US011382968B2

(12) United States Patent
Georges et al.

(10) Patent No.: US 11,382,968 B2
(45) Date of Patent: Jul. 12, 2022

(54) CORONAVIRUS IMMUNOGENIC COMPOSITIONS AND USES THEREOF

(71) Applicant: Altimmune, Inc, Gaithersburg, MD (US)

(72) Inventors: Bertrand Victor Gilbert Georges, Leeds (GB); M. Scot Roberts, Gaithersburg, MD (US)

(73) Assignee: Altimmune Inc., Gaithersburg, MD (US)

( * ) Notice: Subject to any disclaimer, the term of this patent is extended or adjusted under 35 U.S.C. 154(b) by 0 days.

(21) Appl. No.: 17/342,769

(22) Filed: Jun. 9, 2021

(65) Prior Publication Data

US 2022/0072121 A1 Mar. 10, 2022

Related U.S. Application Data

(63) Continuation of application No. 17/175,144, filed on Feb. 12, 2021.

(60) Provisional application No. 63/148,374, filed on Feb. 11, 2021, provisional application No. 63/142,077, filed on Jan. 27, 2021, provisional application No. 63/140,128, filed on Jan. 21, 2021, provisional application No. 63/088,736, filed on Oct. 7, 2020, provisional application No. 63/069,792, filed on Aug. 25, 2020, provisional application No. 63/050,844, filed on Jul. 12, 2020, provisional application No. 63/016,902, filed on Apr. 28, 2020, provisional application No. 63/005,923, filed on Apr. 6, 2020, provisional application No. 62/992,553, filed on Mar. 20, 2020, provisional application No. 62/977,078, filed on Feb. 14, 2020.

(51) Int. Cl.

| | |
|---|---|
| ***A61K 39/215*** | (2006.01) |
| ***A61P 31/14*** | (2006.01) |
| ***C12N 15/86*** | (2006.01) |
| ***A61K 9/00*** | (2006.01) |
| ***C12N 7/00*** | (2006.01) |
| *A61K 39/00* | (2006.01) |

(52) U.S. Cl.

CPC .......... *A61K 39/215* (2013.01); *A61K 9/0043* (2013.01); *A61P 31/14* (2018.01); *C12N 7/00* (2013.01); *C12N 15/86* (2013.01); *A61K 2039/5256* (2013.01); *A61K 2039/543* (2013.01); *C12N 2750/14023* (2013.01); *C12N 2750/14034* (2013.01); *C12N 2750/14143* (2013.01); *C12N 2750/14171* (2013.01)

(58) Field of Classification Search

None

See application file for complete search history.

(56) References Cited

U.S. PATENT DOCUMENTS

| | | | | |
|---|---|---|---|---|
| 7,005,498 | B1 * | 2/2006 | Steinaa | A61P 35/00 530/324 |
| 2021/0246170 | A1 * | 8/2021 | Langedijk | C12N 15/86 |

OTHER PUBLICATIONS

Wu et al., Nature, vol. 579, Mar. 12, 202, published online Feb. 3, 2020, pp. 265-269 plus extended data/figures. (Year: 2020).*

Gen Bank Accession No. MN908947.3, 2020. (Year: 2020).*

Gen Bank Accession No. QHD43416.1, 2020. (Year: 2020).*

* cited by examiner

*Primary Examiner* — Stacy B Chen

(74) *Attorney, Agent, or Firm* — Koren Anderson; Duane Morris LLP

(57) ABSTRACT

Provided in the present disclosure are immunogenic compounds, pharmaceutical formulations thereof and their use for inducing a protective immune response against 2019 novel coronavirus (SARS-CoV-2) infection and variants in a mammal.

19 Claims, 109 Drawing Sheets

Specification includes a Sequence Listing.

FIGURE 1A

SEQ ID NO: 1

*Wuhan seafood market pneumonia virus isolate Wuhan-Hu-1, complete genome*

(GenBank: MN908947.3)

1 attaaaggtt tataccttcc caggtaacaa accaaccaac tttcgatctc ttgtagatct
61 gttctctaaa cgaactttaa aatctgtgtg gctgtcactc ggctgcatgc ttagtgcact
121 cacgcagtat aattaataac taattactgt cgttgacagg acacgagtaa ctcgtctatc
181 ttctgcaggc tgcttacggt ttcgtccgtg ttgcagccga tcatcagcac atctaggttt
241 cgtccgggtg tgaccgaaag gtaagatgga gagccttgtc cctggtttca acgagaaaac
301 acacgtccaa ctcagtttgc ctgttttaca ggttcgcgac gtgctcgtac gtggctttgg
361 agactccgtg gaggaggtct tatcagaggc acgtcaacat cttaaagatg gcacttgtgg
421 cttagtagaa gttgaaaaag gcgttttgcc tcaacttgaa cagccctatg tgttcatcaa
481 acgttcggat gctcgaactg cacctcatgg tcatgttatg gttgagctgg tagcagaact
541 cgaaggcatt cagtacggtc gtagtggtga gacacttggt gtccttgtcc ctcatgtggg
601 cgaaatacca gtggcttacc gcaaggttct tcttcgtaag aacggtaata aaggagctgg
661 tggccatagt tacggcgccg atctaaagtc atttgactta ggcgacgagc ttggcactga
721 tccttatgaa gattttcaag aaaactggaa cactaaacat agcagtggtg ttacccgtga
781 actcatgcgt gagcttaacg gaggggcata cactcgctat gtcgataaca acttctgtgg
841 ccctgatggc taccctcttg agtgcattaa agaccttcta gcacgtgctg gtaaagcttc
901 atgcactttg tccgaacaac tggactttat tgacactaag aggggtgtat actgctgccg
961 tgaacatgag catgaaattg cttggtacac ggaacgttct gaaaagagct atgaattgca
1021 gacacctttt gaaattaaat tggcaaagaa atttgacacc ttcaatgggg aatgtccaaa
1081 ttttgtattt cccttaaatt ccataatcaa gactattcaa ccaagggttg aaaagaaaaa
1141 gcttgatggc tttatgggta gaattcgatc tgtctatcca gttgcgtcac caaatgaatg
1201 caaccaaatg tgcctttcaa ctctcatgaa gtgtgatcat tgtggtgaaa cttcatggca
1261 gacgggcgat tttgttaaag ccacttgcga attttgtggc actgagaatt tgactaaaga
1321 aggtgccact acttgtggtt acttacccca aatgctgttg ttaaaattta ttgtccagc
1381 atgtcacaat tcagaagtag gacctgagca tagtcttgcc gaataccata atgaatctgg
1441 cttgaaaacc attcttcgta agggtggtcg cactattgcc tttggaggct gtgtgttctc
1501 ttatgttggt tgccataaca agtgtgccta ttgggttcca cgtgctagcg ctaacatagg
1561 ttgtaaccat acaggtgttg ttggagaagg ttccgaaggt cttaatgaca accttcttga
1621 aatactccaa aaagagaaag tcaacatcaa tattgttggt gactttaaac ttaatgaaga
1681 gatcgccatt attttggcat ctttttctgc ttccacaagt gcttttgtgg aaactgtgaa
1741 aggtttggat tataaagcat tcaaacaaat tgttgaatcc tgtggtaatt ttaaagttac
1801 aaaaggaaaa gctaaaaaag gtgcctggaa tattggtgaa cagaaatcaa tactgagtcc
1861 tctttatgca tttgcatcag aggctgctcg tgttgtacga tcaattttct cccgcactct
1921 tgaaactgct caaaattctg tgcgtgtttt acagaaggcc gctataacaa tactagatgg
1981 aatttcacag tattcactga gactcattga tgctatgatg ttcacatctg atttggctac
2041 taacaatcta gttgtaatgg cctacattac aggtggtgtt gttcagttga cttcgcagtg
2101 gctaactaac atctttggca ctgtttatga aaaactcaaa cccgtccttg attggcttga
2161 agagaagttt aaggaaggtg tagagtttct tagagacggt tgggaaattg ttaaatttat
2221 ctcaacctgt gcttgtgaaa ttgtcggtgg acaaattgtc acctgtgcaa aggaaattaa
2281 ggagagtgtt cagacattct ttaagcttgt aaataaattt ttggctttgt gtgctgactc
2341 tatcattatt ggtggagcta aacttaaagc cttgaattta ggtgaaacat ttgtcacgca
2401 ctcaaaggga ttgtacagaa agtgtgttaa atccagagaa gaaactggcc tactcatgcc
2461 tctaaaagcc ccaaaagaaa ttatcttctt agagggagaa acacttccca cagaagtgtt
2521 aacagaggaa gttgtcttga aaactggtga tttacaacca ttagaacaac ctactagtga
2581 agctgttgaa gctccattgg ttggtacacc agtttgtatt aacgggctta tgttgctcga
2641 aatcaaagac acagaaaagt actgtgccct tgcacctaat atgatggtaa caaacaatac
2701 cttcacactc aaaggcggtg caccaacaaa ggttactttt ggtgatgaca ctgtgataga
2761 agtgcaaggt tacaagagtg tgaatatcac ttttgaactt gatgaaagga ttgataaagt
2821 acttaatgag aagtgctctg cctatacagt tgaactcggt acagaagtaa atgagttcgc
2881 ctgtgttgtg gcagatgctg tcataaaaac tttgcaacca gtatctgaat tacttacacc
2941 actgggcatt gatttagatg agtggagtat ggctacatac tacttatttg atgagtctgg
3001 tgagtttaaa ttggcttcac atatgtattg ttctttctac cctccagatg aggatgaaga
3061 agaaggtgat tgtgaagaag aagagtttga gccatcaact caatatgagt atggtactga
3121 agatgattac caaggtaaac ctttggaatt tggtgccact tctgctgctc ttcaacctga

FIGURE 1B

SEQ ID NO: 1 (continued)

```
3181 agaagagcaa gaagaagatt ggttagatga tgatagtcaa caaactgttg gtcaacaaga
3241 cggcagtgag gacaatcaga caactactat tcaaacaatt gttgaggttc aacctcaatt
3301 agagatggaa cttacaccag ttgttcagac tattgaagtg aatagtttta gtggttattt
3361 aaaacttact gacaatgtat acattaaaaa tgcagacatt gtggaagaag ctaaaaaggt
3421 aaaaccaaca gtggttgtta atgcagccaa tgtttacctt aaacatggag gaggtgttgc
3481 aggagcctta aataaggcta ctaacaatgc catgcaagtt gaatctgatg attacatagc
3541 tactaatgga ccacttaaag tgggtggtag ttgtgtttta agcggacaca atcttgctaa
3601 acactgtctt catgttgtcg gcccaaatgt taacaaaggt gaagacattc aacttcttaa
3661 gagtgcttat gaaaatttta atcagcacga agttctactt gcaccattat tatcagctgg
3721 tatttttggt gctgacccta tacattcttt aagagtttgt gtagatactg ttcgcacaaa
3781 tgtctactta gctgtctttg ataaaaatct ctatgacaaa cttgtttcaa gctttttgga
3841 aatgaagagt gaaaagcaag ttgaacaaaa gatcgctgag attcctaaag aggaagttaa
3901 gccatttata actgaaagta aaccttcagt tgaacagaga aaacaagatg ataagaaaat
3961 caaagcttgt gttgaagaag ttacaacaac tctggaagaa actaagttcc tcacagaaaa
4021 cttgttactt tatattgaca ttaatggcaa tcttcatcca gattctgcca ctcttgttag
4081 tgacattgac atcactttct taaagaaaga tgctccatat atagtgggtg atgttgttca
4141 agagggtgtt ttaactgctg tggttatacc tactaaaaag gctggtggca ctactgaaat
4201 gctagcgaaa gctttgagaa aagtgccaac agacaattat ataaccactt acccgggtca
4261 gggtttaaat ggttacactg tagaggaggc aaagacagtg cttaaaaagt gtaaaagtgc
4321 cttttacatt ctaccatcta ttatctctaa tgagaagcaa gaaattcttg gaactgtttc
4381 ttggaatttg cgagaaatgc ttgcacatgc agaagaaaca cgcaaattaa tgcctgtctg
4441 tgtggaaact aaagccatag tttcaactat acagcgtaaa tataagggta ttaaaataca
4501 agagggtgtg gttgattatg gtgctagatt ttacttttac accagtaaaa caactgtagc
4561 gtcacttatc aacacactta acgatctaaa tgaaactctt gttacaatgc cacttggcta
4621 tgtaacacat ggcttaaatt tggaagaagc tgctcggtat atgagatctc tcaaagtgcc
4681 agctacagtt tctgtttctt cacctgatgc tgttacagcg tataatggtt atcttacttc
4741 ttcttctaaa acacctgaag aacattttat tgaaaccatc tcacttgctg gttcctataa
4801 agattggtcc tattctggac aatctacaca actaggtata gaatttctta agagaggtga
4861 taaaagtgta tattacacta gtaatcctac cacattccac ctagatggtg aagttatcac
4921 ctttgacaat cttaagacac ttctttcttt gagagaagtg aggactatta aggtgtttac
4981 aacagtagac aacattaacc tccacacgca agttgtggac atgtcaatga catatggaca
5041 acagtttggt ccaacttatt tggatggagc tgatgttact aaaataaaac ctcataattc
5101 acatgaaggt aaaacatttt atgttttacc taatgatgac actctacgtg ttgaggcttt
5161 tgagtactac cacacaactg atcctagttt tctgggtagg tacatgtcag cattaaatca
5221 cactaaaaag tggaaatacc cacaagttaa tggtttaact tctattaaat gggcagataa
5281 caactgttat cttgccactg cattgttaac actccaacaa atagagttga agtttaatcc
5341 acctgctcta caagatgctt attacagagc aagggctggt gaagctgcta acttttgtgc
5401 acttatctta gcctactgta ataagacagt aggtgagtta ggtgatgtta gagaaacaat
5461 gagttacttg tttcaacatg ccaatttaga ttcttgcaaa agagtcttga acgtggtgtg
5521 taaaacttgt ggacaacagc agacaaccct taagggtgta gaagctgtta tgtacatggg
5581 cacactttct tatgaacaat ttaagaaagg tgttcagata ccttgtacgt gtggtaaaca
5641 agctacaaaa tatctagtac aacaggagtc accttttgtt atgatgtcag caccacctgc
5701 tcagtatgaa cttaagcatg gtacatttac ttgtgctagt gagtacactg gtaattacca
5761 gtgtggtcac tataaacata taacttctaa agaaactttg tattgcatag acggtgcttt
5821 acttacaaag tcctcagaat acaaaggtcc tattacggat gttttctaca aagaaaacag
5881 ttacacaaca accataaaac cagttactta taaattggat ggtgttgttt gtacagaaat
5941 tgaccctaag ttggacaatt attataagaa agacaattct tatttcacag agcaaccaat
6001 tgatcttgta ccaaaccaac catatccaaa cgcaagcttc gataattta agtttgtatg
6061 tgataatatc aaatttgctg atgatttaaa ccagttaact ggttataaga aacctgcttc
6121 aagagagctt aaagttacat ttttccctga cttaaatggt gatgtggtgg ctattgatta
6181 taaacactac acaccctctt ttaagaaagg agctaaattg ttacataaac ctattgtttg
6241 gcatgttaac aatgcaacta ataaagccac gtataaacca aatacctggt gtatacgttg
6301 tctttggagc acaaaaccag ttgaaacatc aaattcgttt gatgtactga agtcagagga
6361 cgcgcaggga atggataatc ttgcctgcga agatctaaaa ccagtctctg aagaagtagt
```

FIGURE 1C
SEQ ID NO: 1 (continued)

```
6421 ggaaaatcct accatacaga aagacgttct tgagtgtaat gtgaaaacta ccgaagttgt
6481 aggagacatt atacttaaac cagcaaataa tagtttaaaa attacagaag aggttggcca
6541 cacagatcta atggctgctt atgtagacaa ttctagtctt actattaaga aacctaatga
6601 attatctaga gtattaggtt tgaaaaccct tgctactcat ggtttagctg ctgttaatag
6661 tgtcccttgg gatactatag ctaattatgc taagcctttt cttaacaaag ttgttagtac
6721 aactactaac atagttacac ggtgtttaaa ccgtgtttgt actaattata tgccttattt
6781 ctttacttta ttgctacaat tgtgtacttt tactagaagt acaaattcta gaattaaagc
6841 atctatgccg actactatag caaagaatac tgttaagagt gtcggtaaat tttgtctaga
6901 ggcttcattt aattatttga agtcacctaa tttttctaaa ctgataaata ttataatttg
6961 gtttttacta ttaagtgttt gcctaggttc tttaatctac tcaaccgctg ctttaggtgt
7021 tttaatgtct aatttaggca tgccttctta ctgtactggt tacagagaag gctatttgaa
7081 ctctactaat gtcactattg caacctactg tactggttct ataccttgta gtgtttgtct
7141 tagtggttta gattctttag acacctatcc ttctttagaa actatacaaa ttaccatttc
7201 atcttttaaa tgggatttaa ctgcttttgg cttagttgca gagtggtttt tggcatatat
7261 tcttttcact aggtttttct atgtacttgg attggctgca atcatgcaat tgtttttcag
7321 ctattttgca gtacatttta ttagtaattc ttggcttatg tggttaataa ttaatcttgt
7381 acaaatggcc ccgatttcag ctatggttag aatgtacatc ttctttgcat catttatatta
7441 tgtatggaaa agttatgtgc atgttgtaga cggttgtaat tcatcaactt gtatgatgtg
7501 ttacaaacgt aatagagcaa caagagtcga atgtacaact attgttaatg gtgttagaag
7561 gtccttttat gtctatgcta atggaggtaa aggcttttgc aaactacaca attggaattg
7621 tgttaattgt gatacattct gtgctggtag tacatttatt agtgatgaag ttgcgagaga
7681 cttgtcacta cagtttaaaa gaccaataaa tcctactgac cagtcttctt acatcgttga
7741 tagtgttaca gtgaagaatg gttccatcca tctttacttt gataaagctg gtcaaaagac
7801 ttatgaaaga cattctctct ctcattttgt taacttagac aacctgagag ctaataacac
7861 taaaggttca ttgcctatta atgttatagt tttgatggt aaatcaaaat gtgaagaatc
7921 atctgcaaaa tcagcgtctg tttactacag tcagcttatg tgtcaaccta tactgttact
7981 agatcaggca ttagtgtctg atgttggtga tagtgcggaa gttgcagtta aaatgtttga
8041 tgcttacgtt aatacgtttt catcaacttt taacgtacca atggaaaaac tcaaaacact
8101 agttgcaact gcagaagctg aacttgcaaa gaatgtgtcc ttagacaatg tcttatctac
8161 ttttatttca gcagctcggc aagggtttgt tgattcagat gtagaaacta aagatgttgt
8221 tgaatgtctt aaattgtcac atcaatctga catagaagtt actggcgata gttgtaataa
8281 ctatatgctc acctataaca aagttgaaaa catgacaccc cgtgaccttg gtgcttgtat
8341 tgactgtagt gcgcgtcata ttaatgcgca ggtagcaaaa agtcacaaca ttgctttgat
8401 atggaacgtt aaagatttca tgtcattgtc tgaacaacta cgaaaacaaa tacgtagtgc
8461 tgctaaaaag aataacttac cttttaagtt gacatgtgca actactagac aagttgttaa
8521 tgttgtaaca acaaagatag cacttaaggg tggtaaaatt gttaataatt ggttgaagca
8581 gttaattaaa gttacacttg tgttcctttt tgttgctgct attttctatt taataacacc
8641 tgttcatgtc atgtctaaac atactgactt ttcaagtgaa atcataggat acaaggctat
8701 tgatggtggt gtcactcgtg acatagcatc tacagatact tgttttgcta acaaacatgc
8761 tgattttgac acatggttta gccagcgtgg tggtagttat actaatgaca aagcttgccc
8821 attgattgct gcagtcataa caagagaagt gggttttgtc gtgcctggtt tgcctggcac
8881 gatattacgc acaactaatg gtgacttttt gcatttctta cctagagttt ttagtgcagt
8941 tggtaacatc tgttacacac catcaaaact tatagagtac actgactttg caacatcagc
9001 ttgtgttttg gctgctgaat gtacaatttt taaagatgct tctggtaagc cagtaccata
9061 ttgttatgat accaatgtac tagaaggttc tgttgcttat gaaagtttac gccctgacac
9121 acgttatgtg ctcatggatg gctctattat tcaatttcct aacacctacc ttgaaggttc
9181 tgttagagtg gtaacaactt ttgattctga gtactgtagg cacggcactt gtgaaagatc
9241 agaagctggt gtttgtgtat ctactagtgg tagatgggta cttaacaatg attattacag
9301 atctttacca ggagttttct gtggtgtaga tgctgtaaat ttacttacta atatgtttac
9361 accactaatt caacctattg gtgctttgga catatcagca tctatagtag ctggtggtat
9421 tgtagctatc gtagtaacat gccttgccta ctattttatg aggtttagaa gagcttttgg
9481 tgaatacagt catgtagttg cctttaatac tttactattc cttatgtcat tcactgtact
9541 ctgtttaaca ccagtttact cattcttacc tggtgtttat tctgttattt acttgtactt
9601 gacattttat cttactaatg atgtttcttt tttagcacat attcagtgga tggttatgtt
```

FIGURE 1D
SEQ ID NO: 1 (continued)

```
 9661 cacaccttta gtacctttct ggataacaat tgcttatatc atttgtattt ccacaaagca
 9721 tttctattgg ttctttagta attacctaaa gagacgtgta gtctttaatg gtgtttcctt
 9781 tagtactttt gaagaagctg cgctgtgcac ctttttgtta aataaagaaa tgtatctaaa
 9841 gttgcgtagt gatgtgctat tacctcttac gcaatataat agatacttag ctctttataa
 9901 taagtacaag tattttagtg gagcaatgga tacaactagc tacagagaag ctgcttgttg
 9961 tcatctcgca aaggctctca atgacttcag taactcaggt tctgatgttc tttaccaacc
10021 accacaaacc tctatcacct cagctgtttt gcagagtggt tttagaaaaa tggcattccc
10081 atctggtaaa gttgagggtt gtatggtaca agtaacttgt ggtacaacta cacttaacgg
10141 tctttggctt gatgacgtag tttactgtcc aagacatgtg atctgcacct ctgaagacat
10201 gcttaaccct aattatgaag atttactcat tcgtaagtct aatcataatt tcttggtaca
10261 ggctggtaat gttcaactca gggttattgg acattctatg caaaattgtg tacttaagct
10321 taaggttgat acagccaatc ctaagacacc taagtataag tttgttcgca ttcaaccagg
10381 acagactttt tcagtgttag cttgttacaa tggttcacca tctggtgttt accaatgtgc
10441 tatgaggccc aatttcacta ttaagggttc attccttaat ggttcatgtg gtagtgttgg
10501 ttttaacata gattatgact gtgtctcttt ttgttacatg caccatatgg aattaccaac
10561 tggagttcat gctggcacag acttagaagg taacttttat ggacctttg ttgacaggca
10621 aacagcacaa gcagctggta cggacacaac tattacagtt aatgttttag cttggttgta
10681 cgctgctgtt ataaatggag acaggtggtt tctcaatcga tttaccacaa ctcttaatga
10741 ctttaacctt gtggctatga agtacaatta tgaacctcta acacaagacc atgttgacat
10801 actaggacct ctttctgctc aaactggaat tgccgtttta gatatgtgtg cttcattaaa
10861 agaattactg caaaatggta tgaatggacg taccatattg ggtagtgctt tattagaaga
10921 tgaatttaca ccttttgatg ttgttagaca atgctcaggt gttactttcc aaagtgcagt
10981 gaaaagaaca atcaagggta cacaccactg gttgttactc acaattttga cttcactttt
11041 agttttagtc cagagtactc aatggtcttt gttctttttt ttgtatgaaa atgccttttt
11101 acctttttgct atgggtatta ttgctatgtc tgcttttgca atgatgtttg tcaaacataa
11161 gcatgcattt ctctgtttgt ttttgttacc ttctcttgcc actgtagctt attttaatat
11221 ggtctatatg cctgctagtt gggtgatgcg tattatgaca tggttggata tggttgatac
11281 tagtttgtct ggttttaagc taaaagactg tgttatgtat gcatcagctg tagtgttact
11341 aatccttatg acagcaagaa ctgtgtatga tgatggtgct aggagagtgt ggacacttat
11401 gaatgtcttg acactcgttt ataaagttta ttatggtaat gctttagatc aagccatttc
11461 catgtgggct cttataatct ctgttacttc taactactca ggtgtagtta caactgtcat
11521 gtttttggcc agaggtattg tttttatgtg tgttgagtat tgccctattt tcttcataac
11581 tggtaataca cttcagtgta taatgctagt ttattgtttc ttaggctatt tttgtacttg
11641 ttactttggc ctcttttgtt tactcaaccg ctactttaga ctgactcttg gtgtttatga
11701 ttacttagtt tctacacagg agtttagata tatgaattca cagggactac tcccacccaa
11761 gaatagcata gatgccttca aactcaacat taaattgttg ggtgttggtg gcaaaccttg
11821 tatcaaagta gccactgtac agtctaaaat gtcagatgta aagtgcacat cagtagtctt
11881 actctcagtt ttgcaacaac tcagagtaga atcatcatct aaattgtggg ctcaatgtgt
11941 ccagttacac aatgacattc tcttagctaa agatactact gaagcctttg aaaaaatggt
12001 ttcactactt tctgttttgc tttccatgca gggtgctgta gacataaaca agctttgtga
12061 agaaatgctg gacaacaggg caaccttaca agctatagcc tcagagttta gttcccttcc
12121 atcatatgca gcttttgcta ctgctcaaga agcttatgag caggctgttg ctaatggtga
12181 ttctgaagtt gttcttaaaa agttgaagaa gtctttgaat gtggctaaat ctgaatttga
12241 ccgtgatgca gccatgcaac gtaagttgga aaagatggct gatcaagcta tgacccaaat
12301 gtataaacag gctagatctg aggacaagag ggcaaaagtt actagtgcta tgcagacaat
12361 gcttttcact atgcttagaa agttggataa tgatgcactc aacaacatta tcaacaatgc
12421 aagagatggt tgtgttccct tgaacataat acctcttaca acagcagcca aactaatggt
12481 tgtcatacca gactataaca catataaaaa tacgtgtgat ggtacaacat ttacttatgc
12541 atcagcattg tgggaaatcc aacaggttgt agatgcagat agtaaaattg ttcaacttag
12601 tgaaattagt atggacaatt cacctaattt agcatggcct cttattgtaa cagctttaag
12661 ggccaattct gctgtcaaat tacagaataa tgagcttagt cctgttgcac tacgacagat
12721 gtcttgtgct gccggtacta cacaaactgc ttgcactgat gacaatgcgt tagcttacta
12781 caacacaaca aagggaggta ggtttgtact tgcactgtta tccgatttac aggatttgaa
12841 atgggctaga ttccctaaga gtgatggaac tggtactatc tatacagaac tggaaccacc
```

FIGURE 1E
SEQ ID NO: 1 (continued)

```
12901 ttgtaggttt gttacagaca cacctaaagg tcctaaagtg aagtatttat actttattaa
12961 aggattaaac aacctaaata gaggtatggt acttggtagt ttagctgcca cagtacgtct
13021 acaagctggt aatgcaacag aagtgcctgc caattcaact gtattatctt tctgtgcttt
13081 tgctgtagat gctgctaaag cttacaaaga ttatctagct agtgggggac aaccaatcac
13141 taattgtgtt aagatgttgt gtacacacac tggtactggt caggcaataa cagttacacc
13201 ggaagccaat atggatcaag aatcctttgg tggtgcatcg tgttgtctgt actgccgttg
13261 ccacatagat catccaaatc ctaaaggatt ttgtgactta aaaggtaagt atgtacaaat
13321 acctacaact tgtgctaatg accctgtggg ttttacactt aaaaacacag tctgtaccgt
13381 ctgcggtatg tggaaaggtt atggctgtag ttgtgatcaa ctccgcgaac ccatgcttca
13441 gtcagctgat gcacaatcgt ttttaaacgg gtttgcggtg taagtgcagc ccgtcttaca
13501 ccgtgcggca caggcactag tactgatgtc gtatacaggg cttttgacat ctacaatgat
13561 aaagtagctg gttttgctaa attcctaaaa actaattgtt gtcgcttcca agaaaaggac
13621 gaagatgaca atttaattga ttcttacttt gtagttaaga gacacacttt ctctaactac
13681 caacatgaag aaacaattta taatttactt aaggattgtc cagctgttgc taaacatgac
13741 ttctttaagt ttagaataga cggtgacatg gtaccacata tatcacgtca acgtcttact
13801 aaatacacaa tggcagacct cgtctatgct ttaaggcatt ttgatgaagg taattgtgac
13861 acattaaaag aaatacttgt cacatacaat tgttgtgatg atgattattt caataaaaag
13921 gactggtatg attttgtaga aaacccagat atattacgcg tatacgccaa cttaggtgaa
13981 cgtgtacgcc aagctttgtt aaaaacagta caattctgtg atgccatgcg aaatgctggt
14041 attgttggtg tactgacatt agataatcaa gatctcaatg gtaactggta tgatttcggt
14101 gatttcatac aaaccacgcc aggtagtgga gttcctgttg tagattctta ttattcattg
14161 ttaatgccta tattaacctt gaccagggct ttaactgcag agtcacatgt tgacactgac
14221 ttaacaaagc cttacattaa gtgggatttg ttaaaatatg acttcacgga agagaggtta
14281 aaactctttg accgttattt taaatattgg gatcagacat accacccaaa ttgtgttaac
14341 tgtttggatg acagatgcat tctgcattgt gcaaacttta atgttttatt ctctacagtg
14401 ttcccaccta caagttttgg accactagtg agaaaaatat ttgttgatgg tgttccattt
14461 gtagtttcaa ctggatacca cttcagagag ctaggtgttg tacataatca ggatgtaaac
14521 ttacatagct ctagacttag ttttaaggaa ttacttgtgt atgctgctga ccctgctatg
14581 cacgctgctt ctggtaatct attactagat aaacgcacta cgtgcttttc agtagctgca
14641 cttactaaca atgttgcttt tcaaactgtc aaacccggta attttaacaa agacttctat
14701 gactttgctg tgtctaaggg tttctttaag gaaggaagtt ctgttgaatt aaaacacttc
14761 ttctttgctc aggatggtaa tgctgctatc agcgattatg actactatcg ttataatcta
14821 ccaacaatgt gtgatatcag acaactacta tttgtagttg aagttgttga taagtacttt
14881 gattgttacg atggtggctg tattaatgct aaccaagtca tcgtcaacaa cctagacaaa
14941 tcagctggtt ttccatttaa taaatggggt aaggctagac tttattatga ttcaatgagt
15001 tatgaggatc aagatgcact tttcgcatat acaaaacgta atgtcatccc tactataact
15061 caaatgaatc ttaagtatgc cattagtgca aagaatagag ctcgcaccgt agctggtgtc
15121 tctatctgta gtactatgac caatagacag tttcatcaaa aattattgaa atcaatagcc
15181 gccactagag gagctactgt agtaattgga acaagcaaat tctatggtgg ttggcacaac
15241 atgttaaaaa ctgtttatag tgatgtagaa aaccctcacc ttatgggttg ggattatcct
15301 aaatgtgata gagccatgcc taacatgctt agaattatgg cctcacttgt tcttgctcgc
15361 aaacatacaa cgtgttgtag cttgtcacac cgtttctata gattagctaa tgagtgtgct
15421 caagtattga gtgaaatggt catgtgtggc ggttcactat atgttaaacc aggtggaacc
15481 tcatcaggag atgccacaac tgcttatgct aatagtgttt ttaacatttg tcaagctgtc
15541 acggccaatg ttaatgcact tttatctact gatggtaaca aaattgccga taagtatgtc
15601 cgcaatttac aacacagact ttatgagtgt ctctatagaa atagagatgt tgacacagac
15661 tttgtgaatg agttttacgc atatttgcgt aaacatttct caatgatgat actctctgac
15721 gatgctgttg tgtgtttcaa tagcacttat gcatctcaag gtctagtggc tagcataaag
15781 aactttaagt cagttcttta ttatcaaaac aatgttttta tgtctgaagc aaaatgttgg
15841 actgagactg accttactaa aggacctcat gaattttgct ctcaacatac aatgctagtt
15901 aaacagggtg atgattatgt gtaccttcct tacccagatc catcaagaat cctaggggcc
15961 ggctgttttg tagatgatat cgtaaaaaca gatggtacac ttatgattga acggttcgtg
16021 tctttagcta tagatgctta cccacttact aaacatccta atcaggagta tgctgatgtc
16081 tttcatttgt acttacaata cataagaaag ctacatgatg agttaacagg acacatgtta
```

FIGURE 1F
SEQ ID NO: 1 (continued)

```
16141 gacatgtatt ctgttatgct tactaatgat aacacttcaa ggtattggga acctgagttt
16201 tatgaggcta tgtacacacc gcatacagtc ttacaggctg ttggggcttg tgttctttgc
16261 aattcacaga cttcattaag atgtggtgct tgcatacgta gaccattctt atgttgtaaa
16321 tgctgttacg accatgtcat atcaacatca cataaattag tcttgtctgt taatccgtat
16381 gtttgcaatg ctccaggttg tgatgtcaca gatgtgactc aactttactt aggaggtatg
16441 agctattatt gtaaatcaca taaaccaccc attagttttc cattgtgtgc taatggacaa
16501 gtttttggtt tatataaaaa tacatgtgtt ggtagcgata atgttactga ctttaatgca
16561 attgcaacat gtgactggac aaatgctggt gattacattt tagctaacac ctgtactgaa
16621 agactcaagc tttttgcagc agaaacgctc aaagctactg aggagacatt taaactgtct
16681 tatggtattg ctactgtacg tgaagtgctg tctgacagag aattacatct ttcatgggaa
16741 gttggtaaac ctagaccacc acttaaccga aattatgtct ttactggtta tcgtgtaact
16801 aaaaacagta aagtacaaat aggagagtac acctttgaaa aaggtgacta tggtgatgct
16861 gttgtttacc gaggtacaac aacttacaaa ttaaatgttg gtgattattt tgtgctgaca
16921 tcacatacag taatgccatt aagtgcacct acactagtgc cacaagagca ctatgttaga
16981 attactggct tatacccaac actcaatatc tcagatgagt tttctagcaa tgttgcaaat
17041 tatcaaaagg ttggtatgca aaagtattct acactccagg gaccacctgg tactggtaag
17101 agtcattttg ctattggcct agctctctac tacccttctg ctcgcatagt gtatacagct
17161 tgctctcatg ccgctgttga tgcactatgt gagaaggcat taaaatattt gcctatagat
17221 aaatgtagta gaattatacc tgcacgtgct cgtgtagagt gttttgataa attcaaagtg
17281 aattcaacat tagaacagta tgtcttttgt actgtaaatg cattgcctga gacgacagca
17341 gatatagttg tctttgatga aatttcaatg gccacaaatt atgatttgag tgttgtcaat
17401 gccagattac gtgctaagca ctatgtgtac attggcgacc ctgctcaatt acctgcacca
17461 cgcacattgc taactaaggg cacactagaa ccagaatatt tcaattcagt gtgtagactt
17521 atgaaaacta taggtccaga catgttcctc ggaacttgtc ggcgttgtcc tgctgaaatt
17581 gttgacactg tgagtgcttt ggtttatgat aataagctta aagcacataa agacaaatca
17641 gctcaatgct ttaaaatgtt ttataagggt gttatcacgc atgatgtttc atctgcaatt
17701 aacaggccac aaataggcgt ggtaagagaa ttccttacac gtaaccctgc ttggagaaaa
17761 gctgtcttta tttcacctta taattcacag aatgctgtag cctcaaagat tttgggacta
17821 ccaactcaaa ctgttgattc atcacagggc tcagaatatg actatgtcat attcactcaa
17881 accactgaaa cagctcactc ttgtaatgta aacagattta atgttgctat taccagagca
17941 aaagtaggca tactttgcat aatgtctgat agagaccttt atgacaagtt gcaatttaca
18001 agtcttgaaa ttccacgtag gaatgtggca actttacaag ctgaaaatgt aacaggactc
18061 tttaaagatt gtagtaaggt aatcactggg ttacatccta cacaggcacc tacacacctc
18121 agtgttgaca ctaaattcaa aactgaaggt ttatgtgttg acatacctgg catacctaag
18181 gacatgacct atagaagact catctctatg atgggtttta aaatgaatta tcaagttaat
18241 ggttacccta acatgtttat cacccgcgaa gaagctataa gacatgtacg tgcatggatt
18301 ggcttcgatg tcgaggggtg tcatgctact agagaagctg ttggtaccaa tttaccttta
18361 cagctaggtt tttctacagg tgttaaccta gttgctgtac ctacaggtta tgttgataca
18421 cctaataata cagatttttc cagagttagt gctaaaccac cgcctggaga tcaatttaaa
18481 cacctcatac cacttatgta caaaggactt ccttggaatg tagtgcgtat aaagattgta
18541 caaatgttaa gtgacacact taaaaatctc tctgacagag tcgtatttgt cttatgggca
18601 catggctttg agttgacatc tatgaagtat tttgtgaaaa taggacctga gcgcacctgt
18661 tgtctatgtg atagacgtgc cacatgcttt tccactgctt cagacactta tgcctgttgg
18721 catcattcta ttggatttga ttacgtctat aatccgttta tgattgatgt tcaacaatgg
18781 ggttttacag gtaacctaca aagcaaccat gatctgtatt gtcaagtcca tggtaatgca
18841 catgtagcta gttgtgatgc aatcatgact aggtgtctag ctgtccacga gtgctttgtt
18901 aagcgtgttg actggactat tgaatatcct ataattggtg atgaactgaa gattaatgcg
18961 gcttgtagaa aggttcaaca catggttgtt aaagctgcat tattagcaga caaattccca
19021 gttcttcacg acattggtaa ccctaaagct attaagtgtg tacctcaagc tgatgtagaa
19081 tggaagttct atgatgcaca gccttgtagt gacaaagctt ataaaataga agaattattc
19141 tattcttatg ccacacattc tgacaaattc acagatggtg tatgcctatt ttggaattgc
19201 aatgtcgata gatatcctgc taattccatt gtttgtagat ttgacactag agtgctatct
19261 aaccttaact tgcctggttg tgatggtggc agtttgtatg taaataaaca tgcattccac
19321 acaccagctt ttgataaaag tgcttttgtt aatttaaaac aattaccatt tttctattac
```

FIGURE 1G
SEQ ID NO: 1 (continued)

```
19381 tctgacagtc catgtgagtc tcatggaaaa caagtagtgt cagatataga ttatgtacca
19441 ctaaagtctg ctacgtgtat aacacgttgc aatttaggtg gtgctgtctg tagacatcat
19501 gctaatgagt acagattgta tctcgatgct tataacatga tgatctcagc tggctttagc
19561 ttgtgggttt acaaacaatt tgatacttat aacctctgga acacttttac aagacttcag
19621 agtttagaaa atgtggcttt taatgttgta aataagggac actttgatgg acaacagggt
19681 gaagtaccag tttctatcat taataacact gtttacacaa aagttgatgg tgttgatgta
19741 gaattgtttg aaaataaaac aacattacct gttaatgtag catttgagct ttgggctaag
19801 cgcaacatta aaccagtacc agaggtgaaa atactcaata atttgggtgt ggacattgct
19861 gctaatactg tgatctggga ctacaaaaga gatgctccag cacatatatc tactattggt
19921 gtttgttcta tgactgacat agccaagaaa ccaactgaaa cgatttgtgc accactcact
19981 gtcttttttg atggtagagt tgatggtcaa gtagacttat ttagaaatgc ccgtaatggt
20041 gttcttatta cagaaggtag tgttaaaggt ttacaaccat ctgtaggtcc caaacaagct
20101 agtcttaatg gagtcacatt aattggagaa gccgtaaaaa cacagttcaa ttattataag
20161 aaagttgatg gtgttgtcca acaattacct gaaacttact ttactcagag tagaaattta
20221 caagaattta aacccaggag tcaaatggaa attgatttct tagaattagc tatggatgaa
20281 ttcattgaac ggtataaatt agaaggctat gccttcgaac atatcgttta tggagatttt
20341 agtcatagtc agttaggtgg tttacatcta ctgattggac tagctaaacg ttttaaggaa
20401 tcaccttttg aattagaaga ttttattcct atggacagta cagttaaaaa ctatttcata
20461 acagatgcgc aaacaggttc atctaagtgt gtgtgttctg ttattgattt attacttgat
20521 gattttgttg aaataataaa atcccaagat ttatctgtag tttctaaggt tgtcaaagtg
20581 actattgact atacagaaat ttcatttatg ctttggtgta aagatggcca tgtagaaaca
20641 ttttacccaa aattacaatc tagtcaagcg tggcaaccgg gtgttgctat gcctaatctt
20701 tacaaaatgc aaagaatgct attagaaaag tgtgaccttc aaaattatgg tgatagtgca
20761 acattaccta aaggcataat gatgaatgtc gcaaaatata ctcaactgtg tcaatattta
20821 aacacattaa cattagctgt accctataat atgagagtta tacattttgg tgctggttct
20881 gataaaggag ttgcaccagg tacagctgtt ttaagacagt ggttgcctac gggtacgctg
20941 cttgtcgatt cagatcttaa tgactttgtc tctgatgcag attcaacttt gattggtgat
21001 tgtgcaactg tacatacagc taataaatgg gatctcatta ttagtgatat gtacgaccct
21061 aagactaaaa atgttacaaa agaaaatgac tctaaagagg gtttttttcac ttacatttgt
21121 gggtttatac aacaaaagct agctcttgga ggttccgtgg ctataaagat aacagaacat
21181 tcttggaatg ctgatcttta taagctcatg ggacacttcg catggtggac agcctttgtt
21241 actaatgtga atgcgtcatc atctgaagca tttttaattg gatgtaatta tcttggcaaa
21301 ccacgcgaac aaatagatgg ttatgtcatg catgcaaatt acatattttg gaggaataca
21361 aatccaattc agttgtcttc ctattcttta tttgacatga gtaaatttcc ccttaaatta
21421 aggggtactg ctgttatgtc tttaaaagaa ggtcaaatca atgatatgat tttatctctt
21481 cttagtaaag gtagacttat aattagagaa aacaacagag ttgttatttc tagtgatgtt
21541 cttgttaaca actaaacgaa caatgtttgt ttttcttgtt ttattgccac tagtctctag
21601 tcagtgtgtt aatcttacaa ccagaactca attaccccct gcatacacta attctttcac
21661 acgtggtgtt tattaccctg acaaagtttt cagatcctca gttttacatt caactcagga
21721 cttgttctta cctttctttt ccaatgttac ttggttccat gctatacatg tctctgggac
21781 caatggtact aagaggtttg ataaccctgt cctaccattt aatgatggtg tttattttgc
21841 ttccactgag aagtctaaca taataagagg ctggattttt ggtactactt tagattcgaa
21901 gacccagtcc ctacttattg ttaataacgc tactaatgtt gttattaaag tctgtgaatt
21961 tcaattttgt aatgatccat ttttgggtgt ttattaccac aaaaacaaca aaagttggat
22021 ggaaagtgag ttcagagttt attctagtgc gaataattgc acttttgaat atgtctctca
22081 gccttttctt atggaccttg aaggaaaaca gggtaatttc aaaaatctta gggaatttgt
22141 gtttaagaat attgatggtt attttaaaat atattctaag cacacgccta ttaatttagt
22201 gcgtgatctc cctcagggtt tttcggcttt agaaccattg gtagatttgc caataggtat
22261 taacatcact aggtttcaaa ctttacttgc tttacataga agttatttga ctcctggtga
22321 ttcttcttca ggttggacag ctggtgctgc agcttattat gtgggttatc ttcaacctag
22381 gacttttcta ttaaaatata atgaaaatgg aaccattaca gatgctgtag actgtgcact
22441 tgaccctctc tcagaaacaa agtgtacgtt gaaatccttc actgtagaaa aaggaatcta
22501 tcaaacttct aactttagag tccaaccaac agaatctatt gttagatttc ctaatattac
22561 aaacttgtgc ccttttggtg aagtttttaa cgccaccaga tttgcatctg tttatgcttg
```

FIGURE 1H
SEQ ID NO: 1 (continued)

```
22621 gaacaggaag agaatcagca actgtgttgc tgattattct gtcctatata attccgcatc
22681 attttccact tttaagtgtt atggagtgtc tcctactaaa ttaaatgatc tctgctttac
22741 taatgtctat gcagattcat ttgtaattag aggtgatgaa gtcagacaaa tcgctccagg
22801 gcaaactgga aagattgctg attataatta taaattacca gatgatttta caggctgcgt
22861 tatagcttgg aattctaaca atcttgattc taaggttggt ggtaattata attacctgta
22921 tagattgttt aggaagtcta atctcaaacc ttttgagaga gatatttcaa ctgaaatcta
22981 tcaggccggt agcacacctt gtaatggtgt tgaaggtttt aattgttact ttcctttaca
23041 atcatatggt ttccaaccca ctaatggtgt tggttaccaa ccatacagag tagtagtact
23101 ttcttttgaa cttctacatg caccagcaac tgtttgtgga cctaaaaagt ctactaattt
23161 ggttaaaaac aaatgtgtca atttcaactt caatggttta acaggcacag gtgttcttac
23221 tgagtctaac aaaaagtttc tgcctttcca acaatttggc agagacattg ctgacactac
23281 tgatgctgtc cgtgatccac agacacttga gattcttgac attacaccat gttcttttgg
23341 tggtgtcagt gttataacac caggaacaaa tacttctaac caggttgctg ttctttatca
23401 ggatgttaac tgcacagaag tccctgttgc tattcatgca gatcaactta ctcctacttg
23461 gcgtgtttat tctacaggtt ctaatgtttt tcaaacacgt gcaggctgtt taatagggc
23521 tgaacatgtc aacaactcat atgagtgtga catacccatt ggtgcaggta tatgcgctag
23581 ttatcagact cagactaatt ctcctcggcg ggcacgtagt gtagctagtc aatccatcat
23641 tgcctacact atgtcacttg gtgcagaaaa ttcagttgct tactctaata actctattgc
23701 catacccaca aattttacta ttagtgttac cacagaaatt ctaccagtgt ctatgaccaa
23761 gacatcagta gattgtacaa tgtacatttg tggtgattca actgaatgca gcaatctttt
23821 gttgcaatat ggcagttttt gtacacaatt aaaccgtgct ttaactggaa tagctgttga
23881 acaagacaaa aacacccaag aagtttttgc acaagtcaaa caaatttaca aaacaccacc
23941 aattaaagat tttggtggtt ttaatttttc acaaatatta ccagatccat caaaaccaag
24001 caagaggtca tttattgaag atctactttt caacaaagtg acacttgcag atgctggctt
24061 catcaaacaa tatggtgatt gccttggtga tattgctgct agagacctca tttgtgcaca
24121 aaagtttaac ggccttactg ttttgccacc tttgctcaca gatgaaatga ttgctcaata
24181 cacttctgca ctgttagcgg gtacaatcac ttctggttgg acctttggtg caggtgctgc
24241 attacaaata ccatttgcta tgcaaatggc ttataggttt aatggtattg gagttacaca
24301 gaatgttctc tatgagaacc aaaaattgat tgccaaccaa tttaatagtg ctattggcaa
24361 aattcaagac tcactttctt ccacagcaag tgcacttgga aaacttcaag atgtggtcaa
24421 ccaaaatgca caagctttaa acacgcttgt taaacaactt agctccaatt ttggtgcaat
24481 ttcaagtgtt ttaaatgata tcctttcacg tcttgacaaa gttgaggctg aagtgcaaat
24541 tgataggttg atcacaggca gacttcaaag tttgcagaca tatgtgactc aacaattaat
24601 tagagctgca gaaatcagag cttctgctaa tcttgctgct actaaaatgt cagagtgtgt
24661 acttggacaa tcaaaaagag ttgatttttg tggaaagggc tatcatctta tgtccttccc
24721 tcagtcagca cctcatggtg tagtcttctt gcatgtgact tatgtccctg cacaagaaaa
24781 gaacttcaca actgctcctg ccatttgtca tgatggaaaa gcacactttc ctcgtgaagg
24841 tgtctttgtt tcaaatggca cacactggtt tgtaacacaa aggaattttt atgaaccaca
24901 aatcattact acagacaaca catttgtgtc tggtaactgt gatgttgtaa taggaattgt
24961 caacaacaca gtttatgatc ctttgcaacc tgaattagac tcattcaagg aggagttaga
25021 taaatatttt aagaatcata catcaccaga tgttgattta ggtgacatct ctggcattaa
25081 tgcttcagtt gtaaacattc aaaaagaaat tgaccgcctc aatgaggttg ccaagaattt
25141 aaatgaatct ctcatcgatc tccaagaact tggaaagtat gagcagtata taaaatggcc
25201 atggtacatt tggctaggtt ttatagctgg cttgattgcc atagtaatgg tgacaattat
25261 gctttgctgt atgaccagtt gctgtagttg tctcaagggc tgttgttctt gtggatcctg
25321 ctgcaaattt gatgaagacg actctgagcc agtgctcaaa ggagtcaaat tacattacac
25381 ataaacgaac ttatggattt gtttatgaga atcttcacaa ttggaactgt aactttgaag
25441 caaggtgaaa tcaaggatgc tactccttca gattttgttc gcgctactgc aacgataccg
25501 atacaagcct cactcccttt cggatggctt attgttggcg ttgcacttct tgctgttttt
25561 cagagcgctt ccaaaatcat aaccctcaaa aagagatggc aactagcact ctccaagggt
25621 gttcactttg tttgcaactt gctgttgttg tttgtaacag tttactcaca ccttttgctc
25681 gttgctgctg gccttgaagc cccttttctc tatctttatg ctttagtcta cttcttgcag
25741 agtataaact ttgtaagaat aataatgagg ctttggcttt gctggaaatg ccgttccaaa
25801 aacccattac tttatgatgc caactatttt ctttgctggc atactaattg ttacgactat
```

FIGURE 1I
SEQ ID NO: 1 (continued)

```
25861 tgtatacctt acaatagtgt aacttcttca attgtcatta cttcaggtga tggcacaaca
25921 agtcctattt ctgaacatga ctaccagatt ggtggttata ctgaaaaatg ggaatctgga
25981 gtaaaagact gtgttgtatt acacagttac ttcacttcag actattacca gctgtactca
26041 actcaattga gtacagacac tggtgttgaa catgttacct tcttcatcta caataaaatt
26101 gttgatgagc ctgaagaaca tgtccaaatt cacacaatcg acggttcatc cggagttgtt
26161 aatccagtaa tggaaccaat ttatgatgaa ccgacgacga ctactagcgt gcctttgtaa
26221 gcacaagctg atgagtacga acttatgtac tcattcgttt cggaagagac aggtacgtta
26281 atagttaata gcgtacttct ttttcttgct ttcgtggtat tcttgctagt tacactagcc
26341 atccttactg cgcttcgatt gtgtgcgtac tgctgcaata ttgttaacgt gagtcttgta
26401 aaaccttctt tttacgttta ctctcgtgtt aaaaatctga attcttctag agttcctgat
26461 cttctggtct aaacgaacta aatattatat tagtttttct gtttggaact ttaattttag
26521 ccatggcaga ttccaacggt actattaccg ttgaagagct taaaaagctc cttgaacaat
26581 ggaacctagt aataggtttc ctattcctta catggatttg tcttctacaa tttgcctatg
26641 ccaacaggaa taggtttttg tatataatta agttaatttt cctctggctg ttatggccag
26701 taactttagc ttgttttgtg cttgctgctg tttacagaat aaattggatc accggtggaa
26761 ttgctatcgc aatggcttgt cttgtaggct tgatgtggct cagctacttc attgcttctt
26821 tcagactgtt tgcgcgtacg cgttccatgt ggtcattcaa tccagaaact aacattcttc
26881 tcaacgtgcc actccatggc actattctga ccagaccgct tctagaaagt gaactcgtaa
26941 tcggagctgt gatccttcgt ggacatcttc gtattgctgg acaccatcta ggacgctgtg
27001 acatcaagga cctgcctaaa gaaatcactg ttgctacatc acgaacgctt tcttattaca
27061 aattgggagc ttcgcagcgt gtagcaggtg actcaggttt tgctgcatac agtcgctaca
27121 ggattggcaa ctataaatta aacacagacc attccagtag cagtgacaat attgctttgc
27181 ttgtacagta agtgacaaca gatgtttcat ctcgttgact ttcaggttac tatagcagag
27241 atattactaa ttattatgag gacttttaaa gtttccattt ggaatcttga ttacatcata
27301 aacctcataa ttaaaaattt atctaagtca ctaactgaga ataaatattc tcaattagat
27361 gaagagcaac caatggagat tgattaaacg aacatgaaaa ttattctttt cttggcactg
27421 ataacactcg ctacttgtga gctttatcac taccaagagt gtgttagagg tacaacagta
27481 cttttaaaag aaccttgctc ttctggaaca tacgagggca attcaccatt tcatcctcta
27541 gctgataaca aatttgcact gacttgcttt agcactcaat ttgcttttgc ttgtcctgac
27601 ggcgtaaaac acgtctatca gttacgtgcc agatcagttt cacctaaact gttcatcaga
27661 caagaggaag ttcaagaact ttactctcca atttttctta ttgttgcggc aatagtgttt
27721 ataacacttt gcttcacact caaaagaaag acagaatgat tgaactttca ttaattgact
27781 tctatttgtg ctttttagcc tttctgctat tccttgtttt aattatgctt attatctttt
27841 ggttctcact tgaactgcaa gatcataatg aaacttgtca cgcctaaacg aacatgaaat
27901 ttcttgtttt cttaggaatc atcacaactg tagctgcatt tcaccaagaa tgtagtttac
27961 agtcatgtac tcaacatcaa ccatatgtag ttgatgaccc gtgtcctatt cacttctatt
28021 ctaaatggta tattagagta ggagctagaa aatcagcacc tttaattgaa ttgtgcgtgg
28081 atgaggctgg ttctaaatca cccattcagt acatcgatat cggtaattat acagtttcct
28141 gtttaccttt tacaattaat tgccaggaac ctaaattggg tagtcttgta gtgcgttgtt
28201 cgttctatga agacttttta gagtatcatg acgttcgtgt tgttttagat ttcatctaaa
28261 cgaacaaact aaaatgtctg ataatggacc ccaaaatcag cgaaatgcac cccgcattac
28321 gtttggtgga ccctcagatt caactggcag taaccagaat ggagaacgca gtggggcgcg
28381 atcaaaacaa cgtcggcccc aaggtttacc caataatact gcgtcttggt tcaccgctct
28441 cactcaacat ggcaaggaag accttaaatt ccctcgagga caaggcgttc caattaacac
28501 caatagcagt ccagatgacc aaattggcta ctaccgaaga gctaccagac gaattcgtgg
28561 tggtgacggt aaaatgaaag atctcagtcc aagatggtat ttctactacc taggaactgg
28621 gccagaagct ggacttccct atggtgctaa caaagacggc atcatatggg ttgcaactga
28681 gggagccttg aatacaccaa aagatcacat tggcacccgc aatcctgcta acaatgctgc
28741 aatcgtgcta caacttcctc aaggaacaac attgccaaaa ggcttctacg cagaagggag
28801 cagaggcggc agtcaagcct cttctcgttc ctcatcacgt agtcgcaaca gttcaagaaa
28861 ttcaactcca ggcagcagta ggggaacttc tcctgctaga atggctggca atggcggtga
28921 tgctgctctt gctttgctgc tgcttgacag attgaaccag cttgagagca aaatgtctgg
28981 taaaggccaa caacaacaag gccaaactgt cactaagaaa tctgctgctg aggcttctaa
29041 gaagcctcgg caaaaacgta ctgccactaa agcatacaat gtaacacaag ctttcggcag
```

FIGURE 1J
SEQ ID NO: 1 (continued)

```
29101 acgtggtcca gaacaaaccc aaggaaattt tggggaccag gaactaatca gacaaggaac
29161 tgattacaaa cattggccgc aaattgcaca atttgccccc agcgcttcag cgttcttcgg
29221 aatgtcgcgc attggcatgg aagtcacacc ttcgggaacg tggttgacct acacaggtgc
29281 catcaaattg gatgacaaag atccaaattt caaagatcaa gtcattttgc tgaataagca
29341 tattgacgca tacaaaacat tcccaccaac agagcctaaa aaggacaaaa agaagaaggc
29401 tgatgaaact caagccttac cgcagagaca gaagaaacag caaactgtga ctcttcttcc
29461 tgctgcagat ttggatgatt tctccaaaca attgcaacaa tccatgagca gtgctgactc
29521 aactcaggcc taaactcatg cagaccacac aaggcagatg ggctatataa acgttttcgc
29581 ttttccgttt acgatatata gtctactctt gtgcagaatg aattctcgta actacatagc
29641 acaagtagat gtagttaact ttaatctcac atagcaatct ttaatcagtg tgtaacatta
29701 gggaggactt gaaagagcca ccacattttc accgaggcca cgcggagtac gatcgagtgt
29761 acagtgaaca atgctaggga gagctgccta tatggaagag ccctaatgtg taaaattaat
29821 tttagtagtg ctatccccat gtgattttaa tagcttctta ggagaatgac aaaaaaaaaa
29881 aaaaaaaaaa aaaaaaaaaa aaa (SEQ ID NO: 1)
```

FIGURE 2A

SEQ ID NO: 2

(SARS-CoV-2 Polyprotein; GenBank: QHD43415.1)

MESLVPGFNEKTHVQLSLPVLQVRDVLVRGFGDSVEEVLSEARQ

HLKDGTCGLVEVEKGVLPQLEQPYVFIKRSDARTAPHGHVMVELVAELEGIQYGRSGE

TLGVLVPHVGEIPVAYRKVLLRKNGNKGAGGHSYGADLKSFDLGDELGTDPYEDFQEN

WNTKHSSGVTRELMRELNGGAYTRYVDNNFCGPDGYPLECIKDLLARAGKASCTLSEQ

LDFIDTKRGVYCCREHEHEIAWYTERSEKSYELQTPFEIKLAKKFDTFNGECPNFVFP

LNSIIKTIQPRVEKKKLDGFMGRIRSVYPVASPNECNQMCLSTLMKCDHCGETSWQTG

DFVKATCEFCGTENLTKEGATTCGYLPQNAVVKIYCPACHNSEVGPEHSLAEYHNESG

LKTILRKGGRTIAFGGCVFSYVGCHNKCAYWVPRASANIGCNHTGVVGEGSEGLNDNL

LEILQKEKVNINIVGDFKLNEEIAIILASFSASTSAFVETVKGLDYKAFKQIVESCGN

FKVTKGKAKKGAWNIGEQKSILSPLYAFASEAARVVRSIFSRTLETAQNSVRVLQKAA

ITILDGISQYSLRLIDAMMFTSDLATNNLVVMAYITGGVVQLTSQWLTNIFGTVYEKL

KPVLDWLEEKFKEGVEFLRDGWEIVKFISTCACEIVGGQIVTCAKEIKESVQTFFKLV

NKFLALCADSIIIGGAKLKALNLGETFVTHSKGLYRKCVKSREETGLLMPLKAPKEII

FLEGETLPTEVLTEEVVLKTGDLQPLEQPTSEAVEAPLVGTPVCINGLMLLEIKDTEK

YCALAPNMMVTNNTFTLKGGAPTKVTFGDDTVIEVQGYKSVNITFELDERIDKVLNEK

CSAYTVELGTEVNEFACVVADAVIKTLQPVSELLTPLGIDLDEWSMATYYLFDESGEF

KLASHMYCSFYPPDEDEEEGDCEEEEFEPSTQYEYGTEDDYQGKPLEFGATSAALQPE

EEQEEDWLDDDSQQTVGQQDGSEDNQTTTIQTIVEVQPQLEMELTPVVQTIEVNSFSG

YLKLTDNVYIKNADIVEEAKKVKPTVVVNAANVYLKHGGGVAGALNKATNNAMQVESD

DYIATNGPLKVGGSCVLSGHNLAKHCLHVVGPNVNKGEDIQLLKSAYENFNQHEVLLA

PLLSAGIFGADPIHSLRVCVDTVRTNVYLAVFDKNLYDKLVSSFLEMKSEKQVEQKIA

EIPKEEVKPFITESKPSVEQRKQDDKKIKACVEEVTTTLEETKFLTENLLLYIDINGN

LHPDSATLVSDIDITFLKKDAPYIVGDVVQEGVLTAVVIPTKKAGGTTEMLAKALRKV

PTDNYITTYPGQGLNGYTVEEAKTVLKKCKSAFYILPSIISNEKQEILGTVSWNLREM

LAHAEETRKLMPVCVETKAIVSTIQRKYKGIKIQEGVVDYGARFYFYTSKTTVASLIN

TLNDLNETLVTMPLGYVTHGLNLEEAARYMRSLKVPATVSVSSPDAVTAYNGYLTSSS

FIGURE 2B
SEQ ID NO: 2 (continued)

KTPEEHFIETISLAGSYKDWSYSGQSTQLGIEFLKRGDKSVYYTSNPTTFHLDGEVIT

FDNLKTLLSLREVRTIKVFTTVDNINLHTQVVDMSMTYGQQFGPTYLDGADVTKIKPH

NSHEGKTFYVLPNDDTLRVEAFEYYHTTDPSFLGRYMSALNHTKKWKYPQVNGLTSIK

WADNNCYLATALLTLQQIELKFNPPALQDAYYRARAGEAANFCALILAYCNKTVGELG

DVRETMSYLFQHANLDSCKRVLNVVCKTCGQQQTTLKGVEAVMYMGTLSYEQFKKGVQ

IPCTCGKQATKYLVQQESPFVMMSAPPAQYELKHGTFTCASEYTGNYQCGHYKHITSK

ETLYCIDGALLTKSSEYKGPITDVFYKENSYTTTIKPVTYKLDGVVCTEIDPKLDNYY

KKDNSYFTEQPIDLVPNQPYPNASFDNFKFVCDNIKFADDLNQLTGYKKPASRELKVT

FFPDLNGDVVAIDYKHYTPSFKKGAKLLHKPIVWHVNNATNKATYKPNTWCIRCLWST

KPVETSNSFDVLKSEDAQGMDNLACEDLKPVSEEVVENPTIQKDVLECNVKTTEVVGD

IILKPANNSLKITEEVGHTDLMAAYVDNSSLTIKKPNELSRVLGLKTLATHGLAAVNS

VPWDTIANYAKPFLNKVVSTTTNIVTRCLNRVCTNYMPYFFTLLLQLCTFTRSTNSRI

KASMPTTIAKNTVKSVGKFCLEASFNYLKSPNFSKLINIIIWFLLLSVCLGSLIYSTA

ALGVLMSNLGMPSYCTGYREGYLNSTNVTIATYCTGSIPCSVCLSGLDSLDTYPSLET

IQITISSFKWDLTAFGLVAEWFLAYILFTRFFYVLGLAAIMQLFFSYFAVHFISNSWL

MWLIINLVQMAPISAMVRMYIFFASFYYVWKSYVHVVDGCNSSTCMMCYKRNRATRVE

CTTIVNGVRRSFYVYANGGKGFCKLHNWNCVNCDTFCAGSTFISDEVARDLSLQFKRP

INPTDQSSYIVDSVTVKNGSIHLYFDKAGQKTYERHSLSHFVNLDNLRANNTKGSLPI

NVIVFDGKSKCEESSAKSASVYYSQLMCQPILLLDQALVSDVGDSAEVAVKMFDAYVN

TFSSTFNVPMEKLKTLVATAEAELAKNVSLDNVLSTFISAARQGFVDSDVETKDVVEC

LKLSHQSDIEVTGDSCNNYMLTYNKVENMTPRDLGACIDCSARHINAQVAKSHNIALI

WNVKDFMSLSEQLRKQIRSAAKKNNLPFKLTCATTRQVVNVVTTKIALKGGKIVNNWL

KQLIKVTLVFLFVAAIFYLITPVHVMSKHTDFSSEIIGYKAIDGGVTRDIASTDTCFA

NKHADFDTWFSQRGGSYTNDKACPLIAAVITREVGFVVPGLPGTILRTTNGDFLHFLP

RVFSAVGNICYTPSKLIEYTDFATSACVLAAECTIFKDASGKPVPYCYDTNVLEGSVA

YESLRPDTRYVLMDGSIIQFPNTYLEGSVRVVTTFDSEYCRHGTCERSEAGVCVSTSG

RWVLNNDYYRSLPGVFCGVDAVNLLTNMFTPLIQPIGALDISASIVAGGIVAIVVTCL

FIGURE 2C

SEQ ID NO: 2 (continued)

AYYFMRFRRAFGEYSHVVAFNTLLFLMSFTVLCLTPVYSFLPGVYSVIYLYLTFYLTN

DVSFLAHIQWMVMFTPLVPFWITIAYIICISTKHFYWFFSNYLKRRVVFNGVSFSTFE

EAALCTFLLNKEMYLKLRSDVLLPLTQYNRYLALYNKYKYFSGAMDTTSYREAACCHL

AKALNDFSNSGSDVLYQPPQTSITSAVLQSGFRKMAFPSGKVEGCMVQVTCGTTTLNG

LWLDDVVYCPRHVICTSEDMLNPNYEDLLIRKSNHNFLVQAGNVQLRVIGHSMQNCVL

KLKVDTANPKTPKYKFVRIQPGQTFSVLACYNGSPSGVYQCAMRPNFTIKGSFLNGSC

GSVGFNIDYDCVSFCYMHHMELPTGVHAGTDLEGNFYGPFVDRQTAQAAGTDTTITVN

VLAWLYAAVINGDRWFLNRFTTTLNDFNLVAMKYNYEPLTQDHVDILGPLSAQTGIAV

LDMCASLKELLQNGMNGRTILGSALLEDEFTPFDVVRQCSGVTFQSAVKRTIKGTHHW

LLLTILTSLLVLVQSTQWSLFFFLYENAFLPFAMGIIAMSAFAMMFVKHKHAFLCLFL

LPSLATVAYFNMVYMPASWVMRIMTWLDMVDTSLSGFKLKDCVMYASAVVLLILMTAR

TVYDDGARRVWTLMNVLTLVYKVYYGNALDQAISMWALIISVTSNYSGVVTTVMFLAR

GIVFMCVEYCPIFFITGNTLQCIMLVYCFLGYFCTCYFGLFCLLNRYFRLTLGVYDYL

VSTQEFRYMNSQGLLPPKNSIDAFKLNIKLLGVGGKPCIKVATVQSKMSDVKCTSVVL

LSVLQQLRVESSSKLWAQCVQLHNDILLAKDTTEAFEKMVSLLSVLLSMQGAVDINKL

CEEMLDNRATLQAIASEFSSLPSYAAFATAQEAYEQAVANGDSEVVLKKLKKSLNVAK

SEFDRDAAMQRKLEKMADQAMTQMYKQARSEDKRAKVTSAMQTMLFTMLRKLDNDALN

NIINNARDGCVPLNIIPLTTAAKLMVVIPDYNTYKNTCDGTTFTYASALWEIQQVVDA

DSKIVQLSEISMDNSPNLAWPLIVTALRANSAVKLQNNELSPVALRQMSCAAGTTQTA

CTDDNALAYYNTTKGGRFVLALLSDLQDLKWARFPKSDGTGTIYTELEPPCRFVTDTP

KGPKVKYLYFIKGLNNLNRGMVLGSLAATVRLQAGNATEVPANSTVLSFCAFAVDAAK

AYKDYLASGGQPITNCVKMLCTHTGTGQAITVTPEANMDQESFGGASCCLYCRCHIDH

PNPKGFCDLKGKYVQIPTTCANDPVGFTLKNTVCTVCGMWKGYGCSCDQLREPMLQSA

DAQSFLNRVCGVSAARLTPCGTGTSTDVVYRAFDIYNDKVAGFAKFLKTNCCRFQEKD

EDDNLIDSYFVVKRHTFSNYQHEETIYNLLKDCPAVAKHDFFKFRIDGDMVPHISRQR

LTKYTMADLVYALRHFDEGNCDTLKEILVTYNCCDDDYFNKKDWYDFVENPDILRVYA

NLGERVRQALLKTVQFCDAMRNAGIVGVLTLDNQDLNGNWYDFGDFIQTTPGSGVPVV

FIGURE 2D
SEQ ID NO: 2 (continued)

DSYYSLLMPILTLTRALTAESHVDTDLTKPYIKWDLLKYDFTEERLKLFDRYFKYWDQ

TYHPNCVNCLDDRCILHCANFNVLFSTVFPPTSFGPLVRKIFVDGVPFVVSTGYHFRE

LGVVHNQDVNLHSSRLSFKELLVYAADPAMHAASGNLLLDKRTTCFSVAALTNNVAFQ

TVKPGNFNKDFYDFAVSKGFFKEGSSVELKHFFFAQDGNAAISDYDYYRYNLPTMCDI

RQLLFVVEVVDKYFDCYDGGCINANQVIVNNLDKSAGFPFNKWGKARLYYDSMSYEDQ

DALFAYTKRNVIPTITQMNLKYAISAKNRARTVAGVSICSTMTNRQFHQKLLKSIAAT

RGATVVIGTSKFYGGWHNMLKTVYSDVENPHLMGWDYPKCDRAMPNMLRIMASLVLAR

KHTTCCSLSHRFYRLANECAQVLSEMVMCGGSLYVKPGGTSSGDATTAYANSVFNICQ

AVTANVNALLSTDGNKIADKYVRNLQHRLYECLYRNRDVDTDFVNEFYAYLRKHFSMM

ILSDDAVVCFNSTYASQGLVASIKNFKSVLYYQNNVFMSEAKCWTETDLTKGPHEFCS

QHTMLVKQGDDYVYLPYPDPSRILGAGCFVDDIVKTDGTLMIERFVSLAIDAYPLTKH

PNQEYADVFHLYLQYIRKLHDELTGHMLDMYSVMLTNDNTSRYWEPEFYEAMYTPHTV

LQAVGACVLCNSQTSLRCGACIRRPFLCCKCCYDHVISTSHKLVLSVNPYVCNAPGCD

VTDVTQLYLGGMSYYCKSHKPPISFPLCANGQVFGLYKNTCVGSDNVTDFNAIATCDW

TNAGDYILANTCTERLKLFAAETLKATEETFKLSYGIATVREVLSDRELHLSWEVGKP

RPPLNRNYVFTGYRVTKNSKVQIGEYTFEKGDYGDAVVYRGTTTYKLNVGDYFVLTSH

TVMPLSAPTLVPQEHYVRITGLYPTLNISDEFSSNVANYQKVGMQKYSTLQGPPGTGK

SHFAIGLALYYPSARIVYTACSHAAVDALCEKALKYLPIDKCSRIIPARARVECFDKF

KVNSTLEQYVFCTVNALPETTADIVVFDEISMATNYDLSVVNARLRAKHYVYIGDPAQ

LPAPRTLLTKGTLEPEYFNSVCRLMKTIGPDMFLGTCRRCPAEIVDTVSALVYDNKLK

AHKDKSAQCFKMFYKGVITHDVSSAINRPQIGVVREFLTRNPAWRKAVFISPYNSQNA

VASKILGLPTQTVDSSQGSEYDYVIFTQTTETAHSCNVNRFNVAITRAKVGILCIMSD

RDLYDKLQFTSLEIPRRNVATLQAENVTGLFKDCSKVITGLHPTQAPTHLSVDTKFKT

EGLCVDIPGIPKDMTYRRLISMMGFKMNYQVNGYPNMFITREEAIRHVRAWIGFDVEG

CHATREAVGTNLPLQLGFSTGVNLVAVPTGYVDTPNNTDFSRVSAKPPPGDQFKHLIP

LMYKGLPWNVVRIKIVQMLSDTLKNLSDRVVFVLWAHGFELTSMKYFVKIGPERTCCL

CDRRATCFSTASDTYACWHHSIGFDYVYNPFMIDVQQWGFTGNLQSNHDLYCQVHGNA

FIGURE 2E
SEQ ID NO: 2 (continued)

HVASCDAIMTRCLAVHECFVKRVDWTIEYPIIGDELKINAACRKVQHMVVKAALLADK

FPVLHDIGNPKAIKCVPQADVEWKFYDAQPCSDKAYKIEELFYSYATHSDKFTDGVCL

FWNCNVDRYPANSIVCRFDTRVLSNLNLPGCDGGSLYVNKHAFHTPAFDKSAFVNLKQ

LPFFYYSDSPCESHGKQVVSDIDYVPLKSATCITRCNLGGAVCRHHANEYRLYLDAYN

MMISAGFSLWVYKQFDTYNLWNTFTRLQSLENVAFNVVNKGHFDGQQGEVPVSIINNT

VYTKVDGVDVELFENKTTLPVNVAFELWAKRNIKPVPEVKILNNLGVDIAANTVIWDY

KRDAPAHISTIGVCSMTDIAKKPTETICAPLTVFFDGRVDGQVDLFRNARNGVLITEG

SVKGLQPSVGPKQASLNGVTLIGEAVKTQFNYYKKVDGVVQQLPETYFTQSRNLQEFK

PRSQMEIDFLELAMDEFIERYKLEGYAFEHIVYGDFSHSQLGGLHLLIGLAKRFKESP

FELEDFIPMDSTVKNYFITDAQTGSSKCVCSVIDLLLDDFVEIIKSQDLSVVSKVVKV

TIDYTEISFMLWCKDGHVETFYPKLQSSQAWQPGVAMPNLYKMQRMLLEKCDLQNYGD

SATLPKGIMMNVAKYTQLCQYLNTLTLAVPYNMRVIHFGAGSDKGVAPGTAVLRQWLP

TGTLLVDSDLNDFVSDADSTLIGDCATVHTANKWDLIISDMYDPKTKNVTKENDSKEG

FFTYICGFIQQKLALGGSVAIKITEHSWNADLYKLMGHFAWWTAFVTNVNASSSEAFL

IGCNYLGKPREQIDGYVMHANYIFWRNTNPIQLSSYSLFDMSKFPLKLRGTAVMSLKE

GQINDMILSLLSKGRLIIRENNRVVISSDVLVNN (SEQ ID NO:2)

FIGURE 3A
SEQ ID NO: 3
(SARS-CoV-2 surface glycoprotein (spike protein); GenBank: QHD43416.1)

MFVFLVLLPLVSSQCVNLTTRTQLPPAYTNSFTRGVYYPDKVFRSSVLHSTQDLFLPFFSNVTWFHAIHVSGTNGTK

RFDNPVLPFNDGVYFASTEKSNIIRGWIFGTTLDSKTQSLLIVNNATNVVIKVCEFQFCNDPFLGVYYHKNNKSWME

SEFRVYSSANNCTFEYVSQPFLMDLEGKQGNFKNLREFVFKNIDGYFKIYSKHTPINLVRDLPQGFSALEPLVDLPI

GINITRFQTLLALHRSYLTPGDSSSGWTAGAAAYYVGYLQPRTFLLKYNENGTITDAVDCALDPLSETKCTLKSFTV

EKGIYQTSNFRVQPTESIVRFPNITNLCPFGEVFNATRFASVYAWNRKRISNCVADYSVLYNSASFSTFKCYGVSPT

KLNDLCFTNVYADSFVIRGDEVRQIAPGQTGKIADYNYKLPDDFTGCVIAWNSNNLDSKVGGNYNYLYRLFRKSNLK

PFERDISTEIYQAGSTPCNGVEGFNCYFPLQSYGFQPTNGVGYQPYRVVVLSFELLHAPATVCGPKKSTNLVKNKCV

NFNFNGLTGTGVLTESNKKFLPFQQFGRDIADTTDAVRDPQTLEILDITPCSFGGVSVITPGTNTSNQVAVLYQDVN

CTEVPVAIHADQLTPTWRVYSTGSNVFQTRAGCLIGAEHVNNSYECDIPIGAGICASYQTQTNSPRRARSVASQSII

AYTMSLGAENSVAYSNNSIAIPTNFTISVTTEILPVSMTKTSVDCTMYICGDSTECSNLLLQYGSFCTQLNRALTGI

AVEQDKNTQEVFAQVKQIYKTPPIKDFGGFNFSQILPDPSKPSKRSFIEDLLFNKVTLADAGFIKQYGDCLGDIAAR

DLICAQKFNGLTVLPPLLTDEMIAQYTSALLAGTITSGWTFGAGAALQIPFAMQMAYRFNGIGVTQNVLYENQKLIA

NQFNSAIGKIQDSLSSTASALGKLQDVVNQNAQALNTLVKQLSSNFGAISSVLNDILSRLDKVEAEVQIDRLITGRL

QSLQTYVTQQLIRAAEIRASANLAATKMSECVLGQSKRVDFCGKGYHLMSFPQSAPHGVVFLHVTYVPAQEKNFTTA

PAICHDGKAHFPREGVFVSNGTHWFVTQRNFYEPQIITTDNTFVSGNCDVVIGIVNNTVYDPLQPELDSFKEELDKY

FKNHTSPDVDLGDISGINASVVNIQKEIDRLNEVAKNLNESLIDLQELGKYEQYIKWPWYIWLGFIAGLIAIVMVTI

MLCCMTSCCSCLKGCCSCGSCCKFDEDDSEPVLKGVKLHYT (SEQ ID NO:3)

FIGURE 3B (RBD region of spike protein)

NITNLCPFGEVFNATRFASVYAWNRKRISNCVADYSVLYNSASFSTFKCYGVSPTKLNDLCFTNVYADSFVIRGDEV

RQIAPGQTGKIADYNYKLPDDFTGCVIAWNSNNLDSKVGGNYNYLYRLFRKSNLKPFERDISTEIYQAGSTPCNGVE

GFNCYFPLQSYGFQPTNGVGYQPYRVVVLSFELLHAPATVCGP (SEQ ID NO: 446)

FIGURE 4
SEQ ID NO: 4
(SARS-CoV-2 ORF3A protein; GenBank: QHD43417.1)

MDLFMRIFTIGTVTLKQGEIKDATPSDFVRATATIPIQASLPFGWLIVGVALLAVFQSASKIITLKKRWQLALSKGV
HFVCNLLLLFVTVYSHLLLVAAGLEAPFLYLYALVYFLQSINFVRIIMRLWLCWKCRSKNPLLYDANYFLCWHTNCY
DYCIPYNSVTSSIVITSGDGTTSPISEHDYQIGGYTEKWESGVKDCVVLHSYFTSDYYQLYSTQLSTDTGVEHVTFF
IYNKIVDEPEEHVQIHTIDGSSGVVNPVMEPIYDEPTTTTSVPL (SEQ ID NO:4)

FIGURE 5
SEQ ID NO: 5
(SARS-CoV-2 envelope protein; GenBank: QHD43418.1)

MYSFVSEETGTLIVNSVLLFLAFVVFLLVTLAILTALRLCAYCCNIVNVSLVKPSFYVYSRVKNLNSSRVPDLLV
(SEQ ID NO: 5)

FIGURE 6
SEQ ID NO: 6
(SARS-CoV-2 membrane glycoprotein; GenBank: QHD43419.1)

MADSNGTITVEELKKLLEQWNLVIGFLFLTWICLLQFAYANRNRFLYIIKLIFLWLLWPVTLACFVLAAVYRINWIT
GGIAIAMACLVGLMWLSYFIASFRLFARTRSMWSFNPETNILLNVPLHGTILTRPLLESELVIGAVILRGHLRIAGH
HLGRCDIKDLPKEITVATSRTLSYYKLGASQRVAGDSGFAAYSRYRIGNYKLNTDHSSSSDNIA (SEQ ID
NO:6)

FIGURE 7
SEQ ID NO: 7
(SARS-CoV-2 ORF6 protein; GenBank: QHD43420.1)

MFHLVDFQVTIAEILLIIMRTFKVSIWNLDYIINLIIKNLSKSLTENKYSQLDEEQPMEID (SEQ ID NO:7)

FIGURE 8

SEQ ID NO: 8

(SARS-CoV-2 ORF7a protein; GenBank: QHD43421.1)

MKIILFLALITLATCELYHYQECVRGTTVLLKEPCSSGTYEGNSPFHPLADNKFALTCFSTQFAFACPDGVKHVYQL

RARSVSPKLFIRQEEVQELYSPIFLIVAAIVFITLCFTLKRKTE (SEQ ID NO:8)

FIGURE 9

SEQ ID NO: 9

(SARS-CoV-2 ORF8 protein; GenBank: QHD43422.1)

MKFLVFLGIITTVAAFHQECSLQSCTQHQPYVVDDPCPIHFYSKWYIRVGARKSAPLIELCVDEAGSKSPIQYIDIG

NYTVSCLPFTINCQEPKLGSLVVRCSFYEDFLEYHDVRVVLDFI (SEQ ID NO:9)

FIGURE 10

SEQ ID NO: 10

(SARS-CoV-2 nucleocapsid phosphoprotein; GenBank: QHD43423.2)

MSDNGPQNQRNAPRITFGGPSDSTGSNQNGERSGARSKQRRPQGLPNNTASWFTALTQHGKEDLKFPRGQGVPINTN

SSPDDQIGYYRRATRRIRGGDGKMKDLSPRWYFYYLGTGPEAGLPYGANKDGIIWVATEGALNTPKDHIGTRNPANN

AAIVLQLPQGTTLPKGFYAEGSRGGSQASSRSSSRSRNSSRNSTPGSSRGTSPARMAGNGGDAALALLLLDRLNQLE

SKMSGKGQQQQGQTVTKKSAAEASKKPRQKRTATKAYNVTQAFGRRGPEQTQGNFGDQELIRQGTDYKHWPQIAQFA

PSASAFFGMSRIGMEVTPSGTWLTYTGAIKLDDKDPNFKDQVILLNKHIDAYKTFPPTEPKKDKKKKADETQALPQR

QKKQQTVTLLPAADLDDFSKQLQQSMSSADSTQA (SEQ ID NO:10)

FIGURE 11

SEQ ID NO: 11

(SARS-CoV-2 ORF10 protein; GenBank: QHI42199.1)

MGYINVFAFPFTIYSLLLCRMNSRNYIAQVDVVNFNLT (SEQ ID NO:11)

Wuhan seafood market pneumonia virus isolate Wuhan-Hu-1, complete genome
NCBI Reference Sequence: NC_045512.2

| [illegible] | [illegible] |
|---|---|
| ORF1a | 4405 a.a. |
| ORF1b | 2595 a.a. |
| S | 1282 a.a. |
| ORF3a | 275 a.a. |
| E | 75 a.a. |
| M | 222 a.a. |
| ORF6 | 61 a.a. |
| ORF7a | 121 a.a. |
| ORF8 | 121 a.a. |
| N | 419 a.a. |
| ORF10 | 38 a.a. |

Figure 13

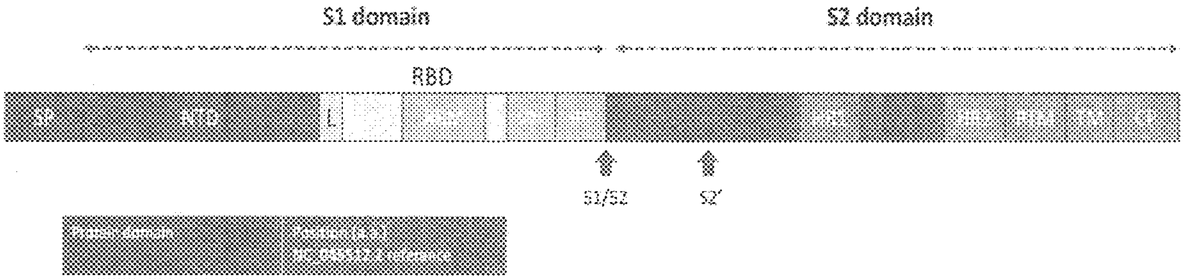

| Protein domain | [illegible] |
|---|---|
| Signal peptide (SP) | 1-15 |
| S1 domain | 16-685 |
| S2 domain | 686-1273 |
| S1/S2 cleavage | 685/686 |
| S2' cleavage | 815/816 |
| N-terminal domain (NTD) | 16-305 |
| Linker | 306-330 |
| Receptor binding domain (RBD) | 331-527 |
| Receptor binding motif (RBM) | 438-508 |
| Sub-domain 1 (SD1) | 528-589 |
| Sub-domain 2 (SD2) | 590-676 |
| Heptad repeat 1 (HR1) | 920-970 |
| Heptad repeat 2 (HR2) | 1163-1202 |
| Pre-transmembrane (PTM) | 1203-1220 |
| Transmembrane domain (TM) | 1214-1234 |
| Putative fusion peptide 1 | 788-806 |
| Putative fusion peptide 2 | 891-906 |
| Putative fusion peptide 3 | 816-837 |
| Putative fusion peptide 4 | 816-855 |

Figure 14

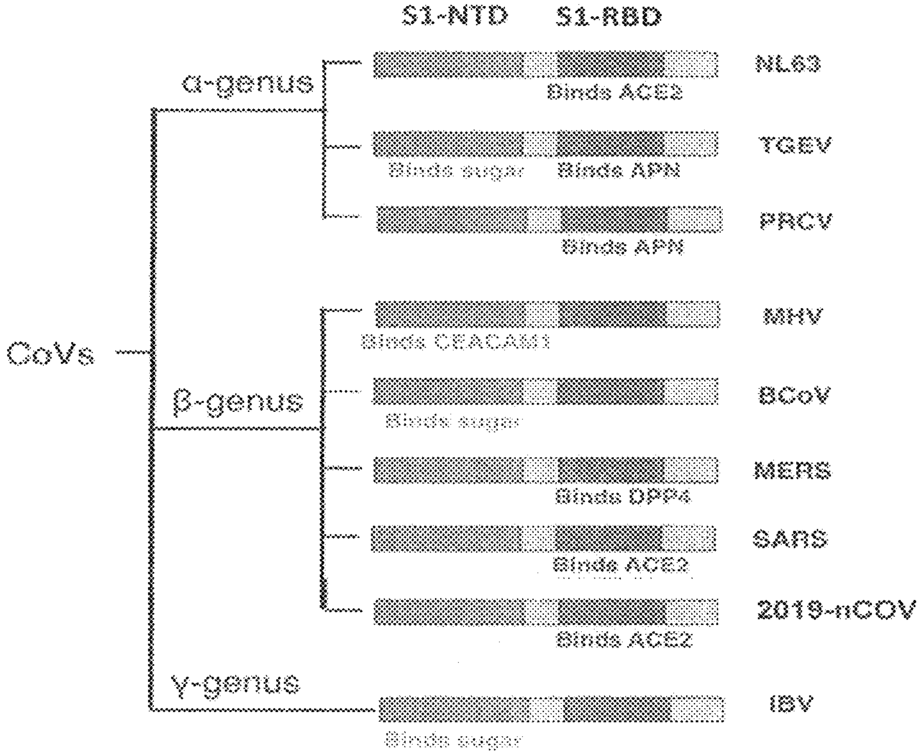

FIGURE 15

| Position | 455 | 486 | 493 | 494 | 501 |
|---|---|---|---|---|---|
| Amino acid residues | L | F | Q | S | N |
| | Y | L | N | D | T |
| | Y | L | K | D | S |
| | Y | P | N | G | S |
| | Y | P | R | G | S |
| | F | F | N | D | S |
| | F or Y | F, L or P | N, R or K | D or G | T or S |
| | F | F | N | D | T |
| | Y or F | P, L or F | R, K or N | G or D | T or S |
| | Y | P | R | G | T |
| | S | F | N | D | N |
| | Y, F, L or S | L, F or P | N, Q, R or K | D, G or S | T, S or N |
| | Aliphatic, Aromatic or small residues | Aliphatic, Aromatic, or P | Uncharged polar or positively charged residues | Small residues or negatively charged residues | Small residues or uncharged polar |

FIGURE 16

SEQ ID NO: 12

(SARS-CoV-2 spike protein; (GenBank: QHD43416.1) with pTA signal sequence and RBD sequences underlined)

MDAMKRGLCCVLLLCGAVFVSPSGTGSVNLTTRTQLPPAYTNSFTRGVYYPDKVFRSSVLHSTQDLFLPFFSNVTWF

HAIHVSGTNGTKRFDNPVLPFNDGVYFASTEKSNIIRGWIFGTTLDSKTQSLLIVNNATNVVIKVCEFQFCNDPFLG

VYYHKNNKSWMESEFRVYSSANNCTFEYVSQPFLMDLEGKQGNFKNLREFVFKNIDGYFKIYSKHTPINLVRDLPQG

FSALEPLVDLPIGINITRFQTLLALHRSYLTPGDSSSGWTAGAAAYYVGYLQPRTFLLKYNENGTITDAVDCALDPL

SETKCTLKSFTVEKGIYQTSNFRVQPTESIVRFPNITNLCPFGEVFNATRFASVYAWNRKRISNCVADYSVLYNSAS

FSTFKCYGVSPTKLNDLCFTNVYADSFVIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPTNGVGYQPYRVVVLSFELLHAPATVCGP

KKSTNLVKNKCVNFNFNGLTGTGVLTESNKKFLPFQQFGRDIADTTDAVRDPQTLEILDITPCSFGGVSVITPGTNT

SNQVAVLYQDVNCTEVPVAIHADQLTPTWRVYSTGSNVFQTRAGCLIGAEHVNNSYECDIPIGAGICASYQTQTNSP

RRARSVASQSIIAYTMSLGAENSVAYSNNSIAIPTNFTISVTTEILPVSMTKTSVDCTMYICGDSTECSNLLLQYGS

FCTQLNRALTGIAVEQDKNTQEVFAQVKQIYKTPPIKDFGGFNFSQILPDPSKPSKRSFIEDLLFNKVTLADAGFIK

QYGDCLGDIAARDLICAQKFNGLTVLPPLLTDEMIAQYTSALLAGTITSGWTFGAGAALQIPFAMQMAYRFNGIGVT

QNVLYENQKLIANQFNSAIGKIQDSLSSTASALGKLQDVVNQNAQALNTLVKQLSSNFGAISSVLNDILSRLDKVEA

EVQIDRLITGRLQSLQTYVTQQLIRAAEIRASANLAATKMSECVLGQSKRVDFCGKGYHLMSFPQSAPHGVVFLHVT

YVPAQEKNFTTAPAICHDGKAHFPREGVFVSNGTHWFVTQRNFYEPQIITTDNTFVSGNCDVVIGIVNNTVYDPLQP

ELDSFKEELDKYFKNHTSPDVDLGDISGINASVVNIQKEIDRLNEVAKNLNESLIDLQELGKYEQYIKWPWYIWLGF

IAGLIAIVMVTIMLCCMTSCCSCLKGCCSCGSCCKFDEDDSEPVLKGVKLHYT (SEQ ID NO: 12)

FIGURE 17A

SEQ ID NO: 13

(SARS-CoV-2 spike protein S1 domain; with pTA signal sequence and RBD sequence underlined)

MDAMKRGLCCVLLLCGAVFVSPSGTGSVNLTTRTQLPPAYTNSFTRGVYYPDKVFRSSVLHSTQDLFLPFFSNVTWF

HAIHVSGTNGTKRFDNPVLPFNDGVYFASTEKSNIIRGWIFGTTLDSKTQSLLIVNNATNVVIKVCEFQFCNDPFLG

VYYHKNNKSWMESEFRVYSSANNCTFEYVSQPFLMDLEGKQGNFKNLREFVFKNIDGYFKIYSKHTPINLVRDLPQG

FSALEPLVDLPIGINITRFQTLLALHRSYLTPGDSSSGWTAGAAAYYVGYLQPRTFLLKYNENGTITDAVDCALDPL

SETKCTLKSFTVEKGIYQTSNFRVQPTESIVRFPNITNLCPFGEVFNATRFASVYAWNRKRISNCVADYSVLYNSAS

FSTFKCYGVSPTKLNDLCFTNVYADSFVIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPTNGVGYQPYRVVVLSFELLHAPATVCGP

KKSTNLVKNKCVNFNFNGLTGTGVLTESNKKFLPFQQFGRDIADTTDAVRDPQTLEILDITPCSFGGVSVITPGTNT

SNQVAVLYQDVNCTEVPVAIHADQLTPTWRVYSTGSNVFQTRAGCLIGAEHVNNSYECDIPIGAGICASYQTQTNSP

RRAR (SEQ ID NO: 13)

FIGURE 17B

SEQ ID NO: 411

```
          302     310       320       330       340       350       360
          :       :         :         :         :         :         :
Sequence  TLKSPTVEKGIYQTSNFRVQPTESIVRFPNITNLCPFGEVFNATRFASVYAWNRKRISNC
Mutations                                QTCALLVKFLSSSKISFLLSSDSSRLNKT
                                         I FRS D IC TITCP   VLKTRIT  I
                                             R      P   V   IRS N    S
                                                        T     E

          362     370       380       390       400       410       420
          :       :         :         :         :         :         :
Sequence  VADYSVLYNSASFSTFKCYGVSPTKLNDLCFTNVYADSFVIRGDEVRQIAPGQTGKIADY
Mutations FPYHLFPCKPTLLPILNVMRLDSALQT PGLPYI PYP LVKKCQAIEVS VRS NVS
          L N YLK S V  F NRF KM LI  G H   K       LSAVDIK  D RKI T
          P    I    S    HE   E KS                     RT    APP K
               S              S                        G     EA
               A                                              I
                                                              E

          422     430       440       450       460       470       480
          :       :         :         :         :         :         :
Sequence  NYKLPDDFTGCVIAWNSNNLDSKVGGNYNYLYRLFRKSNLKPFERDISTEIYQAGSTPCN
Mutations   L LYGLASNAMS S KKNH RAV  ND RF FLKQYTNLL D VVPIQVV VSNIS D
               NI NWFNL      FK NGS  K  M    FRKS NS    FAAG    ARKL H
                      K      I  WFA  S  Q    TNF   K    T ND     TR
                                 I                 R    L        GA
                                 R                              A
                                 E                              I
                                 M
                                 Y

          482     490       500       510       520       530       540 543
          :       :         :         :         :         :         :  :
Sequence  GVEGFNCYFPLQSYGFQPTNGVGYQPYRVVVLSFELLHAPATVCGPKKSTNLVKNKCVNFNF
Mutations SAKRL   LR LPNV  HIYRLVHHHHKL  FAVLFINSRVNLNS
           FQSS   SS KLFS  S TDIDEKSN    RFLQ AQELSAW
           ID      L       R SCFSW        Y V  GVQPE
            A                    C             PCSI
            R                                   TTG
```

FIGURE 18

SEQ ID NO: 14

(SARS-CoV-2 spike protein Receptor Binding Domain (RBD) of the S1 domain; with pTA signal sequence (italics) and underlined short flanking sequence)

*MDAMKRGLCCVLLLCGAVFVSPSGTGS*RVQPTESIVRFPNITNLCPFGEVFNATRFASVYAWNRKRISNCVADYSVL
YNSASFSTFKCYGVSPTKLNDLCFTNVYADSFVIRGDEVRQIAPGQTGKIADYNYKLPDDFTGCVIAWNSNNLDSKV
GGNYNYLYRLFRKSNLKPFERDISTEIYQAGSTPCNGVEGFNCYFPLQSYGFQPTNGVGYQPYRVVVLSFELLHAPA
TVCGPKKSTNLVKNK (SEQ ID NO: 14)

FIGURE 19

SEQ ID NO: 15

(SARS-CoV-2 spike protein Receptor Binding Domain (RBD) of the S1 domain; with pTA signal sequence (italics) and underlined and long flanking sequence)

*MDAMKRGLCCVLLLCGAVFVSPSGTGS*TLKSFTVEKGIYQTSNFRVQPTESIVRFPNITNLCPFGEVFNATRFASVY
AWNRKRISNCVADYSVLYNSASFSTFKCYGVSPTKLNDLCFTNVYADSFVIRGDEVRQIAPGQTGKIADYNYKLPDD
FTGCVIAWNSNNLDSKVGGNYNYLYRLFRKSNLKPFERDISTEIYQAGSTPCNGVEGFNCYFPLQSYGFQPTNGVGY
QPYRVVVLSFELLHAPATVCGPKKSTNLVKNKCVNFNF (SEQ ID NO: 15)

FIGURE 20

SEQ ID NO: 16

(SARS-CoV-2 spike protein Receptor Binding Domain (RBD) of the S1 domain with conservative substitutions at positions 455, 486, 493, 494 and 501)

NITNLCPFGEVFNATRFASVYAWNRKRISNCVADYSVLYNSASFSTFKCYGVSPTKLNDLCFTNVYADSFVIRGDEV
RQIAPGQTGKIADYNYKLPDDFTGCVIAWNSNNLDSKVGGNYNYLYR(455)FRKSNLKPFERDISTEIYQAGSTPC
NGVEG(486)NCYFPL(493)(494)YGFQPT(501)GVGYQPYRVVVLSFELLHAPATVCGP (SEQ ID NO:
16)

FIGURE 21
SEQ ID NO: 17
(SARS-CoV-2 spike protein Receptor Binding Domain (RBD) of the S1 domain with conservative substitutions at positions 455, 486, 493, 494 and 501)

NSNNLDSKVGGNYNYLYR(455)FRKSNLKPFERDISTEIYQAGSTPCNGVEG(486)NCYFPL(493)(494)YGF

QPT(501)GVGYQPYRVVVLSFELLHAPATVCGP (SEQ ID NO: 17)

FIGURE 22

SEQ ID NO: 18

(SARS-CoV-2 spike protein; with pTA signal sequence underlined and substitutions at the S1/S2, S2′ and HR1 sites)

MDAMKRGLCCVLLLCGAVFVSPSGTGSVNLTTRTQLPPAYTNSFTRGVYYPDKVFRSSVLHSTQDLFLPF
FSNVTWFHAIHVSGTNGTKRFDNPVLPFNDGVYFASTEKSNIIRGWIFGTTLDSKTQSLLIVNNATNVVI
KVCEFQFCNDPFLGVYYHKNNKSWMESEFRVYSSANNCTFEYVSQPFLMDLEGKQGNFKNLREFVFKNID
GYFKIYSKHTPINLVRDLPQGFSALEPLVDLPIGINITRFQTLLALHRSYLTPGDSSSGWTAGAAAYYVG
YLQPRTFLLKYNENGTITDAVDCALDPLSETKCTLKSFTVEKGIYQTSNFRVQPTESIVRFPNITNLCPF
GEVFNATRFASVYAWNRKRISNCVADYSVLYNSASFSTFKCYGVSPTKLNDLCFTNVYADSFVIRGDEVR
QIAPGQTGKIADYNYKLPDDFTGCVIAWNSNNLDSKVGGNYNYLYRLFRKSNLKPFERDISTEIYQAGST
PCNGVEGFNCYFPLQSYGFQPTNGVGYQPYRVVVLSFELLHAPATVCGPKKSTNLVKNKCVNFNFNGLTG
TGVLTESNKKFLPFQQFGRDIADTTDAVRDPQTLEILDITPCSFGGVSVITPGTNTSNQVAVLYQDVNCT
EVPVAIHADQLTPTWRVYSTGSNVFQTRAGCLIGAEHVNNSYECDIPIGAGICASYQTQTNSPQQAQSVA
SQSIIAYTMSLGAENSVAYSNNSIAIPTNFTISVTTEILPVSMTKTSVDCTMYICGDSTECSNLLLQYGS
FCTQLNRALTGIAVEQDKNTQEVFAQVKQIYKTPPIKDFGGFNFSQILPDPSKPSKRSFIADAGFIKQYG
DCLGDIAARDLICAQKFNGLTVLPPLLTDEMIAQYTSALLAGTITSGWTFGAGAALQIPFAMQMAYRFNG
IGVTQNVLYENQKLIANQFNSAIGKIQDSLSSTASALGKLQDVVNQNAQALNTLVKQLSSNFGAISSVLN
DILSRLDPPEAEVQIDRLITGRLQSLQTYVTQQLIRAAEIRASANLAATKMSECVLGQSKRVDFCGKGYH
LMSFPQSAPHGVVFLHVTYVPAQEKNFTTAPAICHDGKAHFPREGVFVSNGTHWFVTQRNFYEPQIITTD
NTFVSGNCDVVIGIVNNTVYDPLQPELDSFKEELDKYFKNHTSPDVDLGDISGINASVVNIQKEIDRLNE
VAKNLNESLIDLQELGKYEQYIKWPWYIWLGFIAGLIAIVMVTIMLCCMTSCCSCLKGCCSCGSCCKFDE
DDSEPVLKGVKLHYT

| | |
|---|---|
| S1/S2 site | RRAR substituted by QQAQ |
| S2′ site | FIEDLLFNKVTLAD substituted by FI----------AD |
| HR1 site | LDKV substituted by LDPP |

FIGURE 23

SEQ ID NO: 19

(SARS-CoV-2 spike protein; with pTA signal sequence underlined and substitutions at the S1/S2, S2′ and HR1 sites)

MDAMKRGLCCVLLLCGAVFVSPSGTGSVNLTTRTQLPPAYTNSFTRGVYYPDKVFRSSVLHSTQDLFLPF
FSNVTWFHAIHVSGTNGTKRFDNPVLPFNDGVYFASTEKSNIIRGWIFGTTLDSKTQSLLIVNNATNVVI
KVCEFQFCNDPFLGVYYHKNNKSWMESEFRVYSSANNCTFEYVSQPFLMDLEGKQGNFKNLREFVFKNID
GYFKIYSKHTPINLVRDLPQGFSALEPLVDLPIGINITRFQTLLALHRSYLTPGDSSSGWTAGAAAYYVG
YLQPRTFLLKYNENGTITDAVDCALDPLSETKCTLKSFTVEKGIYQTSNFRVQPTESIVRFPNITNLCPF
GEVFNATRFASVYAWNRKRISNCVADYSVLYNSASFSTFKCYGVSPTKLNDLCFTNVYADSFVIRGDEVR
QIAPGQTGKIADYNYKLPDDFTGCVIAWNSNNLDSKVGGNYNYLYRLFRKSNLKPFERDISTEIYQAGST
PCNGVEGFNCYFPLQSYGFQPTNGVGYQPYRVVVLSFELLHAPATVCGPKKSTNLVKNKCVNFNFNGLTG
TGVLTESNKKFLPFQQFGRDIADTTDAVRDPQTLEILDITPCSFGGVSVITPGTNTSNQVAVLYQDVNCT
EVPVAIHADQLTPTWRVYSTGSNVFQTRAGCLIGAEHVNNSYECDIPIGAGICASYQTQTNSPSGAGSVA
SQSIIAYTMSLGAENSVAYSNNSIAIPTNFTISVTTEILPVSMTKTSVDCTMYICGDSTECSNLLLQYGS
FCTQLNRALTGIAVEQDKNTQEVFAQVKQIYKTPPIKDFGGFNFSQILPDPSKPSKQSFIEDLLFNKVTL
ADAGFIKQYGDCLGDIAARDLICAQKFNGLTVLPPLLTDEMIAQYTSALLAGTITSGWTFGAGAALQIPF
AMQMAYRFNGIGVTQNVLYENQKLIANQFNSAIGKIQDSLSSTASALGKLQDVVNQNAQALNTLVKQLSS
NFGAISSVLNDILSRLDPPEAEVQIDRLITGRLQSLQTYVTQQLIRAAEIRASANLAATKMSECVLGQSK
RVDFCGKGYHLMSFPQSAPHGVVFLHVTYVPAQEKNFTTAPAICHDGKAHFPREGVFVSNGTHWFVTQRN
FYEPQIITTDNTFVSGNCDVVIGIVNNTVYDPLQPELDSFKEELDKYFKNHTSPDVDLGDISGINASVVN
IQKEIDRLNEVAKNLNESLIDLQELGKYEQYIKWPWYIWLGFIAGLIAIVMVTIMLCCMTSCCSCLKGCC
SCGSCCKFDEDDSEPVLKGVKLHYT

| | | |
|---|---|---|
| S1/S2 site | RRAR substituted by SGAG |
| S2′ site | PSKR substituted by PSKQ |
| HR1 site | LDKV substituted by LDPP |

FIGURE 24

SEQ ID NO: 20

(SARS-CoV-2 spike protein; with pTA signal sequence underlined and substitutions at the S1/S2, S2′, HR1, fusion peptide and ER retention motif sits)

MDAMKRGLCCVLLLCGAVFVSPSGTGSVNLTTRTQLPPAYTNSFTRGVYYPDKVFRSSVLHSTQDLFLPF
FSNVTWFHAIHVSGTNGTKRFDNPVLPFNDGVYFASTEKSNIIRGWIFGTTLDSKTQSLLIVNNATNVVI
KVCEFQFCNDPFLGVYYHKNNKSWMESEFRVYSSANNCTFEYVSQPFLMDLEGKQGNFKNLREFVFKNID
GYFKIYSKHTPINLVRDLPQGFSALEPLVDLPIGINITRFQTLLALHRSYLTPGDSSSGWTAGAAAYYVG
YLQPRTFLLKYNENGTITDAVDCALDPLSETKCTLKSFTVEKGIYQTSNFRVQPTESIVRFPNITNLCPF
GEVFNATRFASVYAWNRKRISNCVADYSVLYNSASFSTFKCYGVSPTKLNDLCFTNVYADSFVIRGDEVR
QIAPGQTGKIADYNYKLPDDFTGCVIAWNSNNLDSKVGGNYNYLYRLFRKSNLKPFERDISTEIYQAGST
PCNGVEGFNCYFPLQSYGFQPTNGVGYQPYRVVVLSFELLHAPATVCGPKKSTNLVKNKCVNFNFNGLTG
TGVLTESNKKFLPFQQFGRDIADTTDAVRDPQTLEILDITPCSFGGVSVITPGTNTSNQVAVLYQDVNCT
EVPVAIHADQLTPTWRVYSTGSNVFQTRAGCLIGAEHVNNSYECDIPIGAGICASYQTQTNSPSGAGSVA
SQSIIAYTMSLGAENSVAYSNNSIAIPTNFTISVTTEILPVSMTKTSVDCTMYICGDSTECSNLLLQYGS
FCTQLNRALTGIAVEQDKNTQEVFAQVKQIYKTPPIKDFGGFNFSQILPDPSKPSKQSFIEDPLFNKVTL
ADPGFIKQYGDCLGDIAARDLICAQKFNGLTVLPPLLTDEMIAQYTSALLAGTITSGWTFGAGAALQIPF
AMQMAYRFNGIGVTQNVLYENQKLIANQFNSAIGKIQDSLSSTASALGKLQDVVNQNAQALNTLVKQLSS
NFGAISSVLNDILSRLDPPEAEVQIDRLITGRLQSLQTYVTQQLIRAAEIRASANLAATKMSECVLGQSK
RVDFCGKGYHLMSFPQSAPHGVVFLHVTYVPAQEKNFTTAPAICHDGKAHFPREGVFVSNGTHWFVTQRN
FYEPQIITTDNTFVSGNCDVVIGIVNNTVYDPLQPELDSFKEELDKYFKNHTSPDVDLGDISGINASVVN
IQKEIDRLNEVAKNLNESLIDLQELGKYEQYIKWPWYIWLGFIAGLIAIVMVTIMLCCMTSCCSCLKGCC
SCGSCCKFDEDDSEPVLKGVALAYT

| | |
|---|---|
| S1/S2 site | RRAR substituted by SGAG |
| S2′ site | PSKR substituted by PSKQ |
| HR1 site | LDKV substituted by LDPP |
| Fusion peptide | SFIEDLLFNKVTLADAGF substituted by SFIEDPLFNKVTLADPGF |
| ER retention motif | KLHYT substituted by ALAYT |

| | Ad5 PCR Positive (%) | | |
|---|---|---|---|
| | $10^9$ vp n=15 | $10^{10}$ vp n=15 | $10^{11}$ vp n=15 |
| Day 4 | 47% | 60% | 80% |
| Day 8 | 7% | 13% | 20% |
| Day 15 | 0% | 0% | 0% |

| GMR Ad5 Antibody Day 29 vs Baseline (95% CI) | | |
|---|---|---|
| $10^9$ vp n=15 | $10^{10}$ vp n=15 | $10^{11}$ vp n=15 |
| 1.67 (0.96 – 2.93) | 1.58 (1.06 – 2.35) | 2.34 (1.37 – 4.13) |

*Profiles of high affinity HLA class I and HLA class II binding motifs across the entire SARS-CoV-2 proteome*

*Profiles of high and moderate affinity HLA class I and HLA class II binding motifs across the entire SARS-CoV-2 proteome*

+FIGURE 29

*Map of HLA class I and HLA class II binding motifs for SEQ ID NO: 328*

*Map of HLA class I and HLA class II binding motifs for SEQ ID NO: 329*

*Map of HLA class I and HLA class II binding motifs for SEQ ID NO: 330*

*Map of HLA class I and HLA class II binding motifs for SEQ ID NO: 331*

*Map of HLA class I and HLA class II binding motifs for SEQ ID NO: 332*

*Map of HLA class I and HLA class II binding motifs for SEQ ID NO: 333*

*Map of HLA class I and HLA class II binding motifs for SEQ ID NO: 334*

*Map of HLA class I and HLA class II binding motifs for SEQ ID NO: 335*

*Map of HLA class I and HLA class II binding motifs for SEQ ID NO: 336*

*Map of HLA class I and HLA class II binding motifs for SEQ ID NO: 337*

*Map of HLA class I and HLA class II binding motifs for SEQ ID NO: 338*

*Map of HLA class I and HLA class II binding motifs for SEQ ID NO: 339*

*Map of HLA class I and HLA class II binding motifs for SEQ ID NO: 340*

*Map of HLA class I and HLA class II binding motifs for SEQ ID NO: 341*

*Map of HLA class I and HLA class II binding motifs for SEQ ID NO: 342*

*Map of HLA class I and HLA class II binding motifs for SEQ ID NO: 343*

*Map of HLA class I and HLA class II binding motifs for SEQ ID NO: 344*

*Map of HLA class I and HLA class II binding motifs for SEQ ID NO: 345*

*Map of HLA class I and HLA class II binding motifs for SEQ ID NO: 346*

*Map of HLA class I and HLA class II binding motifs for SEQ ID NO: 347*

*Map of HLA class I and HLA class II binding motifs for SEQ ID NO: 348*

*Map of HLA class I and HLA class II binding motifs for SEQ ID NO: 349*

*Map of HLA class I and HLA class II binding motifs for SEQ ID NO: 350*

*Map of HLA class I and HLA class II binding motifs for SEQ ID NO: 351*

*Map of HLA class I and HLA class II binding motifs for SEQ ID NO: 352*

*Map of HLA class I and HLA class II binding motifs for SEQ ID NO: 353*

*Map of HLA class I and HLA class II binding motifs for SEQ ID NO: 354*

*Map of HLA class I and HLA class II binding motifs for SEQ ID NO: 355*

*Map of HLA class I and HLA class II binding motifs for SEQ ID NO: 356*

*Map of HLA class I and HLA class II binding motifs for SEQ ID NO: 357*

*Map of HLA class I and HLA class II binding motifs for SEQ ID NO: 358*

*Map of HLA class I and HLA class II binding motifs for SEQ ID NO: 359*

*Map of HLA class I and HLA class II binding motifs for SEQ ID NO: 360*

*Map of HLA class I and HLA class II binding motifs for SEQ ID NO: 361*

*Map of HLA class I and HLA class II binding motifs for SEQ ID NO: 362*

*Map of HLA class I and HLA class II binding motifs for SEQ ID NO: 363*

*Map of HLA class I and HLA class II binding motifs for SEQ ID NO: 364*

*Map of HLA class I and HLA class II binding motifs for SEQ ID NO: 365*

*Map of HLA class I and HLA class II binding motifs for SEQ ID NO: 366*

*Map of HLA class I and HLA class II binding motifs for SEQ ID NO: 367*

*Map of HLA class I and HLA class II binding motifs for SEQ ID NO: 368*

*Map of HLA class I and HLA class II binding motifs for SEQ ID NO: 369*

Figure 74
FIGURE 74A
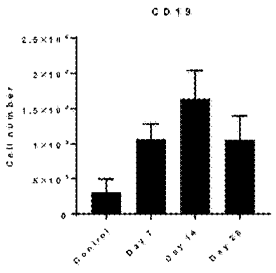
FIGURE 74B
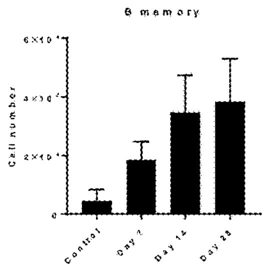
FIGURE 74C
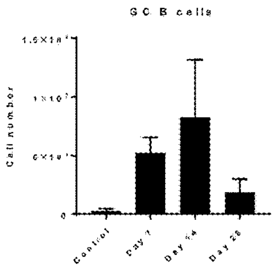
FIGURE 74D
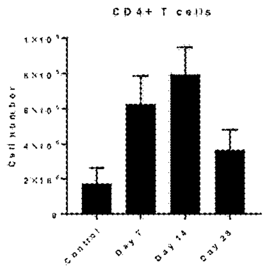
FIGURE 74E
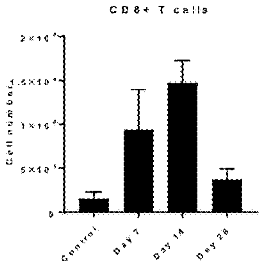
FIGURE 74F
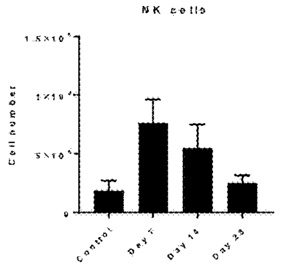
FIGURE 74G
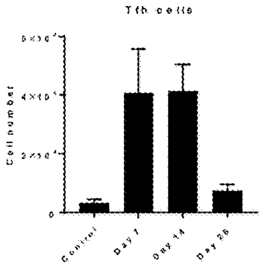
FIGURE 74H
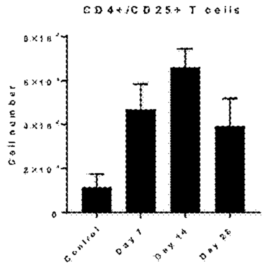
FIGURE 74I
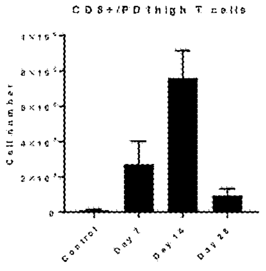
FIGURE 74J
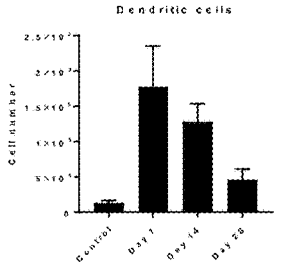
FIGURE 74K
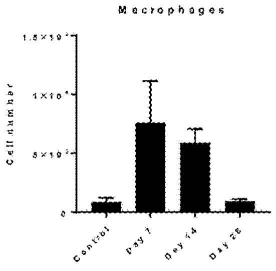
FIGURE 74L
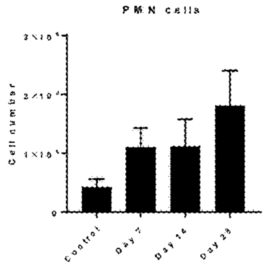

Figure 75
FIGURE 75A
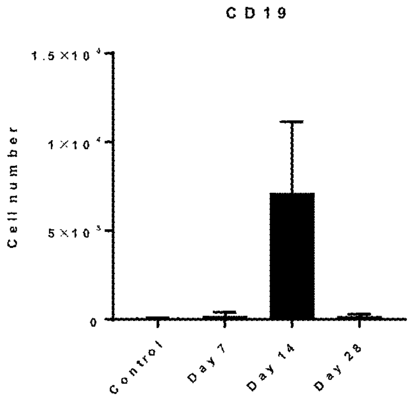
FIGURE 75B
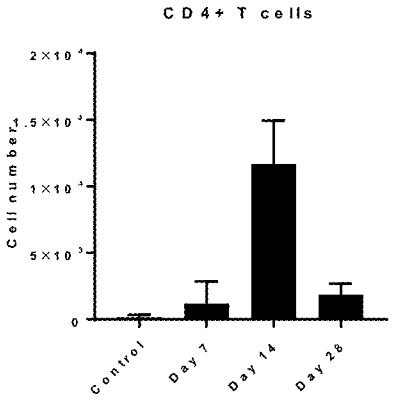
FIGURE 75C
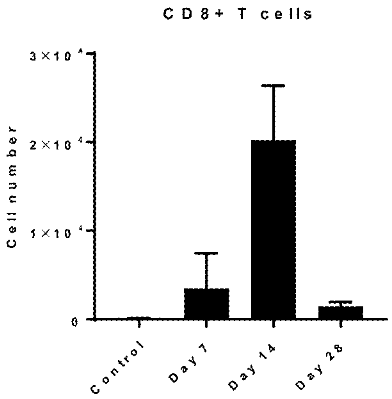
FIGURE 75D
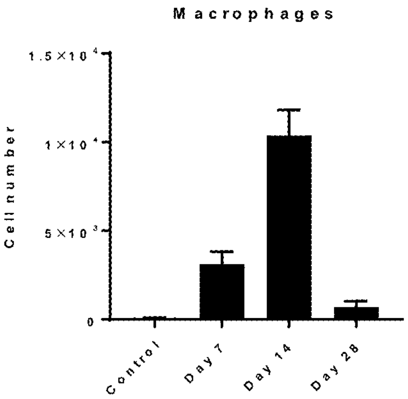
FIGURE 75E
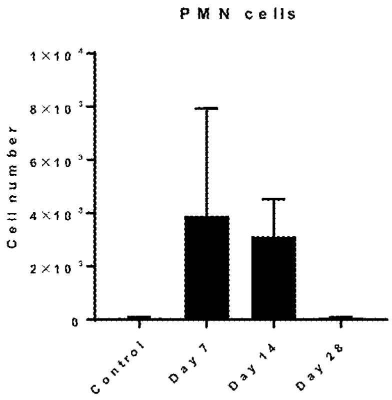

Figure 76
FIGURE 76A
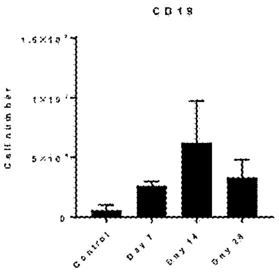
FIGURE 76B
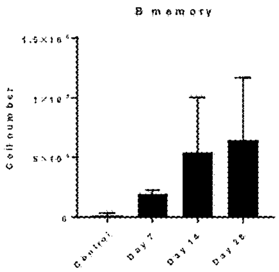
FIGURE 76C
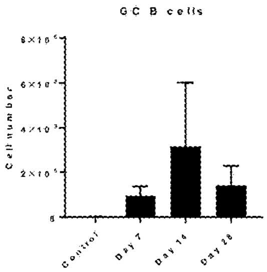
FIGURE 76D
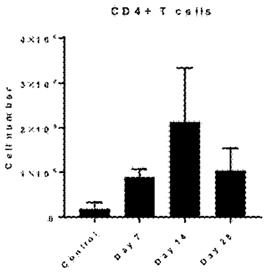
FIGURE 76E
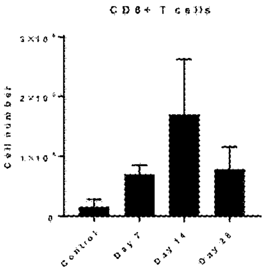
FIGURE 76F
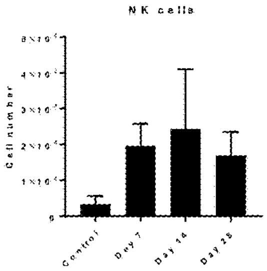
FIGURE 76G
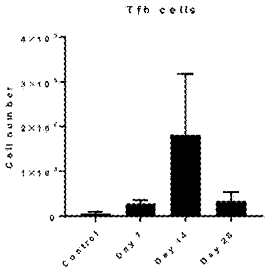
FIGURE 76H
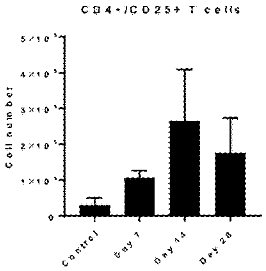
FIGURE 76I
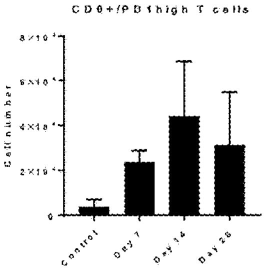
FIGURE 76J
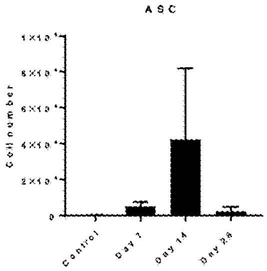

Figure 77
FIGURE 77A
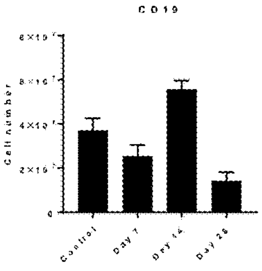
FIGURE 77B
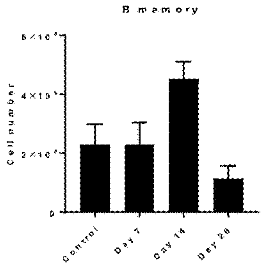
FIGURE 77C
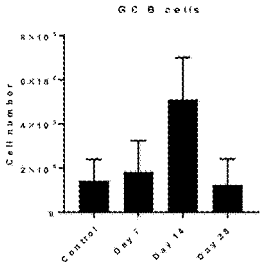
FIGURE 77D
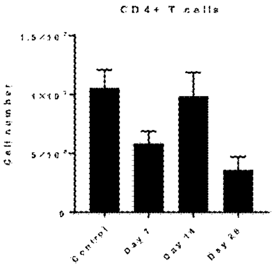
FIGURE 77E
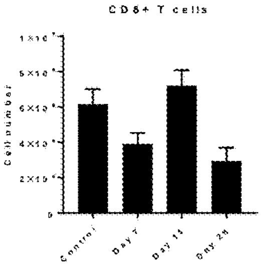
FIGURE 77F
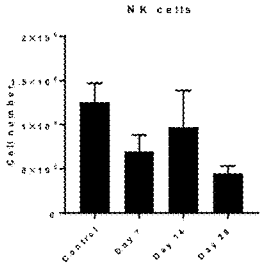
FIGURE 77G
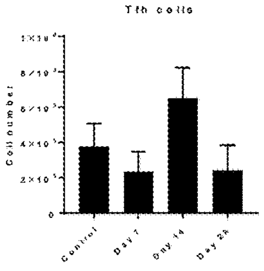
FIGURE 77H
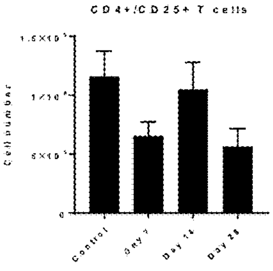
FIGURE 77I
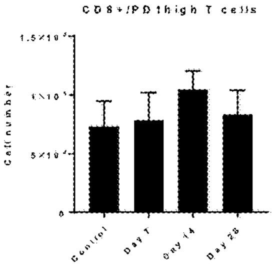
FIGURE 77J
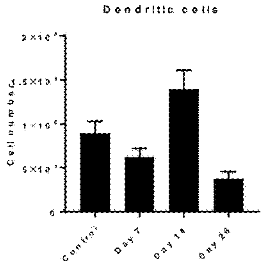
FIGURE 77K
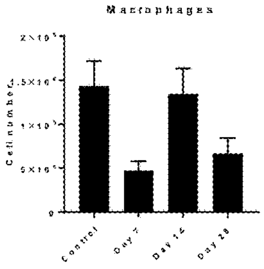
FIGURE 77L
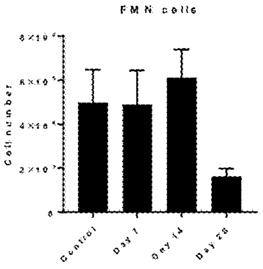

Figure 79
FIGURE 79A
V1A_V1A.1
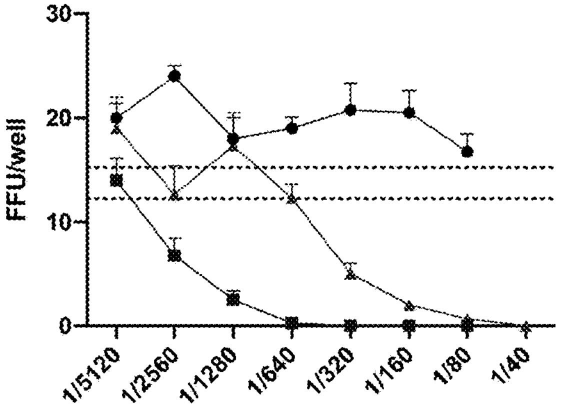
FIGURE 79B
V1A_V1A.2
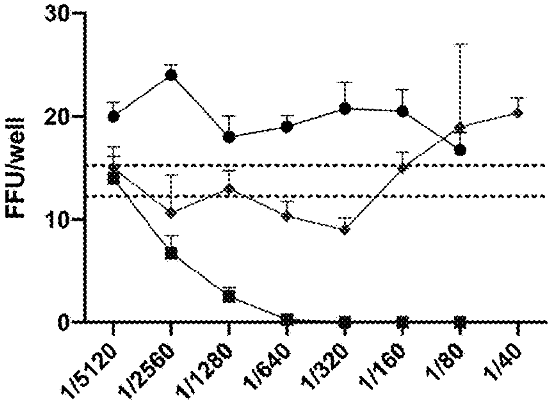
FIGURE 79C
V1A_V1A.3
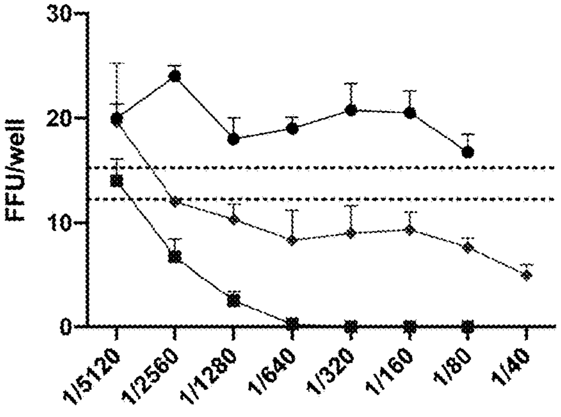
FIGURE 79D
V1A_V1A.7
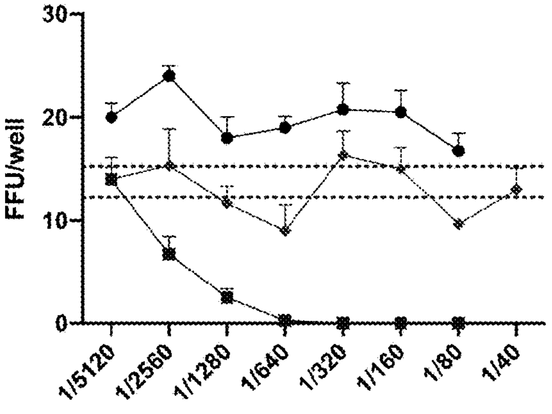

Figure 80
FIGURE 80A
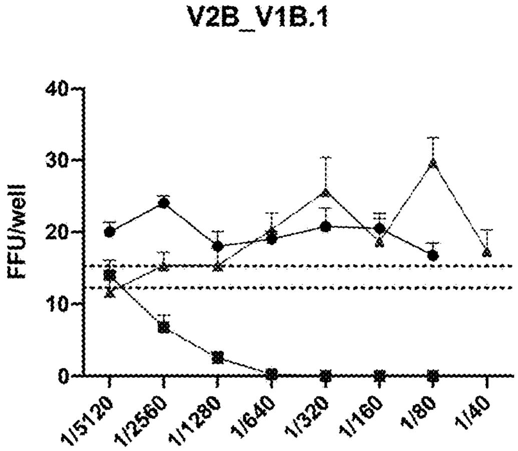
FIGURE 80B
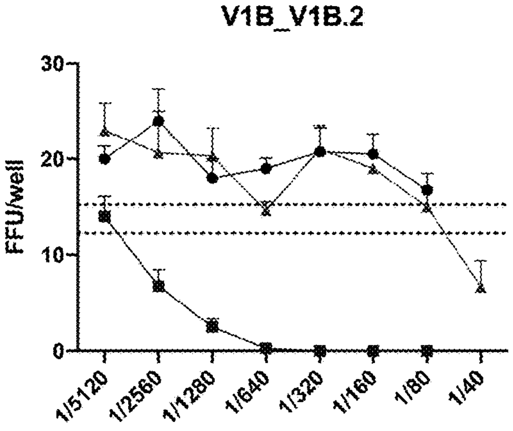
FIGURE 80C
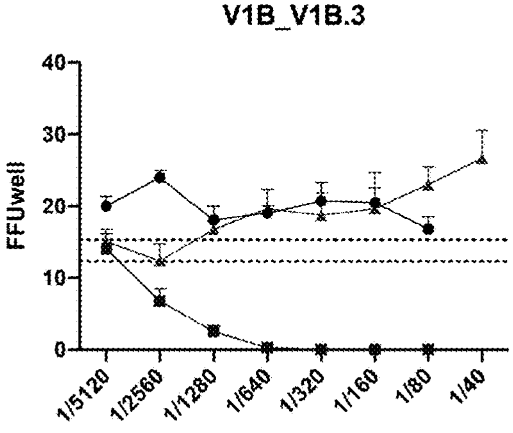
FIGURE 80D
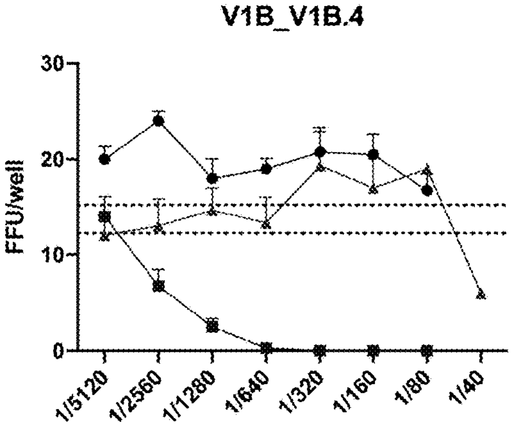

Figure 82
FIGURE 82A
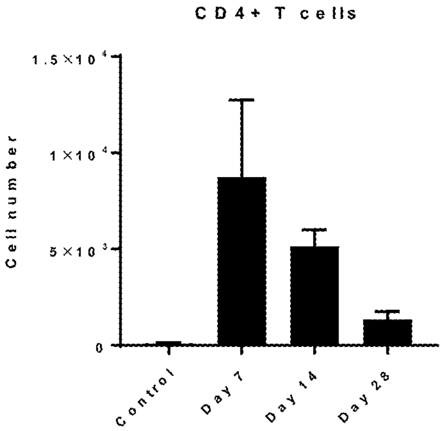
FIGURE 82B
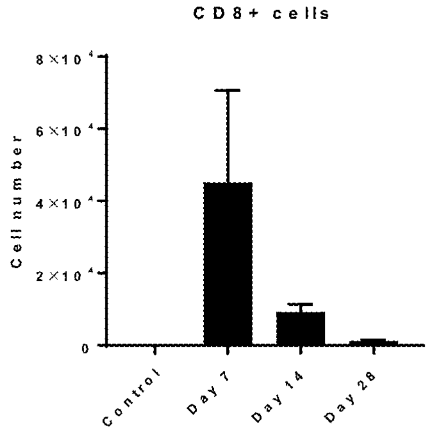
FIGURE 82C
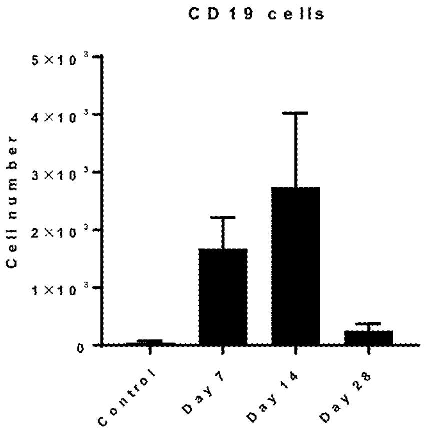
FIGURE 82D
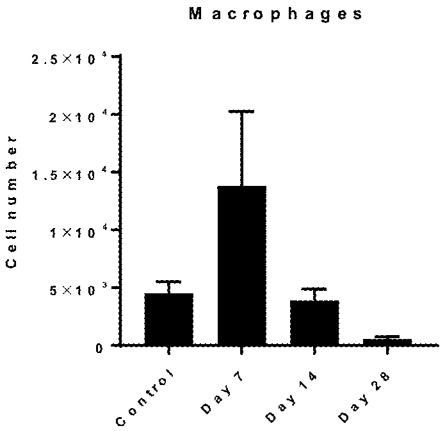
FIGURE 82E
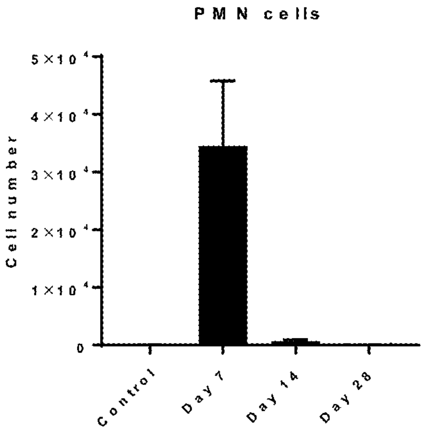

Figure 83
FIGURE 83A
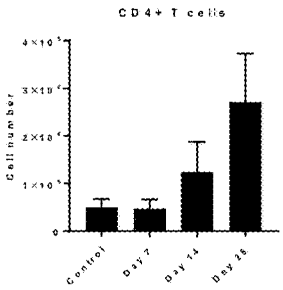
FIGURE 83B
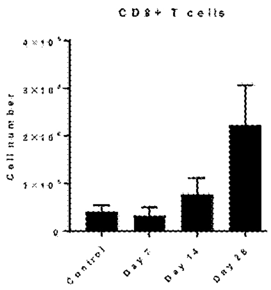
FIGURE 83C
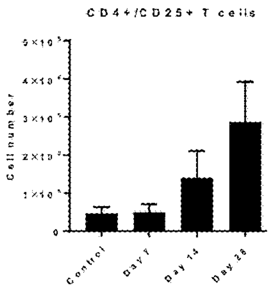
FIGURE 83D
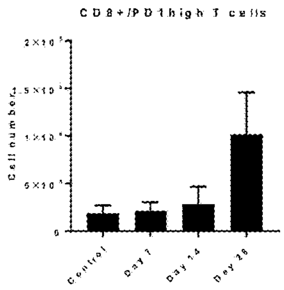
FIGURE 83E
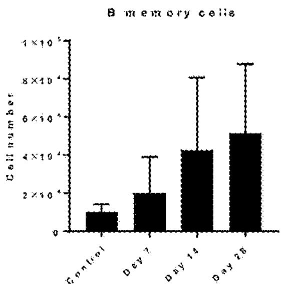
FIGURE 83F
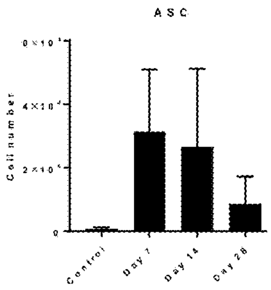
FIGURE 83G
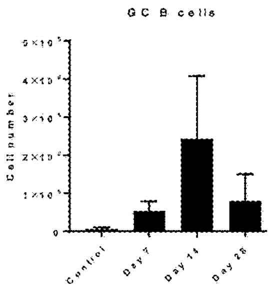
FIGURE 83H
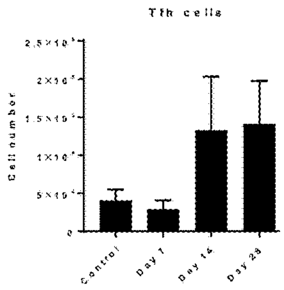
FIGURE 83I
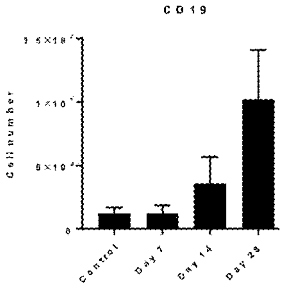
FIGURE 83J
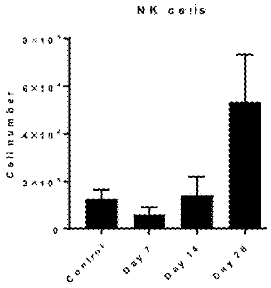

Figure 84
FIGURE 84A
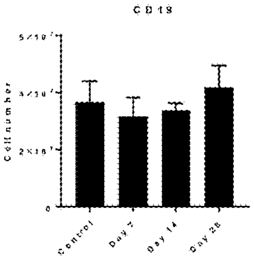
FIGURE 84B
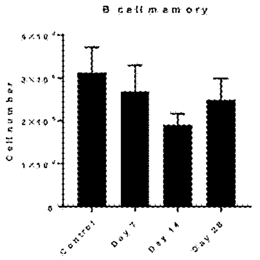
FIGURE 84C
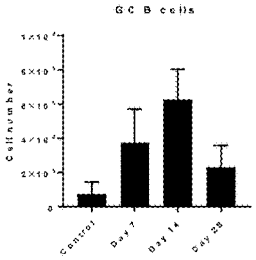
FIGURE 84D
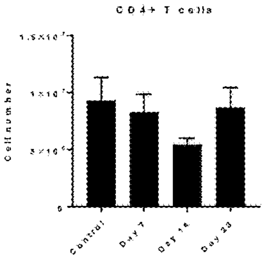
FIGURE 84E
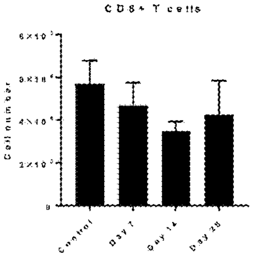
FIGURE 84F
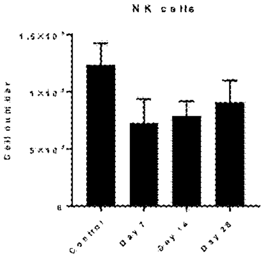
FIGURE 84G
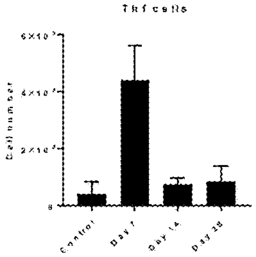
FIGURE 84H
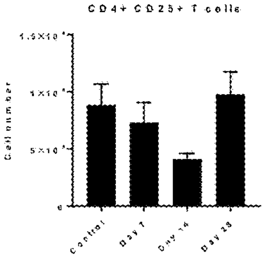
FIGURE 84I
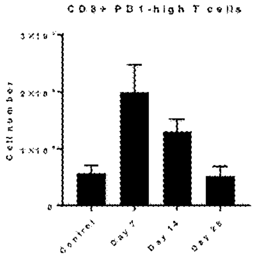
FIGURE 84J
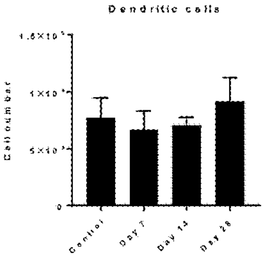
FIGURE 84K
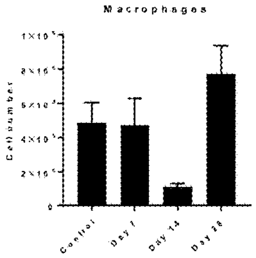
FIGURE 84L
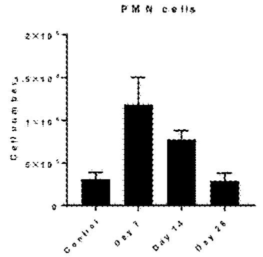

Figure 87A

SEQ ID NO: 410

(SARS-CoV-2 concatenated Polyprotein; Derived from SEQ ID NO: 1 (GenBank: MN908947.3))

MESLVPGFNEKTHVQLSLPVLQVRDVLVRGFGDSVEEVLSEARQHLKDGTCGLVEVEKGVLPQLEQPYVFIKRS

DARTAPHGHVMVELVAELEGIQYGRSGETLGVLVPHVGEIPVAYRKVLLRKNGNKGAGGHSYGADLKSFDLGDE

LGTDPYEDFQENWNTKHSSGVTRELMRELNGGAYTRYVDNNFCGPDGYPLECIKDLLARAGKASCTLSEQLDFI

DTKRGVYCCREHEHEIAWYTERSEKSYELQTPFEIKLAKKFDTFNGECPNFVFPLNSIIKTIQPRVEKKKLDGF

MGRIRSVYPVASPNECNQMCLSTLMKCDHCGETSWQTGDFVKATCEFCGTENLTKEGATTCGYLPQNAVVKIYC

PACHNSEVGPEHSLAEYHNESGLKTILRKGGRTIAFGGCVFSYVGCHNKCAYWVPRASANIGCNHTGVVGEGSE

GLNDNLLEILQKEKVNINIVGDFKLNEEIAIILASFSASTSAFVETVKGLDYKAFKQIVESCGNFKVTKGKAKK

GAWNIGEQKSILSPLYAFASEAARVVRSIFSRTLETAQNSVRVLQKAAITILDGISQYSLRLIDAMMFTSDLAT

NNLVVMAYITGGVVQLTSQWLTNIFGTVYEKLKPVLDWLEEKFKEGVEFLRDGWEIVKFISTCACEIVGGQIVT

CAKEIKESVQTFFKLVNKFLALCADSIIIGGAKLKALNLGETFVTHSKGLYRKCVKSREETGLLMPLKAPKEII

FLEGETLPTEVLTEEVVLKTGDLQPLEQPTSEAVEAPLVGTPVCINGLMLLEIKDTEKYCALAPNMMVTNNTFT

LKGGAPTKVTFGDDTVIEVQGYKSVNITFELDERIDKVLNEKCSAYTVELGTEVNEFACVVADAVIKTLQPVSE

LLTPLGIDLDEWSMATYYLFDESGEFKLASHMYCSFYPPDEDEEEGDCEEEEFEPSTQYEYGTEDDYQGKPLEF

GATSAALQPEEEQEEDWLDDDSQQTVGQQDGSEDNQTTTIQTIVEVQPQLEMELTPVVQTIEVNSFSGYLKLTD

NVYIKNADIVEEAKKVKPTVVVNAANVYLKHGGGVAGALNKATNNAMQVESDDYIATNGPLKVGGSCVLSGHNL

AKHCLHVVGPNVNKGEDIQLLKSAYENFNQHEVLLAPLLSAGIFGADPIHSLRVCVDTVRTNVYLAVFDKNLYD

KLVSSFLEMKSEKQVEQKIAEIPKEEVKPFITESKPSVEQRKQDDKKIKACVEEVTTTLEETKFLTENLLLYID

INGNLHPDSATLVSDIDITFLKKDAPYIVGDVVQEGVLTAVVIPTKKAGGTTEMLAKALRKVPTDNYITTYPGQ

GLNGYTVEEAKTVLKKCKSAFYILPSIISNEKQEILGTVSWNLREMLAHAEETRKLMPVCVETKAIVSTIQRKY

KGIKIQEGVVDYGARFYFYTSKTTVASLINTLNDLNETLVTMPLGYVTHGLNLEEAARYMRSLKVPATVSVSSP

DAVTAYNGYLTSSSKTPEEHFIETISLAGSYKDWSYSGQSTQLGIEFLKRGDKSVYYTSNPTTFHLDGEVITFD

NLKTLLSLREVRTIKVFTTVDNINLHTQVVDMSMTYGQQFGPTYLDGADVTKIKPHNSHEGKTFYVLPNDDTLR

VEAFEYYHTTDPSFLGRYMSALNHTKKWKYPQVNGLTSIKWADNNCYLATALLTLQQIELKFNPPALQDAYYRA

Figure 87B

SEQ ID NO: 410 (continued)

RAGEAANFCALILAYCNKTVGELGDVRETMSYLFQHANLDSCKRVLNVVCKTCGQQQTTLKGVEAVMYMGTLSY

EQFKKGVQIPCTCGKQATKYLVQQESPFVMMSAPPAQYELKHGTFTCASEYTGNYQCGHYKHITSKETLYCIDG

ALLTKSSEYKGPITDVFYKENSYTTTIKPVTYKLDGVVCTEIDPKLDNYYKKDNSYFTEQPIDLVPNQPYPNAS

FDNFKFVCDNIKFADDLNQLTGYKKPASRELKVTFFPDLNGDVVAIDYKHYTPSFKKGAKLLHKPIVWHVNNAT

NKATYKPNTWCIRCLWSTKPVETSNSFDVLKSEDAQGMDNLACEDLKPVSEEVVENPTIQKDVLECNVKTTEVV

GDIILKPANNSLKITEEVGHTDLMAAYVDNSSLTIKKPNELSRVLGLKTLATHGLAAVNSVPWDTIANYAKPFL

NKVVSTTTNIVTRCLNRVCTNYMPYFFTLLLQLCTFTRSTNSRIKASMPTTIAKNTVKSVGKFCLEASFNYLKS

PNFSKLINIIIWFLLLSVCLGSLIYSTAALGVLMSNLGMPSYCTGYREGYLNSTNVTIATYCTGSIPCSVCLSG

LDSLDTYPSLETIQITISSFKWDLTAFGLVAEWFLAYILFTRFFYVLGLAAIMQLFFSYFAVHFISNSWLMWLI

INLVQMAPISAMVRMYIFFASFYYVWKSYVHVVDGCNSSTCMMCYKRNRATRVECTTIVNGVRRSFYVYANGGK

GFCKLHNWNCVNCDTFCAGSTFISDEVARDLSLQFKRPINPTDQSSYIVDSVTVKNGSIHLYFDKAGQKTYERH

SLSHFVNLDNLRANNTKGSLPINVIVFDGKSKCEESSAKSASVYYSQLMCQPILLLDQALVSDVGDSAEVAVKM

FDAYVNTFSSTFNVPMEKLKTLVATAEAELAKNVSLDNVLSTFISAARQGFVDSDVETKDVVECLKLSHQSDIE

VTGDSCNNYMLTYNKVENMTPRDLGACIDCSARHINAQVAKSHNIALIWNVKDFMSLSEQLRKQIRSAAKKNNL

PFKLTCATTRQVVNVVTTKIALKGGKIVNNWLKQLIKVTLVFLFVAAIFYLITPVHVMSKHTDFSSEIIGYKAI

DGGVTRDIASTDTCFANKHADFDTWFSQRGGSYTNDKACPLIAAVITREVGFVVPGLPGTILRTTNGDFLHFLP

RVFSAVGNICYTPSKLIEYTDFATSACVLAAECTIFKDASGKPVPYCYDTNVLEGSVAYESLRPDTRYVLMDGS

IIQFPNTYLEGSVRVVTTFDSEYCRHGTCERSEAGVCVSTSGRWVLNNDYYRSLPGVFCGVDAVNLLTNMFTPL

IQPIGALDISASIVAGGIVAIVVTCLAYYFMRFRRAFGEYSHVVAFNTLLFLMSFTVLCLTPVYSFLPGVYSVI

YLYLTFYLTNDVSFLAHIQWMVMFTPLVPFWITIAYIICISTKHFYWFFSNYLKRRVVFNGVSFSTFEEAALCT

FLLNKEMYLKLRSDVLLPLTQYNRYLALYNKYKYFSGAMDTTSYREAACCHLAKALNDFSNSGSDVLYQPPQTS

ITSAVLQSGFRKMAFPSGKVEGCMVQVTCGTTTLNGLWLDDVVYCPRHVICTSEDMLNPNYEDLLIRKSNHNFL

VQAGNVQLRVIGHSMQNCVLKLKVDTANPKTPKYKFVRIQPGQTFSVLACYNGSPSGVYQCAMRPNFTIKGSFL

NGSCGSVGFNIDYDCVSFCYMHHMELPTGVHAGTDLEGNFYGPFVDRQTAQAAGTDTTITVNVLAWLYAAVING

DRWFLNRFTTTLNDFNLVAMKYNYEPLTQDHVDILGPLSAQTGIAVLDMCASLKELLQNGMNGRTILGSALLED

EFTPFDVVRQCSGVTFQSAVKRTIKGTHHWLLLTILTSLLVLVQSTQWSLFFFLYENAFLPFAMGIIAMSAFAM

MFVKHKHAFLCLFLLPSLATVAYFNMVYMPASWVMRIMTWLDMVDTSLSGFKLKDCVMYASAVVLLILMTARTV

Figure 87C

SEQ ID NO: 410 (continued)

YDDGARRVWTLMNVLTLVYKVYYGNALDQAISMWALIISVTSNYSGVVTTVMFLARGIVFMCVEYCPIFFITGN

TLQCIMLVYCFLGYFCTCYFGLFCLLNRYFRLTLGVYDYLVSTQEFRYMNSQGLLPPKNSIDAFKLNIKLLGVG

GKPCIKVATVQSKMSDVKCTSVVLLSVLQQLRVESSSKLWAQCVQLHNDILLAKDTTEAFEKMVSLLSVLLSMQ

GAVDINKLCEEMLDNRATLQAIASEFSSLPSYAAFATAQEAYEQAVANGDSEVVLKKLKKSLNVAKSEFDRDAA

MQRKLEKMADQAMTQMYKQARSEDKRAKVTSAMQTMLFTMLRKLDNDALNNIINNARDGCVPLNIIPLTTAAKL

MVVIPDYNTYKNTCDGTTFTYASALWEIQQVVDADSKIVQLSEISMDNSPNLAWPLIVTALRANSAVKLQNNEL

SPVALRQMSCAAGTTQTACTDDNALAYYNTTKGGRFVLALLSDLQDLKWARFPKSDGTGTIYTELEPPCRFVTD

TPKGPKVKYLYFIKGLNNLNRGMVLGSLAATVRLQAGNATEVPANSTVLSFCAFAVDAAKAYKDYLASGGQPIT

NCVKMLCTHTGTGQAITVTPEANMDQESFGGASCCLYCRCHIDHPNPKGFCDLKGKYVQIPTTCANDPVGFTLK

NTVCTVCGMWKGYGCSCDQLREPMLQSADAQSFLNRVCGVSAARLTPCGTGTSTDVVYRAFDIYNDKVAGFAKF

LKTNCCRFQEKDEDDNLIDSYFVVKRHTFSNYQHEETIYNLLKDCPAVAKHDFFKFRIDGDMVPHISRQRLTKY

TMADLVYALRHFDEGNCDTLKEILVTYNCCDDDYFNKKDWYDFVENPDILRVYANLGERVRQALLKTVQFCDAM

RNAGIVGVLTLDNQDLNGNWYDFGDFIQTTPGSGVPVVDSYYSLLMPILTLTRALTAESHVDTDLTKPYIKWDL

LKYDFTEERLKLFDRYFKYWDQTYHPNCVNCLDDRCILHCANFNVLFSTVFPPTSFGPLVRKIFVDGVPFVVST

GYHFRELGVVHNQDVNLHSSRLSFKELLVYAADPAMHAASGNLLLDKRTTCFSVAALTNNVAFQTVKPGNFNKD

FYDFAVSKGFFKEGSSVELKHFFFAQDGNAAISDYDYYRYNLPTMCDIRQLLFVVEVVDKYFDCYDGGCINANQ

VIVNNLDKSAGFPFNKWGKARLYYDSMSYEDQDALFAYTKRNVIPTITQMNLKYAISAKNRARTVAGVSICSTM

TNRQFHQKLLKSIAATRGATVVIGTSKFYGGWHNMLKTVYSDVENPHLMGWDYPKCDRAMPNMLRIMASLVLAR

KHTTCCSLSHRFYRLANECAQVLSEMVMCGGSLYVKPGGTSSGDATTAYANSVFNICQAVTANVNALLSTDGNK

IADKYVRNLQHRLYECLYRNRDVDTDFVNEFYAYLRKHFSMMILSDDAVVCFNSTYASQGLVASIKNFKSVLYY

QNNVFMSEAKCWTETDLTKGPHEFCSQHTMLVKQGDDYVYLPYPDPSRILGAGCFVDDIVKTDGTLMIERFVSL

AIDAYPLTKHPNQEYADVFHLYLQYIRKLHDELTGHMLDMYSVMLTNDNTSRYWEPEFYEAMYTPHTVLQAVGA

CVLCNSQTSLRCGACIRRPFLCCKCCYDHVISTSHKLVLSVNPYVCNAPGCDVTDVTQLYLGGMSYYCKSHKPP

ISFPLCANGQVFGLYKNTCVGSDNVTDFNAIATCDWTNAGDYILANTCTERLKLFAAETLKATEETFKLSYGIA

TVREVLSDRELHLSWEVGKPRPPLNRNYVFTGYRVTKNSKVQIGEYTFEKGDYGDAVVYRGTTTYKLNVGDYFV

LTSHTVMPLSAPTLVPQEHYVRITGLYPTLNISDEFSSNVANYQKVGMQKYSTLQGPPGTGKSHFAIGLALYYP

SARIVYTACSHAAVDALCEKALKYLPIDKCSRIIPARARVECFDKFKVNSTLEQYVFCTVNALPETTADIVVFD

Figure 87D

SEQ ID NO: 410 (continued)

EISMATNYDLSVVNARLRAKHYVYIGDPAQLPAPRTLLTKGTLEPEYFNSVCRLMKTIGPDMFLGTCRRCPAEI

VDTVSALVYDNKLKAHKDKSAQCFKMFYKGVITHDVSSAINRPQIGVVREFLTRNPAWRKAVFISPYNSQNAVA

SKILGLPTQTVDSSQGSEYDYVIFTQTTETAHSCNVNRFNVAITRAKVGILCIMSDRDLYDKLQFTSLEIPRRN

VATLQAENVTGLFKDCSKVITGLHPTQAPTHLSVDTKFKTEGLCVDIPGIPKDMTYRRLISMMGFKMNYQVNGY

PNMFITREEAIRHVRAWIGFDVEGCHATREAVGTNLPLQLGFSTGVNLVAVPTGYVDTPNNTDFSRVSAKPPPG

DQFKHLIPLMYKGLPWNVVRIKIVQMLSDTLKNLSDRVVFVLWAHGFELTSMKYFVKIGPERTCCLCDRRATCF

STASDTYACWHHSIGFDYVYNPFMIDVQQWGFTGNLQSNHDLYCQVHGNAHVASCDAIMTRCLAVHECFVKRVD

WTIEYPIIGDELKINAACRKVQHMVVKAALLADKFPVLHDIGNPKAIKCVPQADVEWKFYDAQPCSDKAYKIEE

LFYSYATHSDKFTDGVCLFWNCNVDRYPANSIVCRFDTRVLSNLNLPGCDGGSLYVNKHAFHTPAFDKSAFVNL

KQLPFFYYSDSPCESHGKQVVSDIDYVPLKSATCITRCNLGGAVCRHHANEYRLYLDAYNMMISAGFSLWVYKQ

FDTYNLWNTFTRLQSLENVAFNVVNKGHFDGQQGEVPVSIINNTVYTKVDGVDVELFENKTTLPVNVAFELWAK

RNIKPVPEVKILNNLGVDIAANTVIWDYKRDAPAHISTIGVCSMTDIAKKPTETICAPLTVFFDGRVDGQVDLF

RNARNGVLITEGSVKGLQPSVGPKQASLNGVTLIGEAVKTQFNYYKKVDGVVQQLPETYFTQSRNLQEFKPRSQ

MEIDFLELAMDEFIERYKLEGYAFEHIVYGDFSHSQLGGLHLLIGLAKRFKESPFELEDFIPMDSTVKNYFITD

AQTGSSKCVCSVIDLLLDDFVEIIKSQDLSVVSKVVKVTIDYTEISFMLWCKDGHVETFYPKLQSSQAWQPGVA

MPNLYKMQRMLLEKCDLQNYGDSATLPKGIMMNVAKYTQLCQYLNTLTLAVPYNMRVIHFGAGSDKGVAPGTAV

LRQWLPTGTLLVDSDLNDFVSDADSTLIGDCATVHTANKWDLIISDMYDPKTKNVTKENDSKEGFFTYICGFIQ

QKLALGGSVAIKITEHSWNADLYKLMGHFAWWTAFVTNVNASSSEAFLIGCNYLGKPREQIDGYVMHANYIFWR

NTNPIQLSSYSLFDMSKFPLKLRGTAVMSLKEGQINDMILSLLSKGRLIIRENNRVVISSDVLVNNMFVFLVLL

PLVSSQCVNLTTRTQLPPAYTNSFTRGVYYPDKVFRSSVLHSTQDLFLPFFSNVTWFHAIHVSGTNGTKRFDNP

VLPFNDGVYFASTEKSNIIRGWIFGTTLDSKTQSLLIVNNATNVVIKVCEFQFCNDPFLGVYYHKNNKSWMESE

FRVYSSANNCTFEYVSQPFLMDLEGKQGNFKNLREFVFKNIDGYFKIYSKHTPINLVRDLPQGFSALEPLVDLP

IGINITRFQTLLALHRSYLTPGDSSSGWTAGAAAYYVGYLQPRTFLLKYNENGTITDAVDCALDPLSETKCTLK

SFTVEKGIYQTSNFRVQPTESIVRFPNITNLCPFGEVFNATRFASVYAWNRKRISNCVADYSVLYNSASFSTFK

CYGVSPTKLNDLCFTNVYADSFVIRGDEVRQIAPGQTGKIADYNYKLPDDFTGCVIAWNSNNLDSKVGGNYNYL

YRLFRKSNLKPFERDISTEIYQAGSTPCNGVEGFNCYFPLQSYGFQPTNGVGYQPYRVVVLSFELLHAPATVCG

PKKSTNLVKNKCVNFNFNGLTGTGVLTESNKKFLPFQQFGRDIADTTDAVRDPQTLEILDITPCSFGGVSVITP

Figure 87E

SEQ ID NO: 410 (continued)

GTNTSNQVAVLYQDVNCTEVPVAIHADQLTPTWRVYSTGSNVFQTRAGCLIGAEHVNNSYECDIPIGAGICASY

QTQTNSPRRARSVASQSIIAYTMSLGAENSVAYSNNSIAIPTNFTISVTTEILPVSMTKTSVDCTMYICGDSTE

CSNLLLQYGSFCTQLNRALTGIAVEQDKNTQEVFAQVKQIYKTPPIKDFGGFNFSQILPDPSKPSKRSFIEDLL

FNKVTLADAGFIKQYGDCLGDIAARDLICAQKFNGLTVLPPLLTDEMIAQYTSALLAGTITSGWTFGAGAALQI

PFAMQMAYRFNGIGVTQNVLYENQKLIANQFNSAIGKIQDSLSSTASALGKLQDVVNQNAQALNTLVKQLSSNF

GAISSVLNDILSRLDKVEAEVQIDRLITGRLQSLQTYVTQQLIRAAEIRASANLAATKMSECVLGQSKRVDFCG

KGYHLMSFPQSAPHGVVFLHVTYVPAQEKNFTTAPAICHDGKAHFPREGVFVSNGTHWFVTQRNFYEPQIITTD

NTFVSGNCDVVIGIVNNTVYDPLQPELDSFKEELDKYFKNHTSPDVDLGDISGINASVVNIQKEIDRLNEVAKN

LNESLIDLQELGKYEQYIKWPWYIWLGFIAGLIAIVMVTIMLCCMTSCCSCLKGCCSCGSCCKFDEDDSEPVLK

GVKLHYTMDLFMRIFTIGTVTLKQGEIKDATPSDFVRATATIPIQASLPFGWLIVGVALLAVFQSASKIITLKK

RWQLALSKGVHFVCNLLLLFVTVYSHLLLVAAGLEAPFLYLYALVYFLQSINFVRIIMRLWLCWKCRSKNPLLY

DANYFLCWHTNCYDYCIPYNSVTSSIVITSGDGTTSPISEHDYQIGGYTEKWESGVKDCVVLHSYFTSDYYQLY

STQLSTDTGVEHVTFFIYNKIVDEPEEHVQIHTIDGSSGVVNPVMEPIYDEPTTTTSVPLMYSFVSEETGTLIV

NSVLLFLAFVVFLLVTLAILTALRLCAYCCNIVNVSLVKPSFYVYSRVKNLNSSRVPDLLVMADSNGTITVEEL

KKLLEQWNLVIGFLFLTWICLLQFAYANRNRFLYIIKLIFLWLLWPVTLACFVLAAVYRINWITGGIAIAMACL

VGLMWLSYFIASFRLFARTRSMWSFNPETNILLNVPLHGTILTRPLLESELVIGAVILRGHLRIAGHHLGRCDI

KDLPKEITVATSRTLSYYKLGASQRVAGDSGFAAYSRYRIGNYKLNTDHSSSSDNIALLVQMFHLVDFQVTIAE

ILLIIMRTFKVSIWNLDYIINLIIKNLSKSLTENKYSQLDEEQPMEIDMKIILFLALITLATCELYHYQECVRG

TTVLLKEPCSSGTYEGNSPFHPLADNKFALTCFSTQFAFACPDGVKHVYQLRARSVSPKLFIRQEEVQELYSPI

FLIVAAIVFITLCFTLKRKTEMIELSLIDFYLCFLAFLLFLVLIMLIIFWFSLELQDHNETCHAMKFLVFLGII

TTVAAFHQECSLQSCTQHQPYVVDDPCPIHFYSKWYIRVGARKSAPLIELCVDEAGSKSPIQYIDIGNYTVSCL

PFTINCQEPKLGSLVVRCSFYEDFLEYHDVRVVLDFIMSDNGPQNQRNAPRITFGGPSDSTGSNQNGERSGARS

KQRRPQGLPNNTASWFTALTQHGKEDLKFPRGQGVPINTNSSPDDQIGYYRRATRRIRGGDGKMKDLSPRWYFY

YLGTGPEAGLPYGANKDGIIWVATEGALNTPKDHIGTRNPANNAAIVLQLPQGTTLPKGFYAEGSRGGSQASSR

SSSRSRNSSRNSTPGSSRGTSPARMAGNGGDAALALLLLDRLNQLESKMSGKGQQQQGQTVTKKSAAEASKKPR

QKRTATKAYNVTQAFGRRGPEQTQGNFGDQELIRQGTDYKHWPQIAQFAPSASAFFGMSRIGMEVTPSGTWLTY

TGAIKLDDKDPNFKDQVILLNKHIDAYKTFPPTEPKKDKKKKADETQALPQRQKKQQTVTLLPAADLDDFSKQL

QQSMSSADSTQAMGYINVFAFPFTIYSLLLCRMNSRNYIAQVDVVNFNLT

SEQUENCE LISTING

<160> NUMBER OF SEQ ID NOS: 476

<210> SEQ ID NO 1
<211> LENGTH: 29903
<212> TYPE: DNA
<213> ORGANISM: Unknown
<220> FEATURE:
<223> OTHER INFORMATION: Wuhan-Hu-1

<400> SEQUENCE: 1

```
attaaaggtt tataccttcc caggtaacaa accaaccaac tttcgatctc ttgtagatct     60

gttctctaaa cgaactttaa aatctgtgtg gctgtcactc ggctgcatgc ttagtgcact    120

cacgcagtat aattaataac taattactgt cgttgacagg acacgagtaa ctcgtctatc    180

ttctgcaggc tgcttacggt ttcgtccgtg ttgcagccga tcatcagcac atctaggttt    240

cgtccgggtg tgaccgaaag gtaagatgga gagccttgtc cctggtttca acgagaaaac    300

acacgtccaa ctcagtttgc ctgttttaca ggttcgcgac gtgctcgtac gtggctttgg    360

agactccgtg gaggaggtct tatcagaggc acgtcaacat cttaaagatg gcacttgtgg    420

cttagtagaa gttgaaaaag gcgttttgcc tcaacttgaa cagccctatg tgttcatcaa    480

acgttcggat gctcgaactg cacctcatgg tcatgttatg gttgagctgg tagcagaact    540

cgaaggcatt cagtacggtc gtagtggtga gacacttggt gtccttgtcc ctcatgtggg    600

cgaaatacca gtggcttacc gcaaggttct tcttcgtaag aacggtaata aaggagctgg    660

tggccatagt tacggcgccg atctaaagtc atttgactta ggcgacgagc ttggcactga    720

tccttatgaa gattttcaag aaaactggaa cactaaacat agcagtggtg ttacccgtga    780

actcatgcgt gagcttaacg gaggggcata cactcgctat gtcgataaca acttctgtgg    840

ccctgatggc taccctcttg agtgcattaa agaccttcta gcacgtgctg gtaaagcttc    900

atgcactttg tccgaacaac tggactttat tgacactaag aggggtgtat actgctgccg    960

tgaacatgag catgaaattg cttggtacac ggaacgttct gaaaagagct atgaattgca   1020

gacacctttt gaaattaaat tggcaaagaa atttgacacc ttcaatgggg aatgtccaaa   1080

ttttgtattt cccttaaatt ccataatcaa gactattcaa ccaagggttg aaaagaaaaa   1140

gcttgatggc tttatgggta gaattcgatc tgtctatcca gttgcgtcac caaatgaatg   1200

caaccaaatg tgcctttcaa ctctcatgaa gtgtgatcat tgtggtgaaa cttcatggca   1260

gacgggcgat tttgttaaag ccacttgcga attttgtggc actgagaatt tgactaaaga   1320

aggtgccact acttgtggtt acttacccca aaatgctgtt gttaaaattt attgtccagc   1380

atgtcacaat tcagaagtag gacctgagca tagtcttgcc gaataccata atgaatctgg   1440

cttgaaaacc attcttcgta agggtggtcg cactattgcc tttggaggct gtgtgttctc   1500

ttatgttggt tgccataaca agtgtgccta ttgggttcca cgtgctagcg ctaacatagg   1560

ttgtaaccat acaggtgttg ttggagaagg ttccgaaggt cttaatgaca accttcttga   1620

aatactccaa aaagagaaag tcaacatcaa tattgttggt gactttaaac ttaatgaaga   1680

gatcgccatt attttggcat ctttttctgc ttccacaagt gcttttgtgg aaactgtgaa   1740

aggtttggat tataaagcat tcaaacaaat tgttgaatcc tgtggtaatt ttaaagttac   1800

aaaaggaaaa gctaaaaaag gtgcctggaa tattggtgaa cagaaatcaa tactgagtcc   1860
```

-continued

```
tctttatgca tttgcatcag aggctgctcg tgttgtacga tcaattttct cccgcactct   1920
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
gctaactaac atctttggca ctgtttatga aaaactcaaa cccgtccttg attggcttga   2160
agagaagttt aaggaaggtg tagagtttct tagagacggt tgggaaattg ttaaatttat   2220
ctcaacctgt gcttgtgaaa ttgtcggtgg acaaattgtc acctgtgcaa aggaaattaa   2280
ggagagtgtt cagacattct ttaagcttgt aaataaattt ttggctttgt gtgctgactc   2340
tatcattatt ggtggagcta aacttaaagc cttgaattta ggtgaaacat ttgtcacgca   2400
ctcaaaggga ttgtacagaa agtgtgttaa atccagagaa gaaactggcc tactcatgcc   2460
tctaaaagcc ccaaaagaaa ttatcttctt agagggagaa acacttccca cagaagtgtt   2520
aacagaggaa gttgtcttga aaactggtga tttacaacca ttagaacaac ctactagtga   2580
agctgttgaa gctccattgg ttggtacacc agtttgtatt aacgggctta tgttgctcga   2640
aatcaaagac acagaaaagt actgtgccct tgcacctaat atgatggtaa caaacaatac   2700
cttcacactc aaaggcggtg caccaacaaa ggttactttt ggtgatgaca ctgtgataga   2760
agtgcaaggt tacaagagtg tgaatatcac ttttgaactt gatgaaagga ttgataaagt   2820
acttaatgag aagtgctctg cctatacagt tgaactcggt acagaagtaa atgagttcgc   2880
ctgtgttgtg gcagatgctg tcataaaaac tttgcaacca gtatctgaat tacttacacc   2940
actgggcatt gatttagatg agtggagtat ggctacatac tacttatttg atgagtctgg   3000
tgagtttaaa ttggcttcac atatgtattg ttctttctac cctccagatg aggatgaaga   3060
agaaggtgat tgtgaagaag aagagtttga gccatcaact caatatgagt atggtactga   3120
agatgattac caaggtaaac ctttggaatt tggtgccact tctgctgctc ttcaacctga   3180
agaagagcaa gaagaagatt ggttagatga tgatagtcaa caaactgttg gtcaacaaga   3240
cggcagtgag gacaatcaga caactactat tcaaacaatt gttgaggttc aacctcaatt   3300
agagatggaa cttacaccag ttgttcagac tattgaagtg aatagtttta gtggttattt   3360
aaaacttact gacaatgtat acattaaaaa tgcagacatt gtggaagaag ctaaaaaggt   3420
aaaaccaaca gtggttgtta atgcagccaa tgtttacctt aaacatggag gaggtgttgc   3480
aggagcctta aataaggcta ctaacaatgc catgcaagtt gaatctgatg attacatagc   3540
tactaatgga ccacttaaag tgggtggtag ttgtgtttta agcggacaca atcttgctaa   3600
acactgtctt catgttgtcg gcccaaatgt taacaaaggt gaagacattc aacttcttaa   3660
gagtgcttat gaaaatttta atcagcacga agttctactt gcaccattat tatcagctgg   3720
tatttttggt gctgacccta tacattcttt aagagtttgt gtagatactg ttcgcacaaa   3780
tgtctactta gctgtctttg ataaaaatct ctatgacaaa cttgtttcaa gctttttgga   3840
aatgaagagt gaaaagcaag ttgaacaaaa gatcgctgag attcctaaag aggaagttaa   3900
gccatttata actgaaagta aaccttcagt tgaacagaga aaacaagatg ataagaaaat   3960
caaagcttgt gttgaagaag ttacaacaac tctggaagaa actaagttcc tcacagaaaa   4020
cttgttactt tatattgaca ttaatggcaa tcttcatcca gattctgcca ctcttgttag   4080
tgacattgac atcactttct taaagaaaga tgctccatat atagtgggtg atgttgttca   4140
agagggtgtt ttaactgctg tggttatacc tactaaaaag gctggtggca ctactgaaat   4200
gctagcgaaa gctttgagaa aagtgccaac agacaattat ataaccactt acccgggtca   4260
```

-continued

```
gggtttaaat ggttacactg tagaggaggc aaagacagtg cttaaaaagt gtaaaagtgc   4320
cttttacatt ctaccatcta ttatctctaa tgagaagcaa gaaattcttg gaactgtttc   4380
ttggaatttg cgagaaatgc ttgcacatgc agaagaaaca cgcaaattaa tgcctgtctg   4440
tgtggaaact aaagccatag tttcaactat acagcgtaaa tataagggta ttaaaataca   4500
agagggtgtg gttgattatg gtgctagatt ttacttttac accagtaaaa caactgtagc   4560
gtcacttatc aacacactta acgatctaaa tgaaactctt gttacaatgc cacttggcta   4620
tgtaacacat ggcttaaatt tggaagaagc tgctcggtat atgagatctc tcaaagtgcc   4680
agctacagtt tctgtttctt cacctgatgc tgttacagcg tataatggtt atcttacttc   4740
ttcttctaaa acacctgaag aacattttat tgaaaccatc tcacttgctg gttcctataa   4800
agattggtcc tattctggac aatctacaca actaggtata gaatttctta agagaggtga   4860
taaaagtgta tattacacta gtaatcctac cacattccac ctagatggtg aagttatcac   4920
ctttgacaat cttaagacac ttctttcttt gagagaagtg aggactatta aggtgtttac   4980
aacagtagac aacattaacc tccacacgca agttgtggac atgtcaatga catatggaca   5040
acagtttggt ccaacttatt tggatggagc tgatgttact aaaataaaac ctcataattc   5100
acatgaaggt aaaacatttt atgttttacc taatgatgac actctacgtg ttgaggcttt   5160
tgagtactac cacacaactg atcctagttt tctgggtagg tacatgtcag cattaaatca   5220
cactaaaaag tggaaatacc cacaagttaa tggtttaact tctattaaat gggcagataa   5280
caactgttat cttgccactg cattgttaac actccaacaa atagagttga agtttaatcc   5340
acctgctcta caagatgctt attacagagc aagggctggt gaagctgcta acttttgtgc   5400
acttatctta gcctactgta ataagacagt aggtgagtta ggtgatgtta gagaaacaat   5460
gagttacttg tttcaacatg ccaatttaga ttcttgcaaa agagtcttga acgtggtgtg   5520
taaaacttgt ggacaacagc agacaaccct taagggtgta gaagctgtta tgtacatggg   5580
cacactttct tatgaacaat ttaagaaagg tgttcagata ccttgtacgt gtggtaaaca   5640
agctacaaaa tatctagtac aacaggagtc accttttgtt atgatgtcag caccacctgc   5700
tcagtatgaa cttaagcatg gtacatttac ttgtgctagt gagtacactg gtaattacca   5760
gtgtggtcac tataaacata taacttctaa agaaactttg tattgcatag acggtgcttt   5820
acttacaaag tcctcagaat acaaaggtcc tattacggat gttttctaca aagaaaacag   5880
ttacacaaca accataaaac cagttactta taaattggat ggtgttgttt gtacagaaat   5940
tgaccctaag ttggacaatt attataagaa agacaattct tatttcacag agcaaccaat   6000
tgatcttgta ccaaaccaac catatccaaa cgcaagcttc gataatttta agtttgtatg   6060
tgataatatc aaatttgctg atgatttaaa ccagttaact ggttataaga aacctgcttc   6120
aagagagctt aaagttacat ttttccctga cttaaatggt gatgtggtgg ctattgatta   6180
taaacactac acaccctctt ttaagaaagg agctaaattg ttacataaac ctattgtttg   6240
gcatgttaac aatgcaacta ataaagccac gtataaacca aatacctggt gtatacgttg   6300
tctttggagc acaaaaccag ttgaaacatc aaattcgttt gatgtactga agtcagagga   6360
cgcgcaggga atggataatc ttgcctgcga agatctaaaa ccagtctctg aagaagtagt   6420
ggaaaatcct accatacaga aagacgttct tgagtgtaat gtgaaaacta ccgaagttgt   6480
aggagacatt atacttaaac cagcaaataa tagtttaaaa attacagaag aggttggcca   6540
cacagatcta atggctgctt atgtagacaa ttctagtctt actattaaga aacctaatga   6600
```

-continued

```
attatctaga gtattaggtt tgaaaaccct tgctactcat ggtttagctg ctgttaatag   6660
tgtcccttgg gatactatag ctaattatgc taagcctttt cttaacaaag ttgttagtac   6720
aactactaac atagttacac ggtgtttaaa ccgtgtttgt actaattata tgccttattt   6780
ctttacttta ttgctacaat tgtgtacttt tactagaagt acaaattcta gaattaaagc   6840
atctatgccg actactatag caaagaatac tgttaagagt gtcggtaaat tttgtctaga   6900
ggcttcattt aattatttga agtcacctaa tttttctaaa ctgataaata ttataatttg   6960
gtttttacta ttaagtgttt gcctaggttc tttaatctac tcaaccgctg ctttaggtgt   7020
tttaatgtct aatttaggca tgccttctta ctgtactggt tacagagaag gctatttgaa   7080
ctctactaat gtcactattg caacctactg tactggttct ataccttgta gtgtttgtct   7140
tagtggttta gattctttag acacctatcc ttctttagaa actatacaaa ttaccatttc   7200
atcttttaaa tgggatttaa ctgcttttgg cttagttgca gagtggtttt tggcatatat   7260
tcttttcact aggtttttct atgtacttgg attggctgca atcatgcaat tgtttttcag   7320
ctattttgca gtacatttta ttagtaattc ttggcttatg tggttaataa ttaatcttgt   7380
acaaatggcc ccgatttcag ctatggttag aatgtacatc ttctttgcat cattttatta   7440
tgtatggaaa agttatgtgc atgttgtaga cggttgtaat tcatcaactt gtatgatgtg   7500
ttacaaacgt aatagagcaa caagagtcga atgtacaact attgttaatg gtgttagaag   7560
gtccttttat gtctatgcta atggaggtaa aggcttttgc aaactacaca attggaattg   7620
tgttaattgt gatacattct gtgctggtag tacatttatt agtgatgaag ttgcgagaga   7680
cttgtcacta cagtttaaaa gaccaataaa tcctactgac cagtcttctt acatcgttga   7740
tagtgttaca gtgaagaatg gttccatcca tctttacttt gataaagctg gtcaaaagac   7800
ttatgaaaga cattctctct ctcattttgt taacttagac aacctgagag ctaataacac   7860
taaaggttca ttgcctatta atgttatagt tttgatggt aaatcaaaat gtgaagaatc   7920
atctgcaaaa tcagcgtctg tttactacag tcagcttatg tgtcaaccta tactgttact   7980
agatcaggca ttagtgtctg atgttggtga tagtgcggaa gttgcagtta aaatgtttga   8040
tgcttacgtt aatacgtttt catcaacttt taacgtacca atggaaaaac tcaaaacact   8100
agttgcaact gcagaagctg aacttgcaaa gaatgtgtcc ttagacaatg tcttatctac   8160
ttttatttca gcagctcggc aagggtttgt tgattcagat gtagaaacta aagatgttgt   8220
tgaatgtctt aaattgtcac atcaatctga catagaagtt actggcgata gttgtaataa   8280
ctatatgctc acctataaca aagttgaaaa catgacaccc cgtgaccttg gtgcttgtat   8340
tgactgtagt gcgcgtcata ttaatgcgca ggtagcaaaa agtcacaaca ttgctttgat   8400
atggaacgtt aaagatttca tgtcattgtc tgaacaacta cgaaaacaaa tacgtagtgc   8460
tgctaaaaag aataacttac cttttaagtt gacatgtgca actactagac aagttgttaa   8520
tgttgtaaca acaaagatag cacttaaggg tggtaaaatt gttaataatt ggttgaagca   8580
gttaattaaa gttacacttg tgttcctttt tgttgctgct attttctatt taataacacc   8640
tgttcatgtc atgtctaaac atactgactt ttcaagtgaa atcataggat acaaggctat   8700
tgatggtggt gtcactcgtg acatagcatc tacagatact tgttttgcta acaaacatgc   8760
tgattttgac acatggttta gccagcgtgg tggtagttat actaatgaca aagcttgccc   8820
attgattgct gcagtcataa caagagaagt gggttttgtc gtgcctggtt tgcctggcac   8880
gatattacgc acaactaatg gtgacttttt gcatttctta cctagagttt ttagtgcagt   8940
tggtaacatc tgttacacac catcaaaact tatagagtac actgactttg caacatcagc   9000
```

-continued

```
ttgtgttttg gctgctgaat gtacaatttt taaagatgct tctggtaagc cagtaccata   9060
ttgttatgat accaatgtac tagaaggttc tgttgcttat gaaagtttac gccctgacac   9120
acgttatgtg ctcatggatg gctctattat tcaatttcct aacacctacc ttgaaggttc   9180
tgttagagtg gtaacaactt ttgattctga gtactgtagg cacggcactt gtgaaagatc   9240
agaagctggt gtttgtgtat ctactagtgg tagatgggta cttaacaatg attattacag   9300
atctttacca ggagttttct gtggtgtaga tgctgtaaat ttacttacta atatgtttac   9360
accactaatt caacctattg gtgctttgga catatcagca tctatagtag ctggtggtat   9420
tgtagctatc gtagtaacat gccttgccta ctattttatg aggtttagaa gagcttttgg   9480
tgaatacagt catgtagttg cctttaatac tttactattc cttatgtcat tcactgtact   9540
ctgtttaaca ccagtttact cattcttacc tggtgtttat tctgttattt acttgtactt   9600
gacattttat cttactaatg atgtttcttt tttagcacat attcagtgga tggttatgtt   9660
cacaccttta gtacctttct ggataacaat tgcttatatc atttgtattt ccacaaagca   9720
tttctattgg ttctttagta attacctaaa gagacgtgta gtctttaatg gtgtttcctt   9780
tagtactttt gaagaagctg cgctgtgcac ctttttgtta aataaagaaa tgtatctaaa   9840
gttgcgtagt gatgtgctat tacctcttac gcaatataat agatacttag ctctttataa   9900
taagtacaag tattttagtg gagcaatgga tacaactagc tacagagaag ctgcttgttg   9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
acctttgct  atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
```

aatccttatg acagcaagaa ctgtgtatga tgatggtgct aggagagtgt ggacacttat 11400
gaatgtcttg acactcgttt ataaagttta ttatggtaat gctttagatc aagccatttc 11460
catgtgggct cttataatct ctgttacttc taactactca ggtgtagtta caactgtcat 11520
gtttttggcc agaggtattg tttttatgtg tgttgagtat tgccctattt tcttcataac 11580
tggtaataca cttcagtgta taatgctagt ttattgtttc ttaggctatt tttgtacttg 11640
ttactttggc ctcttttgtt tactcaaccg ctactttaga ctgactcttg gtgtttatga 11700
ttacttagtt tctacacagg agtttagata tatgaattca cagggactac tcccacccaa 11760
gaatagcata gatgccttca aactcaacat taaattgttg ggtgttggtg gcaaaccttg 11820
tatcaaagta gccactgtac agtctaaaat gtcagatgta aagtgcacat cagtagtctt 11880
actctcagtt ttgcaacaac tcagagtaga atcatcatct aaattgtggg ctcaatgtgt 11940
ccagttacac aatgacattc tcttagctaa agatactact gaagcctttg aaaaaatggt 12000
ttcactactt tctgttttgc tttccatgca gggtgctgta gacataaaca agctttgtga 12060
agaaatgctg gacaacaggg caaccttaca agctatagcc tcagagttta gttcccttcc 12120
atcatatgca gcttttgcta ctgctcaaga agcttatgag caggctgttg ctaatggtga 12180
ttctgaagtt gttcttaaaa agttgaagaa gtctttgaat gtggctaaat ctgaatttga 12240
ccgtgatgca gccatgcaac gtaagttgga aaagatggct gatcaagcta tgacccaaat 12300
gtataaacag gctagatctg aggacaagag ggcaaaagtt actagtgcta tgcagacaat 12360
gcttttcact atgcttagaa agttggataa tgatgcactc aacaacatta tcaacaatgc 12420
aagagatggt tgtgttccct tgaacataat acctcttaca acagcagcca aactaatggt 12480
tgtcatacca gactataaca catataaaaa tacgtgtgat ggtacaacat ttacttatgc 12540
atcagcattg tgggaaatcc aacaggttgt agatgcagat agtaaaattg ttcaacttag 12600
tgaaattagt atggacaatt cacctaattt agcatggcct cttattgtaa cagctttaag 12660
ggccaattct gctgtcaaat tacagaataa tgagcttagt cctgttgcac tacgacagat 12720
gtcttgtgct gccggtacta cacaaactgc ttgcactgat gacaatgcgt tagcttacta 12780
caacacaaca aagggaggta ggtttgtact tgcactgtta tccgatttac aggatttgaa 12840
atgggctaga ttccctaaga gtgatggaac tggtactatc tatacagaac tggaaccacc 12900
ttgtaggttt gttacagaca cacctaaagg tcctaaagtg aagtatttat actttattaa 12960
aggattaaac aacctaaata gaggtatggt acttggtagt ttagctgcca cagtacgtct 13020
acaagctggt aatgcaacag aagtgcctgc caattcaact gtattatctt tctgtgcttt 13080
tgctgtagat gctgctaaag cttacaaaga ttatctagct agtgggggac aaccaatcac 13140
taattgtgtt aagatgttgt gtacacacac tggtactggt caggcaataa cagttacacc 13200
ggaagccaat atggatcaag aatcctttgg tggtgcatcg tgttgtctgt actgccgttg 13260
ccacatagat catccaaatc ctaaaggatt ttgtgactta aaaggtaagt atgtacaaat 13320
acctacaact tgtgctaatg accctgtggg ttttacactt aaaaacacag tctgtaccgt 13380
ctgcggtatg tggaaaggtt atggctgtag ttgtgatcaa ctccgcgaac ccatgcttca 13440
gtcagctgat gcacaatcgt ttttaaacgg gtttgcggtg taagtgcagc ccgtcttaca 13500
ccgtgcggca caggcactag tactgatgtc gtatacaggg cttttgacat ctacaatgat 13560
aaagtagctg gttttgctaa attcctaaaa actaattgtt gtcgcttcca agaaaaggac 13620
gaagatgaca atttaattga ttcttacttt gtagttaaga gacacacttt ctctaactac 13680
caacatgaag aaacaattta taatttactt aaggattgtc cagctgttgc taaacatgac 13740

-continued ttctttaagt ttagaataga cggtgacatg gtaccacata tatcacgtca acgtcttact 13800
aaatacacaa tggcagacct cgtctatgct ttaaggcatt ttgatgaagg taattgtgac 13860
acattaaaag aaatacttgt cacatacaat tgttgtgatg atgattattt caataaaaag 13920
gactggtatg attttgtaga aaacccagat atattacgcg tatacgccaa cttaggtgaa 13980
cgtgtacgcc aagctttgtt aaaaacagta caattctgtg atgccatgcg aaatgctggt 14040
attgttggtg tactgacatt agataatcaa gatctcaatg gtaactggta tgatttcggt 14100
gatttcatac aaaccacgcc aggtagtgga gttcctgttg tagattctta ttattcattg 14160
ttaatgccta tattaacctt gaccagggct ttaactgcag agtcacatgt tgacactgac 14220
ttaacaaagc cttacattaa gtgggatttg ttaaaatatg acttcacgga agagaggtta 14280
aaactctttg accgttattt taaatattgg gatcagacat accacccaaa ttgtgttaac 14340
tgtttggatg acagatgcat tctgcattgt gcaaacttta atgttttatt ctctacagtg 14400
ttcccaccta caagttttgg accactagtg agaaaaatat ttgttgatgg tgttccattt 14460
gtagtttcaa ctggatacca cttcagagag ctaggtgttg tacataatca ggatgtaaac 14520
ttacatagct ctagacttag ttttaaggaa ttacttgtgt atgctgctga ccctgctatg 14580
cacgctgctt ctggtaatct attactagat aaacgcacta cgtgcttttc agtagctgca 14640
cttactaaca atgttgcttt tcaaactgtc aaacccggta attttaacaa agacttctat 14700
gactttgctg tgtctaaggg tttctttaag gaaggaagtt ctgttgaatt aaaacacttc 14760
ttctttgctc aggatggtaa tgctgctatc agcgattatg actactatcg ttataatcta 14820
ccaacaatgt gtgatatcag acaactacta tttgtagttg aagttgttga taagtacttt 14880
gattgttacg atggtggctg tattaatgct aaccaagtca tcgtcaacaa cctagacaaa 14940
tcagctggtt ttccatttaa taaatggggt aaggctagac tttattatga ttcaatgagt 15000
tatgaggatc aagatgcact tttcgcatat acaaaacgta atgtcatccc tactataact 15060
caaatgaatc ttaagtatgc cattagtgca aagaatagag ctcgcaccgt agctggtgtc 15120
tctatctgta gtactatgac caatagacag tttcatcaaa aattattgaa atcaatagcc 15180
gccactagag gagctactgt agtaattgga acaagcaaat tctatggtgg ttggcacaac 15240
atgttaaaaa ctgtttatag tgatgtagaa aaccctcacc ttatgggttg ggattatcct 15300
aaatgtgata gagccatgcc taacatgctt agaattatgg cctcacttgt tcttgctcgc 15360
aaacatacaa cgtgttgtag cttgtcacac cgtttctata gattagctaa tgagtgtgct 15420
caagtattga gtgaaatggt catgtgtggc ggttcactat atgttaaacc aggtggaacc 15480
tcatcaggag atgccacaac tgcttatgct aatagtgttt ttaacatttg tcaagctgtc 15540
acggccaatg ttaatgcact tttatctact gatggtaaca aaattgccga taagtatgtc 15600
cgcaatttac aacacagact ttatgagtgt ctctatagaa atagagatgt tgacacagac 15660
tttgtgaatg agttttacgc atatttgcgt aaacatttct caatgatgat actctctgac 15720
gatgctgttg tgtgtttcaa tagcacttat gcatctcaag gtctagtggc tagcataaag 15780
aactttaagt cagttcttta ttatcaaaac aatgttttta tgtctgaagc aaaatgttgg 15840
actgagactg accttactaa aggacctcat gaattttgct ctcaacatac aatgctagtt 15900
aaacagggtg atgattatgt gtaccttcct tacccagatc catcaagaat cctaggggcc 15960
ggctgttttg tagatgatat cgtaaaaaca gatggtacac ttatgattga acggttcgtg 16020
tctttagcta tagatgctta cccacttact aaacatccta atcaggagta tgctgatgtc 16080

-continued

```
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac tacccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagatttttc cagagttagt gctaaaccac cgcctggaga tcaatttaaa  18480
```

cacctcatac cacttatgta caaaggactt ccttggaatg tagtgcgtat aaagattgta 18540
caaatgttaa gtgacacact taaaaatctc tctgacagag tcgtatttgt cttatgggca 18600
catggctttg agttgacatc tatgaagtat tttgtgaaaa taggacctga gcgcacctgt 18660
tgtctatgtg atagacgtgc cacatgcttt tccactgctt cagacactta tgcctgttgg 18720
catcattcta ttggatttga ttacgtctat aatccgttta tgattgatgt tcaacaatgg 18780
ggttttacag gtaacctaca aagcaaccat gatctgtatt gtcaagtcca tggtaatgca 18840
catgtagcta gttgtgatgc aatcatgact aggtgtctag ctgtccacga gtgctttgtt 18900
aagcgtgttg actggactat tgaatatcct ataattggtg atgaactgaa gattaatgcg 18960
gcttgtagaa aggttcaaca catggttgtt aaagctgcat tattagcaga caaattccca 19020
gttcttcacg acattggtaa ccctaaagct attaagtgtg tacctcaagc tgatgtagaa 19080
tggaagttct atgatgcaca gccttgtagt gacaaagctt ataaaataga agaattattc 19140
tattcttatg ccacacattc tgacaaattc acagatggtg tatgcctatt ttggaattgc 19200
aatgtcgata gatatcctgc taattccatt gtttgtagat ttgacactag agtgctatct 19260
aaccttaact tgcctggttg tgatggtggc agtttgtatg taaataaaca tgcattccac 19320
acaccagctt ttgataaaag tgcttttgtt aatttaaaac aattaccatt tttctattac 19380
tctgacagtc catgtgagtc tcatggaaaa caagtagtgt cagatataga ttatgtacca 19440
ctaaagtctg ctacgtgtat aacacgttgc aatttaggtg gtgctgtctg tagacatcat 19500
gctaatgagt acagattgta tctcgatgct tataacatga tgatctcagc tggctttagc 19560
ttgtgggttt acaaacaatt tgatacttat aacctctgga acacttttac aagacttcag 19620
agtttagaaa atgtggcttt taatgttgta aataagggac actttgatgg acaacagggt 19680
gaagtaccag tttctatcat taataacact gtttacacaa aagttgatgg tgttgatgta 19740
gaattgtttg aaaataaaac aacattacct gttaatgtag catttgagct ttgggctaag 19800
cgcaacatta aaccagtacc agaggtgaaa atactcaata atttgggtgt ggacattgct 19860
gctaatactg tgatctggga ctacaaaaga gatgctccag cacatatatc tactattggt 19920
gtttgttcta tgactgacat agccaagaaa ccaactgaaa cgatttgtgc accactcact 19980
gtcttttttg atggtagagt tgatggtcaa gtagacttat ttagaaatgc ccgtaatggt 20040
gttcttatta cagaaggtag tgttaaaggt ttacaaccat ctgtaggtcc caaacaagct 20100
agtcttaatg gagtcacatt aattggagaa gccgtaaaaa cacagttcaa ttattataag 20160
aaagttgatg gtgttgtcca acaattacct gaaacttact ttactcagag tagaaattta 20220
caagaattta aacccaggag tcaaatggaa attgatttct tagaattagc tatggatgaa 20280
ttcattgaac ggtataaatt agaaggctat gccttcgaac atatcgttta tggagatttt 20340
agtcatagtc agttaggtgg tttacatcta ctgattggac tagctaaacg ttttaaggaa 20400
tcaccttttg aattagaaga ttttattcct atggacagta cagttaaaaa ctatttcata 20460
acagatgcgc aaacaggttc atctaagtgt gtgtgttctg ttattgattt attacttgat 20520
gattttgttg aaataataaa atcccaagat ttatctgtag tttctaaggt tgtcaaagtg 20580
actattgact atacagaaat ttcatttatg ctttggtgta aagatggcca tgtagaaaca 20640
ttttacccaa aattacaatc tagtcaagcg tggcaaccgg gtgttgctat gcctaatctt 20700
tacaaaatgc aaagaatgct attagaaaag tgtgaccttc aaaattatgg tgatagtgca 20760
acattaccta aaggcataat gatgaatgtc gcaaaatata ctcaactgtg tcaatattta 20820

-continued

```
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attacccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc ctaatattac  22560
aaacttgtgc ccttttggtg aagtttttaa cgccaccaga tttgcatctg tttatgcttg  22620
gaacaggaag agaatcagca actgtgttgc tgattattct gtcctatata attccgcatc  22680
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
gcaaactgga aagattgctg attataatta taaattacca gatgatttta caggctgcgt  22860
tatagcttgg aattctaaca atcttgattc taaggttggt ggtaattata attacctgta  22920
tagattgttt aggaagtcta atctcaaacc ttttgagaga gatatttcaa ctgaaatcta  22980
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
```

-continued tgagtctaac aaaaagtttc tgcctttcca acaatttggc agagacattg ctgacactac 23280
tgatgctgtc cgtgatccac agacacttga gattcttgac attacaccat gttcttttgg 23340
tggtgtcagt gttataacac caggaacaaa tacttctaac caggttgctg ttctttatca 23400
ggatgttaac tgcacagaag tccctgttgc tattcatgca gatcaactta ctcctacttg 23460
gcgtgtttat tctacaggtt ctaatgtttt tcaaacacgt gcaggctgtt taataggggc 23520
tgaacatgtc aacaactcat atgagtgtga catacccatt ggtgcaggta tatgcgctag 23580
ttatcagact cagactaatt ctcctcggcg ggcacgtagt gtagctagtc aatccatcat 23640
tgcctacact atgtcacttg gtgcagaaaa ttcagttgct tactctaata actctattgc 23700
catacccaca aattttacta ttagtgttac cacagaaatt ctaccagtgt ctatgaccaa 23760
gacatcagta gattgtacaa tgtacatttg tggtgattca actgaatgca gcaatctttt 23820
gttgcaatat ggcagttttt gtacacaatt aaaccgtgct ttaactggaa tagctgttga 23880
acaagacaaa aacacccaag aagtttttgc acaagtcaaa caaatttaca aaacaccacc 23940
aattaaagat tttggtggtt ttaatttttc acaaatatta ccagatccat caaaaccaag 24000
caagaggtca tttattgaag atctactttt caacaaagtg acacttgcag atgctggctt 24060
catcaaacaa tatggtgatt gccttggtga tattgctgct agagacctca tttgtgcaca 24120
aaagtttaac ggccttactg ttttgccacc tttgctcaca gatgaaatga ttgctcaata 24180
cacttctgca ctgttagcgg gtacaatcac ttctggttgg acctttggtg caggtgctgc 24240
attacaaata ccatttgcta tgcaaatggc ttataggttt aatggtattg gagttacaca 24300
gaatgttctc tatgagaacc aaaaattgat tgccaaccaa tttaatagtg ctattggcaa 24360
aattcaagac tcactttctt ccacagcaag tgcacttgga aaacttcaag atgtggtcaa 24420
ccaaaatgca caagctttaa acacgcttgt taaacaactt agctccaatt ttggtgcaat 24480
ttcaagtgtt ttaaatgata tcctttcacg tcttgacaaa gttgaggctg aagtgcaaat 24540
tgataggttg atcacaggca gacttcaaag tttgcagaca tatgtgactc aacaattaat 24600
tagagctgca gaaatcagag cttctgctaa tcttgctgct actaaaatgt cagagtgtgt 24660
acttggacaa tcaaaaagag ttgatttttg tggaaagggc tatcatctta tgtccttccc 24720
tcagtcagca cctcatggtg tagtcttctt gcatgtgact tatgtccctg cacaagaaaa 24780
gaacttcaca actgctcctg ccatttgtca tgatggaaaa gcacactttc ctcgtgaagg 24840
tgtctttgtt tcaaatggca cacactggtt tgtaacacaa aggaattttt atgaaccaca 24900
aatcattact acagacaaca catttgtgtc tggtaactgt gatgttgtaa taggaattgt 24960
caacaacaca gtttatgatc ctttgcaacc tgaattagac tcattcaagg aggagttaga 25020
taaatatttt aagaatcata catcaccaga tgttgattta ggtgacatct ctggcattaa 25080
tgcttcagtt gtaaacattc aaaaagaaat tgaccgcctc aatgaggttg ccaagaattt 25140
aaatgaatct ctcatcgatc tccaagaact tggaaagtat gagcagtata taaaatggcc 25200
atggtacatt tggctaggtt ttatagctgg cttgattgcc atagtaatgg tgacaattat 25260
gctttgctgt atgaccagtt gctgtagttg tctcaagggc tgttgttctt gtggatcctg 25320
ctgcaaattt gatgaagacg actctgagcc agtgctcaaa ggagtcaaat tacattacac 25380
ataaacgaac ttatggattt gtttatgaga atcttcacaa ttggaactgt aactttgaag 25440
caaggtgaaa tcaaggatgc tactccttca gattttgttc gcgctactgc aacgataccg 25500
atacaagcct cactcccttt cggatggctt attgttggcg ttgcacttct tgctgttttt 25560

-continued

```
cagagcgctt ccaaaatcat aaccctcaaa aagagatggc aactagcact ctccaagggt  25620
gttcactttg tttgcaactt gctgttgttg tttgtaacag tttactcaca ccttttgctc  25680
gttgctgctg gccttgaagc cccttttctc tatctttatg ctttagtcta cttcttgcag  25740
agtataaact ttgtaagaat aataatgagg ctttggcttt gctggaaatg ccgttccaaa  25800
aacccattac tttatgatgc caactatttt ctttgctggc atactaattg ttacgactat  25860
tgtatacctt acaatagtgt aacttcttca attgtcatta cttcaggtga tggcacaaca  25920
agtcctattt ctgaacatga ctaccagatt ggtggttata ctgaaaaatg ggaatctgga  25980
gtaaaagact gtgttgtatt acacagttac ttcacttcag actattacca gctgtactca  26040
actcaattga gtacagacac tggtgttgaa catgttacct tcttcatcta caataaaatt  26100
gttgatgagc ctgaagaaca tgtccaaatt cacacaatcg acggttcatc cggagttgtt  26160
aatccagtaa tggaaccaat ttatgatgaa ccgacgacga ctactagcgt gcctttgtaa  26220
gcacaagctg atgagtacga acttatgtac tcattcgttt cggaagagac aggtacgtta  26280
atagttaata gcgtacttct ttttcttgct ttcgtggtat tcttgctagt tacactagcc  26340
atccttactg cgcttcgatt gtgtgcgtac tgctgcaata ttgttaacgt gagtcttgta  26400
aaaccttctt tttacgttta ctctcgtgtt aaaaatctga attcttctag agttcctgat  26460
cttctggtct aaacgaacta aatattatat tagtttttct gtttggaact ttaattttag  26520
ccatggcaga ttccaacggt actattaccg ttgaagagct taaaaagctc cttgaacaat  26580
ggaacctagt aataggtttc ctattcctta catggatttg tcttctacaa tttgcctatg  26640
ccaacaggaa taggtttttg tatataatta agttaatttt cctctggctg ttatggccag  26700
taactttagc ttgttttgtg cttgctgctg tttacagaat aaattggatc accggtggaa  26760
ttgctatcgc aatggcttgt cttgtaggct tgatgtggct cagctacttc attgcttctt  26820
tcagactgtt tgcgcgtacg cgttccatgt ggtcattcaa tccagaaact aacattcttc  26880
tcaacgtgcc actccatggc actattctga ccagaccgct tctagaaagt gaactcgtaa  26940
tcggagctgt gatccttcgt ggacatcttc gtattgctgg acaccatcta ggacgctgtg  27000
acatcaagga cctgcctaaa gaaatcactg ttgctacatc acgaacgctt tcttattaca  27060
aattgggagc ttcgcagcgt gtagcaggtg actcaggttt tgctgcatac agtcgctaca  27120
ggattggcaa ctataaatta aacacagacc attccagtag cagtgacaat attgctttgc  27180
ttgtacagta agtgacaaca gatgtttcat ctcgttgact ttcaggttac tatagcagag  27240
atattactaa ttattatgag gacttttaaa gtttccattt ggaatcttga ttacatcata  27300
aacctcataa ttaaaaattt atctaagtca ctaactgaga ataaatattc tcaattagat  27360
gaagagcaac caatggagat tgattaaacg aacatgaaaa ttattctttt cttggcactg  27420
ataacactcg ctacttgtga gctttatcac taccaagagt gtgttagagg tacaacagta  27480
cttttaaaag aaccttgctc ttctggaaca tacgagggca attcaccatt tcatcctcta  27540
gctgataaca aatttgcact gacttgcttt agcactcaat ttgcttttgc ttgtcctgac  27600
ggcgtaaaac acgtctatca gttacgtgcc agatcagttt cacctaaact gttcatcaga  27660
caagaggaag ttcaagaact ttactctcca atttttctta ttgttgcggc aatagtgttt  27720
ataacacttt gcttcacact caaaagaaag acagaatgat tgaactttca ttaattgact  27780
tctatttgtg ctttttagcc tttctgctat tccttgtttt aattatgctt attatctttt  27840
ggttctcact tgaactgcaa gatcataatg aaacttgtca cgcctaaacg aacatgaaat  27900
ttcttgtttt cttaggaatc atcacaactg tagctgcatt tcaccaagaa tgtagtttac  27960
```

-continued

```
agtcatgtac tcaacatcaa ccatatgtag ttgatgaccc gtgtcctatt cacttctatt  28020

ctaaatggta tattagagta ggagctagaa aatcagcacc tttaattgaa ttgtgcgtgg  28080

atgaggctgg ttctaaatca cccattcagt acatcgatat cggtaattat acagtttcct  28140

gtttaccttt tacaattaat tgccaggaac ctaaattggg tagtcttgta gtgcgttgtt  28200

cgttctatga agacttttta gagtatcatg acgttcgtgt tgttttagat ttcatctaaa  28260

cgaacaaact aaaatgtctg ataatggacc ccaaaatcag cgaaatgcac cccgcattac  28320

gtttggtgga ccctcagatt caactggcag taaccagaat ggagaacgca gtggggcgcg  28380

atcaaaacaa cgtcggcccc aaggtttacc caataatact gcgtcttggt tcaccgctct  28440

cactcaacat ggcaaggaag accttaaatt ccctcgagga caaggcgttc caattaacac  28500

caatagcagt ccagatgacc aaattggcta ctaccgaaga gctaccagac gaattcgtgg  28560

tggtgacggt aaaatgaaag atctcagtcc aagatggtat ttctactacc taggaactgg  28620

gccagaagct ggacttccct atggtgctaa caaagacggc atcatatggg ttgcaactga  28680

gggagccttg aatacaccaa aagatcacat tggcacccgc aatcctgcta acaatgctgc  28740

aatcgtgcta caacttcctc aaggaacaac attgccaaaa ggcttctacg cagaagggag  28800

cagaggcggc agtcaagcct cttctcgttc ctcatcacgt agtcgcaaca gttcaagaaa  28860

ttcaactcca ggcagcagta ggggaacttc tcctgctaga atggctggca atggcggtga  28920

tgctgctctt gctttgctgc tgcttgacag attgaaccag cttgagagca aaatgtctgg  28980

taaaggccaa caacaacaag gccaaactgt cactaagaaa tctgctgctg aggcttctaa  29040

gaagcctcgg caaaaacgta ctgccactaa agcatacaat gtaacacaag ctttcggcag  29100

acgtggtcca gaacaaaccc aaggaaattt tggggaccag gaactaatca gacaaggaac  29160

tgattacaaa cattggccgc aaattgcaca atttgccccc agcgcttcag cgttcttcgg  29220

aatgtcgcgc attggcatgg aagtcacacc ttcgggaacg tggttgacct acacaggtgc  29280

catcaaattg gatgacaaag atccaaattt caaagatcaa gtcattttgc tgaataagca  29340

tattgacgca tacaaaacat tcccaccaac agagcctaaa aaggacaaaa agaagaaggc  29400

tgatgaaact caagccttac cgcagagaca gaagaaacag caaactgtga ctcttcttcc  29460

tgctgcagat ttggatgatt tctccaaaca attgcaacaa tccatgagca gtgctgactc  29520

aactcaggcc taaactcatg cagaccacac aaggcagatg ggctatataa acgttttcgc  29580

ttttccgttt acgatatata gtctactctt gtgcagaatg aattctcgta actacatagc  29640

acaagtagat gtagttaact ttaatctcac atagcaatct ttaatcagtg tgtaacatta  29700

gggaggactt gaaagagcca ccacattttc accgaggcca cgcggagtac gatcgagtgt  29760

acagtgaaca atgctaggga gagctgccta tatggaagag ccctaatgtg taaaattaat  29820

tttagtagtg ctatccccat gtgattttaa tagcttctta ggagaatgac aaaaaaaaaa  29880

aaaaaaaaaa aaaaaaaaaa aaa                                          29903
```

<210> SEQ ID NO 2
<211> LENGTH: 7096
<212> TYPE: PRT
<213> ORGANISM: Unknown
<220> FEATURE:
<223> OTHER INFORMATION: SARS-CoV-2 Polyprotein

<400> SEQUENCE: 2

```
Met Glu Ser Leu Val Pro Gly Phe Asn Glu Lys Thr His Val Gln Leu
1               5                   10                  15
```

```
Ser Leu Pro Val Leu Gln Val Arg Asp Val Leu Val Arg Gly Phe Gly
            20                  25                  30

Asp Ser Val Glu Glu Val Leu Ser Glu Ala Arg Gln His Leu Lys Asp
        35                  40                  45

Gly Thr Cys Gly Leu Val Glu Val Glu Lys Gly Val Leu Pro Gln Leu
    50                  55                  60

Glu Gln Pro Tyr Val Phe Ile Lys Arg Ser Asp Ala Arg Thr Ala Pro
65                  70                  75                  80

His Gly His Val Met Val Glu Leu Val Ala Glu Leu Glu Gly Ile Gln
                85                  90                  95

Tyr Gly Arg Ser Gly Glu Thr Leu Gly Val Leu Val Pro His Val Gly
            100                 105                 110

Glu Ile Pro Val Ala Tyr Arg Lys Val Leu Leu Arg Lys Asn Gly Asn
        115                 120                 125

Lys Gly Ala Gly Gly His Ser Tyr Gly Ala Asp Leu Lys Ser Phe Asp
    130                 135                 140

Leu Gly Asp Glu Leu Gly Thr Asp Pro Tyr Glu Asp Phe Gln Glu Asn
145                 150                 155                 160

Trp Asn Thr Lys His Ser Ser Gly Val Thr Arg Glu Leu Met Arg Glu
                165                 170                 175

Leu Asn Gly Gly Ala Tyr Thr Arg Tyr Val Asp Asn Asn Phe Cys Gly
            180                 185                 190

Pro Asp Gly Tyr Pro Leu Glu Cys Ile Lys Asp Leu Leu Ala Arg Ala
        195                 200                 205

Gly Lys Ala Ser Cys Thr Leu Ser Glu Gln Leu Asp Phe Ile Asp Thr
    210                 215                 220

Lys Arg Gly Val Tyr Cys Cys Arg Glu His Glu His Glu Ile Ala Trp
225                 230                 235                 240

Tyr Thr Glu Arg Ser Glu Lys Ser Tyr Glu Leu Gln Thr Pro Phe Glu
                245                 250                 255

Ile Lys Leu Ala Lys Lys Phe Asp Thr Phe Asn Gly Glu Cys Pro Asn
            260                 265                 270

Phe Val Phe Pro Leu Asn Ser Ile Ile Lys Thr Ile Gln Pro Arg Val
        275                 280                 285

Glu Lys Lys Lys Leu Asp Gly Phe Met Gly Arg Ile Arg Ser Val Tyr
    290                 295                 300

Pro Val Ala Ser Pro Asn Glu Cys Asn Gln Met Cys Leu Ser Thr Leu
305                 310                 315                 320

Met Lys Cys Asp His Cys Gly Glu Thr Ser Trp Gln Thr Gly Asp Phe
                325                 330                 335

Val Lys Ala Thr Cys Glu Phe Cys Gly Thr Glu Asn Leu Thr Lys Glu
            340                 345                 350

Gly Ala Thr Thr Cys Gly Tyr Leu Pro Gln Asn Ala Val Val Lys Ile
        355                 360                 365

Tyr Cys Pro Ala Cys His Asn Ser Glu Val Gly Pro Glu His Ser Leu
    370                 375                 380

Ala Glu Tyr His Asn Glu Ser Gly Leu Lys Thr Ile Leu Arg Lys Gly
385                 390                 395                 400

Gly Arg Thr Ile Ala Phe Gly Gly Cys Val Phe Ser Tyr Val Gly Cys
                405                 410                 415

His Asn Lys Cys Ala Tyr Trp Val Pro Arg Ala Ser Ala Asn Ile Gly
            420                 425                 430
```

-continued

```
Cys Asn His Thr Gly Val Val Gly Glu Gly Ser Glu Gly Leu Asn Asp
        435                 440                 445

Asn Leu Leu Glu Ile Leu Gln Lys Glu Lys Val Asn Ile Asn Ile Val
    450                 455                 460

Gly Asp Phe Lys Leu Asn Glu Glu Ile Ala Ile Ile Leu Ala Ser Phe
465                 470                 475                 480

Ser Ala Ser Thr Ser Ala Phe Val Glu Thr Val Lys Gly Leu Asp Tyr
                485                 490                 495

Lys Ala Phe Lys Gln Ile Val Glu Ser Cys Gly Asn Phe Lys Val Thr
            500                 505                 510

Lys Gly Lys Ala Lys Lys Gly Ala Trp Asn Ile Gly Glu Gln Lys Ser
        515                 520                 525

Ile Leu Ser Pro Leu Tyr Ala Phe Ala Ser Glu Ala Ala Arg Val Val
    530                 535                 540

Arg Ser Ile Phe Ser Arg Thr Leu Glu Thr Ala Gln Asn Ser Val Arg
545                 550                 555                 560

Val Leu Gln Lys Ala Ala Ile Thr Ile Leu Asp Gly Ile Ser Gln Tyr
                565                 570                 575

Ser Leu Arg Leu Ile Asp Ala Met Met Phe Thr Ser Asp Leu Ala Thr
            580                 585                 590

Asn Asn Leu Val Val Met Ala Tyr Ile Thr Gly Gly Val Val Gln Leu
        595                 600                 605

Thr Ser Gln Trp Leu Thr Asn Ile Phe Gly Thr Val Tyr Glu Lys Leu
    610                 615                 620

Lys Pro Val Leu Asp Trp Leu Glu Glu Lys Phe Lys Glu Gly Val Glu
625                 630                 635                 640

Phe Leu Arg Asp Gly Trp Glu Ile Val Lys Phe Ile Ser Thr Cys Ala
                645                 650                 655

Cys Glu Ile Val Gly Gly Gln Ile Val Thr Cys Ala Lys Glu Ile Lys
            660                 665                 670

Glu Ser Val Gln Thr Phe Phe Lys Leu Val Asn Lys Phe Leu Ala Leu
        675                 680                 685

Cys Ala Asp Ser Ile Ile Ile Gly Gly Ala Lys Leu Lys Ala Leu Asn
    690                 695                 700

Leu Gly Glu Thr Phe Val Thr His Ser Lys Gly Leu Tyr Arg Lys Cys
705                 710                 715                 720

Val Lys Ser Arg Glu Glu Thr Gly Leu Leu Met Pro Leu Lys Ala Pro
                725                 730                 735

Lys Glu Ile Ile Phe Leu Glu Gly Glu Thr Leu Pro Thr Glu Val Leu
            740                 745                 750

Thr Glu Glu Val Val Leu Lys Thr Gly Asp Leu Gln Pro Leu Glu Gln
        755                 760                 765

Pro Thr Ser Glu Ala Val Glu Ala Pro Leu Val Gly Thr Pro Val Cys
    770                 775                 780

Ile Asn Gly Leu Met Leu Leu Glu Ile Lys Asp Thr Glu Lys Tyr Cys
785                 790                 795                 800

Ala Leu Ala Pro Asn Met Met Val Thr Asn Asn Thr Phe Thr Leu Lys
                805                 810                 815

Gly Gly Ala Pro Thr Lys Val Thr Phe Gly Asp Asp Thr Val Ile Glu
            820                 825                 830

Val Gln Gly Tyr Lys Ser Val Asn Ile Thr Phe Glu Leu Asp Glu Arg
        835                 840                 845

Ile Asp Lys Val Leu Asn Glu Lys Cys Ser Ala Tyr Thr Val Glu Leu
```

```
    850                 855                 860

Gly Thr Glu Val Asn Glu Phe Ala Cys Val Val Ala Asp Ala Val Ile
865                 870                 875                 880

Lys Thr Leu Gln Pro Val Ser Glu Leu Leu Thr Pro Leu Gly Ile Asp
                885                 890                 895

Leu Asp Glu Trp Ser Met Ala Thr Tyr Tyr Leu Phe Asp Glu Ser Gly
            900                 905                 910

Glu Phe Lys Leu Ala Ser His Met Tyr Cys Ser Phe Tyr Pro Pro Asp
        915                 920                 925

Glu Asp Glu Glu Glu Gly Asp Cys Glu Glu Glu Glu Phe Glu Pro Ser
    930                 935                 940

Thr Gln Tyr Glu Tyr Gly Thr Glu Asp Asp Tyr Gln Gly Lys Pro Leu
945                 950                 955                 960

Glu Phe Gly Ala Thr Ser Ala Ala Leu Gln Pro Glu Glu Glu Gln Glu
                965                 970                 975

Glu Asp Trp Leu Asp Asp Asp Ser Gln Gln Thr Val Gly Gln Gln Asp
            980                 985                 990

Gly Ser Glu Asp Asn Gln Thr Thr  Thr Ile Gln Thr Ile  Val Glu Val
        995                 1000                1005

Gln Pro  Gln Leu Glu Met Glu  Leu Thr Pro Val Val  Gln Thr Ile
    1010                 1015                 1020

Glu Val  Asn Ser Phe Ser Gly  Tyr Leu Lys Leu Thr  Asp Asn Val
    1025                 1030                 1035

Tyr Ile  Lys Asn Ala Asp Ile  Val Glu Glu Ala Lys  Lys Val Lys
    1040                 1045                 1050

Pro Thr  Val Val Val Asn Ala  Ala Asn Val Tyr Leu  Lys His Gly
    1055                 1060                 1065

Gly Gly  Val Ala Gly Ala Leu  Asn Lys Ala Thr Asn  Asn Ala Met
    1070                 1075                 1080

Gln Val  Glu Ser Asp Asp Tyr  Ile Ala Thr Asn Gly  Pro Leu Lys
    1085                 1090                 1095

Val Gly  Gly Ser Cys Val Leu  Ser Gly His Asn Leu  Ala Lys His
    1100                 1105                 1110

Cys Leu  His Val Val Gly Pro  Asn Val Asn Lys Gly  Glu Asp Ile
    1115                 1120                 1125

Gln Leu  Leu Lys Ser Ala Tyr  Glu Asn Phe Asn Gln  His Glu Val
    1130                 1135                 1140

Leu Leu  Ala Pro Leu Leu Ser  Ala Gly Ile Phe Gly  Ala Asp Pro
    1145                 1150                 1155

Ile His  Ser Leu Arg Val Cys  Val Asp Thr Val Arg  Thr Asn Val
    1160                 1165                 1170

Tyr Leu  Ala Val Phe Asp Lys  Asn Leu Tyr Asp Lys  Leu Val Ser
    1175                 1180                 1185

Ser Phe  Leu Glu Met Lys Ser  Glu Lys Gln Val Glu  Gln Lys Ile
    1190                 1195                 1200

Ala Glu  Ile Pro Lys Glu Glu  Val Lys Pro Phe Ile  Thr Glu Ser
    1205                 1210                 1215

Lys Pro  Ser Val Glu Gln Arg  Lys Gln Asp Asp Lys  Lys Ile Lys
    1220                 1225                 1230

Ala Cys  Val Glu Glu Val Thr  Thr Thr Leu Glu Glu  Thr Lys Phe
    1235                 1240                 1245

Leu Thr  Glu Asn Leu Leu Leu  Tyr Ile Asp Ile Asn  Gly Asn Leu
    1250                 1255                 1260
```

```
His Pro  Asp Ser Ala Thr Leu  Val Ser Asp Ile Asp  Ile Thr Phe
    1265                 1270                 1275

Leu Lys  Lys Asp Ala Pro Tyr  Ile Val Gly Asp Val  Val Gln Glu
    1280                 1285                 1290

Gly Val  Leu Thr Ala Val Val  Ile Pro Thr Lys Lys  Ala Gly Gly
    1295                 1300                 1305

Thr Thr  Glu Met Leu Ala Lys  Ala Leu Arg Lys Val  Pro Thr Asp
    1310                 1315                 1320

Asn Tyr  Ile Thr Thr Tyr Pro  Gly Gln Gly Leu Asn  Gly Tyr Thr
    1325                 1330                 1335

Val Glu  Glu Ala Lys Thr Val  Leu Lys Lys Cys Lys  Ser Ala Phe
    1340                 1345                 1350

Tyr Ile  Leu Pro Ser Ile Ile  Ser Asn Glu Lys Gln  Glu Ile Leu
    1355                 1360                 1365

Gly Thr  Val Ser Trp Asn Leu  Arg Glu Met Leu Ala  His Ala Glu
    1370                 1375                 1380

Glu Thr  Arg Lys Leu Met Pro  Val Cys Val Glu Thr  Lys Ala Ile
    1385                 1390                 1395

Val Ser  Thr Ile Gln Arg Lys  Tyr Lys Gly Ile Lys  Ile Gln Glu
    1400                 1405                 1410

Gly Val  Val Asp Tyr Gly Ala  Arg Phe Tyr Phe Tyr  Thr Ser Lys
    1415                 1420                 1425

Thr Thr  Val Ala Ser Leu Ile  Asn Thr Leu Asn Asp  Leu Asn Glu
    1430                 1435                 1440

Thr Leu  Val Thr Met Pro Leu  Gly Tyr Val Thr His  Gly Leu Asn
    1445                 1450                 1455

Leu Glu  Glu Ala Ala Arg Tyr  Met Arg Ser Leu Lys  Val Pro Ala
    1460                 1465                 1470

Thr Val  Ser Val Ser Ser Pro  Asp Ala Val Thr Ala  Tyr Asn Gly
    1475                 1480                 1485

Tyr Leu  Thr Ser Ser Ser Lys  Thr Pro Glu Glu His  Phe Ile Glu
    1490                 1495                 1500

Thr Ile  Ser Leu Ala Gly Ser  Tyr Lys Asp Trp Ser  Tyr Ser Gly
    1505                 1510                 1515

Gln Ser  Thr Gln Leu Gly Ile  Glu Phe Leu Lys Arg  Gly Asp Lys
    1520                 1525                 1530

Ser Val  Tyr Tyr Thr Ser Asn  Pro Thr Thr Phe His  Leu Asp Gly
    1535                 1540                 1545

Glu Val  Ile Thr Phe Asp Asn  Leu Lys Thr Leu Leu  Ser Leu Arg
    1550                 1555                 1560

Glu Val  Arg Thr Ile Lys Val  Phe Thr Thr Val Asp  Asn Ile Asn
    1565                 1570                 1575

Leu His  Thr Gln Val Val Asp  Met Ser Met Thr Tyr  Gly Gln Gln
    1580                 1585                 1590

Phe Gly  Pro Thr Tyr Leu Asp  Gly Ala Asp Val Thr  Lys Ile Lys
    1595                 1600                 1605

Pro His  Asn Ser His Glu Gly  Lys Thr Phe Tyr Val  Leu Pro Asn
    1610                 1615                 1620

Asp Asp  Thr Leu Arg Val Glu  Ala Phe Glu Tyr Tyr  His Thr Thr
    1625                 1630                 1635

Asp Pro  Ser Phe Leu Gly Arg  Tyr Met Ser Ala Leu  Asn His Thr
    1640                 1645                 1650
```

-continued

```
Lys Lys  Trp Lys Tyr Pro Gln  Val Asn Gly Leu Thr  Ser Ile Lys
    1655                 1660                 1665

Trp Ala  Asp Asn Asn Cys Tyr  Leu Ala Thr Ala Leu  Leu Thr Leu
    1670                 1675                 1680

Gln Gln  Ile Glu Leu Lys Phe  Asn Pro Pro Ala Leu  Gln Asp Ala
    1685                 1690                 1695

Tyr Tyr  Arg Ala Arg Ala Gly  Glu Ala Ala Asn Phe  Cys Ala Leu
    1700                 1705                 1710

Ile Leu  Ala Tyr Cys Asn Lys  Thr Val Gly Glu Leu  Gly Asp Val
    1715                 1720                 1725

Arg Glu  Thr Met Ser Tyr Leu  Phe Gln His Ala Asn  Leu Asp Ser
    1730                 1735                 1740

Cys Lys  Arg Val Leu Asn Val  Val Cys Lys Thr Cys  Gly Gln Gln
    1745                 1750                 1755

Gln Thr  Thr Leu Lys Gly Val  Glu Ala Val Met Tyr  Met Gly Thr
    1760                 1765                 1770

Leu Ser  Tyr Glu Gln Phe Lys  Lys Gly Val Gln Ile  Pro Cys Thr
    1775                 1780                 1785

Cys Gly  Lys Gln Ala Thr Lys  Tyr Leu Val Gln Gln  Glu Ser Pro
    1790                 1795                 1800

Phe Val  Met Met Ser Ala Pro  Pro Ala Gln Tyr Glu  Leu Lys His
    1805                 1810                 1815

Gly Thr  Phe Thr Cys Ala Ser  Glu Tyr Thr Gly Asn  Tyr Gln Cys
    1820                 1825                 1830

Gly His  Tyr Lys His Ile Thr  Ser Lys Glu Thr Leu  Tyr Cys Ile
    1835                 1840                 1845

Asp Gly  Ala Leu Leu Thr Lys  Ser Ser Glu Tyr Lys  Gly Pro Ile
    1850                 1855                 1860

Thr Asp  Val Phe Tyr Lys Glu  Asn Ser Tyr Thr Thr  Thr Ile Lys
    1865                 1870                 1875

Pro Val  Thr Tyr Lys Leu Asp  Gly Val Val Cys Thr  Glu Ile Asp
    1880                 1885                 1890

Pro Lys  Leu Asp Asn Tyr Tyr  Lys Lys Asp Asn Ser  Tyr Phe Thr
    1895                 1900                 1905

Glu Gln  Pro Ile Asp Leu Val  Pro Asn Gln Pro Tyr  Pro Asn Ala
    1910                 1915                 1920

Ser Phe  Asp Asn Phe Lys Phe  Val Cys Asp Asn Ile  Lys Phe Ala
    1925                 1930                 1935

Asp Asp  Leu Asn Gln Leu Thr  Gly Tyr Lys Lys Pro  Ala Ser Arg
    1940                 1945                 1950

Glu Leu  Lys Val Thr Phe Phe  Pro Asp Leu Asn Gly  Asp Val Val
    1955                 1960                 1965

Ala Ile  Asp Tyr Lys His Tyr  Thr Pro Ser Phe Lys  Lys Gly Ala
    1970                 1975                 1980

Lys Leu  Leu His Lys Pro Ile  Val Trp His Val Asn  Asn Ala Thr
    1985                 1990                 1995

Asn Lys  Ala Thr Tyr Lys Pro  Asn Thr Trp Cys Ile  Arg Cys Leu
    2000                 2005                 2010

Trp Ser  Thr Lys Pro Val Glu  Thr Ser Asn Ser Phe  Asp Val Leu
    2015                 2020                 2025

Lys Ser  Glu Asp Ala Gln Gly  Met Asp Asn Leu Ala  Cys Glu Asp
    2030                 2035                 2040

Leu Lys  Pro Val Ser Glu Glu  Val Val Glu Asn Pro  Thr Ile Gln
```

2045 2050 2055

Lys Asp Val Leu Glu Cys Asn Val Lys Thr Thr Glu Val Val Gly
2060 2065 2070

Asp Ile Ile Leu Lys Pro Ala Asn Asn Ser Leu Lys Ile Thr Glu
2075 2080 2085

Glu Val Gly His Thr Asp Leu Met Ala Ala Tyr Val Asp Asn Ser
2090 2095 2100

Ser Leu Thr Ile Lys Lys Pro Asn Glu Leu Ser Arg Val Leu Gly
2105 2110 2115

Leu Lys Thr Leu Ala Thr His Gly Leu Ala Ala Val Asn Ser Val
2120 2125 2130

Pro Trp Asp Thr Ile Ala Asn Tyr Ala Lys Pro Phe Leu Asn Lys
2135 2140 2145

Val Val Ser Thr Thr Thr Asn Ile Val Thr Arg Cys Leu Asn Arg
2150 2155 2160

Val Cys Thr Asn Tyr Met Pro Tyr Phe Phe Thr Leu Leu Leu Gln
2165 2170 2175

Leu Cys Thr Phe Thr Arg Ser Thr Asn Ser Arg Ile Lys Ala Ser
2180 2185 2190

Met Pro Thr Thr Ile Ala Lys Asn Thr Val Lys Ser Val Gly Lys
2195 2200 2205

Phe Cys Leu Glu Ala Ser Phe Asn Tyr Leu Lys Ser Pro Asn Phe
2210 2215 2220

Ser Lys Leu Ile Asn Ile Ile Ile Trp Phe Leu Leu Leu Ser Val
2225 2230 2235

Cys Leu Gly Ser Leu Ile Tyr Ser Thr Ala Ala Leu Gly Val Leu
2240 2245 2250

Met Ser Asn Leu Gly Met Pro Ser Tyr Cys Thr Gly Tyr Arg Glu
2255 2260 2265

Gly Tyr Leu Asn Ser Thr Asn Val Thr Ile Ala Thr Tyr Cys Thr
2270 2275 2280

Gly Ser Ile Pro Cys Ser Val Cys Leu Ser Gly Leu Asp Ser Leu
2285 2290 2295

Asp Thr Tyr Pro Ser Leu Glu Thr Ile Gln Ile Thr Ile Ser Ser
2300 2305 2310

Phe Lys Trp Asp Leu Thr Ala Phe Gly Leu Val Ala Glu Trp Phe
2315 2320 2325

Leu Ala Tyr Ile Leu Phe Thr Arg Phe Phe Tyr Val Leu Gly Leu
2330 2335 2340

Ala Ala Ile Met Gln Leu Phe Phe Ser Tyr Phe Ala Val His Phe
2345 2350 2355

Ile Ser Asn Ser Trp Leu Met Trp Leu Ile Ile Asn Leu Val Gln
2360 2365 2370

Met Ala Pro Ile Ser Ala Met Val Arg Met Tyr Ile Phe Phe Ala
2375 2380 2385

Ser Phe Tyr Tyr Val Trp Lys Ser Tyr Val His Val Val Asp Gly
2390 2395 2400

Cys Asn Ser Ser Thr Cys Met Met Cys Tyr Lys Arg Asn Arg Ala
2405 2410 2415

Thr Arg Val Glu Cys Thr Thr Ile Val Asn Gly Val Arg Arg Ser
2420 2425 2430

Phe Tyr Val Tyr Ala Asn Gly Gly Lys Gly Phe Cys Lys Leu His
2435 2440 2445

```
Asn Trp  Asn Cys Val Asn Cys  Asp Thr Phe Cys Ala  Gly Ser Thr
    2450                 2455                 2460

Phe Ile  Ser Asp Glu Val Ala  Arg Asp Leu Ser Leu  Gln Phe Lys
    2465                 2470                 2475

Arg Pro  Ile Asn Pro Thr Asp  Gln Ser Ser Tyr Ile  Val Asp Ser
    2480                 2485                 2490

Val Thr  Val Lys Asn Gly Ser  Ile His Leu Tyr Phe  Asp Lys Ala
    2495                 2500                 2505

Gly Gln  Lys Thr Tyr Glu Arg  His Ser Leu Ser His  Phe Val Asn
    2510                 2515                 2520

Leu Asp  Asn Leu Arg Ala Asn  Asn Thr Lys Gly Ser  Leu Pro Ile
    2525                 2530                 2535

Asn Val  Ile Val Phe Asp Gly  Lys Ser Lys Cys Glu  Glu Ser Ser
    2540                 2545                 2550

Ala Lys  Ser Ala Ser Val Tyr  Tyr Ser Gln Leu Met  Cys Gln Pro
    2555                 2560                 2565

Ile Leu  Leu Leu Asp Gln Ala  Leu Val Ser Asp Val  Gly Asp Ser
    2570                 2575                 2580

Ala Glu  Val Ala Val Lys Met  Phe Asp Ala Tyr Val  Asn Thr Phe
    2585                 2590                 2595

Ser Ser  Thr Phe Asn Val Pro  Met Glu Lys Leu Lys  Thr Leu Val
    2600                 2605                 2610

Ala Thr  Ala Glu Ala Glu Leu  Ala Lys Asn Val Ser  Leu Asp Asn
    2615                 2620                 2625

Val Leu  Ser Thr Phe Ile Ser  Ala Ala Arg Gln Gly  Phe Val Asp
    2630                 2635                 2640

Ser Asp  Val Glu Thr Lys Asp  Val Val Glu Cys Leu  Lys Leu Ser
    2645                 2650                 2655

His Gln  Ser Asp Ile Glu Val  Thr Gly Asp Ser Cys  Asn Asn Tyr
    2660                 2665                 2670

Met Leu  Thr Tyr Asn Lys Val  Glu Asn Met Thr Pro  Arg Asp Leu
    2675                 2680                 2685

Gly Ala  Cys Ile Asp Cys Ser  Ala Arg His Ile Asn  Ala Gln Val
    2690                 2695                 2700

Ala Lys  Ser His Asn Ile Ala  Leu Ile Trp Asn Val  Lys Asp Phe
    2705                 2710                 2715

Met Ser  Leu Ser Glu Gln Leu  Arg Lys Gln Ile Arg  Ser Ala Ala
    2720                 2725                 2730

Lys Lys  Asn Asn Leu Pro Phe  Lys Leu Thr Cys Ala  Thr Thr Arg
    2735                 2740                 2745

Gln Val  Val Asn Val Val Thr  Thr Lys Ile Ala Leu  Lys Gly Gly
    2750                 2755                 2760

Lys Ile  Val Asn Asn Trp Leu  Lys Gln Leu Ile Lys  Val Thr Leu
    2765                 2770                 2775

Val Phe  Leu Phe Val Ala Ala  Ile Phe Tyr Leu Ile  Thr Pro Val
    2780                 2785                 2790

His Val  Met Ser Lys His Thr  Asp Phe Ser Ser Glu  Ile Ile Gly
    2795                 2800                 2805

Tyr Lys  Ala Ile Asp Gly Gly  Val Thr Arg Asp Ile  Ala Ser Thr
    2810                 2815                 2820

Asp Thr  Cys Phe Ala Asn Lys  His Ala Asp Phe Asp  Thr Trp Phe
    2825                 2830                 2835
```

```
Ser Gln  Arg Gly Gly Ser Tyr  Thr Asn Asp Lys Ala  Cys Pro Leu
    2840                 2845                 2850

Ile Ala  Ala Val Ile Thr Arg  Glu Val Gly Phe Val  Val Pro Gly
    2855                 2860                 2865

Leu Pro  Gly Thr Ile Leu Arg  Thr Thr Asn Gly Asp  Phe Leu His
    2870                 2875                 2880

Phe Leu  Pro Arg Val Phe Ser  Ala Val Gly Asn Ile  Cys Tyr Thr
    2885                 2890                 2895

Pro Ser  Lys Leu Ile Glu Tyr  Thr Asp Phe Ala Thr  Ser Ala Cys
    2900                 2905                 2910

Val Leu  Ala Ala Glu Cys Thr  Ile Phe Lys Asp Ala  Ser Gly Lys
    2915                 2920                 2925

Pro Val  Pro Tyr Cys Tyr Asp  Thr Asn Val Leu Glu  Gly Ser Val
    2930                 2935                 2940

Ala Tyr  Glu Ser Leu Arg Pro  Asp Thr Arg Tyr Val  Leu Met Asp
    2945                 2950                 2955

Gly Ser  Ile Ile Gln Phe Pro  Asn Thr Tyr Leu Glu  Gly Ser Val
    2960                 2965                 2970

Arg Val  Val Thr Thr Phe Asp  Ser Glu Tyr Cys Arg  His Gly Thr
    2975                 2980                 2985

Cys Glu  Arg Ser Glu Ala Gly  Val Cys Val Ser Thr  Ser Gly Arg
    2990                 2995                 3000

Trp Val  Leu Asn Asn Asp Tyr  Tyr Arg Ser Leu Pro  Gly Val Phe
    3005                 3010                 3015

Cys Gly  Val Asp Ala Val Asn  Leu Leu Thr Asn Met  Phe Thr Pro
    3020                 3025                 3030

Leu Ile  Gln Pro Ile Gly Ala  Leu Asp Ile Ser Ala  Ser Ile Val
    3035                 3040                 3045

Ala Gly  Gly Ile Val Ala Ile  Val Val Thr Cys Leu  Ala Tyr Tyr
    3050                 3055                 3060

Phe Met  Arg Phe Arg Arg Ala  Phe Gly Glu Tyr Ser  His Val Val
    3065                 3070                 3075

Ala Phe  Asn Thr Leu Leu Phe  Leu Met Ser Phe Thr  Val Leu Cys
    3080                 3085                 3090

Leu Thr  Pro Val Tyr Ser Phe  Leu Pro Gly Val Tyr  Ser Val Ile
    3095                 3100                 3105

Tyr Leu  Tyr Leu Thr Phe Tyr  Leu Thr Asn Asp Val  Ser Phe Leu
    3110                 3115                 3120

Ala His  Ile Gln Trp Met Val  Met Phe Thr Pro Leu  Val Pro Phe
    3125                 3130                 3135

Trp Ile  Thr Ile Ala Tyr Ile  Ile Cys Ile Ser Thr  Lys His Phe
    3140                 3145                 3150

Tyr Trp  Phe Phe Ser Asn Tyr  Leu Lys Arg Arg Val  Val Phe Asn
    3155                 3160                 3165

Gly Val  Ser Phe Ser Thr Phe  Glu Glu Ala Ala Leu  Cys Thr Phe
    3170                 3175                 3180

Leu Leu  Asn Lys Glu Met Tyr  Leu Lys Leu Arg Ser  Asp Val Leu
    3185                 3190                 3195

Leu Pro  Leu Thr Gln Tyr Asn  Arg Tyr Leu Ala Leu  Tyr Asn Lys
    3200                 3205                 3210

Tyr Lys  Tyr Phe Ser Gly Ala  Met Asp Thr Thr Ser  Tyr Arg Glu
    3215                 3220                 3225

Ala Ala  Cys Cys His Leu Ala  Lys Ala Leu Asn Asp  Phe Ser Asn
```

```
    3230                3235                3240

Ser Gly Ser Asp Val Leu Tyr Gln Pro Pro Gln Thr Ser Ile Thr
    3245                3250                3255

Ser Ala Val Leu Gln Ser Gly Phe Arg Lys Met Ala Phe Pro Ser
    3260                3265                3270

Gly Lys Val Glu Gly Cys Met Val Gln Val Thr Cys Gly Thr Thr
    3275                3280                3285

Thr Leu Asn Gly Leu Trp Leu Asp Asp Val Val Tyr Cys Pro Arg
    3290                3295                3300

His Val Ile Cys Thr Ser Glu Asp Met Leu Asn Pro Asn Tyr Glu
    3305                3310                3315

Asp Leu Leu Ile Arg Lys Ser Asn His Asn Phe Leu Val Gln Ala
    3320                3325                3330

Gly Asn Val Gln Leu Arg Val Ile Gly His Ser Met Gln Asn Cys
    3335                3340                3345

Val Leu Lys Leu Lys Val Asp Thr Ala Asn Pro Lys Thr Pro Lys
    3350                3355                3360

Tyr Lys Phe Val Arg Ile Gln Pro Gly Gln Thr Phe Ser Val Leu
    3365                3370                3375

Ala Cys Tyr Asn Gly Ser Pro Ser Gly Val Tyr Gln Cys Ala Met
    3380                3385                3390

Arg Pro Asn Phe Thr Ile Lys Gly Ser Phe Leu Asn Gly Ser Cys
    3395                3400                3405

Gly Ser Val Gly Phe Asn Ile Asp Tyr Asp Cys Val Ser Phe Cys
    3410                3415                3420

Tyr Met His His Met Glu Leu Pro Thr Gly Val His Ala Gly Thr
    3425                3430                3435

Asp Leu Glu Gly Asn Phe Tyr Gly Pro Phe Val Asp Arg Gln Thr
    3440                3445                3450

Ala Gln Ala Ala Gly Thr Asp Thr Thr Ile Thr Val Asn Val Leu
    3455                3460                3465

Ala Trp Leu Tyr Ala Ala Val Ile Asn Gly Asp Arg Trp Phe Leu
    3470                3475                3480

Asn Arg Phe Thr Thr Thr Leu Asn Asp Phe Asn Leu Val Ala Met
    3485                3490                3495

Lys Tyr Asn Tyr Glu Pro Leu Thr Gln Asp His Val Asp Ile Leu
    3500                3505                3510

Gly Pro Leu Ser Ala Gln Thr Gly Ile Ala Val Leu Asp Met Cys
    3515                3520                3525

Ala Ser Leu Lys Glu Leu Leu Gln Asn Gly Met Asn Gly Arg Thr
    3530                3535                3540

Ile Leu Gly Ser Ala Leu Leu Glu Asp Glu Phe Thr Pro Phe Asp
    3545                3550                3555

Val Val Arg Gln Cys Ser Gly Val Thr Phe Gln Ser Ala Val Lys
    3560                3565                3570

Arg Thr Ile Lys Gly Thr His His Trp Leu Leu Leu Thr Ile Leu
    3575                3580                3585

Thr Ser Leu Leu Val Leu Val Gln Ser Thr Gln Trp Ser Leu Phe
    3590                3595                3600

Phe Phe Leu Tyr Glu Asn Ala Phe Leu Pro Phe Ala Met Gly Ile
    3605                3610                3615

Ile Ala Met Ser Ala Phe Ala Met Met Phe Val Lys His Lys His
    3620                3625                3630
```

-continued

```
Ala Phe  Leu Cys Leu Phe Leu  Leu Pro Ser Leu Ala  Thr Val Ala
    3635                 3640                 3645

Tyr Phe  Asn Met Val Tyr Met  Pro Ala Ser Trp Val  Met Arg Ile
    3650                 3655                 3660

Met Thr  Trp Leu Asp Met Val  Asp Thr Ser Leu Ser  Gly Phe Lys
    3665                 3670                 3675

Leu Lys  Asp Cys Val Met Tyr  Ala Ser Ala Val Val  Leu Leu Ile
    3680                 3685                 3690

Leu Met  Thr Ala Arg Thr Val  Tyr Asp Asp Gly Ala  Arg Arg Val
    3695                 3700                 3705

Trp Thr  Leu Met Asn Val Leu  Thr Leu Val Tyr Lys  Val Tyr Tyr
    3710                 3715                 3720

Gly Asn  Ala Leu Asp Gln Ala  Ile Ser Met Trp Ala  Leu Ile Ile
    3725                 3730                 3735

Ser Val  Thr Ser Asn Tyr Ser  Gly Val Val Thr Thr  Val Met Phe
    3740                 3745                 3750

Leu Ala  Arg Gly Ile Val Phe  Met Cys Val Glu Tyr  Cys Pro Ile
    3755                 3760                 3765

Phe Phe  Ile Thr Gly Asn Thr  Leu Gln Cys Ile Met  Leu Val Tyr
    3770                 3775                 3780

Cys Phe  Leu Gly Tyr Phe Cys  Thr Cys Tyr Phe Gly  Leu Phe Cys
    3785                 3790                 3795

Leu Leu  Asn Arg Tyr Phe Arg  Leu Thr Leu Gly Val  Tyr Asp Tyr
    3800                 3805                 3810

Leu Val  Ser Thr Gln Glu Phe  Arg Tyr Met Asn Ser  Gln Gly Leu
    3815                 3820                 3825

Leu Pro  Pro Lys Asn Ser Ile  Asp Ala Phe Lys Leu  Asn Ile Lys
    3830                 3835                 3840

Leu Leu  Gly Val Gly Gly Lys  Pro Cys Ile Lys Val  Ala Thr Val
    3845                 3850                 3855

Gln Ser  Lys Met Ser Asp Val  Lys Cys Thr Ser Val  Val Leu Leu
    3860                 3865                 3870

Ser Val  Leu Gln Gln Leu Arg  Val Glu Ser Ser Ser  Lys Leu Trp
    3875                 3880                 3885

Ala Gln  Cys Val Gln Leu His  Asn Asp Ile Leu Leu  Ala Lys Asp
    3890                 3895                 3900

Thr Thr  Glu Ala Phe Glu Lys  Met Val Ser Leu Leu  Ser Val Leu
    3905                 3910                 3915

Leu Ser  Met Gln Gly Ala Val  Asp Ile Asn Lys Leu  Cys Glu Glu
    3920                 3925                 3930

Met Leu  Asp Asn Arg Ala Thr  Leu Gln Ala Ile Ala  Ser Glu Phe
    3935                 3940                 3945

Ser Ser  Leu Pro Ser Tyr Ala  Ala Phe Ala Thr Ala  Gln Glu Ala
    3950                 3955                 3960

Tyr Glu  Gln Ala Val Ala Asn  Gly Asp Ser Glu Val  Val Leu Lys
    3965                 3970                 3975

Lys Leu  Lys Lys Ser Leu Asn  Val Ala Lys Ser Glu  Phe Asp Arg
    3980                 3985                 3990

Asp Ala  Ala Met Gln Arg Lys  Leu Glu Lys Met Ala  Asp Gln Ala
    3995                 4000                 4005

Met Thr  Gln Met Tyr Lys Gln  Ala Arg Ser Glu Asp  Lys Arg Ala
    4010                 4015                 4020
```

-continued

Lys Val Thr Ser Ala Met Gln Thr Met Leu Phe Thr Met Leu Arg
4025 4030 4035

Lys Leu Asp Asn Asp Ala Leu Asn Asn Ile Ile Asn Asn Ala Arg
4040 4045 4050

Asp Gly Cys Val Pro Leu Asn Ile Ile Pro Leu Thr Thr Ala Ala
4055 4060 4065

Lys Leu Met Val Val Ile Pro Asp Tyr Asn Thr Tyr Lys Asn Thr
4070 4075 4080

Cys Asp Gly Thr Thr Phe Thr Tyr Ala Ser Ala Leu Trp Glu Ile
4085 4090 4095

Gln Gln Val Val Asp Ala Asp Ser Lys Ile Val Gln Leu Ser Glu
4100 4105 4110

Ile Ser Met Asp Asn Ser Pro Asn Leu Ala Trp Pro Leu Ile Val
4115 4120 4125

Thr Ala Leu Arg Ala Asn Ser Ala Val Lys Leu Gln Asn Asn Glu
4130 4135 4140

Leu Ser Pro Val Ala Leu Arg Gln Met Ser Cys Ala Ala Gly Thr
4145 4150 4155

Thr Gln Thr Ala Cys Thr Asp Asp Asn Ala Leu Ala Tyr Tyr Asn
4160 4165 4170

Thr Thr Lys Gly Gly Arg Phe Val Leu Ala Leu Leu Ser Asp Leu
4175 4180 4185

Gln Asp Leu Lys Trp Ala Arg Phe Pro Lys Ser Asp Gly Thr Gly
4190 4195 4200

Thr Ile Tyr Thr Glu Leu Glu Pro Pro Cys Arg Phe Val Thr Asp
4205 4210 4215

Thr Pro Lys Gly Pro Lys Val Lys Tyr Leu Tyr Phe Ile Lys Gly
4220 4225 4230

Leu Asn Asn Leu Asn Arg Gly Met Val Leu Gly Ser Leu Ala Ala
4235 4240 4245

Thr Val Arg Leu Gln Ala Gly Asn Ala Thr Glu Val Pro Ala Asn
4250 4255 4260

Ser Thr Val Leu Ser Phe Cys Ala Phe Ala Val Asp Ala Ala Lys
4265 4270 4275

Ala Tyr Lys Asp Tyr Leu Ala Ser Gly Gly Gln Pro Ile Thr Asn
4280 4285 4290

Cys Val Lys Met Leu Cys Thr His Thr Gly Thr Gly Gln Ala Ile
4295 4300 4305

Thr Val Thr Pro Glu Ala Asn Met Asp Gln Glu Ser Phe Gly Gly
4310 4315 4320

Ala Ser Cys Cys Leu Tyr Cys Arg Cys His Ile Asp His Pro Asn
4325 4330 4335

Pro Lys Gly Phe Cys Asp Leu Lys Gly Lys Tyr Val Gln Ile Pro
4340 4345 4350

Thr Thr Cys Ala Asn Asp Pro Val Gly Phe Thr Leu Lys Asn Thr
4355 4360 4365

Val Cys Thr Val Cys Gly Met Trp Lys Gly Tyr Gly Cys Ser Cys
4370 4375 4380

Asp Gln Leu Arg Glu Pro Met Leu Gln Ser Ala Asp Ala Gln Ser
4385 4390 4395

Phe Leu Asn Arg Val Cys Gly Val Ser Ala Ala Arg Leu Thr Pro
4400 4405 4410

Cys Gly Thr Gly Thr Ser Thr Asp Val Val Tyr Arg Ala Phe Asp

-continued

```
    4415                4420                4425

Ile Tyr  Asn Asp Lys Val Ala  Gly Phe Ala Lys Phe  Leu Lys Thr
    4430                4435                4440

Asn Cys  Cys Arg Phe Gln Glu  Lys Asp Glu Asp Asp  Asn Leu Ile
    4445                4450                4455

Asp Ser  Tyr Phe Val Val Lys  Arg His Thr Phe Ser  Asn Tyr Gln
    4460                4465                4470

His Glu  Glu Thr Ile Tyr Asn  Leu Leu Lys Asp Cys  Pro Ala Val
    4475                4480                4485

Ala Lys  His Asp Phe Phe Lys  Phe Arg Ile Asp Gly  Asp Met Val
    4490                4495                4500

Pro His  Ile Ser Arg Gln Arg  Leu Thr Lys Tyr Thr  Met Ala Asp
    4505                4510                4515

Leu Val  Tyr Ala Leu Arg His  Phe Asp Glu Gly Asn  Cys Asp Thr
    4520                4525                4530

Leu Lys  Glu Ile Leu Val Thr  Tyr Asn Cys Cys Asp  Asp Asp Tyr
    4535                4540                4545

Phe Asn  Lys Lys Asp Trp Tyr  Asp Phe Val Glu Asn  Pro Asp Ile
    4550                4555                4560

Leu Arg  Val Tyr Ala Asn Leu  Gly Glu Arg Val Arg  Gln Ala Leu
    4565                4570                4575

Leu Lys  Thr Val Gln Phe Cys  Asp Ala Met Arg Asn  Ala Gly Ile
    4580                4585                4590

Val Gly  Val Leu Thr Leu Asp  Asn Gln Asp Leu Asn  Gly Asn Trp
    4595                4600                4605

Tyr Asp  Phe Gly Asp Phe Ile  Gln Thr Thr Pro Gly  Ser Gly Val
    4610                4615                4620

Pro Val  Val Asp Ser Tyr Tyr  Ser Leu Leu Met Pro  Ile Leu Thr
    4625                4630                4635

Leu Thr  Arg Ala Leu Thr Ala  Glu Ser His Val Asp  Thr Asp Leu
    4640                4645                4650

Thr Lys  Pro Tyr Ile Lys Trp  Asp Leu Leu Lys Tyr  Asp Phe Thr
    4655                4660                4665

Glu Glu  Arg Leu Lys Leu Phe  Asp Arg Tyr Phe Lys  Tyr Trp Asp
    4670                4675                4680

Gln Thr  Tyr His Pro Asn Cys  Val Asn Cys Leu Asp  Asp Arg Cys
    4685                4690                4695

Ile Leu  His Cys Ala Asn Phe  Asn Val Leu Phe Ser  Thr Val Phe
    4700                4705                4710

Pro Pro  Thr Ser Phe Gly Pro  Leu Val Arg Lys Ile  Phe Val Asp
    4715                4720                4725

Gly Val  Pro Phe Val Val Ser  Thr Gly Tyr His Phe  Arg Glu Leu
    4730                4735                4740

Gly Val  Val His Asn Gln Asp  Val Asn Leu His Ser  Ser Arg Leu
    4745                4750                4755

Ser Phe  Lys Glu Leu Leu Val  Tyr Ala Ala Asp Pro  Ala Met His
    4760                4765                4770

Ala Ala  Ser Gly Asn Leu Leu  Leu Asp Lys Arg Thr  Thr Cys Phe
    4775                4780                4785

Ser Val  Ala Ala Leu Thr Asn  Asn Val Ala Phe Gln  Thr Val Lys
    4790                4795                4800

Pro Gly  Asn Phe Asn Lys Asp  Phe Tyr Asp Phe Ala  Val Ser Lys
    4805                4810                4815
```

```
Gly Phe Phe Lys Glu Gly Ser Ser Val Glu Leu Lys His Phe Phe
    4820                4825                4830

Phe Ala Gln Asp Gly Asn Ala Ala Ile Ser Asp Tyr Asp Tyr Tyr
    4835                4840                4845

Arg Tyr Asn Leu Pro Thr Met Cys Asp Ile Arg Gln Leu Leu Phe
    4850                4855                4860

Val Val Glu Val Val Asp Lys Tyr Phe Asp Cys Tyr Asp Gly Gly
    4865                4870                4875

Cys Ile Asn Ala Asn Gln Val Ile Val Asn Asn Leu Asp Lys Ser
    4880                4885                4890

Ala Gly Phe Pro Phe Asn Lys Trp Gly Lys Ala Arg Leu Tyr Tyr
    4895                4900                4905

Asp Ser Met Ser Tyr Glu Asp Gln Asp Ala Leu Phe Ala Tyr Thr
    4910                4915                4920

Lys Arg Asn Val Ile Pro Thr Ile Thr Gln Met Asn Leu Lys Tyr
    4925                4930                4935

Ala Ile Ser Ala Lys Asn Arg Ala Arg Thr Val Ala Gly Val Ser
    4940                4945                4950

Ile Cys Ser Thr Met Thr Asn Arg Gln Phe His Gln Lys Leu Leu
    4955                4960                4965

Lys Ser Ile Ala Ala Thr Arg Gly Ala Thr Val Val Ile Gly Thr
    4970                4975                4980

Ser Lys Phe Tyr Gly Gly Trp His Asn Met Leu Lys Thr Val Tyr
    4985                4990                4995

Ser Asp Val Glu Asn Pro His Leu Met Gly Trp Asp Tyr Pro Lys
    5000                5005                5010

Cys Asp Arg Ala Met Pro Asn Met Leu Arg Ile Met Ala Ser Leu
    5015                5020                5025

Val Leu Ala Arg Lys His Thr Thr Cys Cys Ser Leu Ser His Arg
    5030                5035                5040

Phe Tyr Arg Leu Ala Asn Glu Cys Ala Gln Val Leu Ser Glu Met
    5045                5050                5055

Val Met Cys Gly Gly Ser Leu Tyr Val Lys Pro Gly Gly Thr Ser
    5060                5065                5070

Ser Gly Asp Ala Thr Thr Ala Tyr Ala Asn Ser Val Phe Asn Ile
    5075                5080                5085

Cys Gln Ala Val Thr Ala Asn Val Asn Ala Leu Leu Ser Thr Asp
    5090                5095                5100

Gly Asn Lys Ile Ala Asp Lys Tyr Val Arg Asn Leu Gln His Arg
    5105                5110                5115

Leu Tyr Glu Cys Leu Tyr Arg Asn Arg Asp Val Asp Thr Asp Phe
    5120                5125                5130

Val Asn Glu Phe Tyr Ala Tyr Leu Arg Lys His Phe Ser Met Met
    5135                5140                5145

Ile Leu Ser Asp Asp Ala Val Val Cys Phe Asn Ser Thr Tyr Ala
    5150                5155                5160

Ser Gln Gly Leu Val Ala Ser Ile Lys Asn Phe Lys Ser Val Leu
    5165                5170                5175

Tyr Tyr Gln Asn Asn Val Phe Met Ser Glu Ala Lys Cys Trp Thr
    5180                5185                5190

Glu Thr Asp Leu Thr Lys Gly Pro His Glu Phe Cys Ser Gln His
    5195                5200                5205
```

```
Thr Met  Leu Val Lys Gln Gly  Asp Asp Tyr Val Tyr  Leu Pro Tyr
    5210                 5215                 5220

Pro Asp  Pro Ser Arg Ile Leu  Gly Ala Gly Cys Phe  Val Asp Asp
    5225                 5230                 5235

Ile Val  Lys Thr Asp Gly Thr  Leu Met Ile Glu Arg  Phe Val Ser
    5240                 5245                 5250

Leu Ala  Ile Asp Ala Tyr Pro  Leu Thr Lys His Pro  Asn Gln Glu
    5255                 5260                 5265

Tyr Ala  Asp Val Phe His Leu  Tyr Leu Gln Tyr Ile  Arg Lys Leu
    5270                 5275                 5280

His Asp  Glu Leu Thr Gly His  Met Leu Asp Met Tyr  Ser Val Met
    5285                 5290                 5295

Leu Thr  Asn Asp Asn Thr Ser  Arg Tyr Trp Glu Pro  Glu Phe Tyr
    5300                 5305                 5310

Glu Ala  Met Tyr Thr Pro His  Thr Val Leu Gln Ala  Val Gly Ala
    5315                 5320                 5325

Cys Val  Leu Cys Asn Ser Gln  Thr Ser Leu Arg Cys  Gly Ala Cys
    5330                 5335                 5340

Ile Arg  Arg Pro Phe Leu Cys  Cys Lys Cys Cys Tyr  Asp His Val
    5345                 5350                 5355

Ile Ser  Thr Ser His Lys Leu  Val Leu Ser Val Asn  Pro Tyr Val
    5360                 5365                 5370

Cys Asn  Ala Pro Gly Cys Asp  Val Thr Asp Val Thr  Gln Leu Tyr
    5375                 5380                 5385

Leu Gly  Gly Met Ser Tyr Tyr  Cys Lys Ser His Lys  Pro Pro Ile
    5390                 5395                 5400

Ser Phe  Pro Leu Cys Ala Asn  Gly Gln Val Phe Gly  Leu Tyr Lys
    5405                 5410                 5415

Asn Thr  Cys Val Gly Ser Asp  Asn Val Thr Asp Phe  Asn Ala Ile
    5420                 5425                 5430

Ala Thr  Cys Asp Trp Thr Asn  Ala Gly Asp Tyr Ile  Leu Ala Asn
    5435                 5440                 5445

Thr Cys  Thr Glu Arg Leu Lys  Leu Phe Ala Ala Glu  Thr Leu Lys
    5450                 5455                 5460

Ala Thr  Glu Glu Thr Phe Lys  Leu Ser Tyr Gly Ile  Ala Thr Val
    5465                 5470                 5475

Arg Glu  Val Leu Ser Asp Arg  Glu Leu His Leu Ser  Trp Glu Val
    5480                 5485                 5490

Gly Lys  Pro Arg Pro Pro Leu  Asn Arg Asn Tyr Val  Phe Thr Gly
    5495                 5500                 5505

Tyr Arg  Val Thr Lys Asn Ser  Lys Val Gln Ile Gly  Glu Tyr Thr
    5510                 5515                 5520

Phe Glu  Lys Gly Asp Tyr Gly  Asp Ala Val Val Tyr  Arg Gly Thr
    5525                 5530                 5535

Thr Thr  Tyr Lys Leu Asn Val  Gly Asp Tyr Phe Val  Leu Thr Ser
    5540                 5545                 5550

His Thr  Val Met Pro Leu Ser  Ala Pro Thr Leu Val  Pro Gln Glu
    5555                 5560                 5565

His Tyr  Val Arg Ile Thr Gly  Leu Tyr Pro Thr Leu  Asn Ile Ser
    5570                 5575                 5580

Asp Glu  Phe Ser Ser Asn Val  Ala Asn Tyr Gln Lys  Val Gly Met
    5585                 5590                 5595

Gln Lys  Tyr Ser Thr Leu Gln  Gly Pro Pro Gly Thr  Gly Lys Ser
```

5600 5605 5610

His Phe Ala Ile Gly Leu Ala Leu Tyr Tyr Pro Ser Ala Arg Ile
5615 5620 5625

Val Tyr Thr Ala Cys Ser His Ala Ala Val Asp Ala Leu Cys Glu
5630 5635 5640

Lys Ala Leu Lys Tyr Leu Pro Ile Asp Lys Cys Ser Arg Ile Ile
5645 5650 5655

Pro Ala Arg Ala Arg Val Glu Cys Phe Asp Lys Phe Lys Val Asn
5660 5665 5670

Ser Thr Leu Glu Gln Tyr Val Phe Cys Thr Val Asn Ala Leu Pro
5675 5680 5685

Glu Thr Thr Ala Asp Ile Val Val Phe Asp Glu Ile Ser Met Ala
5690 5695 5700

Thr Asn Tyr Asp Leu Ser Val Val Asn Ala Arg Leu Arg Ala Lys
5705 5710 5715

His Tyr Val Tyr Ile Gly Asp Pro Ala Gln Leu Pro Ala Pro Arg
5720 5725 5730

Thr Leu Leu Thr Lys Gly Thr Leu Glu Pro Glu Tyr Phe Asn Ser
5735 5740 5745

Val Cys Arg Leu Met Lys Thr Ile Gly Pro Asp Met Phe Leu Gly
5750 5755 5760

Thr Cys Arg Arg Cys Pro Ala Glu Ile Val Asp Thr Val Ser Ala
5765 5770 5775

Leu Val Tyr Asp Asn Lys Leu Lys Ala His Lys Asp Lys Ser Ala
5780 5785 5790

Gln Cys Phe Lys Met Phe Tyr Lys Gly Val Ile Thr His Asp Val
5795 5800 5805

Ser Ser Ala Ile Asn Arg Pro Gln Ile Gly Val Val Arg Glu Phe
5810 5815 5820

Leu Thr Arg Asn Pro Ala Trp Arg Lys Ala Val Phe Ile Ser Pro
5825 5830 5835

Tyr Asn Ser Gln Asn Ala Val Ala Ser Lys Ile Leu Gly Leu Pro
5840 5845 5850

Thr Gln Thr Val Asp Ser Ser Gln Gly Ser Glu Tyr Asp Tyr Val
5855 5860 5865

Ile Phe Thr Gln Thr Thr Glu Thr Ala His Ser Cys Asn Val Asn
5870 5875 5880

Arg Phe Asn Val Ala Ile Thr Arg Ala Lys Val Gly Ile Leu Cys
5885 5890 5895

Ile Met Ser Asp Arg Asp Leu Tyr Asp Lys Leu Gln Phe Thr Ser
5900 5905 5910

Leu Glu Ile Pro Arg Arg Asn Val Ala Thr Leu Gln Ala Glu Asn
5915 5920 5925

Val Thr Gly Leu Phe Lys Asp Cys Ser Lys Val Ile Thr Gly Leu
5930 5935 5940

His Pro Thr Gln Ala Pro Thr His Leu Ser Val Asp Thr Lys Phe
5945 5950 5955

Lys Thr Glu Gly Leu Cys Val Asp Ile Pro Gly Ile Pro Lys Asp
5960 5965 5970

Met Thr Tyr Arg Arg Leu Ile Ser Met Met Gly Phe Lys Met Asn
5975 5980 5985

Tyr Gln Val Asn Gly Tyr Pro Asn Met Phe Ile Thr Arg Glu Glu
5990 5995 6000

```
Ala Ile  Arg His Val Arg Ala  Trp Ile Gly Phe Asp  Val Glu Gly
    6005                 6010                 6015

Cys His  Ala Thr Arg Glu Ala  Val Gly Thr Asn Leu  Pro Leu Gln
    6020                 6025                 6030

Leu Gly  Phe Ser Thr Gly Val  Asn Leu Val Ala Val  Pro Thr Gly
    6035                 6040                 6045

Tyr Val  Asp Thr Pro Asn Asn  Thr Asp Phe Ser Arg  Val Ser Ala
    6050                 6055                 6060

Lys Pro  Pro Pro Gly Asp Gln  Phe Lys His Leu Ile  Pro Leu Met
    6065                 6070                 6075

Tyr Lys  Gly Leu Pro Trp Asn  Val Val Arg Ile Lys  Ile Val Gln
    6080                 6085                 6090

Met Leu  Ser Asp Thr Leu Lys  Asn Leu Ser Asp Arg  Val Val Phe
    6095                 6100                 6105

Val Leu  Trp Ala His Gly Phe  Glu Leu Thr Ser Met  Lys Tyr Phe
    6110                 6115                 6120

Val Lys  Ile Gly Pro Glu Arg  Thr Cys Cys Leu Cys  Asp Arg Arg
    6125                 6130                 6135

Ala Thr  Cys Phe Ser Thr Ala  Ser Asp Thr Tyr Ala  Cys Trp His
    6140                 6145                 6150

His Ser  Ile Gly Phe Asp Tyr  Val Tyr Asn Pro Phe  Met Ile Asp
    6155                 6160                 6165

Val Gln  Gln Trp Gly Phe Thr  Gly Asn Leu Gln Ser  Asn His Asp
    6170                 6175                 6180

Leu Tyr  Cys Gln Val His Gly  Asn Ala His Val Ala  Ser Cys Asp
    6185                 6190                 6195

Ala Ile  Met Thr Arg Cys Leu  Ala Val His Glu Cys  Phe Val Lys
    6200                 6205                 6210

Arg Val  Asp Trp Thr Ile Glu  Tyr Pro Ile Ile Gly  Asp Glu Leu
    6215                 6220                 6225

Lys Ile  Asn Ala Ala Cys Arg  Lys Val Gln His Met  Val Val Lys
    6230                 6235                 6240

Ala Ala  Leu Leu Ala Asp Lys  Phe Pro Val Leu His  Asp Ile Gly
    6245                 6250                 6255

Asn Pro  Lys Ala Ile Lys Cys  Val Pro Gln Ala Asp  Val Glu Trp
    6260                 6265                 6270

Lys Phe  Tyr Asp Ala Gln Pro  Cys Ser Asp Lys Ala  Tyr Lys Ile
    6275                 6280                 6285

Glu Glu  Leu Phe Tyr Ser Tyr  Ala Thr His Ser Asp  Lys Phe Thr
    6290                 6295                 6300

Asp Gly  Val Cys Leu Phe Trp  Asn Cys Asn Val Asp  Arg Tyr Pro
    6305                 6310                 6315

Ala Asn  Ser Ile Val Cys Arg  Phe Asp Thr Arg Val  Leu Ser Asn
    6320                 6325                 6330

Leu Asn  Leu Pro Gly Cys Asp  Gly Gly Ser Leu Tyr  Val Asn Lys
    6335                 6340                 6345

His Ala  Phe His Thr Pro Ala  Phe Asp Lys Ser Ala  Phe Val Asn
    6350                 6355                 6360

Leu Lys  Gln Leu Pro Phe Phe  Tyr Tyr Ser Asp Ser  Pro Cys Glu
    6365                 6370                 6375

Ser His  Gly Lys Gln Val Val  Ser Asp Ile Asp Tyr  Val Pro Leu
    6380                 6385                 6390
```

```
Lys Ser Ala Thr Cys Ile Thr Arg Cys Asn Leu Gly Gly Ala Val
    6395                6400                6405

Cys Arg His His Ala Asn Glu Tyr Arg Leu Tyr Leu Asp Ala Tyr
    6410                6415                6420

Asn Met Met Ile Ser Ala Gly Phe Ser Leu Trp Val Tyr Lys Gln
    6425                6430                6435

Phe Asp Thr Tyr Asn Leu Trp Asn Thr Phe Thr Arg Leu Gln Ser
    6440                6445                6450

Leu Glu Asn Val Ala Phe Asn Val Val Asn Lys Gly His Phe Asp
    6455                6460                6465

Gly Gln Gln Gly Glu Val Pro Val Ser Ile Ile Asn Asn Thr Val
    6470                6475                6480

Tyr Thr Lys Val Asp Gly Val Asp Val Glu Leu Phe Glu Asn Lys
    6485                6490                6495

Thr Thr Leu Pro Val Asn Val Ala Phe Glu Leu Trp Ala Lys Arg
    6500                6505                6510

Asn Ile Lys Pro Val Pro Glu Val Lys Ile Leu Asn Asn Leu Gly
    6515                6520                6525

Val Asp Ile Ala Ala Asn Thr Val Ile Trp Asp Tyr Lys Arg Asp
    6530                6535                6540

Ala Pro Ala His Ile Ser Thr Ile Gly Val Cys Ser Met Thr Asp
    6545                6550                6555

Ile Ala Lys Lys Pro Thr Glu Thr Ile Cys Ala Pro Leu Thr Val
    6560                6565                6570

Phe Phe Asp Gly Arg Val Asp Gly Gln Val Asp Leu Phe Arg Asn
    6575                6580                6585

Ala Arg Asn Gly Val Leu Ile Thr Glu Gly Ser Val Lys Gly Leu
    6590                6595                6600

Gln Pro Ser Val Gly Pro Lys Gln Ala Ser Leu Asn Gly Val Thr
    6605                6610                6615

Leu Ile Gly Glu Ala Val Lys Thr Gln Phe Asn Tyr Tyr Lys Lys
    6620                6625                6630

Val Asp Gly Val Val Gln Gln Leu Pro Glu Thr Tyr Phe Thr Gln
    6635                6640                6645

Ser Arg Asn Leu Gln Glu Phe Lys Pro Arg Ser Gln Met Glu Ile
    6650                6655                6660

Asp Phe Leu Glu Leu Ala Met Asp Glu Phe Ile Glu Arg Tyr Lys
    6665                6670                6675

Leu Glu Gly Tyr Ala Phe Glu His Ile Val Tyr Gly Asp Phe Ser
    6680                6685                6690

His Ser Gln Leu Gly Gly Leu His Leu Leu Ile Gly Leu Ala Lys
    6695                6700                6705

Arg Phe Lys Glu Ser Pro Phe Glu Leu Glu Asp Phe Ile Pro Met
    6710                6715                6720

Asp Ser Thr Val Lys Asn Tyr Phe Ile Thr Asp Ala Gln Thr Gly
    6725                6730                6735

Ser Ser Lys Cys Val Cys Ser Val Ile Asp Leu Leu Leu Asp Asp
    6740                6745                6750

Phe Val Glu Ile Ile Lys Ser Gln Asp Leu Ser Val Val Ser Lys
    6755                6760                6765

Val Val Lys Val Thr Ile Asp Tyr Thr Glu Ile Ser Phe Met Leu
    6770                6775                6780

Trp Cys Lys Asp Gly His Val Glu Thr Phe Tyr Pro Lys Leu Gln
```

```
    6785                6790                6795

Ser Ser  Gln Ala Trp Gln Pro  Gly Val Ala Met Pro  Asn Leu Tyr
    6800                6805                6810

Lys Met  Gln Arg Met Leu Leu  Glu Lys Cys Asp Leu  Gln Asn Tyr
    6815                6820                6825

Gly Asp  Ser Ala Thr Leu Pro  Lys Gly Ile Met Met  Asn Val Ala
    6830                6835                6840

Lys Tyr  Thr Gln Leu Cys Gln  Tyr Leu Asn Thr Leu  Thr Leu Ala
    6845                6850                6855

Val Pro  Tyr Asn Met Arg Val  Ile His Phe Gly Ala  Gly Ser Asp
    6860                6865                6870

Lys Gly  Val Ala Pro Gly Thr  Ala Val Leu Arg Gln  Trp Leu Pro
    6875                6880                6885

Thr Gly  Thr Leu Leu Val Asp  Ser Asp Leu Asn Asp  Phe Val Ser
    6890                6895                6900

Asp Ala  Asp Ser Thr Leu Ile  Gly Asp Cys Ala Thr  Val His Thr
    6905                6910                6915

Ala Asn  Lys Trp Asp Leu Ile  Ile Ser Asp Met Tyr  Asp Pro Lys
    6920                6925                6930

Thr Lys  Asn Val Thr Lys Glu  Asn Asp Ser Lys Glu  Gly Phe Phe
    6935                6940                6945

Thr Tyr  Ile Cys Gly Phe Ile  Gln Gln Lys Leu Ala  Leu Gly Gly
    6950                6955                6960

Ser Val  Ala Ile Lys Ile Thr  Glu His Ser Trp Asn  Ala Asp Leu
    6965                6970                6975

Tyr Lys  Leu Met Gly His Phe  Ala Trp Trp Thr Ala  Phe Val Thr
    6980                6985                6990

Asn Val  Asn Ala Ser Ser Ser  Glu Ala Phe Leu Ile  Gly Cys Asn
    6995                7000                7005

Tyr Leu  Gly Lys Pro Arg Glu  Gln Ile Asp Gly Tyr  Val Met His
    7010                7015                7020

Ala Asn  Tyr Ile Phe Trp Arg  Asn Thr Asn Pro Ile  Gln Leu Ser
    7025                7030                7035

Ser Tyr  Ser Leu Phe Asp Met  Ser Lys Phe Pro Leu  Lys Leu Arg
    7040                7045                7050

Gly Thr  Ala Val Met Ser Leu  Lys Glu Gly Gln Ile  Asn Asp Met
    7055                7060                7065

Ile Leu  Ser Leu Leu Ser Lys  Gly Arg Leu Ile Ile  Arg Glu Asn
    7070                7075                7080

Asn Arg  Val Val Ile Ser Ser  Asp Val Leu Val Asn  Asn
    7085                7090                7095
```

<210> SEQ ID NO 3
<211> LENGTH: 1273
<212> TYPE: PRT
<213> ORGANISM: Unknown
<220> FEATURE:
<223> OTHER INFORMATION: SARS-CoV-2 surface glycoprotein

<400> SEQUENCE: 3

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
```

```
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460
```

```
Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880
```

```
Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr
    1265                1270
```

```
<210> SEQ ID NO 4
<211> LENGTH: 275
<212> TYPE: PRT
<213> ORGANISM: Unknown
<220> FEATURE:
<223> OTHER INFORMATION: SARS-CoV-2 ORF3A

<400> SEQUENCE: 4

Met Asp Leu Phe Met Arg Ile Phe Thr Ile Gly Thr Val Thr Leu Lys
1               5                   10                  15

Gln Gly Glu Ile Lys Asp Ala Thr Pro Ser Asp Phe Val Arg Ala Thr
            20                  25                  30

Ala Thr Ile Pro Ile Gln Ala Ser Leu Pro Phe Gly Trp Leu Ile Val
        35                  40                  45

Gly Val Ala Leu Leu Ala Val Phe Gln Ser Ala Ser Lys Ile Ile Thr
    50                  55                  60

Leu Lys Lys Arg Trp Gln Leu Ala Leu Ser Lys Gly Val His Phe Val
65                  70                  75                  80

Cys Asn Leu Leu Leu Leu Phe Val Thr Val Tyr Ser His Leu Leu Leu
                85                  90                  95

Val Ala Ala Gly Leu Glu Ala Pro Phe Leu Tyr Leu Tyr Ala Leu Val
            100                 105                 110

Tyr Phe Leu Gln Ser Ile Asn Phe Val Arg Ile Ile Met Arg Leu Trp
        115                 120                 125

Leu Cys Trp Lys Cys Arg Ser Lys Asn Pro Leu Leu Tyr Asp Ala Asn
    130                 135                 140

Tyr Phe Leu Cys Trp His Thr Asn Cys Tyr Asp Tyr Cys Ile Pro Tyr
145                 150                 155                 160

Asn Ser Val Thr Ser Ser Ile Val Ile Thr Ser Gly Asp Gly Thr Thr
                165                 170                 175

Ser Pro Ile Ser Glu His Asp Tyr Gln Ile Gly Gly Tyr Thr Glu Lys
            180                 185                 190

Trp Glu Ser Gly Val Lys Asp Cys Val Val Leu His Ser Tyr Phe Thr
        195                 200                 205

Ser Asp Tyr Tyr Gln Leu Tyr Ser Thr Gln Leu Ser Thr Asp Thr Gly
    210                 215                 220

Val Glu His Val Thr Phe Phe Ile Tyr Asn Lys Ile Val Asp Glu Pro
225                 230                 235                 240

Glu Glu His Val Gln Ile His Thr Ile Asp Gly Ser Ser Gly Val Val
                245                 250                 255

Asn Pro Val Met Glu Pro Ile Tyr Asp Glu Pro Thr Thr Thr Thr Ser
            260                 265                 270

Val Pro Leu
        275


<210> SEQ ID NO 5
<211> LENGTH: 75
<212> TYPE: PRT
<213> ORGANISM: Unknown
<220> FEATURE:
<223> OTHER INFORMATION: SARS-CoV-2 envelope

<400> SEQUENCE: 5

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30
```

-continued

```
Ile Leu Thr Ala Leu Arg Leu Cys Ala Tyr Cys Cys Asn Ile Val Asn
        35                  40                  45

Val Ser Leu Val Lys Pro Ser Phe Tyr Val Tyr Ser Arg Val Lys Asn
    50                  55                  60

Leu Asn Ser Ser Arg Val Pro Asp Leu Leu Val
65                  70                  75
```

<210> SEQ ID NO 6
<211> LENGTH: 218
<212> TYPE: PRT
<213> ORGANISM: Unknown
<220> FEATURE:
<223> OTHER INFORMATION: SARS-CoV-2 membrane glycoprotein

<400> SEQUENCE: 6

```
Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
            20                  25                  30

Cys Leu Leu Gln Phe Ala Tyr Ala Asn Arg Asn Arg Phe Leu Tyr Ile
        35                  40                  45

Ile Lys Leu Ile Phe Leu Trp Leu Leu Trp Pro Val Thr Leu Ala Cys
    50                  55                  60

Phe Val Leu Ala Ala Val Tyr Arg Ile Asn Trp Ile Thr Gly Gly Ile
65                  70                  75                  80

Ala Ile Ala Met Ala Cys Leu Val Gly Leu Met Trp Leu Ser Tyr Phe
                85                  90                  95

Ile Ala Ser Phe Arg Leu Phe Ala Arg Thr Arg Ser Met Trp Ser Phe
            100                 105                 110

Asn Pro Glu Thr Asn Ile Leu Leu Asn Val Pro Leu His Gly Thr Ile
        115                 120                 125

Leu Thr Arg Pro Leu Leu Glu Ser Glu Leu Val Ile Gly Ala Val Ile
    130                 135                 140

Leu Arg Gly His Leu Arg Ile Ala Gly His His Leu Gly Arg Cys Asp
145                 150                 155                 160

Ile Lys Asp Leu Pro Lys Glu Ile Thr Val Ala Thr Ser Arg Thr Leu
                165                 170                 175

Ser Tyr Tyr Lys Leu Gly Ala Ser Gln Arg Val Ala Gly Asp Ser Gly
            180                 185                 190

Phe Ala Ala Tyr Ser Arg Tyr Arg Ile Gly Asn Tyr Lys Leu Asn Thr
        195                 200                 205

Asp His Ser Ser Ser Ser Asp Asn Ile Ala
    210                 215
```

<210> SEQ ID NO 7
<211> LENGTH: 61
<212> TYPE: PRT
<213> ORGANISM: Unknown
<220> FEATURE:
<223> OTHER INFORMATION: SARS-CoV-2 ORF6

<400> SEQUENCE: 7

```
Met Phe His Leu Val Asp Phe Gln Val Thr Ile Ala Glu Ile Leu Leu
1               5                   10                  15

Ile Ile Met Arg Thr Phe Lys Val Ser Ile Trp Asn Leu Asp Tyr Ile
            20                  25                  30

Ile Asn Leu Ile Ile Lys Asn Leu Ser Lys Ser Leu Thr Glu Asn Lys
        35                  40                  45
```

```
Tyr Ser Gln Leu Asp Glu Glu Gln Pro Met Glu Ile Asp
    50                  55                  60


<210> SEQ ID NO 8
<211> LENGTH: 121
<212> TYPE: PRT
<213> ORGANISM: Unknown
<220> FEATURE:
<223> OTHER INFORMATION: SARS-CoV-2 ORF7a

<400> SEQUENCE: 8

Met Lys Ile Ile Leu Phe Leu Ala Leu Ile Thr Leu Ala Thr Cys Glu
1               5                   10                  15

Leu Tyr His Tyr Gln Glu Cys Val Arg Gly Thr Thr Val Leu Leu Lys
            20                  25                  30

Glu Pro Cys Ser Ser Gly Thr Tyr Glu Gly Asn Ser Pro Phe His Pro
        35                  40                  45

Leu Ala Asp Asn Lys Phe Ala Leu Thr Cys Phe Ser Thr Gln Phe Ala
    50                  55                  60

Phe Ala Cys Pro Asp Gly Val Lys His Val Tyr Gln Leu Arg Ala Arg
65                  70                  75                  80

Ser Val Ser Pro Lys Leu Phe Ile Arg Gln Glu Glu Val Gln Glu Leu
                85                  90                  95

Tyr Ser Pro Ile Phe Leu Ile Val Ala Ala Ile Val Phe Ile Thr Leu
            100                 105                 110

Cys Phe Thr Leu Lys Arg Lys Thr Glu
        115                 120


<210> SEQ ID NO 9
<211> LENGTH: 121
<212> TYPE: PRT
<213> ORGANISM: Unknown
<220> FEATURE:
<223> OTHER INFORMATION: SARS-CoV-2 ORF8

<400> SEQUENCE: 9

Met Lys Phe Leu Val Phe Leu Gly Ile Ile Thr Thr Val Ala Ala Phe
1               5                   10                  15

His Gln Glu Cys Ser Leu Gln Ser Cys Thr Gln His Gln Pro Tyr Val
            20                  25                  30

Val Asp Asp Pro Cys Pro Ile His Phe Tyr Ser Lys Trp Tyr Ile Arg
        35                  40                  45

Val Gly Ala Arg Lys Ser Ala Pro Leu Ile Glu Leu Cys Val Asp Glu
    50                  55                  60

Ala Gly Ser Lys Ser Pro Ile Gln Tyr Ile Asp Ile Gly Asn Tyr Thr
65                  70                  75                  80

Val Ser Cys Leu Pro Phe Thr Ile Asn Cys Gln Glu Pro Lys Leu Gly
                85                  90                  95

Ser Leu Val Val Arg Cys Ser Phe Tyr Glu Asp Phe Leu Glu Tyr His
            100                 105                 110

Asp Val Arg Val Val Leu Asp Phe Ile
        115                 120


<210> SEQ ID NO 10
<211> LENGTH: 419
<212> TYPE: PRT
<213> ORGANISM: Unknown
<220> FEATURE:
<223> OTHER INFORMATION: SARS-CoV-2 nucleocapsid phosphoprotein
```

<400> SEQUENCE: 10

```
Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
    210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Lys Ala Asp Glu Thr Gln Ala Leu Pro Gln
    370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
```

```
                405                 410                 415

Thr Gln Ala


<210> SEQ ID NO 11
<211> LENGTH: 38
<212> TYPE: PRT
<213> ORGANISM: Unknown
<220> FEATURE:
<223> OTHER INFORMATION: SARS-CoV-2 ORF10

<400> SEQUENCE: 11

Met Gly Tyr Ile Asn Val Phe Ala Phe Pro Phe Thr Ile Tyr Ser Leu
1               5                   10                  15

Leu Leu Cys Arg Met Asn Ser Arg Asn Tyr Ile Ala Gln Val Asp Val
            20                  25                  30

Val Asn Phe Asn Leu Thr
        35


<210> SEQ ID NO 12
<211> LENGTH: 1285
<212> TYPE: PRT
<213> ORGANISM: Unknown
<220> FEATURE:
<223> OTHER INFORMATION: SARS-CoV-2 spike protein

<400> SEQUENCE: 12

Met Asp Ala Met Lys Arg Gly Leu Cys Cys Val Leu Leu Leu Cys Gly
1               5                   10                  15

Ala Val Phe Val Ser Pro Ser Gly Thr Gly Ser Val Asn Leu Thr Thr
            20                  25                  30

Arg Thr Gln Leu Pro Pro Ala Tyr Thr Asn Ser Phe Thr Arg Gly Val
        35                  40                  45

Tyr Tyr Pro Asp Lys Val Phe Arg Ser Ser Val Leu His Ser Thr Gln
    50                  55                  60

Asp Leu Phe Leu Pro Phe Phe Ser Asn Val Thr Trp Phe His Ala Ile
65                  70                  75                  80

His Val Ser Gly Thr Asn Gly Thr Lys Arg Phe Asp Asn Pro Val Leu
                85                  90                  95

Pro Phe Asn Asp Gly Val Tyr Phe Ala Ser Thr Glu Lys Ser Asn Ile
            100                 105                 110

Ile Arg Gly Trp Ile Phe Gly Thr Thr Leu Asp Ser Lys Thr Gln Ser
        115                 120                 125

Leu Leu Ile Val Asn Asn Ala Thr Asn Val Val Ile Lys Val Cys Glu
    130                 135                 140

Phe Gln Phe Cys Asn Asp Pro Phe Leu Gly Val Tyr Tyr His Lys Asn
145                 150                 155                 160

Asn Lys Ser Trp Met Glu Ser Glu Phe Arg Val Tyr Ser Ser Ala Asn
                165                 170                 175

Asn Cys Thr Phe Glu Tyr Val Ser Gln Pro Phe Leu Met Asp Leu Glu
            180                 185                 190

Gly Lys Gln Gly Asn Phe Lys Asn Leu Arg Glu Phe Val Phe Lys Asn
        195                 200                 205

Ile Asp Gly Tyr Phe Lys Ile Tyr Ser Lys His Thr Pro Ile Asn Leu
    210                 215                 220

Val Arg Asp Leu Pro Gln Gly Phe Ser Ala Leu Glu Pro Leu Val Asp
225                 230                 235                 240

Leu Pro Ile Gly Ile Asn Ile Thr Arg Phe Gln Thr Leu Leu Ala Leu
```

-continued

```
            245                 250                 255

His Arg Ser Tyr Leu Thr Pro Gly Asp Ser Ser Ser Gly Trp Thr Ala
            260                 265                 270

Gly Ala Ala Ala Tyr Tyr Val Gly Tyr Leu Gln Pro Arg Thr Phe Leu
        275                 280                 285

Leu Lys Tyr Asn Glu Asn Gly Thr Ile Thr Asp Ala Val Asp Cys Ala
    290                 295                 300

Leu Asp Pro Leu Ser Glu Thr Lys Cys Thr Leu Lys Ser Phe Thr Val
305                 310                 315                 320

Glu Lys Gly Ile Tyr Gln Thr Ser Asn Phe Arg Val Gln Pro Thr Glu
                325                 330                 335

Ser Ile Val Arg Phe Pro Asn Ile Thr Asn Leu Cys Pro Phe Gly Glu
            340                 345                 350

Val Phe Asn Ala Thr Arg Phe Ala Ser Val Tyr Ala Trp Asn Arg Lys
        355                 360                 365

Arg Ile Ser Asn Cys Val Ala Asp Tyr Ser Val Leu Tyr Asn Ser Ala
    370                 375                 380

Ser Phe Ser Thr Phe Lys Cys Tyr Gly Val Ser Pro Thr Lys Leu Asn
385                 390                 395                 400

Asp Leu Cys Phe Thr Asn Val Tyr Ala Asp Ser Phe Val Ile Arg Gly
                405                 410                 415

Asp Glu Val Arg Gln Ile Ala Pro Gly Gln Thr Gly Lys Ile Ala Asp
            420                 425                 430

Tyr Asn Tyr Lys Leu Pro Asp Asp Phe Thr Gly Cys Val Ile Ala Trp
        435                 440                 445

Asn Ser Asn Asn Leu Asp Ser Lys Val Gly Gly Asn Tyr Asn Tyr Leu
    450                 455                 460

Tyr Arg Leu Phe Arg Lys Ser Asn Leu Lys Pro Phe Glu Arg Asp Ile
465                 470                 475                 480

Ser Thr Glu Ile Tyr Gln Ala Gly Ser Thr Pro Cys Asn Gly Val Glu
                485                 490                 495

Gly Phe Asn Cys Tyr Phe Pro Leu Gln Ser Tyr Gly Phe Gln Pro Thr
            500                 505                 510

Asn Gly Val Gly Tyr Gln Pro Tyr Arg Val Val Val Leu Ser Phe Glu
        515                 520                 525

Leu Leu His Ala Pro Ala Thr Val Cys Gly Pro Lys Lys Ser Thr Asn
    530                 535                 540

Leu Val Lys Asn Lys Cys Val Asn Phe Asn Phe Asn Gly Leu Thr Gly
545                 550                 555                 560

Thr Gly Val Leu Thr Glu Ser Asn Lys Lys Phe Leu Pro Phe Gln Gln
                565                 570                 575

Phe Gly Arg Asp Ile Ala Asp Thr Thr Asp Ala Val Arg Asp Pro Gln
            580                 585                 590

Thr Leu Glu Ile Leu Asp Ile Thr Pro Cys Ser Phe Gly Gly Val Ser
        595                 600                 605

Val Ile Thr Pro Gly Thr Asn Thr Ser Asn Gln Val Ala Val Leu Tyr
    610                 615                 620

Gln Asp Val Asn Cys Thr Glu Val Pro Val Ala Ile His Ala Asp Gln
625                 630                 635                 640

Leu Thr Pro Thr Trp Arg Val Tyr Ser Thr Gly Ser Asn Val Phe Gln
                645                 650                 655

Thr Arg Ala Gly Cys Leu Ile Gly Ala Glu His Val Asn Asn Ser Tyr
            660                 665                 670
```

```
Glu Cys Asp Ile Pro Ile Gly Ala Gly Ile Cys Ala Ser Tyr Gln Thr
        675                 680                 685

Gln Thr Asn Ser Pro Arg Arg Ala Arg Ser Val Ala Ser Gln Ser Ile
    690                 695                 700

Ile Ala Tyr Thr Met Ser Leu Gly Ala Glu Asn Ser Val Ala Tyr Ser
705                 710                 715                 720

Asn Asn Ser Ile Ala Ile Pro Thr Asn Phe Thr Ile Ser Val Thr Thr
                725                 730                 735

Glu Ile Leu Pro Val Ser Met Thr Lys Thr Ser Val Asp Cys Thr Met
            740                 745                 750

Tyr Ile Cys Gly Asp Ser Thr Glu Cys Ser Asn Leu Leu Leu Gln Tyr
        755                 760                 765

Gly Ser Phe Cys Thr Gln Leu Asn Arg Ala Leu Thr Gly Ile Ala Val
    770                 775                 780

Glu Gln Asp Lys Asn Thr Gln Glu Val Phe Ala Gln Val Lys Gln Ile
785                 790                 795                 800

Tyr Lys Thr Pro Pro Ile Lys Asp Phe Gly Gly Phe Asn Phe Ser Gln
                805                 810                 815

Ile Leu Pro Asp Pro Ser Lys Pro Ser Lys Arg Ser Phe Ile Glu Asp
            820                 825                 830

Leu Leu Phe Asn Lys Val Thr Leu Ala Asp Ala Gly Phe Ile Lys Gln
        835                 840                 845

Tyr Gly Asp Cys Leu Gly Asp Ile Ala Ala Arg Asp Leu Ile Cys Ala
    850                 855                 860

Gln Lys Phe Asn Gly Leu Thr Val Leu Pro Pro Leu Leu Thr Asp Glu
865                 870                 875                 880

Met Ile Ala Gln Tyr Thr Ser Ala Leu Leu Ala Gly Thr Ile Thr Ser
                885                 890                 895

Gly Trp Thr Phe Gly Ala Gly Ala Ala Leu Gln Ile Pro Phe Ala Met
            900                 905                 910

Gln Met Ala Tyr Arg Phe Asn Gly Ile Gly Val Thr Gln Asn Val Leu
        915                 920                 925

Tyr Glu Asn Gln Lys Leu Ile Ala Asn Gln Phe Asn Ser Ala Ile Gly
    930                 935                 940

Lys Ile Gln Asp Ser Leu Ser Ser Thr Ala Ser Ala Leu Gly Lys Leu
945                 950                 955                 960

Gln Asp Val Val Asn Gln Asn Ala Gln Ala Leu Asn Thr Leu Val Lys
                965                 970                 975

Gln Leu Ser Ser Asn Phe Gly Ala Ile Ser Ser Val Leu Asn Asp Ile
            980                 985                 990

Leu Ser Arg Leu Asp Lys Val Glu  Ala Glu Val Gln Ile  Asp Arg Leu
        995                 1000                1005

Ile Thr  Gly Arg Leu Gln Ser  Leu Gln Thr Tyr Val  Thr Gln Gln
    1010                1015                1020

Leu Ile  Arg Ala Ala Glu Ile  Arg Ala Ser Ala Asn  Leu Ala Ala
    1025                1030                1035

Thr Lys  Met Ser Glu Cys Val  Leu Gly Gln Ser Lys  Arg Val Asp
    1040                1045                1050

Phe Cys  Gly Lys Gly Tyr His  Leu Met Ser Phe Pro  Gln Ser Ala
    1055                1060                1065

Pro His  Gly Val Val Phe Leu  His Val Thr Tyr Val  Pro Ala Gln
    1070                1075                1080
```

```
Glu Lys  Asn Phe Thr Thr Ala  Pro Ala Ile Cys His  Asp Gly Lys
    1085                 1090                 1095

Ala His  Phe Pro Arg Glu Gly  Val Phe Val Ser Asn  Gly Thr His
    1100                 1105                 1110

Trp Phe  Val Thr Gln Arg Asn  Phe Tyr Glu Pro Gln  Ile Ile Thr
    1115                 1120                 1125

Thr Asp  Asn Thr Phe Val Ser  Gly Asn Cys Asp Val  Val Ile Gly
    1130                 1135                 1140

Ile Val  Asn Asn Thr Val Tyr  Asp Pro Leu Gln Pro  Glu Leu Asp
    1145                 1150                 1155

Ser Phe  Lys Glu Glu Leu Asp  Lys Tyr Phe Lys Asn  His Thr Ser
    1160                 1165                 1170

Pro Asp  Val Asp Leu Gly Asp  Ile Ser Gly Ile Asn  Ala Ser Val
    1175                 1180                 1185

Val Asn  Ile Gln Lys Glu Ile  Asp Arg Leu Asn Glu  Val Ala Lys
    1190                 1195                 1200

Asn Leu  Asn Glu Ser Leu Ile  Asp Leu Gln Glu Leu  Gly Lys Tyr
    1205                 1210                 1215

Glu Gln  Tyr Ile Lys Trp Pro  Trp Tyr Ile Trp Leu  Gly Phe Ile
    1220                 1225                 1230

Ala Gly  Leu Ile Ala Ile Val  Met Val Thr Ile Met  Leu Cys Cys
    1235                 1240                 1245

Met Thr  Ser Cys Cys Ser Cys  Leu Lys Gly Cys Cys  Ser Cys Gly
    1250                 1255                 1260

Ser Cys  Cys Lys Phe Asp Glu  Asp Asp Ser Glu Pro  Val Leu Lys
    1265                 1270                 1275

Gly Val  Lys Leu His Tyr Thr
    1280                 1285


<210> SEQ ID NO 13
<211> LENGTH: 697
<212> TYPE: PRT
<213> ORGANISM: Unknown
<220> FEATURE:
<223> OTHER INFORMATION: SARS-CoV-2 spike protein

<400> SEQUENCE: 13

Met Asp Ala Met Lys Arg Gly Leu Cys Cys Val Leu Leu Leu Cys Gly
1               5                   10                  15

Ala Val Phe Val Ser Pro Ser Gly Thr Gly Ser Val Asn Leu Thr Thr
            20                  25                  30

Arg Thr Gln Leu Pro Pro Ala Tyr Thr Asn Ser Phe Thr Arg Gly Val
        35                  40                  45

Tyr Tyr Pro Asp Lys Val Phe Arg Ser Ser Val Leu His Ser Thr Gln
    50                  55                  60

Asp Leu Phe Leu Pro Phe Phe Ser Asn Val Thr Trp Phe His Ala Ile
65                  70                  75                  80

His Val Ser Gly Thr Asn Gly Thr Lys Arg Phe Asp Asn Pro Val Leu
                85                  90                  95

Pro Phe Asn Asp Gly Val Tyr Phe Ala Ser Thr Glu Lys Ser Asn Ile
            100                 105                 110

Ile Arg Gly Trp Ile Phe Gly Thr Thr Leu Asp Ser Lys Thr Gln Ser
        115                 120                 125

Leu Leu Ile Val Asn Asn Ala Thr Asn Val Val Ile Lys Val Cys Glu
    130                 135                 140
```

-continued

```
Phe Gln Phe Cys Asn Asp Pro Phe Leu Gly Val Tyr Tyr His Lys Asn
145                 150                 155                 160

Asn Lys Ser Trp Met Glu Ser Glu Phe Arg Val Tyr Ser Ser Ala Asn
                165                 170                 175

Asn Cys Thr Phe Glu Tyr Val Ser Gln Pro Phe Leu Met Asp Leu Glu
            180                 185                 190

Gly Lys Gln Gly Asn Phe Lys Asn Leu Arg Glu Phe Val Phe Lys Asn
        195                 200                 205

Ile Asp Gly Tyr Phe Lys Ile Tyr Ser Lys His Thr Pro Ile Asn Leu
    210                 215                 220

Val Arg Asp Leu Pro Gln Gly Phe Ser Ala Leu Glu Pro Leu Val Asp
225                 230                 235                 240

Leu Pro Ile Gly Ile Asn Ile Thr Arg Phe Gln Thr Leu Leu Ala Leu
                245                 250                 255

His Arg Ser Tyr Leu Thr Pro Gly Asp Ser Ser Ser Gly Trp Thr Ala
            260                 265                 270

Gly Ala Ala Ala Tyr Tyr Val Gly Tyr Leu Gln Pro Arg Thr Phe Leu
        275                 280                 285

Leu Lys Tyr Asn Glu Asn Gly Thr Ile Thr Asp Ala Val Asp Cys Ala
    290                 295                 300

Leu Asp Pro Leu Ser Glu Thr Lys Cys Thr Leu Lys Ser Phe Thr Val
305                 310                 315                 320

Glu Lys Gly Ile Tyr Gln Thr Ser Asn Phe Arg Val Gln Pro Thr Glu
                325                 330                 335

Ser Ile Val Arg Phe Pro Asn Ile Thr Asn Leu Cys Pro Phe Gly Glu
            340                 345                 350

Val Phe Asn Ala Thr Arg Phe Ala Ser Val Tyr Ala Trp Asn Arg Lys
        355                 360                 365

Arg Ile Ser Asn Cys Val Ala Asp Tyr Ser Val Leu Tyr Asn Ser Ala
    370                 375                 380

Ser Phe Ser Thr Phe Lys Cys Tyr Gly Val Ser Pro Thr Lys Leu Asn
385                 390                 395                 400

Asp Leu Cys Phe Thr Asn Val Tyr Ala Asp Ser Phe Val Ile Arg Gly
                405                 410                 415

Asp Glu Val Arg Gln Ile Ala Pro Gly Gln Thr Gly Lys Ile Ala Asp
            420                 425                 430

Tyr Asn Tyr Lys Leu Pro Asp Asp Phe Thr Gly Cys Val Ile Ala Trp
        435                 440                 445

Asn Ser Asn Asn Leu Asp Ser Lys Val Gly Gly Asn Tyr Asn Tyr Leu
    450                 455                 460

Tyr Arg Leu Phe Arg Lys Ser Asn Leu Lys Pro Phe Glu Arg Asp Ile
465                 470                 475                 480

Ser Thr Glu Ile Tyr Gln Ala Gly Ser Thr Pro Cys Asn Gly Val Glu
                485                 490                 495

Gly Phe Asn Cys Tyr Phe Pro Leu Gln Ser Tyr Gly Phe Gln Pro Thr
            500                 505                 510

Asn Gly Val Gly Tyr Gln Pro Tyr Arg Val Val Val Leu Ser Phe Glu
        515                 520                 525

Leu Leu His Ala Pro Ala Thr Val Cys Gly Pro Lys Lys Ser Thr Asn
    530                 535                 540

Leu Val Lys Asn Lys Cys Val Asn Phe Asn Phe Asn Gly Leu Thr Gly
545                 550                 555                 560

Thr Gly Val Leu Thr Glu Ser Asn Lys Lys Phe Leu Pro Phe Gln Gln
```

```
                565                 570                 575

Phe Gly Arg Asp Ile Ala Asp Thr Thr Asp Ala Val Arg Asp Pro Gln
            580                 585                 590

Thr Leu Glu Ile Leu Asp Ile Thr Pro Cys Ser Phe Gly Gly Val Ser
        595                 600                 605

Val Ile Thr Pro Gly Thr Asn Thr Ser Asn Gln Val Ala Val Leu Tyr
    610                 615                 620

Gln Asp Val Asn Cys Thr Glu Val Pro Val Ala Ile His Ala Asp Gln
625                 630                 635                 640

Leu Thr Pro Thr Trp Arg Val Tyr Ser Thr Gly Ser Asn Val Phe Gln
                645                 650                 655

Thr Arg Ala Gly Cys Leu Ile Gly Ala Glu His Val Asn Asn Ser Tyr
            660                 665                 670

Glu Cys Asp Ile Pro Ile Gly Ala Gly Ile Cys Ala Ser Tyr Gln Thr
        675                 680                 685

Gln Thr Asn Ser Pro Arg Arg Ala Arg
    690                 695


<210> SEQ ID NO 14
<211> LENGTH: 246
<212> TYPE: PRT
<213> ORGANISM: Unknown
<220> FEATURE:
<223> OTHER INFORMATION: SARS-CoV-2 spike protein

<400> SEQUENCE: 14

Met Asp Ala Met Lys Arg Gly Leu Cys Cys Val Leu Leu Leu Cys Gly
1               5                   10                  15

Ala Val Phe Val Ser Pro Ser Gly Thr Gly Ser Arg Val Gln Pro Thr
            20                  25                  30

Glu Ser Ile Val Arg Phe Pro Asn Ile Thr Asn Leu Cys Pro Phe Gly
        35                  40                  45

Glu Val Phe Asn Ala Thr Arg Phe Ala Ser Val Tyr Ala Trp Asn Arg
    50                  55                  60

Lys Arg Ile Ser Asn Cys Val Ala Asp Tyr Ser Val Leu Tyr Asn Ser
65                  70                  75                  80

Ala Ser Phe Ser Thr Phe Lys Cys Tyr Gly Val Ser Pro Thr Lys Leu
                85                  90                  95

Asn Asp Leu Cys Phe Thr Asn Val Tyr Ala Asp Ser Phe Val Ile Arg
            100                 105                 110

Gly Asp Glu Val Arg Gln Ile Ala Pro Gly Gln Thr Gly Lys Ile Ala
        115                 120                 125

Asp Tyr Asn Tyr Lys Leu Pro Asp Asp Phe Thr Gly Cys Val Ile Ala
    130                 135                 140

Trp Asn Ser Asn Asn Leu Asp Ser Lys Val Gly Gly Asn Tyr Asn Tyr
145                 150                 155                 160

Leu Tyr Arg Leu Phe Arg Lys Ser Asn Leu Lys Pro Phe Glu Arg Asp
                165                 170                 175

Ile Ser Thr Glu Ile Tyr Gln Ala Gly Ser Thr Pro Cys Asn Gly Val
            180                 185                 190

Glu Gly Phe Asn Cys Tyr Phe Pro Leu Gln Ser Tyr Gly Phe Gln Pro
        195                 200                 205

Thr Asn Gly Val Gly Tyr Gln Pro Tyr Arg Val Val Val Leu Ser Phe
    210                 215                 220

Glu Leu Leu His Ala Pro Ala Thr Val Cys Gly Pro Lys Lys Ser Thr
```

```
225                 230                 235                 240

Asn Leu Val Lys Asn Lys
                245


<210> SEQ ID NO 15
<211> LENGTH: 269
<212> TYPE: PRT
<213> ORGANISM: Unknown
<220> FEATURE:
<223> OTHER INFORMATION: SARS-CoV-2 spike protein

<400> SEQUENCE: 15

Met Asp Ala Met Lys Arg Gly Leu Cys Cys Val Leu Leu Leu Cys Gly
1               5                   10                  15

Ala Val Phe Val Ser Pro Ser Gly Thr Gly Ser Thr Leu Lys Ser Phe
            20                  25                  30

Thr Val Glu Lys Gly Ile Tyr Gln Thr Ser Asn Phe Arg Val Gln Pro
        35                  40                  45

Thr Glu Ser Ile Val Arg Phe Pro Asn Ile Thr Asn Leu Cys Pro Phe
    50                  55                  60

Gly Glu Val Phe Asn Ala Thr Arg Phe Ala Ser Val Tyr Ala Trp Asn
65                  70                  75                  80

Arg Lys Arg Ile Ser Asn Cys Val Ala Asp Tyr Ser Val Leu Tyr Asn
                85                  90                  95

Ser Ala Ser Phe Ser Thr Phe Lys Cys Tyr Gly Val Ser Pro Thr Lys
            100                 105                 110

Leu Asn Asp Leu Cys Phe Thr Asn Val Tyr Ala Asp Ser Phe Val Ile
        115                 120                 125

Arg Gly Asp Glu Val Arg Gln Ile Ala Pro Gly Gln Thr Gly Lys Ile
    130                 135                 140

Ala Asp Tyr Asn Tyr Lys Leu Pro Asp Asp Phe Thr Gly Cys Val Ile
145                 150                 155                 160

Ala Trp Asn Ser Asn Asn Leu Asp Ser Lys Val Gly Gly Asn Tyr Asn
                165                 170                 175

Tyr Leu Tyr Arg Leu Phe Arg Lys Ser Asn Leu Lys Pro Phe Glu Arg
            180                 185                 190

Asp Ile Ser Thr Glu Ile Tyr Gln Ala Gly Ser Thr Pro Cys Asn Gly
        195                 200                 205

Val Glu Gly Phe Asn Cys Tyr Phe Pro Leu Gln Ser Tyr Gly Phe Gln
    210                 215                 220

Pro Thr Asn Gly Val Gly Tyr Gln Pro Tyr Arg Val Val Val Leu Ser
225                 230                 235                 240

Phe Glu Leu Leu His Ala Pro Ala Thr Val Cys Gly Pro Lys Lys Ser
                245                 250                 255

Thr Asn Leu Val Lys Asn Lys Cys Val Asn Phe Asn Phe
            260                 265


<210> SEQ ID NO 16
<211> LENGTH: 192
<212> TYPE: PRT
<213> ORGANISM: Unknown
<220> FEATURE:
<223> OTHER INFORMATION: SARS-CoV-2 spike protein

<400> SEQUENCE: 16

Asn Ile Thr Asn Leu Cys Pro Phe Gly Glu Val Phe Asn Ala Thr Arg
1               5                   10                  15
```

```
Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Asn Cys Tyr Phe Pro Leu
145                 150                 155                 160

Tyr Gly Phe Gln Pro Thr Gly Val Gly Tyr Gln Pro Tyr Arg Val Val
                165                 170                 175

Val Leu Ser Phe Glu Leu Leu His Ala Pro Ala Thr Val Cys Gly Pro
            180                 185                 190


<210> SEQ ID NO 17
<211> LENGTH: 86
<212> TYPE: PRT
<213> ORGANISM: Unknown
<220> FEATURE:
<223> OTHER INFORMATION: SARS-CoV-2 spike protein

<400> SEQUENCE: 17

Asn Ser Asn Asn Leu Asp Ser Lys Val Gly Gly Asn Tyr Asn Tyr Leu
1               5                   10                  15

Tyr Arg Phe Arg Lys Ser Asn Leu Lys Pro Phe Glu Arg Asp Ile Ser
            20                  25                  30

Thr Glu Ile Tyr Gln Ala Gly Ser Thr Pro Cys Asn Gly Val Glu Gly
        35                  40                  45

Asn Cys Tyr Phe Pro Leu Tyr Gly Phe Gln Pro Thr Gly Val Gly Tyr
    50                  55                  60

Gln Pro Tyr Arg Val Val Val Leu Ser Phe Glu Leu Leu His Ala Pro
65                  70                  75                  80

Ala Thr Val Cys Gly Pro
                85


<210> SEQ ID NO 18
<211> LENGTH: 1275
<212> TYPE: PRT
<213> ORGANISM: Unknown
<220> FEATURE:
<223> OTHER INFORMATION: SARS-CoV-2 spike protein

<400> SEQUENCE: 18

Met Asp Ala Met Lys Arg Gly Leu Cys Cys Val Leu Leu Leu Cys Gly
1               5                   10                  15

Ala Val Phe Val Ser Pro Ser Gly Thr Gly Ser Val Asn Leu Thr Thr
            20                  25                  30

Arg Thr Gln Leu Pro Pro Ala Tyr Thr Asn Ser Phe Thr Arg Gly Val
        35                  40                  45
```

```
Tyr Tyr Pro Asp Lys Val Phe Arg Ser Ser Val Leu His Ser Thr Gln
    50                  55                  60

Asp Leu Phe Leu Pro Phe Phe Ser Asn Val Thr Trp Phe His Ala Ile
65                  70                  75                  80

His Val Ser Gly Thr Asn Gly Thr Lys Arg Phe Asp Asn Pro Val Leu
                85                  90                  95

Pro Phe Asn Asp Gly Val Tyr Phe Ala Ser Thr Glu Lys Ser Asn Ile
            100                 105                 110

Ile Arg Gly Trp Ile Phe Gly Thr Thr Leu Asp Ser Lys Thr Gln Ser
        115                 120                 125

Leu Leu Ile Val Asn Asn Ala Thr Asn Val Val Ile Lys Val Cys Glu
    130                 135                 140

Phe Gln Phe Cys Asn Asp Pro Phe Leu Gly Val Tyr Tyr His Lys Asn
145                 150                 155                 160

Asn Lys Ser Trp Met Glu Ser Glu Phe Arg Val Tyr Ser Ser Ala Asn
                165                 170                 175

Asn Cys Thr Phe Glu Tyr Val Ser Gln Pro Phe Leu Met Asp Leu Glu
            180                 185                 190

Gly Lys Gln Gly Asn Phe Lys Asn Leu Arg Glu Phe Val Phe Lys Asn
        195                 200                 205

Ile Asp Gly Tyr Phe Lys Ile Tyr Ser Lys His Thr Pro Ile Asn Leu
    210                 215                 220

Val Arg Asp Leu Pro Gln Gly Phe Ser Ala Leu Glu Pro Leu Val Asp
225                 230                 235                 240

Leu Pro Ile Gly Ile Asn Ile Thr Arg Phe Gln Thr Leu Leu Ala Leu
                245                 250                 255

His Arg Ser Tyr Leu Thr Pro Gly Asp Ser Ser Ser Gly Trp Thr Ala
            260                 265                 270

Gly Ala Ala Ala Tyr Tyr Val Gly Tyr Leu Gln Pro Arg Thr Phe Leu
        275                 280                 285

Leu Lys Tyr Asn Glu Asn Gly Thr Ile Thr Asp Ala Val Asp Cys Ala
    290                 295                 300

Leu Asp Pro Leu Ser Glu Thr Lys Cys Thr Leu Lys Ser Phe Thr Val
305                 310                 315                 320

Glu Lys Gly Ile Tyr Gln Thr Ser Asn Phe Arg Val Gln Pro Thr Glu
                325                 330                 335

Ser Ile Val Arg Phe Pro Asn Ile Thr Asn Leu Cys Pro Phe Gly Glu
            340                 345                 350

Val Phe Asn Ala Thr Arg Phe Ala Ser Val Tyr Ala Trp Asn Arg Lys
        355                 360                 365

Arg Ile Ser Asn Cys Val Ala Asp Tyr Ser Val Leu Tyr Asn Ser Ala
    370                 375                 380

Ser Phe Ser Thr Phe Lys Cys Tyr Gly Val Ser Pro Thr Lys Leu Asn
385                 390                 395                 400

Asp Leu Cys Phe Thr Asn Val Tyr Ala Asp Ser Phe Val Ile Arg Gly
                405                 410                 415

Asp Glu Val Arg Gln Ile Ala Pro Gly Gln Thr Gly Lys Ile Ala Asp
            420                 425                 430

Tyr Asn Tyr Lys Leu Pro Asp Asp Phe Thr Gly Cys Val Ile Ala Trp
        435                 440                 445

Asn Ser Asn Asn Leu Asp Ser Lys Val Gly Gly Asn Tyr Asn Tyr Leu
    450                 455                 460
```

-continued

```
Tyr Arg Leu Phe Arg Lys Ser Asn Leu Lys Pro Phe Glu Arg Asp Ile
465                 470                 475                 480

Ser Thr Glu Ile Tyr Gln Ala Gly Ser Thr Pro Cys Asn Gly Val Glu
                485                 490                 495

Gly Phe Asn Cys Tyr Phe Pro Leu Gln Ser Tyr Gly Phe Gln Pro Thr
            500                 505                 510

Asn Gly Val Gly Tyr Gln Pro Tyr Arg Val Val Val Leu Ser Phe Glu
        515                 520                 525

Leu Leu His Ala Pro Ala Thr Val Cys Gly Pro Lys Lys Ser Thr Asn
    530                 535                 540

Leu Val Lys Asn Lys Cys Val Asn Phe Asn Phe Asn Gly Leu Thr Gly
545                 550                 555                 560

Thr Gly Val Leu Thr Glu Ser Asn Lys Lys Phe Leu Pro Phe Gln Gln
                565                 570                 575

Phe Gly Arg Asp Ile Ala Asp Thr Thr Asp Ala Val Arg Asp Pro Gln
            580                 585                 590

Thr Leu Glu Ile Leu Asp Ile Thr Pro Cys Ser Phe Gly Gly Val Ser
        595                 600                 605

Val Ile Thr Pro Gly Thr Asn Thr Ser Asn Gln Val Ala Val Leu Tyr
    610                 615                 620

Gln Asp Val Asn Cys Thr Glu Val Pro Val Ala Ile His Ala Asp Gln
625                 630                 635                 640

Leu Thr Pro Thr Trp Arg Val Tyr Ser Thr Gly Ser Asn Val Phe Gln
                645                 650                 655

Thr Arg Ala Gly Cys Leu Ile Gly Ala Glu His Val Asn Asn Ser Tyr
            660                 665                 670

Glu Cys Asp Ile Pro Ile Gly Ala Gly Ile Cys Ala Ser Tyr Gln Thr
        675                 680                 685

Gln Thr Asn Ser Pro Gln Gln Ala Gln Ser Val Ala Ser Gln Ser Ile
    690                 695                 700

Ile Ala Tyr Thr Met Ser Leu Gly Ala Glu Asn Ser Val Ala Tyr Ser
705                 710                 715                 720

Asn Asn Ser Ile Ala Ile Pro Thr Asn Phe Thr Ile Ser Val Thr Thr
                725                 730                 735

Glu Ile Leu Pro Val Ser Met Thr Lys Thr Ser Val Asp Cys Thr Met
            740                 745                 750

Tyr Ile Cys Gly Asp Ser Thr Glu Cys Ser Asn Leu Leu Leu Gln Tyr
        755                 760                 765

Gly Ser Phe Cys Thr Gln Leu Asn Arg Ala Leu Thr Gly Ile Ala Val
    770                 775                 780

Glu Gln Asp Lys Asn Thr Gln Glu Val Phe Ala Gln Val Lys Gln Ile
785                 790                 795                 800

Tyr Lys Thr Pro Pro Ile Lys Asp Phe Gly Gly Phe Asn Phe Ser Gln
                805                 810                 815

Ile Leu Pro Asp Pro Ser Lys Pro Ser Lys Arg Ser Phe Ile Ala Asp
            820                 825                 830

Ala Gly Phe Ile Lys Gln Tyr Gly Asp Cys Leu Gly Asp Ile Ala Ala
        835                 840                 845

Arg Asp Leu Ile Cys Ala Gln Lys Phe Asn Gly Leu Thr Val Leu Pro
    850                 855                 860

Pro Leu Leu Thr Asp Glu Met Ile Ala Gln Tyr Thr Ser Ala Leu Leu
865                 870                 875                 880

Ala Gly Thr Ile Thr Ser Gly Trp Thr Phe Gly Ala Gly Ala Ala Leu
```

```
                885                 890                 895

Gln Ile Pro Phe Ala Met Gln Met Ala Tyr Arg Phe Asn Gly Ile Gly
            900                 905                 910

Val Thr Gln Asn Val Leu Tyr Glu Asn Gln Lys Leu Ile Ala Asn Gln
        915                 920                 925

Phe Asn Ser Ala Ile Gly Lys Ile Gln Asp Ser Leu Ser Ser Thr Ala
    930                 935                 940

Ser Ala Leu Gly Lys Leu Gln Asp Val Val Asn Gln Asn Ala Gln Ala
945                 950                 955                 960

Leu Asn Thr Leu Val Lys Gln Leu Ser Ser Asn Phe Gly Ala Ile Ser
                965                 970                 975

Ser Val Leu Asn Asp Ile Leu Ser Arg Leu Asp Pro Pro Glu Ala Glu
            980                 985                 990

Val Gln Ile Asp Arg Leu Ile Thr  Gly Arg Leu Gln Ser  Leu Gln Thr
        995                 1000                1005

Tyr Val  Thr Gln Gln Leu Ile  Arg Ala Ala Glu Ile  Arg Ala Ser
    1010                 1015                 1020

Ala Asn  Leu Ala Ala Thr Lys  Met Ser Glu Cys Val  Leu Gly Gln
    1025                 1030                 1035

Ser Lys  Arg Val Asp Phe Cys  Gly Lys Gly Tyr His  Leu Met Ser
    1040                 1045                 1050

Phe Pro  Gln Ser Ala Pro His  Gly Val Val Phe Leu  His Val Thr
    1055                 1060                 1065

Tyr Val  Pro Ala Gln Glu Lys  Asn Phe Thr Thr Ala  Pro Ala Ile
    1070                 1075                 1080

Cys His  Asp Gly Lys Ala His  Phe Pro Arg Glu Gly  Val Phe Val
    1085                 1090                 1095

Ser Asn  Gly Thr His Trp Phe  Val Thr Gln Arg Asn  Phe Tyr Glu
    1100                 1105                 1110

Pro Gln  Ile Ile Thr Thr Asp  Asn Thr Phe Val Ser  Gly Asn Cys
    1115                 1120                 1125

Asp Val  Val Ile Gly Ile Val  Asn Asn Thr Val Tyr  Asp Pro Leu
    1130                 1135                 1140

Gln Pro  Glu Leu Asp Ser Phe  Lys Glu Glu Leu Asp  Lys Tyr Phe
    1145                 1150                 1155

Lys Asn  His Thr Ser Pro Asp  Val Asp Leu Gly Asp  Ile Ser Gly
    1160                 1165                 1170

Ile Asn  Ala Ser Val Val Asn  Ile Gln Lys Glu Ile  Asp Arg Leu
    1175                 1180                 1185

Asn Glu  Val Ala Lys Asn Leu  Asn Glu Ser Leu Ile  Asp Leu Gln
    1190                 1195                 1200

Glu Leu  Gly Lys Tyr Glu Gln  Tyr Ile Lys Trp Pro  Trp Tyr Ile
    1205                 1210                 1215

Trp Leu  Gly Phe Ile Ala Gly  Leu Ile Ala Ile Val  Met Val Thr
    1220                 1225                 1230

Ile Met  Leu Cys Cys Met Thr  Ser Cys Cys Ser Cys  Leu Lys Gly
    1235                 1240                 1245

Cys Cys  Ser Cys Gly Ser Cys  Cys Lys Phe Asp Glu  Asp Asp Ser
    1250                 1255                 1260

Glu Pro  Val Leu Lys Gly Val  Lys Leu His Tyr Thr
    1265                 1270                 1275
```

<210> SEQ ID NO 19

<211> LENGTH: 1285
<212> TYPE: PRT
<213> ORGANISM: Unknown
<220> FEATURE:
<223> OTHER INFORMATION: SARS-CoV-2 spike protein

<400> SEQUENCE: 19

```
Met Asp Ala Met Lys Arg Gly Leu Cys Cys Val Leu Leu Leu Cys Gly
1               5                   10                  15

Ala Val Phe Val Ser Pro Ser Gly Thr Gly Ser Val Asn Leu Thr Thr
            20                  25                  30

Arg Thr Gln Leu Pro Pro Ala Tyr Thr Asn Ser Phe Thr Arg Gly Val
        35                  40                  45

Tyr Tyr Pro Asp Lys Val Phe Arg Ser Ser Val Leu His Ser Thr Gln
    50                  55                  60

Asp Leu Phe Leu Pro Phe Phe Ser Asn Val Thr Trp Phe His Ala Ile
65                  70                  75                  80

His Val Ser Gly Thr Asn Gly Thr Lys Arg Phe Asp Asn Pro Val Leu
                85                  90                  95

Pro Phe Asn Asp Gly Val Tyr Phe Ala Ser Thr Glu Lys Ser Asn Ile
            100                 105                 110

Ile Arg Gly Trp Ile Phe Gly Thr Thr Leu Asp Ser Lys Thr Gln Ser
        115                 120                 125

Leu Leu Ile Val Asn Asn Ala Thr Asn Val Val Ile Lys Val Cys Glu
    130                 135                 140

Phe Gln Phe Cys Asn Asp Pro Phe Leu Gly Val Tyr Tyr His Lys Asn
145                 150                 155                 160

Asn Lys Ser Trp Met Glu Ser Glu Phe Arg Val Tyr Ser Ser Ala Asn
                165                 170                 175

Asn Cys Thr Phe Glu Tyr Val Ser Gln Pro Phe Leu Met Asp Leu Glu
            180                 185                 190

Gly Lys Gln Gly Asn Phe Lys Asn Leu Arg Glu Phe Val Phe Lys Asn
        195                 200                 205

Ile Asp Gly Tyr Phe Lys Ile Tyr Ser Lys His Thr Pro Ile Asn Leu
    210                 215                 220

Val Arg Asp Leu Pro Gln Gly Phe Ser Ala Leu Glu Pro Leu Val Asp
225                 230                 235                 240

Leu Pro Ile Gly Ile Asn Ile Thr Arg Phe Gln Thr Leu Leu Ala Leu
                245                 250                 255

His Arg Ser Tyr Leu Thr Pro Gly Asp Ser Ser Ser Gly Trp Thr Ala
            260                 265                 270

Gly Ala Ala Ala Tyr Tyr Val Gly Tyr Leu Gln Pro Arg Thr Phe Leu
        275                 280                 285

Leu Lys Tyr Asn Glu Asn Gly Thr Ile Thr Asp Ala Val Asp Cys Ala
    290                 295                 300

Leu Asp Pro Leu Ser Glu Thr Lys Cys Thr Leu Lys Ser Phe Thr Val
305                 310                 315                 320

Glu Lys Gly Ile Tyr Gln Thr Ser Asn Phe Arg Val Gln Pro Thr Glu
                325                 330                 335

Ser Ile Val Arg Phe Pro Asn Ile Thr Asn Leu Cys Pro Phe Gly Glu
            340                 345                 350

Val Phe Asn Ala Thr Arg Phe Ala Ser Val Tyr Ala Trp Asn Arg Lys
        355                 360                 365

Arg Ile Ser Asn Cys Val Ala Asp Tyr Ser Val Leu Tyr Asn Ser Ala
    370                 375                 380
```

```
Ser Phe Ser Thr Phe Lys Cys Tyr Gly Val Ser Pro Thr Lys Leu Asn
385                 390                 395                 400

Asp Leu Cys Phe Thr Asn Val Tyr Ala Asp Ser Phe Val Ile Arg Gly
                405                 410                 415

Asp Glu Val Arg Gln Ile Ala Pro Gly Gln Thr Gly Lys Ile Ala Asp
            420                 425                 430

Tyr Asn Tyr Lys Leu Pro Asp Asp Phe Thr Gly Cys Val Ile Ala Trp
        435                 440                 445

Asn Ser Asn Asn Leu Asp Ser Lys Val Gly Gly Asn Tyr Asn Tyr Leu
    450                 455                 460

Tyr Arg Leu Phe Arg Lys Ser Asn Leu Lys Pro Phe Glu Arg Asp Ile
465                 470                 475                 480

Ser Thr Glu Ile Tyr Gln Ala Gly Ser Thr Pro Cys Asn Gly Val Glu
                485                 490                 495

Gly Phe Asn Cys Tyr Phe Pro Leu Gln Ser Tyr Gly Phe Gln Pro Thr
            500                 505                 510

Asn Gly Val Gly Tyr Gln Pro Tyr Arg Val Val Val Leu Ser Phe Glu
        515                 520                 525

Leu Leu His Ala Pro Ala Thr Val Cys Gly Pro Lys Lys Ser Thr Asn
    530                 535                 540

Leu Val Lys Asn Lys Cys Val Asn Phe Asn Phe Asn Gly Leu Thr Gly
545                 550                 555                 560

Thr Gly Val Leu Thr Glu Ser Asn Lys Lys Phe Leu Pro Phe Gln Gln
                565                 570                 575

Phe Gly Arg Asp Ile Ala Asp Thr Thr Asp Ala Val Arg Asp Pro Gln
            580                 585                 590

Thr Leu Glu Ile Leu Asp Ile Thr Pro Cys Ser Phe Gly Gly Val Ser
        595                 600                 605

Val Ile Thr Pro Gly Thr Asn Thr Ser Asn Gln Val Ala Val Leu Tyr
    610                 615                 620

Gln Asp Val Asn Cys Thr Glu Val Pro Val Ala Ile His Ala Asp Gln
625                 630                 635                 640

Leu Thr Pro Thr Trp Arg Val Tyr Ser Thr Gly Ser Asn Val Phe Gln
                645                 650                 655

Thr Arg Ala Gly Cys Leu Ile Gly Ala Glu His Val Asn Asn Ser Tyr
            660                 665                 670

Glu Cys Asp Ile Pro Ile Gly Ala Gly Ile Cys Ala Ser Tyr Gln Thr
        675                 680                 685

Gln Thr Asn Ser Pro Ser Gly Ala Gly Ser Val Ala Ser Gln Ser Ile
    690                 695                 700

Ile Ala Tyr Thr Met Ser Leu Gly Ala Glu Asn Ser Val Ala Tyr Ser
705                 710                 715                 720

Asn Asn Ser Ile Ala Ile Pro Thr Asn Phe Thr Ile Ser Val Thr Thr
                725                 730                 735

Glu Ile Leu Pro Val Ser Met Thr Lys Thr Ser Val Asp Cys Thr Met
            740                 745                 750

Tyr Ile Cys Gly Asp Ser Thr Glu Cys Ser Asn Leu Leu Leu Gln Tyr
        755                 760                 765

Gly Ser Phe Cys Thr Gln Leu Asn Arg Ala Leu Thr Gly Ile Ala Val
    770                 775                 780

Glu Gln Asp Lys Asn Thr Gln Glu Val Phe Ala Gln Val Lys Gln Ile
785                 790                 795                 800
```

-continued

```
Tyr Lys Thr Pro Pro Ile Lys Asp Phe Gly Gly Phe Asn Phe Ser Gln
                805                 810                 815

Ile Leu Pro Asp Pro Ser Lys Pro Ser Lys Gln Ser Phe Ile Glu Asp
            820                 825                 830

Leu Leu Phe Asn Lys Val Thr Leu Ala Asp Ala Gly Phe Ile Lys Gln
        835                 840                 845

Tyr Gly Asp Cys Leu Gly Asp Ile Ala Ala Arg Asp Leu Ile Cys Ala
    850                 855                 860

Gln Lys Phe Asn Gly Leu Thr Val Leu Pro Pro Leu Leu Thr Asp Glu
865                 870                 875                 880

Met Ile Ala Gln Tyr Thr Ser Ala Leu Leu Ala Gly Thr Ile Thr Ser
                885                 890                 895

Gly Trp Thr Phe Gly Ala Gly Ala Ala Leu Gln Ile Pro Phe Ala Met
            900                 905                 910

Gln Met Ala Tyr Arg Phe Asn Gly Ile Gly Val Thr Gln Asn Val Leu
        915                 920                 925

Tyr Glu Asn Gln Lys Leu Ile Ala Asn Gln Phe Asn Ser Ala Ile Gly
    930                 935                 940

Lys Ile Gln Asp Ser Leu Ser Ser Thr Ala Ser Ala Leu Gly Lys Leu
945                 950                 955                 960

Gln Asp Val Val Asn Gln Asn Ala Gln Ala Leu Asn Thr Leu Val Lys
                965                 970                 975

Gln Leu Ser Ser Asn Phe Gly Ala Ile Ser Ser Val Leu Asn Asp Ile
            980                 985                 990

Leu Ser Arg Leu Asp Pro Pro Glu  Ala Glu Val Gln Ile  Asp Arg Leu
        995                 1000                1005

Ile Thr  Gly Arg Leu Gln Ser  Leu Gln Thr Tyr Val  Thr Gln Gln
    1010                 1015                 1020

Leu Ile  Arg Ala Ala Glu Ile  Arg Ala Ser Ala Asn  Leu Ala Ala
    1025                 1030                 1035

Thr Lys  Met Ser Glu Cys Val  Leu Gly Gln Ser Lys  Arg Val Asp
    1040                 1045                 1050

Phe Cys  Gly Lys Gly Tyr His  Leu Met Ser Phe Pro  Gln Ser Ala
    1055                 1060                 1065

Pro His  Gly Val Val Phe Leu  His Val Thr Tyr Val  Pro Ala Gln
    1070                 1075                 1080

Glu Lys  Asn Phe Thr Thr Ala  Pro Ala Ile Cys His  Asp Gly Lys
    1085                 1090                 1095

Ala His  Phe Pro Arg Glu Gly  Val Phe Val Ser Asn  Gly Thr His
    1100                 1105                 1110

Trp Phe  Val Thr Gln Arg Asn  Phe Tyr Glu Pro Gln  Ile Ile Thr
    1115                 1120                 1125

Thr Asp  Asn Thr Phe Val Ser  Gly Asn Cys Asp Val  Val Ile Gly
    1130                 1135                 1140

Ile Val  Asn Asn Thr Val Tyr  Asp Pro Leu Gln Pro  Glu Leu Asp
    1145                 1150                 1155

Ser Phe  Lys Glu Glu Leu Asp  Lys Tyr Phe Lys Asn  His Thr Ser
    1160                 1165                 1170

Pro Asp  Val Asp Leu Gly Asp  Ile Ser Gly Ile Asn  Ala Ser Val
    1175                 1180                 1185

Val Asn  Ile Gln Lys Glu Ile  Asp Arg Leu Asn Glu  Val Ala Lys
    1190                 1195                 1200

Asn Leu  Asn Glu Ser Leu Ile  Asp Leu Gln Glu Leu  Gly Lys Tyr
```

```
    1205                1210                1215

Glu Gln  Tyr Ile Lys Trp Pro  Trp Tyr Ile Trp Leu  Gly Phe Ile
    1220                1225                1230

Ala Gly  Leu Ile Ala Ile Val  Met Val Thr Ile Met  Leu Cys Cys
    1235                1240                1245

Met Thr  Ser Cys Cys Ser Cys  Leu Lys Gly Cys Cys  Ser Cys Gly
    1250                1255                1260

Ser Cys  Cys Lys Phe Asp Glu  Asp Asp Ser Glu Pro  Val Leu Lys
    1265                1270                1275

Gly Val  Lys Leu His Tyr Thr
    1280                1285


<210> SEQ ID NO 20
<211> LENGTH: 1285
<212> TYPE: PRT
<213> ORGANISM: Unknown
<220> FEATURE:
<223> OTHER INFORMATION: SARS-CoV-2 spike protein

<400> SEQUENCE: 20

Met Asp Ala Met Lys Arg Gly Leu Cys Cys Val Leu Leu Leu Cys Gly
1               5                   10                  15

Ala Val Phe Val Ser Pro Ser Gly Thr Gly Ser Val Asn Leu Thr Thr
            20                  25                  30

Arg Thr Gln Leu Pro Pro Ala Tyr Thr Asn Ser Phe Thr Arg Gly Val
        35                  40                  45

Tyr Tyr Pro Asp Lys Val Phe Arg Ser Ser Val Leu His Ser Thr Gln
    50                  55                  60

Asp Leu Phe Leu Pro Phe Phe Ser Asn Val Thr Trp Phe His Ala Ile
65                  70                  75                  80

His Val Ser Gly Thr Asn Gly Thr Lys Arg Phe Asp Asn Pro Val Leu
                85                  90                  95

Pro Phe Asn Asp Gly Val Tyr Phe Ala Ser Thr Glu Lys Ser Asn Ile
            100                 105                 110

Ile Arg Gly Trp Ile Phe Gly Thr Thr Leu Asp Ser Lys Thr Gln Ser
        115                 120                 125

Leu Leu Ile Val Asn Asn Ala Thr Asn Val Val Ile Lys Val Cys Glu
    130                 135                 140

Phe Gln Phe Cys Asn Asp Pro Phe Leu Gly Val Tyr Tyr His Lys Asn
145                 150                 155                 160

Asn Lys Ser Trp Met Glu Ser Glu Phe Arg Val Tyr Ser Ser Ala Asn
                165                 170                 175

Asn Cys Thr Phe Glu Tyr Val Ser Gln Pro Phe Leu Met Asp Leu Glu
            180                 185                 190

Gly Lys Gln Gly Asn Phe Lys Asn Leu Arg Glu Phe Val Phe Lys Asn
        195                 200                 205

Ile Asp Gly Tyr Phe Lys Ile Tyr Ser Lys His Thr Pro Ile Asn Leu
    210                 215                 220

Val Arg Asp Leu Pro Gln Gly Phe Ser Ala Leu Glu Pro Leu Val Asp
225                 230                 235                 240

Leu Pro Ile Gly Ile Asn Ile Thr Arg Phe Gln Thr Leu Leu Ala Leu
                245                 250                 255

His Arg Ser Tyr Leu Thr Pro Gly Asp Ser Ser Ser Gly Trp Thr Ala
            260                 265                 270

Gly Ala Ala Ala Tyr Tyr Val Gly Tyr Leu Gln Pro Arg Thr Phe Leu
```

-continued

```
        275                 280                 285

Leu Lys Tyr Asn Glu Asn Gly Thr Ile Thr Asp Ala Val Asp Cys Ala
    290                 295                 300

Leu Asp Pro Leu Ser Glu Thr Lys Cys Thr Leu Lys Ser Phe Thr Val
305                 310                 315                 320

Glu Lys Gly Ile Tyr Gln Thr Ser Asn Phe Arg Val Gln Pro Thr Glu
                325                 330                 335

Ser Ile Val Arg Phe Pro Asn Ile Thr Asn Leu Cys Pro Phe Gly Glu
            340                 345                 350

Val Phe Asn Ala Thr Arg Phe Ala Ser Val Tyr Ala Trp Asn Arg Lys
        355                 360                 365

Arg Ile Ser Asn Cys Val Ala Asp Tyr Ser Val Leu Tyr Asn Ser Ala
    370                 375                 380

Ser Phe Ser Thr Phe Lys Cys Tyr Gly Val Ser Pro Thr Lys Leu Asn
385                 390                 395                 400

Asp Leu Cys Phe Thr Asn Val Tyr Ala Asp Ser Phe Val Ile Arg Gly
                405                 410                 415

Asp Glu Val Arg Gln Ile Ala Pro Gly Gln Thr Gly Lys Ile Ala Asp
            420                 425                 430

Tyr Asn Tyr Lys Leu Pro Asp Asp Phe Thr Gly Cys Val Ile Ala Trp
        435                 440                 445

Asn Ser Asn Asn Leu Asp Ser Lys Val Gly Gly Asn Tyr Asn Tyr Leu
    450                 455                 460

Tyr Arg Leu Phe Arg Lys Ser Asn Leu Lys Pro Phe Glu Arg Asp Ile
465                 470                 475                 480

Ser Thr Glu Ile Tyr Gln Ala Gly Ser Thr Pro Cys Asn Gly Val Glu
                485                 490                 495

Gly Phe Asn Cys Tyr Phe Pro Leu Gln Ser Tyr Gly Phe Gln Pro Thr
            500                 505                 510

Asn Gly Val Gly Tyr Gln Pro Tyr Arg Val Val Val Leu Ser Phe Glu
        515                 520                 525

Leu Leu His Ala Pro Ala Thr Val Cys Gly Pro Lys Lys Ser Thr Asn
    530                 535                 540

Leu Val Lys Asn Lys Cys Val Asn Phe Asn Phe Asn Gly Leu Thr Gly
545                 550                 555                 560

Thr Gly Val Leu Thr Glu Ser Asn Lys Lys Phe Leu Pro Phe Gln Gln
                565                 570                 575

Phe Gly Arg Asp Ile Ala Asp Thr Thr Asp Ala Val Arg Asp Pro Gln
            580                 585                 590

Thr Leu Glu Ile Leu Asp Ile Thr Pro Cys Ser Phe Gly Gly Val Ser
        595                 600                 605

Val Ile Thr Pro Gly Thr Asn Thr Ser Asn Gln Val Ala Val Leu Tyr
    610                 615                 620

Gln Asp Val Asn Cys Thr Glu Val Pro Val Ala Ile His Ala Asp Gln
625                 630                 635                 640

Leu Thr Pro Thr Trp Arg Val Tyr Ser Thr Gly Ser Asn Val Phe Gln
                645                 650                 655

Thr Arg Ala Gly Cys Leu Ile Gly Ala Glu His Val Asn Asn Ser Tyr
            660                 665                 670

Glu Cys Asp Ile Pro Ile Gly Ala Gly Ile Cys Ala Ser Tyr Gln Thr
        675                 680                 685

Gln Thr Asn Ser Pro Ser Gly Ala Gly Ser Val Ala Ser Gln Ser Ile
    690                 695                 700
```

-continued

```
Ile Ala Tyr Thr Met Ser Leu Gly Ala Glu Asn Ser Val Ala Tyr Ser
705                 710                 715                 720

Asn Asn Ser Ile Ala Ile Pro Thr Asn Phe Thr Ile Ser Val Thr Thr
                725                 730                 735

Glu Ile Leu Pro Val Ser Met Thr Lys Thr Ser Val Asp Cys Thr Met
            740                 745                 750

Tyr Ile Cys Gly Asp Ser Thr Glu Cys Ser Asn Leu Leu Leu Gln Tyr
        755                 760                 765

Gly Ser Phe Cys Thr Gln Leu Asn Arg Ala Leu Thr Gly Ile Ala Val
    770                 775                 780

Glu Gln Asp Lys Asn Thr Gln Glu Val Phe Ala Gln Val Lys Gln Ile
785                 790                 795                 800

Tyr Lys Thr Pro Pro Ile Lys Asp Phe Gly Gly Phe Asn Phe Ser Gln
                805                 810                 815

Ile Leu Pro Asp Pro Ser Lys Pro Ser Lys Gln Ser Phe Ile Glu Asp
            820                 825                 830

Pro Leu Phe Asn Lys Val Thr Leu Ala Asp Pro Gly Phe Ile Lys Gln
        835                 840                 845

Tyr Gly Asp Cys Leu Gly Asp Ile Ala Ala Arg Asp Leu Ile Cys Ala
    850                 855                 860

Gln Lys Phe Asn Gly Leu Thr Val Leu Pro Pro Leu Leu Thr Asp Glu
865                 870                 875                 880

Met Ile Ala Gln Tyr Thr Ser Ala Leu Leu Ala Gly Thr Ile Thr Ser
                885                 890                 895

Gly Trp Thr Phe Gly Ala Gly Ala Ala Leu Gln Ile Pro Phe Ala Met
            900                 905                 910

Gln Met Ala Tyr Arg Phe Asn Gly Ile Gly Val Thr Gln Asn Val Leu
        915                 920                 925

Tyr Glu Asn Gln Lys Leu Ile Ala Asn Gln Phe Asn Ser Ala Ile Gly
    930                 935                 940

Lys Ile Gln Asp Ser Leu Ser Ser Thr Ala Ser Ala Leu Gly Lys Leu
945                 950                 955                 960

Gln Asp Val Val Asn Gln Asn Ala Gln Ala Leu Asn Thr Leu Val Lys
                965                 970                 975

Gln Leu Ser Ser Asn Phe Gly Ala Ile Ser Ser Val Leu Asn Asp Ile
            980                 985                 990

Leu Ser Arg Leu Asp Pro Pro Glu  Ala Glu Val Gln Ile  Asp Arg Leu
        995                 1000                1005

Ile Thr  Gly Arg Leu Gln Ser  Leu Gln Thr Tyr Val  Thr Gln Gln
    1010                1015                1020

Leu Ile  Arg Ala Ala Glu Ile  Arg Ala Ser Ala Asn  Leu Ala Ala
    1025                1030                1035

Thr Lys  Met Ser Glu Cys Val  Leu Gly Gln Ser Lys  Arg Val Asp
    1040                1045                1050

Phe Cys  Gly Lys Gly Tyr His  Leu Met Ser Phe Pro  Gln Ser Ala
    1055                1060                1065

Pro His  Gly Val Val Phe Leu  His Val Thr Tyr Val  Pro Ala Gln
    1070                1075                1080

Glu Lys  Asn Phe Thr Thr Ala  Pro Ala Ile Cys His  Asp Gly Lys
    1085                1090                1095

Ala His  Phe Pro Arg Glu Gly  Val Phe Val Ser Asn  Gly Thr His
    1100                1105                1110
```

-continued

Trp Phe Val Thr Gln Arg Asn Phe Tyr Glu Pro Gln Ile Ile Thr
1115 1120 1125

Thr Asp Asn Thr Phe Val Ser Gly Asn Cys Asp Val Val Ile Gly
1130 1135 1140

Ile Val Asn Asn Thr Val Tyr Asp Pro Leu Gln Pro Glu Leu Asp
1145 1150 1155

Ser Phe Lys Glu Glu Leu Asp Lys Tyr Phe Lys Asn His Thr Ser
1160 1165 1170

Pro Asp Val Asp Leu Gly Asp Ile Ser Gly Ile Asn Ala Ser Val
1175 1180 1185

Val Asn Ile Gln Lys Glu Ile Asp Arg Leu Asn Glu Val Ala Lys
1190 1195 1200

Asn Leu Asn Glu Ser Leu Ile Asp Leu Gln Glu Leu Gly Lys Tyr
1205 1210 1215

Glu Gln Tyr Ile Lys Trp Pro Trp Tyr Ile Trp Leu Gly Phe Ile
1220 1225 1230

Ala Gly Leu Ile Ala Ile Val Met Val Thr Ile Met Leu Cys Cys
1235 1240 1245

Met Thr Ser Cys Cys Ser Cys Leu Lys Gly Cys Cys Ser Cys Gly
1250 1255 1260

Ser Cys Cys Lys Phe Asp Glu Asp Asp Ser Glu Pro Val Leu Lys
1265 1270 1275

Gly Val Ala Leu Ala Tyr Thr
1280 1285

<210> SEQ ID NO 21
<211> LENGTH: 615
<212> TYPE: PRT
<213> ORGANISM: Unknown
<220> FEATURE:
<223> OTHER INFORMATION: SARS-CoV-2 spike protein

<400> SEQUENCE: 21

Met Asp Ala Met Lys Arg Gly Leu Cys Cys Val Leu Leu Leu Cys Gly
1 5 10 15

Ala Val Phe Val Ser Pro Ser Gly Thr Gly Ser Ser Val Ala Ser Gln
20 25 30

Ser Ile Ile Ala Tyr Thr Met Ser Leu Gly Ala Glu Asn Ser Val Ala
35 40 45

Tyr Ser Asn Asn Ser Ile Ala Ile Pro Thr Asn Phe Thr Ile Ser Val
50 55 60

Thr Thr Glu Ile Leu Pro Val Ser Met Thr Lys Thr Ser Val Asp Cys
65 70 75 80

Thr Met Tyr Ile Cys Gly Asp Ser Thr Glu Cys Ser Asn Leu Leu Leu
85 90 95

Gln Tyr Gly Ser Phe Cys Thr Gln Leu Asn Arg Ala Leu Thr Gly Ile
100 105 110

Ala Val Glu Gln Asp Lys Asn Thr Gln Glu Val Phe Ala Gln Val Lys
115 120 125

Gln Ile Tyr Lys Thr Pro Pro Ile Lys Asp Phe Gly Gly Phe Asn Phe
130 135 140

Ser Gln Ile Leu Pro Asp Pro Ser Lys Pro Ser Lys Arg Ser Phe Ile
145 150 155 160

Glu Asp Leu Leu Phe Asn Lys Val Thr Leu Ala Asp Ala Gly Phe Ile
165 170 175

-continued

```
Lys Gln Tyr Gly Asp Cys Leu Gly Asp Ile Ala Ala Arg Asp Leu Ile
            180                 185                 190

Cys Ala Gln Lys Phe Asn Gly Leu Thr Val Leu Pro Pro Leu Leu Thr
        195                 200                 205

Asp Glu Met Ile Ala Gln Tyr Thr Ser Ala Leu Leu Ala Gly Thr Ile
    210                 215                 220

Thr Ser Gly Trp Thr Phe Gly Ala Gly Ala Ala Leu Gln Ile Pro Phe
225                 230                 235                 240

Ala Met Gln Met Ala Tyr Arg Phe Asn Gly Ile Gly Val Thr Gln Asn
                245                 250                 255

Val Leu Tyr Glu Asn Gln Lys Leu Ile Ala Asn Gln Phe Asn Ser Ala
            260                 265                 270

Ile Gly Lys Ile Gln Asp Ser Leu Ser Ser Thr Ala Ser Ala Leu Gly
        275                 280                 285

Lys Leu Gln Asp Val Val Asn Gln Asn Ala Gln Ala Leu Asn Thr Leu
    290                 295                 300

Val Lys Gln Leu Ser Ser Asn Phe Gly Ala Ile Ser Ser Val Leu Asn
305                 310                 315                 320

Asp Ile Leu Ser Arg Leu Asp Lys Val Glu Ala Glu Val Gln Ile Asp
                325                 330                 335

Arg Leu Ile Thr Gly Arg Leu Gln Ser Leu Gln Thr Tyr Val Thr Gln
            340                 345                 350

Gln Leu Ile Arg Ala Ala Glu Ile Arg Ala Ser Ala Asn Leu Ala Ala
        355                 360                 365

Thr Lys Met Ser Glu Cys Val Leu Gly Gln Ser Lys Arg Val Asp Phe
    370                 375                 380

Cys Gly Lys Gly Tyr His Leu Met Ser Phe Pro Gln Ser Ala Pro His
385                 390                 395                 400

Gly Val Val Phe Leu His Val Thr Tyr Val Pro Ala Gln Glu Lys Asn
                405                 410                 415

Phe Thr Thr Ala Pro Ala Ile Cys His Asp Gly Lys Ala His Phe Pro
            420                 425                 430

Arg Glu Gly Val Phe Val Ser Asn Gly Thr His Trp Phe Val Thr Gln
        435                 440                 445

Arg Asn Phe Tyr Glu Pro Gln Ile Ile Thr Thr Asp Asn Thr Phe Val
    450                 455                 460

Ser Gly Asn Cys Asp Val Val Ile Gly Ile Val Asn Asn Thr Val Tyr
465                 470                 475                 480

Asp Pro Leu Gln Pro Glu Leu Asp Ser Phe Lys Glu Glu Leu Asp Lys
                485                 490                 495

Tyr Phe Lys Asn His Thr Ser Pro Asp Val Asp Leu Gly Asp Ile Ser
            500                 505                 510

Gly Ile Asn Ala Ser Val Val Asn Ile Gln Lys Glu Ile Asp Arg Leu
        515                 520                 525

Asn Glu Val Ala Lys Asn Leu Asn Glu Ser Leu Ile Asp Leu Gln Glu
    530                 535                 540

Leu Gly Lys Tyr Glu Gln Tyr Ile Lys Trp Pro Trp Tyr Ile Trp Leu
545                 550                 555                 560

Gly Phe Ile Ala Gly Leu Ile Ala Ile Val Met Val Thr Ile Met Leu
                565                 570                 575

Cys Cys Met Thr Ser Cys Cys Ser Cys Leu Lys Gly Cys Cys Ser Cys
            580                 585                 590

Gly Ser Cys Cys Lys Phe Asp Glu Asp Asp Ser Glu Pro Val Leu Lys
```

```
        595                 600                 605

Gly Val Lys Leu His Tyr Thr
    610                 615


<210> SEQ ID NO 22
<211> LENGTH: 485
<212> TYPE: PRT
<213> ORGANISM: Unknown
<220> FEATURE:
<223> OTHER INFORMATION: SARS-CoV-2 spike protein

<400> SEQUENCE: 22

Met Asp Ala Met Lys Arg Gly Leu Cys Cys Val Leu Leu Leu Cys Gly
1               5                   10                  15

Ala Val Phe Val Ser Pro Ser Gly Thr Gly Ser Ser Phe Ile Glu Asp
            20                  25                  30

Leu Leu Phe Asn Lys Val Thr Leu Ala Asp Ala Gly Phe Ile Lys Gln
        35                  40                  45

Tyr Gly Asp Cys Leu Gly Asp Ile Ala Ala Arg Asp Leu Ile Cys Ala
    50                  55                  60

Gln Lys Phe Asn Gly Leu Thr Val Leu Pro Pro Leu Leu Thr Asp Glu
65                  70                  75                  80

Met Ile Ala Gln Tyr Thr Ser Ala Leu Leu Ala Gly Thr Ile Thr Ser
                85                  90                  95

Gly Trp Thr Phe Gly Ala Gly Ala Ala Leu Gln Ile Pro Phe Ala Met
            100                 105                 110

Gln Met Ala Tyr Arg Phe Asn Gly Ile Gly Val Thr Gln Asn Val Leu
        115                 120                 125

Tyr Glu Asn Gln Lys Leu Ile Ala Asn Gln Phe Asn Ser Ala Ile Gly
    130                 135                 140

Lys Ile Gln Asp Ser Leu Ser Ser Thr Ala Ser Ala Leu Gly Lys Leu
145                 150                 155                 160

Gln Asp Val Val Asn Gln Asn Ala Gln Ala Leu Asn Thr Leu Val Lys
                165                 170                 175

Gln Leu Ser Ser Asn Phe Gly Ala Ile Ser Ser Val Leu Asn Asp Ile
            180                 185                 190

Leu Ser Arg Leu Asp Lys Val Glu Ala Glu Val Gln Ile Asp Arg Leu
        195                 200                 205

Ile Thr Gly Arg Leu Gln Ser Leu Gln Thr Tyr Val Thr Gln Gln Leu
    210                 215                 220

Ile Arg Ala Ala Glu Ile Arg Ala Ser Ala Asn Leu Ala Ala Thr Lys
225                 230                 235                 240

Met Ser Glu Cys Val Leu Gly Gln Ser Lys Arg Val Asp Phe Cys Gly
                245                 250                 255

Lys Gly Tyr His Leu Met Ser Phe Pro Gln Ser Ala Pro His Gly Val
            260                 265                 270

Val Phe Leu His Val Thr Tyr Val Pro Ala Gln Glu Lys Asn Phe Thr
        275                 280                 285

Thr Ala Pro Ala Ile Cys His Asp Gly Lys Ala His Phe Pro Arg Glu
    290                 295                 300

Gly Val Phe Val Ser Asn Gly Thr His Trp Phe Val Thr Gln Arg Asn
305                 310                 315                 320

Phe Tyr Glu Pro Gln Ile Ile Thr Thr Asp Asn Thr Phe Val Ser Gly
                325                 330                 335

Asn Cys Asp Val Val Ile Gly Ile Val Asn Asn Thr Val Tyr Asp Pro
```

```
            340                 345                 350

Leu Gln Pro Glu Leu Asp Ser Phe Lys Glu Glu Leu Asp Lys Tyr Phe
        355                 360                 365

Lys Asn His Thr Ser Pro Asp Val Asp Leu Gly Asp Ile Ser Gly Ile
    370                 375                 380

Asn Ala Ser Val Val Asn Ile Gln Lys Glu Ile Asp Arg Leu Asn Glu
385                 390                 395                 400

Val Ala Lys Asn Leu Asn Glu Ser Leu Ile Asp Leu Gln Glu Leu Gly
                405                 410                 415

Lys Tyr Glu Gln Tyr Ile Lys Trp Pro Trp Tyr Ile Trp Leu Gly Phe
            420                 425                 430

Ile Ala Gly Leu Ile Ala Ile Val Met Val Thr Ile Met Leu Cys Cys
        435                 440                 445

Met Thr Ser Cys Cys Ser Cys Leu Lys Gly Cys Cys Ser Cys Gly Ser
    450                 455                 460

Cys Cys Lys Phe Asp Glu Asp Asp Ser Glu Pro Val Leu Lys Gly Val
465                 470                 475                 480

Lys Leu His Tyr Thr
                485


<210> SEQ ID NO 23
<211> LENGTH: 393
<212> TYPE: PRT
<213> ORGANISM: Unknown
<220> FEATURE:
<223> OTHER INFORMATION: SARS-CoV-2 spike protein

<400> SEQUENCE: 23

Met Asp Ala Met Lys Arg Gly Leu Cys Cys Val Leu Leu Leu Cys Gly
1               5                   10                  15

Ala Val Phe Val Ser Pro Ser Gly Thr Gly Ser Gly Ile Gly Val Thr
            20                  25                  30

Gln Asn Val Leu Tyr Glu Asn Gln Lys Leu Ile Ala Asn Gln Phe Asn
        35                  40                  45

Ser Ala Ile Gly Lys Ile Gln Asp Ser Leu Ser Ser Thr Ala Ser Ala
    50                  55                  60

Leu Gly Lys Leu Gln Asp Val Val Asn Gln Asn Ala Gln Ala Leu Asn
65                  70                  75                  80

Thr Leu Val Lys Gln Leu Ser Ser Asn Phe Gly Ala Ile Ser Ser Val
                85                  90                  95

Leu Asn Asp Ile Leu Ser Arg Leu Asp Lys Val Glu Ala Glu Val Gln
            100                 105                 110

Ile Asp Arg Leu Ile Thr Gly Arg Leu Gln Ser Leu Gln Thr Tyr Val
        115                 120                 125

Thr Gln Gln Leu Ile Arg Ala Ala Glu Ile Arg Ala Ser Ala Asn Leu
    130                 135                 140

Ala Ala Thr Lys Met Ser Glu Cys Val Leu Gly Gln Ser Lys Arg Val
145                 150                 155                 160

Asp Phe Cys Gly Lys Gly Tyr His Leu Met Ser Phe Pro Gln Ser Ala
                165                 170                 175

Pro His Gly Val Val Phe Leu His Val Thr Tyr Val Pro Ala Gln Glu
            180                 185                 190

Lys Asn Phe Thr Thr Ala Pro Ala Ile Cys His Asp Gly Lys Ala His
        195                 200                 205

Phe Pro Arg Glu Gly Val Phe Val Ser Asn Gly Thr His Trp Phe Val
```

```
    210                 215                 220

Thr Gln Arg Asn Phe Tyr Glu Pro Gln Ile Ile Thr Thr Asp Asn Thr
225                 230                 235                 240

Phe Val Ser Gly Asn Cys Asp Val Val Ile Gly Ile Val Asn Asn Thr
                245                 250                 255

Val Tyr Asp Pro Leu Gln Pro Glu Leu Asp Ser Phe Lys Glu Glu Leu
            260                 265                 270

Asp Lys Tyr Phe Lys Asn His Thr Ser Pro Asp Val Asp Leu Gly Asp
        275                 280                 285

Ile Ser Gly Ile Asn Ala Ser Val Val Asn Ile Gln Lys Glu Ile Asp
    290                 295                 300

Arg Leu Asn Glu Val Ala Lys Asn Leu Asn Glu Ser Leu Ile Asp Leu
305                 310                 315                 320

Gln Glu Leu Gly Lys Tyr Glu Gln Tyr Ile Lys Trp Pro Trp Tyr Ile
                325                 330                 335

Trp Leu Gly Phe Ile Ala Gly Leu Ile Ala Ile Val Met Val Thr Ile
            340                 345                 350

Met Leu Cys Cys Met Thr Ser Cys Cys Ser Cys Leu Lys Gly Cys Cys
        355                 360                 365

Ser Cys Gly Ser Cys Cys Lys Phe Asp Glu Asp Asp Ser Glu Pro Val
    370                 375                 380

Leu Lys Gly Val Lys Leu His Tyr Thr
385                 390
```

<210> SEQ ID NO 24
<211> LENGTH: 444
<212> TYPE: PRT
<213> ORGANISM: Unknown
<220> FEATURE:
<223> OTHER INFORMATION: SARS-CoV-2 spike protein

<400> SEQUENCE: 24

```
Gly Pro Pro Leu Ser Ser Ser Leu Gly Leu Ala Leu Leu Leu Leu Leu
1               5                   10                  15

Leu Ala Leu Leu Phe Trp Leu Tyr Ile Val Met Gly Leu Thr Val Leu
            20                  25                  30

Pro Pro Leu Leu Thr Asp Glu Met Ile Ala Gln Tyr Thr Ser Ala Leu
        35                  40                  45

Leu Ala Gly Thr Ile Thr Ser Gly Trp Thr Phe Gly Ala Gly Ala Ala
    50                  55                  60

Leu Gln Ile Pro Phe Ala Met Gln Met Ala Tyr Arg Phe Asn Gly Ile
65                  70                  75                  80

Gly Val Thr Gln Asn Val Leu Tyr Glu Asn Gln Lys Leu Ile Ala Asn
                85                  90                  95

Gln Phe Asn Ser Ala Ile Gly Lys Ile Gln Asp Ser Leu Ser Ser Thr
            100                 105                 110

Ala Ser Ala Leu Gly Lys Leu Gln Asp Val Val Asn Gln Asn Ala Gln
        115                 120                 125

Ala Leu Asn Thr Leu Val Lys Gln Leu Ser Ser Asn Phe Gly Ala Ile
    130                 135                 140

Ser Ser Val Leu Asn Asp Ile Leu Ser Arg Leu Asp Lys Val Glu Ala
145                 150                 155                 160

Glu Val Gln Ile Asp Arg Leu Ile Thr Gly Arg Leu Gln Ser Leu Gln
                165                 170                 175

Thr Tyr Val Thr Gln Gln Leu Ile Arg Ala Ala Glu Ile Arg Ala Ser
```

180 185 190

Ala Asn Leu Ala Ala Thr Lys Met Ser Glu Cys Val Leu Gly Gln Ser
195 200 205

Lys Arg Val Asp Phe Cys Gly Lys Gly Tyr His Leu Met Ser Phe Pro
210 215 220

Gln Ser Ala Pro His Gly Val Val Phe Leu His Val Thr Tyr Val Pro
225 230 235 240

Ala Gln Glu Lys Asn Phe Thr Thr Ala Pro Ala Ile Cys His Asp Gly
245 250 255

Lys Ala His Phe Pro Arg Glu Gly Val Phe Val Ser Asn Gly Thr His
260 265 270

Trp Phe Val Thr Gln Arg Asn Phe Tyr Glu Pro Gln Ile Ile Thr Thr
275 280 285

Asp Asn Thr Phe Val Ser Gly Asn Cys Asp Val Val Ile Gly Ile Val
290 295 300

Asn Asn Thr Val Tyr Asp Pro Leu Gln Pro Glu Leu Asp Ser Phe Lys
305 310 315 320

Glu Glu Leu Asp Lys Tyr Phe Lys Asn His Thr Ser Pro Asp Val Asp
325 330 335

Leu Gly Asp Ile Ser Gly Ile Asn Ala Ser Val Val Asn Ile Gln Lys
340 345 350

Glu Ile Asp Arg Leu Asn Glu Val Ala Lys Asn Leu Asn Glu Ser Leu
355 360 365

Ile Asp Leu Gln Glu Leu Gly Lys Tyr Glu Gln Tyr Ile Lys Trp Pro
370 375 380

Trp Tyr Ile Trp Leu Gly Phe Ile Ala Gly Leu Ile Ala Ile Val Met
385 390 395 400

Val Thr Ile Met Leu Cys Cys Met Thr Ser Cys Cys Ser Cys Leu Lys
405 410 415

Gly Cys Cys Ser Cys Gly Ser Cys Cys Lys Phe Asp Glu Asp Asp Ser
420 425 430

Glu Pro Val Leu Lys Gly Val Lys Leu His Tyr Thr
435 440

<210> SEQ ID NO 25
<211> LENGTH: 16
<212> TYPE: PRT
<213> ORGANISM: Unknown
<220> FEATURE:
<223> OTHER INFORMATION: SARS-CoV-2 spike protein

<400> SEQUENCE: 25

Gln Thr Gln Thr Asn Ser Pro Arg Arg Ala Arg Ser Val Ala Ser Gln
1 5 10 15

<210> SEQ ID NO 26
<211> LENGTH: 9
<212> TYPE: PRT
<213> ORGANISM: Unknown
<220> FEATURE:
<223> OTHER INFORMATION: SARS-CoV-2 spike protein

<400> SEQUENCE: 26

Pro Ser Lys Pro Ser Lys Arg Ser Phe
1 5

<210> SEQ ID NO 27
<211> LENGTH: 8

<212> TYPE: PRT
<213> ORGANISM: Unknown
<220> FEATURE:
<223> OTHER INFORMATION: peptide

<400> SEQUENCE: 27

Ile Leu Leu Asn Lys His Ile Asp
1 5

<210> SEQ ID NO 28
<211> LENGTH: 18
<212> TYPE: PRT
<213> ORGANISM: Unknown
<220> FEATURE:
<223> OTHER INFORMATION: peptide

<400> SEQUENCE: 28

Ala Phe Phe Gly Met Ser Arg Ile Gly Met Glu Val Thr Pro Ser Gly
1 5 10 15

Thr Trp

<210> SEQ ID NO 29
<211> LENGTH: 10
<212> TYPE: PRT
<213> ORGANISM: Unknown
<220> FEATURE:
<223> OTHER INFORMATION: peptide

<400> SEQUENCE: 29

Met Glu Val Thr Pro Ser Gly Thr Trp Leu
1 5 10

<210> SEQ ID NO 30
<211> LENGTH: 9
<212> TYPE: PRT
<213> ORGANISM: Unknown
<220> FEATURE:
<223> OTHER INFORMATION: peptide

<400> SEQUENCE: 30

Gly Met Ser Arg Ile Gly Met Glu Val
1 5

<210> SEQ ID NO 31
<211> LENGTH: 9
<212> TYPE: PRT
<213> ORGANISM: Unknown
<220> FEATURE:
<223> OTHER INFORMATION: peptide

<400> SEQUENCE: 31

Ile Leu Leu Asn Lys His Ile Asp Ala
1 5

<210> SEQ ID NO 32
<211> LENGTH: 9
<212> TYPE: PRT
<213> ORGANISM: Unknown
<220> FEATURE:
<223> OTHER INFORMATION: peptide

<400> SEQUENCE: 32

Ala Leu Asn Thr Pro Lys Asp His Ile
1 5

<210> SEQ ID NO 33

<211> LENGTH: 17
<212> TYPE: PRT
<213> ORGANISM: Unknown
<220> FEATURE:
<223> OTHER INFORMATION: peptide

<400> SEQUENCE: 33

Ile Arg Gln Gly Thr Asp Tyr Lys His Trp Pro Gln Ile Ala Gln Phe
1 5 10 15

Ala

<210> SEQ ID NO 34
<211> LENGTH: 17
<212> TYPE: PRT
<213> ORGANISM: Unknown
<220> FEATURE:
<223> OTHER INFORMATION: peptide

<400> SEQUENCE: 34

Lys His Trp Pro Gln Ile Ala Gln Phe Ala Pro Ser Ala Ser Ala Phe
1 5 10 15

Phe

<210> SEQ ID NO 35
<211> LENGTH: 9
<212> TYPE: PRT
<213> ORGANISM: Unknown
<220> FEATURE:
<223> OTHER INFORMATION: peptide

<400> SEQUENCE: 35

Leu Ala Leu Leu Leu Leu Asp Arg Leu
1 5

<210> SEQ ID NO 36
<211> LENGTH: 9
<212> TYPE: PRT
<213> ORGANISM: Unknown
<220> FEATURE:
<223> OTHER INFORMATION: pepdite

<400> SEQUENCE: 36

Leu Leu Leu Asp Arg Leu Asn Gln Leu
1 5

<210> SEQ ID NO 37
<211> LENGTH: 18
<212> TYPE: PRT
<213> ORGANISM: Unknown
<220> FEATURE:
<223> OTHER INFORMATION: peptide

<400> SEQUENCE: 37

Leu Leu Asn Lys His Ile Asp Ala Tyr Lys Thr Phe Pro Pro Thr Glu
1 5 10 15

Pro Lys

<210> SEQ ID NO 38
<211> LENGTH: 9
<212> TYPE: PRT
<213> ORGANISM: Unknown
<220> FEATURE:
<223> OTHER INFORMATION: peptide

<400> SEQUENCE: 38

Leu Gln Leu Pro Gln Gly Thr Thr Leu
1               5

<210> SEQ ID NO 39
<211> LENGTH: 15
<212> TYPE: PRT
<213> ORGANISM: Unknown
<220> FEATURE:
<223> OTHER INFORMATION: peptide

<400> SEQUENCE: 39

Ala Gln Phe Ala Pro Ser Ala Ser Ala Phe Phe Gly Met Ser Arg
1               5                   10                  15

<210> SEQ ID NO 40
<211> LENGTH: 18
<212> TYPE: PRT
<213> ORGANISM: Unknown
<220> FEATURE:
<223> OTHER INFORMATION: peptide

<400> SEQUENCE: 40

Ala Gln Phe Ala Pro Ser Ala Ser Ala Phe Phe Gly Met Ser Arg Ile
1               5                   10                  15

Gly Met

<210> SEQ ID NO 41
<211> LENGTH: 15
<212> TYPE: PRT
<213> ORGANISM: Unknown
<220> FEATURE:
<223> OTHER INFORMATION: peptide

<400> SEQUENCE: 41

Arg Arg Pro Gln Gly Leu Pro Asn Asn Thr Ala Ser Trp Phe Thr
1               5                   10                  15

<210> SEQ ID NO 42
<211> LENGTH: 16
<212> TYPE: PRT
<213> ORGANISM: Unknown
<220> FEATURE:
<223> OTHER INFORMATION: peptide

<400> SEQUENCE: 42

Tyr Lys Thr Phe Pro Pro Thr Glu Pro Lys Lys Asp Lys Lys Lys Lys
1               5                   10                  15

<210> SEQ ID NO 43
<211> LENGTH: 16
<212> TYPE: PRT
<213> ORGANISM: Unknown
<220> FEATURE:
<223> OTHER INFORMATION: peptide

<400> SEQUENCE: 43

Gly Ala Ala Leu Gln Ile Pro Phe Ala Met Gln Met Ala Tyr Arg Phe
1               5                   10                  15

<210> SEQ ID NO 44
<211> LENGTH: 16
<212> TYPE: PRT
<213> ORGANISM: Unknown
<220> FEATURE:
<223> OTHER INFORMATION: peptide

<400> SEQUENCE: 44

-continued

```
Met Ala Tyr Arg Phe Asn Gly Ile Gly Val Thr Gln Asn Val Leu Tyr
1               5                   10                  15


<210> SEQ ID NO 45
<211> LENGTH: 18
<212> TYPE: PRT
<213> ORGANISM: Unknown
<220> FEATURE:
<223> OTHER INFORMATION: peptide

<400> SEQUENCE: 45

Gln Leu Ile Arg Ala Ala Glu Ile Arg Ala Ser Ala Asn Leu Ala Ala
1               5                   10                  15

Thr Lys


<210> SEQ ID NO 46
<211> LENGTH: 16
<212> TYPE: PRT
<213> ORGANISM: Unknown
<220> FEATURE:
<223> OTHER INFORMATION: peptide

<400> SEQUENCE: 46

Pro Glu Pro Thr Ile Asp Glu Phe Ile Ala Gly Leu Ile Ala Ile Val
1               5                   10                  15


<210> SEQ ID NO 47
<211> LENGTH: 9
<212> TYPE: PRT
<213> ORGANISM: Unknown
<220> FEATURE:
<223> OTHER INFORMATION: peptide

<400> SEQUENCE: 47

Ala Leu Asn Thr Leu Val Lys Gln Leu
1               5


<210> SEQ ID NO 48
<211> LENGTH: 9
<212> TYPE: PRT
<213> ORGANISM: Unknown
<220> FEATURE:
<223> OTHER INFORMATION: peptide

<400> SEQUENCE: 48

Leu Ile Thr Gly Arg Leu Gln Ser Leu
1               5


<210> SEQ ID NO 49
<211> LENGTH: 9
<212> TYPE: PRT
<213> ORGANISM: Unknown
<220> FEATURE:
<223> OTHER INFORMATION: peptide

<400> SEQUENCE: 49

Asn Leu Asn Glu Ser Leu Ile Asp Leu
1               5


<210> SEQ ID NO 50
<211> LENGTH: 17
<212> TYPE: PRT
<213> ORGANISM: Unknown
<220> FEATURE:
<223> OTHER INFORMATION: peptide
```

<400> SEQUENCE: 50

Gln Ala Leu Asn Thr Leu Val Lys Gln Leu Ser Ser Asn Phe Gly Ala
1 5 10 15

Ile

<210> SEQ ID NO 51
<211> LENGTH: 9
<212> TYPE: PRT
<213> ORGANISM: Unknown
<220> FEATURE:
<223> OTHER INFORMATION: peptide

<400> SEQUENCE: 51

Arg Leu Asn Glu Val Ala Lys Asn Leu
1 5

<210> SEQ ID NO 52
<211> LENGTH: 9
<212> TYPE: PRT
<213> ORGANISM: Unknown
<220> FEATURE:
<223> OTHER INFORMATION: peptide

<400> SEQUENCE: 52

Val Leu Asn Asp Ile Leu Ser Arg Leu
1 5

<210> SEQ ID NO 53
<211> LENGTH: 9
<212> TYPE: PRT
<213> ORGANISM: Unknown
<220> FEATURE:
<223> OTHER INFORMATION: peptide

<400> SEQUENCE: 53

Val Val Phe Leu His Val Thr Tyr Val
1 5

<210> SEQ ID NO 54
<211> LENGTH: 9
<212> TYPE: PRT
<213> ORGANISM: Unknown
<220> FEATURE:
<223> OTHER INFORMATION: peptide

<400> SEQUENCE: 54

Ser Glu Glu Thr Gly Thr Leu Ile Val
1 5

<210> SEQ ID NO 55
<211> LENGTH: 9
<212> TYPE: PRT
<213> ORGANISM: Unknown
<220> FEATURE:
<223> OTHER INFORMATION: peptide

<400> SEQUENCE: 55

Phe Leu Trp Leu Leu Trp Pro Val Thr
1 5

<210> SEQ ID NO 56
<211> LENGTH: 10
<212> TYPE: PRT
<213> ORGANISM: Unknown
<220> FEATURE:
<223> OTHER INFORMATION: peptide

<400> SEQUENCE: 56

Phe Leu Trp Leu Leu Trp Pro Val Thr Leu
1 5 10

<210> SEQ ID NO 57
<211> LENGTH: 15
<212> TYPE: PRT
<213> ORGANISM: Unknown
<220> FEATURE:
<223> OTHER INFORMATION: peptide

<400> SEQUENCE: 57

Phe Leu Trp Leu Leu Trp Pro Val Thr Leu Ala Cys Phe Val Leu
1 5 10 15

<210> SEQ ID NO 58
<211> LENGTH: 15
<212> TYPE: PRT
<213> ORGANISM: Unknown
<220> FEATURE:
<223> OTHER INFORMATION: peptide

<400> SEQUENCE: 58

Ile Lys Asp Leu Pro Lys Glu Ile Thr Val Ala Thr Ser Arg Thr
1 5 10 15

<210> SEQ ID NO 59
<211> LENGTH: 10
<212> TYPE: PRT
<213> ORGANISM: Unknown
<220> FEATURE:
<223> OTHER INFORMATION: peptide

<400> SEQUENCE: 59

Leu Glu Gln Trp Asn Leu Val Ile Gly Phe
1 5 10

<210> SEQ ID NO 60
<211> LENGTH: 9
<212> TYPE: PRT
<213> ORGANISM: Unknown
<220> FEATURE:
<223> OTHER INFORMATION: peptide

<400> SEQUENCE: 60

Leu Phe Ala Arg Thr Arg Ser Met Trp
1 5

<210> SEQ ID NO 61
<211> LENGTH: 9
<212> TYPE: PRT
<213> ORGANISM: Unknown
<220> FEATURE:
<223> OTHER INFORMATION: peptide

<400> SEQUENCE: 61

Leu Trp Leu Leu Trp Pro Val Thr Leu
1 5

<210> SEQ ID NO 62
<211> LENGTH: 9
<212> TYPE: PRT
<213> ORGANISM: Unknown
<220> FEATURE:
<223> OTHER INFORMATION: peptide

<400> SEQUENCE: 62

Leu Trp Pro Val Thr Leu Ala Cys Phe
1 5

<210> SEQ ID NO 63
<211> LENGTH: 9
<212> TYPE: PRT
<213> ORGANISM: Unknown
<220> FEATURE:
<223> OTHER INFORMATION: peptide

<400> SEQUENCE: 63

Ser Glu Glu Thr Gly Thr Leu Ile Val
1 5

<210> SEQ ID NO 64
<211> LENGTH: 10
<212> TYPE: PRT
<213> ORGANISM: Unknown
<220> FEATURE:
<223> OTHER INFORMATION: peptide

<400> SEQUENCE: 64

Met Trp Ser Phe Asn Pro Glu Thr Asn Ile
1 5 10

<210> SEQ ID NO 65
<211> LENGTH: 9
<212> TYPE: PRT
<213> ORGANISM: Unknown
<220> FEATURE:
<223> OTHER INFORMATION: peptide

<400> SEQUENCE: 65

Asn Leu Val Ile Gly Phe Leu Phe Leu
1 5

<210> SEQ ID NO 66
<211> LENGTH: 15
<212> TYPE: PRT
<213> ORGANISM: Unknown
<220> FEATURE:
<223> OTHER INFORMATION: peptide

<400> SEQUENCE: 66

Pro Lys Glu Ile Thr Val Ala Thr Ser Arg Thr Leu Ser Tyr Tyr
1 5 10 15

<210> SEQ ID NO 67
<211> LENGTH: 9
<212> TYPE: PRT
<213> ORGANISM: Unknown
<220> FEATURE:
<223> OTHER INFORMATION: peptide

<400> SEQUENCE: 67

Ala Thr Ser Arg Thr Leu Ser Tyr Tyr
1 5

<210> SEQ ID NO 68
<211> LENGTH: 10
<212> TYPE: PRT
<213> ORGANISM: Unknown
<220> FEATURE:
<223> OTHER INFORMATION: peptide

<400> SEQUENCE: 68

Ala Thr Ser Arg Thr Leu Ser Tyr Tyr Lys
1 5 10

<210> SEQ ID NO 69
<211> LENGTH: 10
<212> TYPE: PRT
<213> ORGANISM: Unknown
<220> FEATURE:
<223> OTHER INFORMATION: peptide

<400> SEQUENCE: 69

Gln Trp Asn Leu Val Ile Gly Phe Leu Phe
1 5 10

<210> SEQ ID NO 70
<211> LENGTH: 9
<212> TYPE: PRT
<213> ORGANISM: Unknown
<220> FEATURE:
<223> OTHER INFORMATION: peptide

<400> SEQUENCE: 70

Arg Tyr Arg Ile Gly Asn Tyr Lys Leu
1 5

<210> SEQ ID NO 71
<211> LENGTH: 9
<212> TYPE: PRT
<213> ORGANISM: Unknown
<220> FEATURE:
<223> OTHER INFORMATION: peptide

<400> SEQUENCE: 71

Ser Glu Leu Val Ile Gly Ala Val Ile
1 5

<210> SEQ ID NO 72
<211> LENGTH: 9
<212> TYPE: PRT
<213> ORGANISM: Unknown
<220> FEATURE:
<223> OTHER INFORMATION: peptide

<400> SEQUENCE: 72

Ser Phe Asn Pro Glu Thr Asn Ile Leu
1 5

<210> SEQ ID NO 73
<211> LENGTH: 9
<212> TYPE: PRT
<213> ORGANISM: Unknown
<220> FEATURE:
<223> OTHER INFORMATION: peptide

<400> SEQUENCE: 73

Ser Met Trp Ser Phe Asn Pro Glu Thr
1 5

<210> SEQ ID NO 74
<211> LENGTH: 9
<212> TYPE: PRT
<213> ORGANISM: Unknown
<220> FEATURE:
<223> OTHER INFORMATION: peptide

<400> SEQUENCE: 74

```
Thr Ser Arg Thr Leu Ser Tyr Tyr Lys
1               5


<210> SEQ ID NO 75
<211> LENGTH: 10
<212> TYPE: PRT
<213> ORGANISM: Unknown
<220> FEATURE:
<223> OTHER INFORMATION: peptide

<400> SEQUENCE: 75

Thr Val Ala Thr Ser Arg Thr Leu Ser Tyr
1               5                   10


<210> SEQ ID NO 76
<211> LENGTH: 9
<212> TYPE: PRT
<213> ORGANISM: Unknown
<220> FEATURE:
<223> OTHER INFORMATION: peptide

<400> SEQUENCE: 76

Trp Leu Leu Trp Pro Val Thr Leu Ala
1               5


<210> SEQ ID NO 77
<211> LENGTH: 10
<212> TYPE: PRT
<213> ORGANISM: Unknown
<220> FEATURE:
<223> OTHER INFORMATION: peptide

<400> SEQUENCE: 77

Trp Pro Val Thr Leu Ala Cys Phe Val Leu
1               5                   10


<210> SEQ ID NO 78
<211> LENGTH: 8
<212> TYPE: PRT
<213> ORGANISM: Unknown
<220> FEATURE:
<223> OTHER INFORMATION: peptide

<400> SEQUENCE: 78

Ile Leu Leu Asn Lys His Ile Asp
1               5


<210> SEQ ID NO 79
<211> LENGTH: 9
<212> TYPE: PRT
<213> ORGANISM: Unknown
<220> FEATURE:
<223> OTHER INFORMATION: peptide

<400> SEQUENCE: 79

Phe Pro Arg Gly Gln Gly Val Pro Ile
1               5


<210> SEQ ID NO 80
<211> LENGTH: 10
<212> TYPE: PRT
<213> ORGANISM: Unknown
<220> FEATURE:
<223> OTHER INFORMATION: peptide

<400> SEQUENCE: 80

Met Glu Val Thr Pro Ser Gly Thr Trp Leu
```

```
1               5                   10


<210> SEQ ID NO 81
<211> LENGTH: 11
<212> TYPE: PRT
<213> ORGANISM: Unknown
<220> FEATURE:
<223> OTHER INFORMATION: peptide

<400> SEQUENCE: 81

Gly Met Glu Val Thr Pro Ser Gly Thr Trp Leu
1               5                   10


<210> SEQ ID NO 82
<211> LENGTH: 9
<212> TYPE: PRT
<213> ORGANISM: Unknown
<220> FEATURE:
<223> OTHER INFORMATION: peptide

<400> SEQUENCE: 82

Leu Leu Leu Leu Asp Arg Leu Asn Gln
1               5


<210> SEQ ID NO 83
<211> LENGTH: 9
<212> TYPE: PRT
<213> ORGANISM: Unknown
<220> FEATURE:
<223> OTHER INFORMATION: peptide

<400> SEQUENCE: 83

Gly Met Ser Arg Ile Gly Met Glu Val
1               5


<210> SEQ ID NO 84
<211> LENGTH: 9
<212> TYPE: PRT
<213> ORGANISM: Unknown
<220> FEATURE:
<223> OTHER INFORMATION: peptide

<400> SEQUENCE: 84

Gly Thr Thr Leu Pro Lys Gly Phe Tyr
1               5


<210> SEQ ID NO 85
<211> LENGTH: 9
<212> TYPE: PRT
<213> ORGANISM: Unknown
<220> FEATURE:
<223> OTHER INFORMATION: peptide

<400> SEQUENCE: 85

Ala Leu Ala Leu Leu Leu Leu Asp Arg
1               5


<210> SEQ ID NO 86
<211> LENGTH: 15
<212> TYPE: PRT
<213> ORGANISM: Unknown
<220> FEATURE:
<223> OTHER INFORMATION: peptide

<400> SEQUENCE: 86

Ile Asp Ala Tyr Lys Thr Phe Pro Pro Thr Glu Pro Lys Lys Asp
1               5                   10                  15
```

<210> SEQ ID NO 87
<211> LENGTH: 9
<212> TYPE: PRT
<213> ORGANISM: Unknown
<220> FEATURE:
<223> OTHER INFORMATION: peptide

<400> SEQUENCE: 87

Ile Leu Leu Asn Lys His Ile Asp Ala
1 5

<210> SEQ ID NO 88
<211> LENGTH: 9
<212> TYPE: PRT
<213> ORGANISM: Unknown
<220> FEATURE:
<223> OTHER INFORMATION: peptide

<400> SEQUENCE: 88

Ala Leu Asn Thr Pro Lys Asp His Ile
1 5

<210> SEQ ID NO 89
<211> LENGTH: 9
<212> TYPE: PRT
<213> ORGANISM: Unknown
<220> FEATURE:
<223> OTHER INFORMATION: peptide

<400> SEQUENCE: 89

Lys Thr Phe Pro Pro Thr Glu Pro Lys
1 5

<210> SEQ ID NO 90
<211> LENGTH: 10
<212> TYPE: PRT
<213> ORGANISM: Unknown
<220> FEATURE:
<223> OTHER INFORMATION: peptide

<400> SEQUENCE: 90

Lys Thr Phe Pro Pro Thr Glu Pro Lys Lys
1 5 10

<210> SEQ ID NO 91
<211> LENGTH: 9
<212> TYPE: PRT
<213> ORGANISM: Unknown
<220> FEATURE:
<223> OTHER INFORMATION: peptide

<400> SEQUENCE: 91

Leu Ala Leu Leu Leu Leu Asp Arg Leu
1 5

<210> SEQ ID NO 92
<211> LENGTH: 9
<212> TYPE: PRT
<213> ORGANISM: Unknown
<220> FEATURE:
<223> OTHER INFORMATION: peptide

<400> SEQUENCE: 92

Leu Leu Leu Asp Arg Leu Asn Gln Leu
1 5

<210> SEQ ID NO 93
<211> LENGTH: 10
<212> TYPE: PRT
<213> ORGANISM: Unknown
<220> FEATURE:
<223> OTHER INFORMATION: peptide

<400> SEQUENCE: 93

Leu Leu Leu Leu Asp Arg Leu Asn Gln Leu
1 5 10

<210> SEQ ID NO 94
<211> LENGTH: 10
<212> TYPE: PRT
<213> ORGANISM: Unknown
<220> FEATURE:
<223> OTHER INFORMATION: peptide

<400> SEQUENCE: 94

Ala Pro Ser Ala Ser Ala Phe Phe Gly Met
1 5 10

<210> SEQ ID NO 95
<211> LENGTH: 9
<212> TYPE: PRT
<213> ORGANISM: Unknown
<220> FEATURE:
<223> OTHER INFORMATION: peptide

<400> SEQUENCE: 95

Leu Gln Leu Pro Gln Gly Thr Thr Leu
1 5

<210> SEQ ID NO 96
<211> LENGTH: 9
<212> TYPE: PRT
<213> ORGANISM: Unknown
<220> FEATURE:
<223> OTHER INFORMATION: peptide

<400> SEQUENCE: 96

Ala Gln Phe Ala Pro Ser Ala Ser Ala
1 5

<210> SEQ ID NO 97
<211> LENGTH: 9
<212> TYPE: PRT
<213> ORGANISM: Unknown
<220> FEATURE:
<223> OTHER INFORMATION: peptide

<400> SEQUENCE: 97

Leu Ser Pro Arg Trp Tyr Phe Tyr Tyr
1 5

<210> SEQ ID NO 98
<211> LENGTH: 15
<212> TYPE: PRT
<213> ORGANISM: Unknown
<220> FEATURE:
<223> OTHER INFORMATION: peptide

<400> SEQUENCE: 98

Met Ser Arg Ile Gly Met Glu Val Thr Pro Ser Gly Thr Trp Leu
1 5 10 15

<210> SEQ ID NO 99
<211> LENGTH: 9
<212> TYPE: PRT
<213> ORGANISM: Unknown
<220> FEATURE:
<223> OTHER INFORMATION: peptide

<400> SEQUENCE: 99

Ala Ser Ala Phe Phe Gly Met Ser Arg
1               5

<210> SEQ ID NO 100
<211> LENGTH: 15
<212> TYPE: PRT
<213> ORGANISM: Unknown
<220> FEATURE:
<223> OTHER INFORMATION: peptide

<400> SEQUENCE: 100

Asn Lys His Ile Asp Ala Tyr Lys Thr Phe Pro Pro Thr Glu Pro
1               5                   10                  15

<210> SEQ ID NO 101
<211> LENGTH: 10
<212> TYPE: PRT
<213> ORGANISM: Unknown
<220> FEATURE:
<223> OTHER INFORMATION: peptide

<400> SEQUENCE: 101

Ala Thr Glu Gly Ala Leu Asn Thr Pro Lys
1               5                   10

<210> SEQ ID NO 102
<211> LENGTH: 10
<212> TYPE: PRT
<213> ORGANISM: Unknown
<220> FEATURE:
<223> OTHER INFORMATION: peptide

<400> SEQUENCE: 102

Gln Leu Pro Gln Gly Thr Thr Leu Pro Lys
1               5                   10

<210> SEQ ID NO 103
<211> LENGTH: 9
<212> TYPE: PRT
<213> ORGANISM: Unknown
<220> FEATURE:
<223> OTHER INFORMATION: peptide

<400> SEQUENCE: 103

Gln Gln Gln Gly Gln Thr Val Thr Lys
1               5

<210> SEQ ID NO 104
<211> LENGTH: 10
<212> TYPE: PRT
<213> ORGANISM: Unknown
<220> FEATURE:
<223> OTHER INFORMATION: peptide

<400> SEQUENCE: 104

Gln Gln Gln Gln Gly Gln Thr Val Thr Lys
1               5                   10

<210> SEQ ID NO 105

<211> LENGTH: 9
<212> TYPE: PRT
<213> ORGANISM: Unknown
<220> FEATURE:
<223> OTHER INFORMATION: peptide

<400> SEQUENCE: 105

Ala Leu Asn Thr Leu Val Lys Gln Leu
1               5

<210> SEQ ID NO 106
<211> LENGTH: 15
<212> TYPE: PRT
<213> ORGANISM: Unknown
<220> FEATURE:
<223> OTHER INFORMATION: peptide

<400> SEQUENCE: 106

Ile Ser Gly Ile Asn Ala Ser Val Val Asn Ile Gln Lys Glu Ile
1               5                   10                  15

<210> SEQ ID NO 107
<211> LENGTH: 15
<212> TYPE: PRT
<213> ORGANISM: Unknown
<220> FEATURE:
<223> OTHER INFORMATION: peptide

<400> SEQUENCE: 107

Leu Asp Lys Tyr Phe Lys Asn His Thr Ser Pro Asp Val Asp Leu
1               5                   10                  15

<210> SEQ ID NO 108
<211> LENGTH: 10
<212> TYPE: PRT
<213> ORGANISM: Unknown
<220> FEATURE:
<223> OTHER INFORMATION: peptide

<400> SEQUENCE: 108

Ala Pro His Gly Val Val Phe Leu His Val
1               5                   10

<210> SEQ ID NO 109
<211> LENGTH: 15
<212> TYPE: PRT
<213> ORGANISM: Unknown
<220> FEATURE:
<223> OTHER INFORMATION: peptide

<400> SEQUENCE: 109

Leu Gly Asp Ile Ser Gly Ile Asn Ala Ser Val Val Asn Ile Gln
1               5                   10                  15

<210> SEQ ID NO 110
<211> LENGTH: 15
<212> TYPE: PRT
<213> ORGANISM: Unknown
<220> FEATURE:
<223> OTHER INFORMATION: peptide

<400> SEQUENCE: 110

Leu Gly Phe Ile Ala Gly Leu Ile Ala Ile Val Met Val Thr Ile
1               5                   10                  15

<210> SEQ ID NO 111
<211> LENGTH: 10

<212> TYPE: PRT
<213> ORGANISM: Unknown
<220> FEATURE:
<223> OTHER INFORMATION: peptide

<400> SEQUENCE: 111

Leu Ile Asp Leu Gln Glu Leu Gly Lys Tyr
1 5 10

<210> SEQ ID NO 112
<211> LENGTH: 9
<212> TYPE: PRT
<213> ORGANISM: Unknown
<220> FEATURE:
<223> OTHER INFORMATION: peptide

<400> SEQUENCE: 112

Leu Ile Thr Gly Arg Leu Gln Ser Leu
1 5

<210> SEQ ID NO 113
<211> LENGTH: 9
<212> TYPE: PRT
<213> ORGANISM: Unknown
<220> FEATURE:
<223> OTHER INFORMATION: peptide

<400> SEQUENCE: 113

Leu Leu Leu Gln Tyr Gly Ser Phe Cys
1 5

<210> SEQ ID NO 114
<211> LENGTH: 9
<212> TYPE: PRT
<213> ORGANISM: Unknown
<220> FEATURE:
<223> OTHER INFORMATION: peptide

<400> SEQUENCE: 114

Leu Leu Gln Tyr Gly Ser Phe Cys Thr
1 5

<210> SEQ ID NO 115
<211> LENGTH: 15
<212> TYPE: PRT
<213> ORGANISM: Unknown
<220> FEATURE:
<223> OTHER INFORMATION: peptide

<400> SEQUENCE: 115

Leu Asn Thr Leu Val Lys Gln Leu Ser Ser Asn Phe Gly Ala Ile
1 5 10 15

<210> SEQ ID NO 116
<211> LENGTH: 15
<212> TYPE: PRT
<213> ORGANISM: Unknown
<220> FEATURE:
<223> OTHER INFORMATION: peptide

<400> SEQUENCE: 116

Leu Gln Asp Val Val Asn Gln Asn Ala Gln Ala Leu Asn Thr Leu
1 5 10 15

<210> SEQ ID NO 117
<211> LENGTH: 9
<212> TYPE: PRT

<213> ORGANISM: Unknown
<220> FEATURE:
<223> OTHER INFORMATION: peptide

<400> SEQUENCE: 117

Leu Gln Ile Pro Phe Ala Met Gln Met
1 5

<210> SEQ ID NO 118
<211> LENGTH: 15
<212> TYPE: PRT
<213> ORGANISM: Unknown
<220> FEATURE:
<223> OTHER INFORMATION: peptide

<400> SEQUENCE: 118

Leu Gln Ser Leu Gln Thr Tyr Val Thr Gln Gln Leu Ile Arg Ala
1 5 10 15

<210> SEQ ID NO 119
<211> LENGTH: 15
<212> TYPE: PRT
<213> ORGANISM: Unknown
<220> FEATURE:
<223> OTHER INFORMATION: peptide

<400> SEQUENCE: 119

Leu Gln Thr Tyr Val Thr Gln Gln Leu Ile Arg Ala Ala Glu Ile
1 5 10 15

<210> SEQ ID NO 120
<211> LENGTH: 9
<212> TYPE: PRT
<213> ORGANISM: Unknown
<220> FEATURE:
<223> OTHER INFORMATION: peptide

<400> SEQUENCE: 120

Ala Gln Ala Leu Asn Thr Leu Val Lys
1 5

<210> SEQ ID NO 121
<211> LENGTH: 15
<212> TYPE: PRT
<213> ORGANISM: Unknown
<220> FEATURE:
<223> OTHER INFORMATION: peptide

<400> SEQUENCE: 121

Ala Gln Lys Phe Asn Gly Leu Thr Val Leu Pro Pro Leu Leu Thr
1 5 10 15

<210> SEQ ID NO 122
<211> LENGTH: 9
<212> TYPE: PRT
<213> ORGANISM: Unknown
<220> FEATURE:
<223> OTHER INFORMATION: peptide

<400> SEQUENCE: 122

Met Thr Ser Cys Cys Ser Cys Leu Lys
1 5

<210> SEQ ID NO 123
<211> LENGTH: 9
<212> TYPE: PRT
<213> ORGANISM: Unknown

<220> FEATURE:
<223> OTHER INFORMATION: peptide

<400> SEQUENCE: 123

Ala Ser Ala Asn Leu Ala Ala Thr Lys
1 5

<210> SEQ ID NO 124
<211> LENGTH: 9
<212> TYPE: PRT
<213> ORGANISM: Unknown
<220> FEATURE:
<223> OTHER INFORMATION: peptide

<400> SEQUENCE: 124

Asn Leu Asn Glu Ser Leu Ile Asp Leu
1 5

<210> SEQ ID NO 125
<211> LENGTH: 15
<212> TYPE: PRT
<213> ORGANISM: Unknown
<220> FEATURE:
<223> OTHER INFORMATION: peptide

<400> SEQUENCE: 125

Pro Cys Ser Phe Gly Gly Val Ser Val Ile Thr Pro Gly Thr Asn
1 5 10 15

<210> SEQ ID NO 126
<211> LENGTH: 9
<212> TYPE: PRT
<213> ORGANISM: Unknown
<220> FEATURE:
<223> OTHER INFORMATION: peptide

<400> SEQUENCE: 126

Pro Tyr Arg Val Val Val Leu Ser Phe
1 5

<210> SEQ ID NO 127
<211> LENGTH: 10
<212> TYPE: PRT
<213> ORGANISM: Unknown
<220> FEATURE:
<223> OTHER INFORMATION: peptide

<400> SEQUENCE: 127

Gln Glu Leu Gly Lys Tyr Glu Gln Tyr Ile
1 5 10

<210> SEQ ID NO 128
<211> LENGTH: 15
<212> TYPE: PRT
<213> ORGANISM: Unknown
<220> FEATURE:
<223> OTHER INFORMATION: peptide

<400> SEQUENCE: 128

Gln Ile Pro Phe Ala Met Gln Met Ala Tyr Arg Phe Asn Gly Ile
1 5 10 15

<210> SEQ ID NO 129
<211> LENGTH: 10
<212> TYPE: PRT
<213> ORGANISM: Unknown
<220> FEATURE:

<223> OTHER INFORMATION: peptide

<400> SEQUENCE: 129

Gln Pro Tyr Arg Val Val Val Leu Ser Phe
1 5 10

<210> SEQ ID NO 130
<211> LENGTH: 15
<212> TYPE: PRT
<213> ORGANISM: Unknown
<220> FEATURE:
<223> OTHER INFORMATION: peptide

<400> SEQUENCE: 130

Gln Gln Leu Ile Arg Ala Ala Glu Ile Arg Ala Ser Ala Asn Leu
1 5 10 15

<210> SEQ ID NO 131
<211> LENGTH: 15
<212> TYPE: PRT
<213> ORGANISM: Unknown
<220> FEATURE:
<223> OTHER INFORMATION: peptide

<400> SEQUENCE: 131

Gln Thr Tyr Val Thr Gln Gln Leu Ile Arg Ala Ala Glu Ile Arg
1 5 10 15

<210> SEQ ID NO 132
<211> LENGTH: 9
<212> TYPE: PRT
<213> ORGANISM: Unknown
<220> FEATURE:
<223> OTHER INFORMATION: peptide

<400> SEQUENCE: 132

Arg Leu Asp Lys Val Glu Ala Glu Val
1 5

<210> SEQ ID NO 133
<211> LENGTH: 9
<212> TYPE: PRT
<213> ORGANISM: Unknown
<220> FEATURE:
<223> OTHER INFORMATION: peptide

<400> SEQUENCE: 133

Arg Leu Asn Glu Val Ala Lys Asn Leu
1 5

<210> SEQ ID NO 134
<211> LENGTH: 9
<212> TYPE: PRT
<213> ORGANISM: Unknown
<220> FEATURE:
<223> OTHER INFORMATION: peptide

<400> SEQUENCE: 134

Arg Leu Gln Ser Leu Gln Thr Tyr Val
1 5

<210> SEQ ID NO 135
<211> LENGTH: 9
<212> TYPE: PRT
<213> ORGANISM: Unknown
<220> FEATURE:
<223> OTHER INFORMATION: peptide

<400> SEQUENCE: 135

Arg Val Asp Phe Cys Gly Lys Gly Tyr
1 5

<210> SEQ ID NO 136
<211> LENGTH: 15
<212> TYPE: PRT
<213> ORGANISM: Unknown
<220> FEATURE:
<223> OTHER INFORMATION: peptide

<400> SEQUENCE: 136

Ala Tyr Arg Phe Asn Gly Ile Gly Val Thr Gln Asn Val Leu Tyr
1 5 10 15

<210> SEQ ID NO 137
<211> LENGTH: 10
<212> TYPE: PRT
<213> ORGANISM: Unknown
<220> FEATURE:
<223> OTHER INFORMATION: peptide

<400> SEQUENCE: 137

Ser Leu Ile Asp Leu Gln Glu Leu Gly Lys
1 5 10

<210> SEQ ID NO 138
<211> LENGTH: 15
<212> TYPE: PRT
<213> ORGANISM: Unknown
<220> FEATURE:
<223> OTHER INFORMATION: peptide

<400> SEQUENCE: 138

Ser Ser Asn Phe Gly Ala Ile Ser Ser Val Leu Asn Asp Ile Leu
1 5 10 15

<210> SEQ ID NO 139
<211> LENGTH: 9
<212> TYPE: PRT
<213> ORGANISM: Unknown
<220> FEATURE:
<223> OTHER INFORMATION: peptide

<400> SEQUENCE: 139

Ser Val Leu Asn Asp Ile Leu Ser Arg
1 5

<210> SEQ ID NO 140
<211> LENGTH: 15
<212> TYPE: PRT
<213> ORGANISM: Unknown
<220> FEATURE:
<223> OTHER INFORMATION: peptide

<400> SEQUENCE: 140

Thr Gly Arg Leu Gln Ser Leu Gln Thr Tyr Val Thr Gln Gln Leu
1 5 10 15

<210> SEQ ID NO 141
<211> LENGTH: 10
<212> TYPE: PRT
<213> ORGANISM: Unknown
<220> FEATURE:
<223> OTHER INFORMATION: peptide

<400> SEQUENCE: 141

Thr Gln Asn Val Leu Tyr Glu Asn Gln Lys
1               5                   10

<210> SEQ ID NO 142
<211> LENGTH: 10
<212> TYPE: PRT
<213> ORGANISM: Unknown
<220> FEATURE:
<223> OTHER INFORMATION: peptide

<400> SEQUENCE: 142

Cys Met Thr Ser Cys Cys Ser Cys Leu Lys
1               5                   10

<210> SEQ ID NO 143
<211> LENGTH: 9
<212> TYPE: PRT
<213> ORGANISM: Unknown
<220> FEATURE:
<223> OTHER INFORMATION: peptide

<400> SEQUENCE: 143

Val Leu Asn Asp Ile Leu Ser Arg Leu
1               5

<210> SEQ ID NO 144
<211> LENGTH: 10
<212> TYPE: PRT
<213> ORGANISM: Unknown
<220> FEATURE:
<223> OTHER INFORMATION: peptide

<400> SEQUENCE: 144

Val Gln Ile Asp Arg Leu Ile Thr Gly Arg
1               5                   10

<210> SEQ ID NO 145
<211> LENGTH: 9
<212> TYPE: PRT
<213> ORGANISM: Unknown
<220> FEATURE:
<223> OTHER INFORMATION: peptide

<400> SEQUENCE: 145

Val Arg Phe Pro Asn Ile Thr Asn Leu
1               5

<210> SEQ ID NO 146
<211> LENGTH: 9
<212> TYPE: PRT
<213> ORGANISM: Unknown
<220> FEATURE:
<223> OTHER INFORMATION: peptide

<400> SEQUENCE: 146

Val Val Phe Leu His Val Thr Tyr Val
1               5

<210> SEQ ID NO 147
<211> LENGTH: 15
<212> TYPE: PRT
<213> ORGANISM: Unknown
<220> FEATURE:
<223> OTHER INFORMATION: peptide

<400> SEQUENCE: 147

```
Trp Leu Gly Phe Ile Ala Gly Leu Ile Ala Ile Val Met Val Thr
1               5                   10                  15


<210> SEQ ID NO 148
<211> LENGTH: 15
<212> TYPE: PRT
<213> ORGANISM: Unknown
<220> FEATURE:
<223> OTHER INFORMATION: peptide

<400> SEQUENCE: 148

Cys Val Asn Phe Asn Phe Asn Gly Leu Thr Gly Thr Gly Val Leu
1               5                   10                  15


<210> SEQ ID NO 149
<211> LENGTH: 10
<212> TYPE: PRT
<213> ORGANISM: Unknown
<220> FEATURE:
<223> OTHER INFORMATION: peptide

<400> SEQUENCE: 149

Tyr Glu Gln Tyr Ile Lys Trp Pro Trp Tyr
1               5                   10


<210> SEQ ID NO 150
<211> LENGTH: 15
<212> TYPE: PRT
<213> ORGANISM: Unknown
<220> FEATURE:
<223> OTHER INFORMATION: peptide

<400> SEQUENCE: 150

Asp Lys Tyr Phe Lys Asn His Thr Ser Pro Asp Val Asp Leu Gly
1               5                   10                  15


<210> SEQ ID NO 151
<211> LENGTH: 10
<212> TYPE: PRT
<213> ORGANISM: Unknown
<220> FEATURE:
<223> OTHER INFORMATION: peptide

<400> SEQUENCE: 151

Ala Glu Ile Arg Ala Ser Ala Asn Leu Ala
1               5                   10


<210> SEQ ID NO 152
<211> LENGTH: 16
<212> TYPE: PRT
<213> ORGANISM: Unknown
<220> FEATURE:
<223> OTHER INFORMATION: peptide

<400> SEQUENCE: 152

Gly Ala Ala Leu Gln Ile Pro Phe Ala Met Gln Met Ala Tyr Arg Phe
1               5                   10                  15


<210> SEQ ID NO 153
<211> LENGTH: 16
<212> TYPE: PRT
<213> ORGANISM: Unknown
<220> FEATURE:
<223> OTHER INFORMATION: peptide

<400> SEQUENCE: 153
```

Met Ala Tyr Arg Phe Asn Gly Ile Gly Val Thr Gln Asn Val Leu Tyr
1 5 10 15

<210> SEQ ID NO 154
<211> LENGTH: 18
<212> TYPE: PRT
<213> ORGANISM: Unknown
<220> FEATURE:
<223> OTHER INFORMATION: peptide

<400> SEQUENCE: 154

Gln Leu Ile Arg Ala Ala Glu Ile Arg Ala Ser Ala Asn Leu Ala Ala
1 5 10 15

Thr Lys

<210> SEQ ID NO 155
<211> LENGTH: 10
<212> TYPE: PRT
<213> ORGANISM: Unknown
<220> FEATURE:
<223> OTHER INFORMATION: peptide

<400> SEQUENCE: 155

Ser Ala Ser Ala Phe Phe Gly Met Ser Arg
1 5 10

<210> SEQ ID NO 156
<211> LENGTH: 9
<212> TYPE: PRT
<213> ORGANISM: Unknown
<220> FEATURE:
<223> OTHER INFORMATION: peptide

<400> SEQUENCE: 156

Ser Pro Arg Trp Tyr Phe Tyr Tyr Leu
1 5

<210> SEQ ID NO 157
<211> LENGTH: 10
<212> TYPE: PRT
<213> ORGANISM: Unknown
<220> FEATURE:
<223> OTHER INFORMATION: peptide

<400> SEQUENCE: 157

Ser Gln Ala Ser Ser Arg Ser Ser Ser Arg
1 5 10

<210> SEQ ID NO 158
<211> LENGTH: 9
<212> TYPE: PRT
<213> ORGANISM: Unknown
<220> FEATURE:
<223> OTHER INFORMATION: peptide

<400> SEQUENCE: 158

Thr Pro Ser Gly Thr Trp Leu Thr Tyr
1 5

<210> SEQ ID NO 159
<211> LENGTH: 9
<212> TYPE: PRT
<213> ORGANISM: Unknown
<220> FEATURE:
<223> OTHER INFORMATION: peptide

<400> SEQUENCE: 159

Thr Thr Leu Pro Lys Gly Phe Tyr Ala
1 5

<210> SEQ ID NO 160
<211> LENGTH: 10
<212> TYPE: PRT
<213> ORGANISM: Unknown
<220> FEATURE:
<223> OTHER INFORMATION: peptide

<400> SEQUENCE: 160

Val Leu Gln Leu Pro Gln Gly Thr Thr Leu
1 5 10

<210> SEQ ID NO 161
<211> LENGTH: 15
<212> TYPE: PRT
<213> ORGANISM: Unknown
<220> FEATURE:
<223> OTHER INFORMATION: peptide

<400> SEQUENCE: 161

Val Leu Gln Leu Pro Gln Gly Thr Thr Leu Pro Lys Gly Phe Tyr
1 5 10 15

<210> SEQ ID NO 162
<211> LENGTH: 10
<212> TYPE: PRT
<213> ORGANISM: Unknown
<220> FEATURE:
<223> OTHER INFORMATION: peptide

<400> SEQUENCE: 162

Val Thr Pro Ser Gly Thr Trp Leu Thr Tyr
1 5 10

<210> SEQ ID NO 163
<211> LENGTH: 10
<212> TYPE: PRT
<213> ORGANISM: Unknown
<220> FEATURE:
<223> OTHER INFORMATION: peptide

<400> SEQUENCE: 163

Ala Glu Gly Ser Arg Gly Gly Ser Gln Ala
1 5 10

<210> SEQ ID NO 164
<211> LENGTH: 10
<212> TYPE: PRT
<213> ORGANISM: Unknown
<220> FEATURE:
<223> OTHER INFORMATION: peptide

<400> SEQUENCE: 164

Phe Leu Cys Leu Phe Leu Leu Pro Ser Leu
1 5 10

<210> SEQ ID NO 165
<211> LENGTH: 9
<212> TYPE: PRT
<213> ORGANISM: Unknown
<220> FEATURE:
<223> OTHER INFORMATION: peptide

<400> SEQUENCE: 165

Phe Leu Gly Arg Tyr Met Ser Ala Leu
1               5

<210> SEQ ID NO 166
<211> LENGTH: 9
<212> TYPE: PRT
<213> ORGANISM: Unknown
<220> FEATURE:
<223> OTHER INFORMATION: peptide

<400> SEQUENCE: 166

Phe Leu Leu Asn Lys Glu Met Tyr Leu
1               5

<210> SEQ ID NO 167
<211> LENGTH: 9
<212> TYPE: PRT
<213> ORGANISM: Unknown
<220> FEATURE:
<223> OTHER INFORMATION: peptide

<400> SEQUENCE: 167

Phe Leu Leu Pro Ser Leu Ala Thr Val
1               5

<210> SEQ ID NO 168
<211> LENGTH: 9
<212> TYPE: PRT
<213> ORGANISM: Unknown
<220> FEATURE:
<223> OTHER INFORMATION: peptide

<400> SEQUENCE: 168

Phe Leu Asn Gly Ser Cys Gly Ser Val
1               5

<210> SEQ ID NO 169
<211> LENGTH: 9
<212> TYPE: PRT
<213> ORGANISM: Unknown
<220> FEATURE:
<223> OTHER INFORMATION: peptide

<400> SEQUENCE: 169

Phe Leu Asn Arg Phe Thr Thr Thr Leu
1               5

<210> SEQ ID NO 170
<211> LENGTH: 9
<212> TYPE: PRT
<213> ORGANISM: Unknown
<220> FEATURE:
<223> OTHER INFORMATION: peptide

<400> SEQUENCE: 170

Phe Leu Pro Arg Val Phe Ser Ala Val
1               5

<210> SEQ ID NO 171
<211> LENGTH: 9
<212> TYPE: PRT
<213> ORGANISM: Unknown
<220> FEATURE:
<223> OTHER INFORMATION: peptide

<400> SEQUENCE: 171

Phe Arg Tyr Met Asn Ser Gln Gly Leu 1 5

<210> SEQ ID NO 172
<211> LENGTH: 10
<212> TYPE: PRT
<213> ORGANISM: Unknown
<220> FEATURE:
<223> OTHER INFORMATION: peptide

<400> SEQUENCE: 172

Phe Thr Tyr Ala Ser Ala Leu Trp Glu Ile
1 5 10

<210> SEQ ID NO 173
<211> LENGTH: 9
<212> TYPE: PRT
<213> ORGANISM: Unknown
<220> FEATURE:
<223> OTHER INFORMATION: peptide

<400> SEQUENCE: 173

Ala Ile Ile Leu Ala Ser Phe Ser Ala
1 5

<210> SEQ ID NO 174
<211> LENGTH: 9
<212> TYPE: PRT
<213> ORGANISM: Unknown
<220> FEATURE:
<223> OTHER INFORMATION: peptide

<400> SEQUENCE: 174

Gly Val Tyr Asp Tyr Leu Val Ser Thr
1 5

<210> SEQ ID NO 175
<211> LENGTH: 9
<212> TYPE: PRT
<213> ORGANISM: Unknown
<220> FEATURE:
<223> OTHER INFORMATION: peptide

<400> SEQUENCE: 175

Ile Leu Ala Ser Phe Ser Ala Ser Thr
1 5

<210> SEQ ID NO 176
<211> LENGTH: 9
<212> TYPE: PRT
<213> ORGANISM: Unknown
<220> FEATURE:
<223> OTHER INFORMATION: peptide

<400> SEQUENCE: 176

Ile Leu Gly Thr Val Ser Trp Asn Leu
1 5

<210> SEQ ID NO 177
<211> LENGTH: 9
<212> TYPE: PRT
<213> ORGANISM: Unknown
<220> FEATURE:
<223> OTHER INFORMATION: peptide

<400> SEQUENCE: 177

Ile Gln Pro Gly Gln Thr Phe Ser Val
1 5

<210> SEQ ID NO 178
<211> LENGTH: 9
<212> TYPE: PRT
<213> ORGANISM: Unknown
<220> FEATURE:
<223> OTHER INFORMATION: peptide

<400> SEQUENCE: 178

Ala Leu Arg Ala Asn Ser Ala Val Lys
1 5

<210> SEQ ID NO 179
<211> LENGTH: 9
<212> TYPE: PRT
<213> ORGANISM: Unknown
<220> FEATURE:
<223> OTHER INFORMATION: peptide

<400> SEQUENCE: 179

Ala Leu Trp Glu Ile Gln Gln Val Val
1 5

<210> SEQ ID NO 180
<211> LENGTH: 9
<212> TYPE: PRT
<213> ORGANISM: Unknown
<220> FEATURE:
<223> OTHER INFORMATION: peptide

<400> SEQUENCE: 180

Lys Leu Trp Ala Gln Cys Val Gln Leu
1 5

<210> SEQ ID NO 181
<211> LENGTH: 9
<212> TYPE: PRT
<213> ORGANISM: Unknown
<220> FEATURE:
<223> OTHER INFORMATION: peptide

<400> SEQUENCE: 181

Leu Leu Ser Ala Gly Ile Phe Gly Ala
1 5

<210> SEQ ID NO 182
<211> LENGTH: 9
<212> TYPE: PRT
<213> ORGANISM: Unknown
<220> FEATURE:
<223> OTHER INFORMATION: peptide

<400> SEQUENCE: 182

Met Pro Ala Ser Trp Val Met Arg Ile
1 5

<210> SEQ ID NO 183
<211> LENGTH: 9
<212> TYPE: PRT
<213> ORGANISM: Unknown
<220> FEATURE:
<223> OTHER INFORMATION: peptide

<400> SEQUENCE: 183

Asn Val Leu Ala Trp Leu Tyr Ala Ala
1 5

<210> SEQ ID NO 184
<211> LENGTH: 9
<212> TYPE: PRT
<213> ORGANISM: Unknown
<220> FEATURE:
<223> OTHER INFORMATION: peptide

<400> SEQUENCE: 184

Gln Leu Met Cys Gln Pro Ile Leu Leu
1               5

<210> SEQ ID NO 185
<211> LENGTH: 10
<212> TYPE: PRT
<213> ORGANISM: Unknown
<220> FEATURE:
<223> OTHER INFORMATION: peptide

<400> SEQUENCE: 185

Gln Leu Met Cys Gln Pro Ile Leu Leu Leu
1               5                   10

<210> SEQ ID NO 186
<211> LENGTH: 9
<212> TYPE: PRT
<213> ORGANISM: Unknown
<220> FEATURE:
<223> OTHER INFORMATION: peptide

<400> SEQUENCE: 186

Ala Val Leu Gln Ser Gly Phe Arg Lys
1               5

<210> SEQ ID NO 187
<211> LENGTH: 9
<212> TYPE: PRT
<213> ORGANISM: Unknown
<220> FEATURE:
<223> OTHER INFORMATION: peptide

<400> SEQUENCE: 187

Ser Leu Leu Ser Val Leu Leu Ser Met
1               5

<210> SEQ ID NO 188
<211> LENGTH: 9
<212> TYPE: PRT
<213> ORGANISM: Unknown
<220> FEATURE:
<223> OTHER INFORMATION: peptide

<400> SEQUENCE: 188

Thr Leu Gly Val Tyr Asp Tyr Leu Val
1               5

<210> SEQ ID NO 189
<211> LENGTH: 9
<212> TYPE: PRT
<213> ORGANISM: Unknown
<220> FEATURE:
<223> OTHER INFORMATION: peptide

<400> SEQUENCE: 189

Thr Val Leu Ser Phe Cys Ala Phe Ala
1               5

<210> SEQ ID NO 190
<211> LENGTH: 9
<212> TYPE: PRT
<213> ORGANISM: Unknown
<220> FEATURE:
<223> OTHER INFORMATION: peptide

<400> SEQUENCE: 190

Val Leu Ala Trp Leu Tyr Ala Ala Val
1               5

<210> SEQ ID NO 191
<211> LENGTH: 9
<212> TYPE: PRT
<213> ORGANISM: Unknown
<220> FEATURE:
<223> OTHER INFORMATION: peptide

<400> SEQUENCE: 191

Val Leu Ser Phe Cys Ala Phe Ala Val
1               5

<210> SEQ ID NO 192
<211> LENGTH: 9
<212> TYPE: PRT
<213> ORGANISM: Unknown
<220> FEATURE:
<223> OTHER INFORMATION: peptide

<400> SEQUENCE: 192

Tyr Ile Phe Phe Ala Ser Phe Tyr Tyr
1               5

<210> SEQ ID NO 193
<211> LENGTH: 9
<212> TYPE: PRT
<213> ORGANISM: Unknown
<220> FEATURE:
<223> OTHER INFORMATION: peptide

<400> SEQUENCE: 193

Phe Pro Pro Thr Ser Phe Gly Pro Leu
1               5

<210> SEQ ID NO 194
<211> LENGTH: 9
<212> TYPE: PRT
<213> ORGANISM: Unknown
<220> FEATURE:
<223> OTHER INFORMATION: peptide

<400> SEQUENCE: 194

Phe Val Asp Gly Val Pro Phe Val Val
1               5

<210> SEQ ID NO 195
<211> LENGTH: 9
<212> TYPE: PRT
<213> ORGANISM: Unknown
<220> FEATURE:
<223> OTHER INFORMATION: peptide

<400> SEQUENCE: 195

Ala Ile Met Thr Arg Cys Leu Ala Val
1               5

<210> SEQ ID NO 196

<211> LENGTH: 9
<212> TYPE: PRT
<213> ORGANISM: Unknown
<220> FEATURE:
<223> OTHER INFORMATION: peptide

<400> SEQUENCE: 196

Gly Val Ala Met Pro Asn Leu Tyr Lys
1 5

<210> SEQ ID NO 197
<211> LENGTH: 9
<212> TYPE: PRT
<213> ORGANISM: Unknown
<220> FEATURE:
<223> OTHER INFORMATION: peptide

<400> SEQUENCE: 197

Ala Leu Leu Ala Asp Lys Phe Pro Val
1 5

<210> SEQ ID NO 198
<211> LENGTH: 9
<212> TYPE: PRT
<213> ORGANISM: Unknown
<220> FEATURE:
<223> OTHER INFORMATION: peptide

<400> SEQUENCE: 198

Ile Leu Gly Leu Pro Thr Gln Thr Val
1 5

<210> SEQ ID NO 199
<211> LENGTH: 9
<212> TYPE: PRT
<213> ORGANISM: Unknown
<220> FEATURE:
<223> OTHER INFORMATION: peptide

<400> SEQUENCE: 199

Ile Leu His Cys Ala Asn Phe Asn Val
1 5

<210> SEQ ID NO 200
<211> LENGTH: 9
<212> TYPE: PRT
<213> ORGANISM: Unknown
<220> FEATURE:
<223> OTHER INFORMATION: peptide

<400> SEQUENCE: 200

Ile Pro Arg Arg Asn Val Ala Thr Leu
1 5

<210> SEQ ID NO 201
<211> LENGTH: 9
<212> TYPE: PRT
<213> ORGANISM: Unknown
<220> FEATURE:
<223> OTHER INFORMATION: peptide

<400> SEQUENCE: 201

Ile Ser Asp Tyr Asp Tyr Tyr Arg Tyr
1 5

<210> SEQ ID NO 202
<211> LENGTH: 9

<212> TYPE: PRT
<213> ORGANISM: Unknown
<220> FEATURE:
<223> OTHER INFORMATION: peptide

<400> SEQUENCE: 202

Ile Val Asp Thr Val Ser Ala Leu Val
1               5

<210> SEQ ID NO 203
<211> LENGTH: 9
<212> TYPE: PRT
<213> ORGANISM: Unknown
<220> FEATURE:
<223> OTHER INFORMATION: peptide

<400> SEQUENCE: 203

Lys Leu Phe Ala Ala Glu Thr Leu Lys
1               5

<210> SEQ ID NO 204
<211> LENGTH: 9
<212> TYPE: PRT
<213> ORGANISM: Unknown
<220> FEATURE:
<223> OTHER INFORMATION: peptide

<400> SEQUENCE: 204

Lys Leu Asn Val Gly Asp Tyr Phe Val
1               5

<210> SEQ ID NO 205
<211> LENGTH: 9
<212> TYPE: PRT
<213> ORGANISM: Unknown
<220> FEATURE:
<223> OTHER INFORMATION: peptide

<400> SEQUENCE: 205

Lys Leu Ser Tyr Gly Ile Ala Thr Val
1               5

<210> SEQ ID NO 206
<211> LENGTH: 9
<212> TYPE: PRT
<213> ORGANISM: Unknown
<220> FEATURE:
<223> OTHER INFORMATION: peptide

<400> SEQUENCE: 206

Lys Met Gln Arg Met Leu Leu Glu Lys
1               5

<210> SEQ ID NO 207
<211> LENGTH: 9
<212> TYPE: PRT
<213> ORGANISM: Unknown
<220> FEATURE:
<223> OTHER INFORMATION: peptide

<400> SEQUENCE: 207

Lys Gln Phe Asp Thr Tyr Asn Leu Trp
1               5

<210> SEQ ID NO 208
<211> LENGTH: 9
<212> TYPE: PRT

<213> ORGANISM: Unknown
<220> FEATURE:
<223> OTHER INFORMATION: peptide

<400> SEQUENCE: 208

Leu Leu Asp Asp Phe Val Glu Ile Ile
1 5

<210> SEQ ID NO 209
<211> LENGTH: 9
<212> TYPE: PRT
<213> ORGANISM: Unknown
<220> FEATURE:
<223> OTHER INFORMATION: peptide

<400> SEQUENCE: 209

Leu Leu Leu Asp Asp Phe Val Glu Ile
1 5

<210> SEQ ID NO 210
<211> LENGTH: 9
<212> TYPE: PRT
<213> ORGANISM: Unknown
<220> FEATURE:
<223> OTHER INFORMATION: peptide

<400> SEQUENCE: 210

Leu Leu Met Pro Ile Leu Thr Leu Thr
1 5

<210> SEQ ID NO 211
<211> LENGTH: 9
<212> TYPE: PRT
<213> ORGANISM: Unknown
<220> FEATURE:
<223> OTHER INFORMATION: peptide

<400> SEQUENCE: 211

Leu Met Ile Glu Arg Phe Val Ser Leu
1 5

<210> SEQ ID NO 212
<211> LENGTH: 9
<212> TYPE: PRT
<213> ORGANISM: Unknown
<220> FEATURE:
<223> OTHER INFORMATION: peptide

<400> SEQUENCE: 212

Leu Gln Leu Gly Phe Ser Thr Gly Val
1 5

<210> SEQ ID NO 213
<211> LENGTH: 9
<212> TYPE: PRT
<213> ORGANISM: Unknown
<220> FEATURE:
<223> OTHER INFORMATION: peptide

<400> SEQUENCE: 213

Leu Val Leu Ser Val Asn Pro Tyr Val
1 5

<210> SEQ ID NO 214
<211> LENGTH: 9
<212> TYPE: PRT
<213> ORGANISM: Unknown

<220> FEATURE:
<223> OTHER INFORMATION: peptide

<400> SEQUENCE: 214

Met Leu Trp Cys Lys Asp Gly His Val
1               5

<210> SEQ ID NO 215
<211> LENGTH: 9
<212> TYPE: PRT
<213> ORGANISM: Unknown
<220> FEATURE:
<223> OTHER INFORMATION: peptide

<400> SEQUENCE: 215

Met Met Ile Ser Ala Gly Phe Ser Leu
1               5

<210> SEQ ID NO 216
<211> LENGTH: 10
<212> TYPE: PRT
<213> ORGANISM: Unknown
<220> FEATURE:
<223> OTHER INFORMATION: peptide

<400> SEQUENCE: 216

Met Val Met Cys Gly Gly Ser Leu Tyr Val
1               5                   10

<210> SEQ ID NO 217
<211> LENGTH: 9
<212> TYPE: PRT
<213> ORGANISM: Unknown
<220> FEATURE:
<223> OTHER INFORMATION: peptide

<400> SEQUENCE: 217

Asn Leu Trp Asn Thr Phe Thr Arg Leu
1               5

<210> SEQ ID NO 218
<211> LENGTH: 9
<212> TYPE: PRT
<213> ORGANISM: Unknown
<220> FEATURE:
<223> OTHER INFORMATION: peptide

<400> SEQUENCE: 218

Asn Met Leu Arg Ile Met Ala Ser Leu
1               5

<210> SEQ ID NO 219
<211> LENGTH: 9
<212> TYPE: PRT
<213> ORGANISM: Unknown
<220> FEATURE:
<223> OTHER INFORMATION: peptide

<400> SEQUENCE: 219

Ala Thr Val Val Ile Gly Thr Ser Lys
1               5

<210> SEQ ID NO 220
<211> LENGTH: 9
<212> TYPE: PRT
<213> ORGANISM: Unknown
<220> FEATURE:

<223> OTHER INFORMATION: peptide

<400> SEQUENCE: 220

Arg Ile Leu Gly Ala Gly Cys Phe Val
1               5

<210> SEQ ID NO 221
<211> LENGTH: 9
<212> TYPE: PRT
<213> ORGANISM: Unknown
<220> FEATURE:
<223> OTHER INFORMATION: peptide

<400> SEQUENCE: 221

Arg Leu Tyr Tyr Asp Ser Met Ser Tyr
1               5

<210> SEQ ID NO 222
<211> LENGTH: 9
<212> TYPE: PRT
<213> ORGANISM: Unknown
<220> FEATURE:
<223> OTHER INFORMATION: peptide

<400> SEQUENCE: 222

Arg Gln Leu Leu Phe Val Val Glu Val
1               5

<210> SEQ ID NO 223
<211> LENGTH: 9
<212> TYPE: PRT
<213> ORGANISM: Unknown
<220> FEATURE:
<223> OTHER INFORMATION: peptide

<400> SEQUENCE: 223

Ser Ser Asn Val Ala Asn Tyr Gln Lys
1               5

<210> SEQ ID NO 224
<211> LENGTH: 9
<212> TYPE: PRT
<213> ORGANISM: Unknown
<220> FEATURE:
<223> OTHER INFORMATION: peptide

<400> SEQUENCE: 224

Thr Leu Ile Gly Asp Cys Ala Thr Val
1               5

<210> SEQ ID NO 225
<211> LENGTH: 9
<212> TYPE: PRT
<213> ORGANISM: Unknown
<220> FEATURE:
<223> OTHER INFORMATION: peptide

<400> SEQUENCE: 225

Thr Leu Val Pro Gln Glu His Tyr Val
1               5

<210> SEQ ID NO 226
<211> LENGTH: 9
<212> TYPE: PRT
<213> ORGANISM: Unknown
<220> FEATURE:
<223> OTHER INFORMATION: peptide

<400> SEQUENCE: 226

Thr Met Ala Asp Leu Val Tyr Ala Leu
1               5

<210> SEQ ID NO 227
<211> LENGTH: 9
<212> TYPE: PRT
<213> ORGANISM: Unknown
<220> FEATURE:
<223> OTHER INFORMATION: peptide

<400> SEQUENCE: 227

Thr Thr Leu Pro Val Asn Val Ala Phe
1               5

<210> SEQ ID NO 228
<211> LENGTH: 9
<212> TYPE: PRT
<213> ORGANISM: Unknown
<220> FEATURE:
<223> OTHER INFORMATION: peptide

<400> SEQUENCE: 228

Val Leu Gln Ala Val Gly Ala Cys Val
1               5

<210> SEQ ID NO 229
<211> LENGTH: 9
<212> TYPE: PRT
<213> ORGANISM: Unknown
<220> FEATURE:
<223> OTHER INFORMATION: peptide

<400> SEQUENCE: 229

Val Leu Trp Ala His Gly Phe Glu Leu
1               5

<210> SEQ ID NO 230
<211> LENGTH: 9
<212> TYPE: PRT
<213> ORGANISM: Unknown
<220> FEATURE:
<223> OTHER INFORMATION: peptide

<400> SEQUENCE: 230

Val Met Cys Gly Gly Ser Leu Tyr Val
1               5

<210> SEQ ID NO 231
<211> LENGTH: 9
<212> TYPE: PRT
<213> ORGANISM: Unknown
<220> FEATURE:
<223> OTHER INFORMATION: peptide

<400> SEQUENCE: 231

Val Val Asp Lys Tyr Phe Asp Cys Tyr
1               5

<210> SEQ ID NO 232
<211> LENGTH: 9
<212> TYPE: PRT
<213> ORGANISM: Unknown
<220> FEATURE:
<223> OTHER INFORMATION: peptide

<400> SEQUENCE: 232

Val Val Tyr Arg Gly Thr Thr Thr Tyr
1               5

<210> SEQ ID NO 233
<211> LENGTH: 9
<212> TYPE: PRT
<213> ORGANISM: Unknown
<220> FEATURE:
<223> OTHER INFORMATION: peptide

<400> SEQUENCE: 233

Tyr Leu Asp Ala Tyr Asn Met Met Ile
1               5

<210> SEQ ID NO 234
<211> LENGTH: 9
<212> TYPE: PRT
<213> ORGANISM: Unknown
<220> FEATURE:
<223> OTHER INFORMATION: peptide

<400> SEQUENCE: 234

Tyr Leu Asn Thr Leu Thr Leu Ala Val
1               5

<210> SEQ ID NO 235
<211> LENGTH: 9
<212> TYPE: PRT
<213> ORGANISM: Unknown
<220> FEATURE:
<223> OTHER INFORMATION: peptide

<400> SEQUENCE: 235

Tyr Gln Lys Val Gly Met Gln Lys Tyr
1               5

<210> SEQ ID NO 236
<211> LENGTH: 9
<212> TYPE: PRT
<213> ORGANISM: Unknown
<220> FEATURE:
<223> OTHER INFORMATION: peptide

<400> SEQUENCE: 236

Tyr Thr Met Ala Asp Leu Val Tyr Ala
1               5

<210> SEQ ID NO 237
<211> LENGTH: 9
<212> TYPE: PRT
<213> ORGANISM: Unknown
<220> FEATURE:
<223> OTHER INFORMATION: peptide

<400> SEQUENCE: 237

Tyr Val Phe Cys Thr Val Asn Ala Leu
1               5

<210> SEQ ID NO 238
<211> LENGTH: 9
<212> TYPE: PRT
<213> ORGANISM: Unknown
<220> FEATURE:
<223> OTHER INFORMATION: peptide

<400> SEQUENCE: 238

His Leu Val Asp Phe Gln Val Thr Ile
1 5

<210> SEQ ID NO 239
<211> LENGTH: 10
<212> TYPE: PRT
<213> ORGANISM: Unknown
<220> FEATURE:
<223> OTHER INFORMATION: peptide

<400> SEQUENCE: 239

His Pro Leu Ala Asp Asn Lys Phe Ala Leu
1 5 10

<210> SEQ ID NO 240
<211> LENGTH: 9
<212> TYPE: PRT
<213> ORGANISM: Unknown
<220> FEATURE:
<223> OTHER INFORMATION: peptide

<400> SEQUENCE: 240

Lys Leu Phe Ile Arg Gln Glu Glu Val
1 5

<210> SEQ ID NO 241
<211> LENGTH: 15
<212> TYPE: PRT
<213> ORGANISM: Unknown
<220> FEATURE:
<223> OTHER INFORMATION: peptide

<400> SEQUENCE: 241

Gln Glu Cys Val Arg Gly Thr Thr Val Leu Leu Lys Glu Pro Cys
1 5 10 15

<210> SEQ ID NO 242
<211> LENGTH: 10
<212> TYPE: PRT
<213> ORGANISM: Unknown
<220> FEATURE:
<223> OTHER INFORMATION: peptide

<400> SEQUENCE: 242

Cys Glu Leu Tyr His Tyr Gln Glu Cys Val
1 5 10

<210> SEQ ID NO 243
<211> LENGTH: 9
<212> TYPE: PRT
<213> ORGANISM: Unknown
<220> FEATURE:
<223> OTHER INFORMATION: peptide

<400> SEQUENCE: 243

Ser Val Ser Pro Lys Leu Phe Ile Arg
1 5

<210> SEQ ID NO 244
<211> LENGTH: 10
<212> TYPE: PRT
<213> ORGANISM: Unknown
<220> FEATURE:
<223> OTHER INFORMATION: peptide

<400> SEQUENCE: 244

Tyr Glu Gly Asn Ser Pro Phe His Pro Leu
1 5 10

<210> SEQ ID NO 245
<211> LENGTH: 9
<212> TYPE: PRT
<213> ORGANISM: Unknown
<220> FEATURE:
<223> OTHER INFORMATION: peptide

<400> SEQUENCE: 245

Ala Phe Leu Leu Phe Leu Val Leu Ile
1 5

<210> SEQ ID NO 246
<211> LENGTH: 15
<212> TYPE: PRT
<213> ORGANISM: Unknown
<220> FEATURE:
<223> OTHER INFORMATION: peptide

<400> SEQUENCE: 246

Ala Phe Leu Leu Phe Leu Val Leu Ile Met Leu Ile Ile Phe Trp
1 5 10 15

<210> SEQ ID NO 247
<211> LENGTH: 9
<212> TYPE: PRT
<213> ORGANISM: Unknown
<220> FEATURE:
<223> OTHER INFORMATION: peptide

<400> SEQUENCE: 247

Phe Leu Ala Phe Leu Leu Phe Leu Val
1 5

<210> SEQ ID NO 248
<211> LENGTH: 10
<212> TYPE: PRT
<213> ORGANISM: Unknown
<220> FEATURE:
<223> OTHER INFORMATION: peptide

<400> SEQUENCE: 248

Phe Leu Ala Phe Leu Leu Phe Leu Val Leu
1 5 10

<210> SEQ ID NO 249
<211> LENGTH: 15
<212> TYPE: PRT
<213> ORGANISM: Unknown
<220> FEATURE:
<223> OTHER INFORMATION: peptide

<400> SEQUENCE: 249

Phe Leu Ala Phe Leu Leu Phe Leu Val Leu Ile Met Leu Ile Ile
1 5 10 15

<210> SEQ ID NO 250
<211> LENGTH: 9
<212> TYPE: PRT
<213> ORGANISM: Unknown
<220> FEATURE:
<223> OTHER INFORMATION: peptide

<400> SEQUENCE: 250

Phe Leu Leu Phe Leu Val Leu Ile Met 1 5

<210> SEQ ID NO 251
<211> LENGTH: 10
<212> TYPE: PRT
<213> ORGANISM: Unknown
<220> FEATURE:
<223> OTHER INFORMATION: peptide

<400> SEQUENCE: 251

Phe Leu Leu Phe Leu Val Leu Ile Met Leu
1 5 10

<210> SEQ ID NO 252
<211> LENGTH: 15
<212> TYPE: PRT
<213> ORGANISM: Unknown
<220> FEATURE:
<223> OTHER INFORMATION: peptide

<400> SEQUENCE: 252

Phe Leu Leu Phe Leu Val Leu Ile Met Leu Ile Ile Phe Trp Phe
1 5 10 15

<210> SEQ ID NO 253
<211> LENGTH: 9
<212> TYPE: PRT
<213> ORGANISM: Unknown
<220> FEATURE:
<223> OTHER INFORMATION: peptide

<400> SEQUENCE: 253

Phe Leu Val Leu Ile Met Leu Ile Ile
1 5

<210> SEQ ID NO 254
<211> LENGTH: 15
<212> TYPE: PRT
<213> ORGANISM: Unknown
<220> FEATURE:
<223> OTHER INFORMATION: peptide

<400> SEQUENCE: 254

Phe Leu Val Leu Ile Met Leu Ile Ile Phe Trp Phe Ser Leu Glu
1 5 10 15

<210> SEQ ID NO 255
<211> LENGTH: 9
<212> TYPE: PRT
<213> ORGANISM: Unknown
<220> FEATURE:
<223> OTHER INFORMATION: peptide

<400> SEQUENCE: 255

Phe Tyr Leu Cys Phe Leu Ala Phe Leu
1 5

<210> SEQ ID NO 256
<211> LENGTH: 10
<212> TYPE: PRT
<213> ORGANISM: Unknown
<220> FEATURE:
<223> OTHER INFORMATION: peptide

<400> SEQUENCE: 256

Phe Tyr Leu Cys Phe Leu Ala Phe Leu Leu
1 5 10

<210> SEQ ID NO 257
<211> LENGTH: 10
<212> TYPE: PRT
<213> ORGANISM: Unknown
<220> FEATURE:
<223> OTHER INFORMATION: peptide

<400> SEQUENCE: 257

Ile Asp Phe Tyr Leu Cys Phe Leu Ala Phe
1 5 10

<210> SEQ ID NO 258
<211> LENGTH: 10
<212> TYPE: PRT
<213> ORGANISM: Unknown
<220> FEATURE:
<223> OTHER INFORMATION: peptide

<400> SEQUENCE: 258

Ile Met Leu Ile Ile Phe Trp Phe Ser Leu
1 5 10

<210> SEQ ID NO 259
<211> LENGTH: 15
<212> TYPE: PRT
<213> ORGANISM: Unknown
<220> FEATURE:
<223> OTHER INFORMATION: peptide

<400> SEQUENCE: 259

Leu Ala Phe Leu Leu Phe Leu Val Leu Ile Met Leu Ile Ile Phe
1 5 10 15

<210> SEQ ID NO 260
<211> LENGTH: 15
<212> TYPE: PRT
<213> ORGANISM: Unknown
<220> FEATURE:
<223> OTHER INFORMATION: peptide

<400> SEQUENCE: 260

Leu Phe Leu Val Leu Ile Met Leu Ile Ile Phe Trp Phe Ser Leu
1 5 10 15

<210> SEQ ID NO 261
<211> LENGTH: 9
<212> TYPE: PRT
<213> ORGANISM: Unknown
<220> FEATURE:
<223> OTHER INFORMATION: peptide

<400> SEQUENCE: 261

Leu Ile Asp Phe Tyr Leu Cys Phe Leu
1 5

<210> SEQ ID NO 262
<211> LENGTH: 9
<212> TYPE: PRT
<213> ORGANISM: Unknown
<220> FEATURE:
<223> OTHER INFORMATION: peptide

<400> SEQUENCE: 262

Leu Leu Phe Leu Val Leu Ile Met Leu
1 5

<210> SEQ ID NO 263
<211> LENGTH: 10
<212> TYPE: PRT
<213> ORGANISM: Unknown
<220> FEATURE:
<223> OTHER INFORMATION: peptide

<400> SEQUENCE: 263

Leu Leu Phe Leu Val Leu Ile Met Leu Ile
1 5 10

<210> SEQ ID NO 264
<211> LENGTH: 15
<212> TYPE: PRT
<213> ORGANISM: Unknown
<220> FEATURE:
<223> OTHER INFORMATION: peptide

<400> SEQUENCE: 264

Leu Leu Phe Leu Val Leu Ile Met Leu Ile Ile Phe Trp Phe Ser
1 5 10 15

<210> SEQ ID NO 265
<211> LENGTH: 9
<212> TYPE: PRT
<213> ORGANISM: Unknown
<220> FEATURE:
<223> OTHER INFORMATION: peptide

<400> SEQUENCE: 265

Met Leu Ile Ile Phe Trp Phe Ser Leu
1 5

<210> SEQ ID NO 266
<211> LENGTH: 9
<212> TYPE: PRT
<213> ORGANISM: Unknown
<220> FEATURE:
<223> OTHER INFORMATION: peptide

<400> SEQUENCE: 266

Tyr Leu Cys Phe Leu Ala Phe Leu Leu
1 5

<210> SEQ ID NO 267
<211> LENGTH: 15
<212> TYPE: PRT
<213> ORGANISM: Unknown
<220> FEATURE:
<223> OTHER INFORMATION: peptide

<400> SEQUENCE: 267

Tyr Leu Cys Phe Leu Ala Phe Leu Leu Phe Leu Val Leu Ile Met
1 5 10 15

<210> SEQ ID NO 268
<211> LENGTH: 10
<212> TYPE: PRT
<213> ORGANISM: Unknown
<220> FEATURE:
<223> OTHER INFORMATION: peptide

<400> SEQUENCE: 268

Asp Ser Phe Lys Glu Glu Leu Asp Lys Tyr
1 5 10

<210> SEQ ID NO 269
<211> LENGTH: 9
<212> TYPE: PRT
<213> ORGANISM: Unknown
<220> FEATURE:
<223> OTHER INFORMATION: peptide

<400> SEQUENCE: 269

Ala Glu Val Gln Ile Asp Arg Leu Ile
1               5

<210> SEQ ID NO 270
<211> LENGTH: 10
<212> TYPE: PRT
<213> ORGANISM: Unknown
<220> FEATURE:
<223> OTHER INFORMATION: peptide

<400> SEQUENCE: 270

Ala Glu Val Gln Ile Asp Arg Leu Ile Thr
1               5                   10

<210> SEQ ID NO 271
<211> LENGTH: 9
<212> TYPE: PRT
<213> ORGANISM: Unknown
<220> FEATURE:
<223> OTHER INFORMATION: peptide

<400> SEQUENCE: 271

Phe Ile Ala Gly Leu Ile Ala Ile Val
1               5

<210> SEQ ID NO 272
<211> LENGTH: 10
<212> TYPE: PRT
<213> ORGANISM: Unknown
<220> FEATURE:
<223> OTHER INFORMATION: peptide

<400> SEQUENCE: 272

Phe Pro Asn Ile Thr Asn Leu Cys Pro Phe
1               5                   10

<210> SEQ ID NO 273
<211> LENGTH: 15
<212> TYPE: PRT
<213> ORGANISM: Unknown
<220> FEATURE:
<223> OTHER INFORMATION: peptide

<400> SEQUENCE: 273

Gly Ala Ala Leu Gln Ile Pro Phe Ala Met Gln Met Ala Tyr Arg
1               5                   10                  15

<210> SEQ ID NO 274
<211> LENGTH: 10
<212> TYPE: PRT
<213> ORGANISM: Unknown
<220> FEATURE:
<223> OTHER INFORMATION: peptide

<400> SEQUENCE: 274

Gly Leu Ile Ala Ile Val Met Val Thr Ile
1               5                   10

<210> SEQ ID NO 275

<211> LENGTH: 9
<212> TYPE: PRT
<213> ORGANISM: Unknown
<220> FEATURE:
<223> OTHER INFORMATION: peptide

<400> SEQUENCE: 275

Gly Arg Leu Gln Ser Leu Gln Thr Tyr
1               5

<210> SEQ ID NO 276
<211> LENGTH: 9
<212> TYPE: PRT
<213> ORGANISM: Unknown
<220> FEATURE:
<223> OTHER INFORMATION: peptide

<400> SEQUENCE: 276

Gly Ser Phe Cys Thr Gln Leu Asn Arg
1               5

<210> SEQ ID NO 277
<211> LENGTH: 9
<212> TYPE: PRT
<213> ORGANISM: Unknown
<220> FEATURE:
<223> OTHER INFORMATION: peptide

<400> SEQUENCE: 277

Gly Val Val Phe Leu His Val Thr Tyr
1               5

<210> SEQ ID NO 278
<211> LENGTH: 15
<212> TYPE: PRT
<213> ORGANISM: Unknown
<220> FEATURE:
<223> OTHER INFORMATION: peptide

<400> SEQUENCE: 278

Gly Trp Thr Phe Gly Ala Gly Ala Ala Leu Gln Ile Pro Phe Ala
1               5                   10                  15

<210> SEQ ID NO 279
<211> LENGTH: 10
<212> TYPE: PRT
<213> ORGANISM: Unknown
<220> FEATURE:
<223> OTHER INFORMATION: peptide

<400> SEQUENCE: 279

Gly Tyr Gln Pro Tyr Arg Val Val Val Leu
1               5                   10

<210> SEQ ID NO 280
<211> LENGTH: 15
<212> TYPE: PRT
<213> ORGANISM: Unknown
<220> FEATURE:
<223> OTHER INFORMATION: peptide

<400> SEQUENCE: 280

Ile Asp Arg Leu Ile Thr Gly Arg Leu Gln Ser Leu Gln Thr Tyr
1               5                   10                  15

<210> SEQ ID NO 281
<211> LENGTH: 9

<212> TYPE: PRT
<213> ORGANISM: Unknown
<220> FEATURE:
<223> OTHER INFORMATION: peptide

<400> SEQUENCE: 281

Ile Gly Ala Gly Ile Cys Ala Ser Tyr
1               5

<210> SEQ ID NO 282
<211> LENGTH: 9
<212> TYPE: PRT
<213> ORGANISM: Unknown
<220> FEATURE:
<223> OTHER INFORMATION: peptide

<400> SEQUENCE: 282

Ile Ile Thr Thr Asp Asn Thr Phe Val
1               5

<210> SEQ ID NO 283
<211> LENGTH: 17
<212> TYPE: PRT
<213> ORGANISM: Unknown
<220> FEATURE:
<223> OTHER INFORMATION: epitope

<400> SEQUENCE: 283

Asp Val Val Asn Gln Asn Ala Gln Ala Leu Asn Thr Leu Val Lys Gln
1               5                   10                  15

Leu

<210> SEQ ID NO 284
<211> LENGTH: 17
<212> TYPE: PRT
<213> ORGANISM: Unknown
<220> FEATURE:
<223> OTHER INFORMATION: epitope

<400> SEQUENCE: 284

Phe Phe Gly Met Ser Arg Ile Gly Met Glu Val Thr Pro Ser Gly Thr
1               5                   10                  15

Trp

<210> SEQ ID NO 285
<211> LENGTH: 17
<212> TYPE: PRT
<213> ORGANISM: Unknown
<220> FEATURE:
<223> OTHER INFORMATION: epitope

<400> SEQUENCE: 285

Glu Ala Glu Val Gln Ile Asp Arg Leu Ile Thr Gly Arg Leu Gln Ser
1               5                   10                  15

Leu

<210> SEQ ID NO 286
<211> LENGTH: 18
<212> TYPE: PRT
<213> ORGANISM: Unknown
<220> FEATURE:
<223> OTHER INFORMATION: epitope

<400> SEQUENCE: 286

Gly Leu Pro Asn Asn Thr Ala Ser Trp Phe Thr Ala Leu Thr Gln His 1 5 10 15

Gly Lys

<210> SEQ ID NO 287
<211> LENGTH: 28
<212> TYPE: PRT
<213> ORGANISM: Unknown
<220> FEATURE:
<223> OTHER INFORMATION: epitope

<400> SEQUENCE: 287

Glu Ile Asp Arg Leu Asn Glu Val Ala Lys Asn Leu Asn Glu Ser Leu
1 5 10 15

Ile Asp Leu Gln Glu Leu Gly Lys Tyr Glu Gln Tyr
20 25

<210> SEQ ID NO 288
<211> LENGTH: 6
<212> TYPE: PRT
<213> ORGANISM: Unknown
<220> FEATURE:
<223> OTHER INFORMATION: epitope

<400> SEQUENCE: 288

Gly Thr Thr Leu Pro Lys
1 5

<210> SEQ ID NO 289
<211> LENGTH: 17
<212> TYPE: PRT
<213> ORGANISM: Unknown
<220> FEATURE:
<223> OTHER INFORMATION: epitope

<400> SEQUENCE: 289

Glu Val Ala Lys Asn Leu Asn Glu Ser Leu Ile Asp Leu Gln Glu Leu
1 5 10 15

Gly

<210> SEQ ID NO 290
<211> LENGTH: 17
<212> TYPE: PRT
<213> ORGANISM: Unknown
<220> FEATURE:
<223> OTHER INFORMATION: epitope

<400> SEQUENCE: 290

Ile Arg Gln Gly Thr Asp Tyr Lys His Trp Pro Gln Ile Ala Gln Phe
1 5 10 15

Ala

<210> SEQ ID NO 291
<211> LENGTH: 17
<212> TYPE: PRT
<213> ORGANISM: Unknown
<220> FEATURE:
<223> OTHER INFORMATION: epitope

<400> SEQUENCE: 291

Gly Ala Ala Leu Gln Ile Pro Phe Ala Met Gln Met Ala Tyr Arg Phe
1 5 10 15

Asn

<210> SEQ ID NO 292
<211> LENGTH: 20
<212> TYPE: PRT
<213> ORGANISM: Unknown
<220> FEATURE:
<223> OTHER INFORMATION: epitope

<400> SEQUENCE: 292

Lys His Ile Asp Ala Tyr Lys Thr Phe Pro Pro Thr Glu Pro Lys Lys
1 5 10 15

Asp Lys Lys Lys
20

<210> SEQ ID NO 293
<211> LENGTH: 8
<212> TYPE: PRT
<213> ORGANISM: Unknown
<220> FEATURE:
<223> OTHER INFORMATION: epitope

<400> SEQUENCE: 293

Gly Ala Gly Ile Cys Ala Ser Tyr
1 5

<210> SEQ ID NO 294
<211> LENGTH: 17
<212> TYPE: PRT
<213> ORGANISM: Unknown
<220> FEATURE:
<223> OTHER INFORMATION: epitope

<400> SEQUENCE: 294

Lys His Trp Pro Gln Ile Ala Gln Phe Ala Pro Ser Ala Ser Ala Phe
1 5 10 15

Phe

<210> SEQ ID NO 295
<211> LENGTH: 17
<212> TYPE: PRT
<213> ORGANISM: Unknown
<220> FEATURE:
<223> OTHER INFORMATION: epitope

<400> SEQUENCE: 295

Ala Ile Ser Ser Val Leu Asn Asp Ile Leu Ser Arg Leu Asp Lys Val
1 5 10 15

Glu

<210> SEQ ID NO 296
<211> LENGTH: 19
<212> TYPE: PRT
<213> ORGANISM: Unknown
<220> FEATURE:
<223> OTHER INFORMATION: epitope

<400> SEQUENCE: 296

Tyr Asn Val Thr Gln Ala Phe Gly Arg Arg Gly Pro Glu Gln Thr Gln
1 5 10 15

Gly Asn Phe

<210> SEQ ID NO 297
<211> LENGTH: 8
<212> TYPE: PRT
<213> ORGANISM: Unknown
<220> FEATURE:

<223> OTHER INFORMATION: epitope

<400> SEQUENCE: 297

Gly Ser Phe Cys Thr Gln Leu Asn
1 5

<210> SEQ ID NO 298
<211> LENGTH: 15
<212> TYPE: PRT
<213> ORGANISM: Unknown
<220> FEATURE:
<223> OTHER INFORMATION: epitope

<400> SEQUENCE: 298

Lys Thr Phe Pro Pro Thr Glu Pro Lys Lys Asp Lys Lys Lys Lys
1 5 10 15

<210> SEQ ID NO 299
<211> LENGTH: 17
<212> TYPE: PRT
<213> ORGANISM: Unknown
<220> FEATURE:
<223> OTHER INFORMATION: epitope

<400> SEQUENCE: 299

Ile Leu Ser Arg Leu Asp Lys Val Glu Ala Glu Val Gln Ile Asp Arg
1 5 10 15

Leu

<210> SEQ ID NO 300
<211> LENGTH: 6
<212> TYPE: PRT
<213> ORGANISM: Unknown
<220> FEATURE:
<223> OTHER INFORMATION: epitope

<400> SEQUENCE: 300

Leu Leu Pro Ala Ala Asp
1 5

<210> SEQ ID NO 301
<211> LENGTH: 8
<212> TYPE: PRT
<213> ORGANISM: Unknown
<220> FEATURE:
<223> OTHER INFORMATION: epitope

<400> SEQUENCE: 301

Lys Gly Ile Tyr Gln Thr Ser Asn
1 5

<210> SEQ ID NO 302
<211> LENGTH: 17
<212> TYPE: PRT
<213> ORGANISM: Unknown
<220> FEATURE:
<223> OTHER INFORMATION: epitope

<400> SEQUENCE: 302

Leu Asn Lys His Ile Asp Ala Tyr Lys Thr Phe Pro Pro Thr Glu Pro
1 5 10 15

Lys

<210> SEQ ID NO 303
<211> LENGTH: 8

<212> TYPE: PRT
<213> ORGANISM: Unknown
<220> FEATURE:
<223> OTHER INFORMATION: epitope

<400> SEQUENCE: 303

Ala Met Gln Met Ala Tyr Arg Phe
1 5

<210> SEQ ID NO 304
<211> LENGTH: 10
<212> TYPE: PRT
<213> ORGANISM: Unknown
<220> FEATURE:
<223> OTHER INFORMATION: epitope

<400> SEQUENCE: 304

Leu Pro Gln Gly Thr Thr Leu Pro Lys Gly
1 5 10

<210> SEQ ID NO 305
<211> LENGTH: 17
<212> TYPE: PRT
<213> ORGANISM: Unknown
<220> FEATURE:
<223> OTHER INFORMATION: epitope

<400> SEQUENCE: 305

Lys Asn His Thr Ser Pro Asp Val Asp Leu Gly Asp Ile Ser Gly Ile
1 5 10 15

Asn

<210> SEQ ID NO 306
<211> LENGTH: 8
<212> TYPE: PRT
<213> ORGANISM: Unknown
<220> FEATURE:
<223> OTHER INFORMATION: epitope

<400> SEQUENCE: 306

Leu Pro Gln Arg Gln Lys Lys Gln
1 5

<210> SEQ ID NO 307
<211> LENGTH: 17
<212> TYPE: PRT
<213> ORGANISM: Unknown
<220> FEATURE:
<223> OTHER INFORMATION: epitope

<400> SEQUENCE: 307

Met Ala Tyr Arg Phe Asn Gly Ile Gly Val Thr Gln Asn Val Leu Tyr
1 5 10 15

Glu

<210> SEQ ID NO 308
<211> LENGTH: 18
<212> TYPE: PRT
<213> ORGANISM: Unknown
<220> FEATURE:
<223> OTHER INFORMATION: epitope

<400> SEQUENCE: 308

Pro Lys Gly Phe Tyr Ala Glu Gly Ser Arg Gly Gly Ser Gln Ala Ser
1 5 10 15

Ser Arg

<210> SEQ ID NO 309
<211> LENGTH: 17
<212> TYPE: PRT
<213> ORGANISM: Unknown
<220> FEATURE:
<223> OTHER INFORMATION: epitope

<400> SEQUENCE: 309

Ala Ala Thr Lys Met Ser Glu Cys Val Leu Gly Gln Ser Lys Arg Val
1 5 10 15

Asp

<210> SEQ ID NO 310
<211> LENGTH: 17
<212> TYPE: PRT
<213> ORGANISM: Unknown
<220> FEATURE:
<223> OTHER INFORMATION: epitope

<400> SEQUENCE: 310

Gln Phe Ala Pro Ser Ala Ser Ala Phe Phe Gly Met Ser Arg Ile Gly
1 5 10 15

Met

<210> SEQ ID NO 311
<211> LENGTH: 17
<212> TYPE: PRT
<213> ORGANISM: Unknown
<220> FEATURE:
<223> OTHER INFORMATION: epitope

<400> SEQUENCE: 311

Pro Phe Ala Met Gln Met Ala Tyr Arg Phe Asn Gly Ile Gly Val Thr
1 5 10 15

Gln

<210> SEQ ID NO 312
<211> LENGTH: 8
<212> TYPE: PRT
<213> ORGANISM: Unknown
<220> FEATURE:
<223> OTHER INFORMATION: epitope

<400> SEQUENCE: 312

Gln Gly Thr Asp Tyr Lys His Trp
1 5

<210> SEQ ID NO 313
<211> LENGTH: 17
<212> TYPE: PRT
<213> ORGANISM: Unknown
<220> FEATURE:
<223> OTHER INFORMATION: epitope

<400> SEQUENCE: 313

Gln Ala Leu Asn Thr Leu Val Lys Gln Leu Ser Ser Asn Phe Gly Ala
1 5 10 15

Ile

<210> SEQ ID NO 314
<211> LENGTH: 15
<212> TYPE: PRT

```
<213> ORGANISM: Unknown
<220> FEATURE:
<223> OTHER INFORMATION: epitope

<400> SEQUENCE: 314

Gln Leu Pro Gln Gly Thr Thr Leu Pro Lys Gly Phe Tyr Ala Glu
1               5                   10                  15


<210> SEQ ID NO 315
<211> LENGTH: 17
<212> TYPE: PRT
<213> ORGANISM: Unknown
<220> FEATURE:
<223> OTHER INFORMATION: epitope

<400> SEQUENCE: 315

Gln Leu Ile Arg Ala Ala Glu Ile Arg Ala Ser Ala Asn Leu Ala Ala
1               5                   10                  15

Thr


<210> SEQ ID NO 316
<211> LENGTH: 18
<212> TYPE: PRT
<213> ORGANISM: Unknown
<220> FEATURE:
<223> OTHER INFORMATION: epitope

<400> SEQUENCE: 316

Gln Leu Pro Gln Gly Thr Thr Leu Pro Lys Gly Phe Tyr Ala Glu Gly
1               5                   10                  15

Ser Arg


<210> SEQ ID NO 317
<211> LENGTH: 6
<212> TYPE: PRT
<213> ORGANISM: Unknown
<220> FEATURE:
<223> OTHER INFORMATION: epitope

<400> SEQUENCE: 317

Gln Gln Phe Gly Arg Asp
1               5


<210> SEQ ID NO 318
<211> LENGTH: 22
<212> TYPE: PRT
<213> ORGANISM: Unknown
<220> FEATURE:
<223> OTHER INFORMATION: epitope

<400> SEQUENCE: 318

Gln Leu Pro Gln Gly Thr Thr Leu Pro Lys Gly Phe Tyr Ala Glu Gly
1               5                   10                  15

Ser Arg Gly Gly Ser Gln
            20


<210> SEQ ID NO 319
<211> LENGTH: 17
<212> TYPE: PRT
<213> ORGANISM: Unknown
<220> FEATURE:
<223> OTHER INFORMATION: epitope

<400> SEQUENCE: 319

Arg Ala Ser Ala Asn Leu Ala Ala Thr Lys Met Ser Glu Cys Val Leu
```

1 5 10 15

Gly

<210> SEQ ID NO 320
<211> LENGTH: 8
<212> TYPE: PRT
<213> ORGANISM: Unknown
<220> FEATURE:
<223> OTHER INFORMATION: epitope

<400> SEQUENCE: 320

Thr Phe Pro Pro Thr Glu Pro Lys
1 5

<210> SEQ ID NO 321
<211> LENGTH: 17
<212> TYPE: PRT
<213> ORGANISM: Unknown
<220> FEATURE:
<223> OTHER INFORMATION: epitope

<400> SEQUENCE: 321

Arg Leu Ile Thr Gly Arg Leu Gln Ser Leu Gln Thr Tyr Val Thr Gln
1 5 10 15

Gln

<210> SEQ ID NO 322
<211> LENGTH: 15
<212> TYPE: PRT
<213> ORGANISM: Unknown
<220> FEATURE:
<223> OTHER INFORMATION: epitope

<400> SEQUENCE: 322

Arg Arg Pro Gln Gly Leu Pro Asn Asn Thr Ala Ser Trp Phe Thr
1 5 10 15

<210> SEQ ID NO 323
<211> LENGTH: 28
<212> TYPE: PRT
<213> ORGANISM: Unknown
<220> FEATURE:
<223> OTHER INFORMATION: epitope

<400> SEQUENCE: 323

Glu Ile Asp Arg Leu Asn Glu Val Ala Lys Asn Leu Asn Glu Ser Leu
1 5 10 15

Ile Asp Leu Gln Glu Leu Gly Lys Tyr Glu Gln Tyr
20 25

<210> SEQ ID NO 324
<211> LENGTH: 8
<212> TYPE: PRT
<213> ORGANISM: Unknown
<220> FEATURE:
<223> OTHER INFORMATION: epitope

<400> SEQUENCE: 324

Ser Gln Ala Ser Ser Arg Ser Ser
1 5

<210> SEQ ID NO 325
<211> LENGTH: 17
<212> TYPE: PRT
<213> ORGANISM: Unknown

<220> FEATURE:
<223> OTHER INFORMATION: epitope

<400> SEQUENCE: 325

Ser Leu Gln Thr Tyr Val Thr Gln Gln Leu Ile Arg Ala Ala Glu Ile
1 5 10 15

Arg

<210> SEQ ID NO 326
<211> LENGTH: 16
<212> TYPE: PRT
<213> ORGANISM: Unknown
<220> FEATURE:
<223> OTHER INFORMATION: epitope

<400> SEQUENCE: 326

Ser Arg Gly Gly Ser Gln Ala Ser Ser Arg Ser Ser Ser Arg Ser Arg
1 5 10 15

<210> SEQ ID NO 327
<211> LENGTH: 17
<212> TYPE: PRT
<213> ORGANISM: Unknown
<220> FEATURE:
<223> OTHER INFORMATION: epitope

<400> SEQUENCE: 327

Asp Leu Gly Asp Ile Ser Gly Ile Asn Ala Ser Val Val Asn Ile Gln
1 5 10 15

Lys

<210> SEQ ID NO 328
<211> LENGTH: 66
<212> TYPE: PRT
<213> ORGANISM: Unknown
<220> FEATURE:
<223> OTHER INFORMATION: peptide

<400> SEQUENCE: 328

Val Gly Asp Ser Ala Glu Val Ala Val Lys Met Phe Asp Ala Tyr Val
1 5 10 15

Asn Thr Phe Ser Ser Thr Phe Asn Val Pro Met Glu Lys Leu Lys Thr
20 25 30

Leu Val Ala Thr Ala Glu Ala Glu Leu Ala Lys Asn Val Ser Leu Asp
35 40 45

Asn Val Leu Ser Thr Phe Ile Ser Ala Ala Arg Gln Gly Phe Val Asp
50 55 60

Ser Asp
65

<210> SEQ ID NO 329
<211> LENGTH: 41
<212> TYPE: PRT
<213> ORGANISM: Unknown
<220> FEATURE:
<223> OTHER INFORMATION: peptide

<400> SEQUENCE: 329

Met Ser Tyr Glu Asp Gln Asp Ala Leu Phe Ala Tyr Thr Lys Arg Asn
1 5 10 15

Val Ile Pro Thr Ile Thr Gln Met Asn Leu Lys Tyr Ala Ile Ser Ala
20 25 30

```
Lys Asn Arg Ala Arg Thr Val Ala Gly
        35                  40


<210> SEQ ID NO 330
<211> LENGTH: 87
<212> TYPE: PRT
<213> ORGANISM: Unknown
<220> FEATURE:
<223> OTHER INFORMATION: peptide

<400> SEQUENCE: 330

Asp Ile Val Lys Thr Asp Gly Thr Leu Met Ile Glu Arg Phe Val Ser
1               5                   10                  15

Leu Ala Ile Asp Ala Tyr Pro Leu Thr Lys His Pro Asn Gln Glu Tyr
            20                  25                  30

Ala Asp Val Phe His Leu Tyr Leu Gln Tyr Ile Arg Lys Leu His Asp
        35                  40                  45

Glu Leu Thr Gly His Met Leu Asp Met Tyr Ser Val Met Leu Thr Asn
    50                  55                  60

Asp Asn Thr Ser Arg Tyr Trp Glu Pro Glu Phe Tyr Glu Ala Met Tyr
65                  70                  75                  80

Thr Pro His Thr Val Leu Gln
                85


<210> SEQ ID NO 331
<211> LENGTH: 46
<212> TYPE: PRT
<213> ORGANISM: Unknown
<220> FEATURE:
<223> OTHER INFORMATION: peptide

<400> SEQUENCE: 331

Ala Val Cys Arg His His Ala Asn Glu Tyr Arg Leu Tyr Leu Asp Ala
1               5                   10                  15

Tyr Asn Met Met Ile Ser Ala Gly Phe Ser Leu Trp Val Tyr Lys Gln
            20                  25                  30

Phe Asp Thr Tyr Asn Leu Trp Asn Thr Phe Thr Arg Leu Gln
        35                  40                  45


<210> SEQ ID NO 332
<211> LENGTH: 98
<212> TYPE: PRT
<213> ORGANISM: Unknown
<220> FEATURE:
<223> OTHER INFORMATION: peptide

<400> SEQUENCE: 332

Asn Phe Asn Val Leu Phe Ser Thr Val Phe Pro Pro Thr Ser Phe Gly
1               5                   10                  15

Pro Leu Val Arg Lys Ile Phe Val Asp Gly Val Pro Phe Val Val Ser
            20                  25                  30

Thr Gly Tyr His Phe Arg Glu Leu Gly Val Val His Asn Gln Asp Val
        35                  40                  45

Asn Leu His Ser Ser Arg Leu Ser Phe Lys Glu Leu Leu Val Tyr Ala
    50                  55                  60

Ala Asp Pro Ala Met His Ala Ala Ser Gly Asn Leu Leu Leu Asp Lys
65                  70                  75                  80

Arg Thr Thr Cys Phe Ser Val Ala Ala Leu Thr Asn Asn Val Ala Phe
                85                  90                  95

Gln Thr
```

<210> SEQ ID NO 333
<211> LENGTH: 83
<212> TYPE: PRT
<213> ORGANISM: Unknown
<220> FEATURE:
<223> OTHER INFORMATION: peptide

<400> SEQUENCE: 333

Glu Cys Asp Ile Pro Ile Gly Ala Gly Ile Cys Ala Ser Tyr Gln Thr
1 5 10 15

Gln Thr Asn Ser Pro Arg Arg Ala Arg Ser Val Ala Ser Gln Ser Ile
20 25 30

Ile Ala Tyr Thr Met Ser Leu Gly Ala Glu Asn Ser Val Ala Tyr Ser
35 40 45

Asn Asn Ser Ile Ala Ile Pro Thr Asn Phe Thr Ile Ser Val Thr Thr
50 55 60

Glu Ile Leu Pro Val Ser Met Thr Lys Thr Ser Val Asp Cys Thr Met
65 70 75 80

Tyr Ile Cys

<210> SEQ ID NO 334
<211> LENGTH: 70
<212> TYPE: PRT
<213> ORGANISM: Unknown
<220> FEATURE:
<223> OTHER INFORMATION: peptide

<400> SEQUENCE: 334

Asp Lys Ser Val Tyr Tyr Thr Ser Asn Pro Thr Thr Phe His Leu Asp
1 5 10 15

Gly Glu Val Ile Thr Phe Asp Asn Leu Lys Thr Leu Leu Ser Leu Arg
20 25 30

Glu Val Arg Thr Ile Lys Val Phe Thr Thr Val Asp Asn Ile Asn Leu
35 40 45

His Thr Gln Val Val Asp Met Ser Met Thr Tyr Gly Gln Gln Phe Gly
50 55 60

Pro Thr Tyr Leu Asp Gly
65 70

<210> SEQ ID NO 335
<211> LENGTH: 82
<212> TYPE: PRT
<213> ORGANISM: Unknown
<220> FEATURE:
<223> OTHER INFORMATION: peptide

<400> SEQUENCE: 335

Ala Gln Lys Phe Asn Gly Leu Thr Val Leu Pro Pro Leu Leu Thr Asp
1 5 10 15

Glu Met Ile Ala Gln Tyr Thr Ser Ala Leu Leu Ala Gly Thr Ile Thr
20 25 30

Ser Gly Trp Thr Phe Gly Ala Gly Ala Ala Leu Gln Ile Pro Phe Ala
35 40 45

Met Gln Met Ala Tyr Arg Phe Asn Gly Ile Gly Val Thr Gln Asn Val
50 55 60

Leu Tyr Glu Asn Gln Lys Leu Ile Ala Asn Gln Phe Asn Ser Ala Ile
65 70 75 80

Gly Lys

<210> SEQ ID NO 336
<211> LENGTH: 117
<212> TYPE: PRT
<213> ORGANISM: Unknown
<220> FEATURE:
<223> OTHER INFORMATION: peptide

<400> SEQUENCE: 336

```
Asp Ala Val Val Tyr Arg Gly Thr Thr Thr Tyr Lys Leu Asn Val Gly
1               5                   10                  15

Asp Tyr Phe Val Leu Thr Ser His Thr Val Met Pro Leu Ser Ala Pro
            20                  25                  30

Thr Leu Val Pro Gln Glu His Tyr Val Arg Ile Thr Gly Leu Tyr Pro
        35                  40                  45

Thr Leu Asn Ile Ser Asp Glu Phe Ser Ser Asn Val Ala Asn Tyr Gln
    50                  55                  60

Lys Val Gly Met Gln Lys Tyr Ser Thr Leu Gln Gly Pro Pro Gly Thr
65                  70                  75                  80

Gly Lys Ser His Phe Ala Ile Gly Leu Ala Leu Tyr Tyr Pro Ser Ala
                85                  90                  95

Arg Ile Val Tyr Thr Ala Cys Ser His Ala Ala Val Asp Ala Leu Cys
            100                 105                 110

Glu Lys Ala Leu Lys
        115
```

<210> SEQ ID NO 337
<211> LENGTH: 84
<212> TYPE: PRT
<213> ORGANISM: Unknown
<220> FEATURE:
<223> OTHER INFORMATION: peptide

<400> SEQUENCE: 337

```
Cys Arg Glu His Glu His Glu Ile Ala Trp Tyr Thr Glu Arg Ser Glu
1               5                   10                  15

Lys Ser Tyr Glu Leu Gln Thr Pro Phe Glu Ile Lys Leu Ala Lys Lys
            20                  25                  30

Phe Asp Thr Phe Asn Gly Glu Cys Pro Asn Phe Val Phe Pro Leu Asn
        35                  40                  45

Ser Ile Ile Lys Thr Ile Gln Pro Arg Val Glu Lys Lys Lys Leu Asp
    50                  55                  60

Gly Phe Met Gly Arg Ile Arg Ser Val Tyr Pro Val Ala Ser Pro Asn
65                  70                  75                  80

Glu Cys Asn Gln
```

<210> SEQ ID NO 338
<211> LENGTH: 85
<212> TYPE: PRT
<213> ORGANISM: Unknown
<220> FEATURE:
<223> OTHER INFORMATION: peptide

<400> SEQUENCE: 338

```
Ala Ala Tyr Val Asp Asn Ser Ser Leu Thr Ile Lys Lys Pro Asn Glu
1               5                   10                  15

Leu Ser Arg Val Leu Gly Leu Lys Thr Leu Ala Thr His Gly Leu Ala
            20                  25                  30

Ala Val Asn Ser Val Pro Trp Asp Thr Ile Ala Asn Tyr Ala Lys Pro
```

```
        35                  40                  45

Phe Leu Asn Lys Val Val Ser Thr Thr Thr Asn Ile Val Thr Arg Cys
    50                  55                  60

Leu Asn Arg Val Cys Thr Asn Tyr Met Pro Tyr Phe Phe Thr Leu Leu
65                  70                  75                  80

Leu Gln Leu Cys Thr
                85


<210> SEQ ID NO 339
<211> LENGTH: 86
<212> TYPE: PRT
<213> ORGANISM: Unknown
<220> FEATURE:
<223> OTHER INFORMATION: peptide

<400> SEQUENCE: 339

Ile Ala Asp Lys Tyr Val Arg Asn Leu Gln His Arg Leu Tyr Glu Cys
1               5                   10                  15

Leu Tyr Arg Asn Arg Asp Val Asp Thr Asp Phe Val Asn Glu Phe Tyr
            20                  25                  30

Ala Tyr Leu Arg Lys His Phe Ser Met Met Ile Leu Ser Asp Asp Ala
        35                  40                  45

Val Val Cys Phe Asn Ser Thr Tyr Ala Ser Gln Gly Leu Val Ala Ser
    50                  55                  60

Ile Lys Asn Phe Lys Ser Val Leu Tyr Tyr Gln Asn Asn Val Phe Met
65                  70                  75                  80

Ser Glu Ala Lys Cys Trp
                85


<210> SEQ ID NO 340
<211> LENGTH: 80
<212> TYPE: PRT
<213> ORGANISM: Unknown
<220> FEATURE:
<223> OTHER INFORMATION: peptide

<400> SEQUENCE: 340

Arg Gln Phe His Gln Lys Leu Leu Lys Ser Ile Ala Ala Thr Arg Gly
1               5                   10                  15

Ala Thr Val Val Ile Gly Thr Ser Lys Phe Tyr Gly Gly Trp His Asn
            20                  25                  30

Met Leu Lys Thr Val Tyr Ser Asp Val Glu Asn Pro His Leu Met Gly
        35                  40                  45

Trp Asp Tyr Pro Lys Cys Asp Arg Ala Met Pro Asn Met Leu Arg Ile
    50                  55                  60

Met Ala Ser Leu Val Leu Ala Arg Lys His Thr Thr Cys Cys Ser Leu
65                  70                  75                  80


<210> SEQ ID NO 341
<211> LENGTH: 80
<212> TYPE: PRT
<213> ORGANISM: Unknown
<220> FEATURE:
<223> OTHER INFORMATION: peptide

<400> SEQUENCE: 341

Gly His Phe Asp Gly Gln Gln Gly Glu Val Pro Val Ser Ile Ile Asn
1               5                   10                  15

Asn Thr Val Tyr Thr Lys Val Asp Gly Val Asp Val Glu Leu Phe Glu
            20                  25                  30
```

Asn Lys Thr Thr Leu Pro Val Asn Val Ala Phe Glu Leu Trp Ala Lys
        35                  40                  45

Arg Asn Ile Lys Pro Val Pro Glu Val Lys Ile Leu Asn Asn Leu Gly
    50                  55                  60

Val Asp Ile Ala Ala Asn Thr Val Ile Trp Asp Tyr Lys Arg Asp Ala
65                  70                  75                  80

<210> SEQ ID NO 342
<211> LENGTH: 92
<212> TYPE: PRT
<213> ORGANISM: Unknown
<220> FEATURE:
<223> OTHER INFORMATION: peptide

<400> SEQUENCE: 342

Leu His Pro Thr Gln Ala Pro Thr His Leu Ser Val Asp Thr Lys Phe
1               5                   10                  15

Lys Thr Glu Gly Leu Cys Val Asp Ile Pro Gly Ile Pro Lys Asp Met
            20                  25                  30

Thr Tyr Arg Arg Leu Ile Ser Met Met Gly Phe Lys Met Asn Tyr Gln
        35                  40                  45

Val Asn Gly Tyr Pro Asn Met Phe Ile Thr Arg Glu Glu Ala Ile Arg
    50                  55                  60

His Val Arg Ala Trp Ile Gly Phe Asp Val Glu Gly Cys His Ala Thr
65                  70                  75                  80

Arg Glu Ala Val Gly Thr Asn Leu Pro Leu Gln Leu
                85                  90

<210> SEQ ID NO 343
<211> LENGTH: 55
<212> TYPE: PRT
<213> ORGANISM: Unknown
<220> FEATURE:
<223> OTHER INFORMATION: peptide

<400> SEQUENCE: 343

Asp Thr Asn Val Leu Glu Gly Ser Val Ala Tyr Glu Ser Leu Arg Pro
1               5                   10                  15

Asp Thr Arg Tyr Val Leu Met Asp Gly Ser Ile Ile Gln Phe Pro Asn
            20                  25                  30

Thr Tyr Leu Glu Gly Ser Val Arg Val Val Thr Thr Phe Asp Ser Glu
        35                  40                  45

Tyr Cys Arg His Gly Thr Cys
    50                  55

<210> SEQ ID NO 344
<211> LENGTH: 96
<212> TYPE: PRT
<213> ORGANISM: Unknown
<220> FEATURE:
<223> OTHER INFORMATION: peptide

<400> SEQUENCE: 344

Asp Lys Arg Thr Thr Cys Phe Ser Val Ala Ala Leu Thr Asn Asn Val
1               5                   10                  15

Ala Phe Gln Thr Val Lys Pro Gly Asn Phe Asn Lys Asp Phe Tyr Asp
            20                  25                  30

Phe Ala Val Ser Lys Gly Phe Phe Lys Glu Gly Ser Ser Val Glu Leu
        35                  40                  45

```
Lys His Phe Phe Phe Ala Gln Asp Gly Asn Ala Ala Ile Ser Asp Tyr
    50                  55                  60

Asp Tyr Tyr Arg Tyr Asn Leu Pro Thr Met Cys Asp Ile Arg Gln Leu
65                  70                  75                  80

Leu Phe Val Val Glu Val Val Asp Lys Tyr Phe Asp Cys Tyr Asp Gly
                85                  90                  95


<210> SEQ ID NO 345
<211> LENGTH: 107
<212> TYPE: PRT
<213> ORGANISM: Unknown
<220> FEATURE:
<223> OTHER INFORMATION: peptide

<400> SEQUENCE: 345

Lys Val Thr Phe Gly Asp Asp Thr Val Ile Glu Val Gln Gly Tyr Lys
1               5                   10                  15

Ser Val Asn Ile Thr Phe Glu Leu Asp Glu Arg Ile Asp Lys Val Leu
            20                  25                  30

Asn Glu Lys Cys Ser Ala Tyr Thr Val Glu Leu Gly Thr Glu Val Asn
        35                  40                  45

Glu Phe Ala Cys Val Val Ala Asp Ala Val Ile Lys Thr Leu Gln Pro
    50                  55                  60

Val Ser Glu Leu Leu Thr Pro Leu Gly Ile Asp Leu Asp Glu Trp Ser
65                  70                  75                  80

Met Ala Thr Tyr Tyr Leu Phe Asp Glu Ser Gly Glu Phe Lys Leu Ala
                85                  90                  95

Ser His Met Tyr Cys Ser Phe Tyr Pro Pro Asp
            100                 105


<210> SEQ ID NO 346
<211> LENGTH: 80
<212> TYPE: PRT
<213> ORGANISM: Unknown
<220> FEATURE:
<223> OTHER INFORMATION: peptide

<400> SEQUENCE: 346

Lys Gly Ile Tyr Gln Thr Ser Asn Phe Arg Val Gln Pro Thr Glu Ser
1               5                   10                  15

Ile Val Arg Phe Pro Asn Ile Thr Asn Leu Cys Pro Phe Gly Glu Val
            20                  25                  30

Phe Asn Ala Thr Arg Phe Ala Ser Val Tyr Ala Trp Asn Arg Lys Arg
        35                  40                  45

Ile Ser Asn Cys Val Ala Asp Tyr Ser Val Leu Tyr Asn Ser Ala Ser
    50                  55                  60

Phe Ser Thr Phe Lys Cys Tyr Gly Val Ser Pro Thr Lys Leu Asn Asp
65                  70                  75                  80


<210> SEQ ID NO 347
<211> LENGTH: 91
<212> TYPE: PRT
<213> ORGANISM: Unknown
<220> FEATURE:
<223> OTHER INFORMATION: peptide

<400> SEQUENCE: 347

Glu Phe Val Phe Lys Asn Ile Asp Gly Tyr Phe Lys Ile Tyr Ser Lys
1               5                   10                  15

His Thr Pro Ile Asn Leu Val Arg Asp Leu Pro Gln Gly Phe Ser Ala
```

```
            20                  25                  30

Leu Glu Pro Leu Val Asp Leu Pro Ile Gly Ile Asn Ile Thr Arg Phe
        35                  40                  45

Gln Thr Leu Leu Ala Leu His Arg Ser Tyr Leu Thr Pro Gly Asp Ser
    50                  55                  60

Ser Ser Gly Trp Thr Ala Gly Ala Ala Ala Tyr Tyr Val Gly Tyr Leu
65                  70                  75                  80

Gln Pro Arg Thr Phe Leu Leu Lys Tyr Asn Glu
                85                  90


<210> SEQ ID NO 348
<211> LENGTH: 102
<212> TYPE: PRT
<213> ORGANISM: Unknown
<220> FEATURE:
<223> OTHER INFORMATION: peptide

<400> SEQUENCE: 348

Glu Ala Val Lys Thr Gln Phe Asn Tyr Tyr Lys Lys Val Asp Gly Val
1               5                   10                  15

Val Gln Gln Leu Pro Glu Thr Tyr Phe Thr Gln Ser Arg Asn Leu Gln
            20                  25                  30

Glu Phe Lys Pro Arg Ser Gln Met Glu Ile Asp Phe Leu Glu Leu Ala
        35                  40                  45

Met Asp Glu Phe Ile Glu Arg Tyr Lys Leu Glu Gly Tyr Ala Phe Glu
    50                  55                  60

His Ile Val Tyr Gly Asp Phe Ser His Ser Gln Leu Gly Gly Leu His
65                  70                  75                  80

Leu Leu Ile Gly Leu Ala Lys Arg Phe Lys Glu Ser Pro Phe Glu Leu
                85                  90                  95

Glu Asp Phe Ile Pro Met
            100


<210> SEQ ID NO 349
<211> LENGTH: 97
<212> TYPE: PRT
<213> ORGANISM: Unknown
<220> FEATURE:
<223> OTHER INFORMATION: peptide

<400> SEQUENCE: 349

Ser Gln Ala Trp Gln Pro Gly Val Ala Met Pro Asn Leu Tyr Lys Met
1               5                   10                  15

Gln Arg Met Leu Leu Glu Lys Cys Asp Leu Gln Asn Tyr Gly Asp Ser
            20                  25                  30

Ala Thr Leu Pro Lys Gly Ile Met Met Asn Val Ala Lys Tyr Thr Gln
        35                  40                  45

Leu Cys Gln Tyr Leu Asn Thr Leu Thr Leu Ala Val Pro Tyr Asn Met
    50                  55                  60

Arg Val Ile His Phe Gly Ala Gly Ser Asp Lys Gly Val Ala Pro Gly
65                  70                  75                  80

Thr Ala Val Leu Arg Gln Trp Leu Pro Thr Gly Thr Leu Leu Val Asp
                85                  90                  95

Ser


<210> SEQ ID NO 350
<211> LENGTH: 77
<212> TYPE: PRT
```

<213> ORGANISM: Unknown
<220> FEATURE:
<223> OTHER INFORMATION: peptide

<400> SEQUENCE: 350

Asp Cys Val Val Leu His Ser Tyr Phe Thr Ser Asp Tyr Tyr Gln Leu
1               5                   10                  15

Tyr Ser Thr Gln Leu Ser Thr Asp Thr Gly Val Glu His Val Thr Phe
            20                  25                  30

Phe Ile Tyr Asn Lys Ile Val Asp Glu Pro Glu Glu His Val Gln Ile
        35                  40                  45

His Thr Ile Asp Gly Ser Ser Gly Val Val Asn Pro Val Met Glu Pro
    50                  55                  60

Ile Tyr Asp Glu Pro Thr Thr Thr Thr Ser Val Pro Leu
65                  70                  75

<210> SEQ ID NO 351
<211> LENGTH: 37
<212> TYPE: PRT
<213> ORGANISM: Unknown
<220> FEATURE:
<223> OTHER INFORMATION: peptide

<400> SEQUENCE: 351

Leu Cys Ala Tyr Cys Cys Asn Ile Val Asn Val Ser Leu Val Lys Pro
1               5                   10                  15

Ser Phe Tyr Val Tyr Ser Arg Val Lys Asn Leu Asn Ser Ser Arg Val
            20                  25                  30

Pro Asp Leu Leu Val
        35

<210> SEQ ID NO 352
<211> LENGTH: 124
<212> TYPE: PRT
<213> ORGANISM: Unknown
<220> FEATURE:
<223> OTHER INFORMATION: peptide

<400> SEQUENCE: 352

Ser Phe Arg Leu Phe Ala Arg Thr Arg Ser Met Trp Ser Phe Asn Pro
1               5                   10                  15

Glu Thr Asn Ile Leu Leu Asn Val Pro Leu His Gly Thr Ile Leu Thr
            20                  25                  30

Arg Pro Leu Leu Glu Ser Glu Leu Val Ile Gly Ala Val Ile Leu Arg
        35                  40                  45

Gly His Leu Arg Ile Ala Gly His His Leu Gly Arg Cys Asp Ile Lys
    50                  55                  60

Asp Leu Pro Lys Glu Ile Thr Val Ala Thr Ser Arg Thr Leu Ser Tyr
65                  70                  75                  80

Tyr Lys Leu Gly Ala Ser Gln Arg Val Ala Gly Asp Ser Gly Phe Ala
                85                  90                  95

Ala Tyr Ser Arg Tyr Arg Ile Gly Asn Tyr Lys Leu Asn Thr Asp His
            100                 105                 110

Ser Ser Ser Ser Asp Asn Ile Ala Leu Leu Val Gln
        115                 120

<210> SEQ ID NO 353
<211> LENGTH: 85
<212> TYPE: PRT
<213> ORGANISM: Unknown

```
<220> FEATURE:
<223> OTHER INFORMATION: peptide

<400> SEQUENCE: 353

Ser Gly Thr Tyr Glu Gly Asn Ser Pro Phe His Pro Leu Ala Asp Asn
1               5                   10                  15

Lys Phe Ala Leu Thr Cys Phe Ser Thr Gln Phe Ala Phe Ala Cys Pro
            20                  25                  30

Asp Gly Val Lys His Val Tyr Gln Leu Arg Ala Arg Ser Val Ser Pro
        35                  40                  45

Lys Leu Phe Ile Arg Gln Glu Glu Val Gln Glu Leu Tyr Ser Pro Ile
    50                  55                  60

Phe Leu Ile Val Ala Ala Ile Val Phe Ile Thr Leu Cys Phe Thr Leu
65                  70                  75                  80

Lys Arg Lys Thr Glu
                85


<210> SEQ ID NO 354
<211> LENGTH: 107
<212> TYPE: PRT
<213> ORGANISM: Unknown
<220> FEATURE:
<223> OTHER INFORMATION: peptide

<400> SEQUENCE: 354

Thr Lys Ala Tyr Asn Val Thr Gln Ala Phe Gly Arg Arg Gly Pro Glu
1               5                   10                  15

Gln Thr Gln Gly Asn Phe Gly Asp Gln Glu Leu Ile Arg Gln Gly Thr
            20                  25                  30

Asp Tyr Lys His Trp Pro Gln Ile Ala Gln Phe Ala Pro Ser Ala Ser
        35                  40                  45

Ala Phe Phe Gly Met Ser Arg Ile Gly Met Glu Val Thr Pro Ser Gly
    50                  55                  60

Thr Trp Leu Thr Tyr Thr Gly Ala Ile Lys Leu Asp Asp Lys Asp Pro
65                  70                  75                  80

Asn Phe Lys Asp Gln Val Ile Leu Leu Asn Lys His Ile Asp Ala Tyr
                85                  90                  95

Lys Thr Phe Pro Pro Thr Glu Pro Lys Lys Asp
            100                 105


<210> SEQ ID NO 355
<211> LENGTH: 81
<212> TYPE: PRT
<213> ORGANISM: Unknown
<220> FEATURE:
<223> OTHER INFORMATION: peptide

<400> SEQUENCE: 355

Ser Thr Lys His Phe Tyr Trp Phe Phe Ser Asn Tyr Leu Lys Arg Arg
1               5                   10                  15

Val Val Phe Asn Gly Val Ser Phe Ser Thr Phe Glu Glu Ala Ala Leu
            20                  25                  30

Cys Thr Phe Leu Leu Asn Lys Glu Met Tyr Leu Lys Leu Arg Ser Asp
        35                  40                  45

Val Leu Leu Pro Leu Thr Gln Tyr Asn Arg Tyr Leu Ala Leu Tyr Asn
    50                  55                  60

Lys Tyr Lys Tyr Phe Ser Gly Ala Met Asp Thr Thr Ser Tyr Arg Glu
65                  70                  75                  80
```

Ala

<210> SEQ ID NO 356
<211> LENGTH: 84
<212> TYPE: PRT
<213> ORGANISM: Unknown
<220> FEATURE:
<223> OTHER INFORMATION: peptide

<400> SEQUENCE: 356

```
Val Pro Leu Asn Ile Ile Pro Leu Thr Thr Ala Ala Lys Leu Met Val
1               5                   10                  15

Val Ile Pro Asp Tyr Asn Thr Tyr Lys Asn Thr Cys Asp Gly Thr Thr
            20                  25                  30

Phe Thr Tyr Ala Ser Ala Leu Trp Glu Ile Gln Gln Val Val Asp Ala
        35                  40                  45

Asp Ser Lys Ile Val Gln Leu Ser Glu Ile Ser Met Asp Asn Ser Pro
    50                  55                  60

Asn Leu Ala Trp Pro Leu Ile Val Thr Ala Leu Arg Ala Asn Ser Ala
65                  70                  75                  80

Val Lys Leu Gln
```

<210> SEQ ID NO 357
<211> LENGTH: 80
<212> TYPE: PRT
<213> ORGANISM: Unknown
<220> FEATURE:
<223> OTHER INFORMATION: peptide

<400> SEQUENCE: 357

```
Glu Gly Ser Glu Gly Leu Asn Asp Asn Leu Leu Glu Ile Leu Gln Lys
1               5                   10                  15

Glu Lys Val Asn Ile Asn Ile Val Gly Asp Phe Lys Leu Asn Glu Glu
            20                  25                  30

Ile Ala Ile Ile Leu Ala Ser Phe Ser Ala Ser Thr Ser Ala Phe Val
        35                  40                  45

Glu Thr Val Lys Gly Leu Asp Tyr Lys Ala Phe Lys Gln Ile Val Glu
    50                  55                  60

Ser Cys Gly Asn Phe Lys Val Thr Lys Gly Lys Ala Lys Lys Gly Ala
65                  70                  75                  80
```

<210> SEQ ID NO 358
<211> LENGTH: 108
<212> TYPE: PRT
<213> ORGANISM: Unknown
<220> FEATURE:
<223> OTHER INFORMATION: peptide

<400> SEQUENCE: 358

```
Ile Gly Glu Gln Lys Ser Ile Leu Ser Pro Leu Tyr Ala Phe Ala Ser
1               5                   10                  15

Glu Ala Ala Arg Val Val Arg Ser Ile Phe Ser Arg Thr Leu Glu Thr
            20                  25                  30

Ala Gln Asn Ser Val Arg Val Leu Gln Lys Ala Ala Ile Thr Ile Leu
        35                  40                  45

Asp Gly Ile Ser Gln Tyr Ser Leu Arg Leu Ile Asp Ala Met Met Phe
    50                  55                  60

Thr Ser Asp Leu Ala Thr Asn Asn Leu Val Val Met Ala Tyr Ile Thr
65                  70                  75                  80
```

Gly Gly Val Val Gln Leu Thr Ser Gln Trp Leu Thr Asn Ile Phe Gly
                85                  90                  95

Thr Val Tyr Glu Lys Leu Lys Pro Val Leu Asp Trp
            100                 105

<210> SEQ ID NO 359
<211> LENGTH: 77
<212> TYPE: PRT
<213> ORGANISM: Unknown
<220> FEATURE:
<223> OTHER INFORMATION: peptide

<400> SEQUENCE: 359

Gly Ser Glu Asp Asn Gln Thr Thr Thr Ile Gln Thr Ile Val Glu Val
1               5                   10                  15

Gln Pro Gln Leu Glu Met Glu Leu Thr Pro Val Val Gln Thr Ile Glu
            20                  25                  30

Val Asn Ser Phe Ser Gly Tyr Leu Lys Leu Thr Asp Asn Val Tyr Ile
        35                  40                  45

Lys Asn Ala Asp Ile Val Glu Glu Ala Lys Lys Val Lys Pro Thr Val
    50                  55                  60

Val Val Asn Ala Ala Asn Val Tyr Leu Lys His Gly Gly
65                  70                  75

<210> SEQ ID NO 360
<211> LENGTH: 81
<212> TYPE: PRT
<213> ORGANISM: Unknown
<220> FEATURE:
<223> OTHER INFORMATION: peptide

<400> SEQUENCE: 360

Asn Lys Gly Glu Asp Ile Gln Leu Leu Lys Ser Ala Tyr Glu Asn Phe
1               5                   10                  15

Asn Gln His Glu Val Leu Leu Ala Pro Leu Leu Ser Ala Gly Ile Phe
            20                  25                  30

Gly Ala Asp Pro Ile His Ser Leu Arg Val Cys Val Asp Thr Val Arg
        35                  40                  45

Thr Asn Val Tyr Leu Ala Val Phe Asp Lys Asn Leu Tyr Asp Lys Leu
    50                  55                  60

Val Ser Ser Phe Leu Glu Met Lys Ser Glu Lys Gln Val Glu Gln Lys
65                  70                  75                  80

Ile

<210> SEQ ID NO 361
<211> LENGTH: 104
<212> TYPE: PRT
<213> ORGANISM: Unknown
<220> FEATURE:
<223> OTHER INFORMATION: peptide

<400> SEQUENCE: 361

Ser Ala Phe Tyr Ile Leu Pro Ser Ile Ile Ser Asn Glu Lys Gln Glu
1               5                   10                  15

Ile Leu Gly Thr Val Ser Trp Asn Leu Arg Glu Met Leu Ala His Ala
            20                  25                  30

Glu Glu Thr Arg Lys Leu Met Pro Val Cys Val Glu Thr Lys Ala Ile
        35                  40                  45

Val Ser Thr Ile Gln Arg Lys Tyr Lys Gly Ile Lys Ile Gln Glu Gly
    50                  55                  60

```
Val Val Asp Tyr Gly Ala Arg Phe Tyr Phe Tyr Thr Ser Lys Thr Thr
65                  70                  75                  80

Val Ala Ser Leu Ile Asn Thr Leu Asn Asp Leu Asn Glu Thr Leu Val
                85                  90                  95

Thr Met Pro Leu Gly Tyr Val Thr
            100


<210> SEQ ID NO 362
<211> LENGTH: 104
<212> TYPE: PRT
<213> ORGANISM: Unknown
<220> FEATURE:
<223> OTHER INFORMATION: peptide

<400> SEQUENCE: 362

Ile Lys Ile Gln Glu Gly Val Val Asp Tyr Gly Ala Arg Phe Tyr Phe
1               5                   10                  15

Tyr Thr Ser Lys Thr Thr Val Ala Ser Leu Ile Asn Thr Leu Asn Asp
            20                  25                  30

Leu Asn Glu Thr Leu Val Thr Met Pro Leu Gly Tyr Val Thr His Gly
        35                  40                  45

Leu Asn Leu Glu Glu Ala Ala Arg Tyr Met Arg Ser Leu Lys Val Pro
    50                  55                  60

Ala Thr Val Ser Val Ser Ser Pro Asp Ala Val Thr Ala Tyr Asn Gly
65                  70                  75                  80

Tyr Leu Thr Ser Ser Ser Lys Thr Pro Glu Glu His Phe Ile Glu Thr
                85                  90                  95

Ile Ser Leu Ala Gly Ser Tyr Lys
            100


<210> SEQ ID NO 363
<211> LENGTH: 82
<212> TYPE: PRT
<213> ORGANISM: Unknown
<220> FEATURE:
<223> OTHER INFORMATION: peptide

<400> SEQUENCE: 363

Asn Ser His Glu Gly Lys Thr Phe Tyr Val Leu Pro Asn Asp Asp Thr
1               5                   10                  15

Leu Arg Val Glu Ala Phe Glu Tyr Tyr His Thr Thr Asp Pro Ser Phe
            20                  25                  30

Leu Gly Arg Tyr Met Ser Ala Leu Asn His Thr Lys Lys Trp Lys Tyr
        35                  40                  45

Pro Gln Val Asn Gly Leu Thr Ser Ile Lys Trp Ala Asp Asn Asn Cys
    50                  55                  60

Tyr Leu Ala Thr Ala Leu Leu Thr Leu Gln Gln Ile Glu Leu Lys Phe
65                  70                  75                  80

Asn Pro


<210> SEQ ID NO 364
<211> LENGTH: 76
<212> TYPE: PRT
<213> ORGANISM: Unknown
<220> FEATURE:
<223> OTHER INFORMATION: peptide

<400> SEQUENCE: 364

Thr Thr Arg Thr Gln Leu Pro Pro Ala Tyr Thr Asn Ser Phe Thr Arg
```

```
1               5                   10                  15

Gly Val Tyr Tyr Pro Asp Lys Val Phe Arg Ser Ser Val Leu His Ser
            20                  25                  30

Thr Gln Asp Leu Phe Leu Pro Phe Phe Ser Asn Val Thr Trp Phe His
        35                  40                  45

Ala Ile His Val Ser Gly Thr Asn Gly Thr Lys Arg Phe Asp Asn Pro
    50                  55                  60

Val Leu Pro Phe Asn Asp Gly Val Tyr Phe Ala Ser
65                  70                  75


<210> SEQ ID NO 365
<211> LENGTH: 83
<212> TYPE: PRT
<213> ORGANISM: Unknown
<220> FEATURE:
<223> OTHER INFORMATION: peptide

<400> SEQUENCE: 365

Arg Glu Gln Ile Asp Gly Tyr Val Met His Ala Asn Tyr Ile Phe Trp
1               5                   10                  15

Arg Asn Thr Asn Pro Ile Gln Leu Ser Ser Tyr Ser Leu Phe Asp Met
            20                  25                  30

Ser Lys Phe Pro Leu Lys Leu Arg Gly Thr Ala Val Met Ser Leu Lys
        35                  40                  45

Glu Gly Gln Ile Asn Asp Met Ile Leu Ser Leu Leu Ser Lys Gly Arg
    50                  55                  60

Leu Ile Ile Arg Glu Asn Asn Arg Val Val Ile Ser Ser Asp Val Leu
65                  70                  75                  80

Val Asn Asn


<210> SEQ ID NO 366
<211> LENGTH: 61
<212> TYPE: PRT
<213> ORGANISM: Unknown
<220> FEATURE:
<223> OTHER INFORMATION: peptide

<400> SEQUENCE: 366

Met Phe His Leu Val Asp Phe Gln Val Thr Ile Ala Glu Ile Leu Leu
1               5                   10                  15

Ile Ile Met Arg Thr Phe Lys Val Ser Ile Trp Asn Leu Asp Tyr Ile
            20                  25                  30

Ile Asn Leu Ile Ile Lys Asn Leu Ser Lys Ser Leu Thr Glu Asn Lys
        35                  40                  45

Tyr Ser Gln Leu Asp Glu Glu Gln Pro Met Glu Ile Asp
    50                  55                  60


<210> SEQ ID NO 367
<211> LENGTH: 84
<212> TYPE: PRT
<213> ORGANISM: Unknown
<220> FEATURE:
<223> OTHER INFORMATION: peptide

<400> SEQUENCE: 367

Asp Val Val Asn Gln Asn Ala Gln Ala Leu Asn Thr Leu Val Lys Gln
1               5                   10                  15

Leu Ser Ser Asn Phe Gly Ala Ile Ser Ser Val Leu Asn Asp Ile Leu
            20                  25                  30
```

Ser Arg Leu Asp Lys Val Glu Ala Glu Val Gln Ile Asp Arg Leu Ile
35 40 45

Thr Gly Arg Leu Gln Ser Leu Gln Thr Tyr Val Thr Gln Gln Leu Ile
50 55 60

Arg Ala Ala Glu Ile Arg Ala Ser Ala Asn Leu Ala Ala Thr Lys Met
65 70 75 80

Ser Glu Cys Val

<210> SEQ ID NO 368
<211> LENGTH: 63
<212> TYPE: PRT
<213> ORGANISM: Unknown
<220> FEATURE:
<223> OTHER INFORMATION: peptide

<400> SEQUENCE: 368

Ala Ile Ala Ser Glu Phe Ser Ser Leu Pro Ser Tyr Ala Ala Phe Ala
1 5 10 15

Thr Ala Gln Glu Ala Tyr Glu Gln Ala Val Ala Asn Gly Asp Ser Glu
20 25 30

Val Val Leu Lys Lys Leu Lys Lys Ser Leu Asn Val Ala Lys Ser Glu
35 40 45

Phe Asp Arg Asp Ala Ala Met Gln Arg Lys Leu Glu Lys Met Ala
50 55 60

<210> SEQ ID NO 369
<211> LENGTH: 80
<212> TYPE: PRT
<213> ORGANISM: Unknown
<220> FEATURE:
<223> OTHER INFORMATION: peptide

<400> SEQUENCE: 369

Thr Thr Lys Gly Gly Arg Phe Val Leu Ala Leu Leu Ser Asp Leu Gln
1 5 10 15

Asp Leu Lys Trp Ala Arg Phe Pro Lys Ser Asp Gly Thr Gly Thr Ile
20 25 30

Tyr Thr Glu Leu Glu Pro Pro Cys Arg Phe Val Thr Asp Thr Pro Lys
35 40 45

Gly Pro Lys Val Lys Tyr Leu Tyr Phe Ile Lys Gly Leu Asn Asn Leu
50 55 60

Asn Arg Gly Met Val Leu Gly Ser Leu Ala Ala Thr Val Arg Leu Gln
65 70 75 80

<210> SEQ ID NO 370
<211> LENGTH: 45
<212> TYPE: PRT
<213> ORGANISM: Unknown
<220> FEATURE:
<223> OTHER INFORMATION: peptide

<400> SEQUENCE: 370

Lys Met Phe Asp Ala Tyr Val Asn Thr Phe Ser Ser Thr Phe Asn Val
1 5 10 15

Pro Met Glu Lys Leu Lys Thr Leu Val Ala Thr Ala Glu Ala Glu Leu
20 25 30

Ala Lys Asn Val Ser Leu Asp Asn Val Leu Ser Thr Phe
35 40 45

<210> SEQ ID NO 371

<211> LENGTH: 41
<212> TYPE: PRT
<213> ORGANISM: Unknown
<220> FEATURE:
<223> OTHER INFORMATION: peptide

<400> SEQUENCE: 371

Met Ser Tyr Glu Asp Gln Asp Ala Leu Phe Ala Tyr Thr Lys Arg Asn
1 5 10 15

Val Ile Pro Thr Ile Thr Gln Met Asn Leu Lys Tyr Ala Ile Ser Ala
20 25 30

Lys Asn Arg Ala Arg Thr Val Ala Gly
35 40

<210> SEQ ID NO 372
<211> LENGTH: 45
<212> TYPE: PRT
<213> ORGANISM: Unknown
<220> FEATURE:
<223> OTHER INFORMATION: peptide

<400> SEQUENCE: 372

Asp Gly Thr Leu Met Ile Glu Arg Phe Val Ser Leu Ala Ile Asp Ala
1 5 10 15

Tyr Pro Leu Thr Lys His Pro Asn Gln Glu Tyr Ala Asp Val Phe His
20 25 30

Leu Tyr Leu Gln Tyr Ile Arg Lys Leu His Asp Glu Leu
35 40 45

<210> SEQ ID NO 373
<211> LENGTH: 43
<212> TYPE: PRT
<213> ORGANISM: Unknown
<220> FEATURE:
<223> OTHER INFORMATION: peptide

<400> SEQUENCE: 373

Arg His His Ala Asn Glu Tyr Arg Leu Tyr Leu Asp Ala Tyr Asn Met
1 5 10 15

Met Ile Ser Ala Gly Phe Ser Leu Trp Val Tyr Lys Gln Phe Asp Thr
20 25 30

Tyr Asn Leu Trp Asn Thr Phe Thr Arg Leu Gln
35 40

<210> SEQ ID NO 374
<211> LENGTH: 41
<212> TYPE: PRT
<213> ORGANISM: Unknown
<220> FEATURE:
<223> OTHER INFORMATION: peptide

<400> SEQUENCE: 374

Asn Phe Asn Val Leu Phe Ser Thr Val Phe Pro Pro Thr Ser Phe Gly
1 5 10 15

Pro Leu Val Arg Lys Ile Phe Val Asp Gly Val Pro Phe Val Val Ser
20 25 30

Thr Gly Tyr His Phe Arg Glu Leu Gly
35 40

<210> SEQ ID NO 375
<211> LENGTH: 45
<212> TYPE: PRT
<213> ORGANISM: Unknown

<220> FEATURE:
<223> OTHER INFORMATION: peptide

<400> SEQUENCE: 375

Arg Ser Val Ala Ser Gln Ser Ile Ile Ala Tyr Thr Met Ser Leu Gly
1               5                   10                  15

Ala Glu Asn Ser Val Ala Tyr Ser Asn Asn Ser Ile Ala Ile Pro Thr
            20                  25                  30

Asn Phe Thr Ile Ser Val Thr Thr Glu Ile Leu Pro Val
        35                  40                  45

<210> SEQ ID NO 376
<211> LENGTH: 47
<212> TYPE: PRT
<213> ORGANISM: Unknown
<220> FEATURE:
<223> OTHER INFORMATION: peptide

<400> SEQUENCE: 376

Asp Lys Ser Val Tyr Tyr Thr Ser Asn Pro Thr Thr Phe His Leu Asp
1               5                   10                  15

Gly Glu Val Ile Thr Phe Asp Asn Leu Lys Thr Leu Leu Ser Leu Arg
            20                  25                  30

Glu Val Arg Thr Ile Lys Val Phe Thr Thr Val Asp Asn Ile Asn
        35                  40                  45

<210> SEQ ID NO 377
<211> LENGTH: 45
<212> TYPE: PRT
<213> ORGANISM: Unknown
<220> FEATURE:
<223> OTHER INFORMATION: peptide

<400> SEQUENCE: 377

Leu Thr Asp Glu Met Ile Ala Gln Tyr Thr Ser Ala Leu Leu Ala Gly
1               5                   10                  15

Thr Ile Thr Ser Gly Trp Thr Phe Gly Ala Gly Ala Ala Leu Gln Ile
            20                  25                  30

Pro Phe Ala Met Gln Met Ala Tyr Arg Phe Asn Gly Ile
        35                  40                  45

<210> SEQ ID NO 378
<211> LENGTH: 45
<212> TYPE: PRT
<213> ORGANISM: Unknown
<220> FEATURE:
<223> OTHER INFORMATION: peptide

<400> SEQUENCE: 378

Ala Val Val Tyr Arg Gly Thr Thr Thr Tyr Lys Leu Asn Val Gly Asp
1               5                   10                  15

Tyr Phe Val Leu Thr Ser His Thr Val Met Pro Leu Ser Ala Pro Thr
            20                  25                  30

Leu Val Pro Gln Glu His Tyr Val Arg Ile Thr Gly Leu
        35                  40                  45

<210> SEQ ID NO 379
<211> LENGTH: 41
<212> TYPE: PRT
<213> ORGANISM: Unknown
<220> FEATURE:
<223> OTHER INFORMATION: peptide

<400> SEQUENCE: 379

Glu Arg Ser Glu Lys Ser Tyr Glu Leu Gln Thr Pro Phe Glu Ile Lys
1 5 10 15

Leu Ala Lys Lys Phe Asp Thr Phe Asn Gly Glu Cys Pro Asn Phe Val
20 25 30

Phe Pro Leu Asn Ser Ile Ile Lys Thr
35 40

<210> SEQ ID NO 380
<211> LENGTH: 45
<212> TYPE: PRT
<213> ORGANISM: Unknown
<220> FEATURE:
<223> OTHER INFORMATION: peptide

<400> SEQUENCE: 380

Ala Ala Tyr Val Asp Asn Ser Ser Leu Thr Ile Lys Lys Pro Asn Glu
1 5 10 15

Leu Ser Arg Val Leu Gly Leu Lys Thr Leu Ala Thr His Gly Leu Ala
20 25 30

Ala Val Asn Ser Val Pro Trp Asp Thr Ile Ala Asn Tyr
35 40 45

<210> SEQ ID NO 381
<211> LENGTH: 41
<212> TYPE: PRT
<213> ORGANISM: Unknown
<220> FEATURE:
<223> OTHER INFORMATION: peptide

<400> SEQUENCE: 381

Val Asp Thr Asp Phe Val Asn Glu Phe Tyr Ala Tyr Leu Arg Lys His
1 5 10 15

Phe Ser Met Met Ile Leu Ser Asp Asp Ala Val Val Cys Phe Asn Ser
20 25 30

Thr Tyr Ala Ser Gln Gly Leu Val Ala
35 40

<210> SEQ ID NO 382
<211> LENGTH: 33
<212> TYPE: PRT
<213> ORGANISM: Unknown
<220> FEATURE:
<223> OTHER INFORMATION: peptide

<400> SEQUENCE: 382

Phe Asn Ser Thr Tyr Ala Ser Gln Gly Leu Val Ala Ser Ile Lys Asn
1 5 10 15

Phe Lys Ser Val Leu Tyr Tyr Gln Asn Asn Val Phe Met Ser Glu Ala
20 25 30

Lys

<210> SEQ ID NO 383
<211> LENGTH: 43
<212> TYPE: PRT
<213> ORGANISM: Unknown
<220> FEATURE:
<223> OTHER INFORMATION: peptide

<400> SEQUENCE: 383

Val Tyr Ser Asp Val Glu Asn Pro His Leu Met Gly Trp Asp Tyr Pro
1 5 10 15

```
Lys Cys Asp Arg Ala Met Pro Asn Met Leu Arg Ile Met Ala Ser Leu
            20                  25                  30

Val Leu Ala Arg Lys His Thr Thr Cys Cys Ser
        35                  40


<210> SEQ ID NO 384
<211> LENGTH: 45
<212> TYPE: PRT
<213> ORGANISM: Unknown
<220> FEATURE:
<223> OTHER INFORMATION: peptide

<400> SEQUENCE: 384

Lys Asp Met Thr Tyr Arg Arg Leu Ile Ser Met Met Gly Phe Lys Met
1               5                   10                  15

Asn Tyr Gln Val Asn Gly Tyr Pro Asn Met Phe Ile Thr Arg Glu Glu
            20                  25                  30

Ala Ile Arg His Val Arg Ala Trp Ile Gly Phe Asp Val
        35                  40                  45


<210> SEQ ID NO 385
<211> LENGTH: 41
<212> TYPE: PRT
<213> ORGANISM: Unknown
<220> FEATURE:
<223> OTHER INFORMATION: peptide

<400> SEQUENCE: 385

Tyr Glu Ser Leu Arg Pro Asp Thr Arg Tyr Val Leu Met Asp Gly Ser
1               5                   10                  15

Ile Ile Gln Phe Pro Asn Thr Tyr Leu Glu Gly Ser Val Arg Val Val
            20                  25                  30

Thr Thr Phe Asp Ser Glu Tyr Cys Arg
        35                  40


<210> SEQ ID NO 386
<211> LENGTH: 41
<212> TYPE: PRT
<213> ORGANISM: Unknown
<220> FEATURE:
<223> OTHER INFORMATION: peptide

<400> SEQUENCE: 386

Ser Lys Gly Phe Phe Lys Glu Gly Ser Ser Val Glu Leu Lys His Phe
1               5                   10                  15

Phe Phe Ala Gln Asp Gly Asn Ala Ala Ile Ser Asp Tyr Asp Tyr Tyr
            20                  25                  30

Arg Tyr Asn Leu Pro Thr Met Cys Asp
        35                  40


<210> SEQ ID NO 387
<211> LENGTH: 43
<212> TYPE: PRT
<213> ORGANISM: Unknown
<220> FEATURE:
<223> OTHER INFORMATION: peptide

<400> SEQUENCE: 387

Lys Thr Leu Gln Pro Val Ser Glu Leu Leu Thr Pro Leu Gly Ile Asp
1               5                   10                  15

Leu Asp Glu Trp Ser Met Ala Thr Tyr Tyr Leu Phe Asp Glu Ser Gly
            20                  25                  30
```

Glu Phe Lys Leu Ala Ser His Met Tyr Cys Ser
35 40

<210> SEQ ID NO 388
<211> LENGTH: 45
<212> TYPE: PRT
<213> ORGANISM: Unknown
<220> FEATURE:
<223> OTHER INFORMATION: peptide

<400> SEQUENCE: 388

Pro Thr Glu Ser Ile Val Arg Phe Pro Asn Ile Thr Asn Leu Cys Pro
1 5 10 15

Phe Gly Glu Val Phe Asn Ala Thr Arg Phe Ala Ser Val Tyr Ala Trp
20 25 30

Asn Arg Lys Arg Ile Ser Asn Cys Val Ala Asp Tyr Ser
35 40 45

<210> SEQ ID NO 389
<211> LENGTH: 43
<212> TYPE: PRT
<213> ORGANISM: Unknown
<220> FEATURE:
<223> OTHER INFORMATION: peptide

<400> SEQUENCE: 389

Phe Ala Ser Val Tyr Ala Trp Asn Arg Lys Arg Ile Ser Asn Cys Val
1 5 10 15

Ala Asp Tyr Ser Val Leu Tyr Asn Ser Ala Ser Phe Ser Thr Phe Lys
20 25 30

Cys Tyr Gly Val Ser Pro Thr Lys Leu Asn Asp
35 40

<210> SEQ ID NO 390
<211> LENGTH: 45
<212> TYPE: PRT
<213> ORGANISM: Unknown
<220> FEATURE:
<223> OTHER INFORMATION: peptide

<400> SEQUENCE: 390

Thr Arg Phe Gln Thr Leu Leu Ala Leu His Arg Ser Tyr Leu Thr Pro
1 5 10 15

Gly Asp Ser Ser Ser Gly Trp Thr Ala Gly Ala Ala Ala Tyr Tyr Val
20 25 30

Gly Tyr Leu Gln Pro Arg Thr Phe Leu Leu Lys Tyr Asn
35 40 45

<210> SEQ ID NO 391
<211> LENGTH: 42
<212> TYPE: PRT
<213> ORGANISM: Unknown
<220> FEATURE:
<223> OTHER INFORMATION: peptide

<400> SEQUENCE: 391

Val Val Leu His Ser Tyr Phe Thr Ser Asp Tyr Tyr Gln Leu Tyr Ser
1 5 10 15

Thr Gln Leu Ser Thr Asp Thr Gly Val Glu His Val Thr Phe Phe Ile
20 25 30

Tyr Asn Lys Ile Val Asp Glu Pro Glu Glu
35 40

<210> SEQ ID NO 392
<211> LENGTH: 31
<212> TYPE: PRT
<213> ORGANISM: Unknown
<220> FEATURE:
<223> OTHER INFORMATION: peptide

<400> SEQUENCE: 392

Asn Ile Val Asn Val Ser Leu Val Lys Pro Ser Phe Tyr Val Tyr Ser
1 5 10 15

Arg Val Lys Asn Leu Asn Ser Ser Arg Val Pro Asp Leu Leu Val
20 25 30

<210> SEQ ID NO 393
<211> LENGTH: 43
<212> TYPE: PRT
<213> ORGANISM: Unknown
<220> FEATURE:
<223> OTHER INFORMATION: peptide

<400> SEQUENCE: 393

Pro Lys Glu Ile Thr Val Ala Thr Ser Arg Thr Leu Ser Tyr Tyr Lys
1 5 10 15

Leu Gly Ala Ser Gln Arg Val Ala Gly Asp Ser Gly Phe Ala Ala Tyr
20 25 30

Ser Arg Tyr Arg Ile Gly Asn Tyr Lys Leu Asn
35 40

<210> SEQ ID NO 394
<211> LENGTH: 42
<212> TYPE: PRT
<213> ORGANISM: Unknown
<220> FEATURE:
<223> OTHER INFORMATION: peptide

<400> SEQUENCE: 394

Val Lys His Val Tyr Gln Leu Arg Ala Arg Ser Val Ser Pro Lys Leu
1 5 10 15

Phe Ile Arg Gln Glu Glu Val Gln Glu Leu Tyr Ser Pro Ile Phe Leu
20 25 30

Ile Val Ala Ala Ile Val Phe Ile Thr Leu
35 40

<210> SEQ ID NO 395
<211> LENGTH: 42
<212> TYPE: PRT
<213> ORGANISM: Unknown
<220> FEATURE:
<223> OTHER INFORMATION: peptide

<400> SEQUENCE: 395

His Trp Pro Gln Ile Ala Gln Phe Ala Pro Ser Ala Ser Ala Phe Phe
1 5 10 15

Gly Met Ser Arg Ile Gly Met Glu Val Thr Pro Ser Gly Thr Trp Leu
20 25 30

Thr Tyr Thr Gly Ala Ile Lys Leu Asp Asp
35 40

<210> SEQ ID NO 396
<211> LENGTH: 46
<212> TYPE: PRT
<213> ORGANISM: Unknown

<220> FEATURE:
<223> OTHER INFORMATION: peptide

<400> SEQUENCE: 396

Ser Thr Lys His Phe Tyr Trp Phe Phe Ser Asn Tyr Leu Lys Arg Arg
1 5 10 15

Val Val Phe Asn Gly Val Ser Phe Ser Thr Phe Glu Glu Ala Ala Leu
20 25 30

Cys Thr Phe Leu Leu Asn Lys Glu Met Tyr Leu Lys Leu Arg
35 40 45

<210> SEQ ID NO 397
<211> LENGTH: 46
<212> TYPE: PRT
<213> ORGANISM: Unknown
<220> FEATURE:
<223> OTHER INFORMATION: peptide

<400> SEQUENCE: 397

Leu Leu Asn Lys Glu Met Tyr Leu Lys Leu Arg Ser Asp Val Leu Leu
1 5 10 15

Pro Leu Thr Gln Tyr Asn Arg Tyr Leu Ala Leu Tyr Asn Lys Tyr Lys
20 25 30

Tyr Phe Ser Gly Ala Met Asp Thr Thr Ser Tyr Arg Glu Ala
35 40 45

<210> SEQ ID NO 398
<211> LENGTH: 44
<212> TYPE: PRT
<213> ORGANISM: Unknown
<220> FEATURE:
<223> OTHER INFORMATION: peptide

<400> SEQUENCE: 398

Val Pro Leu Asn Ile Ile Pro Leu Thr Thr Ala Ala Lys Leu Met Val
1 5 10 15

Val Ile Pro Asp Tyr Asn Thr Tyr Lys Asn Thr Cys Asp Gly Thr Thr
20 25 30

Phe Thr Tyr Ala Ser Ala Leu Trp Glu Ile Gln Gln
35 40

<210> SEQ ID NO 399
<211> LENGTH: 42
<212> TYPE: PRT
<213> ORGANISM: Unknown
<220> FEATURE:
<223> OTHER INFORMATION: peptide

<400> SEQUENCE: 399

Asn Ile Asn Ile Val Gly Asp Phe Lys Leu Asn Glu Glu Ile Ala Ile
1 5 10 15

Ile Leu Ala Ser Phe Ser Ala Ser Thr Ser Ala Phe Val Glu Thr Val
20 25 30

Lys Gly Leu Asp Tyr Lys Ala Phe Lys Gln
35 40

<210> SEQ ID NO 400
<211> LENGTH: 43
<212> TYPE: PRT
<213> ORGANISM: Unknown
<220> FEATURE:
<223> OTHER INFORMATION: peptide

<400> SEQUENCE: 400

Ser Ile Leu Ser Pro Leu Tyr Ala Phe Ala Ser Glu Ala Ala Arg Val
1 5 10 15

Val Arg Ser Ile Phe Ser Arg Thr Leu Glu Thr Ala Gln Asn Ser Val
20 25 30

Arg Val Leu Gln Lys Ala Ala Ile Thr Ile Leu
35 40

<210> SEQ ID NO 401
<211> LENGTH: 43
<212> TYPE: PRT
<213> ORGANISM: Unknown
<220> FEATURE:
<223> OTHER INFORMATION: peptide

<400> SEQUENCE: 401

Ser Glu Asp Asn Gln Thr Thr Thr Ile Gln Thr Ile Val Glu Val Gln
1 5 10 15

Pro Gln Leu Glu Met Glu Leu Thr Pro Val Val Gln Thr Ile Glu Val
20 25 30

Asn Ser Phe Ser Gly Tyr Leu Lys Leu Thr Asp
35 40

<210> SEQ ID NO 402
<211> LENGTH: 43
<212> TYPE: PRT
<213> ORGANISM: Unknown
<220> FEATURE:
<223> OTHER INFORMATION: peptide

<400> SEQUENCE: 402

Phe Gly Ala Asp Pro Ile His Ser Leu Arg Val Cys Val Asp Thr Val
1 5 10 15

Arg Thr Asn Val Tyr Leu Ala Val Phe Asp Lys Asn Leu Tyr Asp Lys
20 25 30

Leu Val Ser Ser Phe Leu Glu Met Lys Ser Glu
35 40

<210> SEQ ID NO 403
<211> LENGTH: 43
<212> TYPE: PRT
<213> ORGANISM: Unknown
<220> FEATURE:
<223> OTHER INFORMATION: peptide

<400> SEQUENCE: 403

Lys Ile Gln Glu Gly Val Val Asp Tyr Gly Ala Arg Phe Tyr Phe Tyr
1 5 10 15

Thr Ser Lys Thr Thr Val Ala Ser Leu Ile Asn Thr Leu Asn Asp Leu
20 25 30

Asn Glu Thr Leu Val Thr Met Pro Leu Gly Tyr
35 40

<210> SEQ ID NO 404
<211> LENGTH: 41
<212> TYPE: PRT
<213> ORGANISM: Unknown
<220> FEATURE:
<223> OTHER INFORMATION: peptide

<400> SEQUENCE: 404

Lys Thr Phe Tyr Val Leu Pro Asn Asp Asp Thr Leu Arg Val Glu Ala 1 5 10 15

Phe Glu Tyr Tyr His Thr Thr Asp Pro Ser Phe Leu Gly Arg Tyr Met
20 25 30

Ser Ala Leu Asn His Thr Lys Lys Trp
35 40

<210> SEQ ID NO 405
<211> LENGTH: 46
<212> TYPE: PRT
<213> ORGANISM: Unknown
<220> FEATURE:
<223> OTHER INFORMATION: peptide

<400> SEQUENCE: 405

His Leu Val Asp Phe Gln Val Thr Ile Ala Glu Ile Leu Leu Ile Ile
1 5 10 15

Met Arg Thr Phe Lys Val Ser Ile Trp Asn Leu Asp Tyr Ile Ile Asn
20 25 30

Leu Ile Ile Lys Asn Leu Ser Lys Ser Leu Thr Glu Asn Lys
35 40 45

<210> SEQ ID NO 406
<211> LENGTH: 44
<212> TYPE: PRT
<213> ORGANISM: Unknown
<220> FEATURE:
<223> OTHER INFORMATION: peptide

<400> SEQUENCE: 406

Val Glu Ala Glu Val Gln Ile Asp Arg Leu Ile Thr Gly Arg Leu Gln
1 5 10 15

Ser Leu Gln Thr Tyr Val Thr Gln Gln Leu Ile Arg Ala Ala Glu Ile
20 25 30

Arg Ala Ser Ala Asn Leu Ala Ala Thr Lys Met Ser
35 40

<210> SEQ ID NO 407
<211> LENGTH: 36
<212> TYPE: PRT
<213> ORGANISM: Unknown
<220> FEATURE:
<223> OTHER INFORMATION: peptide

<400> SEQUENCE: 407

Ala Ile Ala Ser Glu Phe Ser Ser Leu Pro Ser Tyr Ala Ala Phe Ala
1 5 10 15

Thr Ala Gln Glu Ala Tyr Glu Gln Ala Val Ala Asn Gly Asp Ser Glu
20 25 30

Val Val Leu Lys
35

<210> SEQ ID NO 408
<211> LENGTH: 41
<212> TYPE: PRT
<213> ORGANISM: Unknown
<220> FEATURE:
<223> OTHER INFORMATION: peptide

<400> SEQUENCE: 408

Cys Arg Phe Val Thr Asp Thr Pro Lys Gly Pro Lys Val Lys Tyr Leu
1 5 10 15

Tyr Phe Ile Lys Gly Leu Asn Asn Leu Asn Arg Gly Met Val Leu Gly

```
            20                  25                  30

Ser Leu Ala Ala Thr Val Arg Leu Gln
        35                  40


<210> SEQ ID NO 409
<211> LENGTH: 6
<212> TYPE: PRT
<213> ORGANISM: Unknown
<220> FEATURE:
<223> OTHER INFORMATION: peptide

<400> SEQUENCE: 409

Val Lys Leu His Tyr Thr
1               5


<210> SEQ ID NO 410
<211> LENGTH: 9744
<212> TYPE: PRT
<213> ORGANISM: Unknown
<220> FEATURE:
<223> OTHER INFORMATION: SARS-CoV-2 concatenated Polyprotein

<400> SEQUENCE: 410

Met Glu Ser Leu Val Pro Gly Phe Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Val Leu Ser Glu Ala Arg Gln His Leu Lys Asp
        35                  40                  45

Gly Thr Cys Gly Leu Val Glu Val Glu Lys Gly Val Leu Pro Gln Leu
    50                  55                  60

Glu Gln Pro Tyr Val Phe Ile Lys Arg Ser Asp Ala Arg Thr Ala Pro
65                  70                  75                  80

His Gly His Val Met Val Glu Leu Val Ala Glu Leu Glu Gly Ile Gln
                85                  90                  95

Tyr Gly Arg Ser Gly Glu Thr Leu Gly Val Leu Val Pro His Val Gly
            100                 105                 110

Glu Ile Pro Val Ala Tyr Arg Lys Val Leu Leu Arg Lys Asn Gly Asn
        115                 120                 125

Lys Gly Ala Gly Gly His Ser Tyr Gly Ala Asp Leu Lys Ser Phe Asp
    130                 135                 140

Leu Gly Asp Glu Leu Gly Thr Asp Pro Tyr Glu Asp Phe Gln Glu Asn
145                 150                 155                 160

Trp Asn Thr Lys His Ser Ser Gly Val Thr Arg Glu Leu Met Arg Glu
                165                 170                 175

Leu Asn Gly Gly Ala Tyr Thr Arg Tyr Val Asp Asn Asn Phe Cys Gly
            180                 185                 190

Pro Asp Gly Tyr Pro Leu Glu Cys Ile Lys Asp Leu Leu Ala Arg Ala
        195                 200                 205

Gly Lys Ala Ser Cys Thr Leu Ser Glu Gln Leu Asp Phe Ile Asp Thr
    210                 215                 220

Lys Arg Gly Val Tyr Cys Cys Arg Glu His Glu His Glu Ile Ala Trp
225                 230                 235                 240

Tyr Thr Glu Arg Ser Glu Lys Ser Tyr Glu Leu Gln Thr Pro Phe Glu
                245                 250                 255

Ile Lys Leu Ala Lys Lys Phe Asp Thr Phe Asn Gly Glu Cys Pro Asn
            260                 265                 270
```

-continued

```
Phe Val Phe Pro Leu Asn Ser Ile Ile Lys Thr Ile Gln Pro Arg Val
        275                 280                 285

Glu Lys Lys Lys Leu Asp Gly Phe Met Gly Arg Ile Arg Ser Val Tyr
    290                 295                 300

Pro Val Ala Ser Pro Asn Glu Cys Asn Gln Met Cys Leu Ser Thr Leu
305                 310                 315                 320

Met Lys Cys Asp His Cys Gly Glu Thr Ser Trp Gln Thr Gly Asp Phe
                325                 330                 335

Val Lys Ala Thr Cys Glu Phe Cys Gly Thr Glu Asn Leu Thr Lys Glu
            340                 345                 350

Gly Ala Thr Thr Cys Gly Tyr Leu Pro Gln Asn Ala Val Val Lys Ile
        355                 360                 365

Tyr Cys Pro Ala Cys His Asn Ser Glu Val Gly Pro Glu His Ser Leu
    370                 375                 380

Ala Glu Tyr His Asn Glu Ser Gly Leu Lys Thr Ile Leu Arg Lys Gly
385                 390                 395                 400

Gly Arg Thr Ile Ala Phe Gly Gly Cys Val Phe Ser Tyr Val Gly Cys
                405                 410                 415

His Asn Lys Cys Ala Tyr Trp Val Pro Arg Ala Ser Ala Asn Ile Gly
            420                 425                 430

Cys Asn His Thr Gly Val Val Gly Glu Gly Ser Glu Gly Leu Asn Asp
        435                 440                 445

Asn Leu Leu Glu Ile Leu Gln Lys Glu Lys Val Asn Ile Asn Ile Val
    450                 455                 460

Gly Asp Phe Lys Leu Asn Glu Glu Ile Ala Ile Ile Leu Ala Ser Phe
465                 470                 475                 480

Ser Ala Ser Thr Ser Ala Phe Val Glu Thr Val Lys Gly Leu Asp Tyr
                485                 490                 495

Lys Ala Phe Lys Gln Ile Val Glu Ser Cys Gly Asn Phe Lys Val Thr
            500                 505                 510

Lys Gly Lys Ala Lys Lys Gly Ala Trp Asn Ile Gly Glu Gln Lys Ser
        515                 520                 525

Ile Leu Ser Pro Leu Tyr Ala Phe Ala Ser Glu Ala Ala Arg Val Val
    530                 535                 540

Arg Ser Ile Phe Ser Arg Thr Leu Glu Thr Ala Gln Asn Ser Val Arg
545                 550                 555                 560

Val Leu Gln Lys Ala Ala Ile Thr Ile Leu Asp Gly Ile Ser Gln Tyr
                565                 570                 575

Ser Leu Arg Leu Ile Asp Ala Met Met Phe Thr Ser Asp Leu Ala Thr
            580                 585                 590

Asn Asn Leu Val Val Met Ala Tyr Ile Thr Gly Gly Val Val Gln Leu
        595                 600                 605

Thr Ser Gln Trp Leu Thr Asn Ile Phe Gly Thr Val Tyr Glu Lys Leu
    610                 615                 620

Lys Pro Val Leu Asp Trp Leu Glu Glu Lys Phe Lys Glu Gly Val Glu
625                 630                 635                 640

Phe Leu Arg Asp Gly Trp Glu Ile Val Lys Phe Ile Ser Thr Cys Ala
                645                 650                 655

Cys Glu Ile Val Gly Gly Gln Ile Val Thr Cys Ala Lys Glu Ile Lys
            660                 665                 670

Glu Ser Val Gln Thr Phe Phe Lys Leu Val Asn Lys Phe Leu Ala Leu
        675                 680                 685

Cys Ala Asp Ser Ile Ile Ile Gly Gly Ala Lys Leu Lys Ala Leu Asn
```

```
    690                 695                 700

Leu Gly Glu Thr Phe Val Thr His Ser Lys Gly Leu Tyr Arg Lys Cys
705                 710                 715                 720

Val Lys Ser Arg Glu Glu Thr Gly Leu Leu Met Pro Leu Lys Ala Pro
                725                 730                 735

Lys Glu Ile Ile Phe Leu Glu Gly Glu Thr Leu Pro Thr Glu Val Leu
            740                 745                 750

Thr Glu Glu Val Val Leu Lys Thr Gly Asp Leu Gln Pro Leu Glu Gln
        755                 760                 765

Pro Thr Ser Glu Ala Val Glu Ala Pro Leu Val Gly Thr Pro Val Cys
    770                 775                 780

Ile Asn Gly Leu Met Leu Leu Glu Ile Lys Asp Thr Glu Lys Tyr Cys
785                 790                 795                 800

Ala Leu Ala Pro Asn Met Met Val Thr Asn Asn Thr Phe Thr Leu Lys
                805                 810                 815

Gly Gly Ala Pro Thr Lys Val Thr Phe Gly Asp Asp Thr Val Ile Glu
            820                 825                 830

Val Gln Gly Tyr Lys Ser Val Asn Ile Thr Phe Glu Leu Asp Glu Arg
        835                 840                 845

Ile Asp Lys Val Leu Asn Glu Lys Cys Ser Ala Tyr Thr Val Glu Leu
    850                 855                 860

Gly Thr Glu Val Asn Glu Phe Ala Cys Val Val Ala Asp Ala Val Ile
865                 870                 875                 880

Lys Thr Leu Gln Pro Val Ser Glu Leu Leu Thr Pro Leu Gly Ile Asp
                885                 890                 895

Leu Asp Glu Trp Ser Met Ala Thr Tyr Tyr Leu Phe Asp Glu Ser Gly
            900                 905                 910

Glu Phe Lys Leu Ala Ser His Met Tyr Cys Ser Phe Tyr Pro Pro Asp
        915                 920                 925

Glu Asp Glu Glu Glu Gly Asp Cys Glu Glu Glu Phe Glu Pro Ser
    930                 935                 940

Thr Gln Tyr Glu Tyr Gly Thr Glu Asp Asp Tyr Gln Gly Lys Pro Leu
945                 950                 955                 960

Glu Phe Gly Ala Thr Ser Ala Ala Leu Gln Pro Glu Glu Glu Gln Glu
                965                 970                 975

Glu Asp Trp Leu Asp Asp Asp Ser Gln Gln Thr Val Gly Gln Gln Asp
            980                 985                 990

Gly Ser Glu Asp Asn Gln Thr Thr  Thr Ile Gln Thr Ile  Val Glu Val
        995                 1000                1005

Gln Pro  Gln Leu Glu Met Glu  Leu Thr Pro Val Val  Gln Thr Ile
    1010                1015                1020

Glu Val  Asn Ser Phe Ser Gly  Tyr Leu Lys Leu Thr  Asp Asn Val
    1025                1030                1035

Tyr Ile  Lys Asn Ala Asp Ile  Val Glu Glu Ala Lys  Lys Val Lys
    1040                1045                1050

Pro Thr  Val Val Val Asn Ala  Ala Asn Val Tyr Leu  Lys His Gly
    1055                1060                1065

Gly Gly  Val Ala Gly Ala Leu  Asn Lys Ala Thr Asn  Asn Ala Met
    1070                1075                1080

Gln Val  Glu Ser Asp Asp Tyr  Ile Ala Thr Asn Gly  Pro Leu Lys
    1085                1090                1095

Val Gly  Gly Ser Cys Val Leu  Ser Gly His Asn Leu  Ala Lys His
    1100                1105                1110
```

```
Cys Leu  His Val Val Gly Pro  Asn Val Asn Lys Gly  Glu Asp Ile
    1115                 1120                 1125

Gln Leu  Leu Lys Ser Ala Tyr  Glu Asn Phe Asn Gln  His Glu Val
    1130                 1135                 1140

Leu Leu  Ala Pro Leu Leu Ser  Ala Gly Ile Phe Gly  Ala Asp Pro
    1145                 1150                 1155

Ile His  Ser Leu Arg Val Cys  Val Asp Thr Val Arg  Thr Asn Val
    1160                 1165                 1170

Tyr Leu  Ala Val Phe Asp Lys  Asn Leu Tyr Asp Lys  Leu Val Ser
    1175                 1180                 1185

Ser Phe  Leu Glu Met Lys Ser  Glu Lys Gln Val Glu  Gln Lys Ile
    1190                 1195                 1200

Ala Glu  Ile Pro Lys Glu Glu  Val Lys Pro Phe Ile  Thr Glu Ser
    1205                 1210                 1215

Lys Pro  Ser Val Glu Gln Arg  Lys Gln Asp Asp Lys  Lys Ile Lys
    1220                 1225                 1230

Ala Cys  Val Glu Glu Val Thr  Thr Thr Leu Glu Glu  Thr Lys Phe
    1235                 1240                 1245

Leu Thr  Glu Asn Leu Leu Leu  Tyr Ile Asp Ile Asn  Gly Asn Leu
    1250                 1255                 1260

His Pro  Asp Ser Ala Thr Leu  Val Ser Asp Ile Asp  Ile Thr Phe
    1265                 1270                 1275

Leu Lys  Lys Asp Ala Pro Tyr  Ile Val Gly Asp Val  Val Gln Glu
    1280                 1285                 1290

Gly Val  Leu Thr Ala Val Val  Ile Pro Thr Lys Lys  Ala Gly Gly
    1295                 1300                 1305

Thr Thr  Glu Met Leu Ala Lys  Ala Leu Arg Lys Val  Pro Thr Asp
    1310                 1315                 1320

Asn Tyr  Ile Thr Thr Tyr Pro  Gly Gln Gly Leu Asn  Gly Tyr Thr
    1325                 1330                 1335

Val Glu  Glu Ala Lys Thr Val  Leu Lys Lys Cys Lys  Ser Ala Phe
    1340                 1345                 1350

Tyr Ile  Leu Pro Ser Ile Ile  Ser Asn Glu Lys Gln  Glu Ile Leu
    1355                 1360                 1365

Gly Thr  Val Ser Trp Asn Leu  Arg Glu Met Leu Ala  His Ala Glu
    1370                 1375                 1380

Glu Thr  Arg Lys Leu Met Pro  Val Cys Val Glu Thr  Lys Ala Ile
    1385                 1390                 1395

Val Ser  Thr Ile Gln Arg Lys  Tyr Lys Gly Ile Lys  Ile Gln Glu
    1400                 1405                 1410

Gly Val  Val Asp Tyr Gly Ala  Arg Phe Tyr Phe Tyr  Thr Ser Lys
    1415                 1420                 1425

Thr Thr  Val Ala Ser Leu Ile  Asn Thr Leu Asn Asp  Leu Asn Glu
    1430                 1435                 1440

Thr Leu  Val Thr Met Pro Leu  Gly Tyr Val Thr His  Gly Leu Asn
    1445                 1450                 1455

Leu Glu  Glu Ala Ala Arg Tyr  Met Arg Ser Leu Lys  Val Pro Ala
    1460                 1465                 1470

Thr Val  Ser Val Ser Ser Pro  Asp Ala Val Thr Ala  Tyr Asn Gly
    1475                 1480                 1485

Tyr Leu  Thr Ser Ser Ser Lys  Thr Pro Glu Glu His  Phe Ile Glu
    1490                 1495                 1500
```

```
Thr Ile  Ser Leu Ala Gly Ser  Tyr Lys Asp Trp Ser  Tyr Ser Gly
    1505                 1510                 1515

Gln Ser  Thr Gln Leu Gly Ile  Glu Phe Leu Lys Arg  Gly Asp Lys
    1520                 1525                 1530

Ser Val  Tyr Tyr Thr Ser Asn  Pro Thr Thr Phe His  Leu Asp Gly
    1535                 1540                 1545

Glu Val  Ile Thr Phe Asp Asn  Leu Lys Thr Leu Leu  Ser Leu Arg
    1550                 1555                 1560

Glu Val  Arg Thr Ile Lys Val  Phe Thr Thr Val Asp  Asn Ile Asn
    1565                 1570                 1575

Leu His  Thr Gln Val Val Asp  Met Ser Met Thr Tyr  Gly Gln Gln
    1580                 1585                 1590

Phe Gly  Pro Thr Tyr Leu Asp  Gly Ala Asp Val Thr  Lys Ile Lys
    1595                 1600                 1605

Pro His  Asn Ser His Glu Gly  Lys Thr Phe Tyr Val  Leu Pro Asn
    1610                 1615                 1620

Asp Asp  Thr Leu Arg Val Glu  Ala Phe Glu Tyr Tyr  His Thr Thr
    1625                 1630                 1635

Asp Pro  Ser Phe Leu Gly Arg  Tyr Met Ser Ala Leu  Asn His Thr
    1640                 1645                 1650

Lys Lys  Trp Lys Tyr Pro Gln  Val Asn Gly Leu Thr  Ser Ile Lys
    1655                 1660                 1665

Trp Ala  Asp Asn Asn Cys Tyr  Leu Ala Thr Ala Leu  Leu Thr Leu
    1670                 1675                 1680

Gln Gln  Ile Glu Leu Lys Phe  Asn Pro Pro Ala Leu  Gln Asp Ala
    1685                 1690                 1695

Tyr Tyr  Arg Ala Arg Ala Gly  Glu Ala Ala Asn Phe  Cys Ala Leu
    1700                 1705                 1710

Ile Leu  Ala Tyr Cys Asn Lys  Thr Val Gly Glu Leu  Gly Asp Val
    1715                 1720                 1725

Arg Glu  Thr Met Ser Tyr Leu  Phe Gln His Ala Asn  Leu Asp Ser
    1730                 1735                 1740

Cys Lys  Arg Val Leu Asn Val  Val Cys Lys Thr Cys  Gly Gln Gln
    1745                 1750                 1755

Gln Thr  Thr Leu Lys Gly Val  Glu Ala Val Met Tyr  Met Gly Thr
    1760                 1765                 1770

Leu Ser  Tyr Glu Gln Phe Lys  Lys Gly Val Gln Ile  Pro Cys Thr
    1775                 1780                 1785

Cys Gly  Lys Gln Ala Thr Lys  Tyr Leu Val Gln Gln  Glu Ser Pro
    1790                 1795                 1800

Phe Val  Met Met Ser Ala Pro  Pro Ala Gln Tyr Glu  Leu Lys His
    1805                 1810                 1815

Gly Thr  Phe Thr Cys Ala Ser  Glu Tyr Thr Gly Asn  Tyr Gln Cys
    1820                 1825                 1830

Gly His  Tyr Lys His Ile Thr  Ser Lys Glu Thr Leu  Tyr Cys Ile
    1835                 1840                 1845

Asp Gly  Ala Leu Leu Thr Lys  Ser Ser Glu Tyr Lys  Gly Pro Ile
    1850                 1855                 1860

Thr Asp  Val Phe Tyr Lys Glu  Asn Ser Tyr Thr Thr  Thr Ile Lys
    1865                 1870                 1875

Pro Val  Thr Tyr Lys Leu Asp  Gly Val Val Cys Thr  Glu Ile Asp
    1880                 1885                 1890

Pro Lys  Leu Asp Asn Tyr Tyr  Lys Lys Asp Asn Ser  Tyr Phe Thr
```

```
    1895                1900                1905

Glu Gln  Pro Ile Asp Leu Val  Pro Asn Gln Pro Tyr  Pro Asn Ala
    1910                1915                1920

Ser Phe  Asp Asn Phe Lys Phe  Val Cys Asp Asn Ile  Lys Phe Ala
    1925                1930                1935

Asp Asp  Leu Asn Gln Leu Thr  Gly Tyr Lys Lys Pro  Ala Ser Arg
    1940                1945                1950

Glu Leu  Lys Val Thr Phe Phe  Pro Asp Leu Asn Gly  Asp Val Val
    1955                1960                1965

Ala Ile  Asp Tyr Lys His Tyr  Thr Pro Ser Phe Lys  Lys Gly Ala
    1970                1975                1980

Lys Leu  Leu His Lys Pro Ile  Val Trp His Val Asn  Asn Ala Thr
    1985                1990                1995

Asn Lys  Ala Thr Tyr Lys Pro  Asn Thr Trp Cys Ile  Arg Cys Leu
    2000                2005                2010

Trp Ser  Thr Lys Pro Val Glu  Thr Ser Asn Ser Phe  Asp Val Leu
    2015                2020                2025

Lys Ser  Glu Asp Ala Gln Gly  Met Asp Asn Leu Ala  Cys Glu Asp
    2030                2035                2040

Leu Lys  Pro Val Ser Glu Glu  Val Val Glu Asn Pro  Thr Ile Gln
    2045                2050                2055

Lys Asp  Val Leu Glu Cys Asn  Val Lys Thr Thr Glu  Val Val Gly
    2060                2065                2070

Asp Ile  Ile Leu Lys Pro Ala  Asn Asn Ser Leu Lys  Ile Thr Glu
    2075                2080                2085

Glu Val  Gly His Thr Asp Leu  Met Ala Ala Tyr Val  Asp Asn Ser
    2090                2095                2100

Ser Leu  Thr Ile Lys Lys Pro  Asn Glu Leu Ser Arg  Val Leu Gly
    2105                2110                2115

Leu Lys  Thr Leu Ala Thr His  Gly Leu Ala Ala Val  Asn Ser Val
    2120                2125                2130

Pro Trp  Asp Thr Ile Ala Asn  Tyr Ala Lys Pro Phe  Leu Asn Lys
    2135                2140                2145

Val Val  Ser Thr Thr Thr Asn  Ile Val Thr Arg Cys  Leu Asn Arg
    2150                2155                2160

Val Cys  Thr Asn Tyr Met Pro  Tyr Phe Phe Thr Leu  Leu Leu Gln
    2165                2170                2175

Leu Cys  Thr Phe Thr Arg Ser  Thr Asn Ser Arg Ile  Lys Ala Ser
    2180                2185                2190

Met Pro  Thr Thr Ile Ala Lys  Asn Thr Val Lys Ser  Val Gly Lys
    2195                2200                2205

Phe Cys  Leu Glu Ala Ser Phe  Asn Tyr Leu Lys Ser  Pro Asn Phe
    2210                2215                2220

Ser Lys  Leu Ile Asn Ile Ile  Ile Trp Phe Leu Leu  Leu Ser Val
    2225                2230                2235

Cys Leu  Gly Ser Leu Ile Tyr  Ser Thr Ala Ala Leu  Gly Val Leu
    2240                2245                2250

Met Ser  Asn Leu Gly Met Pro  Ser Tyr Cys Thr Gly  Tyr Arg Glu
    2255                2260                2265

Gly Tyr  Leu Asn Ser Thr Asn  Val Thr Ile Ala Thr  Tyr Cys Thr
    2270                2275                2280

Gly Ser  Ile Pro Cys Ser Val  Cys Leu Ser Gly Leu  Asp Ser Leu
    2285                2290                2295
```

```
Asp Thr  Tyr Pro Ser Leu Glu  Thr Ile Gln Ile Thr  Ile Ser Ser
    2300                 2305                 2310

Phe Lys  Trp Asp Leu Thr Ala  Phe Gly Leu Val Ala  Glu Trp Phe
    2315                 2320                 2325

Leu Ala  Tyr Ile Leu Phe Thr  Arg Phe Phe Tyr Val  Leu Gly Leu
    2330                 2335                 2340

Ala Ala  Ile Met Gln Leu Phe  Phe Ser Tyr Phe Ala  Val His Phe
    2345                 2350                 2355

Ile Ser  Asn Ser Trp Leu Met  Trp Leu Ile Ile Asn  Leu Val Gln
    2360                 2365                 2370

Met Ala  Pro Ile Ser Ala Met  Val Arg Met Tyr Ile  Phe Phe Ala
    2375                 2380                 2385

Ser Phe  Tyr Tyr Val Trp Lys  Ser Tyr Val His Val  Val Asp Gly
    2390                 2395                 2400

Cys Asn  Ser Ser Thr Cys Met  Met Cys Tyr Lys Arg  Asn Arg Ala
    2405                 2410                 2415

Thr Arg  Val Glu Cys Thr Thr  Ile Val Asn Gly Val  Arg Arg Ser
    2420                 2425                 2430

Phe Tyr  Val Tyr Ala Asn Gly  Gly Lys Gly Phe Cys  Lys Leu His
    2435                 2440                 2445

Asn Trp  Asn Cys Val Asn Cys  Asp Thr Phe Cys Ala  Gly Ser Thr
    2450                 2455                 2460

Phe Ile  Ser Asp Glu Val Ala  Arg Asp Leu Ser Leu  Gln Phe Lys
    2465                 2470                 2475

Arg Pro  Ile Asn Pro Thr Asp  Gln Ser Ser Tyr Ile  Val Asp Ser
    2480                 2485                 2490

Val Thr  Val Lys Asn Gly Ser  Ile His Leu Tyr Phe  Asp Lys Ala
    2495                 2500                 2505

Gly Gln  Lys Thr Tyr Glu Arg  His Ser Leu Ser His  Phe Val Asn
    2510                 2515                 2520

Leu Asp  Asn Leu Arg Ala Asn  Asn Thr Lys Gly Ser  Leu Pro Ile
    2525                 2530                 2535

Asn Val  Ile Val Phe Asp Gly  Lys Ser Lys Cys Glu  Glu Ser Ser
    2540                 2545                 2550

Ala Lys  Ser Ala Ser Val Tyr  Tyr Ser Gln Leu Met  Cys Gln Pro
    2555                 2560                 2565

Ile Leu  Leu Leu Asp Gln Ala  Leu Val Ser Asp Val  Gly Asp Ser
    2570                 2575                 2580

Ala Glu  Val Ala Val Lys Met  Phe Asp Ala Tyr Val  Asn Thr Phe
    2585                 2590                 2595

Ser Ser  Thr Phe Asn Val Pro  Met Glu Lys Leu Lys  Thr Leu Val
    2600                 2605                 2610

Ala Thr  Ala Glu Ala Glu Leu  Ala Lys Asn Val Ser  Leu Asp Asn
    2615                 2620                 2625

Val Leu  Ser Thr Phe Ile Ser  Ala Ala Arg Gln Gly  Phe Val Asp
    2630                 2635                 2640

Ser Asp  Val Glu Thr Lys Asp  Val Val Glu Cys Leu  Lys Leu Ser
    2645                 2650                 2655

His Gln  Ser Asp Ile Glu Val  Thr Gly Asp Ser Cys  Asn Asn Tyr
    2660                 2665                 2670

Met Leu  Thr Tyr Asn Lys Val  Glu Asn Met Thr Pro  Arg Asp Leu
    2675                 2680                 2685
```

```
Gly Ala  Cys Ile Asp Cys Ser  Ala Arg His Ile Asn  Ala Gln Val
    2690                 2695                 2700

Ala Lys  Ser His Asn Ile Ala  Leu Ile Trp Asn Val  Lys Asp Phe
    2705                 2710                 2715

Met Ser  Leu Ser Glu Gln Leu  Arg Lys Gln Ile Arg  Ser Ala Ala
    2720                 2725                 2730

Lys Lys  Asn Asn Leu Pro Phe  Lys Leu Thr Cys Ala  Thr Thr Arg
    2735                 2740                 2745

Gln Val  Val Asn Val Val Thr  Thr Lys Ile Ala Leu  Lys Gly Gly
    2750                 2755                 2760

Lys Ile  Val Asn Asn Trp Leu  Lys Gln Leu Ile Lys  Val Thr Leu
    2765                 2770                 2775

Val Phe  Leu Phe Val Ala Ala  Ile Phe Tyr Leu Ile  Thr Pro Val
    2780                 2785                 2790

His Val  Met Ser Lys His Thr  Asp Phe Ser Ser Glu  Ile Ile Gly
    2795                 2800                 2805

Tyr Lys  Ala Ile Asp Gly Gly  Val Thr Arg Asp Ile  Ala Ser Thr
    2810                 2815                 2820

Asp Thr  Cys Phe Ala Asn Lys  His Ala Asp Phe Asp  Thr Trp Phe
    2825                 2830                 2835

Ser Gln  Arg Gly Gly Ser Tyr  Thr Asn Asp Lys Ala  Cys Pro Leu
    2840                 2845                 2850

Ile Ala  Ala Val Ile Thr Arg  Glu Val Gly Phe Val  Val Pro Gly
    2855                 2860                 2865

Leu Pro  Gly Thr Ile Leu Arg  Thr Thr Asn Gly Asp  Phe Leu His
    2870                 2875                 2880

Phe Leu  Pro Arg Val Phe Ser  Ala Val Gly Asn Ile  Cys Tyr Thr
    2885                 2890                 2895

Pro Ser  Lys Leu Ile Glu Tyr  Thr Asp Phe Ala Thr  Ser Ala Cys
    2900                 2905                 2910

Val Leu  Ala Ala Glu Cys Thr  Ile Phe Lys Asp Ala  Ser Gly Lys
    2915                 2920                 2925

Pro Val  Pro Tyr Cys Tyr Asp  Thr Asn Val Leu Glu  Gly Ser Val
    2930                 2935                 2940

Ala Tyr  Glu Ser Leu Arg Pro  Asp Thr Arg Tyr Val  Leu Met Asp
    2945                 2950                 2955

Gly Ser  Ile Ile Gln Phe Pro  Asn Thr Tyr Leu Glu  Gly Ser Val
    2960                 2965                 2970

Arg Val  Val Thr Thr Phe Asp  Ser Glu Tyr Cys Arg  His Gly Thr
    2975                 2980                 2985

Cys Glu  Arg Ser Glu Ala Gly  Val Cys Val Ser Thr  Ser Gly Arg
    2990                 2995                 3000

Trp Val  Leu Asn Asn Asp Tyr  Tyr Arg Ser Leu Pro  Gly Val Phe
    3005                 3010                 3015

Cys Gly  Val Asp Ala Val Asn  Leu Leu Thr Asn Met  Phe Thr Pro
    3020                 3025                 3030

Leu Ile  Gln Pro Ile Gly Ala  Leu Asp Ile Ser Ala  Ser Ile Val
    3035                 3040                 3045

Ala Gly  Gly Ile Val Ala Ile  Val Val Thr Cys Leu  Ala Tyr Tyr
    3050                 3055                 3060

Phe Met  Arg Phe Arg Arg Ala  Phe Gly Glu Tyr Ser  His Val Val
    3065                 3070                 3075

Ala Phe  Asn Thr Leu Leu Phe  Leu Met Ser Phe Thr  Val Leu Cys
```

```
    3080                3085                3090

Leu Thr  Pro Val Tyr Ser Phe  Leu Pro Gly Val Tyr  Ser Val Ile
    3095                3100                3105

Tyr Leu  Tyr Leu Thr Phe Tyr  Leu Thr Asn Asp Val  Ser Phe Leu
    3110                3115                3120

Ala His  Ile Gln Trp Met Val  Met Phe Thr Pro Leu  Val Pro Phe
    3125                3130                3135

Trp Ile  Thr Ile Ala Tyr Ile  Ile Cys Ile Ser Thr  Lys His Phe
    3140                3145                3150

Tyr Trp  Phe Phe Ser Asn Tyr  Leu Lys Arg Arg Val  Val Phe Asn
    3155                3160                3165

Gly Val  Ser Phe Ser Thr Phe  Glu Glu Ala Ala Leu  Cys Thr Phe
    3170                3175                3180

Leu Leu  Asn Lys Glu Met Tyr  Leu Lys Leu Arg Ser  Asp Val Leu
    3185                3190                3195

Leu Pro  Leu Thr Gln Tyr Asn  Arg Tyr Leu Ala Leu  Tyr Asn Lys
    3200                3205                3210

Tyr Lys  Tyr Phe Ser Gly Ala  Met Asp Thr Thr Ser  Tyr Arg Glu
    3215                3220                3225

Ala Ala  Cys Cys His Leu Ala  Lys Ala Leu Asn Asp  Phe Ser Asn
    3230                3235                3240

Ser Gly  Ser Asp Val Leu Tyr  Gln Pro Pro Gln Thr  Ser Ile Thr
    3245                3250                3255

Ser Ala  Val Leu Gln Ser Gly  Phe Arg Lys Met Ala  Phe Pro Ser
    3260                3265                3270

Gly Lys  Val Glu Gly Cys Met  Val Gln Val Thr Cys  Gly Thr Thr
    3275                3280                3285

Thr Leu  Asn Gly Leu Trp Leu  Asp Asp Val Val Tyr  Cys Pro Arg
    3290                3295                3300

His Val  Ile Cys Thr Ser Glu  Asp Met Leu Asn Pro  Asn Tyr Glu
    3305                3310                3315

Asp Leu  Leu Ile Arg Lys Ser  Asn His Asn Phe Leu  Val Gln Ala
    3320                3325                3330

Gly Asn  Val Gln Leu Arg Val  Ile Gly His Ser Met  Gln Asn Cys
    3335                3340                3345

Val Leu  Lys Leu Lys Val Asp  Thr Ala Asn Pro Lys  Thr Pro Lys
    3350                3355                3360

Tyr Lys  Phe Val Arg Ile Gln  Pro Gly Gln Thr Phe  Ser Val Leu
    3365                3370                3375

Ala Cys  Tyr Asn Gly Ser Pro  Ser Gly Val Tyr Gln  Cys Ala Met
    3380                3385                3390

Arg Pro  Asn Phe Thr Ile Lys  Gly Ser Phe Leu Asn  Gly Ser Cys
    3395                3400                3405

Gly Ser  Val Gly Phe Asn Ile  Asp Tyr Asp Cys Val  Ser Phe Cys
    3410                3415                3420

Tyr Met  His His Met Glu Leu  Pro Thr Gly Val His  Ala Gly Thr
    3425                3430                3435

Asp Leu  Glu Gly Asn Phe Tyr  Gly Pro Phe Val Asp  Arg Gln Thr
    3440                3445                3450

Ala Gln  Ala Ala Gly Thr Asp  Thr Thr Ile Thr Val  Asn Val Leu
    3455                3460                3465

Ala Trp  Leu Tyr Ala Ala Val  Ile Asn Gly Asp Arg  Trp Phe Leu
    3470                3475                3480
```

```
Asn Arg Phe Thr Thr Thr Leu Asn Asp Phe Asn Leu Val Ala Met
    3485                3490                3495

Lys Tyr Asn Tyr Glu Pro Leu Thr Gln Asp His Val Asp Ile Leu
    3500                3505                3510

Gly Pro Leu Ser Ala Gln Thr Gly Ile Ala Val Leu Asp Met Cys
    3515                3520                3525

Ala Ser Leu Lys Glu Leu Leu Gln Asn Gly Met Asn Gly Arg Thr
    3530                3535                3540

Ile Leu Gly Ser Ala Leu Leu Glu Asp Glu Phe Thr Pro Phe Asp
    3545                3550                3555

Val Val Arg Gln Cys Ser Gly Val Thr Phe Gln Ser Ala Val Lys
    3560                3565                3570

Arg Thr Ile Lys Gly Thr His His Trp Leu Leu Leu Thr Ile Leu
    3575                3580                3585

Thr Ser Leu Leu Val Leu Val Gln Ser Thr Gln Trp Ser Leu Phe
    3590                3595                3600

Phe Phe Leu Tyr Glu Asn Ala Phe Leu Pro Phe Ala Met Gly Ile
    3605                3610                3615

Ile Ala Met Ser Ala Phe Ala Met Met Phe Val Lys His Lys His
    3620                3625                3630

Ala Phe Leu Cys Leu Phe Leu Leu Pro Ser Leu Ala Thr Val Ala
    3635                3640                3645

Tyr Phe Asn Met Val Tyr Met Pro Ala Ser Trp Val Met Arg Ile
    3650                3655                3660

Met Thr Trp Leu Asp Met Val Asp Thr Ser Leu Ser Gly Phe Lys
    3665                3670                3675

Leu Lys Asp Cys Val Met Tyr Ala Ser Ala Val Val Leu Leu Ile
    3680                3685                3690

Leu Met Thr Ala Arg Thr Val Tyr Asp Asp Gly Ala Arg Arg Val
    3695                3700                3705

Trp Thr Leu Met Asn Val Leu Thr Leu Val Tyr Lys Val Tyr Tyr
    3710                3715                3720

Gly Asn Ala Leu Asp Gln Ala Ile Ser Met Trp Ala Leu Ile Ile
    3725                3730                3735

Ser Val Thr Ser Asn Tyr Ser Gly Val Val Thr Thr Val Met Phe
    3740                3745                3750

Leu Ala Arg Gly Ile Val Phe Met Cys Val Glu Tyr Cys Pro Ile
    3755                3760                3765

Phe Phe Ile Thr Gly Asn Thr Leu Gln Cys Ile Met Leu Val Tyr
    3770                3775                3780

Cys Phe Leu Gly Tyr Phe Cys Thr Cys Tyr Phe Gly Leu Phe Cys
    3785                3790                3795

Leu Leu Asn Arg Tyr Phe Arg Leu Thr Leu Gly Val Tyr Asp Tyr
    3800                3805                3810

Leu Val Ser Thr Gln Glu Phe Arg Tyr Met Asn Ser Gln Gly Leu
    3815                3820                3825

Leu Pro Pro Lys Asn Ser Ile Asp Ala Phe Lys Leu Asn Ile Lys
    3830                3835                3840

Leu Leu Gly Val Gly Gly Lys Pro Cys Ile Lys Val Ala Thr Val
    3845                3850                3855

Gln Ser Lys Met Ser Asp Val Lys Cys Thr Ser Val Val Leu Leu
    3860                3865                3870
```

```
Ser Val  Leu Gln Gln Leu Arg  Val Glu Ser Ser Ser  Lys Leu Trp
    3875                 3880                 3885

Ala Gln  Cys Val Gln Leu His  Asn Asp Ile Leu Leu  Ala Lys Asp
    3890                 3895                 3900

Thr Thr  Glu Ala Phe Glu Lys  Met Val Ser Leu Leu  Ser Val Leu
    3905                 3910                 3915

Leu Ser  Met Gln Gly Ala Val  Asp Ile Asn Lys Leu  Cys Glu Glu
    3920                 3925                 3930

Met Leu  Asp Asn Arg Ala Thr  Leu Gln Ala Ile Ala  Ser Glu Phe
    3935                 3940                 3945

Ser Ser  Leu Pro Ser Tyr Ala  Ala Phe Ala Thr Ala  Gln Glu Ala
    3950                 3955                 3960

Tyr Glu  Gln Ala Val Ala Asn  Gly Asp Ser Glu Val  Val Leu Lys
    3965                 3970                 3975

Lys Leu  Lys Lys Ser Leu Asn  Val Ala Lys Ser Glu  Phe Asp Arg
    3980                 3985                 3990

Asp Ala  Ala Met Gln Arg Lys  Leu Glu Lys Met Ala  Asp Gln Ala
    3995                 4000                 4005

Met Thr  Gln Met Tyr Lys Gln  Ala Arg Ser Glu Asp  Lys Arg Ala
    4010                 4015                 4020

Lys Val  Thr Ser Ala Met Gln  Thr Met Leu Phe Thr  Met Leu Arg
    4025                 4030                 4035

Lys Leu  Asp Asn Asp Ala Leu  Asn Asn Ile Ile Asn  Asn Ala Arg
    4040                 4045                 4050

Asp Gly  Cys Val Pro Leu Asn  Ile Ile Pro Leu Thr  Thr Ala Ala
    4055                 4060                 4065

Lys Leu  Met Val Val Ile Pro  Asp Tyr Asn Thr Tyr  Lys Asn Thr
    4070                 4075                 4080

Cys Asp  Gly Thr Thr Phe Thr  Tyr Ala Ser Ala Leu  Trp Glu Ile
    4085                 4090                 4095

Gln Gln  Val Val Asp Ala Asp  Ser Lys Ile Val Gln  Leu Ser Glu
    4100                 4105                 4110

Ile Ser  Met Asp Asn Ser Pro  Asn Leu Ala Trp Pro  Leu Ile Val
    4115                 4120                 4125

Thr Ala  Leu Arg Ala Asn Ser  Ala Val Lys Leu Gln  Asn Asn Glu
    4130                 4135                 4140

Leu Ser  Pro Val Ala Leu Arg  Gln Met Ser Cys Ala  Ala Gly Thr
    4145                 4150                 4155

Thr Gln  Thr Ala Cys Thr Asp  Asp Asn Ala Leu Ala  Tyr Tyr Asn
    4160                 4165                 4170

Thr Thr  Lys Gly Gly Arg Phe  Val Leu Ala Leu Leu  Ser Asp Leu
    4175                 4180                 4185

Gln Asp  Leu Lys Trp Ala Arg  Phe Pro Lys Ser Asp  Gly Thr Gly
    4190                 4195                 4200

Thr Ile  Tyr Thr Glu Leu Glu  Pro Pro Cys Arg Phe  Val Thr Asp
    4205                 4210                 4215

Thr Pro  Lys Gly Pro Lys Val  Lys Tyr Leu Tyr Phe  Ile Lys Gly
    4220                 4225                 4230

Leu Asn  Asn Leu Asn Arg Gly  Met Val Leu Gly Ser  Leu Ala Ala
    4235                 4240                 4245

Thr Val  Arg Leu Gln Ala Gly  Asn Ala Thr Glu Val  Pro Ala Asn
    4250                 4255                 4260

Ser Thr  Val Leu Ser Phe Cys  Ala Phe Ala Val Asp  Ala Ala Lys
```

```
    4265                4270                4275

Ala Tyr  Lys Asp Tyr Leu Ala  Ser Gly Gly Gln Pro  Ile Thr Asn
    4280                4285                4290

Cys Val  Lys Met Leu Cys Thr  His Thr Gly Thr Gly  Gln Ala Ile
    4295                4300                4305

Thr Val  Thr Pro Glu Ala Asn  Met Asp Gln Glu Ser  Phe Gly Gly
    4310                4315                4320

Ala Ser  Cys Cys Leu Tyr Cys  Arg Cys His Ile Asp  His Pro Asn
    4325                4330                4335

Pro Lys  Gly Phe Cys Asp Leu  Lys Gly Lys Tyr Val  Gln Ile Pro
    4340                4345                4350

Thr Thr  Cys Ala Asn Asp Pro  Val Gly Phe Thr Leu  Lys Asn Thr
    4355                4360                4365

Val Cys  Thr Val Cys Gly Met  Trp Lys Gly Tyr Gly  Cys Ser Cys
    4370                4375                4380

Asp Gln  Leu Arg Glu Pro Met  Leu Gln Ser Ala Asp  Ala Gln Ser
    4385                4390                4395

Phe Leu  Asn Arg Val Cys Gly  Val Ser Ala Ala Arg  Leu Thr Pro
    4400                4405                4410

Cys Gly  Thr Gly Thr Ser Thr  Asp Val Val Tyr Arg  Ala Phe Asp
    4415                4420                4425

Ile Tyr  Asn Asp Lys Val Ala  Gly Phe Ala Lys Phe  Leu Lys Thr
    4430                4435                4440

Asn Cys  Cys Arg Phe Gln Glu  Lys Asp Glu Asp Asp  Asn Leu Ile
    4445                4450                4455

Asp Ser  Tyr Phe Val Val Lys  Arg His Thr Phe Ser  Asn Tyr Gln
    4460                4465                4470

His Glu  Glu Thr Ile Tyr Asn  Leu Leu Lys Asp Cys  Pro Ala Val
    4475                4480                4485

Ala Lys  His Asp Phe Phe Lys  Phe Arg Ile Asp Gly  Asp Met Val
    4490                4495                4500

Pro His  Ile Ser Arg Gln Arg  Leu Thr Lys Tyr Thr  Met Ala Asp
    4505                4510                4515

Leu Val  Tyr Ala Leu Arg His  Phe Asp Glu Gly Asn  Cys Asp Thr
    4520                4525                4530

Leu Lys  Glu Ile Leu Val Thr  Tyr Asn Cys Cys Asp  Asp Asp Tyr
    4535                4540                4545

Phe Asn  Lys Lys Asp Trp Tyr  Asp Phe Val Glu Asn  Pro Asp Ile
    4550                4555                4560

Leu Arg  Val Tyr Ala Asn Leu  Gly Glu Arg Val Arg  Gln Ala Leu
    4565                4570                4575

Leu Lys  Thr Val Gln Phe Cys  Asp Ala Met Arg Asn  Ala Gly Ile
    4580                4585                4590

Val Gly  Val Leu Thr Leu Asp  Asn Gln Asp Leu Asn  Gly Asn Trp
    4595                4600                4605

Tyr Asp  Phe Gly Asp Phe Ile  Gln Thr Thr Pro Gly  Ser Gly Val
    4610                4615                4620

Pro Val  Val Asp Ser Tyr Tyr  Ser Leu Leu Met Pro  Ile Leu Thr
    4625                4630                4635

Leu Thr  Arg Ala Leu Thr Ala  Glu Ser His Val Asp  Thr Asp Leu
    4640                4645                4650

Thr Lys  Pro Tyr Ile Lys Trp  Asp Leu Leu Lys Tyr  Asp Phe Thr
    4655                4660                4665
```

Glu Glu Arg Leu Lys Leu Phe Asp Arg Tyr Phe Lys Tyr Trp Asp
4670 4675 4680

Gln Thr Tyr His Pro Asn Cys Val Asn Cys Leu Asp Asp Arg Cys
4685 4690 4695

Ile Leu His Cys Ala Asn Phe Asn Val Leu Phe Ser Thr Val Phe
4700 4705 4710

Pro Pro Thr Ser Phe Gly Pro Leu Val Arg Lys Ile Phe Val Asp
4715 4720 4725

Gly Val Pro Phe Val Val Ser Thr Gly Tyr His Phe Arg Glu Leu
4730 4735 4740

Gly Val Val His Asn Gln Asp Val Asn Leu His Ser Ser Arg Leu
4745 4750 4755

Ser Phe Lys Glu Leu Leu Val Tyr Ala Ala Asp Pro Ala Met His
4760 4765 4770

Ala Ala Ser Gly Asn Leu Leu Leu Asp Lys Arg Thr Thr Cys Phe
4775 4780 4785

Ser Val Ala Ala Leu Thr Asn Asn Val Ala Phe Gln Thr Val Lys
4790 4795 4800

Pro Gly Asn Phe Asn Lys Asp Phe Tyr Asp Phe Ala Val Ser Lys
4805 4810 4815

Gly Phe Phe Lys Glu Gly Ser Ser Val Glu Leu Lys His Phe Phe
4820 4825 4830

Phe Ala Gln Asp Gly Asn Ala Ala Ile Ser Asp Tyr Asp Tyr Tyr
4835 4840 4845

Arg Tyr Asn Leu Pro Thr Met Cys Asp Ile Arg Gln Leu Leu Phe
4850 4855 4860

Val Val Glu Val Val Asp Lys Tyr Phe Asp Cys Tyr Asp Gly Gly
4865 4870 4875

Cys Ile Asn Ala Asn Gln Val Ile Val Asn Asn Leu Asp Lys Ser
4880 4885 4890

Ala Gly Phe Pro Phe Asn Lys Trp Gly Lys Ala Arg Leu Tyr Tyr
4895 4900 4905

Asp Ser Met Ser Tyr Glu Asp Gln Asp Ala Leu Phe Ala Tyr Thr
4910 4915 4920

Lys Arg Asn Val Ile Pro Thr Ile Thr Gln Met Asn Leu Lys Tyr
4925 4930 4935

Ala Ile Ser Ala Lys Asn Arg Ala Arg Thr Val Ala Gly Val Ser
4940 4945 4950

Ile Cys Ser Thr Met Thr Asn Arg Gln Phe His Gln Lys Leu Leu
4955 4960 4965

Lys Ser Ile Ala Ala Thr Arg Gly Ala Thr Val Val Ile Gly Thr
4970 4975 4980

Ser Lys Phe Tyr Gly Gly Trp His Asn Met Leu Lys Thr Val Tyr
4985 4990 4995

Ser Asp Val Glu Asn Pro His Leu Met Gly Trp Asp Tyr Pro Lys
5000 5005 5010

Cys Asp Arg Ala Met Pro Asn Met Leu Arg Ile Met Ala Ser Leu
5015 5020 5025

Val Leu Ala Arg Lys His Thr Thr Cys Cys Ser Leu Ser His Arg
5030 5035 5040

Phe Tyr Arg Leu Ala Asn Glu Cys Ala Gln Val Leu Ser Glu Met
5045 5050 5055

Val Met Cys Gly Gly Ser Leu Tyr Val Lys Pro Gly Gly Thr Ser
5060 5065 5070

Ser Gly Asp Ala Thr Thr Ala Tyr Ala Asn Ser Val Phe Asn Ile
5075 5080 5085

Cys Gln Ala Val Thr Ala Asn Val Asn Ala Leu Leu Ser Thr Asp
5090 5095 5100

Gly Asn Lys Ile Ala Asp Lys Tyr Val Arg Asn Leu Gln His Arg
5105 5110 5115

Leu Tyr Glu Cys Leu Tyr Arg Asn Arg Asp Val Asp Thr Asp Phe
5120 5125 5130

Val Asn Glu Phe Tyr Ala Tyr Leu Arg Lys His Phe Ser Met Met
5135 5140 5145

Ile Leu Ser Asp Asp Ala Val Val Cys Phe Asn Ser Thr Tyr Ala
5150 5155 5160

Ser Gln Gly Leu Val Ala Ser Ile Lys Asn Phe Lys Ser Val Leu
5165 5170 5175

Tyr Tyr Gln Asn Asn Val Phe Met Ser Glu Ala Lys Cys Trp Thr
5180 5185 5190

Glu Thr Asp Leu Thr Lys Gly Pro His Glu Phe Cys Ser Gln His
5195 5200 5205

Thr Met Leu Val Lys Gln Gly Asp Asp Tyr Val Tyr Leu Pro Tyr
5210 5215 5220

Pro Asp Pro Ser Arg Ile Leu Gly Ala Gly Cys Phe Val Asp Asp
5225 5230 5235

Ile Val Lys Thr Asp Gly Thr Leu Met Ile Glu Arg Phe Val Ser
5240 5245 5250

Leu Ala Ile Asp Ala Tyr Pro Leu Thr Lys His Pro Asn Gln Glu
5255 5260 5265

Tyr Ala Asp Val Phe His Leu Tyr Leu Gln Tyr Ile Arg Lys Leu
5270 5275 5280

His Asp Glu Leu Thr Gly His Met Leu Asp Met Tyr Ser Val Met
5285 5290 5295

Leu Thr Asn Asp Asn Thr Ser Arg Tyr Trp Glu Pro Glu Phe Tyr
5300 5305 5310

Glu Ala Met Tyr Thr Pro His Thr Val Leu Gln Ala Val Gly Ala
5315 5320 5325

Cys Val Leu Cys Asn Ser Gln Thr Ser Leu Arg Cys Gly Ala Cys
5330 5335 5340

Ile Arg Arg Pro Phe Leu Cys Cys Lys Cys Cys Tyr Asp His Val
5345 5350 5355

Ile Ser Thr Ser His Lys Leu Val Leu Ser Val Asn Pro Tyr Val
5360 5365 5370

Cys Asn Ala Pro Gly Cys Asp Val Thr Asp Val Thr Gln Leu Tyr
5375 5380 5385

Leu Gly Gly Met Ser Tyr Tyr Cys Lys Ser His Lys Pro Pro Ile
5390 5395 5400

Ser Phe Pro Leu Cys Ala Asn Gly Gln Val Phe Gly Leu Tyr Lys
5405 5410 5415

Asn Thr Cys Val Gly Ser Asp Asn Val Thr Asp Phe Asn Ala Ile
5420 5425 5430

Ala Thr Cys Asp Trp Thr Asn Ala Gly Asp Tyr Ile Leu Ala Asn
5435 5440 5445

Thr Cys Thr Glu Arg Leu Lys Leu Phe Ala Ala Glu Thr Leu Lys

```
    5450                5455                5460

Ala Thr  Glu Glu Thr Phe Lys  Leu Ser Tyr Gly Ile  Ala Thr Val
    5465                5470                5475

Arg Glu  Val Leu Ser Asp Arg  Glu Leu His Leu Ser  Trp Glu Val
    5480                5485                5490

Gly Lys  Pro Arg Pro Pro Leu  Asn Arg Asn Tyr Val  Phe Thr Gly
    5495                5500                5505

Tyr Arg  Val Thr Lys Asn Ser  Lys Val Gln Ile Gly  Glu Tyr Thr
    5510                5515                5520

Phe Glu  Lys Gly Asp Tyr Gly  Asp Ala Val Val Tyr  Arg Gly Thr
    5525                5530                5535

Thr Thr  Tyr Lys Leu Asn Val  Gly Asp Tyr Phe Val  Leu Thr Ser
    5540                5545                5550

His Thr  Val Met Pro Leu Ser  Ala Pro Thr Leu Val  Pro Gln Glu
    5555                5560                5565

His Tyr  Val Arg Ile Thr Gly  Leu Tyr Pro Thr Leu  Asn Ile Ser
    5570                5575                5580

Asp Glu  Phe Ser Ser Asn Val  Ala Asn Tyr Gln Lys  Val Gly Met
    5585                5590                5595

Gln Lys  Tyr Ser Thr Leu Gln  Gly Pro Pro Gly Thr  Gly Lys Ser
    5600                5605                5610

His Phe  Ala Ile Gly Leu Ala  Leu Tyr Tyr Pro Ser  Ala Arg Ile
    5615                5620                5625

Val Tyr  Thr Ala Cys Ser His  Ala Ala Val Asp Ala  Leu Cys Glu
    5630                5635                5640

Lys Ala  Leu Lys Tyr Leu Pro  Ile Asp Lys Cys Ser  Arg Ile Ile
    5645                5650                5655

Pro Ala  Arg Ala Arg Val Glu  Cys Phe Asp Lys Phe  Lys Val Asn
    5660                5665                5670

Ser Thr  Leu Glu Gln Tyr Val  Phe Cys Thr Val Asn  Ala Leu Pro
    5675                5680                5685

Glu Thr  Thr Ala Asp Ile Val  Val Phe Asp Glu Ile  Ser Met Ala
    5690                5695                5700

Thr Asn  Tyr Asp Leu Ser Val  Val Asn Ala Arg Leu  Arg Ala Lys
    5705                5710                5715

His Tyr  Val Tyr Ile Gly Asp  Pro Ala Gln Leu Pro  Ala Pro Arg
    5720                5725                5730

Thr Leu  Leu Thr Lys Gly Thr  Leu Glu Pro Glu Tyr  Phe Asn Ser
    5735                5740                5745

Val Cys  Arg Leu Met Lys Thr  Ile Gly Pro Asp Met  Phe Leu Gly
    5750                5755                5760

Thr Cys  Arg Arg Cys Pro Ala  Glu Ile Val Asp Thr  Val Ser Ala
    5765                5770                5775

Leu Val  Tyr Asp Asn Lys Leu  Lys Ala His Lys Asp  Lys Ser Ala
    5780                5785                5790

Gln Cys  Phe Lys Met Phe Tyr  Lys Gly Val Ile Thr  His Asp Val
    5795                5800                5805

Ser Ser  Ala Ile Asn Arg Pro  Gln Ile Gly Val Val  Arg Glu Phe
    5810                5815                5820

Leu Thr  Arg Asn Pro Ala Trp  Arg Lys Ala Val Phe  Ile Ser Pro
    5825                5830                5835

Tyr Asn  Ser Gln Asn Ala Val  Ala Ser Lys Ile Leu  Gly Leu Pro
    5840                5845                5850
```

Thr Gln Thr Val Asp Ser Ser Gln Gly Ser Glu Tyr Asp Tyr Val
5855 5860 5865

Ile Phe Thr Gln Thr Thr Glu Thr Ala His Ser Cys Asn Val Asn
5870 5875 5880

Arg Phe Asn Val Ala Ile Thr Arg Ala Lys Val Gly Ile Leu Cys
5885 5890 5895

Ile Met Ser Asp Arg Asp Leu Tyr Asp Lys Leu Gln Phe Thr Ser
5900 5905 5910

Leu Glu Ile Pro Arg Arg Asn Val Ala Thr Leu Gln Ala Glu Asn
5915 5920 5925

Val Thr Gly Leu Phe Lys Asp Cys Ser Lys Val Ile Thr Gly Leu
5930 5935 5940

His Pro Thr Gln Ala Pro Thr His Leu Ser Val Asp Thr Lys Phe
5945 5950 5955

Lys Thr Glu Gly Leu Cys Val Asp Ile Pro Gly Ile Pro Lys Asp
5960 5965 5970

Met Thr Tyr Arg Arg Leu Ile Ser Met Met Gly Phe Lys Met Asn
5975 5980 5985

Tyr Gln Val Asn Gly Tyr Pro Asn Met Phe Ile Thr Arg Glu Glu
5990 5995 6000

Ala Ile Arg His Val Arg Ala Trp Ile Gly Phe Asp Val Glu Gly
6005 6010 6015

Cys His Ala Thr Arg Glu Ala Val Gly Thr Asn Leu Pro Leu Gln
6020 6025 6030

Leu Gly Phe Ser Thr Gly Val Asn Leu Val Ala Val Pro Thr Gly
6035 6040 6045

Tyr Val Asp Thr Pro Asn Asn Thr Asp Phe Ser Arg Val Ser Ala
6050 6055 6060

Lys Pro Pro Pro Gly Asp Gln Phe Lys His Leu Ile Pro Leu Met
6065 6070 6075

Tyr Lys Gly Leu Pro Trp Asn Val Val Arg Ile Lys Ile Val Gln
6080 6085 6090

Met Leu Ser Asp Thr Leu Lys Asn Leu Ser Asp Arg Val Val Phe
6095 6100 6105

Val Leu Trp Ala His Gly Phe Glu Leu Thr Ser Met Lys Tyr Phe
6110 6115 6120

Val Lys Ile Gly Pro Glu Arg Thr Cys Cys Leu Cys Asp Arg Arg
6125 6130 6135

Ala Thr Cys Phe Ser Thr Ala Ser Asp Thr Tyr Ala Cys Trp His
6140 6145 6150

His Ser Ile Gly Phe Asp Tyr Val Tyr Asn Pro Phe Met Ile Asp
6155 6160 6165

Val Gln Gln Trp Gly Phe Thr Gly Asn Leu Gln Ser Asn His Asp
6170 6175 6180

Leu Tyr Cys Gln Val His Gly Asn Ala His Val Ala Ser Cys Asp
6185 6190 6195

Ala Ile Met Thr Arg Cys Leu Ala Val His Glu Cys Phe Val Lys
6200 6205 6210

Arg Val Asp Trp Thr Ile Glu Tyr Pro Ile Ile Gly Asp Glu Leu
6215 6220 6225

Lys Ile Asn Ala Ala Cys Arg Lys Val Gln His Met Val Val Lys
6230 6235 6240

```
Ala Ala Leu Leu Ala Asp Lys Phe Pro Val Leu His Asp Ile Gly
    6245                6250                6255

Asn Pro Lys Ala Ile Lys Cys Val Pro Gln Ala Asp Val Glu Trp
    6260                6265                6270

Lys Phe Tyr Asp Ala Gln Pro Cys Ser Asp Lys Ala Tyr Lys Ile
    6275                6280                6285

Glu Glu Leu Phe Tyr Ser Tyr Ala Thr His Ser Asp Lys Phe Thr
    6290                6295                6300

Asp Gly Val Cys Leu Phe Trp Asn Cys Asn Val Asp Arg Tyr Pro
    6305                6310                6315

Ala Asn Ser Ile Val Cys Arg Phe Asp Thr Arg Val Leu Ser Asn
    6320                6325                6330

Leu Asn Leu Pro Gly Cys Asp Gly Gly Ser Leu Tyr Val Asn Lys
    6335                6340                6345

His Ala Phe His Thr Pro Ala Phe Asp Lys Ser Ala Phe Val Asn
    6350                6355                6360

Leu Lys Gln Leu Pro Phe Phe Tyr Tyr Ser Asp Ser Pro Cys Glu
    6365                6370                6375

Ser His Gly Lys Gln Val Val Ser Asp Ile Asp Tyr Val Pro Leu
    6380                6385                6390

Lys Ser Ala Thr Cys Ile Thr Arg Cys Asn Leu Gly Gly Ala Val
    6395                6400                6405

Cys Arg His His Ala Asn Glu Tyr Arg Leu Tyr Leu Asp Ala Tyr
    6410                6415                6420

Asn Met Met Ile Ser Ala Gly Phe Ser Leu Trp Val Tyr Lys Gln
    6425                6430                6435

Phe Asp Thr Tyr Asn Leu Trp Asn Thr Phe Thr Arg Leu Gln Ser
    6440                6445                6450

Leu Glu Asn Val Ala Phe Asn Val Val Asn Lys Gly His Phe Asp
    6455                6460                6465

Gly Gln Gln Gly Glu Val Pro Val Ser Ile Ile Asn Asn Thr Val
    6470                6475                6480

Tyr Thr Lys Val Asp Gly Val Asp Val Glu Leu Phe Glu Asn Lys
    6485                6490                6495

Thr Thr Leu Pro Val Asn Val Ala Phe Glu Leu Trp Ala Lys Arg
    6500                6505                6510

Asn Ile Lys Pro Val Pro Glu Val Lys Ile Leu Asn Asn Leu Gly
    6515                6520                6525

Val Asp Ile Ala Ala Asn Thr Val Ile Trp Asp Tyr Lys Arg Asp
    6530                6535                6540

Ala Pro Ala His Ile Ser Thr Ile Gly Val Cys Ser Met Thr Asp
    6545                6550                6555

Ile Ala Lys Lys Pro Thr Glu Thr Ile Cys Ala Pro Leu Thr Val
    6560                6565                6570

Phe Phe Asp Gly Arg Val Asp Gly Gln Val Asp Leu Phe Arg Asn
    6575                6580                6585

Ala Arg Asn Gly Val Leu Ile Thr Glu Gly Ser Val Lys Gly Leu
    6590                6595                6600

Gln Pro Ser Val Gly Pro Lys Gln Ala Ser Leu Asn Gly Val Thr
    6605                6610                6615

Leu Ile Gly Glu Ala Val Lys Thr Gln Phe Asn Tyr Tyr Lys Lys
    6620                6625                6630

Val Asp Gly Val Val Gln Gln Leu Pro Glu Thr Tyr Phe Thr Gln
```

-continued

```
    6635                6640                6645

Ser Arg  Asn Leu Gln Glu Phe  Lys Pro Arg Ser Gln  Met Glu Ile
    6650                6655                6660

Asp Phe  Leu Glu Leu Ala Met  Asp Glu Phe Ile Glu  Arg Tyr Lys
    6665                6670                6675

Leu Glu  Gly Tyr Ala Phe Glu  His Ile Val Tyr Gly  Asp Phe Ser
    6680                6685                6690

His Ser  Gln Leu Gly Gly Leu  His Leu Leu Ile Gly  Leu Ala Lys
    6695                6700                6705

Arg Phe  Lys Glu Ser Pro Phe  Glu Leu Glu Asp Phe  Ile Pro Met
    6710                6715                6720

Asp Ser  Thr Val Lys Asn Tyr  Phe Ile Thr Asp Ala  Gln Thr Gly
    6725                6730                6735

Ser Ser  Lys Cys Val Cys Ser  Val Ile Asp Leu Leu  Leu Asp Asp
    6740                6745                6750

Phe Val  Glu Ile Ile Lys Ser  Gln Asp Leu Ser Val  Val Ser Lys
    6755                6760                6765

Val Val  Lys Val Thr Ile Asp  Tyr Thr Glu Ile Ser  Phe Met Leu
    6770                6775                6780

Trp Cys  Lys Asp Gly His Val  Glu Thr Phe Tyr Pro  Lys Leu Gln
    6785                6790                6795

Ser Ser  Gln Ala Trp Gln Pro  Gly Val Ala Met Pro  Asn Leu Tyr
    6800                6805                6810

Lys Met  Gln Arg Met Leu Leu  Glu Lys Cys Asp Leu  Gln Asn Tyr
    6815                6820                6825

Gly Asp  Ser Ala Thr Leu Pro  Lys Gly Ile Met Met  Asn Val Ala
    6830                6835                6840

Lys Tyr  Thr Gln Leu Cys Gln  Tyr Leu Asn Thr Leu  Thr Leu Ala
    6845                6850                6855

Val Pro  Tyr Asn Met Arg Val  Ile His Phe Gly Ala  Gly Ser Asp
    6860                6865                6870

Lys Gly  Val Ala Pro Gly Thr  Ala Val Leu Arg Gln  Trp Leu Pro
    6875                6880                6885

Thr Gly  Thr Leu Leu Val Asp  Ser Asp Leu Asn Asp  Phe Val Ser
    6890                6895                6900

Asp Ala  Asp Ser Thr Leu Ile  Gly Asp Cys Ala Thr  Val His Thr
    6905                6910                6915

Ala Asn  Lys Trp Asp Leu Ile  Ile Ser Asp Met Tyr  Asp Pro Lys
    6920                6925                6930

Thr Lys  Asn Val Thr Lys Glu  Asn Asp Ser Lys Glu  Gly Phe Phe
    6935                6940                6945

Thr Tyr  Ile Cys Gly Phe Ile  Gln Gln Lys Leu Ala  Leu Gly Gly
    6950                6955                6960

Ser Val  Ala Ile Lys Ile Thr  Glu His Ser Trp Asn  Ala Asp Leu
    6965                6970                6975

Tyr Lys  Leu Met Gly His Phe  Ala Trp Trp Thr Ala  Phe Val Thr
    6980                6985                6990

Asn Val  Asn Ala Ser Ser Ser  Glu Ala Phe Leu Ile  Gly Cys Asn
    6995                7000                7005

Tyr Leu  Gly Lys Pro Arg Glu  Gln Ile Asp Gly Tyr  Val Met His
    7010                7015                7020

Ala Asn  Tyr Ile Phe Trp Arg  Asn Thr Asn Pro Ile  Gln Leu Ser
    7025                7030                7035
```

Ser Tyr Ser Leu Phe Asp Met Ser Lys Phe Pro Leu Lys Leu Arg
7040 7045 7050

Gly Thr Ala Val Met Ser Leu Lys Glu Gly Gln Ile Asn Asp Met
7055 7060 7065

Ile Leu Ser Leu Leu Ser Lys Gly Arg Leu Ile Ile Arg Glu Asn
7070 7075 7080

Asn Arg Val Val Ile Ser Ser Asp Val Leu Val Asn Asn Met Phe
7085 7090 7095

Val Phe Leu Val Leu Leu Pro Leu Val Ser Ser Gln Cys Val Asn
7100 7105 7110

Leu Thr Thr Arg Thr Gln Leu Pro Pro Ala Tyr Thr Asn Ser Phe
7115 7120 7125

Thr Arg Gly Val Tyr Tyr Pro Asp Lys Val Phe Arg Ser Ser Val
7130 7135 7140

Leu His Ser Thr Gln Asp Leu Phe Leu Pro Phe Phe Ser Asn Val
7145 7150 7155

Thr Trp Phe His Ala Ile His Val Ser Gly Thr Asn Gly Thr Lys
7160 7165 7170

Arg Phe Asp Asn Pro Val Leu Pro Phe Asn Asp Gly Val Tyr Phe
7175 7180 7185

Ala Ser Thr Glu Lys Ser Asn Ile Ile Arg Gly Trp Ile Phe Gly
7190 7195 7200

Thr Thr Leu Asp Ser Lys Thr Gln Ser Leu Leu Ile Val Asn Asn
7205 7210 7215

Ala Thr Asn Val Val Ile Lys Val Cys Glu Phe Gln Phe Cys Asn
7220 7225 7230

Asp Pro Phe Leu Gly Val Tyr Tyr His Lys Asn Asn Lys Ser Trp
7235 7240 7245

Met Glu Ser Glu Phe Arg Val Tyr Ser Ser Ala Asn Asn Cys Thr
7250 7255 7260

Phe Glu Tyr Val Ser Gln Pro Phe Leu Met Asp Leu Glu Gly Lys
7265 7270 7275

Gln Gly Asn Phe Lys Asn Leu Arg Glu Phe Val Phe Lys Asn Ile
7280 7285 7290

Asp Gly Tyr Phe Lys Ile Tyr Ser Lys His Thr Pro Ile Asn Leu
7295 7300 7305

Val Arg Asp Leu Pro Gln Gly Phe Ser Ala Leu Glu Pro Leu Val
7310 7315 7320

Asp Leu Pro Ile Gly Ile Asn Ile Thr Arg Phe Gln Thr Leu Leu
7325 7330 7335

Ala Leu His Arg Ser Tyr Leu Thr Pro Gly Asp Ser Ser Ser Gly
7340 7345 7350

Trp Thr Ala Gly Ala Ala Ala Tyr Tyr Val Gly Tyr Leu Gln Pro
7355 7360 7365

Arg Thr Phe Leu Leu Lys Tyr Asn Glu Asn Gly Thr Ile Thr Asp
7370 7375 7380

Ala Val Asp Cys Ala Leu Asp Pro Leu Ser Glu Thr Lys Cys Thr
7385 7390 7395

Leu Lys Ser Phe Thr Val Glu Lys Gly Ile Tyr Gln Thr Ser Asn
7400 7405 7410

Phe Arg Val Gln Pro Thr Glu Ser Ile Val Arg Phe Pro Asn Ile
7415 7420 7425

-continued

```
Thr Asn  Leu Cys Pro Phe Gly  Glu Val Phe Asn Ala  Thr Arg Phe
    7430                 7435                 7440

Ala Ser  Val Tyr Ala Trp Asn  Arg Lys Arg Ile Ser  Asn Cys Val
    7445                 7450                 7455

Ala Asp  Tyr Ser Val Leu Tyr  Asn Ser Ala Ser Phe  Ser Thr Phe
    7460                 7465                 7470

Lys Cys  Tyr Gly Val Ser Pro  Thr Lys Leu Asn Asp  Leu Cys Phe
    7475                 7480                 7485

Thr Asn  Val Tyr Ala Asp Ser  Phe Val Ile Arg Gly  Asp Glu Val
    7490                 7495                 7500

Arg Gln  Ile Ala Pro Gly Gln  Thr Gly Lys Ile Ala  Asp Tyr Asn
    7505                 7510                 7515

Tyr Lys  Leu Pro Asp Asp Phe  Thr Gly Cys Val Ile  Ala Trp Asn
    7520                 7525                 7530

Ser Asn  Asn Leu Asp Ser Lys  Val Gly Gly Asn Tyr  Asn Tyr Leu
    7535                 7540                 7545

Tyr Arg  Leu Phe Arg Lys Ser  Asn Leu Lys Pro Phe  Glu Arg Asp
    7550                 7555                 7560

Ile Ser  Thr Glu Ile Tyr Gln  Ala Gly Ser Thr Pro  Cys Asn Gly
    7565                 7570                 7575

Val Glu  Gly Phe Asn Cys Tyr  Phe Pro Leu Gln Ser  Tyr Gly Phe
    7580                 7585                 7590

Gln Pro  Thr Asn Gly Val Gly  Tyr Gln Pro Tyr Arg  Val Val Val
    7595                 7600                 7605

Leu Ser  Phe Glu Leu Leu His  Ala Pro Ala Thr Val  Cys Gly Pro
    7610                 7615                 7620

Lys Lys  Ser Thr Asn Leu Val  Lys Asn Lys Cys Val  Asn Phe Asn
    7625                 7630                 7635

Phe Asn  Gly Leu Thr Gly Thr  Gly Val Leu Thr Glu  Ser Asn Lys
    7640                 7645                 7650

Lys Phe  Leu Pro Phe Gln Gln  Phe Gly Arg Asp Ile  Ala Asp Thr
    7655                 7660                 7665

Thr Asp  Ala Val Arg Asp Pro  Gln Thr Leu Glu Ile  Leu Asp Ile
    7670                 7675                 7680

Thr Pro  Cys Ser Phe Gly Gly  Val Ser Val Ile Thr  Pro Gly Thr
    7685                 7690                 7695

Asn Thr  Ser Asn Gln Val Ala  Val Leu Tyr Gln Asp  Val Asn Cys
    7700                 7705                 7710

Thr Glu  Val Pro Val Ala Ile  His Ala Asp Gln Leu  Thr Pro Thr
    7715                 7720                 7725

Trp Arg  Val Tyr Ser Thr Gly  Ser Asn Val Phe Gln  Thr Arg Ala
    7730                 7735                 7740

Gly Cys  Leu Ile Gly Ala Glu  His Val Asn Asn Ser  Tyr Glu Cys
    7745                 7750                 7755

Asp Ile  Pro Ile Gly Ala Gly  Ile Cys Ala Ser Tyr  Gln Thr Gln
    7760                 7765                 7770

Thr Asn  Ser Pro Arg Arg Ala  Arg Ser Val Ala Ser  Gln Ser Ile
    7775                 7780                 7785

Ile Ala  Tyr Thr Met Ser Leu  Gly Ala Glu Asn Ser  Val Ala Tyr
    7790                 7795                 7800

Ser Asn  Asn Ser Ile Ala Ile  Pro Thr Asn Phe Thr  Ile Ser Val
    7805                 7810                 7815

Thr Thr  Glu Ile Leu Pro Val  Ser Met Thr Lys Thr  Ser Val Asp
```

```
    7820                7825                7830

Cys Thr Met Tyr Ile Cys Gly Asp Ser Thr Glu Cys Ser Asn Leu
    7835                7840                7845

Leu Leu Gln Tyr Gly Ser Phe Cys Thr Gln Leu Asn Arg Ala Leu
    7850                7855                7860

Thr Gly Ile Ala Val Glu Gln Asp Lys Asn Thr Gln Glu Val Phe
    7865                7870                7875

Ala Gln Val Lys Gln Ile Tyr Lys Thr Pro Pro Ile Lys Asp Phe
    7880                7885                7890

Gly Gly Phe Asn Phe Ser Gln Ile Leu Pro Asp Pro Ser Lys Pro
    7895                7900                7905

Ser Lys Arg Ser Phe Ile Glu Asp Leu Leu Phe Asn Lys Val Thr
    7910                7915                7920

Leu Ala Asp Ala Gly Phe Ile Lys Gln Tyr Gly Asp Cys Leu Gly
    7925                7930                7935

Asp Ile Ala Ala Arg Asp Leu Ile Cys Ala Gln Lys Phe Asn Gly
    7940                7945                7950

Leu Thr Val Leu Pro Pro Leu Leu Thr Asp Glu Met Ile Ala Gln
    7955                7960                7965

Tyr Thr Ser Ala Leu Leu Ala Gly Thr Ile Thr Ser Gly Trp Thr
    7970                7975                7980

Phe Gly Ala Gly Ala Ala Leu Gln Ile Pro Phe Ala Met Gln Met
    7985                7990                7995

Ala Tyr Arg Phe Asn Gly Ile Gly Val Thr Gln Asn Val Leu Tyr
    8000                8005                8010

Glu Asn Gln Lys Leu Ile Ala Asn Gln Phe Asn Ser Ala Ile Gly
    8015                8020                8025

Lys Ile Gln Asp Ser Leu Ser Ser Thr Ala Ser Ala Leu Gly Lys
    8030                8035                8040

Leu Gln Asp Val Val Asn Gln Asn Ala Gln Ala Leu Asn Thr Leu
    8045                8050                8055

Val Lys Gln Leu Ser Ser Asn Phe Gly Ala Ile Ser Ser Val Leu
    8060                8065                8070

Asn Asp Ile Leu Ser Arg Leu Asp Lys Val Glu Ala Glu Val Gln
    8075                8080                8085

Ile Asp Arg Leu Ile Thr Gly Arg Leu Gln Ser Leu Gln Thr Tyr
    8090                8095                8100

Val Thr Gln Gln Leu Ile Arg Ala Ala Glu Ile Arg Ala Ser Ala
    8105                8110                8115

Asn Leu Ala Ala Thr Lys Met Ser Glu Cys Val Leu Gly Gln Ser
    8120                8125                8130

Lys Arg Val Asp Phe Cys Gly Lys Gly Tyr His Leu Met Ser Phe
    8135                8140                8145

Pro Gln Ser Ala Pro His Gly Val Val Phe Leu His Val Thr Tyr
    8150                8155                8160

Val Pro Ala Gln Glu Lys Asn Phe Thr Thr Ala Pro Ala Ile Cys
    8165                8170                8175

His Asp Gly Lys Ala His Phe Pro Arg Glu Gly Val Phe Val Ser
    8180                8185                8190

Asn Gly Thr His Trp Phe Val Thr Gln Arg Asn Phe Tyr Glu Pro
    8195                8200                8205

Gln Ile Ile Thr Thr Asp Asn Thr Phe Val Ser Gly Asn Cys Asp
    8210                8215                8220
```

```
Val Val Ile Gly Ile Val Asn Asn Thr Val Tyr Asp Pro Leu Gln
    8225                8230                8235

Pro Glu Leu Asp Ser Phe Lys Glu Glu Leu Asp Lys Tyr Phe Lys
    8240                8245                8250

Asn His Thr Ser Pro Asp Val Asp Leu Gly Asp Ile Ser Gly Ile
    8255                8260                8265

Asn Ala Ser Val Val Asn Ile Gln Lys Glu Ile Asp Arg Leu Asn
    8270                8275                8280

Glu Val Ala Lys Asn Leu Asn Glu Ser Leu Ile Asp Leu Gln Glu
    8285                8290                8295

Leu Gly Lys Tyr Glu Gln Tyr Ile Lys Trp Pro Trp Tyr Ile Trp
    8300                8305                8310

Leu Gly Phe Ile Ala Gly Leu Ile Ala Ile Val Met Val Thr Ile
    8315                8320                8325

Met Leu Cys Cys Met Thr Ser Cys Cys Ser Cys Leu Lys Gly Cys
    8330                8335                8340

Cys Ser Cys Gly Ser Cys Cys Lys Phe Asp Glu Asp Asp Ser Glu
    8345                8350                8355

Pro Val Leu Lys Gly Val Lys Leu His Tyr Thr Met Asp Leu Phe
    8360                8365                8370

Met Arg Ile Phe Thr Ile Gly Thr Val Thr Leu Lys Gln Gly Glu
    8375                8380                8385

Ile Lys Asp Ala Thr Pro Ser Asp Phe Val Arg Ala Thr Ala Thr
    8390                8395                8400

Ile Pro Ile Gln Ala Ser Leu Pro Phe Gly Trp Leu Ile Val Gly
    8405                8410                8415

Val Ala Leu Leu Ala Val Phe Gln Ser Ala Ser Lys Ile Ile Thr
    8420                8425                8430

Leu Lys Lys Arg Trp Gln Leu Ala Leu Ser Lys Gly Val His Phe
    8435                8440                8445

Val Cys Asn Leu Leu Leu Leu Phe Val Thr Val Tyr Ser His Leu
    8450                8455                8460

Leu Leu Val Ala Ala Gly Leu Glu Ala Pro Phe Leu Tyr Leu Tyr
    8465                8470                8475

Ala Leu Val Tyr Phe Leu Gln Ser Ile Asn Phe Val Arg Ile Ile
    8480                8485                8490

Met Arg Leu Trp Leu Cys Trp Lys Cys Arg Ser Lys Asn Pro Leu
    8495                8500                8505

Leu Tyr Asp Ala Asn Tyr Phe Leu Cys Trp His Thr Asn Cys Tyr
    8510                8515                8520

Asp Tyr Cys Ile Pro Tyr Asn Ser Val Thr Ser Ser Ile Val Ile
    8525                8530                8535

Thr Ser Gly Asp Gly Thr Thr Ser Pro Ile Ser Glu His Asp Tyr
    8540                8545                8550

Gln Ile Gly Gly Tyr Thr Glu Lys Trp Glu Ser Gly Val Lys Asp
    8555                8560                8565

Cys Val Val Leu His Ser Tyr Phe Thr Ser Asp Tyr Tyr Gln Leu
    8570                8575                8580

Tyr Ser Thr Gln Leu Ser Thr Asp Thr Gly Val Glu His Val Thr
    8585                8590                8595

Phe Phe Ile Tyr Asn Lys Ile Val Asp Glu Pro Glu Glu His Val
    8600                8605                8610
```

-continued

Gln Ile His Thr Ile Asp Gly Ser Ser Gly Val Val Asn Pro Val
8615 8620 8625

Met Glu Pro Ile Tyr Asp Glu Pro Thr Thr Thr Thr Ser Val Pro
8630 8635 8640

Leu Met Tyr Ser Phe Val Ser Glu Glu Thr Gly Thr Leu Ile Val
8645 8650 8655

Asn Ser Val Leu Leu Phe Leu Ala Phe Val Val Phe Leu Leu Val
8660 8665 8670

Thr Leu Ala Ile Leu Thr Ala Leu Arg Leu Cys Ala Tyr Cys Cys
8675 8680 8685

Asn Ile Val Asn Val Ser Leu Val Lys Pro Ser Phe Tyr Val Tyr
8690 8695 8700

Ser Arg Val Lys Asn Leu Asn Ser Ser Arg Val Pro Asp Leu Leu
8705 8710 8715

Val Met Ala Asp Ser Asn Gly Thr Ile Thr Val Glu Glu Leu Lys
8720 8725 8730

Lys Leu Leu Glu Gln Trp Asn Leu Val Ile Gly Phe Leu Phe Leu
8735 8740 8745

Thr Trp Ile Cys Leu Leu Gln Phe Ala Tyr Ala Asn Arg Asn Arg
8750 8755 8760

Phe Leu Tyr Ile Ile Lys Leu Ile Phe Leu Trp Leu Leu Trp Pro
8765 8770 8775

Val Thr Leu Ala Cys Phe Val Leu Ala Ala Val Tyr Arg Ile Asn
8780 8785 8790

Trp Ile Thr Gly Gly Ile Ala Ile Ala Met Ala Cys Leu Val Gly
8795 8800 8805

Leu Met Trp Leu Ser Tyr Phe Ile Ala Ser Phe Arg Leu Phe Ala
8810 8815 8820

Arg Thr Arg Ser Met Trp Ser Phe Asn Pro Glu Thr Asn Ile Leu
8825 8830 8835

Leu Asn Val Pro Leu His Gly Thr Ile Leu Thr Arg Pro Leu Leu
8840 8845 8850

Glu Ser Glu Leu Val Ile Gly Ala Val Ile Leu Arg Gly His Leu
8855 8860 8865

Arg Ile Ala Gly His His Leu Gly Arg Cys Asp Ile Lys Asp Leu
8870 8875 8880

Pro Lys Glu Ile Thr Val Ala Thr Ser Arg Thr Leu Ser Tyr Tyr
8885 8890 8895

Lys Leu Gly Ala Ser Gln Arg Val Ala Gly Asp Ser Gly Phe Ala
8900 8905 8910

Ala Tyr Ser Arg Tyr Arg Ile Gly Asn Tyr Lys Leu Asn Thr Asp
8915 8920 8925

His Ser Ser Ser Ser Asp Asn Ile Ala Leu Leu Val Gln Met Phe
8930 8935 8940

His Leu Val Asp Phe Gln Val Thr Ile Ala Glu Ile Leu Leu Ile
8945 8950 8955

Ile Met Arg Thr Phe Lys Val Ser Ile Trp Asn Leu Asp Tyr Ile
8960 8965 8970

Ile Asn Leu Ile Ile Lys Asn Leu Ser Lys Ser Leu Thr Glu Asn
8975 8980 8985

Lys Tyr Ser Gln Leu Asp Glu Glu Gln Pro Met Glu Ile Asp Met
8990 8995 9000

Lys Ile Ile Leu Phe Leu Ala Leu Ile Thr Leu Ala Thr Cys Glu

```
    9005                9010                9015

Leu Tyr  His Tyr Gln Glu Cys  Val Arg Gly Thr Thr  Val Leu Leu
    9020                9025                9030

Lys Glu  Pro Cys Ser Ser Gly  Thr Tyr Glu Gly Asn  Ser Pro Phe
    9035                9040                9045

His Pro  Leu Ala Asp Asn Lys  Phe Ala Leu Thr Cys  Phe Ser Thr
    9050                9055                9060

Gln Phe  Ala Phe Ala Cys Pro  Asp Gly Val Lys His  Val Tyr Gln
    9065                9070                9075

Leu Arg  Ala Arg Ser Val Ser  Pro Lys Leu Phe Ile  Arg Gln Glu
    9080                9085                9090

Glu Val  Gln Glu Leu Tyr Ser  Pro Ile Phe Leu Ile  Val Ala Ala
    9095                9100                9105

Ile Val  Phe Ile Thr Leu Cys  Phe Thr Leu Lys Arg  Lys Thr Glu
    9110                9115                9120

Met Ile  Glu Leu Ser Leu Ile  Asp Phe Tyr Leu Cys  Phe Leu Ala
    9125                9130                9135

Phe Leu  Leu Phe Leu Val Leu  Ile Met Leu Ile Ile  Phe Trp Phe
    9140                9145                9150

Ser Leu  Glu Leu Gln Asp His  Asn Glu Thr Cys His  Ala Met Lys
    9155                9160                9165

Phe Leu  Val Phe Leu Gly Ile  Ile Thr Thr Val Ala  Ala Phe His
    9170                9175                9180

Gln Glu  Cys Ser Leu Gln Ser  Cys Thr Gln His Gln  Pro Tyr Val
    9185                9190                9195

Val Asp  Asp Pro Cys Pro Ile  His Phe Tyr Ser Lys  Trp Tyr Ile
    9200                9205                9210

Arg Val  Gly Ala Arg Lys Ser  Ala Pro Leu Ile Glu  Leu Cys Val
    9215                9220                9225

Asp Glu  Ala Gly Ser Lys Ser  Pro Ile Gln Tyr Ile  Asp Ile Gly
    9230                9235                9240

Asn Tyr  Thr Val Ser Cys Leu  Pro Phe Thr Ile Asn  Cys Gln Glu
    9245                9250                9255

Pro Lys  Leu Gly Ser Leu Val  Val Arg Cys Ser Phe  Tyr Glu Asp
    9260                9265                9270

Phe Leu  Glu Tyr His Asp Val  Arg Val Val Leu Asp  Phe Ile Met
    9275                9280                9285

Ser Asp  Asn Gly Pro Gln Asn  Gln Arg Asn Ala Pro  Arg Ile Thr
    9290                9295                9300

Phe Gly  Gly Pro Ser Asp Ser  Thr Gly Ser Asn Gln  Asn Gly Glu
    9305                9310                9315

Arg Ser  Gly Ala Arg Ser Lys  Gln Arg Arg Pro Gln  Gly Leu Pro
    9320                9325                9330

Asn Asn  Thr Ala Ser Trp Phe  Thr Ala Leu Thr Gln  His Gly Lys
    9335                9340                9345

Glu Asp  Leu Lys Phe Pro Arg  Gly Gln Gly Val Pro  Ile Asn Thr
    9350                9355                9360

Asn Ser  Ser Pro Asp Asp Gln  Ile Gly Tyr Tyr Arg  Arg Ala Thr
    9365                9370                9375

Arg Arg  Ile Arg Gly Gly Asp  Gly Lys Met Lys Asp  Leu Ser Pro
    9380                9385                9390

Arg Trp  Tyr Phe Tyr Tyr Leu  Gly Thr Gly Pro Glu  Ala Gly Leu
    9395                9400                9405
```

```
Pro Tyr Gly Ala Asn Lys Asp Gly Ile Ile Trp Val Ala Thr Glu
    9410                9415                9420

Gly Ala Leu Asn Thr Pro Lys Asp His Ile Gly Thr Arg Asn Pro
    9425                9430                9435

Ala Asn Asn Ala Ala Ile Val Leu Gln Leu Pro Gln Gly Thr Thr
    9440                9445                9450

Leu Pro Lys Gly Phe Tyr Ala Glu Gly Ser Arg Gly Gly Ser Gln
    9455                9460                9465

Ala Ser Ser Arg Ser Ser Ser Arg Ser Arg Asn Ser Ser Arg Asn
    9470                9475                9480

Ser Thr Pro Gly Ser Ser Arg Gly Thr Ser Pro Ala Arg Met Ala
    9485                9490                9495

Gly Asn Gly Gly Asp Ala Ala Leu Ala Leu Leu Leu Leu Asp Arg
    9500                9505                9510

Leu Asn Gln Leu Glu Ser Lys Met Ser Gly Lys Gly Gln Gln Gln
    9515                9520                9525

Gln Gly Gln Thr Val Thr Lys Lys Ser Ala Ala Glu Ala Ser Lys
    9530                9535                9540

Lys Pro Arg Gln Lys Arg Thr Ala Thr Lys Ala Tyr Asn Val Thr
    9545                9550                9555

Gln Ala Phe Gly Arg Arg Gly Pro Glu Gln Thr Gln Gly Asn Phe
    9560                9565                9570

Gly Asp Gln Glu Leu Ile Arg Gln Gly Thr Asp Tyr Lys His Trp
    9575                9580                9585

Pro Gln Ile Ala Gln Phe Ala Pro Ser Ala Ser Ala Phe Phe Gly
    9590                9595                9600

Met Ser Arg Ile Gly Met Glu Val Thr Pro Ser Gly Thr Trp Leu
    9605                9610                9615

Thr Tyr Thr Gly Ala Ile Lys Leu Asp Asp Lys Asp Pro Asn Phe
    9620                9625                9630

Lys Asp Gln Val Ile Leu Leu Asn Lys His Ile Asp Ala Tyr Lys
    9635                9640                9645

Thr Phe Pro Pro Thr Glu Pro Lys Lys Asp Lys Lys Lys Lys Ala
    9650                9655                9660

Asp Glu Thr Gln Ala Leu Pro Gln Arg Gln Lys Lys Gln Gln Thr
    9665                9670                9675

Val Thr Leu Leu Pro Ala Ala Asp Leu Asp Asp Phe Ser Lys Gln
    9680                9685                9690

Leu Gln Gln Ser Met Ser Ser Ala Asp Ser Thr Gln Ala Met Gly
    9695                9700                9705

Tyr Ile Asn Val Phe Ala Phe Pro Phe Thr Ile Tyr Ser Leu Leu
    9710                9715                9720

Leu Cys Arg Met Asn Ser Arg Asn Tyr Ile Ala Gln Val Asp Val
    9725                9730                9735

Val Asn Phe Asn Leu Thr
    9740
```

<210> SEQ ID NO 411
<211> LENGTH: 242
<212> TYPE: PRT
<213> ORGANISM: Unknown
<220> FEATURE:
<223> OTHER INFORMATION: SARS-CoV-2 spike protein

<400> SEQUENCE: 411

```
Thr Leu Lys Ser Phe Thr Val Glu Lys Gly Ile Tyr Gln Thr Ser Asn
1               5                   10                  15

Phe Arg Val Gln Pro Thr Glu Ser Ile Val Arg Phe Pro Asn Ile Thr
            20                  25                  30

Asn Leu Cys Pro Phe Gly Glu Val Phe Asn Ala Thr Arg Phe Ala Ser
        35                  40                  45

Val Tyr Ala Trp Asn Arg Lys Arg Ile Ser Asn Cys Val Ala Asp Tyr
    50                  55                  60

Ser Val Leu Tyr Asn Ser Ala Ser Phe Ser Thr Phe Lys Cys Tyr Gly
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Lys Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
    130                 135                 140

Gly Gly Asn Tyr Asn Tyr Leu Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Glu Gly Phe Asn Cys Tyr Phe Pro Leu Gln
            180                 185                 190

Ser Tyr Gly Phe Gln Pro Thr Asn Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Cys Val Asn Phe
225                 230                 235                 240

Asn Phe


<210> SEQ ID NO 412
<211> LENGTH: 242
<212> TYPE: PRT
<213> ORGANISM: Unknown
<220> FEATURE:
<223> OTHER INFORMATION: SARS-CoV spike protein

<400> SEQUENCE: 412

Thr Leu Lys Ser Phe Thr Val Glu Lys Gly Ile Tyr Gln Thr Ser Asn
1               5                   10                  15

Phe Arg Val Gln Pro Thr Glu Ser Ile Val Arg Phe Pro Asn Ile Thr
            20                  25                  30

Asn Leu Cys Pro Phe Gly Glu Val Phe Asn Ala Thr Arg Phe Ala Ser
        35                  40                  45

Val Tyr Ala Trp Asn Arg Lys Arg Ile Ser Asn Cys Val Ala Asp Tyr
    50                  55                  60

Ser Val Leu Tyr Asn Ser Ala Ser Phe Ser Thr Phe Lys Cys Tyr Gly
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110
```

```
Gln Thr Gly Lys Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
    130                 135                 140

Gly Gly Asn Tyr Asn Tyr Arg Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Glu Gly Phe Asn Cys Tyr Phe Pro Leu Gln
            180                 185                 190

Ser Tyr Gly Phe Gln Pro Thr Asn Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Cys Val Phe Asn
225                 230                 235                 240

Phe Asn


<210> SEQ ID NO 413
<211> LENGTH: 242
<212> TYPE: PRT
<213> ORGANISM: Unknown
<220> FEATURE:
<223> OTHER INFORMATION: SARS-CoV spike protein

<400> SEQUENCE: 413

Thr Leu Lys Ser Phe Thr Val Glu Lys Gly Ile Tyr Gln Thr Ser Asn
1               5                   10                  15

Phe Arg Val Gln Pro Thr Glu Ser Ile Val Arg Phe Pro Asn Ile Thr
            20                  25                  30

Asn Leu Cys Pro Phe Gly Glu Val Phe Asn Ala Thr Arg Phe Ala Ser
        35                  40                  45

Val Tyr Ala Trp Asn Arg Lys Arg Ile Ser Asn Cys Val Ala Asp Tyr
    50                  55                  60

Ser Val Leu Tyr Asn Ser Ala Ser Phe Ser Thr Phe Lys Cys Tyr Gly
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Lys Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
    130                 135                 140

Gly Gly Asn Tyr Asn Tyr Leu Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Lys Gly Phe Asn Cys Tyr Phe Pro Leu Gln
            180                 185                 190

Ser Tyr Gly Phe Gln Pro Thr Asn Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Cys Val Phe Asn
```

225 230 235 240

Phe Asn

<210> SEQ ID NO 414
<211> LENGTH: 242
<212> TYPE: PRT
<213> ORGANISM: Unknown
<220> FEATURE:
<223> OTHER INFORMATION: SARS-CoV spike protein

<400> SEQUENCE: 414

Thr Leu Lys Ser Phe Thr Val Glu Lys Gly Ile Tyr Gln Thr Ser Asn
1 5 10 15

Phe Arg Val Gln Pro Thr Glu Ser Ile Val Arg Phe Pro Asn Ile Thr
20 25 30

Asn Leu Cys Pro Phe Gly Glu Val Phe Asn Ala Thr Arg Phe Ala Ser
35 40 45

Val Tyr Ala Trp Asn Arg Lys Arg Ile Ser Asn Cys Val Ala Asp Tyr
50 55 60

Ser Val Leu Tyr Asn Ser Ala Ser Phe Ser Thr Phe Lys Cys Tyr Gly
65 70 75 80

Val Ser Pro Thr Lys Leu Asn Asp Leu Cys Phe Thr Asn Val Tyr Ala
85 90 95

Asp Ser Phe Val Ile Arg Gly Asp Glu Val Arg Gln Ile Ala Pro Gly
100 105 110

Gln Thr Gly Lys Ile Ala Asp Tyr Asn Tyr Lys Leu Pro Asp Asp Phe
115 120 125

Thr Gly Cys Val Ile Ala Trp Asn Ser Asn Asn Leu Asp Ser Lys Val
130 135 140

Gly Gly Asn Tyr Asn Tyr Leu Tyr Arg Leu Phe Arg Lys Ser Asn Leu
145 150 155 160

Lys Pro Phe Glu Arg Asp Ile Ser Thr Glu Ile Tyr Gln Ala Gly Ser
165 170 175

Thr Pro Cys Asn Gly Val Glu Gly Phe Asn Cys Tyr Phe Pro Leu Gln
180 185 190

Ser Tyr Gly Phe Gln Pro Thr Tyr Gly Val Gly Tyr Gln Pro Tyr Arg
195 200 205

Val Val Val Leu Ser Phe Glu Leu Leu His Ala Pro Ala Thr Val Cys
210 215 220

Gly Pro Lys Lys Ser Thr Asn Leu Val Lys Asn Lys Cys Val Phe Asn
225 230 235 240

Phe Asn

<210> SEQ ID NO 415
<211> LENGTH: 242
<212> TYPE: PRT
<213> ORGANISM: Unknown
<220> FEATURE:
<223> OTHER INFORMATION: SARS-CoV spike protein

<400> SEQUENCE: 415

Thr Leu Lys Ser Phe Thr Val Glu Lys Gly Ile Tyr Gln Thr Ser Asn
1 5 10 15

Phe Arg Val Gln Pro Thr Glu Ser Ile Val Arg Phe Pro Asn Ile Thr
20 25 30

Asn Leu Cys Pro Phe Gly Glu Val Phe Asn Ala Thr Arg Phe Ala Ser
35 40 45

Val Tyr Ala Trp Asn Arg Lys Arg Ile Ser Asn Cys Val Ala Asp Tyr
50 55 60

Ser Val Leu Tyr Asn Ser Ala Ser Phe Ser Thr Phe Lys Cys Tyr Gly
65 70 75 80

Val Ser Pro Thr Lys Leu Asn Asp Leu Cys Phe Thr Asn Val Tyr Ala
85 90 95

Asp Ser Phe Val Ile Arg Gly Asp Glu Val Arg Gln Ile Ala Pro Gly
100 105 110

Gln Thr Gly Lys Ile Ala Asp Tyr Asn Tyr Lys Leu Pro Asp Asp Phe
115 120 125

Thr Gly Cys Val Ile Ala Trp Asn Ser Asn Asn Leu Asp Ser Lys Val
130 135 140

Gly Gly Asn Tyr Asn Tyr Leu Tyr Arg Leu Phe Arg Lys Ser Asn Leu
145 150 155 160

Lys Pro Phe Glu Arg Asp Ile Ser Thr Glu Ile Tyr Gln Ala Gly Ser
165 170 175

Thr Pro Cys Asn Gly Val Lys Gly Phe Asn Cys Tyr Phe Pro Leu Gln
180 185 190

Ser Tyr Gly Phe Gln Pro Thr Tyr Gly Val Gly Tyr Gln Pro Tyr Arg
195 200 205

Val Val Val Leu Ser Phe Glu Leu Leu His Ala Pro Ala Thr Val Cys
210 215 220

Gly Pro Lys Lys Ser Thr Asn Leu Val Lys Asn Lys Cys Val Phe Asn
225 230 235 240

Phe Asn

<210> SEQ ID NO 416
<211> LENGTH: 242
<212> TYPE: PRT
<213> ORGANISM: Unknown
<220> FEATURE:
<223> OTHER INFORMATION: SARS-CoV spike protein

<400> SEQUENCE: 416

Thr Leu Lys Ser Phe Thr Val Glu Lys Gly Ile Tyr Gln Thr Ser Asn
1 5 10 15

Phe Arg Val Gln Pro Thr Glu Ser Ile Val Arg Phe Pro Asn Ile Thr
20 25 30

Asn Leu Cys Pro Phe Gly Glu Val Phe Asn Ala Thr Arg Phe Ala Ser
35 40 45

Val Tyr Ala Trp Asn Arg Lys Arg Ile Ser Asn Cys Val Ala Asp Tyr
50 55 60

Ser Val Leu Tyr Asn Ser Ala Ser Phe Ser Thr Phe Lys Cys Tyr Gly
65 70 75 80

Val Ser Pro Thr Lys Leu Asn Asp Leu Cys Phe Thr Asn Val Tyr Ala
85 90 95

Asp Ser Phe Val Ile Arg Gly Asp Glu Val Arg Gln Ile Ala Pro Gly
100 105 110

Gln Thr Gly Thr Ile Ala Asp Tyr Asn Tyr Lys Leu Pro Asp Asp Phe
115 120 125

Thr Gly Cys Val Ile Ala Trp Asn Ser Asn Asn Leu Asp Ser Lys Val
130 135 140

Gly Gly Asn Tyr Asn Tyr Leu Tyr Arg Leu Phe Arg Lys Ser Asn Leu
145 150 155 160

```
Lys Pro Phe Glu Arg Asp Ile Ser Thr Glu Ile Tyr Gln Ala Gly Ser
                165                 170                 175

Thr Pro Cys Asn Gly Val Lys Gly Phe Asn Cys Tyr Phe Pro Leu Gln
            180                 185                 190

Ser Tyr Gly Phe Gln Pro Thr Tyr Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Cys Val Phe Asn
225                 230                 235                 240

Phe Asn


<210> SEQ ID NO 417
<211> LENGTH: 242
<212> TYPE: PRT
<213> ORGANISM: Unknown
<220> FEATURE:
<223> OTHER INFORMATION: SARS-CoV spike potein

<400> SEQUENCE: 417

Thr Leu Lys Ser Phe Thr Val Glu Lys Gly Ile Tyr Gln Thr Ser Asn
1               5                   10                  15

Phe Arg Val Gln Pro Thr Glu Ser Ile Val Arg Phe Pro Asn Ile Thr
            20                  25                  30

Asn Leu Cys Pro Phe Gly Glu Val Phe Asn Ala Thr Arg Phe Ala Ser
        35                  40                  45

Val Tyr Ala Trp Asn Arg Lys Arg Ile Ser Asn Cys Val Ala Asp Tyr
    50                  55                  60

Ser Val Leu Tyr Asn Ser Ala Ser Phe Ser Thr Phe Lys Cys Tyr Gly
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Asn Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
    130                 135                 140

Gly Gly Asn Tyr Asn Tyr Leu Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Lys Gly Phe Asn Cys Tyr Phe Pro Leu Gln
            180                 185                 190

Ser Tyr Gly Phe Gln Pro Thr Tyr Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Cys Val Phe Asn
225                 230                 235                 240

Phe Asn


<210> SEQ ID NO 418
<211> LENGTH: 25
<212> TYPE: PRT
<213> ORGANISM: Unknown
```

<220> FEATURE:
<223> OTHER INFORMATION: Human OSM

<400> SEQUENCE: 418

Met Gly Val Leu Leu Thr Gln Arg Thr Leu Leu Ser Leu Val Leu Ala
1 5 10 15

Leu Leu Phe Pro Ser Met Ala Ser Met
20 25

<210> SEQ ID NO 419
<211> LENGTH: 16
<212> TYPE: PRT
<213> ORGANISM: Unknown
<220> FEATURE:
<223> OTHER INFORMATION: VSV-G

<400> SEQUENCE: 419

Met Lys Cys Leu Leu Tyr Leu Ala Phe Leu Phe Ile Gly Val Asn Cys
1 5 10 15

<210> SEQ ID NO 420
<211> LENGTH: 21
<212> TYPE: PRT
<213> ORGANISM: Unknown
<220> FEATURE:
<223> OTHER INFORMATION: Mouse Ig Kappa

<400> SEQUENCE: 420

Met Glu Thr Asp Thr Leu Leu Leu Trp Val Leu Leu Leu Trp Val Pro
1 5 10 15

Gly Ser Thr Gly Asp
20

<210> SEQ ID NO 421
<211> LENGTH: 19
<212> TYPE: PRT
<213> ORGANISM: Unknown
<220> FEATURE:
<223> OTHER INFORMATION: Human IgG2 H

<400> SEQUENCE: 421

Met Gly Trp Ser Cys Ile Ile Leu Phe Leu Val Ala Thr Ala Thr Gly
1 5 10 15

Val His Ser

<210> SEQ ID NO 422
<211> LENGTH: 17
<212> TYPE: PRT
<213> ORGANISM: Unknown
<220> FEATURE:
<223> OTHER INFORMATION: BM40

<400> SEQUENCE: 422

Met Arg Ala Trp Ile Phe Phe Leu Leu Cys Leu Ala Gly Arg Ala Leu
1 5 10 15

Ala

<210> SEQ ID NO 423
<211> LENGTH: 21
<212> TYPE: PRT
<213> ORGANISM: Unknown
<220> FEATURE:
<223> OTHER INFORMATION: Secrecon

<400> SEQUENCE: 423

```
Met Trp Trp Arg Leu Trp Trp Leu Leu Leu Leu Leu Leu Leu Leu Trp
1               5                   10                  15

Pro Met Val Trp Ala
            20


<210> SEQ ID NO 424
<211> LENGTH: 22
<212> TYPE: PRT
<213> ORGANISM: Unknown
<220> FEATURE:
<223> OTHER INFORMATION: Human IgKVIII

<400> SEQUENCE: 424

Met Asp Met Arg Val Pro Ala Gln Leu Leu Gly Leu Leu Leu Leu Trp
1               5                   10                  15

Leu Arg Gly Ala Arg Cys
            20


<210> SEQ ID NO 425
<211> LENGTH: 16
<212> TYPE: PRT
<213> ORGANISM: Unknown
<220> FEATURE:
<223> OTHER INFORMATION: CD33

<400> SEQUENCE: 425

Met Pro Leu Leu Leu Leu Leu Pro Leu Leu Trp Ala Gly Ala Leu Ala
1               5                   10                  15


<210> SEQ ID NO 426
<211> LENGTH: 23
<212> TYPE: PRT
<213> ORGANISM: Unknown
<220> FEATURE:
<223> OTHER INFORMATION: tPA

<400> SEQUENCE: 426

Met Asp Ala Met Lys Arg Gly Leu Cys Cys Val Leu Leu Leu Cys Gly
1               5                   10                  15

Ala Val Phe Val Ser Pro Ser
            20


<210> SEQ ID NO 427
<211> LENGTH: 27
<212> TYPE: PRT
<213> ORGANISM: Unknown
<220> FEATURE:
<223> OTHER INFORMATION: tPA

<400> SEQUENCE: 427

Met Asp Ala Met Lys Arg Gly Leu Cys Cys Val Leu Leu Leu Cys Gly
1               5                   10                  15

Ala Val Phe Val Ser Pro Ser Gly Thr Gly Ser
            20                  25


<210> SEQ ID NO 428
<211> LENGTH: 18
<212> TYPE: PRT
<213> ORGANISM: Unknown
<220> FEATURE:
<223> OTHER INFORMATION: Human Chymotrypsinogen

<400> SEQUENCE: 428

Met Ala Phe Leu Trp Leu Leu Ser Cys Trp Ala Leu Leu Gly Thr Thr
```

1 5 10 15

Phe Gly

<210> SEQ ID NO 429
<211> LENGTH: 15
<212> TYPE: PRT
<213> ORGANISM: Unknown
<220> FEATURE:
<223> OTHER INFORMATION: Human trypsinogen-2

<400> SEQUENCE: 429

Met Asn Leu Leu Leu Ile Leu Thr Phe Val Ala Ala Ala Val Ala
1 5 10 15

<210> SEQ ID NO 430
<211> LENGTH: 20
<212> TYPE: PRT
<213> ORGANISM: Unknown
<220> FEATURE:
<223> OTHER INFORMATION: Human IL-2

<400> SEQUENCE: 430

Met Tyr Arg Met Gln Leu Leu Ser Cys Ile Ala Leu Ser Leu Ala Leu
1 5 10 15

Val Thr Asn Ser
20

<210> SEQ ID NO 431
<211> LENGTH: 17
<212> TYPE: PRT
<213> ORGANISM: Unknown
<220> FEATURE:
<223> OTHER INFORMATION: Gaussia luciferase

<400> SEQUENCE: 431

Met Gly Val Lys Val Leu Phe Ala Leu Ile Cys Ile Ala Val Ala Glu
1 5 10 15

Ala

<210> SEQ ID NO 432
<211> LENGTH: 16
<212> TYPE: PRT
<213> ORGANISM: Unknown
<220> FEATURE:
<223> OTHER INFORMATION: Albumin(HSA)

<400> SEQUENCE: 432

Met Lys Trp Val Thr Phe Ile Ser Leu Leu Phe Ser Ser Ala Tyr Ser
1 5 10 15

<210> SEQ ID NO 433
<211> LENGTH: 16
<212> TYPE: PRT
<213> ORGANISM: Unknown
<220> FEATURE:
<223> OTHER INFORMATION: Influenza Haemagglutinin

<400> SEQUENCE: 433

Met Lys Thr Ile Ile Ala Leu Ser Tyr Ile Phe Cys Leu Val Leu Gly
1 5 10 15

<210> SEQ ID NO 434
<211> LENGTH: 24
<212> TYPE: PRT
<213> ORGANISM: Unknown

<220> FEATURE:
<223> OTHER INFORMATION: Human insulin

<400> SEQUENCE: 434

Met Ala Leu Trp Met Arg Leu Leu Pro Leu Leu Ala Leu Leu Ala Leu
1 5 10 15

Trp Gly Pro Asp Pro Ala Ala Ala
20

<210> SEQ ID NO 435
<211> LENGTH: 16
<212> TYPE: PRT
<213> ORGANISM: Unknown
<220> FEATURE:
<223> OTHER INFORMATION: Silkworm Fibroin LC

<400> SEQUENCE: 435

Met Lys Pro Ile Phe Leu Val Leu Leu Val Val Thr Ser Ala Tyr Ala
1 5 10 15

<210> SEQ ID NO 436
<211> LENGTH: 18
<212> TYPE: PRT
<213> ORGANISM: Unknown
<220> FEATURE:
<223> OTHER INFORMATION: adenovirus protein E3/gp19K

<400> SEQUENCE: 436

Met Arg Tyr Met Ile Leu Gly Leu Leu Ala Leu Ala Ala Val Cys Ser
1 5 10 15

Ala Ala

<210> SEQ ID NO 437
<211> LENGTH: 19
<212> TYPE: PRT
<213> ORGANISM: Unknown
<220> FEATURE:
<223> OTHER INFORMATION: IgG

<400> SEQUENCE: 437

Met Lys His Leu Trp Phe Phe Leu Leu Leu Val Ala Ala Pro Arg Trp
1 5 10 15

Val Leu Ser

<210> SEQ ID NO 438
<211> LENGTH: 242
<212> TYPE: PRT
<213> ORGANISM: Unknown
<220> FEATURE:
<223> OTHER INFORMATION: SARS-CoV spike protein

<400> SEQUENCE: 438

Thr Leu Lys Ser Phe Thr Val Glu Lys Gly Ile Tyr Gln Thr Ser Asn
1 5 10 15

Phe Arg Val Gln Pro Thr Glu Ser Ile Val Arg Phe Pro Asn Ile Thr
20 25 30

Asn Leu Cys Pro Phe Gly Glu Val Phe Asn Ala Thr Arg Phe Ala Ser
35 40 45

Val Tyr Ala Trp Asn Arg Lys Arg Ile Ser Asn Cys Val Ala Asp Tyr
50 55 60

Ser Val Leu Tyr Asn Ser Ala Ser Phe Ser Thr Phe Lys Cys Tyr Gly
65 70 75 80

```
Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Lys Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
    130                 135                 140

Gly Gly Asn Tyr Asn Tyr Leu Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Glu Gly Phe Asn Cys Tyr Phe Pro Leu Gln
            180                 185                 190

Ser Tyr Gly Phe Gln Pro Thr Asn Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Ser Val Asn Phe
225                 230                 235                 240

Thr Phe


<210> SEQ ID NO 439
<211> LENGTH: 242
<212> TYPE: PRT
<213> ORGANISM: Unknown
<220> FEATURE:
<223> OTHER INFORMATION: SARS-CoV spike protein

<400> SEQUENCE: 439

Thr Leu Lys Ser Phe Thr Val Glu Lys Gly Ile Tyr Gln Thr Ser Asn
1               5                   10                  15

Phe Arg Val Gln Pro Thr Glu Ser Ile Val Arg Phe Pro Asn Ile Thr
            20                  25                  30

Asn Leu Cys Pro Phe Gly Glu Val Phe Asn Ala Thr Arg Phe Ala Ser
        35                  40                  45

Val Tyr Ala Trp Asn Arg Lys Arg Ile Ser Asn Cys Val Ala Asp Tyr
    50                  55                  60

Ser Val Leu Tyr Asn Ser Ala Ser Phe Ser Thr Phe Lys Cys Tyr Gly
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Lys Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
    130                 135                 140

Gly Gly Asn Tyr Asn Tyr Arg Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Glu Gly Phe Asn Cys Tyr Phe Pro Leu Gln
            180                 185                 190

Ser Tyr Gly Phe Gln Pro Thr Asn Gly Val Gly Tyr Gln Pro Tyr Arg
```

```
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Ser Val Asn Phe
225                 230                 235                 240

Thr Phe


<210> SEQ ID NO 440
<211> LENGTH: 242
<212> TYPE: PRT
<213> ORGANISM: Unknown
<220> FEATURE:
<223> OTHER INFORMATION: SARS-CoV spike protein

<400> SEQUENCE: 440

Thr Leu Lys Ser Phe Thr Val Glu Lys Gly Ile Tyr Gln Thr Ser Asn
1               5                   10                  15

Phe Arg Val Gln Pro Thr Glu Ser Ile Val Arg Phe Pro Asn Ile Thr
            20                  25                  30

Asn Leu Cys Pro Phe Gly Glu Val Phe Asn Ala Thr Arg Phe Ala Ser
        35                  40                  45

Val Tyr Ala Trp Asn Arg Lys Arg Ile Ser Asn Cys Val Ala Asp Tyr
    50                  55                  60

Ser Val Leu Tyr Asn Ser Ala Ser Phe Ser Thr Phe Lys Cys Tyr Gly
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Lys Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
    130                 135                 140

Gly Gly Asn Tyr Asn Tyr Leu Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Lys Gly Phe Asn Cys Tyr Phe Pro Leu Gln
            180                 185                 190

Ser Tyr Gly Phe Gln Pro Thr Asn Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Ser Val Asn Phe
225                 230                 235                 240

Thr Phe


<210> SEQ ID NO 441
<211> LENGTH: 242
<212> TYPE: PRT
<213> ORGANISM: Unknown
<220> FEATURE:
<223> OTHER INFORMATION: SARS-CoV spike protein

<400> SEQUENCE: 441

Thr Leu Lys Ser Phe Thr Val Glu Lys Gly Ile Tyr Gln Thr Ser Asn
1               5                   10                  15
```

```
Phe Arg Val Gln Pro Thr Glu Ser Ile Val Arg Phe Pro Asn Ile Thr
            20                  25                  30

Asn Leu Cys Pro Phe Gly Glu Val Phe Asn Ala Thr Arg Phe Ala Ser
        35                  40                  45

Val Tyr Ala Trp Asn Arg Lys Arg Ile Ser Asn Cys Val Ala Asp Tyr
    50                  55                  60

Ser Val Leu Tyr Asn Ser Ala Ser Phe Ser Thr Phe Lys Cys Tyr Gly
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Lys Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
    130                 135                 140

Gly Gly Asn Tyr Asn Tyr Leu Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Lys Gly Phe Asn Cys Tyr Phe Pro Leu Gln
            180                 185                 190

Ser Tyr Gly Phe Gln Pro Thr Tyr Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Ser Val Asn Phe
225                 230                 235                 240

Thr Phe


<210> SEQ ID NO 442
<211> LENGTH: 242
<212> TYPE: PRT
<213> ORGANISM: Unknown
<220> FEATURE:
<223> OTHER INFORMATION: SARS-CoV spike protein

<400> SEQUENCE: 442

Thr Leu Lys Ser Phe Thr Val Glu Lys Gly Ile Tyr Gln Thr Ser Asn
1               5                   10                  15

Phe Arg Val Gln Pro Thr Glu Ser Ile Val Arg Phe Pro Asn Ile Thr
            20                  25                  30

Asn Leu Cys Pro Phe Gly Glu Val Phe Asn Ala Thr Arg Phe Ala Ser
        35                  40                  45

Val Tyr Ala Trp Asn Arg Lys Arg Ile Ser Asn Cys Val Ala Asp Tyr
    50                  55                  60

Ser Val Leu Tyr Asn Ser Ala Ser Phe Ser Thr Phe Lys Cys Tyr Gly
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Thr Ile Ala Asp Tyr Asn Tyr Lys Leu Pro Asp Asp Phe
        115                 120                 125
```

-continued

```
Thr Gly Cys Val Ile Ala Trp Asn Ser Asn Asn Leu Asp Ser Lys Val
    130                 135                 140

Gly Gly Asn Tyr Asn Tyr Leu Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Lys Gly Phe Asn Cys Tyr Phe Pro Leu Gln
            180                 185                 190

Ser Tyr Gly Phe Gln Pro Thr Tyr Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Ser Val Asn Phe
225                 230                 235                 240

Thr Phe


<210> SEQ ID NO 443
<211> LENGTH: 242
<212> TYPE: PRT
<213> ORGANISM: Unknown
<220> FEATURE:
<223> OTHER INFORMATION: SARS-CoV spike protein

<400> SEQUENCE: 443

Thr Leu Lys Ser Phe Thr Val Glu Lys Gly Ile Tyr Gln Thr Ser Asn
1               5                   10                  15

Phe Arg Val Gln Pro Thr Glu Ser Ile Val Arg Phe Pro Asn Ile Thr
            20                  25                  30

Asn Leu Cys Pro Phe Gly Glu Val Phe Asn Ala Thr Arg Phe Ala Ser
        35                  40                  45

Val Tyr Ala Trp Asn Arg Lys Arg Ile Ser Asn Cys Val Ala Asp Tyr
    50                  55                  60

Ser Val Leu Tyr Asn Ser Ala Ser Phe Ser Thr Phe Lys Cys Tyr Gly
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Asn Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
    130                 135                 140

Gly Gly Asn Tyr Asn Tyr Leu Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Lys Gly Phe Asn Cys Tyr Phe Pro Leu Gln
            180                 185                 190

Ser Tyr Gly Phe Gln Pro Thr Tyr Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Ser Val Asn Phe
225                 230                 235                 240

Thr Phe
```

<210> SEQ ID NO 444
<211> LENGTH: 756
<212> TYPE: PRT
<213> ORGANISM: Unknown
<220> FEATURE:
<223> OTHER INFORMATION: SARS-CoV spike protein

<400> SEQUENCE: 444

Thr Leu Lys Ser Phe Thr Val Glu Lys Gly Ile Tyr Gln Thr Ser Asn
1 5 10 15

Phe Arg Val Gln Pro Thr Glu Ser Ile Val Arg Phe Pro Asn Ile Thr
20 25 30

Asn Leu Cys Pro Phe Gly Glu Val Phe Asn Ala Thr Arg Phe Ala Ser
35 40 45

Val Tyr Ala Trp Asn Arg Lys Arg Ile Ser Asn Cys Val Ala Asp Tyr
50 55 60

Ser Val Leu Tyr Asn Ser Ala Ser Phe Ser Thr Phe Lys Cys Tyr Gly
65 70 75 80

Val Ser Pro Thr Lys Leu Asn Asp Leu Cys Phe Thr Asn Val Tyr Ala
85 90 95

Asp Ser Phe Val Ile Arg Gly Asp Glu Val Arg Gln Ile Ala Pro Gly
100 105 110

Gln Thr Gly Lys Ile Ala Asp Tyr Asn Tyr Lys Leu Pro Asp Asp Phe
115 120 125

Thr Gly Cys Val Ile Ala Trp Asn Ser Asn Asn Leu Asp Ser Lys Val
130 135 140

Gly Gly Asn Tyr Asn Tyr Leu Tyr Arg Leu Phe Arg Lys Ser Asn Leu
145 150 155 160

Lys Pro Phe Glu Arg Asp Ile Ser Thr Glu Ile Tyr Gln Ala Gly Ser
165 170 175

Thr Pro Cys Asn Gly Val Glu Gly Phe Asn Cys Tyr Phe Pro Leu Gln
180 185 190

Ser Tyr Gly Phe Gln Pro Thr Asn Gly Val Gly Tyr Gln Pro Tyr Arg
195 200 205

Val Val Val Leu Ser Phe Glu Leu Leu His Ala Pro Ala Thr Val Cys
210 215 220

Gly Pro Lys Lys Ser Thr Asn Leu Val Lys Asn Lys Ser Val Asn Phe
225 230 235 240

Thr Phe Gly Gly Gly Gly Ser Gly Gly Gly Gly Ser Gly Gly Gly Gly
245 250 255

Ser Thr Leu Lys Ser Phe Thr Val Glu Lys Gly Ile Tyr Gln Thr Ser
260 265 270

Asn Phe Arg Val Gln Pro Thr Glu Ser Ile Val Arg Phe Pro Asn Ile
275 280 285

Thr Asn Leu Cys Pro Phe Gly Glu Val Phe Asn Ala Thr Arg Phe Ala
290 295 300

Ser Val Tyr Ala Trp Asn Arg Lys Arg Ile Ser Asn Cys Val Ala Asp
305 310 315 320

Tyr Ser Val Leu Tyr Asn Ser Ala Ser Phe Ser Thr Phe Lys Cys Tyr
325 330 335

Gly Val Ser Pro Thr Lys Leu Asn Asp Leu Cys Phe Thr Asn Val Tyr
340 345 350

Ala Asp Ser Phe Val Ile Arg Gly Asp Glu Val Arg Gln Ile Ala Pro
355 360 365

```
Gly Gln Thr Gly Asn Ile Ala Asp Tyr Asn Tyr Lys Leu Pro Asp Asp
    370                 375                 380

Phe Thr Gly Cys Val Ile Ala Trp Asn Ser Asn Asn Leu Asp Ser Lys
385                 390                 395                 400

Val Gly Gly Asn Tyr Asn Tyr Leu Tyr Arg Leu Phe Arg Lys Ser Asn
                405                 410                 415

Leu Lys Pro Phe Glu Arg Asp Ile Ser Thr Glu Ile Tyr Gln Ala Gly
            420                 425                 430

Ser Thr Pro Cys Asn Gly Val Lys Gly Phe Asn Cys Tyr Phe Pro Leu
        435                 440                 445

Gln Ser Tyr Gly Phe Gln Pro Thr Tyr Gly Val Gly Tyr Gln Pro Tyr
    450                 455                 460

Arg Val Val Val Leu Ser Phe Glu Leu Leu His Ala Pro Ala Thr Val
465                 470                 475                 480

Cys Gly Pro Lys Lys Ser Thr Asn Leu Val Lys Asn Lys Ser Val Asn
                485                 490                 495

Phe Thr Phe Gly Gly Gly Gly Ser Gly Gly Gly Gly Ser Gly Gly Gly
            500                 505                 510

Gly Ser Thr Leu Lys Ser Phe Thr Val Glu Lys Gly Ile Tyr Gln Thr
        515                 520                 525

Ser Asn Phe Arg Val Gln Pro Thr Glu Ser Ile Val Arg Phe Pro Asn
    530                 535                 540

Ile Thr Asn Leu Cys Pro Phe Gly Glu Val Phe Asn Ala Thr Arg Phe
545                 550                 555                 560

Ala Ser Val Tyr Ala Trp Asn Arg Lys Arg Ile Ser Asn Cys Val Ala
                565                 570                 575

Asp Tyr Ser Val Leu Tyr Asn Ser Ala Ser Phe Ser Thr Phe Lys Cys
            580                 585                 590

Tyr Gly Val Ser Pro Thr Lys Leu Asn Asp Leu Cys Phe Thr Asn Val
        595                 600                 605

Tyr Ala Asp Ser Phe Val Ile Arg Gly Asp Glu Val Arg Gln Ile Ala
    610                 615                 620

Pro Gly Gln Thr Gly Lys Ile Ala Asp Tyr Asn Tyr Lys Leu Pro Asp
625                 630                 635                 640

Asp Phe Thr Gly Cys Val Ile Ala Trp Asn Ser Asn Asn Leu Asp Ser
                645                 650                 655

Lys Val Gly Gly Asn Tyr Asn Tyr Leu Tyr Arg Leu Phe Arg Lys Ser
            660                 665                 670

Asn Leu Lys Pro Phe Glu Arg Asp Ile Ser Thr Glu Ile Tyr Gln Ala
        675                 680                 685

Gly Ser Thr Pro Cys Asn Gly Val Lys Gly Phe Asn Cys Tyr Phe Pro
    690                 695                 700

Leu Gln Ser Tyr Gly Phe Gln Pro Thr Tyr Gly Val Gly Tyr Gln Pro
705                 710                 715                 720

Tyr Arg Val Val Val Leu Ser Phe Glu Leu Leu His Ala Pro Ala Thr
                725                 730                 735

Val Cys Gly Pro Lys Lys Ser Thr Asn Leu Val Lys Asn Lys Ser Val
            740                 745                 750

Asn Phe Thr Phe
        755
```

<210> SEQ ID NO 445
<211> LENGTH: 778

```
<212> TYPE: PRT
<213> ORGANISM: Unknown
<220> FEATURE:
<223> OTHER INFORMATION: SARS-CoV spike protein

<400> SEQUENCE: 445

Thr Leu Lys Ser Phe Thr Val Glu Lys Gly Ile Tyr Gln Thr Ser Asn
1               5                   10                  15

Phe Arg Val Gln Pro Thr Glu Ser Ile Val Arg Phe Pro Asn Ile Thr
            20                  25                  30

Asn Leu Cys Pro Phe Gly Glu Val Phe Asn Ala Thr Arg Phe Ala Ser
        35                  40                  45

Val Tyr Ala Trp Asn Arg Lys Arg Ile Ser Asn Cys Val Ala Asp Tyr
    50                  55                  60

Ser Val Leu Tyr Asn Ser Ala Ser Phe Ser Thr Phe Lys Cys Tyr Gly
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Lys Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
    130                 135                 140

Gly Gly Asn Tyr Asn Tyr Leu Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Glu Gly Phe Asn Cys Tyr Phe Pro Leu Gln
            180                 185                 190

Ser Tyr Gly Phe Gln Pro Thr Asn Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Ser Val Asn Phe
225                 230                 235                 240

Thr Phe Gly Gly Gly Gly Ser Gly Gly Gly Gly Ser Arg Arg Lys Arg
                245                 250                 255

Ser Val Gly Gly Gly Gly Ser Gly Gly Gly Gly Ser Thr Leu Lys Ser
            260                 265                 270

Phe Thr Val Glu Lys Gly Ile Tyr Gln Thr Ser Asn Phe Arg Val Gln
        275                 280                 285

Pro Thr Glu Ser Ile Val Arg Phe Pro Asn Ile Thr Asn Leu Cys Pro
    290                 295                 300

Phe Gly Glu Val Phe Asn Ala Thr Arg Phe Ala Ser Val Tyr Ala Trp
305                 310                 315                 320

Asn Arg Lys Arg Ile Ser Asn Cys Val Ala Asp Tyr Ser Val Leu Tyr
                325                 330                 335

Asn Ser Ala Ser Phe Ser Thr Phe Lys Cys Tyr Gly Val Ser Pro Thr
            340                 345                 350

Lys Leu Asn Asp Leu Cys Phe Thr Asn Val Tyr Ala Asp Ser Phe Val
        355                 360                 365

Ile Arg Gly Asp Glu Val Arg Gln Ile Ala Pro Gly Gln Thr Gly Asn
    370                 375                 380
```

Ile Ala Asp Tyr Asn Tyr Lys Leu Pro Asp Asp Phe Thr Gly Cys Val
385 390 395 400

Ile Ala Trp Asn Ser Asn Asn Leu Asp Ser Lys Val Gly Gly Asn Tyr
405 410 415

Asn Tyr Leu Tyr Arg Leu Phe Arg Lys Ser Asn Leu Lys Pro Phe Glu
420 425 430

Arg Asp Ile Ser Thr Glu Ile Tyr Gln Ala Gly Ser Thr Pro Cys Asn
435 440 445

Gly Val Lys Gly Phe Asn Cys Tyr Phe Pro Leu Gln Ser Tyr Gly Phe
450 455 460

Gln Pro Thr Tyr Gly Val Gly Tyr Gln Pro Tyr Arg Val Val Val Leu
465 470 475 480

Ser Phe Glu Leu Leu His Ala Pro Ala Thr Val Cys Gly Pro Lys Lys
485 490 495

Ser Thr Asn Leu Val Lys Asn Lys Ser Val Asn Phe Thr Phe Gly Gly
500 505 510

Gly Gly Ser Gly Gly Gly Gly Ser Arg Arg Lys Arg Ser Val Gly Gly
515 520 525

Gly Gly Ser Gly Gly Gly Gly Ser Thr Leu Lys Ser Phe Thr Val Glu
530 535 540

Lys Gly Ile Tyr Gln Thr Ser Asn Phe Arg Val Gln Pro Thr Glu Ser
545 550 555 560

Ile Val Arg Phe Pro Asn Ile Thr Asn Leu Cys Pro Phe Gly Glu Val
565 570 575

Phe Asn Ala Thr Arg Phe Ala Ser Val Tyr Ala Trp Asn Arg Lys Arg
580 585 590

Ile Ser Asn Cys Val Ala Asp Tyr Ser Val Leu Tyr Asn Ser Ala Ser
595 600 605

Phe Ser Thr Phe Lys Cys Tyr Gly Val Ser Pro Thr Lys Leu Asn Asp
610 615 620

Leu Cys Phe Thr Asn Val Tyr Ala Asp Ser Phe Val Ile Arg Gly Asp
625 630 635 640

Glu Val Arg Gln Ile Ala Pro Gly Gln Thr Gly Lys Ile Ala Asp Tyr
645 650 655

Asn Tyr Lys Leu Pro Asp Asp Phe Thr Gly Cys Val Ile Ala Trp Asn
660 665 670

Ser Asn Asn Leu Asp Ser Lys Val Gly Gly Asn Tyr Asn Tyr Leu Tyr
675 680 685

Arg Leu Phe Arg Lys Ser Asn Leu Lys Pro Phe Glu Arg Asp Ile Ser
690 695 700

Thr Glu Ile Tyr Gln Ala Gly Ser Thr Pro Cys Asn Gly Val Lys Gly
705 710 715 720

Phe Asn Cys Tyr Phe Pro Leu Gln Ser Tyr Gly Phe Gln Pro Thr Tyr
725 730 735

Gly Val Gly Tyr Gln Pro Tyr Arg Val Val Val Leu Ser Phe Glu Leu
740 745 750

Leu His Ala Pro Ala Thr Val Cys Gly Pro Lys Lys Ser Thr Asn Leu
755 760 765

Val Lys Asn Lys Ser Val Asn Phe Thr Phe
770 775

<210> SEQ ID NO 446
<211> LENGTH: 197
<212> TYPE: PRT

<213> ORGANISM: Unknown
<220> FEATURE:
<223> OTHER INFORMATION: SARS-CoV-2 surface glycoprotein

<400> SEQUENCE: 446

```
Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro
        195
```

<210> SEQ ID NO 447
<211> LENGTH: 19
<212> TYPE: PRT
<213> ORGANISM: Unknown
<220> FEATURE:
<223> OTHER INFORMATION: SARS Co-V spike protein

<400> SEQUENCE: 447

```
Ser Phe Ile Glu Asp Leu Leu Phe Asn Lys Val Thr Leu Ala Asp Ala
1               5                   10                  15

Gly Phe Ile
```

<210> SEQ ID NO 448
<211> LENGTH: 10
<212> TYPE: PRT
<213> ORGANISM: Unknown
<220> FEATURE:
<223> OTHER INFORMATION: SARS Co-V spike protein

<400> SEQUENCE: 448

```
Ser Arg Leu Asp Lys Val Glu Ala Glu Val
1               5                   10
```

<210> SEQ ID NO 449
<211> LENGTH: 39
<212> TYPE: PRT
<213> ORGANISM: Unknown
<220> FEATURE:

<223> OTHER INFORMATION: SARS Co-V spike protein

<400> SEQUENCE: 449

Cys Cys Met Thr Ser Cys Cys Ser Cys Leu Lys Gly Cys Cys Ser Cys
1 5 10 15

Gly Ser Cys Cys Lys Phe Asp Glu Asp Asp Ser Glu Pro Val Leu Lys
20 25 30

Gly Val Lys Leu His Tyr Thr
35

<210> SEQ ID NO 450
<211> LENGTH: 11
<212> TYPE: PRT
<213> ORGANISM: Unknown
<220> FEATURE:
<223> OTHER INFORMATION: peptide

<400> SEQUENCE: 450

Asn Ser Pro Arg Arg Ala Arg Ser Val Ala Ser
1 5 10

<210> SEQ ID NO 451
<211> LENGTH: 11
<212> TYPE: PRT
<213> ORGANISM: Unknown
<220> FEATURE:
<223> OTHER INFORMATION: peptide

<400> SEQUENCE: 451

Asn Ser Pro Gln Gln Ala Gln Ser Val Ala Ser
1 5 10

<210> SEQ ID NO 452
<211> LENGTH: 18
<212> TYPE: PRT
<213> ORGANISM: Unknown
<220> FEATURE:
<223> OTHER INFORMATION: peptide

<400> SEQUENCE: 452

Lys Arg Ser Phe Ile Glu Asp Leu Leu Phe Asn Lys Val Thr Leu Ala
1 5 10 15

Asp Ala

<210> SEQ ID NO 453
<211> LENGTH: 8
<212> TYPE: PRT
<213> ORGANISM: Unknown
<220> FEATURE:
<223> OTHER INFORMATION: peptide

<400> SEQUENCE: 453

Lys Arg Ser Phe Ile Ala Asp Ala
1 5

<210> SEQ ID NO 454
<211> LENGTH: 10
<212> TYPE: PRT
<213> ORGANISM: Unknown
<220> FEATURE:
<223> OTHER INFORMATION: peptide

<400> SEQUENCE: 454

Ser Arg Leu Asp Lys Val Glu Ala Glu Val
1 5 10

```
<210> SEQ ID NO 455
<211> LENGTH: 10
<212> TYPE: PRT
<213> ORGANISM: Unknown
<220> FEATURE:
<223> OTHER INFORMATION: peptide

<400> SEQUENCE: 455

Ser Arg Leu Asp Pro Pro Glu Ala Glu Val
1               5                   10


<210> SEQ ID NO 456
<211> LENGTH: 11
<212> TYPE: PRT
<213> ORGANISM: Unknown
<220> FEATURE:
<223> OTHER INFORMATION: peptide

<400> SEQUENCE: 456

Asn Ser Pro Ser Gly Ala Gly Ser Val Ala Ser
1               5                   10


<210> SEQ ID NO 457
<211> LENGTH: 9
<212> TYPE: PRT
<213> ORGANISM: Unknown
<220> FEATURE:
<223> OTHER INFORMATION: peptide

<400> SEQUENCE: 457

Pro Ser Lys Pro Ser Lys Gln Ser Phe
1               5


<210> SEQ ID NO 458
<211> LENGTH: 9
<212> TYPE: PRT
<213> ORGANISM: Unknown
<220> FEATURE:
<223> OTHER INFORMATION: pepide

<400> SEQUENCE: 458

Pro Ser Lys Pro Ser Lys Asn Ser Phe
1               5


<210> SEQ ID NO 459
<211> LENGTH: 9
<212> TYPE: PRT
<213> ORGANISM: Unknown
<220> FEATURE:
<223> OTHER INFORMATION: peptide

<400> SEQUENCE: 459

Pro Ser Lys Pro Ser Asn Ala Ser Phe
1               5


<210> SEQ ID NO 460
<211> LENGTH: 242
<212> TYPE: PRT
<213> ORGANISM: Unknown
<220> FEATURE:
<223> OTHER INFORMATION: SARS-CoV spike protein

<400> SEQUENCE: 460

Thr Leu Lys Ser Phe Thr Val Glu Lys Gly Ile Tyr Gln Thr Ser Asn
1               5                   10                  15
```

```
Phe Arg Val Gln Pro Thr Glu Ser Ile Val Arg Phe Pro Asn Ile Thr
            20                  25                  30

Asn Leu Cys Pro Phe Gly Glu Val Phe Asn Ala Thr Arg Phe Ala Ser
        35                  40                  45

Val Tyr Ala Trp Asn Arg Lys Arg Ile Ser Asn Cys Val Ala Asp Tyr
    50                  55                  60

Ser Val Leu Tyr Asn Ser Ala Ser Phe Ser Thr Phe Lys Cys Tyr Gly
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Lys Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
    130                 135                 140

Gly Gly Asn Tyr Asn Tyr Leu Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Lys Gly Phe Asn Cys Tyr Phe Pro Leu Gln
            180                 185                 190

Ser Tyr Gly Phe Gln Pro Thr Tyr Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Ser Val Asn Phe
225                 230                 235                 240

Thr Phe


<210> SEQ ID NO 461
<211> LENGTH: 6
<212> TYPE: PRT
<213> ORGANISM: Unknown
<220> FEATURE:
<223> OTHER INFORMATION: peptide

<400> SEQUENCE: 461

Asn Ser Pro Val Ala Ser
1               5


<210> SEQ ID NO 462
<211> LENGTH: 8
<212> TYPE: PRT
<213> ORGANISM: Unknown
<220> FEATURE:
<223> OTHER INFORMATION: peptide

<400> SEQUENCE: 462

Leu Gln Tyr Gly Ser Phe Cys Thr
1               5


<210> SEQ ID NO 463
<211> LENGTH: 7
<212> TYPE: PRT
<213> ORGANISM: Unknown
<220> FEATURE:
<223> OTHER INFORMATION: peptide

<400> SEQUENCE: 463
```

Gln Glu Ile Asn Ser Ser Tyr
1 5

<210> SEQ ID NO 464
<211> LENGTH: 7
<212> TYPE: PRT
<213> ORGANISM: Unknown
<220> FEATURE:
<223> OTHER INFORMATION: peptide

<400> SEQUENCE: 464

Ser His Pro Arg Leu Ser Ala
1 5

<210> SEQ ID NO 465
<211> LENGTH: 7
<212> TYPE: PRT
<213> ORGANISM: Unknown
<220> FEATURE:
<223> OTHER INFORMATION: peptide

<400> SEQUENCE: 465

Ser Met Pro Asn Pro Met Val
1 5

<210> SEQ ID NO 466
<211> LENGTH: 7
<212> TYPE: PRT
<213> ORGANISM: Unknown
<220> FEATURE:
<223> OTHER INFORMATION: peptide

<400> SEQUENCE: 466

Gly Leu Gln Gln Val Leu Leu
1 5

<210> SEQ ID NO 467
<211> LENGTH: 7
<212> TYPE: PRT
<213> ORGANISM: Unknown
<220> FEATURE:
<223> OTHER INFORMATION: peptide

<400> SEQUENCE: 467

His Glu Leu Ser Val Leu Leu
1 5

<210> SEQ ID NO 468
<211> LENGTH: 7
<212> TYPE: PRT
<213> ORGANISM: Unknown
<220> FEATURE:
<223> OTHER INFORMATION: peptide

<400> SEQUENCE: 468

Tyr Ala Pro Gln Arg Leu Pro
1 5

<210> SEQ ID NO 469
<211> LENGTH: 7
<212> TYPE: PRT
<213> ORGANISM: Unknown
<220> FEATURE:
<223> OTHER INFORMATION: peptide

<400> SEQUENCE: 469

Thr Pro Arg Thr Leu Pro Thr
1 5

<210> SEQ ID NO 470
<211> LENGTH: 7
<212> TYPE: PRT
<213> ORGANISM: Unknown
<220> FEATURE:
<223> OTHER INFORMATION: peptide

<400> SEQUENCE: 470

Ala Pro Val His Ser Ser Ile
1 5

<210> SEQ ID NO 471
<211> LENGTH: 7
<212> TYPE: PRT
<213> ORGANISM: Unknown
<220> FEATURE:
<223> OTHER INFORMATION: peptide

<400> SEQUENCE: 471

Ala Pro Pro His Ala Leu Ser
1 5

<210> SEQ ID NO 472
<211> LENGTH: 7
<212> TYPE: PRT
<213> ORGANISM: Unknown
<220> FEATURE:
<223> OTHER INFORMATION: peptide

<400> SEQUENCE: 472

Thr Phe Ser Asn Arg Phe Ile
1 5

<210> SEQ ID NO 473
<211> LENGTH: 7
<212> TYPE: PRT
<213> ORGANISM: Unknown
<220> FEATURE:
<223> OTHER INFORMATION: peptide

<400> SEQUENCE: 473

Val Val Pro Thr Pro Pro Tyr
1 5

<210> SEQ ID NO 474
<211> LENGTH: 7
<212> TYPE: PRT
<213> ORGANISM: Unknown
<220> FEATURE:
<223> OTHER INFORMATION: peptide

<400> SEQUENCE: 474

Glu Leu Ala Pro Asp Ser Pro
1 5

<210> SEQ ID NO 475
<211> LENGTH: 1527
<212> TYPE: PRT
<213> ORGANISM: Unknown
<220> FEATURE:
<223> OTHER INFORMATION: SARS-CoV spike protein

<400> SEQUENCE: 475

Thr Leu Lys Ser Phe Thr Val Glu Lys Gly Ile Tyr Gln Thr Ser Asn

-continued

```
1               5                   10                  15

Phe Arg Val Gln Pro Thr Glu Ser Ile Val Arg Phe Pro Asn Ile Thr
            20                  25                  30

Asn Leu Cys Pro Phe Gly Glu Val Phe Asn Ala Thr Arg Phe Ala Ser
        35                  40                  45

Val Tyr Ala Trp Asn Arg Lys Arg Ile Ser Asn Cys Val Ala Asp Tyr
    50                  55                  60

Ser Val Leu Tyr Asn Ser Ala Ser Phe Ser Thr Phe Lys Cys Tyr Gly
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Lys Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
    130                 135                 140

Gly Gly Asn Tyr Asn Tyr Arg Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Glu Gly Phe Asn Cys Tyr Phe Pro Leu Gln
            180                 185                 190

Ser Tyr Gly Phe Gln Pro Thr Asn Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Ser Val Asn Phe
225                 230                 235                 240

Thr Phe Gly Gly Gly Gly Ser Gly Gly Gly Gly Ser Gly Gly Gly Gly
                245                 250                 255

Ser Thr Leu Lys Ser Phe Thr Val Glu Lys Gly Ile Tyr Gln Thr Ser
            260                 265                 270

Asn Phe Arg Val Gln Pro Thr Glu Ser Ile Val Arg Phe Pro Asn Ile
        275                 280                 285

Thr Asn Leu Cys Pro Phe Gly Glu Val Phe Asn Ala Thr Arg Phe Ala
    290                 295                 300

Ser Val Tyr Ala Trp Asn Arg Lys Arg Ile Ser Asn Cys Val Ala Asp
305                 310                 315                 320

Tyr Ser Val Leu Tyr Asn Ser Ala Ser Phe Ser Thr Phe Lys Cys Tyr
                325                 330                 335

Gly Val Ser Pro Thr Lys Leu Asn Asp Leu Cys Phe Thr Asn Val Tyr
            340                 345                 350

Ala Asp Ser Phe Val Ile Arg Gly Asp Glu Val Arg Gln Ile Ala Pro
        355                 360                 365

Gly Gln Thr Gly Lys Ile Ala Asp Tyr Asn Tyr Lys Leu Pro Asp Asp
    370                 375                 380

Phe Thr Gly Cys Val Ile Ala Trp Asn Ser Asn Asn Leu Asp Ser Lys
385                 390                 395                 400

Val Gly Gly Asn Tyr Asn Tyr Arg Tyr Arg Leu Phe Arg Lys Ser Asn
                405                 410                 415

Leu Lys Pro Phe Glu Arg Asp Ile Ser Thr Glu Ile Tyr Gln Ala Gly
            420                 425                 430
```

-continued

```
Ser Thr Pro Cys Asn Gly Val Glu Gly Phe Asn Cys Tyr Phe Pro Leu
        435                 440                 445

Gln Ser Tyr Gly Phe Gln Pro Thr Asn Gly Val Gly Tyr Gln Pro Tyr
    450                 455                 460

Arg Val Val Val Leu Ser Phe Glu Leu Leu His Ala Pro Ala Thr Val
465                 470                 475                 480

Cys Gly Pro Lys Lys Ser Thr Asn Leu Val Lys Asn Lys Ser Val Asn
                485                 490                 495

Phe Thr Phe Gly Gly Gly Gly Ser Gly Gly Gly Gly Ser Gly Gly Gly
            500                 505                 510

Gly Ser Thr Leu Lys Ser Phe Thr Val Glu Lys Gly Ile Tyr Gln Thr
        515                 520                 525

Ser Asn Phe Arg Val Gln Pro Thr Glu Ser Ile Val Arg Phe Pro Asn
    530                 535                 540

Ile Thr Asn Leu Cys Pro Phe Gly Glu Val Phe Asn Ala Thr Arg Phe
545                 550                 555                 560

Ala Ser Val Tyr Ala Trp Asn Arg Lys Arg Ile Ser Asn Cys Val Ala
                565                 570                 575

Asp Tyr Ser Val Leu Tyr Asn Ser Ala Ser Phe Ser Thr Phe Lys Cys
            580                 585                 590

Tyr Gly Val Ser Pro Thr Lys Leu Asn Asp Leu Cys Phe Thr Asn Val
        595                 600                 605

Tyr Ala Asp Ser Phe Val Ile Arg Gly Asp Glu Val Arg Gln Ile Ala
    610                 615                 620

Pro Gly Gln Thr Gly Lys Ile Ala Asp Tyr Asn Tyr Lys Leu Pro Asp
625                 630                 635                 640

Asp Phe Thr Gly Cys Val Ile Ala Trp Asn Ser Asn Asn Leu Asp Ser
                645                 650                 655

Lys Val Gly Gly Asn Tyr Asn Tyr Leu Tyr Arg Leu Phe Arg Lys Ser
            660                 665                 670

Asn Leu Lys Pro Phe Glu Arg Asp Ile Ser Thr Glu Ile Tyr Gln Ala
        675                 680                 685

Gly Ser Thr Pro Cys Asn Gly Val Lys Gly Phe Asn Cys Tyr Phe Pro
    690                 695                 700

Leu Gln Ser Tyr Gly Phe Gln Pro Thr Asn Gly Val Gly Tyr Gln Pro
705                 710                 715                 720

Tyr Arg Val Val Val Leu Ser Phe Glu Leu Leu His Ala Pro Ala Thr
                725                 730                 735

Val Cys Gly Pro Lys Lys Ser Thr Asn Leu Val Lys Asn Lys Ser Val
            740                 745                 750

Asn Phe Thr Phe Gly Gly Gly Gly Ser Gly Gly Gly Gly Ser Gly Gly
        755                 760                 765

Gly Gly Ser Thr Leu Lys Ser Phe Thr Val Glu Lys Gly Ile Tyr Gln
    770                 775                 780

Thr Ser Asn Phe Arg Val Gln Pro Thr Glu Ser Ile Val Arg Phe Pro
785                 790                 795                 800

Asn Ile Thr Asn Leu Cys Pro Phe Gly Glu Val Phe Asn Ala Thr Arg
                805                 810                 815

Phe Ala Ser Val Tyr Ala Trp Asn Arg Lys Arg Ile Ser Asn Cys Val
            820                 825                 830

Ala Asp Tyr Ser Val Leu Tyr Asn Ser Ala Ser Phe Ser Thr Phe Lys
        835                 840                 845
```

```
Cys Tyr Gly Val Ser Pro Thr Lys Leu Asn Asp Leu Cys Phe Thr Asn
    850                 855                 860

Val Tyr Ala Asp Ser Phe Val Ile Arg Gly Asp Glu Val Arg Gln Ile
865                 870                 875                 880

Ala Pro Gly Gln Thr Gly Lys Ile Ala Asp Tyr Asn Tyr Lys Leu Pro
                885                 890                 895

Asp Asp Phe Thr Gly Cys Val Ile Ala Trp Asn Ser Asn Asn Leu Asp
            900                 905                 910

Ser Lys Val Gly Gly Asn Tyr Asn Tyr Leu Tyr Arg Leu Phe Arg Lys
        915                 920                 925

Ser Asn Leu Lys Pro Phe Glu Arg Asp Ile Ser Thr Glu Ile Tyr Gln
    930                 935                 940

Ala Gly Ser Thr Pro Cys Asn Gly Val Lys Gly Phe Asn Cys Tyr Phe
945                 950                 955                 960

Pro Leu Gln Ser Tyr Gly Phe Gln Pro Thr Tyr Gly Val Gly Tyr Gln
                965                 970                 975

Pro Tyr Arg Val Val Val Leu Ser Phe Glu Leu Leu His Ala Pro Ala
            980                 985                 990

Thr Val Cys Gly Pro Lys Lys Ser  Thr Asn Leu Val Lys  Asn Lys Ser
        995                 1000                1005

Val Asn  Phe Thr Phe Gly Gly  Gly Gly Ser Gly Gly  Gly Gly Ser
    1010                1015                1020

Gly Gly  Gly Gly Ser Thr Leu  Lys Ser Phe Thr Val  Glu Lys Gly
    1025                1030                1035

Ile Tyr  Gln Thr Ser Asn Phe  Arg Val Gln Pro Thr  Glu Ser Ile
    1040                1045                1050

Val Arg  Phe Pro Asn Ile Thr  Asn Leu Cys Pro Phe  Gly Glu Val
    1055                1060                1065

Phe Asn  Ala Thr Arg Phe Ala  Ser Val Tyr Ala Trp  Asn Arg Lys
    1070                1075                1080

Arg Ile  Ser Asn Cys Val Ala  Asp Tyr Ser Val Leu  Tyr Asn Ser
    1085                1090                1095

Ala Ser  Phe Ser Thr Phe Lys  Cys Tyr Gly Val Ser  Pro Thr Lys
    1100                1105                1110

Leu Asn  Asp Leu Cys Phe Thr  Asn Val Tyr Ala Asp  Ser Phe Val
    1115                1120                1125

Ile Arg  Gly Asp Glu Val Arg  Gln Ile Ala Pro Gly  Gln Thr Gly
    1130                1135                1140

Thr Ile  Ala Asp Tyr Asn Tyr  Lys Leu Pro Asp Asp  Phe Thr Gly
    1145                1150                1155

Cys Val  Ile Ala Trp Asn Ser  Asn Asn Leu Asp Ser  Lys Val Gly
    1160                1165                1170

Gly Asn  Tyr Asn Tyr Leu Tyr  Arg Leu Phe Arg Lys  Ser Asn Leu
    1175                1180                1185

Lys Pro  Phe Glu Arg Asp Ile  Ser Thr Glu Ile Tyr  Gln Ala Gly
    1190                1195                1200

Ser Thr  Pro Cys Asn Gly Val  Lys Gly Phe Asn Cys  Tyr Phe Pro
    1205                1210                1215

Leu Gln  Ser Tyr Gly Phe Gln  Pro Thr Tyr Gly Val  Gly Tyr Gln
    1220                1225                1230

Pro Tyr  Arg Val Val Val Leu  Ser Phe Glu Leu Leu  His Ala Pro
    1235                1240                1245

Ala Thr  Val Cys Gly Pro Lys  Lys Ser Thr Asn Leu  Val Lys Asn
```

```
    1250                1255                1260

Lys Ser  Val Asn Phe Thr Phe  Gly Gly Gly Gly Ser  Gly Gly Gly
    1265                1270                1275

Gly Ser  Gly Gly Gly Gly Ser  Thr Leu Lys Ser Phe  Thr Val Glu
    1280                1285                1290

Lys Gly  Ile Tyr Gln Thr Ser  Asn Phe Arg Val Gln  Pro Thr Glu
    1295                1300                1305

Ser Ile  Val Arg Phe Pro Asn  Ile Thr Asn Leu Cys  Pro Phe Gly
    1310                1315                1320

Glu Val  Phe Asn Ala Thr Arg  Phe Ala Ser Val Tyr  Ala Trp Asn
    1325                1330                1335

Arg Lys  Arg Ile Ser Asn Cys  Val Ala Asp Tyr Ser  Val Leu Tyr
    1340                1345                1350

Asn Ser  Ala Ser Phe Ser Thr  Phe Lys Cys Tyr Gly  Val Ser Pro
    1355                1360                1365

Thr Lys  Leu Asn Asp Leu Cys  Phe Thr Asn Val Tyr  Ala Asp Ser
    1370                1375                1380

Phe Val  Ile Arg Gly Asp Glu  Val Arg Gln Ile Ala  Pro Gly Gln
    1385                1390                1395

Thr Gly  Asn Ile Ala Asp Tyr  Asn Tyr Lys Leu Pro  Asp Asp Phe
    1400                1405                1410

Thr Gly  Cys Val Ile Ala Trp  Asn Ser Asn Asn Leu  Asp Ser Lys
    1415                1420                1425

Val Gly  Gly Asn Tyr Asn Tyr  Leu Tyr Arg Leu Phe  Arg Lys Ser
    1430                1435                1440

Asn Leu  Lys Pro Phe Glu Arg  Asp Ile Ser Thr Glu  Ile Tyr Gln
    1445                1450                1455

Ala Gly  Ser Thr Pro Cys Asn  Gly Val Lys Gly Phe  Asn Cys Tyr
    1460                1465                1470

Phe Pro  Leu Gln Ser Tyr Gly  Phe Gln Pro Thr Tyr  Gly Val Gly
    1475                1480                1485

Tyr Gln  Pro Tyr Arg Val Val  Val Leu Ser Phe Glu  Leu Leu His
    1490                1495                1500

Ala Pro  Ala Thr Val Cys Gly  Pro Lys Lys Ser Thr  Asn Leu Val
    1505                1510                1515

Lys Asn  Lys Ser Val Asn Phe  Thr Phe
    1520                1525


<210> SEQ ID NO 476
<211> LENGTH: 1567
<212> TYPE: PRT
<213> ORGANISM: Unknown
<220> FEATURE:
<223> OTHER INFORMATION: SARS-CoV spike protein

<400> SEQUENCE: 476

Thr Leu Lys Ser Phe Thr Val Glu Lys Gly Ile Tyr Gln Thr Ser Asn
1               5                   10                  15

Phe Arg Val Gln Pro Thr Glu Ser Ile Val Arg Phe Pro Asn Ile Thr
            20                  25                  30

Asn Leu Cys Pro Phe Gly Glu Val Phe Asn Ala Thr Arg Phe Ala Ser
        35                  40                  45

Val Tyr Ala Trp Asn Arg Lys Arg Ile Ser Asn Cys Val Ala Asp Tyr
    50                  55                  60

Ser Val Leu Tyr Asn Ser Ala Ser Phe Ser Thr Phe Lys Cys Tyr Gly
```

-continued

```
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Lys Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
    130                 135                 140

Gly Gly Asn Tyr Asn Tyr Arg Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Glu Gly Phe Asn Cys Tyr Phe Pro Leu Gln
            180                 185                 190

Ser Tyr Gly Phe Gln Pro Thr Asn Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Ser Val Asn Phe
225                 230                 235                 240

Thr Phe Gly Ser Gly Gly Gly Gly Ser Arg Arg Lys Arg Ser Val Gly
                245                 250                 255

Gly Gly Gly Ser Gly Gly Gly Gly Ser Thr Leu Lys Ser Phe Thr Val
            260                 265                 270

Glu Lys Gly Ile Tyr Gln Thr Ser Asn Phe Arg Val Gln Pro Thr Glu
        275                 280                 285

Ser Ile Val Arg Phe Pro Asn Ile Thr Asn Leu Cys Pro Phe Gly Glu
    290                 295                 300

Val Phe Asn Ala Thr Arg Phe Ala Ser Val Tyr Ala Trp Asn Arg Lys
305                 310                 315                 320

Arg Ile Ser Asn Cys Val Ala Asp Tyr Ser Val Leu Tyr Asn Ser Ala
                325                 330                 335

Ser Phe Ser Thr Phe Lys Cys Tyr Gly Val Ser Pro Thr Lys Leu Asn
            340                 345                 350

Asp Leu Cys Phe Thr Asn Val Tyr Ala Asp Ser Phe Val Ile Arg Gly
        355                 360                 365

Asp Glu Val Arg Gln Ile Ala Pro Gly Gln Thr Gly Lys Ile Ala Asp
    370                 375                 380

Tyr Asn Tyr Lys Leu Pro Asp Asp Phe Thr Gly Cys Val Ile Ala Trp
385                 390                 395                 400

Asn Ser Asn Asn Leu Asp Ser Lys Val Gly Gly Asn Tyr Asn Tyr Arg
                405                 410                 415

Tyr Arg Leu Phe Arg Lys Ser Asn Leu Lys Pro Phe Glu Arg Asp Ile
            420                 425                 430

Ser Thr Glu Ile Tyr Gln Ala Gly Ser Thr Pro Cys Asn Gly Val Glu
        435                 440                 445

Gly Phe Asn Cys Tyr Phe Pro Leu Gln Ser Tyr Gly Phe Gln Pro Thr
    450                 455                 460

Asn Gly Val Gly Tyr Gln Pro Tyr Arg Val Val Leu Ser Phe Glu
465                 470                 475                 480

Leu Leu His Ala Pro Ala Thr Val Cys Gly Pro Lys Lys Ser Thr Asn
                485                 490                 495
```

-continued

```
Leu Val Lys Asn Lys Ser Val Asn Phe Thr Phe Gly Ser Gly Gly Gly
            500                 505                 510

Gly Ser Arg Arg Lys Arg Ser Val Gly Gly Gly Gly Ser Gly Gly Gly
        515                 520                 525

Gly Ser Thr Leu Lys Ser Phe Thr Val Glu Lys Gly Ile Tyr Gln Thr
    530                 535                 540

Ser Asn Phe Arg Val Gln Pro Thr Glu Ser Ile Val Arg Phe Pro Asn
545                 550                 555                 560

Ile Thr Asn Leu Cys Pro Phe Gly Glu Val Phe Asn Ala Thr Arg Phe
                565                 570                 575

Ala Ser Val Tyr Ala Trp Asn Arg Lys Arg Ile Ser Asn Cys Val Ala
            580                 585                 590

Asp Tyr Ser Val Leu Tyr Asn Ser Ala Ser Phe Ser Thr Phe Lys Cys
        595                 600                 605

Tyr Gly Val Ser Pro Thr Lys Leu Asn Asp Leu Cys Phe Thr Asn Val
    610                 615                 620

Tyr Ala Asp Ser Phe Val Ile Arg Gly Asp Glu Val Arg Gln Ile Ala
625                 630                 635                 640

Pro Gly Gln Thr Gly Lys Ile Ala Asp Tyr Asn Tyr Lys Leu Pro Asp
                645                 650                 655

Asp Phe Thr Gly Cys Val Ile Ala Trp Asn Ser Asn Asn Leu Asp Ser
            660                 665                 670

Lys Val Gly Gly Asn Tyr Asn Tyr Leu Tyr Arg Leu Phe Arg Lys Ser
        675                 680                 685

Asn Leu Lys Pro Phe Glu Arg Asp Ile Ser Thr Glu Ile Tyr Gln Ala
    690                 695                 700

Gly Ser Thr Pro Cys Asn Gly Val Lys Gly Phe Asn Cys Tyr Phe Pro
705                 710                 715                 720

Leu Gln Ser Tyr Gly Phe Gln Pro Thr Asn Gly Val Gly Tyr Gln Pro
                725                 730                 735

Tyr Arg Val Val Val Leu Ser Phe Glu Leu Leu His Ala Pro Ala Thr
            740                 745                 750

Val Cys Gly Pro Lys Lys Ser Thr Asn Leu Val Lys Asn Lys Ser Val
        755                 760                 765

Asn Phe Thr Phe Gly Ser Gly Gly Gly Gly Ser Arg Arg Lys Arg Ser
    770                 775                 780

Val Gly Gly Gly Gly Ser Gly Gly Gly Gly Ser Thr Leu Lys Ser Phe
785                 790                 795                 800

Thr Val Glu Lys Gly Ile Tyr Gln Thr Ser Asn Phe Arg Val Gln Pro
                805                 810                 815

Thr Glu Ser Ile Val Arg Phe Pro Asn Ile Thr Asn Leu Cys Pro Phe
            820                 825                 830

Gly Glu Val Phe Asn Ala Thr Arg Phe Ala Ser Val Tyr Ala Trp Asn
        835                 840                 845

Arg Lys Arg Ile Ser Asn Cys Val Ala Asp Tyr Ser Val Leu Tyr Asn
    850                 855                 860

Ser Ala Ser Phe Ser Thr Phe Lys Cys Tyr Gly Val Ser Pro Thr Lys
865                 870                 875                 880

Leu Asn Asp Leu Cys Phe Thr Asn Val Tyr Ala Asp Ser Phe Val Ile
                885                 890                 895

Arg Gly Asp Glu Val Arg Gln Ile Ala Pro Gly Gln Thr Gly Lys Ile
            900                 905                 910
```

-continued

```
Ala Asp Tyr Asn Tyr Lys Leu Pro Asp Asp Phe Thr Gly Cys Val Ile
        915                 920                 925

Ala Trp Asn Ser Asn Asn Leu Asp Ser Lys Val Gly Gly Asn Tyr Asn
    930                 935                 940

Tyr Leu Tyr Arg Leu Phe Arg Lys Ser Asn Leu Lys Pro Phe Glu Arg
945                 950                 955                 960

Asp Ile Ser Thr Glu Ile Tyr Gln Ala Gly Ser Thr Pro Cys Asn Gly
                965                 970                 975

Val Lys Gly Phe Asn Cys Tyr Phe Pro Leu Gln Ser Tyr Gly Phe Gln
            980                 985                 990

Pro Thr Tyr Gly Val Gly Tyr Gln  Pro Tyr Arg Val Val  Val Leu Ser
        995                 1000                 1005

Phe Glu  Leu Leu His Ala Pro  Ala Thr Val Cys Gly  Pro Lys Lys
    1010                 1015                 1020

Ser Thr  Asn Leu Val Lys Asn  Lys Ser Val Asn Phe  Thr Phe Gly
    1025                 1030                 1035

Ser Gly  Gly Gly Gly Ser Arg  Arg Lys Arg Ser Val  Gly Gly Gly
    1040                 1045                 1050

Gly Ser  Gly Gly Gly Gly Ser  Thr Leu Lys Ser Phe  Thr Val Glu
    1055                 1060                 1065

Lys Gly  Ile Tyr Gln Thr Ser  Asn Phe Arg Val Gln  Pro Thr Glu
    1070                 1075                 1080

Ser Ile  Val Arg Phe Pro Asn  Ile Thr Asn Leu Cys  Pro Phe Gly
    1085                 1090                 1095

Glu Val  Phe Asn Ala Thr Arg  Phe Ala Ser Val Tyr  Ala Trp Asn
    1100                 1105                 1110

Arg Lys  Arg Ile Ser Asn Cys  Val Ala Asp Tyr Ser  Val Leu Tyr
    1115                 1120                 1125

Asn Ser  Ala Ser Phe Ser Thr  Phe Lys Cys Tyr Gly  Val Ser Pro
    1130                 1135                 1140

Thr Lys  Leu Asn Asp Leu Cys  Phe Thr Asn Val Tyr  Ala Asp Ser
    1145                 1150                 1155

Phe Val  Ile Arg Gly Asp Glu  Val Arg Gln Ile Ala  Pro Gly Gln
    1160                 1165                 1170

Thr Gly  Thr Ile Ala Asp Tyr  Asn Tyr Lys Leu Pro  Asp Asp Phe
    1175                 1180                 1185

Thr Gly  Cys Val Ile Ala Trp  Asn Ser Asn Asn Leu  Asp Ser Lys
    1190                 1195                 1200

Val Gly  Gly Asn Tyr Asn Tyr  Leu Tyr Arg Leu Phe  Arg Lys Ser
    1205                 1210                 1215

Asn Leu  Lys Pro Phe Glu Arg  Asp Ile Ser Thr Glu  Ile Tyr Gln
    1220                 1225                 1230

Ala Gly  Ser Thr Pro Cys Asn  Gly Val Lys Gly Phe  Asn Cys Tyr
    1235                 1240                 1245

Phe Pro  Leu Gln Ser Tyr Gly  Phe Gln Pro Thr Tyr  Gly Val Gly
    1250                 1255                 1260

Tyr Gln  Pro Tyr Arg Val Val  Val Leu Ser Phe Glu  Leu Leu His
    1265                 1270                 1275

Ala Pro  Ala Thr Val Cys Gly  Pro Lys Lys Ser Thr  Asn Leu Val
    1280                 1285                 1290

Lys Asn  Lys Ser Val Asn Phe  Thr Phe Gly Ser Gly  Gly Gly Gly
    1295                 1300                 1305

Ser Arg  Arg Lys Arg Ser Val  Gly Gly Gly Gly Ser  Gly Gly Gly
```

-continued

```
    1310                1315                1320

Gly Ser  Thr Leu Lys Ser Phe  Thr Val Glu Lys Gly  Ile Tyr Gln
    1325                1330                1335

Thr Ser  Asn Phe Arg Val Gln  Pro Thr Glu Ser Ile  Val Arg Phe
    1340                1345                1350

Pro Asn  Ile Thr Asn Leu Cys  Pro Phe Gly Glu Val  Phe Asn Ala
    1355                1360                1365

Thr Arg  Phe Ala Ser Val Tyr  Ala Trp Asn Arg Lys  Arg Ile Ser
    1370                1375                1380

Asn Cys  Val Ala Asp Tyr Ser  Val Leu Tyr Asn Ser  Ala Ser Phe
    1385                1390                1395

Ser Thr  Phe Lys Cys Tyr Gly  Val Ser Pro Thr Lys  Leu Asn Asp
    1400                1405                1410

Leu Cys  Phe Thr Asn Val Tyr  Ala Asp Ser Phe Val  Ile Arg Gly
    1415                1420                1425

Asp Glu  Val Arg Gln Ile Ala  Pro Gly Gln Thr Gly  Asn Ile Ala
    1430                1435                1440

Asp Tyr  Asn Tyr Lys Leu Pro  Asp Asp Phe Thr Gly  Cys Val Ile
    1445                1450                1455

Ala Trp  Asn Ser Asn Asn Leu  Asp Ser Lys Val Gly  Gly Asn Tyr
    1460                1465                1470

Asn Tyr  Leu Tyr Arg Leu Phe  Arg Lys Ser Asn Leu  Lys Pro Phe
    1475                1480                1485

Glu Arg  Asp Ile Ser Thr Glu  Ile Tyr Gln Ala Gly  Ser Thr Pro
    1490                1495                1500

Cys Asn  Gly Val Lys Gly Phe  Asn Cys Tyr Phe Pro  Leu Gln Ser
    1505                1510                1515

Tyr Gly  Phe Gln Pro Thr Tyr  Gly Val Gly Tyr Gln  Pro Tyr Arg
    1520                1525                1530

Val Val  Val Leu Ser Phe Glu  Leu Leu His Ala Pro  Ala Thr Val
    1535                1540                1545

Cys Gly  Pro Lys Lys Ser Thr  Asn Leu Val Lys Asn  Lys Ser Val
    1550                1555                1560

Asn Phe  Thr Phe
    1565
```

CORONAVIRUS IMMUNOGENIC COMPOSITIONS AND USES THEREOF

RELATED APPLICATIONS

This application claims priority to provisional application Nos. U.S. Ser. No. 62/977,078 filed 14 Feb. 2020; U.S. Ser. No. 62/992,553 filed 20 Mar. 2020; U.S. Ser. No. 63/005,923 filed 6 Apr. 2020; U.S. Ser. No. 63/016,902 filed 28 Apr. 2020; U.S. Ser. No. 63/050,844 filed 12 Jul. 2020; U.S. Ser. No. 63/069,792 filed 25 Aug. 2020; U.S. Ser. No. 63/088,736 filed 7 Oct. 2020; U.S. Ser. No. 63/140,128 filed 21 Jan. 2021; U.S. Ser. No. 63/142,077 filed 27 Jan. 2021; and, U.S. Ser. No. 63/148,374 filed 11 Feb. 2021, each of which are hereby incorporated into this application in their entirety.

SEQUENCE LISTING

The instant application contains a Sequence Listing which has been submitted electronically in ASCII format via EFS-Web and hereby incorporated by reference in its entirety. Said ASCII copy, created on 3 May 2021, is named ALT2029US1T_Corr_ST25.txt and is 479,367 bytes in size.

FIELD OF THE DISCLOSURE

This application pertains generally to an adenoviral vectored coronavirus antigen pharmaceutical formulation for administration to a mammalian subject that induces an immune response in the subject and optionally provides protection against novel 2019 Coronavirus (SARS-CoV-2).

BACKGROUND OF THE DISCLOSURE

The coronaviruses are a diverse group of large enveloped, positive-stranded RNA (ss RNA) viruses that cause respiratory and enteric diseases in humans and other animals. For example, Human coronaviruses 229E (HCoV-229E), OC43 (HCoV-OC43), NL63, and HKU1 are endemic in the human population and cause up to 30% of common colds. Coronaviruses of animals (e.g., porcine transmissible gastroenteritis virus (TGEV), murine hepatitis virus (MHV) and avian infectious bronchitis virus (IBV)) cause respiratory, gastrointestinal, neurological, or hepatic disease in their respective hosts.

Coronavirus has a positive-sense, non-segmented, single-stranded RNA genome, which encodes at least 18 viral proteins (such as non-structural proteins (NSP) 1-13, structural proteins E, M, N, S, and an RNA-dependent RNA polymerase). Coronavirus has three major surface glycoproteins (designated S, E, and M), and some coronaviruses have another surface glycoprotein referred to as hemagglutinin esterase (HE), in addition, the N (nucleocapsid) protein is a basic phosphoprotein, which is generally associated with the genome and has been reported to be antigenic (Holmes and Lai, Fields Virology, Chapter 34, 1996). The S (spike) protein, a major antigen of coronavirus, has two domains: S1, which is believed to be involved in receptor binding and S2, believed to mediate membrane fusion between the virus and target cell (Holmes and Lai, 1996, supra).

The S (spike) protein may form non-covalently linked homotrimers (oligomers), which may mediate receptor binding and virus infectivity. Homotrimers of S proteins are likely necessary for presenting the correct native conformation of receptor binding domains and for eliciting a neutralizing antibody response. In addition, intracellular processing of S protein is associated with significant posttranslation oligosaccharide modification. The posttranslation oligosaccharide modification (glycosylation) expected by N-glycan motif analysis indicates that the S protein has as many as 23 sites for such modification. In addition, C-terminal cysteine residues may also participate in protein folding and preserving the native (functional) S protein conformation. The S protein of some coronaviruses can be proteolytically processed near the center of the S protein by a trypsin-like protease in the Golgi apparatus or by extracellularly localized enzymes into to a linked polypeptide, containing an N-terminal S1 and a C-terminal S2 polypeptide. Presently, the coronaviruses are subdivided into α-genus, β-genus (e.g., MERS, SARS, SARS-CoV-2), and γ-genus. See FIG. 14.

Coronavirus infection is achieved through fusion of the lipid bilayer of the viral envelope with host cell membranes. Membrane fusion is mediated by the viral spike (S) glycoprotein on the viral envelope. The S-glycoprotein is synthesized as a precursor of about 180 kDa that oligomerizes in the endoplasmic reticulum and is incorporated into budding virions in a pre-Golgi compartment. S1 contains the receptor-binding site and thus contributes to defining the host range of the virus. S2 is the transmembrane subunit which contributes to mediating fusion between viral and cellular membranes. S2 contains two 4,3-hydrophobic repeat domains (HR) that are predicted to form coiled-coil structures. These regions are denoted HR-1 and HR-2, and are separated by an intervening stretch of amino acid residues called the interhelical domain. These coiled-coil regions may play an important role in defining the oligomeric structure of the spike protein in its native state and its fusogenic ability.

The novel coronovirus SARS-CoV-2 (initially reported as 2019-nCoV and officially named SARS-CoV-2 by the Coronavirus Study Group (a working group of the International Committee on Taxonomy of Viruses) based on phylogeny, taxonomy and established practice (BioRxiv; doi.org/10.1101/2020.02.07.937862)) is a new strain that has not been previously identified in humans and was first reported in Wuhan, Hubei Province, China. SARS-CoV-2 is the cause of the ongoing 2019-20 Wuhan coronavirus outbreak, a global health emergency. Genomic sequencing has shown that it is a positive-sense, single-stranded RNA coronavirus (GenBank Accession No. MN908947.3; RefSeq NC_045512; "Wuhan seafood market pneumonia virus isolate Wuhan-Hu-1"). Coronaviruses are primarily spread through close contact, in particular through respiratory droplets from coughs and sneezes within a range of about 6 feet (1.8 m). Common signs of infection include respiratory symptoms, fever, cough, shortness of breath and breathing difficulties. In more severe cases, infection can cause pneumonia, severe acute respiratory syndrome, kidney failure and even death. There is an urgent need for vectors and immunogenic compositions comprising the same that can be used to induce an immune response against SARS-CoV-2. This disclosure addresses these issues.

SUMMARY OF THE DISCLOSURE

In some embodiments, this disclosure provides reagents, compositions, and methods for inducing and/or improving (e.g., enhancing) an immune response against coronavirus, in particular novel 2019 coronavirus SARS-CoV-2. For instance, in some embodiments, this disclosure provides replication defective adenoviral vectors encoding at least one SARS-CoV-2 antigen(s) (e.g., E1A/E3 deletion human Adenovirus type 5 (hAd5) (hAd5-SARS-CoV-2)), and/or another one or more exogenous antigens of a different type of infectious agent (e.g., a different type of virus such as influenza (e.g., Ad-HA)), or lacking a transgene ("hAdE"; e.g., not encoding at least one antigen or immunogen of an exogenous infectious agent "empty"), which can be referred to herein collectively as "SARS-CoV-2 immunization vectors". As discussed herein, such vectors (and/or immunogenic compositions comprising the same) can be used to induce mucosal, cell-mediated and/or humoral immune responses against SARS-CoV-2 (e.g., against protective SARS-CoV-2 epitopes such as spike (S) protein receptor binding domain (RBD)). In some embodiments, this disclosure describes the administration of such vectors (e.g., hAd5-SARS-CoV-2 and/or hAd5) to animals and/or human beings to induce and/or enhance an immune response (e.g., the production of antibodies and/or $CD8^+$ T cells (and/or other T cells)) having specificity for SARS-CoV-2 T epitope(s) (e.g., a dominant epitopes). In some embodiments, the immune response induced by the vector administered intranasal induce and/or enhance a T cell response with a resident memory phenotypes in the respiratory tract. In some embodiments, such immune response is protective against SARS-CoV-2 and/or effective in ameliorating the symptoms and/or infection by SARS-CoV-2, and in some embodiments can be protective against a SARS-CoV-2 challenge. Thus, in some embodiments, this disclosure describes the use of an immunogenic composition(s) comprising hAd5-SARS-CoV-2 to provide solutions to art-recognized problems regarding SARS-CoV-2 transmission and infection.

In certain embodiments provided herein are immunogenic compositions, formulations thereof and methods of use for treating and/or preventing COVID-19 related diseases caused by SARS-Cov-2 viral infection, wherein the immunogenic composition comprises a replication defective adenoviral (rdAd) vector comprising a nucleic acid sequence encoding SEQ ID NO: 446 or a variant comprising at least 90%, or at least 95% identity to SEQ ID NO: 446. In embodiments, the immunogenic composition comprises a replication defective adenoviral (rdAd) vector comprising a nucleic acid sequence encoding SEQ ID NO: 15, or a variant comprising at least 90%, or at least 95% identity to SEQ ID NO: 15. SEQ ID NO: 15 comprises the RBD sequence (SEQ ID NO: 446) with long flanking sequences of the 51 domain of the spike protein (SEQ ID NO: 3) and a leader sequence. In certain embodiments, the nucleic acid sequence encodes SEQ ID NO: 13 (51 domain). In embodiments, the nucleic acid sequence encodes a sequence comprising one or more point mutations of SEQ ID NO: 3.

As used herein "variant" refers to one or more mutations in the RBD sequence. In certain embodiments, the nucleic acid sequence encodes one or more of SEQ ID NOS: 412-417, SEQ ID NOS: 438-445, SEQ ID NOS: 475-476 and SEQ ID NO: 460 (RBD sequences comprising one or more mutations as compared to the RBD sequence of SEQ ID NO: 3, SEQ ID NO: 446, SEQ ID NO: 13 or SEQ ID NO: 15). In embodiments, the nucleic acid sequence encodes a sequence comprising one or more mutations at positions 333-388, 390-395, 397-399, 401-411, 413-415, 417-419, 424, 426-435, 437, 439-442, 444-446, 449, 450, 452, 453, 455-463, 465, 467-473, 475-479, 481-486, 490, 491, 493-495, 499-510, or 513-526 wherein amino acid numbering corresponds to SEQ ID NO: 411 or SEQ ID NO: 3 (full length spike protein). In embodiments, the nucleic acid sequence encodes a sequence comprising one or more mutations at amino acid positions 367, 403, 439, 417, 446, 447, 449, 452, 453, 455, 456, 470, 473, 475, 476, 477, 478, 484, 486, 487, 490, 493, 494, 496, 499, 500, 501, 502, 503, 504, and/or 505, wherein amino acid numbering corresponds to SEQ ID NO: 411 or SEQ ID NO: 3 (full length spike protein).

In embodiments, the one or more mutations are selected from substitution of amino acid 417 (K) by N; substitution of amino acid 446 (G) by V, S or A; substitution of amino acid 449 (Y) by N; substitution at amino acid 453 (Y) by F; substitution of amino acid 455 (L) by F; substitution of amino acid 456 (F) by L; substitution of amino acid 473 (Y) by V; substitution of amino acid 475 (A) by V; substitution of amino acid 476 (G) by S or A; substitution of amino acid 477 (S) by N, R, T, G, A or I; substitution at amino acid 484 (E) by Q, K, D, A or R; substitution of amino acid 486 (F) by L or S; substitution of amino acid 453 (Y) by F; substitution of amino acid 493 (Q) by L or R; substitution of amino acid 495 (Y) by N or F; substitution of amino acid 500 (T) by I; substitution of amino acid 501 (N) by Y, T or S; substitution of amino acid 502 (G) by R, D or C; substitution of amino acid 503 (V) by L, I or F; or, substitution of amino acid 505 (Y) by H, E, W or C, wherein amino acid numbering corresponds to SEQ ID NO: 411. In embodiments, the nucleic acid sequence encodes a sequence comprising one or more mutations selected from K417T, K417N, E484K, L452R and/or N501Y, wherein amino acid numbering corresponds to SEQ ID NO: 411 or SEQ ID NO: 3 (full length spike protein). In embodiments, the nucleic acid sequence encoding SEQ ID NO: 446 further comprises a leader sequence encoded by a nucleic acid sequence encoding a sequence selected from SEQ ID NOS: 418 to 437.

In embodiments provided herein is an immunogenic composition wherein the coding sequence of the transgene is codon optimized for a mammalian subject. In embodiments, the replication defective adenoviral vector is a bovine adenovirus, a canine adenovirus, a non-human primate adenovirus, a chicken adenovirus, a porcine or swine adenovirus, or a human adenovirus. In embodiments, the non-human primate adenovirus is a chimpanzee or gorilla adenovirus. In embodiments, the replication defective adenoviral vector is a human adenovirus. In embodiments, the human adenovirus is Ad5 or Ad26.

In embodiments provided herein is a pharmaceutical formulation, comprising an effective amount of the immunogenic composition (e.g., comprising a replication defective adenoviral (rdAd) vector comprising a nucleic acid sequence encoding SEQ ID NO: 446 or a variant comprising at least 90%, or at least 95% identity to SEQ ID NO: 446), the composition comprising at least one pharmaceutically acceptable diluent or carrier, optionally wherein the diluent is phosphate-buffered saline. In embodiments, the formulation is configured for non-invasive or intranasal administration, optionally wherein the pharmaceutically acceptable carrier is in a spray or aerosol form.

In embodiments provided herein is a method for inducing an immune response against SARS-CoV-2, the method comprising administering an effective amount of a present immunogenic composition ((e.g., comprising a replication defective adenoviral (rdAd) vector comprising a nucleic acid sequence encoding SEQ ID NO: 446 or a variant comprising at least 90%, or at least 95% identity to SEQ ID NO: 446) to a human being. Ion embodiments, the effective amount is at least $10^8$ viral particles (vp), at least $10^9$ viral particles (vp), or at least $10^{10}$ viral particles (vp). In embodiments, the immunogenic composition is administered intranasally.

In some embodiments, compositions of the disclosure can be used in the treatment or prevention of SARS-CoV-2, and compositions of the disclosure can be used in the manufacture of a medicament to provide treatment or prevention of SARS-Cov-2. Accordingly, while the invention comprehends methods of treating and prevention of SARS-CoV-2, the invention also comprehends use of the compositions of the invention and such uses can parallel any of the inventive methods and involve any or all of the inventive compositions.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

FIG. 1A-J Exemplary SARS-CoV-2 complete genome (Wuhan seafood market pneumonia virus isolate Wuhan-Hu-1, complete genome; GenBank: MN908947.3; SEQ ID NO: 1).

FIG. 2A-E. SARS-CoV-2 ORF lab Polyprotein (GenBank: QHD43415.1; SEQ ID NO: 2).

FIG. 3A. SARS-CoV-2 surface glycoprotein (e.g. Spike protein) including the native leader sequence (GenBank: QHD43416.1; SEQ ID NO: 3).

FIG. 3B. RBD region of SARS-CoV-2 surface glycoprotein spike protein (SEQ ID NO: 446).

FIG. 4. SARS-CoV-2 ORF3A protein (GenBank: QHD43417.1; SEQ ID NO: 4).

FIG. 5. SARS-CoV-2 envelope protein (GenBank: QHD43418.1; SEQ ID NO: 5).

FIG. 6. SARS-CoV-2 membrane glycoprotein (GenBank: QHD43419.1; SEQ ID NO: 6).

FIG. 7. SARS-CoV-2 ORF6 protein (GenBank: QHD43420.1; SEQ ID NO: 7).

FIG. 8. SARS-CoV-2 ORF7a protein (GenBank: QHD43421.1; SEQ ID NO: 8).

FIG. 9. SARS-CoV-2 ORF8 protein (GenBank: QHD43422.1; SEQ ID NO: 9).

FIG. 10. SARS-CoV-2 nucleocapsid phosphoprotein (GenBank: QHD43423.2; SEQ ID NO: 10).

FIG. 11. SARS-CoV-2 ORF10 protein (GenBank: QHI42199.1; SEQ ID NO: 11).

FIG. 13 shows the schematic diagram of the Spike protein polypeptide and its domains (e.g. SEQ ID NO: 3)

FIG. 14 shows the taxonomy of coronavirus via the S1 and S2 domains of coronavirus spike protein.

FIG. 15 shows a table of conservative amino acid substitutions at positions 455, 486, 493, 494 and 501 in the Receptor Binding Domain (RBD) of the 51 portion of Spike protein.

FIG. 16. SARS-CoV-2 surface glycoprotein (e.g. Spike protein) (GenBank: QHD43416.1) with a pTA signal sequence underlined. (SEQ ID NO: 12).

FIG. 17A. SARS-CoV-2 spike protein 51 domain with pTA signal sequence underlined (SEQ ID NO: 13). When SEQ ID NO: 13 is inserted into an adenoviral vector it is herein referred to as "51 vector".

FIG. 17B. SARS-CoV-2 variant mutations in the S1 domain ("Sequence" is SEQ ID NO: 411).

FIG. 18. SARS-CoV-2 spike protein Receptor Binding Domain (RBD) of the S1 domain with pTA signal sequence and short flanking sequence underlined. (SEQ ID NO: 14).

FIG. 19. SARS-CoV-2 spike protein Receptor Binding Domain (RBD) of the S1 domain with pTA signal sequence and long flanking sequence underlined (SEQ ID NO: 15). When SEQ ID NO: 15 is inserted into an adenoviral vector it is herein referred to as "RBD vector".

FIG. 20. SARS-CoV-2 spike protein Receptor Binding Domain (RBD) of the S1 domain with conservative substitutions at positions 455, 486, 493, 494 and 501 (SEQ ID NO: 16).

FIG. 21. SARS-CoV-2 spike protein, portion of the Receptor Binding Domain (RBD) of the S1 domain with conservative substitutions at positions 455, 486, 493, 494 and 501 (SEQ ID NO: 17).

FIG. 22. SARS-CoV-2 surface glycoprotein (e.g. Spike protein) with a pTA signal sequence underlined and substitutions at the S1/S2, S2' and HR1 sites (SEQ ID NO: 18).

FIG. 23. SARS-CoV-2 surface glycoprotein (e.g. Spike protein) with a pTA signal sequence underlined and substitutions at the S1/S2, S2' and HR1 sites (SEQ ID NO: 19).

FIG. 24. SARS-CoV-2 surface glycoprotein (e.g. Spike protein) with a pTA signal sequence underlined and substitutions at the S1/S2, S2', HR1, fusion peptide and ER retention motif sites (SEQ ID NO: 20).

FIG. 74. low cytometry analysis of immune cells in lungs from individual C57BL/6 mice that have received a single intranasal high dose of the replication-deficient Ad5 vector expressing the RBD domain (SEQ ID NO: 15). Results for the groups are expressed as the geometric mean response +/95% confidence interval. Each graph (FIG. 74A through FIG. 74L) corresponds to an individual immune cell type.

FIG. 75. Flow cytometry analysis of immune cells in bronchoalveolar lavages from individual C57BL/6 mice that have received a single intranasal mid dose of the replication-deficient Ad5 vector expressing the RBD domain (SEQ ID NO: 15). Results for the groups are expressed as the geometric mean response +/95% confidence interval. Each graph (FIG. 75A through FIG. 75E) corresponds to an individual immune cell type at three time points.

FIG. 76. Flow cytometry analysis of immune cells in mediastinal lymph nodes from individual C57BL/6 mice that have received a single intranasal high dose of the replication-deficient Ad5 vector expressing the RBD domain (SEQ ID NO: 15). Results for the groups are expressed as the geometric mean response +/95% confidence interval. Each graph (FIG. 76A through FIG. 76J) corresponds to an individual immune cell type at three time points.

FIG. 77. Flow cytometry analysis of immune cells (FIGS. 77A through 77L)_in spleens from individual C57BL/6 mice that have received a single intranasal high dose of the replication-deficient Ad5 vector expressing the RBD domain (SEQ ID NO: 15). Results for the groups are expressed as the geometric mean response +/95% confidence interval. Each graph (FIG. 77A through FIG. 77L) corresponds to an individual immune cell type at three time points.

FIG. 82. Flow cytometry analysis of immune cell in bronchoalveolar lavages from individual C57BL/6 mice that have received a single intranasal mid dose of the replication-deficient Ad5 vector expressing the S1 domain (SEQ ID NO: 13). Results for the groups are expressed as the geometric mean response +/95% confidence interval. Each graph (FIG. 82A through FIG. 82E) corresponds to an individual immune cell type at three time points.

FIG. 83. Flow cytometry analysis of immune cells in mediastinal lymph nodes from individual C57BL/6 mice that have received a single intranasal high dose of the replication-deficient Ad5 vector expressing the S1 domain (SEQ ID NO: 13). Results for the groups are expressed as the geometric mean response +/95% confidence interval. Each graph (FIG. 83A through FIG. 83J) corresponds to an individual immune cell type at three time points.

FIG. 84. Flow cytometry analysis of immune cells in spleens from individual C57BL/6 mice that have received a single intranasal high dose of the replication-deficient Ad5 vector expressing the S1 domain (SEQ ID NO: 13). Results for the groups are expressed as the geometric mean response +/95% confidence interval. Each graph (FIG. 84A through FIG. 84L) corresponds to an individual immune cell type at three time points.

FIGS. 87A through 87E. SARS-CoV-2 concatenated Polyprotein; Derived from SEQ ID NO: 1 (GenBank: MN908947.3).

DETAILED DESCRIPTION

Figure 12:
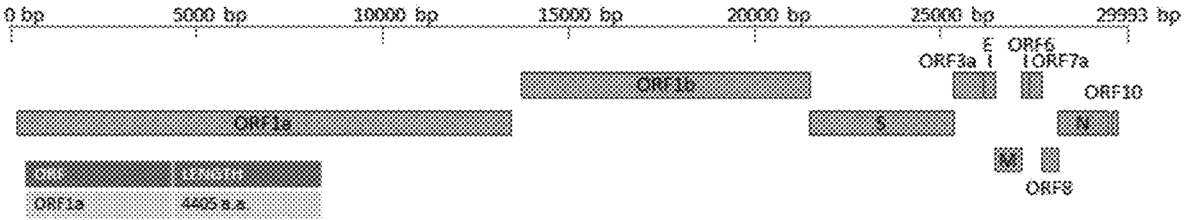
FIG. 12 shows the schematic diagram of the Wuhan-Hu-1 SARS-CoV-2 complete genome (GenBank MN908497; NCBI Reference Sequence: NC_045512.2; SEQ ID NO: 1).

The present disclosure relates to an immunogenic composition (e.g., vaccine) comprising an adenoviral vector encoding at least one 2019 novel coronavirus SARS-CoV-2 antigen(s) ("a SARS-Cov-2 transgene"), compositions comprising the same, and the use thereof for inducing a protective immune response against SARS-CoV-2. Adenovirus is a naturally occurring respiratory virus that has been used frequently as a vector to introduce genetic material into cells, wherein the adenoviral vector can transduce the SARS-CoV-2 antigen genes into cells of the nasal mucosa (via intranasal administration), leading to transient expression of the encoded SARS-CoV-2 antigen proteins or peptides thereof in such cells. Subsequent production of the SARS-CoV-2 antigen in normal human epithelial cells allows for an immune response against the SARS-CoV-2 antigen as it occurs in naturally circulating coronavirus (e.g., SARS-CoV-2). SARS-CoV-2, initially reported as 2019-nCoV is a new and highly pathogenic virus, only emerging in December 2019. In humans, SARS-CoV-2 is responsible for an illness referred to as the coronavirus disease 2019 (COVID-19) as officially defined by the World Health Organization (WHO). The compositions disclosed herein are one of the first to target SARS-CoV-2 and provide protection against COVID-19 and related disease. Accordingly, the immunogenic compositions disclosed herein provide for prevention and treatments for this new and pathogenic SARS-CoV-2 virus, for which prior treatment did not exist and potential for a pandemic remains. In some embodiments, the immunogenic composition prevents and/or reduces severity of COVID-19 as defined by FDA Guidance for Industry "Development and Licensure of Vaccines to Prevent COVID-19" June 2020 and FDA Guidance for Industry "Emergency Use Authorization for Vaccines to Prevent COVID-19" October 2020, each incorporated herein by reference. In some preferred embodiments, the immunogenic composition reduces the incidence of infection or virologically confirmed asymptomatic or symptomatic cases of COVID-19. In some preferred embodiments, the immunogenic composition reduces the incidence of severe and/or non-severe (mild or moderate) COVID-19 or the incidence of COVID-19 related hospital admissions. In some preferred embodiments, the immunogenic composition reduces the incidence of mild or moderate COVID-19.

In some preferred embodiments, the immunogenic composition reduces the incidence of severe COVID-19. In some preferred embodiments, the immunogenic composition reduces the incidence of COVID-19-related Emergency Department visits, COVID-19 hospitalization and/or COVID-19-related death. In some preferred embodiments, the immunogenic composition reduces the severity of COVID-19-related diseases. In some preferred embodiments, the immunogenic composition reduces the transmission of SARS-CoV-2. In some preferred embodiments, the immunogenic composition reduces the transmission of SARS-CoV-2.

In embodiments, this disclosure provides replication defective adenoviral vectors encoding at least one SARS-CoV-2 antigen (e.g., E1A/E3 deletion human Adenovirus type 5 (hAd5) (hAd5-SARS-CoV-2)), and/or another one or more exogenous antigens of a different type of infectious agent (e.g., a different type of virus such as influenza (e.g., Ad-HA)), or lacking a transgene ("hAdE"; e.g., not encoding at least one antigen or immunogen of an exogenous infectious agent "empty"), as well as expression cassettes, e.g., for containing and/or inserting coding sequence(s) into vector(s), comprising a SARS-CoV-2 antigen coding sequence encoding at least one SARS-CoV-2 antigen (and/or another or one or more exogenous antigens of a different type of infectious agent). Such vectors are referred to herein collectively as "SARS-CoV-2 immunization vectors". As discussed herein, such SARS-CoV-2 immunization vectors (and/or immunogenic compositions comprising the same) are preferably used to induce mucosal, cell-mediated and/or humoral immune responses against SARS-CoV-2 (e.g., against protective SARS-CoV-2 epitopes such as spike (S) protein receptor binding domain (RBD)). In some embodiments, such SARS-CoV-2 immunization vectors (and/or immunogenic compositions comprising the same) stimulate an innate immune response supporting the adaptive immunity of the vector if used prophylactically or interfering directly with SARS-CoV-2 infection if administered during the pre-exposure period (few days before infection) or during the post-exposure period. In some embodiments, this disclosure describes the administration of such vectors (e.g., hAd5-SARS-CoV-2 and/or hAd5) to animals and/or human beings to induce and/or enhance an immune response (e.g., the production of antibodies and/or $CD8^+$ T cells (and/or other T cells)) having specificity for SARS-CoV-2 T cell epitope(s) (e.g., a dominant epitopes). In some embodiments, such immune response is protective against SARS-CoV-2 and/or effective in ameliorating the symptoms and/or infection by SARS-CoV-2 and/or reducing transmission of SARS-CoV-2, and in some embodiments can be protective against a SARS-CoV-2 challenge. Thus, in some embodiments, this disclosure describes the use of an immunogenic composition(s) comprising hAd5-SARS-CoV-2 to provide solutions to art-recognized problems regarding SARS-CoV-2 transmission and infection.

In embodiments, the SARS-CoV-2 antigen can be a spike (S) antigen or other SARS-CoV-2 antigen as disclosed herein, or as may be otherwise available to those of ordinary skill in the art. In certain embodiments, the SARS-CoV-2 antigen can be a full length spike (S) protein, an immunogenic fragment thereof, or a consensus spike (S) antigen derived from the sequences of spike antigens from multiple strains of SARS-CoV-2 (or closely related SARS isolates) identified during the 2019/2020 outbreak and initially sequenced and provided in GenBank MN908497; NCBI Reference Sequence: NC_045512.2 "Wuhan seafood market pneumonia virus isolate Wuhan-Hu-1" (incorporated herein by reference); see also Tegally et al., "Sixteen novel lineages of SARS-CoV-2 in South Africa", Nat Med (2021), available via internet at doi.org/10.1038/s41591-021-01255-3 (incorporated herein by reference along with all data and code (including extended data) cited in Tegally, and all references cited in Tegally et al. are also hereby incorporated herein by reference); Conti et al., "The British variant of the new coronavirus-19 (Sars-Cov-2) should not create a vaccine problem", J Biol Regul Homeost Agents", December 30; 35(1) (2020) available via internet at: doi: 10.23812/21-3-E (incorporated herein by reference); Fiorentini et al., "First detection of SARS-Cov-2 spike protein N501 mutation in Italy in August, 2020", Lancet Infect Dis (2021) available online at: doi.org/10.1016/ S1473-3099(21)00007-4 (incorporated herein by reference, along with the references cited in Fiorentini also hereby incorporated herein by reference). In some embodiments, the expression cassette comprising a coding sequence encoding at least one coronavirus antigen comprises at least the 51 and/or S2 domains of spike protein, or immunogenic fragments thereof (e.g., RBD sequence of the 51 domain of the spike protein). See FIGS. 13, 14 and 15. In some embodiments, a pre-fusion stabilized spike protein can be used (e.g., by introducing proline residues in S2 (HR1 domains) as shown improved expression in MERS and SARS (see U.S. Pat. Pub. No. 2020/0061185 A1 (Graham, et al.; see, e.g., FIG. 4 thereof), substituting the wild-type amino acid sequence NSPRRARSVAS (SEQ ID NO: 450) with NSPQQAQSVAS (SEQ ID NO: 451) at the S1/S2 cleavage site (QQAQ mutation), KRSFIEDLLFNKVTLADA (SEQ ID NO: 452) with KRSFIADA (SEQ ID NO: 453) at the S2' cleavage site (fusion peptide truncation, 819-828 deletion), and/or SRLDKVEAEV (SEQ ID NO: 454) with SRLDPPEAEV (SEQ ID NO: 455) (2P mutation, K986P/V987P)). The use of other types of S proteins/antigens is also contemplated herein as would be understood by those of ordinary skill in the art. See Stabilized Spike Protein Antigen Design section below.

In some embodiments, the expression cassette comprising a coding sequence encoding at least one coronavirus antigen comprises the receptor binding domain (RBD) and/or N-terminal domain (NTD) of S1. See, e.g., FIGS. 13, 16-21. In certain embodiments, the expression cassette comprising a coding sequence encoding SEQ ID NO: 3 (FIG. 3A), or at least one domain sequence (e.g., B cell epitope or T cell epitope) of SEQ ID NO: 3, or at least the RBD domain coding sequence encoding SEQ ID NO: 446 (FIG. 3B). In embodiments, the adenoviral vector encoding a SARS-CoV-2 antigen may be monovalent or multivalent (i.e. one, or more than one antigen epitope). In embodiments, the expression cassette comprises a leader sequence (e.g., tPA) for better expression and secretion of the encoded sequence, wherein the coding sequence is optionally codon optimized for the mammalian subject (e.g., human). In embodiments, the expression cassette comprises the RBD sequence (e.g. SEQ ID NO: 446) optionally further comprising long or short flanking sequences native to the SARS-CoV-2 virus (e.g. SEQ ID NOS: 14 and 15), which may enhance expression of the RBD in its native globular conformation. In embodiments, the immunogenic composition comprises one or more recombinant adenovirus, each encoding one or more SARS-CoV-2 antigen(s).

In some embodiments, this disclosure provides compositions and methods for inducing an immune response against coronavirus in a mammalian subject, including human subjects. In certain embodiments provided herein is an immunogenic composition comprising a replication defective adenoviral vector comprising an expression cassette comprising a coding sequence encoding at least one coronavirus antigen or at least one immunogenic fragment thereof. An immunogenic composition as used herein refers to any one or more Ad-vectored compounds or agents or expressed immunogens and/or antigens capable of priming, potentiating, activating, eliciting, stimulating, augmenting, boosting, amplifying, or enhancing an adaptive (specific) immune response, which may be cellular (T cell), humoral (B cell) and/or mucosal, or a combination thereof. The cellular response may be a peripheral T cell response or a resident T cell response in the nasal mucosa or respiratory tract. Also, cellular responses may preferably be driven by CD8+ T cells and/or CD4+ T cells with an antiviral phenotype (e.g. production interferon-gamma). Preferably, the adaptive immune response is protective, which may include neutralization of a virus (decreasing or eliminating virus infectivity) and/or reduction in symptoms or viral shedding (i.e., transmission).

In some embodiments, this disclosure provides immunological compositions comprising an empty (i.e., without an exogenous non-Ad pathogen antigen encoded in the Ad5 genome) adenovirus vector (AdE) as a therapeutic against coronavirus via activation of an innate immune response including a mucosal innate immune response. See Example 2. In some embodiments, a single intranasal administration can provide protection when the AdE is administered about two to about 20 days before exposure to SARS-Cov-2. In some embodiments, administration of the immunogenic composition can induce increased levels of MCP-1 and IFN-γ both post-vaccination and post-challenge, leading to the recruitment of monocytes, neutrophils, and/or lymphocytes, which can then stimulate production of IFN-γ. In some embodiments, administration of such immunogenic compositions can induce significant decreases (e.g., as compared to placebo controls) in IL-1α, IL-6, and/or IL-12p70, cytokines demonstrated to mediate pulmonary interstitial inflammation in COVID-19. See Example 7.

In some embodiments, this disclosure provides reagents (e.g., immunogenic compositions) and methods for intranasal (i.n.) administration of AdE vectors (i.e., replication deficient ΔE1E3 adenovirus type 5 (Ad5)) viral particles without an exogenous non-Ad pathogen antigen encoded in the Ad5 genome) to confer prophylactic therapy against SARS-CoV-2 in mammals, preferably a human being. In preferred embodiments, such AdE immunogenic compositions can be used to induce an anti-SARS-CoV-2 immune response in human beings (e.g., it is an immunogenic composition) and demonstrate an acceptable safety profile. In preferred embodiments, the resultant immune response is statistically significant, and even more preferably, protective (i.e., it is a SARS-CoV-2 vaccine). In preferred embodiments, such AdE immunogenic compositions can be used to treat a human being infected by SARS-CoV-2 (e.g., hospitalized patients). See Example 3.

In some embodiments, this disclosure provides an E1/E3 deleted, replication defective hAd5 comprises an expression cassette comprising a leader sequence (e.g., tissue plasminogen activator (tPA)) and a codon-optimized nucleotide sequence encoding at least one SARS-CoV-2 protein(s) (e.g., any one or more of SEQ ID NOS: 2-11, and/or one or more fragment(s) and/or derivative(s) thereof), operably linked to a promoter (e.g., cytomegalovirus (CMV)), immunogenic compositions and methods for using the same to induce an immune response against SARS-CoV-2. See Example 4. In some embodiments, the SARS-CoV-2 coding sequence are inserted into the E1 region of the hAd5 ("hAd5-SARS-CoV-2"). In some embodiments, the hAd5-SARS-CoV-2 can be based on a replication-deficient, E1- and E3-deleted adenovirus type 5 vector platform (Tang et al 2009) to express the human codon-optimized gene for the S1 domain (residues 16 to 685 (see, e.g., Examples 14, 16)) or RBD domain (residues 331-527 of the S1 domain (see, e.g., Examples 15, 17)) of SARS-CoV-2 spike protein (accession number QHD43416.1 (SEQ ID NO: 3)). In preferred embodiments, such Ad5-vectored S1 and RBD transgenes included a human tissue plasminogen activator leader sequence and can be expressed under the control of the cytomegalovirus immediate early promoter/enhancer (see, e.g., the preferred embodiments of SEQ ID NO: 13 and SEQ ID NO: 15, respectively). In some embodiments, a human being can be intranasally (i.n.) immunized with a sufficient number of hAd5-SARS-CoV-2 viral particles (vp) or infectious units (ifu) (e.g., at least $1\times10^7$, or at least $1\times10^8$, or at least $1\times10^9$, or at least $1\times10^{10}$, or at least $1\times10^{11}$ vp or ifu), such that neutralizing antibodies are induced. In some embodiments, the hAd5-SARS-CoV-2 vaccine can induce a protective response leading to reduce disease severity. In some embodiments, the hAdv5-SARS-CoV-2 composition can be used to induce an anti-SARS-CoV-2 immune response in human beings (i.e., it is an immunogenic composition), and exhibits an acceptable safety profile. It is preferred that that immune response be statistically significant, and even more preferably, a protective immune response (i.e., it is a SARS-CoV-2 vaccine). In some embodiments, such immunogenic compositions can improve the time to clinical improvement and/or recovery in patients (e.g., hospitalized patients) infected with SARS-CoV-2. See Example 5. In some embodiments, a single (or as part of a prime-boost schedule, same or different immunogenic composition) intranasal administration of a replication-deficient Ad5 vector expressing the RBD domain of the Spike protein (see, e.g., preferred embodiment SEQ ID NO: 15) stimulates the production of IgG antibodies in the serum indicating the induction of systemic responses as well as the production of IgG and IgA antibodies in a mammal, preferably a human being. In preferred embodiments, animals that receive a single administration of the high dose vaccine show the presence of neutralizing antibodies (preferably persistent (see, e.g., Example 18) against SARS-CoV-2 as measured by focus reduction neutralization test (FRNT) and/or induces the recruitment and/or proliferation of innate and adaptive immune cells in different immune compartments (see Example 13B). In preferred embodiments, administration of such immunogenic compositions can induce systemic and mucosal T cell immunity (e.g., in preferred embodiments a Th-1-biased response) against SARS-CoV-2 in the mammal, preferably a human being, as can be determined using flow cytometry (see, e.g., Example 17). In preferred embodiments, an immunogenic composition comprising hAd5-SARS-CoV-2, when administered as a single intranasal dose to a mammal can induce an antibody response against the spike protein that is durable for at least 4 months, for at least about 5 months, at least about 6 months, at least about 7 months, at least about 8 months, at least about 9 months, at least about 10 months, at least about 11 months, or at least about 12 months (one year). See Example 18. In some embodiments, administration of the immunogenic compositions (e.g., hAd5-SARS-CoV-2 such as the RBD vector) can induce bone marrow and lung resident memory antibody secreting cells in a mammal, preferably a human being (e.g., in preferred embodiments bone marrow and lung resident memory antibody secreting cells that secrete both anti-spike IgG and IgA). See Example 19. In preferred embodiments, intranasal administration of the replication incompetent Ad5 vector expressing SARS-CoV-2 spike RBD sequence (see, e.g., preferred embodiment SEQ ID NO: 15) can generate humoral and cellular immune responses in both systemic and mucosal sites, particularly within the lung, which represents a major site for infection and clinical disease (see, e.g., Example 20).

In some embodiments, this disclosure provides methods for intranasal (i.n.) administration of a combination of rdAd anti-SARS-CoV-2 vectors (e.g., a "combined SARS-CoV-2 composition") to confer prophylactic therapy against SARS-CoV-2. See Example 10. The components of the combined SARS-CoV-2 composition (e.g., AdE, AdD, and/or hAd5-SARS-CoV-2; "AdD" referring to replication-defective adenoviral vector for use in treating and/or preventing coronavirus infection can be one that does not express one or more coronavirus antigens, but expresses one or more antigens of a different type of infectious agent (e.g., influenza virus); "AdE" referring to an rdAd vector for use in preventing and/or treating coronavirus infection can be one that does not express an exogenous antigen (exogenous as to the adenovirus from the adenoviral vector is derived); and "rdAD" or "rdAd" referring to replication-defective adenoviral) can be contained within a single composition or can be contained in different compositions that can be administered simultaneously or at different times (e.g., as part of a prime-boost protocol) and at the same or different sites on a subject (e.g., a mammal, preferably a human being). Preferred prime boost protocols include the administration of first composition to a mammal, preferably a human being, followed by administration of a second composition an appropriate time later (in some preferred embodiments, seven to 21 days later, preferably 7 days later) (i.e., separate administration of the first and second compositions), wherein the first and second compositions comprise the same or different rdAd anti-SARS-CoV-2 vectors. In preferred embodiments, the combined SARS-CoV-2 compositions are configured to induce neutralizing antibody, IgA and/or cellular immune response(s) and/or other response(s) disclosed herein (e.g., avoiding or shortening the time of hospitalization for Covid-19 a patient) against SARS-CoV-2 in a mammalian subject, preferably a human being, to which said immunogenic composition(s) is/are administered. In preferred embodiments, the combined SARS-CoV-2 composition can be used to induce an anti-SARS-CoV-2 immune response in human beings (e.g., it is an immunogenic composition), and with an acceptable safety profile. It is preferred that that immune response be statistically significant, and even more preferably, a protective immune response (i.e., it is a SARS-CoV-2 vaccine). In preferred embodiments, the data shows the combined SARS-CoV-2 composition can be used to treat subjects infected by SARS-CoV-2 (e.g., hospitalized patients).

In some embodiments, the combined SARS-CoV-2 composition can comprise: a) an rdAd vector lacking a coding sequence encoding an exogenous, non-adenoviral, antigen; b) an rdAd vector comprising an expression cassette comprising a SARS-CoV-2 antigen coding sequence encoding at least one SARS-CoV-2 antigen (i.e., hAd5-SARS-CoV-2), optionally wherein said antigen comprises a SARS-CoV-2 spike (S) protein receptor binding domain (RBD); c) an rdAd vector comprising an expression cassette comprising a coding sequence encoding at least one exogenous antigen of an infectious agent other than SARS-CoV-2; d) a combination of the vectors of a) and b); e) a combination of the vectors of b) and c); f) a combination of any of the rdAd vectors of any of a), b), or c); and/or, g) a combination of two different types of rdAd vectors of b) (i.e., hAd5-SARS-CoV-2), wherein each type comprises an expression cassette encoding at least one SARS-CoV-2 antigen different from that encoded by at least one other type of hAd5-SARS-CoV-2 vector in the combination ("multivalent COVID-19 vaccine"). In some embodiments, the components of the combined SARS-CoV-2 composition can comprise one or both of AdE and/or AdD and/or one or more type of hAd5-SARS-CoV-2. In some embodiments, the combined SARS-CoV-2 composition can comprise a first composition comprising AdE and/or AdD that is administered to a human being, followed by administration of a second composition comprising at least one type of hAd5-SARS-CoV-2. In some embodiments, the combined SARS-CoV-2 composition can comprise at least two types of hAd5-SARS-CoV-2, wherein each type of hAd5-SARS-CoV-2 comprises an expression cassette encoding at least one SARS-CoV-2 antigen different from that encoded by the other type(s) of hAd5-SARS-CoV-2 vectors in the combination. Thus, in some embodiments, the combined SARS-CoV-2 composition can comprise a first type of hAd5-SARS-CoV-2 expressing a first SARS-CoV-2 antigen and a second type of hAd5-SARS-CoV-2 encoding a second SARS-CoV-2 antigen, the second SARS-CoV-2 antigen being different from the first SARS-CoV-2 antigen. In some embodiments, the combined SARS-CoV-2 composition can comprise a first composition comprising AdE, AdD, and/or a first type of hAd5-SARS-CoV-2 that is administered to a human being, which is followed by administration of a second composition comprising at least one second type of hAd5-SARS-CoV-2, different from the first type of hAd5-SARS-CoV-2 (or first where the first composition is AdE or AdD) an appropriate time later (in some preferred embodiments, seven to 21 days later, preferably 7 days later) (i.e., separate administration of the first and second compositions).

In some embodiments, this disclosure provides immunogenic compositions comprising and methods for intranasal (i.n.) administration of AdD vectors (i.e., replication deficient ΔE1E3 adenovirus type 5 (Ad5) viral particles encoding a pathogen antigen derived from an infectious agent other than SARS-CoV-2, e.g., influenza such as NasoVAX which is an AdVector (Ad5) expressing influenza hemagglutinin (HA) antigen, described in, e.g., U.S. application Ser. No. 16/840,723, filed Apr. 6, 2020, claiming priority from U.S. application Ser. No. 62/830,444 filed 6 Apr. 2019, and published as US 2020/0316188, each of which, together with all references cited in each of these applications and publications, is incorporated herein by reference and discloses preparation of NasoVAX; see also U.S. Pat. Nos. 6,706,693; 6,716,823; 6,348,450; and US Patent Publications Nos. 2003/0045492; 2004/0009936; 2005/0271689; 2007/0178115; and 2012/0276138, which may pertain to adenoviral vector(s) prepared for administration to a mammal, which may comprise and express an influenza antigen, each of which, with all references cited in each, being hereby incorporated by reference) to confer prophylactic therapy against SARS-CoV-2 (with it mentioned that while NasoVAX is a particular product, in instances where the term "NasoVAX" is used in this disclosure, the skilled person can read both the particular product and also can broadly read an AdVector (Ad5), advantageously an E1 and/or E3 Ad5 vector, expressing an influenza hemagglutinin (HA) antigen). In such embodiments, the AdD vector can induce an innate immune response, preferably a protective immune response, against both SARS-CoV-2 and the pathogen associated with the expressed exogenous antigen of the AdD vector. For example, NasoVAX (or more broadly an immunogenic composition comprising an AdD vector expressing influenza antigen(s)) can be used to induce an immune response against both influenza and coronavirus including SARS-CoV-2. In this way, AdD is a dual vaccine inducing an innate immune response against two respiratory infectious agents, and a protective adaptive immune response against the expressed antigen. In some embodiments, such immunogenic compositions can be administered to patients already infected by SARS-CoV-2 and can improve time to clinical improvement and/or recovery. In some embodiments, then, the AdD composition can be used to induce an anti-SARS-CoV-2 immune response in human beings (e.g., it is an immunogenic composition) with an acceptable safety profile. It is preferred that that immune response be statistically significant, and even more preferably, a protective immune response (i.e., it is a SARS-CoV-2 vaccine). In preferred embodiments, the data shows the AdD composition can be used to treat subjects infected by SARS-CoV-2 (e.g., hospitalized patients). In some embodiments, NasoVAX can be used as therapy for the early phases of infection or as a concomitant therapy for COVID-19, in some embodiments in combination with direct antiviral agents (e.g., chloroquine, azithromycin). See Example 7. At some juncture, the drug substance could transition into a product in which the vector alone (e.g., sans a transgene as in AdE) is administered. In some embodiments, NasoVAX can be effective in reducing rates of ICU admission and mechanical ventilation in patients with early onset COVID-19, and/or reduce the severity of COVID-19 in patients with early onset COVID-19 who require hospitalization. In some embodiments, a decrease in expression of inflammatory cytokines such as IL-1α, IL-5, IL-6, IL-12, IL-17, MCP-1, tumor necrosis factor alpha (TNF-α), granulocyte macrophage colony stimulating factor (GM-CSF), and/or RANTES (CCL5) (see, e.g., Example 2) following administration of NasoVAX to subjects can occur, and can in some embodiments be used to diagnose COVID-19, and/or predict recovery therefrom and used to adjust treatment protocols (e.g., non-NasoVAX treatments) accordingly. In some embodiments, an increase in MCP1 and/or RANTES shortly after administration of NasoVAX, can be used to predict (e.g., as a marker) recovery from COVID-19 and amelioration of symptoms. It is preferred that that immune response be statistically significant, and even more preferably, a protective immune response (i.e., it is a SARS-CoV-2 vaccine). In preferred embodiments, the data shows that NasoVAX can be used to treat subjects infected by SARS-CoV-2 (e.g., hospitalized patients). In preferred embodiments, such an immunogenic composition can be administered repeatedly (e.g., as a seasonal vaccine administered about once every 11-14 months) without inducing a significant immune response against the adenoviral vector itself. See Example 9.

In some embodiments, this disclosure provides adenoviral vectored vaccine compositions (e.g., AdD, NasoVAX) that is stable for about 3 months at an ambient temperature, such as room temperature (e.g., 15 to 30° C., preferably 20-25° C.). In some embodiments, such adenoviral vectored vaccine compositions can be stored, or shipped, without the need for refrigeration or specific storage conditions. In certain embodiments, such adenoviral vectored vaccine compositions can be configured to induce an immune response against SARS-CoV-2 virus (a pandemic coronavirus strain) infection and/or to ameliorate COVID-19 disease symptoms, and may be shipped directly to the user for administration to patients (preferably intranasal administration). See Example 8.

In some embodiments, as shown in Example 2 herein, administration of AdE to mice decreased the expression of certain cytokines known to be involved in the progression and symptoms of infectious diseases caused by viruses such as influenza. For instance, it was shown that non-infected mice (by influenza), 25 days after administration of AdE, exhibited an increase in expression of monocyte chemoattractant protein (MCP-1 (CCL2)), interferon gamma (IFN-γ), and RANTES (CCL5). At 28 days post-administration of AdE, such non-infected mice exhibited increased expression of MCP-1 and IFN-γ but also a decrease in IL-12 expression. Mice challenged with influenza at day 3 post-administration of AdE, mice were found to exhibit decreased expression of IL-1α, IL-6, IL-12, MCP-1, tumor necrosis factor alpha (TNF-α), granulocyte macrophage colony stimulating factor (GM-CSF), and RANTES. At day six (6) post-administration of AdE, the infected mice exhibited decreased expression of IL-5, IL-6, IL-12, IL-17, MCP-1 and GM-CSF, and increased expression of macrophage inflammatory protein 1 alpha (MIP-1α (CCL3)) and RANTES (CCL5). These results are consistent with the development of a "cytokine storm" during infection by SARS-CoV-2. In some embodiments, then, to prevent and/or treat SARS-CoV-2 infection by, for instance, inhibiting the development of or suppressing a cytokine storm, a SARS-CoV-2 immunogenic composition is administered to a human being with one or more anti-cytokine reagent(s) (e.g., one or more anti-IL-1α reagent(s), one or more anti-IL5 reagent(s), one or more anti-IL-6 reagent(s), one or more anti-IL-12 reagent(s), one or more anti-IL-17 reagent(s), one or more anti-MCP-1 reagent(s), one or more anti-TNF-α reagent(s), one or more anti-GM-CSF reagent(s), and/or one or more anti-RANTES reagent(s). See Example 11. In some embodiments, the one or more anti-cytokine reagents would not include one or more anti-MIPα reagent(s) and/or one or more anti-RANTES reagent(s). Exemplary anti-cytokine reagents that can be used as described herein can include, for example, any of those shown in Table 1 herein. In some embodiments, such anti-cytokine reagents can be administered with the SARS-CoV-2 immunogenic composition at the same time (i.e., simultaneously), or essentially the same time, by a suitable route appropriate for each reagent (e.g., intranasal administration of the SARS-CoV-2 immunogenic composition and subcutaneous injection for the anti-cytokine reagent (s)) in effective amounts. In some embodiments, the one or more anti-cytokine reagent(s) can be co-administered with the SARS-CoV-2 composition and, in some embodiments, the one or more anti-cytokine reagents are subsequently administered as the sole active agents. In preferred embodiments, the combination of SARS-CoV-2 composition(s) and one or more anti-cytokine reagent(s) can be useful for inducing an anti-SARS-CoV-2 immune response in human beings (e.g., it is an immunogenic composition), with an acceptable safety profile, and with alleviation of symptoms related to the deleterious effects of cytokines experienced by some patients (e.g., the aforementioned cytokine storm). In preferred embodiments, the immune response be statistically significant, and even more preferably, that it is a protective and/or curative immune response (i.e., it is a SARS-CoV-2 vaccine). In preferred embodiments, the combination of SARS-CoV-2 composition(s) and one or more anti-cytokine reagent(s) can be used to treat subjects infected by SARS-CoV-2 (e.g., hospitalized patients).

As described herein, the S protein (spike protein) immunogen, fragments, and variants thereof described herein contain one or more epitopes that elicit or induce an immune response, preferably a protective immune response, which may be a humoral response, a mucosal IgA response and/or a cell-mediated immune response. A protective immune response may be manifested by at least one of the following: preventing infection of a host by a coronavirus; modifying or limiting the infection; aiding, improving, enhancing, or stimulating recovery of the host from infection; and generating immunological memory that will prevent or limit a subsequent infection by a coronavirus. A humoral response may include production of antibodies that neutralize infectivity, lyse the virus and/or infected cell, facilitate removal of the virus by host cells (for example, facilitate phagocytosis), and/or bind to and facilitate removal of viral antigenic material. An antibody response may also include a mucosal response, which comprises eliciting or inducing a specific mucosal IgA response. In certain embodiments is provided a method for inducing a combined mucosal, humoral and/or cell-mediated protective immune response in a human subject against SARS-CoV-2 infection.

Provided herein are pharmaceutically acceptable compositions (which may also be referred to as formulations) suitable and/or configured for intranasal administration to a mammalian subject and that are configured to induce an immune response against an antigen (e.g., an immunogen), and optionally induce a protective immune response (i.e., as a vaccine). In some embodiments, the pharmaceutical formulation is an immunogenic composition that upon administration induces an immune response against an antigen in a mammalian subject. In some embodiments, the pharmaceutical formulation is a vaccine or therapeutic composition configured to induce a protective immune response in a mammalian subject, which is protective against foreign infectious agents, and in preferred embodiments induce or stimulate a protective response against SARS-CoV-2 infection.

Definitions

As used herein, the terms "a" or "an" are used, as is common in patent documents, to include one or more than one, independent of any other instances or usages of "at least one" or "one or more."

As used herein, the term "or" is used to refer to a nonexclusive or, such that "A or B" includes "A but not B," "B but not A," and "A and B," unless otherwise indicated.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

The compositions, formulations and methods of the present invention may comprise, consist essentially of, or consist of the components and ingredients of the present invention as well as other ingredients described herein. As used herein, "consisting essentially of" and "consists essentially of" means that the compositions, formulations and methods may include additional steps, components or ingredients, but only if the additional steps, components or ingredients do not materially alter the basic and novel characteristics of the claimed compositions, formulations and methods. Terms such as "comprises", "comprised", "comprising" and the like are synonymous with terms such as "including," "containing," or "characterized by," and are inclusive or open-ended terms that not exclude additional, unrecited elements, components or ingredients or steps. In this regard, it is an object of the invention not to encompass within the invention any previously known product, process of making the product, or method of using the product such that Applicant (s) reserve the right and hereby disclose a disclaimer of any previously known product, process, or method. It is further noted that the invention does not intend to encompass within the scope of the invention any product, process, or making of the product or method of using the product, which does not meet the written description, enablement and/or clarity or definiteness requirements of US Law/the USPTO (e.g. 35 USC § 112(a), (b)) or the sufficiency requirements of EPC/ the EPO (e.g. Article 83 of the EPC), such that Applicant(s) reserve the right and hereby disclose a disclaimer of any subject matter not meeting written description, enablement and/or clarity/definiteness and/or sufficiency requirements and/or that which is a previously described or known product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. All rights to explicitly disclaim that which is in any prior-filed but not prior published patent application or patent is explicitly reserved (with "prior-filed but not prior published" being relative to the filing date accorded this disclosure). Nothing herein is to be construed as a promise. Nor is any citation or identification of any document in this application an admission that such document is available as prior art.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

As used herein, an "adjuvant" refers to a substance that enhances the body's immune response to an antigen. In embodiments, the present monovalent influenza pharmaceutical formulation is a non-adjuvanted vaccine composition.

By "administration" is meant introducing an immunogenic or vaccine composition of the present disclosure into a subject; it may also refer to the act of providing a composition of the present disclosure to a subject (e.g., by prescribing or administering).

As used herein, the term "ambient temperature" is the air temperature for storing the present monovalent influenza pharmaceutical formulation. In embodiments, the ambient temperature is a room temperature, such as selected from any temperature within the range from about 15 to 30° C., preferably from about 20 to 25° C.

The term "therapeutically effective amount" as used herein refers to that amount of the compound being administered which will induce a combined, mucosal, humoral and cell mediated immune response. The term also refers to an amount of the present compositions that will relieve or prevent to some extent one or more of the symptoms of the condition to be treated. In reference to conditions/diseases that can be directly treated with a composition of the disclosure, a therapeutically effective amount refers to that amount which has the effect of preventing the condition/disease from occurring in a mammal that may be predisposed to the disease but does not yet experience or exhibit symptoms of the condition/disease (prophylactic treatment), alleviation of symptoms of the condition/disease, diminishment of extent of the condition/disease, stabilization (e.g., not worsening) of the condition/disease, preventing the spread of condition/di seas e, delaying or slowing of the condition/disease progression, amelioration or palliation of the condition/disease state, and combinations thereof. The term "effective amount" refers to that amount of the compound being administered which will produce a reaction (e.g., a protective immune response and/or as provided by a vaccine) that is distinct from a reaction that would occur in the absence of the compound.

As used herein, the term "percent (%) homology" or "percent (%) identity" and grammatical variations thereof in the context of two sequences (e.g., protein sequences), refers to two or more sequences or subsequences (i.e., fragment thereof) that have at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity (homology), when compared and aligned for maximum correspondence, as measured using one of the well-known sequence comparison algorithms or by visual inspection. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877. Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448. Advantageous for use is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein). In addition, from this definition, when this disclosure speaks about percent (%) homology, the reader can also understand percent (%) identity. In addition, it should be understood that proteins within this invention may differ from the exact sequences illustrated and described in this disclosure. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention. Nucleic acid sequences within the invention, as to such proteins, will similarly vary from this explicitly disclosed herein. The invention thus encompasses nucleotide sequences encoding functionally and/or antigenically equivalent variants and derivatives of the antigens or proteins herein disclosed and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and, phenylalanine/tyrosine/tryptophan.

As used herein, the term "human adenovirus" is intended to encompass all human adenoviruses of the Adenoviridae family, which include members of the Mastadenovirus genera. To date, over fifty-one human serotypes of adenoviruses have been identified (see, e.g., Fields et al., Virology 2, Ch. 67 (3d ed., Lippincott-Raven Publishers)). The adenovirus may be of serogroup A, B, C, D, E, or F. The human adenovirus may be a serotype 1 (Ad 1), serotype 2 (Ad2), serotype 3 (Ad3), serotype 4 (Ad4), serotype 5 (Ad5), serotype 6 (Ad6), serotype 7 (Ad7), serotype 8 (Ad8), serotype 9 (Ad9), serotype 10 (Ad10), serotype 11 (Ad11), serotype 12 (Ad12), serotype 13 (Ad13), serotype 14 (Ad14), serotype 15 (Ad15), serotype 16 (Ad16), serotype 17 (Ad17), serotype 18 (Ad18), serotype 19 (Ad19), serotype 19a (Ad19a), serotype 19p (Ad19p), serotype 20 (Ad20), serotype 21 (Ad21), serotype 22 (Ad22), serotype 23 (Ad23), serotype 24 (Ad24), serotype 25 (Ad25), serotype 26 (Ad26), serotype 27 (Ad27), serotype 28 (Ad28), serotype 29 (Ad29), serotype 30 (Ad30), serotype 31 (Ad31), serotype 32 (Ad32), serotype 33 (Ad33), serotype 34 (Ad34), serotype 35 (Ad35), serotype 36 (Ad36), serotype 37 (Ad37), serotype 38 (Ad38), serotype 39 (Ad39), serotype 40 (Ad40), serotype 41 (Ad41), serotype 42 (Ad42), serotype 43 (Ad43), serotype 44 (Ad44), serotype 45 (Ad45), serotype 46 (Ad46), serotype 47 (Ad47), serotype 48 (Ad48), serotype 49 (Ad49), serotype 50 (Ad50), serotype 51 (Ad51), or combinations thereof, but are not limited to these examples. In certain embodiments, the adenovirus is serotype 5 (Ad5).

As used herein, an "immunogenic composition" refers to a composition, typically comprising at least one type of replication defective adenoviral vector as disclosed herein and at least one pharmaceutically acceptable carrier, that when administered to a host induces and/or enhances an immune response against an antigen and/or infectious agent against which such immune response is directed (e.g., an antigen encoded by a replication defective adenoviral vector, and/or as may be induced/enhanced by an "empty" hAd5 vector). A "vaccine" refers to such an immunogenic composition that when administered induces a protective immune response against an infectious agent (e.g., protects the host against challenge with the infectious agent). In certain embodiments, an immunogenic composition (e.g., vaccine) can comprise one or more viral vector(s) containing and/or expressing an antigen, along with other components of an immunogenic composition (e.g., vaccine) suitable for administration to a mammalian host, including for example one or more adjuvants, slow release compounds, solvents, buffers, etc. In certain embodiments, an immunogenic composition and/or vaccine can comprise a protein and/or carbohydrate and/or lipid and/or other antigen, including but not limited to one or more killed antigen(s) (e.g., a killed or completely inactive virus) or a live attenuated antigen (e.g., an attenuated virus). In some embodiments, the immunogenic composition(s) and/or vaccine(s) improve immune responses to any antigen regardless of the antigen source or its function.

As used herein, a “pharmaceutically acceptable carrier” refers to a carrier or diluent that does not cause significant irritation to the human subject and does not abrogate the biological activity and properties of the administered immunogenic or vaccine compositions.

As used here, the term “seroconversion” is defined as a 4-fold or greater increase in serum neutralization antibody titers (e.g., anti-S1/S2 antibody or anti-RBD of 51 antibody) after vaccination (e.g., administration of a present immunogenic or vaccine composition).

As used herein, the term “seropositive” means a measurable (e.g., detectable in an in vitro assay) in serum neutralization antibody after vaccination (e.g., administration of a present immunogenic composition).

As used herein, the term “protection” indicates that a protective immune response has been elicited, and a protective immune response may be manifested by at least one of the following: preventing infection of a host by a coronavirus; modifying or limiting the infection; aiding, improving, enhancing, or stimulating recovery of the host from infection; and generating immunological memory that will prevent or limit a subsequent infection by a coronavirus. A humoral response may include production of antibodies that neutralize infectivity, lyse the virus and/or infected cell, facilitate removal of the virus by host cells (for example, facilitate phagocytosis), and/or bind to and facilitate removal of viral antigenic material. An antibody response may also include a mucosal response, which comprises eliciting or inducing a specific mucosal IgA response. As used herein, the term “seroprotected” means a subject post vaccination that is protected from infection via generation of serum neutralization antibodies. In a population, this is referred to as a percentage (%) of seroprotected individuals (e.g., 50%). In embodiments, the present immunogenic compositions and methods of use provide seroprotection to the mammalian subject, such as a human subject, against SARS-CoV-2 infection. The duration of protection can be at least about one month to at least about 14 months. Seroprotection can last at least about 1 month, 2 months, 4 months, 6 months, 8 months, 10 months, 12 month or at least about 13 months.

The terms “treat”, “treating”, and “treatment” are an approach for obtaining beneficial or desired clinical results. Specifically, beneficial or desired clinical results include, but are not limited to, alleviation of symptoms, diminishment of extent of disease, stabilization (e.g., not worsening) of disease, delaying or slowing of disease progression, substantially preventing spread of disease, amelioration or palliation of the disease state, and remission (partial or total) whether detectable or undetectable. In addition, “treat”, “treating”, and “treatment” can also mean prolonging survival as compared to expected survival if not receiving treatment and/or can be therapeutic in terms of a partial or complete cure for a disease and/or adverse effect attributable to the disease. As used herein, the terms “prophylactically treat” or “prophylactically treating” refers completely, substantially, or partially preventing a disease/condition or one or more symptoms thereof in a host. Similarly, “delaying the onset of a condition” can also be included in “prophylactically treating” and refers to the act of increasing the time before the actual onset of a condition in a patient that is predisposed to the condition.

In this disclosure, a “vaccine” advantageously refers to a composition comprising a replication defective adenoviral vector containing and expressing a coronavirus antigen or other infectious agent, and/or lacking a coding sequence for an exogenous antigen (e.g., empty Advector), along with other components of a vaccine formulation, including for example adjuvants, slow release compounds, solvents, etc., for inducing a protective immune response. Such compositions within this disclosure that comprise a replication defective adenoviral vector containing and expressing a coronavirus antigen or other infectious agent, and/or lacking a coding sequence for an exogenous antigen (e.g., empty Advector), along with other components of a vaccine formulation, including for example adjuvants, slow release compounds, solvents, etc. can also be for inducing an immune response, and are within “immunogenic compositions” herein-discussed. In embodiments of the invention, vaccines or immunogenic compositions can improve immune responses to any antigen regardless of the antigen source or its function.

As referred to herein, a “vector” carries a genetic code, or a portion thereof, for an antigen, however it is not the antigen itself. In an exemplary aspect, a vector can include a viral vector, such as an adenoviral vector. As referred to herein an “antigen” means a substance that induces and/or enhances a specific immune response against the antigen, and/or an infectious agent expressing such antigen, in a subject, including humans and/or animals. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. In various aspects, the antigen is a virus, bacterium, a subunit of an organism, an auto-antigen, or a cancer antigen.

Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

Immunogenic Compositions and Vaccines

Provided herein are replication-defective adenoviral (“rdAd”) vector and immunogenic compositions comprising the same, (in some embodiments vaccine formulations) suitable and/or configured for administration to a mammalian subject for the prevention and/or treatment of coronavirus infection (“coronavirus pharmaceutical formulations"), preferably wherein the coronavirus is SARS-CoV-2. In some embodiments, any adenoviral vector (Ad-vector) known to one of skill in art, and prepared for administration to a mammal, which may comprise and express a coronavirus antigen, preferably a SARS-CoV-2 antigen, but also may not express an exogenous (i.e., non-Ad) antigen, or may be an empty AdVector (e.g., no exogenous antigen transgene) may be used in the compositions and with the methods of this application. Such Ad-vectors include any of those known to those of ordinary skill in the art including but not limited to those described in U.S. Pat. Nos. 6,706,693; 6,716,823; 6,348,450; and/or US Patent Publication Nos. 2003/0045492; 2004/0009936; 2005/0271689; 2007/0178115; and/or, 2012/0276138; all of which being incorporated herein incorporated by reference in their entireties. In certain embodiments, the non-replicating adenoviral viral vector (rdAd) is a human adenovirus. In alternative embodiments, the adenovirus is a bovine adenovirus, a canine adenovirus, a non-human primate adenovirus (e.g., chimp), a chicken adenovirus, or a porcine or swine adenovirus. In exemplary embodiments, the non-replicating viral vector is a human adenovirus. In some embodiments, the non-replicating adenoviral vectors are particularly useful for gene transfer into eukaryotic cells and immunogenic composition (e.g., vaccine) development, and in animal models.

In certain embodiments the recombinant adenovirus vector may be non-replicating or replication-deficient (RD) requiring complementing E1 activity for replication. In embodiments the recombinant adenovirus vector may include E1-defective, E3-defective, and/or E4-defective adenovirus vectors, or the "gutless" adenovirus vector in which viral genes are deleted. The E1 mutation raises the safety margin of the vector because E1-defective adenovirus mutants are replication incompetent in non-permissive cells. The E3 mutation enhances the immunogenicity of the antigen by disrupting the mechanism whereby adenovirus down-regulates MHC class I molecules. The E4 mutation reduces the immunogenicity of the adenovirus vector by suppressing the late gene expression, thus may allow repeated re-vaccination utilizing the same vector. In exemplary embodiments, the recombinant adenovirus vector is an E1 and E3 defective vector. The "gutless" adenovirus vector replication requires a helper virus and a special human 293 cell line expressing both E1a and Cre, a condition that does not exist in natural environment; the vector is deprived of viral genes, thus the vector as an immunogenic composition (e.g., vaccine) carrier is non-immunogenic and may be inoculated for multiple times for re-vaccination. The "gutless" adenovirus vector also contains 36 kb space for accommodating transgenes, thus allowing co-delivery of a large number of antigen genes into cells. Specific sequence motifs such as the RGD motif may be inserted into the H-I loop of an adenovirus vector to enhance its infectivity. An adenovirus recombinant may be constructed by cloning specific transgenes or fragments of transgenes into any of the adenovirus vectors such as those described below. The adenovirus recombinant vector is used to transduce epidermal cells of a vertebrate in a non-invasive mode for use as an immunizing agent. The adenovirus vector may also be used for invasive administration methods, such as intravenous, intramuscular, or subcutaneous injection.

In some embodiments, such an rdAd vector for use in preventing and/or treating coronavirus infection can be one that does not express an exogenous antigen (exogenous as to the adenovirus from the adenoviral vector is derived), such vectors being referred to herein as "AdE" vectors. In some embodiments, the replication-defective adenoviral vector for use in treating and/or preventing coronavirus infection can be one that does not express one or more coronavirus antigens, but expresses one or more antigens of a different type of infectious agent (e.g., influenza virus) (referred to herein as "AdD"). In certain embodiments is provided an immunogenic composition comprising a rdAd vector comprising an expression cassette comprising a coding sequence encoding at least one SARS-CoV-2 antigen, referred to herein as hAd5-SARS-CoV-2 vectors. In some embodiments, the immunogenic compositions of this disclosure can comprise a different type of such vectors (e.g., AdE, or AdD), alone or in combination with hAd5-SARS-CoV-2 vectors. In some embodiments, these types of vectors can be collectively, or a subset of at least two such vectors, referred to as "rdAd anti-SARS-CoV-2 vectors". A SARS-CoV-2 immunogenic composition (e.g., vaccine) is a pharmaceutical formulation comprising one or more such rdAd anti-SARS-CoV-2 vectors.

An AdE vector is a rdAd vector that does not encode an exogenous antigen (i.e., an antigen exogenous as to the adenovirus from the adenoviral vector is derived, e.g., an antigen of a different type of infectious agent such as influenza). Such hAd5 vectors can also be referred to as "empty", lacking an exogenous transgene, and/or being "transgene-free". In some embodiments, an AdE vector can be a ΔF1E3 Ad5 vector (e.g., lacking the E1 region of the viral genome (nucleotides 343 to 3511) and nucleotides 28132 to 30813 in the E3 region). This disclosure provides some embodiments, comprising immunogenic compositions comprising AdE vectors (including AdE viral particles) and the use of such immunogenic compositions to prevent and/or treat coronavirus infection, preferably wherein the coronavirus is SARS-CoV-2, and methods for doing so. In some embodiments, such AdE vectors can be co-administered with one or more other rdAd anti-SARS-CoV-2 vectors. In some embodiments, such co-administration can refer to administration of a single immunogenic composition comprising AdE vectors and one or more rdAd anti-SARS-CoV-2 vectors, and/or essentially simultaneous and/or sequential administration of multiple immunogenic compositions comprising AdE vectors and another immunogenic composition comprising one or more other rdAd anti-SARS-CoV-2 vectors. Such AdE vectors can also be administered as part of a prime-boost protocol, in which an immunogenic composition comprising AdE is administered before or after (e.g., 7-28 days before and/or after) administration of an immunogenic composition comprising one or more other types of rdAd anti-SARS-CoV-2 vectors. In some embodiments, this disclosure provides methods for inducing (and/or enhancing) an immune response against SARS-CoV-2 in a mammalian subject in need thereof by administering (e.g., intranasally) an effective amount of such composition(s) (e.g., at least about $10^7$ infectious units (ifu) or virus particles (vp) (e.g., at least $1\times10^7$, or at least $1\times10^8$, or at least $1\times10^9$, or at least $1\times10^{10}$, or at least $1\times10^{11}$ vp or ifu of AdE and, where present, at least one other rdAd anti-SARS-CoV-2 vectors). In some embodiments, the immune response against SARS-CoV-2 induced or enhanced by administration of such immunogenic compositions preferably begins within about twenty-four hours of administration and preferably lasts for at least about 21 days. In preferred embodiments, such methods comprise intranasal administration of such immunogenic compositions in an effective amount of (e.g., at least about $10^7$ ifu of the AdE and, where present, at least one other rdAd anti-SARS-CoV-2 vectors). In preferred embodiments, the second rdAd anti-SARS-CoV-2 vector encodes at least one heterologous antigen of SARS-CoV-2 and/or at least one other infectious agent (e.g., AdD), thereby providing a drug-vaccine duo regimen. In some embodiments, the administering of multiple doses of AdE vectors (and/or other rdAd anti-SARS-CoV-2 vectors) can be about any of 7, 10, 14, 21, 28, 35, 42, 49, or 56 days apart. Preferably, such immunogenic compositions can be administered intranasally. In some embodiments, the host is an animal, such as an adult or child human being, optionally wherein the host is immunocompromised. In preferred embodiments, the immune response against the coronavirus lasts for at least about 40-50 days, and can be re-initiated by re-administration of AdE with or without the one or more SARS-CoV-2 vectors. Other embodiments of such AdE vectors, immunogenic compositions, and/or methods are also contemplated herein as would be understood by those of ordinary skill in the art.

An AdD vector is a rdAd vector that encodes an exogenous antigen of an infectious agent other than coronavirus and/or SARS-CoV-2 (e.g., an antigen of a different type of infectious agent such as influenza (e.g., swine influenza, seasonal influenza, avian influenza, H1N1 influenza, or H5N1 influenza). In some embodiments, an AdD vector can be a ΔE1E3 Ad5 vector encoding at least one heterologous (e.g., non-Ad) antigen, preferably optimized for expression in a host (e.g., a mammal). Representative examples of antigens which can be used to produce an immune response against SARS-CoV-2 using the methods described herein can include influenza hemagglutinin, influenza nuclear protein, influenza M2, tetanus toxin C-fragment, anthrax protective antigen, anthrax lethal factor, rabies glycoprotein, HBV surface antigen, HIV gp 120, HIV gp 160, human carcinoembryonic antigen, malaria CSP, malaria SSP, malaria MSP, malaria pfg, and *Mycobacterium tuberculosis* HSP, etc. In one embodiment, an AdD vector can be the AdNC.H1.1 vector encoding the A/New Caledonia/20/99 H1N1 IFV (NC20) HA1 domain (see, e.g., Tang et al. Expert Rev Vaccines 8: 469-481 (2009)). In one embodiment, the AdD vector can contain a genetic insert encoding the hemaglutinnin (HA) surface protein antigen from an A/California/04/2009(H1N1)-like strain of influenza (AdcoCA09.HA "NasoVAX"), preferably manufactured by propagation in replication-permissive PER.C6 cells, followed by purification of the virus from the infected cell harvest, and prepared as a final product including the following excipients: Tris HCl (pH 7.4), histidine, sucrose, sodium chloride, magnesium chloride, polysorbate 80, ethylenediaminetetraacetic acid, and ethanol. This disclosure provides some embodiments, that comprise immunogenic compositions comprising AdD vectors (including AdD viral particles) and the use of such immunogenic compositions to prevent and/or treat coronavirus infection, preferably wherein the coronavirus is SARS-CoV-2, and methods for doing so. In some embodiments, such AdD vectors can be co-administered with one or more other rdAd anti-SARS-CoV-2 vectors. In some embodiments, such co-administration can refer to administration of a single immunogenic composition comprising AdD vectors and one or more rdAd anti-SARS-CoV-2 vectors, and/or essentially simultaneous and/or sequential administration of multiple immunogenic compositions comprising AdD vectors and another immunogenic composition comprising one or more other rdAd anti-SARS-CoV-2 vectors. Such AdD vectors can also be administered as part of a prime-boost protocol, in which an immunogenic composition comprising AdD vectors (e.g., as viral particles) is administered before or after (e.g., 7-21 days before and/or after) administration of an immunogenic composition comprising one or more other types of rdAd anti-SARS-CoV-2 vectors. In some embodiments, this disclosure provides methods for inducing (and/or enhancing) an immune response against SARS-CoV-2 in a mammalian subject in need thereof by administering (e.g., intranasally) an effective amount of such composition(s) (e.g., at least about $10^7$ viral particles (vp) or infectious units (ifu) (e.g., at least $1\times10^7$, or at least $1\times10^8$, or at least $1\times10^9$, or at least $1\times10^{10}$, or at least $1\times10^{11}$ vp or ifu) of each of the AdD vector and, where present, at least one other rdAd anti-SARS-CoV-2 vectors). In some embodiments, the immune response against SARS-CoV-2 induced or enhanced by administration of such immunogenic compositions preferably begins within about twenty-four hours of administration and preferably lasts for at least about 21 days. In preferred embodiments, such methods comprise intranasal administration of such immunogenic compositions in an effective amount of (e.g., at least about $10^7$ vp or ifu (e.g., at least $1\times10^7$, or at least $1\times10^8$, or at least $1\times10^9$, or at least $1\times10^{10}$, or at least $1\times10^{11}$ vp or ifu) of each of the AdD vector and, where present, at least one other rdAd anti-SARS-CoV-2 vectors). In preferred embodiments, the second rdAd anti-SARS-CoV-2 vector is AdE and/or encodes at least one heterologous antigen of SARS-CoV-2 and/or at least one other infectious agent, thereby providing a drug-vaccine duo regimen. In some embodiments, the administering of multiple doses of AdD vectors (and/or other rdAd anti-SARS-CoV-2 vectors) can be about any of 7, 10, 14, 21, 28, 35, 42, 49, or 56 days apart. Preferably, such immunogenic compositions can be administered intranasally. In some embodiments, the host is an animal, such as an adult or child human being, optionally wherein the host is immunocompromised. In preferred embodiments, the immune response against the coronavirus lasts for at least about 40-50 days, and can be re-initiated by re-administration of AdD with or without the one or more SARS-CoV-2 vectors. Other embodiments of such AdD vectors, immunogenic compositions comprising the same, and/or methods for using the same are also contemplated herein as would be understood by those of ordinary skill in the art.

In some embodiments, this disclosure provides an immunogenic composition comprising one or more SARS-CoV-2 vectors comprising a rdAd vector comprising an expression cassette comprising a coding sequence encoding at least one SARS-CoV-spike (S) protein receptor binding domain (RBD), or at least one immunogenic fragment thereof, wherein the composition is configured to induce neutralizing antibody to the spike protein RBD, in a mammalian subject. Putative studies indicate the spike protein via its receptor binding domain of S1 binds to the angiotensin-converting enzyme 2 (ACE2) receptor (Y. Wan et al.; receptor recognition by novel coronavirus from Wuhan: An analysis based on decade-long structural studies of SARS; J. Virol. doi: 10.1128/JVI.00127-20; posted online 29 Jan. 2020). Generating an immune response against at least the RBD of spike protein is an attractive target for inducing neutralization antibodies, wherein spike protein mediates coronavirus entry into host cells by first binding to a host receptor (e.g., ACE2) and then fusing viral and host membranes. The spike protein for SARS-CoV-2 is provided herein as SEQ ID NO: 3 (GenBank: QHD43416.1). See FIG. 3.

In certain embodiments, the immunogenic composition (e.g. vaccine) comprises one or more coronavirus antigens. In certain embodiments, the coronavirus is SARS-CoV-2, wherein the coding sequence for the Wuhan 2019 isolate (SARS-CoV-2) is provided herein as SEQ ID NO: 1. In embodiments, the replication deficient adenoviral vector comprises one or more coding sequences of SEQ ID NO: 1.

Those sequences comprise one or more immunogenic domains such as a B cell and/or T cell epitope. In certain embodiments, the replication deficient adenoviral vector comprises and/or expresses (e.g., comprises an expression cassette encoding) one or more immunogenic domains provided in any of encoded SEQ ID NO: 2 to 20. In preferred embodiments, the replication deficient adenoviral vector comprises and/or expresses (e.g., comprises an expression cassette encoding) SEQ ID NO: 15, or a variant thereof (i.e., in either the RBD sequence (amino acids 57-253 of SEQ ID NO: 15 (comprising SEQ ID NO: 446)), and/or the signal and/or leader and/or flanking sequences). In embodiments, the coding sequence of the replication deficient adenovirus vector encodes at least one or more B cell epitopes, one or more $CD8^+$ T cell epitopes, and/or one or more $CD4^+$ T cell epitopes. One of skill in the art understands how to identify those epitopes within a larger sequence using bioinformatic methodologies such as publicly available tools accessible at the immune epitope database (IEDB), in vitro assay based on PBMCs from infection-positive subjects combined with short linear peptides scanning the antigen sequence or in vitro assay based on serum using short linear or conformational peptides scanning the antigen sequence.

In embodiments, the replication defective adenoviral vector comprises an expression cassette comprising a coding sequence encoding an antigen of SEQ ID NO: 3, SEQ ID NO: 12, SEQ ID NO: 15, the RBD amino acid sequence (amino acids 57-253 of SEQ ID NO: 15 (SEQ ID NO: 446)), or an immunogenic fragment thereof. In embodiments, the replication defective adenoviral vector comprises an expression cassette comprising a coding sequence encoding SARS-CoV-2 spike protein, S1 domain, S2 domain, or an immunogenic fragment thereof. In embodiments, the expression cassette of the immunogenic composition comprises a coding sequence for spike (S) protein (e.g., as in preferred embodiments SEQ ID NO: 3 and SEQ ID NO: 12), 51 domain (e.g., as in preferred embodiment SEQ ID NO: 13) of the spike protein, or an immunogenic fragment thereof (e.g., as in preferred embodiments SEQ ID NOS: 14-17 (FIGS. 17B-21)). In a preferred embodiment, the coding sequence encodes the RBD sequence comprising amino acids 57-253 of SEQ ID NO: 15 (SEQ ID NO: 446). In certain embodiments, those encoded sequences comprise a leader signal sequence, either native or as a recombinant sequence comprising a pTA signal sequence (e.g., preferred embodiment MDAMKRGLCCVLLLCGAVFVSPSGTGS (SEQ ID NO: 427)).

In certain embodiments, the encoded sequence of the immunogenic composition is a sequence, or immunogenic fragment thereof, presented in SEQ ID NO: 3, or a sequence having at least 80% homology to SEQ ID NO: 3. In certain embodiments, the encoded sequence of the immunogenic composition is a sequence with at least about 80%, 81%, 82%, 83%, 84%, 85%, 86%, 87%, 88%, 89%, 90%, 91%, 92%, 93%, 94%, 95%, 96%, 97%, 98%, 99%, homology and/or identity to SEQ ID NO: 3. In certain embodiments, the encoded sequence of the immunogenic composition is a sequence, or immunogenic fragment thereof, presented in SEQ ID NO: 12, or a sequence having at least 80% homology and/or identity to SEQ ID NO: 12. In certain embodiments, the encoded sequence of the immunogenic composition is a sequence with at least about 80%, 81%, 82%, 83%, 84%, 85%, 86%, 87%, 88%, 89%, 90%, 91%, 92%, 93%, 94%, 95%, 96%, 97%, 98%, 99%, homology and/or identity to SEQ ID NO: 12. In certain preferred embodiments, the encoded sequence of the immunogenic composition is a sequence, or immunogenic fragment thereof, presented in SEQ ID NO: 13, or a sequence having at least 80% homology and/or identity to SEQ ID NO: 13. In certain embodiments, the encoded sequence of the immunogenic composition is a sequence with at least about 80%, 81%, 82%, 83%, 84%, 85%, 86%, 87%, 88%, 89%, 90%, 91%, 92%, 93%, 94%, 95%, 96%, 97%, 98%, 99%, homology and/or identity to SEQ ID NO: 13. In certain embodiments, the encoded sequence of the immunogenic composition is a sequence, or immunogenic fragment thereof, presented in SEQ ID NO: 14, or a sequence having at least 80% homology and/or identity to SEQ ID NO: 14. In certain embodiments, the encoded sequence of the immunogenic composition is a sequence with at least about 80%, 81%, 82%, 83%, 84%, 85%, 86%, 87%, 88%, 89%, 90%, 91%, 92%, 93%, 94%, 95%, 96%, 97%, 98%, 99%, homology and/or identity to SEQ ID NO: 14. In certain preferred embodiments, the encoded sequence of the immunogenic composition is a sequence, or immunogenic fragment thereof, presented in SEQ ID NO: 15, or a sequence having at least 80% homology and/or identity to SEQ ID NO: 15. In certain embodiments, the encoded sequence of the immunogenic composition is a sequence with at least about 80%, 81%, 82%, 83%, 84%, 85%, 86%, 87%, 88%, 89%, 90%, 91%, 92%, 93%, 94%, 95%, 96%, 97%, 98%, 99%, homology and/or identity to SEQ ID NO: 15. In certain preferred embodiments, the encoded sequence of the immunogenic composition is a sequence, or immunogenic fragment thereof, presented in SEQ ID NO: 16, or a sequence having at least 80% homology and/or identity to SEQ ID NO: 16. In certain embodiments, the encoded sequence of the immunogenic composition is a sequence with at least about 80%, 81%, 82%, 83%, 84%, 85%, 86%, 87%, 88%, 89%, 90%, 91%, 92%, 93%, 94%, 95%, 96%, 97%, 98%, 99%, homology and/or identity to SEQ ID NO: 16. In certain preferred embodiments, the encoded sequence of the immunogenic composition is a sequence, or immunogenic fragment thereof, presented in SEQ ID NO: 17, or a sequence having at least 80% homology and/or identity to SEQ ID NO: 17. In certain embodiments, the encoded sequence of the immunogenic composition is a sequence with at least about 80%, 81%, 82%, 83%, 84%, 85%, 86%, 87%, 88%, 89%, 90%, 91%, 92%, 93%, 94%, 95%, 96%, 97%, 98%, 99%, homology and/or identity to SEQ ID NO: 17. In certain preferred embodiments, the encoded sequence of the immunogenic composition is a sequence, or immunogenic fragment thereof, presented in SEQ ID NO: 446, or a sequence having at least 80% homology and/or identity to SEQ ID NO: 446. In certain embodiments, the encoded sequence of the immunogenic composition is a sequence with at least about 80%, 81%, 82%, 83%, 84%, 85%, 86%, 87%, 88%, 89%, 90%, 91%, 92%, 93%, 94%, 95%, 96%, 97%, 98%, 99%, homology and/or identity to SEQ ID NO: 446. In certain preferred embodiments, the encoded sequence of the immunogenic composition is a sequence, or immunogenic fragment thereof, presented in any of SEQ ID NOS: 412-417, SEQ ID NOS: 438-445, SEQ ID NO: 460 and SEQ ID NOS: 475-476, or a sequence having at least 80% homology and/or identity to SEQ ID NOS: 412-417, SEQ ID NOS: 438-445, SEQ ID NO: 460 and SEQ ID NOS: 475-476. In certain embodiments, the encoded sequence of the immunogenic composition is a sequence with at least about 80%, 81%, 82%, 83%, 84%, 85%, 86%, 87%, 88%, 89%, 90%, 91%, 92%, 93%, 94%, 95%, 96%, 97%, 98%, 99%, homology and/or identity to any of SEQ ID NOS: 412-420.

In certain other embodiments, the expression cassette of the immunogenic composition comprises a coding sequence for the S1 domain of the spike protein (e.g. SEQ ID NO: 13), or an immunogenic fragment thereof. In certain embodiments, the coding sequence encodes at least amino acid resides 331 to 527 of SEQ ID NO: 3, SEQ ID NO: 12, or SEQ ID NO: 13, wherein the amino acid position numbering is based on the full-length spike protein sequence. In certain embodiments, the encoded sequence of the immunogenic composition is a sequence with at least about 80%, 81%, 82%, 83%, 84%, 85%, 86%, 87%, 88%, 89%, 90%, 91%, 92%, 93%, 94%, 95%, 96%, 97%, 98%, 99%, homology and/or identity to: amino acid resides 331 to 527 of SEQ ID NO: 3; SEQ ID NO: 12; or SEQ ID NO: 13; wherein the amino acid position numbering is based on the full length spike protein sequence (FIG. 3).

In certain embodiments, the expression cassette of the immunogenic composition comprises a coding sequence for the S1 domain of the spike protein (e.g., SEQ ID NO: 13, FIG. 17A), or a fragment (preferably immunogenic fragment) thereof (e.g., SEQ ID NO: 14 or 15), wherein the sequence comprises one or more of the following residues: L455, F486, Q493, S494 and/or N501 (amino acid position numbering based on full-length spike protein). See., e.g., FIGS. 3, 15, and 17B-21. In embodiments, the encoded sequence comprises Q493 and N501. In certain embodiments, the encoded sequence comprises Q493. Those particular amino acid residues of SARS-CoV-2 at positions 455, 486, 493, 494 and/or 501 are believed to directly interact with their receptor. Independently those amino acid residues may be modified via conservative substitutions based on physico-chemical properties of the amino acids of SARS-CoV-2 at positions 455, 486, 493, 494 and 501 of the spike protein. In this way alternative sequences may be generated that would potentially capture escapees (e.g., viral mutations that evade acquired neutralizing antibodies but still bind to a host receptor) wherein the immunogenic compositions would induce neutralizing antibodies based on those alternative sequence(s). In embodiments, the expression cassette of the immunogenic composition comprises a coding sequence for the S1 domain of the spike protein, RBD of S1 domain, or an immunogenic fragment thereof, wherein the sequence comprises SEQ ID NO: 16 wherein 455 (L) is selected from Y, F, L or S; 486 (F) is selected from L, F, S or P; 493 (Q) is selected from L, N, Q, R or K; 494 (S) is selected from D, G, P, L or S; and, 501 (N) is selected from T, S, N or Y. In embodiments, the expression cassette of the immunogenic composition comprises a coding sequence for the S1 domain of the spike protein, RBD of S1, or an immunogenic fragment thereof, wherein the sequence comprises SEQ ID NO: 17 wherein 455 (L) is selected from Y, F, L or S; 486 (F) is selected from L, F, S or P; 493 (Q) is selected from L, N, Q, R or K; 494 (S) is selected from D, G, P, L or S; and, 501 (N) is selected from T, S, N, or Y.

In some embodiments, the expression cassette of the immunogenic composition comprises a coding sequence for modifications of a subsection of the spike protein sequence of SEQ ID NO. 13, the amino acid sequence of that subsection being shown in FIG. 17B ("Sequence") and below:

(SEQ ID NO: 411)

TLKSFTVEKGIYQTSNFRVQPTESIVRFPNITNLCPFGEVFNATRFASVY

AWNRKRISNCVADYSVLYNSASFSTFKCYGVSPTKLNDLCFTNVYADSFV

IRGDEVRQIAPGQTGKIADYNYKLPDDFTGCVIAWNSNNLDSKVGGNYNY

LYRLFRKSNLKPFERDISTEIYQAGSTPCNGVEGFNCYFPLQSYGFQPTN

GVGYQPYRVVVLSFELLHAPATVCGPKKSTNLVKNKCVNFNF

In some embodiments, the coding sequence can encode at least one substitution of any of the amino acids of SEQ ID NO: 411. In some embodiments, the coding sequence can encode at least one substitution ("Mutations") to SEQ ID NO: 411. Preferably, the one or more substitutions to SEQ ID NO: 411 is one of those shown in FIG. 17B. In some embodiments, the one or more substitutions can be to any one or more of amino acids 333-388, 390-395, 397-399, 401-411, 413-415, 417-419, 424, 426-435, 437, 439-442, 444-446, 449, 450, 452, 453, 455-463, 465, 467-473, 475-479, 481-486, 490, 491, 493-495, 499-510, or 513-526, the numbering corresponding to that shown in FIG. 17B. In preferred embodiments, the substitution can be at one or more of the amino acids that serve as main contact residues with the human ACE2 receptor, preferably amino acids 417, 446, 447, 449, 453, 455, 456, 473, 475-477, 484, 486, 487, 493, 495-498, 500-503, and/or 505 (the numbering corresponding to that shown in FIG. 17B). In some embodiments, the substitution to SEQ ID NO: 411 is at least one of: the substitution of amino acid 417 (K) by N; the substitution of amino acid 446 (G) is V, S or A; the substitution of amino acid 449 (Y) is N; the substitution at amino acid 453 (Y) by F; the substitution of amino acid 455 (L) by F; the substitution of amino acid 456 (F) by L; the substitution of amino acid 473 (Y) by V; the substitution of amino acid 475 (A) by V; the substitution of amino acid 476 (G) by S or A; the substitution of amino acid 477 (S) by N, R, T, G, A or I; the substitution at amino acid 484 (E) is Q, K, D, A or R; the substitution of amino acid 486 (F) by L or S; the substitution of amino acid 453 (Y) by F; the substitution of amino acid 493 (Q) by L or R; the substitution of amino acid 495 (Y) by N or F; the substitution of amino acid 500 (T) by I; the substitution of amino acid 501 (N) by Y, T or S; the substitution of amino acid 502 (G) by R, D or C; the substitution of amino acid 503 (V) by L, I or F; and/or, the substitution of amino acid 505 (Y) by H, E, W or C; the numbering corresponding to that shown in FIG. 17B.

In embodiments, the encoded spike protein RBD sequence comprises a residue selected from Y455, F455 or S455. In other embodiments, the encoded spike protein RBD sequence comprises a residue selected from L486 or P486. In certain embodiments, the encoded spike protein RBD sequence comprises a residue selected from N493, R493 or K493. In embodiments, the encoded spike protein RBD sequence comprises a residue selected from D494 or G494. In embodiments, the encoded spike protein RBD sequence comprises a residue selected from T501 or S501.

Stabilized Spike Protein Antigen Design

The development of a viral vector immunogenic composition or vaccine against Covid-19 (e.g. SARS-CoV-2) faces some key challenges related to: (1) the ability of the viral vector to express the protein with a quaternary structure representative of the native pre-fusion protein expressed by the coronavirus and compatible with the induction of neutralizing antibodies against the SARS-CoV-2 virus; and, (2) the ability to propagate the viral vector during its manufacture in a cell-based expression system with limited interference that may be associated with the concomitant expression of the transgenic spike protein.

In embodiments, designing a viral vector expressing a stabilized spike antigen in a pre-fusion trimeric conformation expressed on the surface of infected cells may be desirable for the development of a Covid-19 immunogenic composition or vaccine to address both the antigenicity and manufacturing of the vaccine. In other embodiments, immunogenic fragments thereof (spike protein), such as the S1 or receptor binding domain (RBD), may be desirable for the development of a Covid-19 immunogenic composition or vaccine, which also address both the antigenicity and manufacturing of the immunogenic composition or vaccine. Those challenges are due, in part, to the “fusogenic” properties of the SARS-Cov-2 spike protein, which as used herein refers to the fusion properties of the spike protein to gain entry in a host cell (e.g., as a coat protein on the surface of viral particles) using ACE2 as the entry receptor or when expressed on the host cell to fuse with neighbor cells to form larger syncytia or syncytium (multi-nucleated host cells) as a mean to propagate very rapidly by using this cell-cell fusion independently of the entry receptor. Priming of coronavirus S proteins by host cell proteases is essential for viral entry into cells expressing ACE2 and encompasses S protein cleavage at the S1/S2 and the S2' sites. The S1/S2 cleavage site of SARS-CoV-2 S harbors several arginine residues (multibasic), which indicates high cleavability (Hoffmann et al. SARS-CoV-2 Cell Entry Depends on ACE2 and TMPRSS2 and Is Blocked by a Clinically Proven Protease Inhibitor; Cell; 2020 Apr. 16; 181(2): 271-280.e8). Successful conformational changes of S proteins, leading to membrane fusion, not only require receptor binding, but also appropriate protease activation. There is a furin site between S1 and S2 (amino acids 682-685, RRAR) subunits in SARS-CoV-2 S protein, similar to those found in highly pathogenic influenza viruses. That furin site (RRAR) is not present in other coronavirus S proteins (e.g., See FIG. 1C of Walls et al. Structure, Function, and Antigenicity of the SARS-CoV-2 Spike Glycoprotein; Cell; 2020 Mar. 9, incorporated herein by reference), and may contribute to instability, possibly confounding viral-vectored vaccine development. Therefore, in certain embodiments, those amino acid residues in the SARS-Cov-2 spike protein may be removed and/or modified to ameliorate or remove the furin enzymatic cleave site between S1 and S2 domain present in SARS-Cov-2 spike protein.

Hence, one approach to stabilize the spike protein is to render the protein more resistant to proteolytic degradation (1) during expression of the protein in the cell-based manufacturing such as in E1 complementing cell lines during production of the (adenovirus) viral vector and/or (2) during expression of the protein in a mammal following administration of the viral vector. Proteolytic cleavage sites can be modified by amino-acid substitutions, insertion or deletions in order to prevent or reduce enzymatic degradation. Proteolytic cleavage sites of interest for this type of approach are preferably found in solvent-accessible regions of the protein that form the solvent-facing surface of the three-dimensional structure of the protein trimer complex. These solvent-accessible sites include the S1/S2 junction QTQTNSPRRARSVASQ (SEQ ID NO: 25) and S2' junction PDPSKPSKRSF (SEQ ID NO: 26). Other solvent accessible areas can be identified by known methods that calculate the relative solvent accessible score area (SASA). Potential enzymes involved in proteolytic cleavage of spike protein include Furin, Trypsin, Elastase, Plasmin, TMPRSS2, Chymotrypsin, Cathepsin-L, Cathepsin-B, TMPRSS11D, Dipeptidyl Peptidase IV, MMP-13, MMP-12, MMP-2, MMP-9, MMP-3, Caspase-3, Caspase-8, Caspase-9. Protease cleavage sites can be predicted using known algorithms such as Proper, Properous, PeptideCutter, Pripper, CasCleave, CasCleave 2.0, CASVM and iProt-Sub.

Cleavage of the S1/S2 junction QTQTNSPRRARSVASQ (SEQ ID NO: 25) from SARS-CoV-2 and/or corresponding sequences in other coronaviruses, has been demonstrated to be primarily dependent upon arginine residues such as arginine at positions 685, 682 and/or 683 from SEQ ID NO: 3 and SEQ ID NO: 12. To interfere with proteolytic cleavage, hydrophilic, non-positively charged amino-acids or small amino-acids such as N, Q, D, E, T, S, G or A can be considered for substitution of arginine residues. In addition, the S1/S2 junction can be rendered resistant to proteolytic cleavage by deletion or insertion of amino acids, provided that those sequence modifications do not alter the three-dimensional conformation of the spike antigen so to preserve its antigenicity and ability to stimulate the production of neutralizing antibodies. A similar approach can also be applied to the S2' junction PDPSKPSKRSF (SEQ ID NO: 26) for the Lysine residue at position 814 and Arginine residue at position 815 in sequence SEQ ID NO: 3 and SEQ ID NO: 12. In embodiments, the expression cassette of the immunogenic composition comprises a coding sequence of SEQ ID NO: 18 (a preferred embodiment); SEQ ID NO: 19 (a preferred embodiment); or SEQ ID NO: 20. See FIGS. 22 to 24. Thus, in certain preferred embodiments, the encoded sequence of the immunogenic composition is a sequence, or immunogenic fragment thereof, presented in SEQ ID NO: 18 or SEQ ID NO: 19, or a sequence having at least 80% homology and/or identity to SEQ ID NO: 18 or SEQ ID NO: 19. In certain embodiments, the encoded sequence of the immunogenic composition is a sequence with at least about 80%, 81%, 82%, 83%, 84%, 85%, 86%, 87%, 88%, 89%, 90%, 91%, 92%, 93%, 94%, 95%, 96%, 97%, 98%, 99%, homology and/or identity to SEQ ID NO: 18 or SEQ ID NO: 19.

In other embodiments, another approach for stabilizing the spike protein includes maintaining the metastable spike protein in its prefusion conformation. Modifications of the sequence to stabilize coronavirus spike protein in a prefusion conformation have been previously disclosed in Pallesen et al. 2017 (Immunogenicity and structures of a rationally designed prefusion MERS-CoV spike antigen. Proc Natl Acad Sci USA. 2017 Aug. 29; 114(35):E7348-E7357) and Wrapp et al. 2020 (Cryo-EM structure of the 2019-nCoV spike in the prefusion conformation. Science. 2020 Mar. 13; 367(6483): 1260-1263), showing that proline substitutions in the loop between the first heptad repeat (HR1) and the central helix (CH) restrict premature triggering of the fusion protein and often increase expression yields of prefusion ectodomains. See FIGS. 22 to 24 and SEQ ID NOS: 18, 19 and 20.

In embodiments, other approaches consist of facilitating the expression of the protein at the surface of infected cells. The spike protein may be retained in endoplasmic reticulum and/or the pre-golgi/golgi, a phenomenon associated with the nature of the transmembrane and/or intracellular domain. Preventing intracellular retention can be achieved by modifying the intracellular domain (IC) by substitution of cysteine in cysteine-rich domains or through the modification of the C-terminal endoplasmic reticulum retention motif (VKLHYT (SEQ ID NO: 409)). See FIG. 24 and SEQ ID NO: 20.

In certain embodiments, limiting the toxicity of the transgenic spike protein during manufacturing of the viral vector can be achieved by modifying the fusion peptide contained within the spike antigen sequence. Modification by deletion, insertion of amino-acids and/or substitution of amino-acids can be introduced in the spike sequence to disrupt the alpha-helix conformation of the fusion peptide. Disruption of the alpha helix conformation of the fusion peptide can be achieve by the substitution of specific amino acids by proline residues.

Accordingly, in embodiments the design of a viral vector immunogenic composition or vaccine against Covid-19 expressing a stabilized full-length trimeric spike antigen may comprise one or more of the modifications described above. Example of those modifications are presented in Table 1 (S1/S2, S2' and fusion domains) and Table 2 (HR1/CH and IC domains) (FIGS. 22-24, SEQ ID NOS: 18-20).

TABLE 1

Exemplary modifications for increase the stability or surface expression of full-length spike

| Region | S1/S2 | S2' | Fusion |
|---|---|---|---|
| Sequence from SEQ ID NO: 3 or SEQ ID NO: 12 | QTQTNSPRRARSVASQ (SEQ ID NO: 25) | PSKPSKRSF (SEQ ID NO: 26) | SFIEDLLFNKVTLADAGFI (SEQ ID NO: 447) |
| Modifications | .......XX.X..... | ......X.. | .....P............. |
| | .......QQ.Q..... | ......Q.. | ...............P... |
| | .......SG.G..... | ......N.. | .....P.........P... |
| | .......-----.... | .....NA.. | ....---------...... |
| | | .....--.. | |

"." = conserved amino-acid;
X = N, Q, D, E, T, S, G or A; and,
"-" = deletion.

TABLE 2

Exemplary modifications to increase the stability or surface expression of full-length spike protein

| Region | HR1/CH | IC |
|---|---|---|
| Sequence from SEQ ID NO: 3 or SEQ ID NO: 12 | SRLDKVEAEV (SEQ ID NO: 448) | CCMTSCCSCLKGCCSCGSCCKFDEDDSEPVLKGVKLHYT (SEQ ID NO: 449) |
| Modifications | ....PP.... | ................................------ |
| | | .....................----------------- |
| | | ...........--------------------------- |
| | | .................................Z.#.. |
| | | ...........Z.......................... |
| | | ............Z......................... |
| | | ..............Z....................... |
| | | .................Z.................... |
| | | ..................Z................... |

"." = conserved amino-acid;
Z = N, Q, D, E, T, S, G or A; and,
"-" = deletion

In embodiments, the present immunogenic composition is a multivalent composition. In certain embodiments, the expression cassette of the replication defective adenoviral vector further comprises a coding sequence encoding one or more of SARS-CoV-2 structural proteins envelope (E), membrane (M) or nucleocapsid (N). Each of those structural proteins is presented herein as SEQ ID NO: 5; SEQ ID NO: 6 and SEQ ID NO: 10, respectively. See also FIGS. 5, 6 and 10. In alternative embodiments, those structural proteins may be encoded from a separate replication defective adenoviral vector and provided as a multivalent formulation with a replication defective adenoviral vector comprising an expression cassette comprising a coding sequence encoding at least SARS-CoV-2 (2019 novel coronavirus; 2019-nCoV) spike (S) protein receptor binding domain (RBD), or at least one immunogenic fragment thereof Neutralizing the Post-Fusion Spike Antigen As discussed above, unlike other beta-coronaviruses of subgroup B, the S protein of SARS-CoV-2 harbors a unique S1/S2 furin-recognizable site, indicating that its S protein may possess unique infectious properties. Indeed, in active SARS-CoV-2 infection, syncytium phenomenon were shown to be naturally formed by infected cells, which is rarely reported in SARS-CoV infection, demonstrating a high capacity to mediate membrane fusion (Xu Z. et al. Pathological findings of COVID-19 associated with acute respiratory distress syndrome. Lancet Respir Med. 2020 April; 8(4):420-422.). These cytopathic syncytia are presumably responsible for, at least in part, the pathology observed in COVID-19 patients. Also, the formation of syncytia helps the virus to propagate very rapidly by using this cell-cell fusion mechanism independently of the receptor (receptor independent spread). Therefore, induction of neutralizing antibody against the S antigen in its post-fusion form represents a means for limiting the formation of syncytia and/or preventing the rapid spread of the virus in an entry receptor-independent manner. The post-fusion spike antigen is achieved after cleavage of spike protein by proteases. Cleavage induces a tridimensional rearrangement of the S2 domain as presented in Wall et al. 2017 (Walls, et al. Tectonic conformational changes of a coronavirus spike glycoprotein promote membrane fusion. Proc Natl Acad Sci USA. 2017; 114(42):11157-11162.).

In some embodiments, SARS-CoV-2 immunization vector can also or alternatively comprise a polynucleotide causing expression in a cell of spike antigen without the S1 domain such as the S2 domain of spike (approximately from amino-acid residue 686 of SEQ ID NO: 3) or the S2' domain of spike (approximately from amino-acid residue 816 of SEQ ID NO: 3) or a sequence starting beyond residue 816 of SEQ ID NO: 3 and at minimum comprising the HR1, HR2 and a transmembrane domain. In some preferred embodiments, these SARS-CoV-2 immunization vectors induce an immune response that neutralizes the post-fusion spike protein (e.g. antibodies against the S2 domain) and provide protection by preventing the formation of syncytia and/or by preventing the propagation of the virus in an entry-receptor independent manner. In some embodiments, the expression cassette of the immunogenic composition comprises a coding sequence for the S2 portion of the spike (S) protein (e.g., SEQ ID NO: 21, SEQ ID NO: 22, SEQ ID NO: 23). In some embodiments, the expression cassette of the immunogenic composition comprises a coding sequence for the S2 portion of the spike (S) protein containing an additional transmembrane domain to replace the fusion peptide (e.g., SEQ ID NO: 24). The polypeptides of SEQ ID NOS: 21, 22, 23, and 24 are shown below:

(SEQ ID NO: 21; SARS-CoV-2 spike protein - S2 domain ; with pTA signal)

MDAMKRGLCCVLLLCGAVFVSPSGTGSSVASQSIIAYTMSLGAENSVAYS
NNSIAIPTNFTISVTTEILPVSMTKTSVDCTMYICGDSTECSNLLLQYGS
FCTQLNRALTGIAVEQDKNTQEVFAQVKQIYKTPPIKDFGGFNFSQILPD
PSKPSKRSFIEDLLFNKVTLADAGFIKQYGDCLGDIAARDLICAQKFNGL
TVLPPLLTDEMIAQYTSALLAGTITSGWTFGAGAALQIPFAMQMAYRFNG
IGVTQNVLYENQKLIANQFNSAIGKIQDSLSSTASALGKLQDVVNQNAQA
LNTLVKQLSSNFGAISSVLNDILSRLDKVEAEVQIDRLITGRLQSLQTYV
TQQLIRAAEIRASANLAATKMSECVLGQSKRVDFCGKGYHLMSFPQSAPH
GVVFLHVTYVPAQEKNFTTAPAICHDGKAHFPREGVFVSNGTHWFVTQRN
FYEPQITTTDNTFVSGNCDVVIGIVNNTVYDPLQPELDSFKEELDKYFKN
HTSPDVDLGDISGINASVVNIQKEIDRLNEVAKNLNESLIDLQELGKYEQ
YIKWPWYIWLGFIAGLIAIVMVTIMLCCMTSCCSCLKGCCSCGSCCKFDE
DDSEPVLKGVKLHYT;

(SEQ ID NO: 22; SARS-CoV-2 spike protein - S2' domain ; with pTA signal)

MDAMKRGLCCVLLLCGAVFVSPSGTGSSFIEDLLFNKVTLADAGFIKQYG
DCLGDIAARDLICAQKFNGLTVLPPLLTDEMIAQYTSALLAGTITSGWTF
GAGAALQIPFAMQMAYRFNGIGVTQNVLYENQKLIANQFNSAIGKIQDSL
SSTASALGKLQDVVNQNAQALNTLVKQLSSNFGAISSVLNDILSRLDKVE
AEVQIDRLITGRLQSLQTYVTQQLIRAAEIRASANLAATKMSECVLGQSK
RVDFCGKGYHLMSFPQSAPHGVVFLHVTYVPAQEKNFTTAPAICHDGKAH
FPREGVFVSNGTHWFVTQRNFYEPQIITTDNTFVSGNCDVVIGIVNNTVY
DPLQPELDSFKEELDKYFKNHTSPDVDLGDISGINASVVNIQKEIDRLNE

-continued

VAKNLNESLIDLQELGKYEQYIKWPWYIWLGFIAGLIAIVMVTIMLCCMT
SCCSCLKGCCSCGSCCKFDEDDSEPVLKGVKLHYT;

(SEQ ID NO: 23; SARS-CoV-2 spike protein - HR1 + HR2 domain; with pTA signal)

MDAMKRGLCCVLLLCGAVFVSPSGTGSGIGVTQNVLYENQKLIANQFNSA
IGKIQDSLSSTASALGKLQDVVNQNAQALNTLVKQLSSNFGAISSVLNDI
LSRLDKVEAEVQIDRLITGRLQSLQTYVTQQLIRAAEIRASANLAATKMS
ECVLGQSKRVDFCGKGYHLMSFPQSAPHGVVFLHVTYVPAQEKNFTTAPA
ICHDGKAHFPREGVFVSNGTHWFVTQRNFYEPQIITTDNTFVSGNCDVVI
GIVNNTVYDPLQPELDSFKEELDKYFKNHTSPDVDLGDISGINASVVNIQ
KEIDRLNEVAKNLNESLIDLQELGKYEQYIKWPWYIWLGFIAGLIAIVMV
TIMLCCMTSCCSCLKGCCSCGSCCKFDEDDSEPVLKGVKLHYT;
and, (SEQ ID NO: 24; SARS-CoV-2 spike protein - S2' domain + additional transmembrane domain)

GPPLSSSLGLALLLLLLALLFWLYIVMGLTVLPPLLTDEMIAQYTSALLA
GTITSGWTFGAGAALQIPFAMQMAYRFNGIGVTQNVLYENQKLIANQFNS
AIGKIQDSLSSTASALGKLQDVVNQNAQALNTLVKQLSSNFGAISSVLND
ILSRLDKVEAEVQIDRLITGRLQSLQTYVTQQLIRAAEIRASANLAATKM
SECVLGQSKRVDFCGKGYHLMSFPQSAPHGVVFLHVTYVPAQEKNFTTAP
AICHDGKAHFPREGVFVSNGTHWFVTQRNFYEPQIITTDNTFVSGNCDVV
IGIVNNTVYDPLQPELDSFKEELDKYFKNHTSPDVDLGDISGINASVVNI
QKEIDRLNEVAKNLNESLIDLQELGKYEQYIKWPWYIWLGFIAGLIAIVM
VTIMLCCMTSCCSCLKGCCSCGSCCKFDEDDSEPVLKGVKLHYT.

T Cell Epitope Peptides

In embodiments, the SARS-CoV-2 immunization vectors comprise one or more peptide-encoding sequences from 8 to 60 amino acids in length (and concatenated if more than one), wherein each peptide comprise at least one CD8+ T cell epitope and/or at least one CD4+ T cell epitope. In this case, the concatenated peptide-encoding polynucleotide express a polypeptide where T cell epitopes or T-cell epitope-containing sequences are separated by a spacer sequence containing amino-acids such as glycine, serine or alanine residues. The polynucleotide may further comprise polynucleotide sequences coding for ubiquitin or a signal peptide. In some embodiments, the SARS-CoV-2 immunization vectors comprise one or more polynucleotides encoding one or more S protein antigens. (Ahmed, et al. Preliminary Identification of Potential Vaccine Targets for the COVID-19 Coronavirus (SARS-CoV-2) Based on SARS-CoV Immunological Studies. Viruses, 12: 254 (2020)). The one or more S protein peptide antigens can comprise any T cell epitope, for instance, any of the peptides shown in Table 3A:

TABLE 3A

| SEQ ID NO: | Peptide |
|---|---|
| 27/78 | ILLNKHID |
| 28 | AFFGMSRIGMEVTPSGTW |
| 29/80 | MEVTPSGTWL |

TABLE 3A-continued

| SEQ ID NO: | Peptide |
|---|---|
| 30/83 | GMSRIGMEV |
| 31/87 | ILLNKHIDA |
| 32/88 | ALNTPKDHI |
| 33 | IRQGTDYKHWPQIAQFA |
| 34 | KHWPQIAQFAPSASAFF |
| 35/91 | LALLLLDRL |
| 36/92 | LLLDRLNQL |
| 37 | LLNKHIDAYKTFPPTEPK |
| 38/95 | LQLPQGTTL |
| 39 | AQFAPSASAFFGMSR |
| 40 | AQFAPSASAFFGMSRIGM |
| 41 | RRPQGLPNNTASWFT |
| 42 | YKTFPPTEPKKDKKKK |
| 43/152 | GAALQIPFAMQMAYRF |
| 44/153 | MAYRFNGIGVTQNVLY |
| 45/154 | QLIRAAEIRASANLAATK |
| 46/271 | FIAGLIAIV |
| 47/105 | ALNTLVKQL |
| 48/112 | LITGRLQSL |
| 49/124 | NLNESLIDL |
| 50/313 | QALNTLVKQLSSNFGAI |
| 51/133 | RLNEVAKNL |
| 52/143 | VLNDILSRL |
| 53/146 | VVFLHVTYV |
| 54/63 | SEETGTLIV |
| 55 | FLWLLWPVT |
| 56 | FLWLLWPVTL |
| 57 | FLWLLWPVTLACFVL |
| 58 | IKDLPKEITVATSRT |
| 59 | LEQWNLVIGF |
| 60 | LFARTRSMW |
| 61 | LWLLWPVTL |
| 62 | LWPVTLACF |
| 63/54 | SEETGTLIV |
| 64 | MWSFNPETNI |
| 65 | NLVIGFLFL |
| 66 | PKEITVATSRTLSYY |
| 67 | ATSRTLSYY |

TABLE 3A-continued

| SEQ ID NO: | Peptide |
|---|---|
| 68 | ATSRTLSYYK |
| 69 | QWNLVIGFLF |
| 70 | RYRIGNYKL |
| 71 | SELVIGAVI |
| 72 | SFNPETNIL |
| 73 | SMWSFNPET |
| 74 | TSRTLSYYK |
| 75 | TVATSRTLSY |
| 76 | WLLWPVTLA |
| 77 | WPVTLACFVL |
| 78/27 | ILLNKHID |
| 79 | FPRGQGVPI |
| 80/29 | MEVTPSGTWL |
| 81 | GMEVTPSGTWL |
| 82 | LLLLDRLNQ |
| 83/30 | GMSRIGMEV |
| 84 | GTTLPKGFY |
| 85 | ALALLLLDR |
| 86 | IDAYKTFPPTEPKKD |
| 87/31 | ILLNKHIDA |
| 88/32 | ALNTPKDHI |
| 89 | KTFPPTEPK |
| 90 | KTFPPTEPKK |
| 91/35 | LALLLLDRL |
| 92/36 | LLLDRLNQL |
| 93 | LLLLDRLNQL |
| 94 | APSASAFFGM |
| 95/38 | LQLPQGTTL |
| 96 | AQFAPSASA |
| 97 | LSPRWYFYY |
| 98 | MSRIGMEVTPSGTWL |
| 99 | ASAFFGMSR |
| 100 | NKHIDAYKTFPPTEP |
| 101 | ATEGALNTPK |
| 102 | QLPQGTTLPK |
| 103 | QQQGQTVTK |
| 104 | QQQQGQTVTK |
| 105/47 | ALNTLVKQL |
| 106 | ISGINASVVNIQKEI |

TABLE 3A-continued

| SEQ ID NO: | Peptide |
|---|---|
| 107 | LDKYFKNHTSPDVDL |
| 108 | APHGVVFLHV |
| 109 | LGDISGINASVVNIQ |
| 110 | LGFIAGLIAIVMVTI |
| 111 | LIDLQELGKY |
| 112/48 | LITGRLQSL |
| 113 | LLLQYGSFC |
| 114 | LLQYGSFCT |
| 115 | LNTLVKQLSSNFGAI |
| 116 | LQDVVNQNAQALNTL |
| 117 | LQIPFAMQM |
| 118 | LQSLQTYVTQQLIRA |
| 119 | LQTYVTQQLIRAAEI |
| 120 | AQALNTLVK |
| 121 | AQKFNGLTVLPPLLT |
| 122 | MTSCCSCLK |
| 123 | ASANLAATK |
| 124/49 | NLNESLIDL |
| 125 | PCSFGGVSVITPGTN |
| 126 | PYRVVVLSF |
| 127 | QELGKYEQYI |
| 128 | QIPFAMQMAYRFNGI |
| 129 | QPYRVVVLSF |
| 130 | QQLIRAAEIRASANL |
| 131 | QTYVTQQLIRAAEIR |
| 132 | RLDKVEAEV |
| 133/51 | RLNEVAKNL |
| 134 | RLQSLQTYV |
| 135 | RVDFCGKGY |
| 136 | AYRFNGIGVTQNVLY |
| 137 | SLIDLQELGK |
| 138 | SSNFGAISSVLNDIL |
| 139 | SVLNDILSR |
| 140 | TGRLQSLQTYVTQQL |
| 141 | TQNVLYENQK |
| 142 | CMTSCCSCLK |
| 143/52 | VLNDILSRL |
| 144 | VQIDRLITGR |

TABLE 3A-continued

| SEQ ID NO: | Peptide |
|---|---|
| 145 | VRFPNITNL |
| 146/53 | VVFLHVTYV |
| 147 | WLGFIAGLIAIVMVT |
| 148 | CVNFNFNGLTGTGVL |
| 149 | YEQYIKWPWY |
| 150 | DKYFKNHTSPDVDLG |
| 151 | AEIRASANLA |
| 152/43 | GAALQIPFAMQMAYRF |
| 153/44 | MAYRFNGIGVTQNVLY |
| 154/45 | QLIRAAEIRASANLAATK |
| 155 | SASAFFGMSR |
| 156 | SPRWYFYYL |
| 157 | SQASSRSSSR |
| 158 | TPSGTWLTY |
| 159 | TTLPKGFYA |
| 160 | VLQLPQGTTL |
| 161 | VLQLPQGTTLPKGFY |
| 162 | VTPSGTWLTY |
| 163 | AEGSRGGSQA |
| 164 | FLCLFLLPSL |
| 165 | FLGRYMSAL |
| 166 | FLLNKEMYL |
| 167 | FLLPSLATV |
| 168 | FLNGSCGSV |
| 169 | FLNRFTTTL |
| 170 | FLPRVFSAV |
| 171 | FRYMNSQGL |
| 172 | FTYASALWEI |
| 173 | AIILASFSA |
| 174 | GVYDYLVST |
| 175 | ILASFSAST |
| 176 | ILGTVSWNL |
| 177 | IQPGQTFSV |
| 178 | ALRANSAVK |
| 179 | ALWEIQQVV |
| 180 | KLWAQCVQL |
| 181 | LLSAGIFGA |
| 182 | MPASWVMRI |
| 183 | NVLAWLYAA |

TABLE 3A-continued

| SEQ ID NO: | Peptide |
|---|---|
| 184 | QLMCQPILL |
| 185 | QLMCQPILLL |
| 186 | AVLQSGFRK |
| 187 | SLLSVLLSM |
| 188 | TLGVYDYLV |
| 189 | TVLSFCAFA |
| 190 | VLAWLYAAV |
| 191 | VLSFCAFAV |
| 192 | YIFFASFYY |
| 193 | FPPTSFGPL |
| 194 | FVDGVPFVV |
| 195 | AIMTRCLAV |
| 196 | GVAMPNLYK |
| 197 | ALLADKFPV |
| 198 | ILGLPTQTV |
| 199 | ILHCANFNV |
| 200 | IPRRNVATL |
| 201 | ISDYDYYRY |
| 202 | IVDTVSALV |
| 203 | KLFAAETLK |
| 204 | KLNVGDYFV |
| 205 | KLSYGIATV |
| 206 | KMQRMLLEK |
| 207 | KQFDTYNLW |
| 208 | LLDDFVEII |
| 209 | LLLDDFVEI |
| 210 | LLMPILTLT |
| 211 | LMIERFVSL |
| 212 | LQLGFSTGV |
| 213 | LVLSVNPYV |
| 214 | MLWCKDGHV |
| 215 | MMISAGFSL |
| 216 | MVMCGGSLYV |
| 217 | NLWNTFTRL |
| 218 | NMLRIMASL |
| 219 | ATVVIGTSK |
| 220 | RILGAGCFV |
| 221 | RLYYDSMSY |
| 222 | RQLLFVVEV |
| 223 | SSNVANYQK |
| 224 | TLIGDCATV |
| 225 | TLVPQEHYV |
| 226 | TMADLVYAL |
| 227 | TTLPVNVAF |
| 228 | VLQAVGACV |
| 229 | VLWAHGFEL |
| 230 | VMCGGSLYV |
| 231 | VVDKYFDCY |
| 232 | VVYRGTTTY |
| 233 | YLDAYNMMI |
| 234 | YLNTLTLAV |
| 235 | YQKVGMQKY |
| 236 | YTMADLVYA |
| 237 | YVFCTVNAL |
| 238 | HLVDFQVTI |
| 239 | HPLADNKFAL |
| 240 | KLFIRQEEV |
| 241 | QECVRGTTVLLKEPC |
| 242 | CELYHYQECV |
| 243 | SVSPKLFIR |
| 244 | YEGNSPFHPL |
| 245 | AFLLFLVLI |
| 246 | AFLLFLVLIMLIIFW |
| 247 | FLAFLLFLV |
| 248 | FLAFLLFLVL |
| 249 | FLAFLLFLVLIMLII |
| 250 | FLLFLVLIM |
| 251 | FLLFLVLIML |
| 252 | FLLFLVLIMLIIFWF |
| 253 | FLVLIMLII |
| 254 | FLVLIMLIIFWFSLE |
| 255 | FYLCFLAFL |
| 256 | FYLCFLAFLL |
| 257 | IDFYLCFLAF |
| 258 | IMLIIFWFSL |
| 259 | LAFLLFLVLIMLIIF |
| 260 | LFLVLIMLIIFWFSL |

TABLE 3A-continued

| SEQ ID NO: | Peptide |
|---|---|
| 261 | LIDFYLCFL |
| 262 | LLFLVLIML |
| 263 | LLFLVLIMLI |
| 264 | LLFLVLIMLIIFWFS |
| 265 | MLIIFWFSL |
| 266 | YLCFLAFLL |
| 267 | YLCFLAFLLFLVLIM |
| 268 | DSFKEELDKY |
| 269 | AEVQIDRLI |
| 270 | AEVQIDRLIT |
| 271/46 | FIAGLIAIV |
| 272 | FPNITNLCPF |
| 273 | GAALQIPFAMQMAYR |

TABLE 3A-continued

| SEQ ID NO: | Peptide |
|---|---|
| 274 | GLIAIVMVTI |
| 275 | GRLQSLQTY |
| 276 | GSFCTQLNR |
| 277 | GVVFLHVTY |
| 278 | GWTFGAGAALQIPFA |
| 279 | GYQPYRVVVL |
| 280 | IDRLITGRLQSLQTY |
| 281 | IGAGICASY |
| 282 | IITTDNTFV |

In some preferred embodiments, the vectors can encode multiple epitopes, separately or as part of a single polypeptide (e.g., concatenated, optionally separated by a linker amino acid sequence of two to ten amino acids). In some embodiments, the vectors can encode multiple epitopes as in the exemplary groups shown in Table 3B:

TABLE 3B

| Group | Peptides |
|---|---|
| 1 | FIAGLIAIV (SEQ ID NO: 46), GLIAIVMVTI (SEQ ID NO: 274), IITTDNTFV (SEQ ID NO: 282), ALNTLVKQL (SEQ ID NO: 105), LITGRLQSL (SEQ ID NO: 48), LLLQYGSFC (SEQ ID NO: 113), LQYGSFCT (SEQ ID NO: 465), NLNESLIDL (SEQ ID NO: 49), RLDKVEAEV (SEQ ID NO: 132), RLNEVAKNL (SEQ ID NO: 51), RLQSLQTYV (SEQ ID NO: 134), VLNDILSRL (SEQ ID NO: 52), VVFLHVTYV (SEQ ID NO: 53), ILLNKHID (SEQ ID NO: 27), FPRGQGVPI (SEQ ID NO: 79), LLLLDRLNQ (SEQ ID NO: 82), GMSRIGMEV (SEQ ID NO: 30), ILLNKHIDA (SEQ ID NO: 31), ALNTPKDHI (SEQ ID NO: 32), LALLLLDRL (SEQ ID NO: 35), LLLDRLNQL (SEQ ID NO: 36), LLLLDRLNQL (SEQ ID NO: 93), LQLPQGTTL (SEQ ID NO: 38), AQFAPSASA (SEQ ID NO: 96), TTLPKGFYA (SEQ ID NO: 159), VLQLPQGTTL (SEQ ID NO: 160), VRFPNITNL (SEQ ID NO: 145) and YEQYIKWPWY (SEQ ID NO: 149) |
| 2 | GYQPYRVVVL (SEQ ID NO: 279), PYRVVVLSF (SEQ ID NO: 126) and, LSPRWYFYY (SEQ ID NO: 97) |
| 3 | DSFKEELDKY (SEQ ID NO: 268), LIDLQELGKY (SEQ ID NO: 111), PYRVVVLSF (SEQ ID NO: 126), GTTLPKGFY (SEQ ID NO: 84) and VTPSGTWLTY (SEQ ID NO: 162) |
| 4 | GSFCTQLNR (SEQ ID NO: 276), GVVFLHVTY (SEQ ID NO: 277), AQALNTLVK (SEQ ID NO: 120), MTSCCSCLK (SEQ ID NO: 122), ASANLAATK (SEQ ID NO: 123), SLIDLQELGK (SEQ ID NO: 137), SVLNDILSR (SEQ ID NO: 139), TQNVLYENQK (SEQ ID NO: 141), CMTSCCSCLK (SEQ ID NO: 142), VQIDRLITGR (SEQ ID NO: 144), KTFPPTEPK (SEQ ID NO: 89), and KTFPPTEPKK (SEQ ID NO: 90) |
| 5 | LSPRWYFYY (SEQ ID NO: 97), ASAFFGMSR (SEQ ID NO: 99), ATEGALNTPK (SEQ ID NO: 101), QLPQGTTLPK (SEQ ID NO: 102), QQQGQTVTK (SEQ ID NO: 103), QQQQGQTVTK (SEQ ID NO: 104), SASAFFGMSR (SEQ ID NO: 155), SQASSRSSSR (SEQ ID NO: 157) and TPSGTWLTY (SEQ ID NO: 158) |
| 6 | GSFCTQLNR (SEQ ID NO: 276), GVVFLHVTY (SEQ ID NO: 277), AQALNTLVK (SEQ ID NO: 120), MTSCCSCLK (SEQ ID NO: 122), ASANLAATK (SEQ ID NO: 123), SLIDLQELGK (SEQ ID NO: 137), SVLNDILSR (SEQ ID NO: 139), TQNVLYENQK (SEQ ID NO: 141), CMTSCCSCLK (SEQ ID NO: 142), VQIDRLITGR (SEQ ID NO: 144), KTFPPTEPK (SEQ ID NO: 89), KTFPPTEPKK (SEQ ID NO: 90), LSPRWYFYY (SEQ ID NO: 97), ASAFFGMSR (SEQ ID NO: 99), ATEGALNTPK (SEQ ID NO: 101), QLPQGTTLPK (SEQ ID NO: 102), QQQGQTVTK (SEQ ID NO: 103), QQQQGQTVTK (SEQ ID NO: 104), |

TABLE 3B-continued

| Group | Peptides |
|---|---|
| | SASAFFGMSR (SEQ ID NO: 155), SQASSRSSSR (SEQ ID NO: 157) and TPSGTWLTY (SEQ ID NO: 158) |
| 7 | GYQPYRVVVL (SEQ ID NO: 279), PYRVVVLSF (SEQ ID NO: 126) and LSPRWYFYY (SEQ ID NO: 97) |
| 8 | GSFCTQLNR (SEQ ID NO: 276), GVVFLHVTY (SEQ ID NO: 277), AQALNTLVK (SEQ ID NO: 120), MTSCCSCLK (SEQ ID NO: 122), ASANLAATK (SEQ ID NO: 123), SLIDLQELGK (SEQ ID NO: 137), SVLNDILSR (SEQ ID NO: 139), TQNVLYENQK (SEQ ID NO: 141), CMTSCCSCLK (SEQ ID NO: 142), VQIDRLITGR (SEQ ID NO: 144), KTFPPTEPK (SEQ ID NO: 89), KTFPPTEPKK (SEQ ID NO: 90), LSPRWYFYY (SEQ ID NO: 97), ASAFFGMSR (SEQ ID NO: 99), ATEGALNTPK (SEQ ID NO: 101), QLPQGTTLPK (SEQ ID NO: 102), QQQGQTVTK (SEQ ID NO: 103), QQQQGQTVTK (SEQ ID NO: 104), SASAFFGMSR (SEQ ID NO: 155), SQASSRSSSR (SEQ ID NO: 157) and TPSGTWLTY (SEQ ID NO: 158) |
| 9 | FPNITNLCPF (SEQ ID NO: 272), APHGVVFLHV (SEQ ID NO: 108), FPRGQGVPI (SEQ ID NO: 79) and APSASAFFGM (SEQ ID NO: 94) |
| 10 | GAALQIPFAMQMAYR (SEQ ID NO: 273), GWTFGAGAALQIPFA (SEQ ID NO: 278), IDRLITGRLQSLQTY (SEQ ID NO: 280), ISGINASVVNIQKEI (SEQ ID NO: 106), LDKYFKNHTSPDVDL (SEQ ID NO: 107), LGDISGINASVVNIQ (SEQ ID NO: 109), LGFIAGLIAIVMVTI (SEQ ID NO: 110), LNTLVKQLSSNFGAI (SEQ ID NO: 115), LQDVVNQNAQALNTL (SEQ ID NO: 116), LQSLQTYVTQQLIRA (SEQ ID NO: 118), LQTYVTQQLIRAAEI (SEQ ID NO: 119), AQKFNGLTVLPPLLT (SEQ ID NO: 121), PCSFGGVSVITPGTN (SEQ ID NO: 125), QIPFAMQMAYRFNGI (SEQ ID NO: 128), QQLIRAAEIRASANL (SEQ ID NO: 130), QTYVTQQLIRAAEIR (SEQ ID NO: 131), AYRFNGIGVTQNVLY (SEQ ID NO: 136), SSNFGAISSVLNDIL (SEQ ID NO: 138), TGRLQSLQTYVTQQL (SEQ ID NO: 140), WLGFIAGLIAIVMVT (SEQ ID NO: 147), CVNFNFNGLTGTGVL (SEQ ID NO: 148), DKYFKNHTSPDVDLG (SEQ ID NO: 150), IDAYKTFPPTEPKKD (SEQ ID NO: 86), MSRIGMEVTPSGTWL (SEQ ID NO: 98), NKHIDAYKTFPPTEP (SEQ ID NO: 100) and VLQLPQGTTLPKGFY (SEQ ID NO: 161) |
| 11 | FPNITNLCPF (SEQ ID NO: 272), APHGVVFLHV (SEQ ID NO: 108), FPRGQGVPI (SEQ ID NO: 79) and APSASAFFGM (SEQ ID NO: 94) |
| 12 | LQIPFAMQM (SEQ ID NO: 117) and RVDFCGKGY (SEQ ID NO: 135) |
| 13 | GRLQSLQTY (SEQ ID NO: 275), RVDFCGKGY (SEQ ID NO: 135) and VRFPNITNL (SEQ ID NO: 145) |
| 14 | MTSCCSCLK (SEQ ID NO: 122), SLIDLQELGK (SEQ ID NO: 137), CMTSCCSCLK (SEQ ID NO: 142), VQIDRLITGR (SEQ ID NO: 144), SASAFFGMSR (SEQ ID NO: 155), and SQASSRSSSR (SEQ ID NO: 157) |
| 15 | LQIPFAMQM (SEQ ID NO: 117) and RVDFCGKGY (SEQ ID NO: 135) |

Other combinations of epitopes are also contemplated herein as would be understood by those of ordinary skill in the art.

In some embodiments, the vector(s) can encode one or more of the following epitopes that can be B cell epitopes: DVVNQNAQALNTLVKQL (SEQ ID NO: 283), FFGMSRIGMEVTPSGTW (SEQ ID NO: 284), EAEVQIDRLITGRLQSL (SEQ ID NO: 285), GLPNNTASWFTALTQHGK (SEQ ID NO: 286), EIDRLNEVAKNLNESLIDLQELGKYEQY (SEQ ID NO: 287), GTTLPK (SEQ ID NO: 288), EVAKNLNESLIDLQELG (SEQ ID NO: 289), IRQGTDYKHWPQIAQFA (SEQ ID NO: 290), GAALQIPFAMQMAYRFN (SEQ ID NO: 291), KHIDAYKTFPPTEPKKDKKK (SEQ ID NO: 292), GAGICASY (SEQ ID NO: 293), KHWPQIAQFAPSASAFF (SEQ ID NO: 294), AISSVLNDILSRLDKVE (SEQ ID NO: 295), YNVTQAFGRRGPEQTQGNF (SEQ ID NO: 296), GSFCTQLN (SEQ ID NO: 297), KTFPPTEPKKDKKKK (SEQ ID NO: 298), ILSRLDKVEAEVQIDRL (SEQ ID NO: 299), LLPAAD (SEQ ID NO: 300), KGIYQTSN (SEQ ID NO: 301), LNKHIDAYKTFPPTEPK (SEQ ID NO: 302), AMQMAYRF (SEQ ID NO: 303), LPQGTTLPKG (SEQ ID NO: 304), KNHTSPDVDLGDISGIN (SEQ ID NO: 305), LPQRQKKQ (SEQ ID NO: 306), MAYRFNGIGVTQNVLYE (SEQ ID NO: 307), PKGFYAEGSRGGSQASSR (SEQ ID NO: 308), AATKMSECVLGQSKRVD (SEQ ID NO: 309), QFAPSASAFFGMSRIGM (SEQ ID NO: 310), PFAMQMAYRFNGIGVTQ (SEQ ID NO: 311), QGTDYKHW (SEQ ID NO: 312), QALNTLVKQLSSNFGAI (SEQ ID NOS: 313, 50), QLPQGTTLPKGFYAE (SEQ ID NO: 314), QLIRAAEIRASANLAAT (SEQ ID NO: 315), QLPQGTTLPKGFYAEGSR (SEQ ID NO: 316), QQFGRD (SEQ ID NO: 317), QLPQGTTLPKGFYAEGSRGGSQ (SEQ ID NO: 318), RASANLAATKMSECVLG (SEQ ID NO: 319), TFPPTEPK (SEQ ID NO: 320), RLIT- GRLQSLQTYVTQQ (SEQ ID NO: 321), RRPQGLPNN-TASWFT (SEQ ID NO: 322), EIDRLNEVAKNLNESL-IDLQELGKYEQY (SEQ ID NO: 323), SQASSRSS (SEQ ID NO: 324), SLQTYVTQQLIRAAEIR (SEQ ID NO: 325), SRGGSQASSRSSSRSR (SEQ ID NO: 326), and DLGDIS-GINASVVNIQK (SEQ ID NO: 327); and/or combinations of the same. In some preferred embodiments, the vectors can encode multiple of such epitopes, separately or as part of a single polypeptide (e.g., in some embodiments concatenated, optionally separated by a linker amino acid sequence of two to ten amino acids).

In some embodiments, SARS-CoV-2 peptide sequences encoded by the SARS-CoV-2 immunization vectors can be selected based on the ability to stimulate $CD4^+$ and $CD8^+$ T cell responses, and can in some embodiments be selected based on the prediction of proteome regions containing the highest number of HLA class I and HLA class II binding motifs across a range of selected HLA alleles. In some embodiments, analysis of HLA class II binding motifs across the SARS-CoV-2 sequences can be performed using NetMHCpan EL 4.0 available at IEDB (http://tools.iedb.org/mhci/; Jurtz, et al. NetMHCpan-4.0: Improved Peptide-MHC Class I Interaction Predictions Integrating Eluted Ligand and Peptide Binding Affinity Data. J Immunol. 2017; 199(9):3360-3368). In some embodiments, the NetMHCpan EL 4.0 can be used to identify binding motifs having a length varying from 9 to 11 amino acids to HLA class I molecules and assigned a percentage rank (% Rank). In some embodiments, high affinity binding peptides can be identified as those exhibiting a %-Rank≤0.1 while moderate affinity binding peptides can be considered to have a %-rank comprised between >0.1 and ≤0.5. In preferred embodiments, the NetMHCpan EL 4.0 prediction can be performed with a set of 18 HLA-A alleles, 32 HLA-B alleles and 20 HLA-C alleles shown here: HLA-A*01:01, HLA-A*02:01, HLA-A*02:06, HLA-A*03:01, HLA-A*11:01, HLA-A*23:0, HLA-A*24:02, HLA-A*25:01, HLA-A*26:01, HLA-A*29:02, HLA-A*30:01, HLA-A*30:02, HLA-A*31:01, HLA-A*32:01, HLA-A*33:03, HLA-A*68:01, HLA-A*68:02, HLA-A*74:01, HLA-B*07:02, HLA-B*08:01, HLA-B*13:01, HLA-B*13:02, HLA-B*14:02, HLA-B*15:01, HLA-B*15:02, HLA-B*15:25, HLA-B*18:01, HLA-B*27:02, HLA-B*27:05, HLA-B*35:01, HLA-B*35:03, HLA-B*37:01, HLA-B*38:01, HLA-B*39:01, HLA-B*40:01, HLA-B*40:02, HLA-B*44:02, HLA-B*44:03, HLA-B*46:01, HLA-B*48:01, HLA-B*49:01, HLA-B*50:01, HLA-B*51:01, HLA-B*52:01, HLA-B*53:01, HLA-B*55:01, HLA-B*56:01, HLA-B*57:01, HLA-B*58:01, HLA-B*58:02, HLA-C*01:02, HLA-C*02:02, HLA-C*02:09, HLA-C*03:02, HLA-C*03:03, HLA-C*03:04, HLA-C*04:01, HLA-C*05:01, HLA-C*06:02, HLA-C*07:01, HLA-C*07:02, HLA-C*07:04, HLA-C*08:01, HLA-C*08:02, HLA-C*12:02, HLA-C*12:03, HLA-C*14:02, HLA-C*15:02, HLA-C*16:01 and HLA-C*17:01. Other HLA class I alleles may also be suitable as would be understood by those of ordinary skill in the art.

In some embodiments, HLA class II binding motifs within the SARS-CoV-2 polypeptide sequences can be performed using NetMHCII 2.3 (http://www.cbs.dtu.dk/services/NetMHCII/; Jensen et al. Improved methods for predicting peptide binding affinity to MHC class II molecules. Immunology. 2018 July; 154(3):394-406.) which is based on ensembles of artificial neural networks trained on quantitative peptide binding affinity data from the Immune Epitope Database (IEDB). In some embodiments, NetMHCII 2.3 can be used to identify peptides that can presented by HLA class II molecules by determining, e.g., the percentage rank (%-Rank) (related to the affinity of the peptides for the HLA molecules) and the core nine amino acid binding motif. In some embodiments, high affinity HLA class II binding peptides can be identified as those exhibiting a %-Rank≤2 while moderate affinity binding peptides can be considered to have a %-Rank>2 and 10. In preferred embodiments, the NetMHCII 2.3 system can be based on a set of 20 HLA-DR alleles, 20 HLA-DQ alleles and 9 HLA-DP alleles shown here: DRα1*0101-DRβ1*0101, DRα1*0101-DRβ1*0301, DRα1*0101-DRβ1*0401, DRα1*0101-DRβ1*0701, DRα1*0101-DRβ1*0801, DRα1*0101-DRβ1*0802, DRα1*0101-DRβ1*0901, DRα1*0101-DRβ1*1001, DRα1*0101-DRβ1*1101, DRα1*0101-DRβ1*1201, DRα1*0101-DRβ1*1301, DRα1*0101-DRβ1*1302, DRα1*0101-DRβ1*150, DRα1*0101-DRβ1*1602, DRα1*0101-DRβ3*0101, DRα1*0101-DRβ3*0202, DRα1*0101-DRβ3*0301, DRα1*0101-DRβ4*0101, DRα1*0101-DRβ4*0103, DRα1*0101-DRβ5*0101, DPα1*0103-DPβ1*0301, DPα1*0103-DPβ1*0401, DPα1*0103-DPβ1*0402, DPα1*0103-DPβ1*0601, DPα1*0201-DPβ1*0101, DPα1*0201-DPβ1*0501, DPα1*0201-DPβ1*1401, DPα1*0301-DPβ1*0402, DPα1*0103-DPβ1*0201, DQα1*0101-DQβ1*0501, DQα1*0102-DQβ1*0501, DQα1*0102-DQβ1*0502, DQα1*0102-DQβ1*0602, DQα1*0103-DQβ1*0603, DQα1*0104-DQβ1*0503, DQα1*0201-DQβ1*0202, DQα1*0201-DQβ1*0301, DQα1*0201-DQβ1*0303, DQα1*0201-DQβ1*0402, DQα1*0301-DQβ1*0301, DQα1*0301-DQβ1*0302, DQα1*0303-DQβ1*0402, DQα1*0401-DQβ1*0402, DQα1*0501-DQβ1*0201, DQα1*0501-DQβ1*0301, DQα1*0501-DQβ1*0302, DQα1*0501-DQβ1*0303, DQα1*0501-DQβ1*0402 and DQα1*0601-DQβ1*0402. Other HLA class II alleles may also be suitable as would be understood by those of ordinary skill in the art.

The number of HLA class I binding motifs across the selected 70 HLA class I alleles and the number of HLA class II binding motifs across the selected 49 HLA class II alleles having a high or high plus (+) moderate affinity were respectively calculated for each 41 amino-acid long window scanning the SARS-CoV-2 sequences and presented in FIGS. 27-70. For this analysis, predicted transmembrane domains were deselected due to their high hydrophobicity. Based on this analysis, forty-two (42) long peptide sequences with a length varying from 34 to 124 amino-acids as presented in Table 4 were selected based on the highest content in HLA class I and/or HLA class II motifs across the SARS-CoV-2 proteome (SEQ ID NO. 410).

TABLE 4

Selected SARS-CoV-2 long peptide sequences containing high density HLA class I and/or HLA class II binding motifs (SEQ ID NO: 328 to 369)

| SEQ ID No. | Length | N-terminal position in SEQ ID NO: 410 | C-terminal position in SEQ ID NO: 410 | Sequence |
|---|---|---|---|---|
| 328 | 66 | 2580 | 2645 | VGDSAEVAVKMFDAYVNTFSSTFNVPMEK LKTLVATAEAELAKNVSLDNVLSTFISAAR QGFVDSD |
| 329 | 106 | 4891 | 4996 | DKSAGFPFNKWGKARLYYDSMSYEDQDA LFAYTKRNVIPTITQMNLKYAISAKNRART VAGVSICSTMTNRQFHQKLLKSIAATRGAT VVIGTSKFYGGWHNMLKT |
| 330 | 87 | 5238 | 5324 | DIVKTDGTLMIERFVSLAIDAYPLTKHPNQ EYADVFHLYLQYIRKLHDELTGHMLDMYS VMLTNDNTSRYWEPEFYEAMYTPHTVLQ |
| 331 | 45 | 6407 | 6452 | AVCRHHANEYRLYLDAYNMMISAGFSLW VYKQFDTYNLWNTFTRLQ |
| 332 | 98 | 4704 | 4801 | NFNVLFSTVFPPTSFGPLVRKIFVDGVPFVV STGYHFRELGVVHNQDVNLHSSRLSFKELL VYAADPAMHAASGNLLLDKRTTCFSVAAL TNNVAFQT |
| 333 | 83 | 7757 | 7839 | ECDIPIGAGICASYQTQTNSPRRARSVASQS IIAYTMSLGAENSVAYSNNSIAIPTNFTISVT TEILPVSMTKTSVDCTMYIC |
| 334 | 70 | 1532 | 1601 | DKSVYYTSNPTTFHLDGEVITFDNLKTLLS LREVRTIKVFTTVDNINLHTQVVDMSMTY GQQFGPTYLDG |
| 335 | 82 | 7948 | 8029 | AQKFNGLTVLPPLLTDEMIAQYTSALLAGT ITSGWTFGAGAALQIPFAMQMAYRFNGIG VTQNVLYENQKLIANQFNSAIGK |
| 336 | 117 | 5531 | 5647 | DAVVYRGTTTYKLNVGDYFVLTSHTVMPL SAPTLVPQEHYVRITGLYPTLNISDEFSSNV ANYQKVGMQKYSTLQGPPGTGKSHFAIGL ALYYPSARIVYTACSHAAVDALCEKALK |
| 337 | 84 | 231 | 314 | CREHEHEIAWYTERSEKSYELQTPFEIKLA KKFDTFNGECPNFVFPLNSIIKTIQPRVEKK KLDGFMGRIRSVYPVASPNECNQ |
| 338 | 85 | 2097 | 2181 | AAYVDNSSLTIKKPNELSRVLGLKTLATHG LAAVNSVPWDTIANYAKPFLNKVVSTTTNI VTRCLNRVCTNYMPYFFTLLLQLCT |
| 339 | 86 | 5107 | 5192 | IADKYVRNLQHRLYECLYRNRDVDTDFVN EFYAYLRKHFSMMILSDDAVVCFNSTYAS QGLVASIKNFKSVLYYQNNVFMSEAKCW |
| 340 | 80 | 4961 | 5040 | RQFHQKLLKSIAATRGATVVIGTSKFYGG WHNMLKTVYSDVENPHLMGWDYPKCDR AMPNMLRIMASLVLARKHTTCCSL |
| 341 | 80 | 6465 | 6544 | GHFDGQQGEVPVSIINNTVYTKVDGVDVE LFENKTTLPVNVAFELWAKRNIKPVPEVKI LNNLGVDIAANTVIWDYKRDA |
| 342 | 92 | 5943 | 6034 | LHPTQAPTHLSVDTKFKTEGLCVDIPGIPKD MTYRRLISMMGFKMNYQVNGYPNMFITRE EAIRHVRAWIGFDVEGCHATREAVGTNLP LQL |
| 343 | 55 | 2935 | 2989 | DTNVLEGSVAYESLRPDTRYVLMDGSIIQF PNTYLEGSVRVVTTFDSEYCRHGTC |
| 344 | 96 | 4782 | 4877 | DKRTTCFSVAALTNNVAFQTVKPGNFNKD FYDFAVSKGFFKEGSSVELKHFFFAQDGNA |

TABLE 4-continued

Selected SARS-CoV-2 long peptide sequences containing high density HLA class I and/or HLA class II binding motifs (SEQ ID NO: 328 to 369)

| SEQ ID No. | Length | N-terminal position in SEQ ID NO: 410 | C-terminal position in SEQ ID NO: 410 | Sequence |
|---|---|---|---|---|
| | | | | AISDYDYYRYNLPTMCDIRQLLFVVEVVDKYFDCYDG |
| 345 | 107 | 822 | 928 | KVTFGDDTVIEVQGYKSVNITFELDERIDKVLNEKCSAYTVELGTEVNEFACVVADAVIKTLQPVSELLTPLGIDLDEWSMATYYLFDESGEFKLASHMYCSFYPPD |
| 346 | 80 | 7406 | 7485 | KGIYQTSNFRVQPTESIVRFPNITNLCPFGEVFNATRFASVYAWNRKRISNCVADYSVLYNSASFSTFKCYGVSPTKLND |
| 347 | 91 | 7287 | 7377 | EFVFKNIDGYFKIYSKHTPINLVRDLPQGFSALEPLVDLPIGINITRFQTLLALHRSYLTPGDSSSGWTAGAAAYYVGYLQPRTFLLKYNE |
| 348 | 102 | 6622 | 6723 | EAVKTQFNYYKKVDGVVQQLPETYFTQSRNLQEFKPRSQMEIDFLELAMDEFIERYKLEGYAFEHIVYGDFSHSQLGGLHLLIGLAKRFKESPFELEDFIPM |
| 349 | 97 | 6800 | 6896 | SQAWQPGVAMPNLYKMQRMLLEKCDLQNYGDSATLPKGIMMNVAKYTQLCQYLNTLTLAVPYNMRVIHFGAGSDKGVAPGTAVLRQWLPTGTLLVDS |
| 350 | 77 | 8568 | 8644 | DCVVLHSYFTSDYYQLYSTQLSTDTGVEHVTFFIYNKIVDEPEEHVQIHTIDGSSGVVNPVMEPIYDEPTTTTSVPL |
| 351 | 37 | 8683 | 8719 | LCAYCCNIVNVSLVKPSFYVYSRVKNLNSSRVPDLLV |
| 352 | 124 | 8818 | 8941 | SFRLFARTRSMWSFNPETNILLNVPLHGTILTRPLLESELVIGAVILRGHLRIAGHHLGRCDIKDLPKEITVATSRTLSYYKLGASQRVAGDSGFAAYSRYRIGNYKLNTDHSSSSDNIALLVQ |
| 353 | 85 | 9039 | 9123 | SGTYEGNSPFHPLADNKFALTCFSTQFAFACPDGVKHVYQLRARSVSPKLFIRQEEVQELYSPIFLIVAAIVFITLCFTLKRKTE |
| 354 | 107 | 9552 | 9658 | TKAYNVTQAFGRRGPEQTQGNFGDQELIRQGTDYKHWPQIAQFAPSASAFFGMSRIGMEVTPSGTWLTYTGAIKLDDKDPNFKDQVILLNKHIDAYKTFPPTEPKKD |
| 355 | 81 | 3149 | 3229 | STKHFYWFFSNYLKRRVVFNGVSFSTFEEAALCTFLLNKEMYLKLRSDVLLPLTQYNRYLALYNKYKYFSGAMDTTSYREA |
| 356 | 84 | 4057 | 4140 | VPLNIIPLTTAAKLMVVIPDYNTYKNTCDGTTFTYASALWEIQQVVDADSKIVQLSEISMDNSPNLAWPLIVTALRANSAVKLQ |
| 357 | 80 | 441 | 520 | EGSEGLNDNLLEILQKEKVNINIVGDFKLNEEIAIILASFSASTSAFVETVKGLDYKAFKQIVESCGNFKVTKGKAKKGA |
| 358 | 108 | 523 | 630 | IGEQKSILSPLYAFASEAARVVRSIFSRTLETAQNSVRVLQKAAITILDGISQYSLRLIDAMMFTSDLATNNLVVMAYITGGVVQLTSQWLTNIFGTVYEKLKPVLDW |
| 359 | 77 | 993 | 1069 | GSEDNQTTTIQTIVEVQPQLEMELTPVVQTIEVNSFSGYLKLTDNVYIKNADIVEEAKKVKPTVVVNAANVYLKHGG |

TABLE 4-continued

Selected SARS-CoV-2 long peptide sequences containing high density HLA class I and/or HLA class II binding motifs (SEQ ID NO: 328 to 369)

| SEQ ID No. | Length | N-terminal position in SEQ ID NO: 410 | C-terminal position in SEQ ID NO: 410 | Sequence |
|---|---|---|---|---|
| 360 | 81 | 1123 | 1203 | NKGEDIQLLKSAYENFNQHEVLLAPLLSAG IFGADPIHSLRVCVDTVRTNVYLAVFDKNL YDKLVSSFLEMKSEKQVEQKI |
| 361 | 104 | 1351 | 1454 | SAFYILPSIISNEKQEILGTVSWNLREMLAH AEETRKLMPVCVETKAIVSTIQRKYKGIKIQ EGVVDYGARFYFYTSKTTVASLINTLNDLN ETLVTMPLGYVT |
| 362 | 104 | 1409 | 1512 | IKIQEGVVDYGARFYFYTSKTTVASLINTLN DLNETLVTMPLGYVTHGLNLEEAARYMRS LKVPATVSVSSPDAVTAYNGYLTSSSKTPE EHFIETISLAGSYK |
| 363 | 82 | 1611 | 1692 | NSHEGKTFYVLPNDDTLRVEAFEYYHTTD PSFLGRYMSALNHTKKWKYPQVNGLTSIK WADNNCYLATALLTLQQIELKFNP |
| 364 | 76 | 7115 | 7190 | TTRTQLPPAYTNSFTRGVYYPDKVFRSSVL HSTQDLFLPFFSNVTWFHAIHVSGTNGTKR FDNPVLPFNDGVYFAS |
| 365 | 83 | 7014 | 7096 | REQIDGYVMHANYIFWRNTNPIQLSSYSLF DMSKFPLKLRGTAVMSLKEGQINDMILSLL SKGRLIIRENNRVVISSDVLVNN |
| 366 | 61 | 8942 | 9002 | MFHLVDFQVTIAEILLIIMRTFKVSIWNLDY IINLIIKNLSKSLTENKYSQLDEEQPMEID |
| 367 | 84 | 8046 | 8129 | DVVNQNAQALNTLVKQLSSNFGAISSVLN DILSRLDKVEAEVQIDRLITGRLQSLQTYVT QQLIRAAEIRASANLAATKMSECV |
| 368 | 63 | 3943 | 4005 | AIASEFSSLPSYAAFATAQEAYEQAVANGD SEVVLKKLKKSLNVAKSEFDRDAAMQRKL EKMA |
| 369 | 80 | 4174 | 4253 | TTKGGRFVLALLSDLQDLKWARFPKSDGT GTIYTELEPPCRFVTDTPKGPKVKYLYFIKG LNNLNRGMVLGSLAATVRLQ |

For each selected long sequences SEQ ID NO: 328 to SEQ ID NO: 369, the number of HLA class I and HLA class II alleles for which high or moderate binding was predicted are presented in Table 5.

TABLE 5

Number of HLA class I and HLA class II alleles for which high or moderate binding was predicted within the selected SARS-CoV-2 long peptide sequences containing high density HLA class I and/or HLA class II binding motifs (SEQ ID NO: 328 to 369)

| | | N-terminal position | C-terminal position | Number of HLA class II alleles | | | Number of HLA class I alleles | | |
|---|---|---|---|---|---|---|---|---|---|
| SEQ ID NO. | Length | in SEQ ID NO: 410 | in SEQ ID NO: 410 | Moderate + High affinity | Moderate affinity | Moderate + High affinity | Moderate affinity | High affinity | Moderate + High affinity |
| 328 | 66 | 2580 | 2645 | 40 | 21 | 43 | 64 | 50 | 68 |
| 329 | 106 | 4891 | 4996 | 42 | 26 | 43 | 63 | 48 | 66 |
| 330 | 87 | 5238 | 5324 | 44 | 26 | 46 | 64 | 57 | 69 |
| 331 | 45 | 6407 | 6452 | 38 | 49 | 49 | 66 | 70 | 70 |
| 332 | 98 | 4704 | 4801 | 48 | 24 | 48 | 58 | 49 | 61 |
| 333 | 83 | 7757 | 7839 | 34 | 21 | 36 | 63 | 39 | 64 |
| 334 | 70 | 1532 | 1601 | 32 | 17 | 35 | 60 | 52 | 63 |

TABLE 5-continued

Number of HLA class I and HLA class II alleles for which high or moderate binding was predicted within the selected SARS-CoV-2 long peptide sequences containing high density HLA class I and/or HLA class II binding motifs (SEQ ID NO: 328 to 369)

| | | N-terminal position | C-terminal position | Number of HLA class II alleles | | | Number of HLA class I alleles | | |
|---|---|---|---|---|---|---|---|---|---|
| SEQ ID NO. | Length | in SEQ ID NO: 410 | in SEQ ID NO: 410 | Moderate + High affinity | Moderate affinity | Moderate + High affinity | Moderate affinity | High affinity | Moderate + High affinity |
| 335 | 82 | 7948 | 8029 | 41 | 24 | 43 | 61 | 32 | 62 |
| 336 | 117 | 5531 | 5647 | 46 | 24 | 46 | 68 | 47 | 68 |
| 337 | 84 | 231 | 314 | 37 | 11 | 38 | 61 | 44 | 70 |
| 338 | 85 | 2097 | 2181 | 43 | 16 | 44 | 65 | 45 | 70 |
| 339 | 86 | 5107 | 5192 | 47 | 38 | 49 | 58 | 33 | 59 |
| 340 | 80 | 4961 | 5040 | 39 | 23 | 40 | 59 | 53 | 64 |
| 341 | 80 | 6465 | 6544 | 36 | 9 | 37 | 63 | 41 | 65 |
| 342 | 92 | 5943 | 6034 | 37 | 17 | 43 | 61 | 38 | 64 |
| 343 | 55 | 2935 | 2989 | 29 | 8 | 29 | 59 | 39 | 63 |
| 344 | 96 | 4782 | 4877 | 39 | 17 | 40 | 65 | 46 | 68 |
| 345 | 107 | 822 | 928 | 33 | 15 | 36 | 64 | 48 | 64 |
| 346 | 80 | 7406 | 7485 | 41 | 18 | 42 | 61 | 37 | 64 |
| 347 | 91 | 7287 | 7377 | 47 | 31 | 49 | 63 | 49 | 66 |
| 348 | 102 | 6622 | 6723 | 38 | 18 | 38 | 66 | 49 | 68 |
| 349 | 97 | 6800 | 6896 | 38 | 20 | 40 | 66 | 36 | 66 |
| 350 | 77 | 8568 | 8644 | 32 | 14 | 35 | 54 | 24 | 58 |
| 351 | 37 | 8683 | 8719 | 25 | 9 | 29 | 36 | 27 | 48 |
| 352 | 124 | 8818 | 8941 | 40 | 23 | 41 | 68 | 49 | 70 |
| 353 | 85 | 9039 | 9123 | 38 | 19 | 39 | 65 | 44 | 69 |
| 354 | 107 | 9552 | 9658 | 37 | 13 | 37 | 66 | 47 | 69 |
| 355 | 81 | 3149 | 3229 | 45 | 29 | 45 | 55 | 41 | 60 |
| 356 | 84 | 4057 | 4140 | 44 | 31 | 47 | 65 | 44 | 67 |
| 357 | 80 | 441 | 520 | 39 | 28 | 44 | 50 | 20 | 52 |
| 358 | 108 | 523 | 630 | 48 | 21 | 48 | 70 | 51 | 70 |
| 359 | 77 | 993 | 1069 | 36 | 12 | 37 | 59 | 41 | 62 |
| 360 | 81 | 1123 | 1203 | 41 | 13 | 43 | 64 | 41 | 70 |
| 361 | 104 | 1351 | 1454 | 45 | 24 | 47 | 64 | 38 | 67 |
| 362 | 104 | 1409 | 1512 | 41 | 26 | 44 | 61 | 35 | 63 |
| 363 | 82 | 1611 | 1692 | 41 | 14 | 42 | 59 | 47 | 69 |
| 364 | 76 | 7115 | 7190 | 39 | 17 | 39 | 63 | 26 | 63 |
| 365 | 83 | 7014 | 7096 | 46 | 21 | 46 | 63 | 38 | 67 |
| 366 | 61 | 8942 | 9002 | 37 | 23 | 43 | 44 | 11 | 46 |
| 367 | 84 | 8046 | 8129 | 38 | 19 | 38 | 60 | 35 | 62 |
| 368 | 63 | 3943 | 4005 | 35 | 27 | 40 | 52 | 26 | 56 |
| 369 | 80 | 4174 | 4253 | 46 | 27 | 47 | 64 | 17 | 64 |

In addition to the long peptide sequences SEQ ID NO: 328 to SEQ ID NO: 369, thirty-nine (39) shorter sequences with a length varying from 31 to 47 amino acid residues were also identified. The thirty-nine shorter peptide sequence correspond to portions of sequence within SEQ ID NO: 328 to SEQ ID NO: 369 with the highest number of HLA class I and class II binding motifs are shown in Table 6 (SEQ ID NOS: 370 to 408). In embodiments, these shorter peptides may be concatenated for insertion and expression from the adenoviral vector.

TABLE 6

Selected SARS-CoV-2 shorter peptide sequences motifs (SEQ ID
containing high density HLA class I and/or HLA class II binding NO: 370 to 408)

| SEQ ID No | Contained within SEQ ID NO: | Length | N-term position | C-Term position | Sequence |
|---|---|---|---|---|---|
| 370 | 328 | 45 | 2589 | 2633 | KMFDAYVNTFSSTFNVPMEKLKTLVATAEAELAKNVSLDNVLSTF |
| 371 | 329 | 41 | 4911 | 4951 | MSYEDQDALFAYTKRNVIPTITQMNLKYAISAKNRARTVAG |
| 372 | 330 | 45 | 5243 | 5287 | DGTLMIERFVSLAIDAYPLTKHPNQEYADVFHLYLQYIRKLHDEL |
| 373 | 331 | 43 | 6410 | 6452 | RHHANEYRLYLDAYNMMISAGFSLWVYKQFDTYNLWNTFTRLQ |
| 374 | 332 | 41 | 4704 | 4744 | NFNVLFSTVFPPTSFGPLVRKIFVDGVPFVVSTGYHFRELG |
| 375 | 333 | 45 | 7781 | 7825 | RSVASQSIIAYTMSLGAENSVAYSNNSTATPTNFTISVTTEILPV |
| 376 | 334 | 47 | 1532 | 1578 | DKSVYYTSNPTTFHLDGEVITFDNLKTLLSLREVRTIKVFTTVDNIN |

TABLE 6-continued

Selected SARS-CoV-2 shorter peptide sequences motifs (SEQ ID NO: 370 to 408) containing high density HLA class I and/or HLA class II binding

| SEQ ID No | Contained within SEQ ID NO: | Length | N-term position | C-Term position | Sequence |
|---|---|---|---|---|---|
| 377 | 335 | 45 | 7961 | 8005 | LTDEMIAQYTSALLAGTITSGWTFGAGAALQIPFAMQMAYRFNGI |
| 378 | 336 | 45 | 5532 | 5576 | AVVYRGTTTYKLNVGDYFVLTSHTVMPLSAPTLVPQEHYVRITGL |
| 379 | 337 | 41 | 243 | 283 | ERSEKSYELQTPFEIKLAKKFDTFNGECPNFVFPLNSIIKT |
| 380 | 338 | 45 | 2097 | 2141 | AAYVDNSSLTIKKPNELSRVLGLKTLATHGLAAVNSVPWDTIANY |
| 381 | 339 | 41 | 5129 | 5169 | VDTDFVNEFYAYLRKHFSMMILSDDAVVCFNSTYASQGLVA |
| 382 | 339 | 33 | 5158 | 5190 | FNSTYASQGLVASIKNFKSVLYYQNNVFMSEAK |
| 383 | 340 | 43 | 4997 | 5039 | VYSDVENPHLMGWDYPKCDRAMPNMLRIMASLVLARKHTTCCS |
| 384 | 342 | 45 | 5972 | 6016 | KDMTYRRLISMMGFKMNYQVNGYPNMFITREEAIRHVRAWIGFDV |
| 385 | 343 | 41 | 2945 | 2985 | YESLRPDTRYVLMDGSIIQFPNTYLEGSVRVVTTFDSEYCR |
| 386 | 344 | 41 | 4817 | 4857 | SKGFFKEGSSVELKHFFFAQDGNAAISDYDYYRYNLPTMCD |
| 387 | 345 | 43 | 881 | 923 | KTLQPVSELLTPLGIDLDEWSMATYYLFDESGEFKLASHMYCS |
| 388 | 346 | 45 | 7418 | 7462 | PTESIVRFPNITNLCPFGEVFNATRFASVYAWNRKRISNCVADYS |
| 389 | 346 | 43 | 7443 | 7485 | FASVYAWNRKRISNCVADYSVLYNSASFSTFKCYGVSPTKLND |
| 390 | 347 | 45 | 7332 | 7376 | TRFQTLLALHRSYLTPGDSSSGWTAGAAAYYVGYLQPRTFLLKYN |
| 391 | 350 | 42 | 8570 | 8611 | VVLHSYFTSDYYQLYSTQLSTDTGVEHVTFFIYNKIVDEPEE |
| 392 | 351 | 31 | 8689 | 8719 | NIVNVSLVKPSFYVYSRVKNLNSSRVPDLLV |
| 393 | 352 | 43 | 8884 | 8926 | PKEITVATSRTLSYYKLGASQRVAGDSGFAAYSRYRIGNYKLN |
| 394 | 353 | 42 | 9073 | 9114 | VKHVYQLRARSVSPKLFIRQEEVQELYSPIFLIVAAIVFITL |
| 395 | 354 | 42 | 9587 | 9628 | HWPQIAQFAPSASAFFGMSRIGMEVTPSGTWLTYTGAIKLDD |
| 396 | 355 | 46 | 3149 | 3194 | STKHFYWFFSNYLKRRVVFNGVSFSTFEEAALCTFLLNKEMYLKLR |
| 397 | 355 | 46 | 3184 | 3229 | LLNKEMYLKLRSDVLLPLTQYNRYLALYNKYKYFSGAMDTTSYREA |
| 398 | 356 | 44 | 4057 | 4100 | VPLNIIPLTTAAKLMVVIPDYNTYKNTCDGTTFTYASALWEIQQ |
| 399 | 357 | 42 | 460 | 501 | NINIVGDFKLNEEIAIILASFSASTSAFVETVKGLDYKAFKQ |
| 400 | 358 | 43 | 528 | 570 | SILSPLYAFASEAARVVRSIFSRTLETAQNSVRVLQKAAITIL |
| 401 | 359 | 43 | 994 | 1036 | SEDNQTTTIQTIVEVQPQLEMELTPVVQTIEVNSFSGYLKLTD |
| 402 | 360 | 43 | 1154 | 1196 | FGADPIHSLRVCVDTVRTNVYLAVFDKNLYDKLVSSFLEMKSE |
| 403 | 361 | 43 | 1410 | 1452 | KIQEGVVDYGARFYFYTSKTTVASLINTLNDLNETLVTMPLGY |
| 404 | 363 | 41 | 1616 | 1656 | KTFYVLPNDDTLRVEAFEYYHTTDPSFLGRYMSALNHTKKW |
| 405 | 366 | 46 | 8944 | 8989 | HLVDFQVTIAEILLIIMRTFKVSIWNLDYIINLIIKNLSKSLTENK |
| 406 | 367 | 44 | 8083 | 8126 | VEAEVQIDRLITGRLQSLQTYVTQQLIRAAEIRASANLAATKMS |
| 407 | 368 | 36 | 3943 | 3978 | AIASEFSSLPSYAAFATAQEAYEQAVANGDSEVVLK |
| 408 | 369 | 41 | 4213 | 4253 | CRFVTDTPKGPKVKYLYFIKGLNNLNRGMVLGSLAATVRLQ |

For each of SEQ ID NOS: 370-408 (Table 3), the number of HLA class I and HLA class II alleles for which high or moderate binding was predicted are presented in Table 7.

TABLE 7

Number of HLA class I and HLA class II alleles for which high or moderate binding was predicted within the selected SARS-CoV-2 shorter peptide sequences containing high density HLA class I and/or HLA class II binding motifs (SEQ ID NOS: 370-408)

| SEQ ID NO: | Length | N-terminal position in SEQ ID NO: 410 | C-terminal position in SEQ ID NO: 410 | Number of HLA class II alleles Moderate affinity | High affinity | Moderate + High affinity | Number of HLA class I alleles Moderate affinity | High affinity | Moderate + High affinity |
|---|---|---|---|---|---|---|---|---|---|
| 370 | 45 | 2589 | 2633 | 27 | 14 | 32 | 59 | 50 | 67 |
| 371 | 41 | 4911 | 4951 | 31 | 13 | 32 | 57 | 30 | 65 |
| 372 | 45 | 5243 | 5287 | 37 | 15 | 40 | 61 | 43 | 65 |
| 373 | 43 | 6410 | 6452 | 35 | 15 | 39 | 63 | 37 | 68 |
| 374 | 41 | 4704 | 4744 | 32 | 14 | 35 | 48 | 34 | 55 |
| 375 | 45 | 7781 | 7825 | 31 | 15 | 33 | 54 | 35 | 55 |
| 376 | 47 | 1532 | 1578 | 31 | 16 | 34 | 56 | 41 | 60 |
| 377 | 45 | 7961 | 8005 | 35 | 19 | 37 | 53 | 30 | 55 |
| 378 | 45 | 5532 | 5576 | 38 | 18 | 39 | 59 | 40 | 64 |
| 379 | 41 | 243 | 283 | 28 | 5 | 30 | 47 | 36 | 60 |
| 380 | 45 | 2097 | 2141 | 34 | 10 | 35 | 63 | 36 | 68 |
| 381 | 41 | 5129 | 5169 | 45 | 32 | 49 | 44 | 21 | 47 |
| 382 | 33 | 5158 | 5190 | 33 | 14 | 37 | 37 | 13 | 41 |
| 383 | 43 | 4997 | 5039 | 32 | 15 | 35 | 45 | 37 | 57 |
| 384 | 45 | 5972 | 6016 | 32 | 17 | 38 | 50 | 31 | 56 |
| 385 | 41 | 2945 | 2985 | 24 | 6 | 24 | 56 | 37 | 61 |
| 386 | 41 | 4817 | 4857 | 23 | 6 | 23 | 52 | 32 | 60 |
| 387 | 43 | 881 | 923 | 25 | 7 | 26 | 47 | 36 | 58 |
| 388 | 45 | 7418 | 7462 | 33 | 15 | 35 | 51 | 28 | 58 |
| 389 | 43 | 7443 | 7485 | 31 | 9 | 34 | 33 | 14 | 34 |
| 390 | 45 | 7332 | 7376 | 39 | 24 | 41 | 48 | 37 | 56 |
| 391 | 42 | 8570 | 8611 | 28 | 12 | 31 | 41 | 19 | 47 |
| 392 | 31 | 8689 | 8719 | 25 | 9 | 29 | 36 | 27 | 48 |
| 393 | 43 | 8884 | 8926 | 34 | 16 | 35 | 53 | 24 | 53 |
| 394 | 42 | 9073 | 9114 | 27 | 16 | 31 | 58 | 32 | 67 |
| 395 | 42 | 9587 | 9628 | 29 | 11 | 30 | 54 | 28 | 61 |
| 396 | 46 | 3149 | 3194 | 36 | 24 | 41 | 45 | 23 | 52 |
| 397 | 46 | 3184 | 3229 | 34 | 13 | 35 | 46 | 27 | 53 |
| 398 | 44 | 4057 | 4100 | 34 | 16 | 40 | 43 | 32 | 47 |
| 399 | 42 | 460 | 501 | 33 | 26 | 40 | 46 | 13 | 48 |
| 400 | 43 | 528 | 570 | 42 | 16 | 42 | 62 | 18 | 63 |
| 401 | 43 | 994 | 1036 | 20 | 6 | 23 | 41 | 23 | 47 |
| 402 | 43 | 1154 | 1196 | 33 | 8 | 34 | 56 | 29 | 60 |
| 403 | 43 | 1410 | 1452 | 30 | 16 | 34 | 50 | 28 | 52 |
| 404 | 41 | 1616 | 1656 | 32 | 10 | 35 | 45 | 36 | 58 |
| 405 | 46 | 8944 | 8989 | 36 | 22 | 43 | 42 | 11 | 44 |
| 406 | 44 | 8083 | 8126 | 32 | 14 | 34 | 49 | 18 | 52 |
| 407 | 36 | 3943 | 3978 | 27 | 19 | 30 | 40 | 18 | 45 |
| 408 | 41 | 4213 | 4253 | 36 | 20 | 41 | 43 | 8 | 44 |

For each selected sequence from SEQ ID NO: 328 to SEQ ID NO: 369, a map of HLA class I and HLA class II binding motif are presented in FIGS. 29-70. In FIGS. 29-70, the N-terminal amino acid (i.e., amino acid #1) for each HLA class I and II motif therein is identified by an X or an O, wherein X further indicates a high affinity motif and O indicates moderate affinity for the HLA binding motif. Exemplary HLA binding motifs can be deduced from FIGS. 29 to 70 by including the X or O amino acid residue and including the subsequent eight to ten amino acids in the motif such that each motif includes nine to eleven amino acid residues (i.e., each motif is a 9-11 amino acid peptide), with reference to the SEQ ID number indicated in each figure. Any such binding motifs can be used as immunogens, alone and/or in combination, in the vectors disclosed herein. Other binding motifs of any of SEQ ID NOS. 328-369 may also be suitable for inclusion in the SARS-CoV-2 immunization vectors herein as would be understood by those of ordinary skill in the art.

RBD Sequences Matching Circulating SARS-CoV-2 Variants

As described above, rdAd vectors may be designed to encode sequences homologous to SEQ ID NO: 13, SEQ ID NO: 14, SEQ ID NO: 15 or any sequences comprising SEQ ID NO: 446 with or without additional flanking residues and incorporating single or multiple RBD mutation(s) as those described in FIG. 17B. Preferably, the RBD variant sequences may include single or combined mutations at amino acid positions 367, 403, 439, 417, 446, 447, 449, 452, 453, 455, 456, 470, 473, 475, 476, 477, 478, 484, 486, 487, 490, 493, 494, 496, 499, 500, 501, 502, 503, 504, and/or 505, wherein the amino acid position numbering corresponds to SEQ ID NO: 3 (full length spike protein) (FIG. 17B). More preferably, the RBD sequences include single or combined mutations at position K417T, K417N, E484K, L452R and/or N501Y (FIG. 17B). In preferred embodiments, the RBD variant protein sequences can be selected from the group consisting of SEQ ID NOS: 412-417 wherein the RBD sequence is underlined:

```
Spike RBD from SARS-CoV California CAL.20C B.1.429
lineage:
                                        (SEQ ID NO: 412)
TLKSFTVEKGIYQTSNFRVQPTESIVRFPNITNLCPFGEVFNATRFASVY
```

-continued

AWNRKRISNCVADYSVLYNSASFSTFKCYGVSPTKLNDLCFTNVYADSFV

IRGDEVRQIAPGQTGKIADYNYKLPDDFTGCVIAWNSNNLDSKVGGNYNY

RYRLFRKSNLKPFERDISTEIYQAGSTPCNGVEGFNCYFPLQSYGFQPTN

GVGYQPYRVVVLSFELLHAPATVCGPKKSTNLVKNKCVFNFN

Spike RBD from SARS-CoV Brazil P.2 lineage B.1.1.28.2 lineage:

(SEQ ID NO: 413)

TLKSFTVEKGIYQTSNFRVQPTESIVRFPNITNLCPFGEVFNATRFASVY

AWNRKRISNCVADYSVLYNSASFSTFKCYGVSPTKLNDLCFTNVYADSFV

IRGDEVRQIAPGQTGKIADYNYKLPDDFTGCVIAWNSNNLDSKVGGNYNY

LYRLFRKSNLKPFERDISTEIYQAGSTPCNGVKGFNCYFPLQSYGFQPTN

GVGYQPYRVVVLSFELLHAPATVCGPKKSTNLVKNKCVFNFN

Spike RBD from SARS-CoV UK VOC 202012/01; B.1.1.7 lineage (a.k.a. 20I/501Y.V1):

(SEQ ID NO: 414)

TLKSFTVEKGIYQTSNFRVQPTESIVRFPNITNLCPFGEVFNATRFASVY

AWNRKRISNCVADYSVLYNSASFSTFKCYGVSPTKLNDLCFTNVYADSFV

IRGDEVRQIAPGQTGKIADYNYKLPDDFTGCVIAWNSNNLDSKVGGNYNY

LYRLFRKSNLKPFERDISTEIYQAGSTPCNGVEGFNCYFPLQSYGFQPTY

GVGYQPYRVVVLSFELLHAPATVCGPKKSTNLVKNKCVFNFN

Spike RBD from SARS-CoV UK B.1.1.7 lineage (E484K):

(SEQ ID NO: 415)

TLKSFTVEKGIYQTSNFRVQPTESIVRFPNITNLCPFGEVFNATRFASVY

AWNRKRISNCVADYSVLYNSASFSTFKCYGVSPTKLNDLCFTNVYADSFV

-continued

IRGDEVRQIAPGQTGKIADYNYKLPDDFTGCVIAWNSNNLDSKVGGNYNY

LYRLFRKSNLKPFERDISTEIYQAGSTPCNGVKGFNCYFPLQSYGFQPTY

GVGYQPYRVVVLSFELLHAPATVCGPKKSTNLVKNKCVFNFN

Spike RBD from SARS-CoV Brazil P.1 lineage B.1.1.28.1 lineage (a.k.a. 20J/501Y.V3):

(SEQ ID NO: 416)

TLKSFTVEKGIYQTSNFRVQPTESIVRFPNITNLCPFGEVFNATRFASVY

AWNRKRISNCVADYSVLYNSASFSTFKCYGVSPTKLNDLCFTNVYADSFV

IRGDEVRQIAPGQTGTIADYNYKLPDDFTGCVIAWNSNNLDSKVGGNYNY

LYRLFRKSNLKPFERDISTEIYQAGSTPCNGVKGFNCYFPLQSYGFQPTY

GVGYQPYRVVVLSFELLHAPATVCGPKKSTNLVKNKCVFNFN

South Africa 501Y.V2 B.1.351 lineage (a.k.a. 20H/501Y.V2):

(SEQ ID NO: 417)

TLKSFTVEKGIYQTSNFRVQPTESIVRFPNITNLCPFGEVFNATRFASVY

AWNRKRISNCVADYSVLYNSASFSTFKCYGVSPTKLNDLCFTNVYADSFV

IRGDEVRQIAPGQTGNIADYNYKLPDDFTGCVIAWNSNNLDSKVGGNYNY

LYRLFRKSNLKPFERDISTEIYQAGSTPCNGVKGFNCYFPLQSYGFQPTY

GVGYQPYRVVVLSFELLHAPATVCGPKKSTNLVKNKCVFNFN

In preferred embodiments, the RBD sequences to be expressed by the rdAd (a monovalent RBD vector) will be preceded by a leader/signal peptide sequence to address the expression of the polypeptide the cellular secretory pathway. Commonly used leader peptide sequences for efficient targeting of a recombinant protein expressed in mammalian cells are described in Table 9.

TABLE 9

| Leader sequence name | Sequence |
|---|---|
| Human OSM | MGVLLTQRTLLSLVLALLFPSMASM (SEQ ID NO: 418) |
| VSV-G | MKCLLYLAFLFIGVNC (SEQ ID NO: 419) |
| Mouse Ig Kappa | METDTLLLWVLLLWVPGSTGD (SEQ ID NO: 420) |
| Human IgG2 H | MGWSCIILFLVATATGVHS (SEQ ID NO: 421) |
| BM40 | MRAWIFFLLCLAGRALA (SEQ ID NO: 422) |
| Secrecon | MWWRLWWLLLLLLLLWPMVWA (SEQ ID NO: 423) |
| Human IgK VIII | MDMRVPAQLLGLLLLWLRGARC (SEQ ID NO: 424) |
| CD33 | MPLLLLLPLLWAGALA (SEQ ID NO: 425) |
| tPA | MDAMKRGLCCVLLLCGAVFVSPS (SEQ ID NO: 426)<br>MDAMKRGLCCVLLLCGAVFVSPSGTGS (SEQ ID NO: 427) |
| Human Chymotrypsinogen | MAFLWLLSCWALLGTTFG (SEQ ID NO: 428) |
| Human trypsinogen-2 | MNLLLILTFVAAAVA (SEQ ID NO: 429) |
| Human IL-2 | MYRMQLLSCIALSLALVTNS (SEQ ID NO: 430) |
| Gaussia luciferase | MGVKVLFALICIAVAEA (SEQ ID NO: 431) |
| Albumin(HSA) | MKWVTFISLLFSSAYS (SEQ ID NO: 432) |

TABLE 9-continued

| Leader sequence name | Sequence |
| --- | --- |
| Influenza Haemagglutinin | MKTIIALSYIFCLVLG (SEQ ID NO: 433) |
| Human insulin | MALWMRLLPLLALLALWGPDPAAA (SEQ ID NO: 434) |
| Silkworm Fibroin LC | MKPIFLVLLVVTSAYA (SEQ ID NO: 435) |
| adenovirus protein E3/gp19K | MRYMILGLLALAAVCSAA (SEQ ID NO: 436) |
| IgG | MKHLWFFLLLVAAPRWVLS (SEQ ID NO: 437) |

Variant RBD Sequences and Multivalent Vaccine Compositions

It may be also advantageous to develop multivalent immunogenic compositions or vaccines providing immunity against co-circulating SARS-CoV-2 variants and potentially future variants. In some embodiments, multivalent genetic immunogenic compositions or vaccine compositions can be achieved by combining several monovalent genetic immunogenic compositions or vaccine compositions, each expressing an antigen sequence variant in the same preparation. In some embodiments, a single genetic construct can also be constructed to co-express multiple antigen sequence variants to provide a multivalent RBD SARS-CoV-2 immunogenic compositions or vaccine composition. In some embodiments, for instance, an rdAd vector of this disclosure can comprise one or more expression cassettes comprising a SARS-CoV-2 antigen coding sequence that incorporates one or more mutations in the spike protein RBD region, and that would be able to protect against circulating SARS-CoV-2 variants and potentially future variants. In some embodiments, a single genetic construct may comprise multiple RBD variant units arranged co-linearly within a single expression cassette. RBD variant units may be selected from SEQ ID NO: 13, SEQ ID NO: 14, SEQ ID NO: 15 or any sequences comprising SEQ ID NO: 446 with or without additional flanking residues and incorporating single or multiple RBD mutation(s) as those described in FIG. 17B. Each RBD variant unit can be spaced from other RBD variant in the co-linear arrangement by a flexible spacer sequence comprising, for instance, glycine and serine amino acid residues. In preferred embodiments, the spacer peptide can comprise the amino acid sequence (GGGGS)n, (GGGGA)n, (GGGGQ)n, (GGGPS)n, (GPGPG)n and combinations thereof, where n is comprised between 1 and 10. Other spacers, preferably hydrophilic in nature and comprising polar amino acids may also be suitable as would be understood by those ordinary skill in the art. In some embodiments, spacers can include one or more proteolytic cleavage motifs for proprotein convertases (PCs), also known as eukaryotic subtilases, represented by a group of serine proteases comprising furin (PACE), PC1 (PC3), PC2, PC4, PACE4, PC5 (PC6), and PC7 (LPC, PC8) that generate bioactive proteins and peptides, such as hormones, receptors, and growth factors by cleaving precursor proteins at multi-basic motifs. In preferred embodiments, such multi-basic motifs include the one described in table below:

TABLE 8

| Proprotein convertase names | Cleavage site specificity |
| --- | --- |
| PC1/3 | KR↓ or RR↓ |
| PC2 | KR↓ or RR↓ |
| Furin; PACE | RXK/RR↓ |
|  | RXXR↓ |
|  | RXRXXXR/KR↓ |

TABLE 8-continued

| Proprotein convertase names | Cleavage site specificity |
| --- | --- |
| PC4 | KXXR↓ |
|  | RXK/RR↓ |
| PC5/6A; PC5/6B | RXK/RR↓ |
| PACE4 | RXK/RR↓ |
| PC7; PC8; LPC; SPC7 | RXK/RR↓ |

X = any natural amino-acid;
↓ = Cleavage position

Spacer sequences are preferably optimized to avoid the introduction of neo-epitopes within the pseudo-protein sequence. Moreover, different spacers can be combined in the same sequence. In some embodiments, the spacers may include a flexible portion and a cleavable portion. In some embodiments, different spacer sequences may be used between RBD variant units within the same multivalent construct. In a preferred multivalent RBD vector, the number of RBD variant units arranged colinearly in the same genetic sequence may vary from 2 to 10 units, preferably 2 to 6 units. The respective order of the RBD variant sequence may also vary; the use of spacer being introduced so that each RBD variant unit are immunogenically-independent. Each RBD variant unit can include any single mutation or combination of mutations, as those described in FIG. 17B.

Preferably, the RBD variant sequences may include single or combined mutations at positions 367, 403, 439, 417, 446, 447, 449, 452, 453, 455, 456, 470, 473, 475, 476, 477, 478, 484, 486, 487, 490, 493, 494, 496, 499, 500, 501, 502, 503, 504, and/or 505 (FIG. 17B). More preferably, the RBD sequences include single or combined mutations at position K417T, K417N, E484K, L452R and/or N501Y, wherein the amino acid position numbering corresponds to SEQ ID NO: 3 (full length spike protein) (FIG. 17B). SEQ ID NOS: 438 to 443 and 460 are provided as preferred embodiments of RBD variant sequence that can be used for the design of the multivalent RBD vector. Preferred examples of multivalent RBD sequences comprising multiple RBD variant units are presented as SEQ ID NO: 444, SEQ ID NO: 445, SEQ ID NO: 475 and SEQ ID NO: 476. In preferred embodiments, the multivalent RBD sequences to be expressed by the rdAd (a "multivalent RBD vector", a type of multivalent hAd5-SARS-CoV-2) will be preceded by a leader/signal peptide sequence to address the expression of the polypeptide the cellular secretory pathway. Commonly used leader peptide sequences for efficient targeting of a recombinant protein expressed in mammalian cells are described in Table 9.

In preferred embodiments, the RBD variant protein sequences can be selected from the group consisting of SEQ ID NOS: 438-443 and 460, and exemplary multivalent RBD constructs are shown in SEQ ID NOS: 444, 445, 475 and 476 below, wherein the RBD sequence is underlined:

Spike RBD from SARS-CoV (GenBank: MN908947.3):
(SEQ ID NO: 438)
TLKSFTVEKGIYQTSNFRVQPTESIVRFPNITNLCPFGEVFNATRFASVYAWNRKRISN
CVADYSVLYNSASFSTFKCYGVSPTKLNDLCFTNVYADSFVIRGDEVRQIAPGQTGK
IADYNYKLPDDFTGCVIAWNSNNLDSKVGGNYNYLYRLFRKSNLKPFERDISTEIYQ
AGSTPCNGVEGFNCYFPLQSYGFQPTNGVGYQPYRVVVLSFELLHAPATVCGPKKS
TNLVKNKSVNFTF (CVFNFN substituted by SVNFT)

Spike RBD from SARS-CoV California CAL.20C B.1.429 lineage:
(SEQ ID NO: 439)
TLKSFTVEKGIYQTSNFRVQPTESIVRFPNITNLCPFGEVFNATRFASVYAWNRKRISN
CVADYSVLYNSASFSTFKCYGVSPTKLNDLCFTNVYADSFVIRGDEVRQIAPGQTGK
IADYNYKLPDDFTGCVIAWNSNNLDSKVGGNYNYRYRLFRKSNLKPFERDISTEIYQ
AGSTPCNGVEGFNCYFPLQSYGFQPTNGVGYQPYRVVVLSFELLHAPATVCGPKKS
TNLVKNKSVNFTF (CVFNFN substituted by SVNFT)

Spike RBD from SARS-CoV Brazil P.2 lineage B.1.1.28.2 lineage:
(SEQ ID NO: 440)
TLKSFTVEKGIYQTSNFRVQPTESIVRFPNITNLCPFGEVFNATRFASVYAWNRKRISN
CVADYSVLYNSASFSTFKCYGVSPTKLNDLCFTNVYADSFVIRGDEVRQIAPGQTGK
IADYNYKLPDDFTGCVIAWNSNNLDSKVGGNYNYLYRLFRKSNLKPFERDISTEIYQ
AGSTPCNGVKGFNCYFPLQSYGFQPTNGVGYQPYRVVVLSFELLHAPATVCGPKKS
TNLVKNKSVNFTF (CVFNFN substituted by SVNFT)

Spike RBD from SARS-CoV UK VOC 202012/01; B.1.1.7 lineage (a.k.a. 20I/501Y.V1):
(SEQ ID NO: 460)
TLKSFTVEKGIYQTSNFRVQPTESIVRFPNITNLCPFGEVFNATRFASVYAWNRKRISN
CVADYSVLYNSASFSTFKCYGVSPTKLNDLCFTNVYADSFVIRGDEVRQIAPGQTGK
IADYNYKLPDDFTGCVIAWNSNNLDSKVGGNYNYLYRLFRKSNLKPFERDISTEIYQ
AGSTPCNGVEGFNCYFPLQSYGFQPTYGVGYQPYRVVVLSFELLHAPATVCGPKKS
TNLVKNKSVNFTF (CVFNFN substituted by SVNFT)

Spike RBD from SARS-CoV UK B.1.1.7 lineage (E484K):
(SEQ ID NO: 441)
TLKSFTVEKGIYQTSNFRVQPTESIVRFPNITNLCPFGEVFNATRFASVYAWNRKRISN
CVADYSVLYNSASFSTFKCYGVSPTKLNDLCFTNVYADSFVIRGDEVRQIAPGQTGK
IADYNYKLPDDFTGCVIAWNSNNLDSKVGGNYNYLYRLFRKSNLKPFERDISTEIYQ
AGSTPCNGVKGFNCYFPLQSYGFQPTYGVGYQPYRVVVLSFELLHAPATVCGPKKS
TNLVKNKSVNFTF (CVFNFN substituted by SVNFT)

Spike RBD from SARS-CoV Brazil P.1 lineage B.1.1.28.1 lineage (a.k.a. 20J/501Y.V3):
(SEQ ID NO: 442)
TLKSFTVEKGIYQTSNFRVQPTESIVRFPNITNLCPFGEVFNATRFASVYAWNRKRISN
CVADYSVLYNSASFSTFKCYGVSPTKLNDLCFTNVYADSFVIRGDEVRQIAPGQTGTI
ADYNYKLPDDFTGCVIAWNSNNLDSKVGGNYNYLYRLFRKSNLKPFERDISTEIYQ
AGSTPCNGVKGFNCYFPLQSYGFQPTYGVGYQPYRVVVLSFELLHAPATVCGPKKS
TNLVKNKSVNFTF (CVFNFN substituted by SVNFT)

South Africa 501Y.V2 B.1.351 lineage (a.k.a. 20H/501Y.V2):
(SEQ ID NO: 443)
TLKSFTVEKGIYQTSNFRVQPTESIVRFPNITNLCPFGEVFNATRFASVYAWNRKRISN
CVADYSVLYNSASFSTFKCYGVSPTKLNDLCFTNVYADSFVIRGDEVRQIAPGQTGN -continued

IADYNYKLPDDFTGCVIAWNSNNLDSKVGGNYNYLYRLFRKSNLKPFERDISTEIYQ

AGSTPCNGVKGFNCYFPLQSYGFQPTYGVGYQPYRVVVLSFELLHAPATVCGPKKS

TNLVKNKSVNFTF (CVFNFN substituted by SVNFT)

Multivalent RBD construct combination of comprising SEQ ID NO: 438, SEQ ID NO: 443 and SEQ ID NO: 441:

(SEQ ID NO: 444)

TLKSFTVEKGIYQTSNFRVQPTESIVRFPNITNLCPFGEVFNATRFASVYAWNRKRISN

CVADYSVLYNSASFSTFKCYGVSPTKLNDLCFTNVYADSFVIRGDEVRQIAPGQTGK

IADYNYKLPDDFTGCVIAWNSNNLDSKVGGNYNYLYRLFRKSNLKPFERDISTEIYQ

AGSTPCNGVEGFNCYFPLQSYGFQPTNGVGYQPYRVVVLSFELLHAPATVCGPKKS

TNLVKNKSVNFTFGGGGSGGGGSGGGGSTLKSFTVEKGIYQTSNFRVQPTESIVRFP

NITNLCPFGEVFNATRFASVYAWNRKRISNCVADYSVLYNSASFSTFKCYGVSPTKL

NDLCFTNVYADSFVIRGDEVRQIAPGQTGNIADYNYKLPDDFTGCVIAWNSNNLDS

KVGGNYNYLYRLFRKSNLKPFERDISTEIYQAGSTPCNGVKGFNCYFPLQSYGFQPT

YGVGYQPYRVVVLSFELLHAPATVCGPKKSTNLVKNKSVNFTFGGGGSGGGGSGG

GGSTLKSFTVEKGIYQTSNFRVQPTESIVRFPNITNLCPFGEVFNATRFASVYAWNRK

RISNCVADYSVLYNSASFSTFKCYGVSPTKLNDLCFTNVYADSFVIRGDEVRQIAPGQ

TGKIADYNYKLPDDFTGCVIAWNSNNLDSKVGGNYNYLYRLFRKSNLKPFERDISTE

IYQAGSTPCNGVKGFNCYFPLQSYGFQPTYGVGYQPYRVVVLSFELLHAPATVCGP

KKSTNLVKNKSVNFTF (Spacer $(GGGGS)_3$)

Multivalent RBD construct combination of comprising SEQ ID NO: 438, SEQ ID NO: 443 and SEQ ID NO: 441:

(SEQ ID NO: 445)

TLKSFTVEKGIYQTSNFRVQPTESIVRFPNITNLCPFGEVFNATRFASVYAWNRKRISN

CVADYSVLYNSASFSTFKCYGVSPTKLNDLCFTNVYADSFVIRGDEVRQIAPGQTGK

IADYNYKLPDDFTGCVIAWNSNNLDSKVGGNYNYLYRLFRKSNLKPFERDISTEIYQ

AGSTPCNGVEGFNCYFPLQSYGFQPTNGVGYQPYRVVVLSFELLHAPATVCGPKKS

TNLVKNKSVNFTFGGGGSGGGGSRRKRSVGGGGSGGGGSTLKSFTVEKGIYQTSNF

RVQPTESIVRFPNITNLCPFGEVFNATRFASVYAWNRKRISNCVADYSVLYNSASFST

FKCYGVSPTKLNDLCFTNVYADSFVIRGDEVRQIAPGQTGNIADYNYKLPDDFTGCV

IAWNSNNLDSKVGGNYNYLYRLFRKSNLKPFERDISTEIYQAGSTPCNGVKGFNCYF

PLQSYGFQPTYGVGYQPYRVVVLSFELLHAPATVCGPKKSTNLVKNKSVNFTFGGG

GSGGGGSRRKRSVGGGGSGGGGSTLKSFTVEKGIYQTSNFRVQPTESIVRFPNITNLC

PFGEVFNATRFASVYAWNRKRISNCVADYSVLYNSASFSTFKCYGVSPTKLNDLCFT

NVYADSFVIRGDEVRQIAPGQTGKIADYNYKLPDDFTGCVIAWNSNNLDSKVGGNY

NYLYRLFRKSNLKPFERDISTEIYQAGSTPCNGVKGFNCYFPLQSYGFQPTYGVGYQ

PYRVVVLSFELLHAPATVCGPKKSTNLVKNKSVNFTF (Spacer $(GGGGS)_2$RRKRSV$(GGGGS)_2$)

Multivalent RBD construct combination of comprising SEQ ID NO: 438, SEQ ID NO: 439, SEQ ID NO: 440, SEQ ID NO: 441, SEQ ID NO: 442 and SEQ ID NO: 443

(SEQ ID NO: 475)

TLKSFTVEKGIYQTSNFRVQPTESIVRFPNITNLCPFGEVFNATRFASVYAWNRKRISN

CVADYSVLYNSASFSTFKCYGVSPTKLNDLCFTNVYADSFVIRGDEVRQIAPGQTGK

IADYNYKLPDDFTGCVIAWNSNNLDSKVGGNYNYRYRLFRKSNLKPFERDISTEIYQ

AGSTPCNGVEGFNCYFPLQSYGFQPTNGVGYQPYRVVVLSFELLHAPATVCGPKKS

-continued

TNLVKNKSVNFTFGGGGSGGGGSGGGGSTLKSFTVEKGIYQTSNFRVQPTESIVRFP

NITNLCPFGEVFNATRFASVYAWNRKRISNCVADYSVLYNSASFSTFKCYGVSPTKL

NDLCFTNVYADSFVIRGDEVRQIAPGQTGKIADYNYKLPDDFTGCVIAWNSNNLDS

KVGGNYNYRYRLFRKSNLKPFERDISTEIYQAGSTPCNGVEGFNCYFPLQSYGFQPT

NGVGYQPYRVVVLSFELLHAPATVCGPKKSTNLVKNKSVNFTFGGGGSGGGGSGG

GGSTLKSFTVEKGIYQTSNFRVQPTESIVRFPNITNLCPFGEVFNATRFASVYAWNRK

RISNCVADYSVLYNSASFSTFKCYGVSPTKLNDLCFTNVYADSFVIRGDEVRQIAPGQ

TGKIADYNYKLPDDFTGCVIAWNSNNLDSKVGGNYNYLYRLFRKSNLKPFERDISTE

IYQAGSTPCNGVKGFNCYFPLQSYGFQPTNGVGYQPYRVVVLSFELLHAPATVCGP

KKSTNLVKNKSVNFTFGGGGSGGGGSGGGGSTLKSFTVEKGIYQTSNFRVQPTESIV

RFPNITNLCPFGEVFNATRFASVYAWNRKRISNCVADYSVLYNSASFSTFKCYGVSP

TKLNDLCFTNVYADSFVIRGDEVRQIAPGQTGKIADYNYKLPDDFTGCVIAWNSNNL

DSKVGGNYNYLYRLFRKSNLKPFERDISTEIYQAGSTPCNGVKGFNCYFPLQSYGFQ

PTYGVGYQPYRVVVLSFELLHAPATVCGPKKSTNLVKNKSVNFTFGGGGSGGGGSG

GGGSTLKSFTVEKGIYQTSNFRVQPTESIVRFPNITNLCPFGEVFNATRFASVYAWNR

KRISNCVADYSVLYNSASFSTFKCYGVSPTKLNDLCFTNVYADSFVIRGDEVRQIAPG

QTGTIADYNYKLPDDFTGCVIAWNSNNLDSKVGGNYNYLYRLFRKSNLKPFERDIST

EIYQAGSTPCNGVKGFNCYFPLQSYGFQPTYGVGYQPYRVVVLSFELLHAPATVCGP

KKSTNLVKNKSVNFTFGGGGSGGGGSGGGGSTLKSFTVEKGIYQTSNFRVQPTESIV

RFPNITNLCPFGEVFNATRFASVYAWNRKRISNCVADYSVLYNSASFSTFKCYGVSP

TKLNDLCFTNVYADSFVIRGDEVRQIAPGQTGNIADYNYKLPDDFTGCVIAWNSNNL

DSKVGGNYNYLYRLFRKSNLKPFERDISTEIYQAGSTPCNGVKGFNCYFPLQSYGFQ

PTYGVGYQPYRVVVLSFELLHAPATVCGPKKSTNLVKNKSVNFTF (Spacer $(GGGGS)_2$RRKRSV$(GGGGS)_2$)

Multivalent RBD construct combination of comprising
SEQ ID NO: 438, SEQ ID NO: 439, SEQ ID NO: 440,
SEQ ID NO: 441, SEQ ID NO: 442 and SEQ ID NO: 443
(SEQ ID NO: 476)

TLKSFTVEKGIYQTSNFRVQPTESIVRFPNITNLCPFGEVFNATRFASVYAWNRKRISN

CVADYSVLYNSASFSTFKCYGVSPTKLNDLCFTNVYADSFVIRGDEVRQIAPGQTGK

IADYNYKLPDDFTGCVIAWNSNNLDSKVGGNYNYRYRLFRKSNLKPFERDISTEIYQ

AGSTPCNGVEGFNCYFPLQSYGFQPTNGVGYQPYRVVVLSFELLHAPATVCGPKKS

TNLVKNKSVNFTFGSGGGGSRRKRSVGGGGSGGGGSTLKSFTVEKGIYQTSNFRVQ

PTESIVRFPNITNLCPFGEVFNATRFASVYAWNRKRISNCVADYSVLYNSASFSTFKC

YGVSPTKLNDLCFTNVYADSFVIRGDEVRQIAPGQTGKIADYNYKLPDDFTGCVIAW

NSNNLDSKVGGNYNYRYRLFRKSNLKPFERDISTEIYQAGSTPCNGVEGFNCYFPLQ

SYGFQPTNGVGYQPYRVVVLSFELLHAPATVCGPKKSTNLVKNKSVNFTFGSGGGG

SRRKRSVGGGGSGGGGSTLKSFTVEKGIYQTSNFRVQPTESIVRFPNITNLCPFGEVF

NATRFASVYAWNRKRISNCVADYSVLYNSASFSTFKCYGVSPTKLNDLCFTNVYAD

SFVIRGDEVRQIAPGQTGKIADYNYKLPDDFTGCVIAWNSNNLDSKVGGNYNYLYR

LFRKSNLKPFERDISTEIYQAGSTPCNGVKGFNCYFPLQSYGFQPTNGVGYQPYRVV

VLSFELLHAPATVCGPKKSTNLVKNKSVNFTFGSGGGGSRRKRSVGGGGSGGGGST

-continued

LKSFTVEKGIYQTSNFRVQPTESIVRFPNITNLCPFGEVFNATRFASVYAWNRKRISNC

VADYSVLYNSASFSTFKCYGVSPTKLNDLCFTNVYADSFVIRGDEVRQIAPGQTGKI

ADYNYKLPDDFTGCVIAWNSNNLDSKVGGNYNYLYRLFRKSNLKPFERDISTEIYQ

AGSTPCNGVKGFNCYFPLQSYGFQPTYGVGYQPYRVVVLSFELLHAPATVCGPKKS

TNLVKNKSVNFTFGSGGGGSRRKRSVGGGGSGGGGSTLKSFTVEKGIYQTSNFRVQ

PTESIVRFPNITNLCPFGEVFNATRFASVYAWNRKRISNCVADYSVLYNSASFSTFKC

YGVSPTKLNDLCFTNVYADSFVIRGDEVRQIAPGQTGTIADYNYKLPDDFTGCVIAW

NSNNLDSKVGGNYNYLYRLFRKSNLKPFERDISTEIYQAGSTPCNGVKGFNCYFPLQ

SYGFQPTYGVGYQPYRVVVLSFELLHAPATVCGPKKSTNLVKNKSVNFTFGSGGGG

SRRKRSVGGGGSGGGGSTLKSFTVEKGIYQTSNFRVQPTESIVRFPNITNLCPFGEVF

NATRFASVYAWNRKRISNCVADYSVLYNSASFSTFKCYGVSPTKLNDLCFTNVYAD

SFVIRGDEVRQIAPGQTGNIADYNYKLPDDFTGCVIAWNSNNLDSKVGGNYNYLYR

LFRKSNLKPFERDISTEIYQAGSTPCNGVKGFNCYFPLQSYGFQPTYGVGYQPYRVV

VLSFELLHAPATVCGPKKSTNLVKNKSVNFTF (Spacer $(GGGGS)_2$RRKRSV$(GGGGS)_2$)

Other peptides, polypeptides, constructs, and combinations thereof are also contemplated herein as would be understood by those of ordinary skill in the art.

Receptor Binding Antagonists

In some embodiments, the SARS-CoV-2 immunization vectors (i.e., those expressing one or more exogenous antigens) can comprise polynucleotides encoding one or SARS-CoV-2 blocking proteins (e.g., receptor binding antagonists). For instance, coronaviruses such as SARS-CoV-2 are known to use homotrimers of the spike (S) protein for host cell attachment, fusion and entry into the host cell, and can involve sialic acids and/or ACE2 (a cell membrane C-terminal anchored protein that catalyzes the cleavage of angiotensin 1 into angiotensin 1-9, and of angiotensin II into the vasodilator angiotensin 1-7, thus playing a key role in systemic blood pressure regulation (Alifano, et al. Renin-angiotensin system at the heart of COVID-19 pandemic. Biochimie, 174: 30-33 (2020)). Host cell proteases are known to process coronavirus S protein to generate two subunits (S1 and S2), which remain non-covalently bound in the pre-fusion conformation of the virus (see, e.g., Tortorici, et al. Structural basis for human coronavirus attachment to sialic acid receptors. Nat. Struc. Mol. Biol. 26: 481-489 (2019)). The S1 subunit comprises four domains NTD, RBD, SD1 and SD1 with NTD and RBD separated by a linker sequence as presented in FIG. 13. In some embodiments, SARS-CoV-2 immunization vector can also or alternatively comprise a polynucleotide causing expression in a cell of at least one or both of the S1 domains (NTD and/or RBD) or as part of the full-length S protein (with or without transmembrane domain), and/or an immunogenic fragment of the same that, in some preferred embodiments, induces an immune response that interferes with the binding of the S protein (e.g., an antibody against the S1 RDB and/or NTD domain(s)) to the above-mentioned sialic acids and/or ACE2, thereby interfering with entry of SARS-CoV-2 into a host cell and/or its effect on ACE2. In some embodiments, the SARS-CoV-2 immunization vector can also or alternatively comprise a polynucleotide causing expression in a cell of a protein (e.g., an antibody or fragment thereof, or a peptide (e.g., an ACE2 mimic, RBD binding peptide)) that can bind to S protein (e.g., the S1 RDB and/or NTD domain(s) thereof, and/or S2), thereby interfering with entry of SARS-CoV-2 into a host cell (e.g., blocking the binding of the S protein to its host cells receptors such as ACE2) and/or its effect on ACE2 (collectively referred to as "RBD binding agents"). In some embodiments, the RBD binding agent can be a peptide with at least one domain corresponding to a virus-binding domain of ACE2, e.g., a peptide the conformationally matches the RBD. In some embodiments, the SARS-CoV-2 immunization vector can also or alternatively comprise a polynucleotide causing expression in a cell of a protein that can bind to ACE2 (e.g., an ACE2 binding agent) and/or otherwise prevent attachment of the S protein (e.g., the S1 RDB and/or NTD domain(s) thereof, and/or S2, can be expressed as free proteins) thereto, thereby interfering with entry of SARS-CoV-2 into a host cell and/or its effect on ACE2, preferably without interfering with the normal physiological function of ACE2 (i.e., other than its ability to serve as a receptor for SARS-CoV-2). In some embodiments, such an ACE2 binding agent can be a peptide, such as a peptide that interferes with the binding of SARS-CoV-2 to ACE2. In some embodiments, the SARS-CoV-2 immunization vector can comprise one or more polynucleotides encoding both a RBD binding agent and an ACE2 binding agent, and/or a dual RBD binding and ACE2 binding agent. In preferred embodiments, the RBD binding agent(s) and/or ACE2 binding agent(s) interfere with the interaction of ACE2 and RBD at one or more of the 15 residues from ACE2 (24(Q), 27(T), 30(D), 31(K), 34(H), 35(E), 37(E), 38(D), 41(Y), and 42(Q) are in α1, one residue (residue 82 M) comes from α2, residues 353(K), 354(G), 355(D), and 357(R) come from the linker between β3 and β4) that are currently understood to interact with RBD (Han, et al. Computational Design of ACE2-Based Peptide Inhibitors of SARS-CoV-2. *ACS Nano* 2020, Publication Date: Apr. 14, 2020 (https://doi.org/10.1021/acsnano.0c02857); Yan, et al. Structural Basis for the Recognition of the SARS-CoV-2 by Full-Length Human ACE2. Science 367: 1444-1448 (2020)); preferably without affecting the normal physiological function (i.e., other than its ability to serve as a receptor for SARS-CoV-2) of the ACE2 protein. Thus, in some embodiments, the SARS-CoV-2 immunization vectors of this disclosure can comprise one or more polynucleotides that encode secreted antigens (e.g., S1, NTD, RBD, ACE2 binding agent) that can bind to and block the ACE2 receptor adding additional activity in addition to immunity.

Viral Vectored Adjuvants

In some embodiments, the SARS-CoV-2 immunization vector(s) can also or alternatively comprise at least one polynucleotide encoding a polypeptide and/or peptide that improves or enhances the immunogenicity of the vector(s) (e.g., acts as an adjuvant (e.g., a molecular adjuvant)) that is expressed by a host cells and assists in the induction of an anti-SARS-CoV-2 immune response, and/or enhances an ongoing anti-SARS-CoV-2 immune response, resulting from administration of the vector(s) to a host (e.g., in preferred embodiments without inducing a systemic inflammatory response that could interfere with the recovery of a patient from SARS-CoV-2 infection). For instance, in some embodiments, the SARS-CoV-2 immunization vector(s) can encode one or more: 1) polypeptides or peptides that function as "co-stimulatory" component(s) such as, for instance, polypeptides or peptides that bind members of the CD28 family (i.e., CD28, ICOS; Hutloff, et al. Nature 1999, 397: 263-265; Peach, et al. J Exp Med 1994, 180: 2049-2058) such as the CD28 binding polypeptides B7.1 (CD80; Schwartz, 1992; Chen et al, 1992; Ellis, et al. J. Immunol., 156(8): 2700-9) and B7.2 (CD86; Ellis, et al. J. Immunol., 156(8): 2700-9); members of the integrin family (i.e., LFA-1 (CD11a/CD18); Sedwick, et al. J Immunol 1999, 162: 1367-1375; Wülfing, et al. Science 1998, 282: 2266-2269; Lub, et al. Immunol Today 1995, 16: 479-483) including members of the ICAM family (i.e., ICAM-1, -2 or -3); CD2 family members (i.e., CD2, signalling lymphocyte activation molecule (CDw150 or "SLAM"; Aversa, et al. J Immunol 1997, 158: 4036-4044) such as CD58 (LFA-3; CD2 ligand; Davis, et al. Immunol Today 1996, 17: 177-187) or SLAM ligands (Sayos, et al. Nature 1998, 395: 462-469); heat stable antigen (HSA or CD24; Zhou, et al. Eur J Immunol 1997, 27: 2524-2528); members of the TNF receptor (TNFR) family (i.e., 4-1BB (CD137; Vinay, et al. Semin Immunol 1998, 10: 481-489)), OX40 (CD134; Weinberg, et al. Semin Immunol 1998, 10: 471-480; Higgins, et al. J Immunol 1999, 162: 486-493), and CD27 (Lens, et al. Semin Immunol 1998, 10: 491-499)) such as 4-1BBL (4-1BB ligand; Vinay, et al. Semin Immunol 1998, 10: 481-48; DeBenedette, et al. J Immunol 1997, 158: 551-559), TNFR associated factor-1 (TRAF-1; 4-1BB ligand; Saoulli, et al. J Exp Med 1998, 187: 1849-1862, Arch, et al. Mol Cell Biol 1998, 18: 558-565), TRAF-2 (4-1BB and OX40 ligand; Saoulli, et al. J Exp Med 1998, 187: 1849-1862; Oshima, et al. Int Immunol 1998, 10: 517-526, Kawamata, et al. J Biol Chem 1998, 273: 5808-5814), TRAF-3 (4-1BB and OX40 ligand; Arch, et al. Mol Cell Biol 1998, 18: 558-565; Jang, et al. Biochem Biophys Res Commun 1998, 242: 613-620; Kawamata S, et al. J Biol Chem 1998, 273: 5808-5814), OX40L (OX40 ligand; Gramaglia, et al. J Immunol 1998, 161: 6510-6517), TRAF-5 (OX40 ligand; Arch, et al. Mol Cell Biol 1998, 18: 558-565; Kawamata, et al. J Biol Chem 1998, 273: 5808-5814), and CD70 (CD27 ligand; Couderc, et al. Cancer Gene Ther., 5(3): 163-75). CD154 (CD40 ligand or "CD40L"; Gurunathan, et al. J. Immunol., 1998, 161: 4563-4571; Sine, et al. Hum. Gene Ther., 2001, 12: 1091-1102); 2) one or more cytokines (e.g., as described for retroviruses in Ohs, et al. Interleukin-Encoding Adenoviral Vectors as Genetic Adjuvant for Vaccination against Retroviral Infection. PLos One, 8(12): e82528 (December 2013)), such as interleukin-2 (IL-2) (Rosenberg, et al. Nature Med. 4: 321-327 (1998)), IL-4, IL-5, IL-6 IL-7, IL-12 (reviewed by Pardoll, 1992; Harries, et al. J. Gene Med. 2000 July-August; 2(4):243-9; Rao, et al. J. Immunol. 156: 3357-3365 (1996)), IL-15 (Xin, et al. Vaccine, 17:858-866, 1999), IL-16 (Cruikshank, et al. J. Leuk Biol. 67(6): 757-66, 2000), IL-18 (J. Cancer Res. Clin. Oncol. 2001. 127(12): 718-726), GM-CSF (CSF (Disis, et al. Blood, 88: 202-210 (1996)), IL-23, tumor necrosis factor-alpha (TNF-α), or an interferon (e.g., interferon-gamma (INF-γ)); 3) chemokines such as fusion proteins comprising CXCL10 (IP-10) and CCL7 (MCP-3) fused to a tumor self-antigen have been shown to induce anti-tumor immunity (Biragyn, et al. Nature Biotech. 1999, 17: 253-258), CCL3 (MIP-1α), and/or CCL5 (RANTES) (Boyer, et al. Vaccine, 1999, 17 (Supp. 2): S53-S64); 4) immune inhibitory proteins and/or peptides such as anti-CTLA-4 agent(s) (Shrikant, et al. Immunity, 1996, 14: 145-155; Sutmuller, et al. J. Exp. Med., 2001, 194: 823-832), anti-CD25 agent(s) (Sutmuller, supra), anti-CD4 agent(s) (Matsui, et al. J. Immunol., 1999, 163: 184-193), the fusion protein IL13Rα2-Fc (Terabe, et al. Nature Immunol., 2000, 1: 515-520), anti-cytokine agents (e.g., antibodies or fragments thereof such as anti-IL6, anti-IL6 receptor, anti-IL17 (e.g., BMS-945429 (ALD518), clazakizumab, dupilumab, elsilimomab, olokizumab (CDP6038), siltuximab (Sylvant), sirukumab (CNTO 136), toclizumab (Actemra); see also the agents listed in Table 4 herein); 5) one or more TLR agonist (LPS mimic 7-mer peptide (TLR4 agonist; e.g., Gln Glu Ile Asn Ser Ser Tyr (SEQ ID NO: 463) (RS01); Ser His Pro Arg Leu Ser Ala (SEQ ID NO: 464) (RS02); Ser Met Pro Asn Pro Met Val (SEQ ID NO: 465) (RS03); Gly Leu Gln Gln Val Leu Leu (SEQ ID NO: 466) (RS04); His Glu Leu Ser Val Leu Leu (SEQ ID NO: 467) (RS05); Tyr Ala Pro Gln Arg Leu Pro (SEQ ID NO: 468) (RS06); Thr Pro Arg Thr Leu Pro Thr (SEQ ID NO: 469) (RS07); Ala Pro Val His Ser Ser Ile (SEQ ID NO: 470) (RS08); Ala Pro Pro His Ala Leu Ser (SEQ ID NO: 471) (RS09); Thr Phe Ser Asn Arg Phe Ile (SEQ ID NO: 472) (RS10); Val Val Pro Thr Pro Pro Tyr (SEQ ID NO: 473) (RS11); and, Glu Leu Ala Pro Asp Ser Pro (SEQ ID NO: 474) (RS12)); or, Flagellin (TLR5 agonist (e.g., FliC; Skountzou, et al. *Salmonella flagellins* are potent adjuvants for intranasally administered whole inactivated influenza vaccine, Vaccine. May 28; 28(24): 4103-4112 (2010)); e.g., 51 subunits with integrated TLR agonist sequences (Kim et al. Microneedle array delivered recombinant coronavirus vaccines: Immunogenicity and rapid translational development. EBioMedicine (2020)); and combinations thereof. The use of other types of molecular adjuvants are also contemplated herein as would be understood by those of ordinary skill in the art.

Formulations

In some embodiments, the present replication deficient adenovirus vector that contains and expresses SARS-CoV-2 spike (S) antigen, or immunogenic fragment thereof, that can be codon-optimized for the human subject, may be combined with other coronavirus antigens (e.g. viral vector expressed antigens) to form a multivalent coronavirus pharmaceutical formulation. The other components may be included to induce a humoral response with antibodies to a different epitope than that presented in the instant adenoviral vector containing spike protein antigen. In other embodiments, the other component(s) may be included to induce a different arm of the immune system, such as cell-mediated or mucosal immune response to a coronavirus antigen.

In certain embodiments provided herein is a monovalent or multivalent coronavirus pharmaceutical formulation suitable for intranasal administration to a human subject, comprising: an effective amount of at least $10^7$ viral particles (vp) or infectious units (ifu) (e.g., at least $1\times10^7$, or at least $1\times10^8$, or at least $1\times10^9$, or at least $1\times10^{10}$, or at least $1\times10^{11}$ vp or ifu) of rdAd vector (i.e., one or more SARS-CoV-2 vectors); and, a pharmaceutically acceptable excipient, diluent, and/or carrier. In some embodiments, the rdAd vector contains and expresses SARS-CoV-2 spike antigen, or an immunogenic fragment thereof codon optimized for the human subject; and, a pharmaceutically acceptable excipient, diluent, and/or carrier. In certain embodiments, the effective amount induces a protective immune response configured to provide seroprotection, mucosal protection or cellular protection (e.g., based on a cellular immune response such as T cells) to the human subject for at least 1 month (e.g., 28 days or 4 weeks), at least 2 months, at least 3 months, at least 6 months, at least 8 months, at least 12 months, at least 13 months, or at least 14 months against SARS-CoV-2 infection. The period of at least one month to at least 14 months can be considered a duration of protection. In certain embodiments, the protective immune response comprises a combined mucosal, humoral and/or T cell response. In embodiments, the protective immune response is induced via a single intranasal dose. In alternative embodiments, the protective immune response is induced via two or more intranasal doses, for example a prime dose followed by a boost dose about 2 to 3 weeks later.

In exemplary embodiments provided herein is a SARS-CoV-2 immunogenic composition (e.g., vaccine) pharmaceutical formulation suitable for intranasal administration to a human subject, comprising: an effective amount of at least $10^7$ viral particles (vp) or infectious units (ifu) (e.g., at least $1\times10^7$, or at least $1\times10^8$, or at least $1\times10^9$, or at least $1\times10^{10}$, or at least $1\times10^{11}$ vp or ifu) of a replication defective adenoviral vector comprising an expression cassette comprising a coding sequence encoding at least SARS-CoV-2 spike (S) protein receptor binding domain (RBD), or at least one immunogenic fragment thereof codon optimized for a human subject, wherein the composition is configured to induce neutralizing antibody to the spike protein RBD, in the human subject; and, a pharmaceutically acceptable diluent or carrier.

With respect to dosages, routes of administration, formulations, adjuvants, and uses for recombinant viruses and expression products therefrom, compositions of the invention may be used for parenteral, topical, or mucosal administration, preferably by intradermal, subcutaneous, intranasal or intramuscular routes. When mucosal administration is used, it is possible to use oral, ocular or nasal routes. In exemplary embodiments, the present immunogenic compositions (e.g., vaccine) are administered intranasally. In exemplary embodiments, the present immunogenic compositions (e.g., vaccine) are administered intranasally to the mammalian subject. In some embodiments, the SARS-CoV-2 immunogenic composition can be administered using a device such as a microneedle (e.g., as in Kim et al. EBioMedicine, 00 (2020)).

The immunogenic compositions (e.g., formulations) which comprise the adenovirus vector of interest, can be prepared in accordance with standard techniques well known to those skilled in the pharmaceutical or veterinary art. See Example 1 and 2. Such formulations can be administered in dosages and by techniques well known to those skilled in the clinical arts taking into consideration such factors as the age, sex, weight, and the route of administration. The formulations can be administered alone (i.e., as the sole active agent(s)) or can be co-administered or sequentially administered with compositions, e.g., with "other" immunogenic compositions, or attenuated, inactivated, recombinant immunogenic compositions (e.g., vaccine) or therapeutic compositions thereby providing multivalent or "cocktail" or combination compositions of the invention and methods employing them. In some embodiments, the formulations may comprise sucrose as a cryoprotectant and polysorbate-80 as a non-ionic surfactant. In certain embodiments, the formulations further comprise free-radical oxidation inhibitors ethanol and histidine, the metal-ion chelator ethylenediaminetetraacetic acid (EDTA), or other agents with comparable activity (e.g., block or prevent metal-ion catalyzed free-radical oxidation).

The compositions (e.g., formulations) may be present in a liquid preparation for mucosal administration, e.g., oral, nasal, ocular, etc., formulations such as suspensions and, preparations for parenteral, subcutaneous, intradermal, intramuscular, intravenous (e.g., injectable administration) such as sterile suspensions or emulsions. In such formulations the adenoviral vector may be in admixture with a suitable carrier, diluent, or excipient such as sterile water, physiological saline, viscosity enhancing excipients or the like. Certain specialized formulations for mucosal administration can be used, including mucoadhesives, mucosal penetrants and mucosal disruptants. The formulations can also be lyophilized or frozen. The formulations can contain auxiliary substances such as wetting or emulsifying agents, pH buffering agents, adjuvants, preservatives, and the like, depending upon the route of administration and the preparation desired. The formulations can contain at least one adjuvant compound. In exemplary embodiments, the present immunogenic compositions (e.g., vaccines) are non-adjuvanted. Standard texts, such as "REMINGTON'S PHARMACEUTICAL SCIENCE", 17th edition, 1985, incorporated herein by reference, may be consulted to prepare suitable preparations, without undue experimentation.

In some embodiments, an effective amount (e.g., an amount that induces a protective immune response) of the adenoviral vector is at least $10^7$ viral particle (vp) or infectious units (ifu) (e.g., at least $1\times10^7$, or at least $1\times10^8$, or at least $1\times10^9$, or at least $1\times10^{10}$, or at least $1\times10^{11}$ vp or ifu) of a replication deficient adenoviral vector containing and expressing coronavirus spike protein antigen, or fragment thereof, codon optimized for the human subject. As understood by one of skill in the art, codon optimization improves expression of heterologous genes in a host organism.

In preferred embodiments, an "effective amount" of adenoviral vector and/or immunogenic composition is one administered to a host in a form, dose, and/or administration regimen sufficient to induce an anti-SARS-CoV-2 immune response (e.g., humoral, mucosal and/or cell-mediated immune response) that in some embodiments can be protective from SARS-CoV-2 infection (and/or CoV disease progression). In some embodiments, such as described in the examples herein, a host to which the effective amount was administered can exhibit an induction of (e.g., the appearance of) and/or an increase in the number and/or function of anti-SARS-CoV-2 antibody-producing cells (e.g., B cells, plasma cells) that produce antibodies that bind to CoV and/or antigens (or immunogens) thereof, such as an SARS-CoV-2 specific immunoglobulin G (IgG) response. In some embodiments, such as described in the examples herein, a host to which the effective amount was administered can exhibit an induction of (e.g., the appearance of) and/or an increase in the number and/or function of cells forming an anti-SARS-CoV-2 cell-mediated response (e.g., T cells, granulocytes, natural killer (NK) cells, and the like). In some embodiments, a host to which the effective amount was administered can exhibit an induction of (e.g., the appearance of) and/or an increase in the number and/or function of anti-SARS-CoV-2 antibody-producing cells and cells forming an anti-SARS-CoV-2 cell-mediated response.

In order to determine whether a host to which the effective amount was administered exhibits exhibit an induction of (e.g., the appearance of) and/or an increase in the number and/or function of anti-SARS-CoV-2 antibody-producing cells, in some embodiments, a SARS-CoV-2-specific enzyme-linked immunosorbent assay (ELISA) can be used. As shown in the examples using a murine model, following administration of an immunogenic composition (e.g., 21 days after administration), mice can bled to provide samples for determining the presence of a systemic antibody response using a SARS-CoV-2-specific ELISA (e.g., to determine SARS-CoV-2 specific IgG response has occurred). Briefly, ELISA can be performed by coating polystyrene 96-well plates overnight at 4° C. with 1 μg/ml of SARS-CoV-2 S protein in sodium carbonate buffer (pH 9.3). Plates can be washed (e.g., three times in PBS with 0.02% Tween 20) and blocked (e.g., with non-fat dried milk) for a suitable amount of time and temperature (e.g., one hour at 37° C. with PBS, 2% BSA, and 0.02% Tween 20). Serum from hAd5-SARS-CoV-2 vaccinated mice can be serially diluted (e.g., in PBS) and incubated at an appropriate temperature and time (e.g., 37° C.), washed (e.g., four times with PBS with 0.02% Tween 20) and then incubated with a labeled secondary antibody (e.g., biotin-labeled goat anti-mouse secondary antibody) for an appropriate amount of time (e.g., one hour). The samples can then be washed and incubated with an appropriate reagent (e.g., HRP-conjugated streptavidin), and developed using an appropriate agent (e.g., tetramethylbenzidine substrate), the reaction being stopped with the addition of an appropriate reagent (e.g., 2 N H2504), and emission (450 nm) read using an microplate reader. In some embodiments, administration to a host of an effective amount of an immunogenic composition comprising an adenoviral vector encoding one or more CoV antigens (e.g. Spike protein) can result in the expression of SARS-CoV-2-specific (e.g., CoV S protein-specific) antibodies of a particular type (e.g., IgA, IgM, IgG) and/or amount (e.g., a particular reciprocal mean endpoint indicative of a response (e.g., as compared to naïve hosts). Other assay systems can also be used to determine whether an effective amount has been administered such as, for instance but without limitation, neutralizing antibody assays.

In order to determine whether a host to which the effective amount was administered exhibits exhibit an induction of (e.g., the appearance of) and/or an increase in the number and/or function of cells forming an anti-SARS-CoV-2 cell-mediated response, cell types and/or numbers and/or cytokine expression and/or functional assays can be used. For instance, in some embodiments, T cells of a host to which (or whom) an immunogenic composition was administered can be isolated and studied (e.g., physically isolated from other cells and/or as present within a biological sample such as blood). In some embodiments, an intracellular cytokine staining assay can be performed to determine the type and/or number of cells expressing a particular cytokine, and/or the level of such cytokine being expressed therein. Briefly, a biological sample (e.g., blood, spleen) of a host to which an immunogenic composition has been administered can be isolated at a particular point following administration (e.g., eight to 21 days post-administration). Cells (e.g., approximately $10^6$ cells in cell culture media (e.g., RPMI with 10% FBS and HEPES)) isolated from said biological sample(s) can then be plated in a culture plate(s) (e.g., round bottom 96 well plate), stimulated for an appropriate amount of time, temperature, etc. (e.g., 6 hours at 37° C., 5% $CO_2$) in the presence of stimulator(s) (e.g., 10 μg/ml brefeldin A and either α-CD3 (2C11 clone) or 10 μg of CoV peptide (e.g., the spike antigen SARS-CoV-2 peptide (SEQ ID NO 3) in 90% DMSO). Following CoV peptide stimulation, cells can be washed (e.g., once with phosphate-buffered saline (PBS)) and stained for the following cell surface markers indicating cell type (e.g., α-CD8-PerCP-Cy 5.5 (clone 53-6.7), α-CD3-AF700 (clone 500A2), and α-CD19-BV605 (clone 1D3)). Cells can then be fixed (e.g., using formalin), permeabilized, stained for intracellular cytokine markers (e.g., α-IFN-γ-APC (clone B27)), and analyzed by flow cytometry (e.g., using an Attune-NXT). In some embodiments, an effective amount can be an amount of immunogenic composition that raises the number of cells expressing the cytokine (e.g., IFN-γ) and/or the amount expressed by such cells.

In some embodiments, the anti-SARS-CoV-2 immune response is protective, meaning that it can protect a host from experiencing one or more of the symptoms of SARS-CoV-2 infection. In some embodiments, a protective immune response prevents SARS-CoV-2 infection, which can be demonstrated by challenge of a host to which (or whom) the effective amount was administered. In some embodiments, an immunogenic composition, and/or effective amount thereof, that is protective is a vaccine. To determine if an immunogenic composition is protective, a pre-clinical animal model can be used. For instance, in some embodiments, a SARS-CoV-2 immunogenic composition can be administered to mice susceptible to infection and disease and the mice can be challenged by live SARS-CoV-2 at a subsequent time (e.g., 7-21 days following administration) and monitored for survival and/or symptoms in comparison to the control group. Symptoms of SARS-CoV-2 infection can also be monitored, including clinical signs of disease (e.g., upper and lower respiratory symptoms). Thus, in some embodiments, in order to determine whether an hAd5-SARS-CoV-2 immunogenic composition is protective (i.e., is a vaccine), one of ordinary skill in the art can conduct an animal challenge study.

In some embodiments, an assay to determine the titer of neutralization antibody, following vaccination of an animal model, is performed such as a plaque reduction neutralization test (PRNT) or focus reduction neutralization test (FRNT) which will demonstrate induction of a protective immune response. In this instance, serum or other biological fluids is collected from post-vaccinated animals (e.g. with hAd5-SARS-CoV-2) and mixed with SARS-CoV-2 suspension and incubated for a time period to allow the serum antibodies to react with SARS-CoV-2. The serum antibody/SARS-CoV-2 mixture is poured over a confluent monolayer of host (i.e. SARS-CoV-2 permissive) cells. The surface of the cell layer is covered in a layer of agar or carboxymethyl cellulose to prevent the SARS-CoV-2 virus from spreading indiscriminately. The concentration of plaque forming units (pfu) can be estimated by the number of plaques (regions of infected cells) formed after a few days. The plaque forming units may be measured by microscopic observation, fluorescent antibodies or specific dyes that react with infected cells. The concentration of serum to reduce the number of plaques by 50% compared to the serum free virus gives the measure of how much neutralization antibody is present or how effective it is (i.e. protective). This measurement is denoted as the $PRNT_{50}$ value. Additionally, in an FRNT assay, virus may be visualized using antibody labeling to similarly calculate the $FRNT_{50}$. Other methods using a pseudo-virus neutralization assay or an ACE-2 binding inhibition assay can be used to quantity the presence of neutralizing antibodies against SARS-CoV-2.

In certain embodiments, the present immunogenic composition (e.g., vaccine) comprises an effective amount of about $10^7$ viral particles (vp) or infectious units (ifu) (e.g., at least $1\times10^7$, or at least $1\times10^8$, or at least $1\times10^9$, or at least $1\times10^{10}$, or at least $1\times10^{11}$ vp or ifu) of a replication deficient adenoviral vector. In exemplary embodiments, the present immunogenic composition (e.g., vaccine) comprises an effective amount of about $10^8$ viral particles (vp) of a replication deficient adenoviral vector. In certain other exemplary embodiments, the present immunogenic composition (e.g., vaccine) comprises an effective amount of about $10^9$ viral particles (vp) of a replication deficient adenoviral vector. In certain other exemplary embodiments, the present immunogenic composition (e.g., vaccine) comprises an effective amount of about $10^{10}$, or greater, viral particles (vp) of a replication deficient adenoviral vector. In certain other exemplary embodiments, the present immunogenic composition (e.g., vaccine) comprises an effective amount of about $10^{11}$, or greater, viral particles (vp) of a replication deficient adenoviral vector. In some embodiments, the mammal is a companion or domesticated or food-producing or feed-producing or livestock or game or racing or sport animal such as a cow, a dog, a cat, a goat, a sheep, a rabbit, or a pig or a horse, or even fowl such as turkey, ducks or chicken. In exemplary embodiments the mammalian subject is a human.

Methods of Use

Provided herein is a method for inducing an immune response against coronavirus, the method comprising administering an effective amount of the SARS-CoV-2 immunogenic composition to a mammalian subject. In certain embodiments, is provided a method for transmucosal administration of a pharmaceutical dose of a present therapeutic/immunogenic composition (e.g., vaccine) configured to induce an immune response (e.g., a protective immune response as a vaccine) via intranasal administration. In certain embodiments the present immunogenic compositions comprise a replication defective adenoviral vector comprising an expression cassette comprising a coding sequence encoding at least one coronavirus antigen or at least one immunogenic fragment thereof, wherein the coding sequence encodes at least one or more B cell epitopes, one or more CD8+ T cell epitopes, and/or one or more CD4+ T cell epitopes. In exemplary embodiments the mammalian subject is a human being and the coronavirus antigen is from SARS-CoV-2. In some embodiments, the mammalian subject is a human being infected by SARS-CoV-2 (e.g., a hospitalized human being). In some embodiments, the SARS-CoV-2 immunogenic composition can be used to treat SARS-CoV-2 infection (e.g., in such an infected and/or hospitalized human being).

In some embodiments, the methods of this disclosure can include administration of one or more immunogenic compositions of this disclosure to, in a mammal, preferably a human being: induce an anti-SARS-CoV-2 immune response, preferably statistically significant anti-SARS-CoV-2 immune response; induce a protective and/or curative anti-SARS-CoV-2 immune response; induce an anti-SARS-CoV-2 immune response with an acceptable safety profile; confer prophylactic therapy against SARS-CoV-2; reduce the rates of intensive care unit (ICU) admission and mechanical ventilation in patients with early onset COVID-19; reduce the severity of COVID-19 in patients with early onset COVID-19 who require hospitalization; inhibit, suppress and/or prevent the development of a "cytokine storm" during infection by SARS-CoV-2 (in preferred embodiments, co-administering one or more of immunogenic compositions with one or more anti-cytokine reagents); induce significant decreases (e.g., as compared to placebo controls) in IL-1α, IL-6, and/or IL-12p70, and/or pulmonary interstitial inflammation in a patient having COVID-19 (i.e., a patient infected with SARS-CoV-2); accelerate the time to clinical improvement and/or recovery in patients (e.g., hospitalized patients) infected with SARS-CoV-2; induce anti-SARS-CoV-2 neutralizing antibodies (in preferred embodiments, IgG and/or IgA); induce anti-SARS-CoV-2 T cell immunity (e.g., systemic and/or mucosal); induce bone marrow and lung resident memory antibody secreting cells; induce an immune response (e.g., neutralizing antibodies and/or T cell immunity) that is effective and/or can be detected for at least 4 months, for at least about 5 months, at least about 6 months, at least about 7 months, at least about 8 months, at least about 9 months, at least about 10 months, at least about 11 months, or at least about 12 months; and/or, provide for repeated administration (e.g., as a seasonal vaccine administered about once every 11-14 months) without inducing a significant immune response against the adenoviral vector itself.

Dosage of the immunogenic composition (e.g., Ad-vector SARS-CoV-2 vaccine) when used with or without an adjuvant may range from about $10^7$ to about $10^{12}$ infectious unit or plaque forming unit (ifu or pfu), or the dosage unit may be a viral particle (vp), wherein 1 vp equals about 1-100 ifu or pfu. In one embodiment the dose of Ad-vector SARS-CoV-2 immunogenic composition or vaccine administered to the mammalian subject is about, or at least about, $10^7$ vp or infectious units (ifu) (e.g., at least $1\times10^7$, or at least $1\times10^8$, or at least $1\times10^9$, or at least $1\times10^{10}$, or at least $1\times10^{11}$ vp or ifu). In another aspect the dose of Ad-vector SARS-CoV-2 immunogenic composition or vaccine administered to the mammalian subject is about, or at least about, $10^8$ vp. In yet another aspect, the dose of Ad-vector SARS-CoV-2 immunogenic composition or vaccine administered to the mammalian subject is about, or at least about, $10^9$ vp. In another aspect the dose of Ad-vector SARS-CoV-2 immunogenic composition or vaccine administered to the mammalian subject is about, or at least about, $10^{10}$ vp. In another aspect the dose of Ad-vector SARS-CoV-2 immunogenic composition or vaccine administered to the mammalian subject is about, or at least about, $10^{11}$ vp. In another aspect the dose of Ad-vector SARS-CoV-2 immunogenic composition or vaccine administered to the mammalian subject is about, or at least about, $10^{12}$ vp.

One of skill in the art understands that an effective dose in a mouse may be scaled for larger animals such as a human, dogs, pigs, non-human primates, minks, ferrets, cats, horses/equines, etc.; and, these larger animals are subjects for administration in accordance with this disclosure. In that way, through allometric scaling (also referred to as biological scaling) a dose in a larger animal may be extrapolated from a dose in a mouse to obtain an equivalent dose based on body weight or body surface area of the animal.

In certain embodiments, non-invasive administration of the Ad-vector SARS-CoV-2 immunogenic composition or vaccine includes, but is not limited to, topical application to the skin, and/or intranasal and/or mucosal and/or perlingual and/or buccal and/or oral and/or oral cavity administration. Dosage forms for the application of the Ad-vector SARS-CoV-2 immunogenic composition or vaccine may include liquids, ointments, powders and sprays. The active component may be admixed under sterile conditions with a physiologically acceptable carrier and any preservative, buffers, propellants, or absorption enhancers as may be needed.

In certain embodiments provided herein is a method for transmucosal administration of a therapeutic dose of a non-replicating viral vectored immunogenic composition (e.g., vaccine) to a human subject, wherein the method comprises administering intranasally to the human subject the immunogenic composition (e.g., vaccine) comprising an effective amount of at least $10^7$ viral particle (vp) or infectious units (ifu) (e.g., at least $1\times10^7$, or at least $1\times10^8$, or at least $1\times10^9$, or at least $1\times10^{10}$, or at least $1\times10^{11}$ vp or ifu) of replication deficient adenovirus vector that contains and expresses a heterologous SARS-CoV-2 antigen codon optimized for the mammalian subject; whereby the therapeutic dose administered transmucosally induces a protective immune response.

In embodiments, for (trans)mucosal administration compositions may be in a form and dispensed by a squeeze spray dispenser, pump dispenser, multi-dose dispenser, dropper-type dispenser or aerosol dispenser. Such dispensers may also be employed to deliver the composition to oral or oral cavity (e.g., buccal or perlingual) mucosa. Aerosols are usually under pressure by means of a hydrocarbon. Pump dispensers may preferably dispense a metered dose or, a dose having a particular particle size. The distribution of aerosol particle/droplet size can be expressed in terms of either: the mass median aerodynamic diameter (MMAD)—the droplet size at which half of the mass of the aerosol is contained in smaller droplets and half in larger droplets; volumetric mean diameter (VIVID); mass median diameter (MMD); or the fine particle fraction (FPF)—the percentage of particles that are <5 um in diameter. These measurements may be made by impaction (MMD and MMAD) or by laser (VIVID). For liquid particles, VMD, MMD and MMAD may be the same if environmental conditions are maintained, e.g., standard humidity. However, if humidity is not maintained, MMD and MMAD determinations will be smaller than VMD due to dehydration during impactor measurements. For the purposes of this description, VMD, MMD and MMAD measurements are considered to be under standard conditions such that descriptions of VMD, MMD and MMAD will be comparable. Particles having a mass median aerodynamic diameter (MMAD) of greater than about 5 microns generally do not reach the lung; instead, if administered orally they tend to impact the back of the throat and are swallowed and possibly orally absorbed; and, particles of this size administered nasally will lodge in the nasal mucosa. Particles having diameters of about 1 to about 5 microns are small enough to reach the upper- to mid-pulmonary region (conducting airways) but are too large to reach the alveoli. Smaller particles, i.e., about 0.5 to about 2 microns, are capable of reaching the alveolar region. Particles having diameters smaller than about 0.5 microns can also be deposited in the alveolar region by sedimentation, although very small particles may be exhaled. Depending on whether the desire is to mucosally administer to the nasal mucosa or into the upper-to-mid pulmonary region or into the alveoli, the skilled person can achieve any or all of these targets from this disclosure and the knowledge in the art. In addition, for intranasal administration an atomizer device, such as a LMA MAD300 from Teleflex LLC (Intranasal Mucosal Atomization Device LMA™ #MAD300 Nasal Device Without Syringe, 1.65 inch length, and 0.17 tip diameter) can advantageously be employed. An aerosol device or dispenser such as an atomizer that delivers a mist having a typical particle size of about 30 to about 100 microns to the olfactory mucosa or nasal mucosal membranes can advantageously be employed in the practice of the invention, and advantageous particle sizes of droplets of formulations of this disclosure for the practice of the invention can be from about 30 to about 100 microns, e.g., about 30 or about 40 or about 50 to about 60 or about 70 or about 80 or about 90 or about 100 microns, for intranasal administration.

In embodiments, the present SARS-CoV-2 pharmaceutical formulation is used to provide protection against seasonal coronavirus. In certain other embodiments, the present CoV pharmaceutical formulation is used to provide protection against pandemic SARS-CoV-2. In certain other embodiments, the present SARS-CoV-2 pharmaceutical formulation is used to provide protection against SARS-CoV-2. In embodiments, the seroprotection lasts at least about 1 month, 2 months, 4 months, 6 months, 8 months, 10 months, 12 month or at least about 13 months.

In some embodiments, is provided a method for inducing an immune response against coronavirus, the method comprising administering a single dose of a present immunogenic composition/formulation/dosage to a mammalian subject (e.g. human). In certain embodiments, the method comprises intranasal administration of an effective amount of the immunogenic composition to the mammalian subject, wherein the immune response provides protection against challenge with SARS-CoV-2. In certain embodiments, is provided a method of inducing a combined mucosal, humoral and/or T cell protective immune response in a human subject against coronavirus comprising administering intranasally to a human subject a single dose of the SARS-CoV-2 pharmaceutical formulation (immunogenic composition), or a pharmaceutical dosage thereof, wherein the administration induces serum antibodies, mucosal antibodies and T cells against coronavirus. In embodiments, the human subject is seroprotected at least about 1 month, 2 months, 4 months, 6 months, 8 months, 10 months, 12 month or at least about 13 months. In certain embodiments, the human subject is seroprotected for at least about 9 months.

In alternative embodiments, is provided a method for inducing an immune response against coronavirus wherein the method comprises administering at least a prime and boost dose of a present immunogenic composition/formulation/dosage. In certain embodiments, the boost dose is administered about 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks or 52 weeks after administration of the prime dose.

In embodiments, the prime boost doses are homologous, meaning they are the same formulation. In certain embodiments, the methods and compositions provided include administering a heterologous immunogenic composition or vaccine prime dose and boost dose leading to an induction of an immune response (e.g., T cell, humoral and/or mucosal) where "heterologous" means a prime dose that is different than a boost dose, provided both comprise at least one, or more, of the SARS-Cov-2 antigen epitopes. In certain embodiments, that means a prime dose and boost dose wherein the antigen/immunogens/peptides are presented to the immune system via different delivery carriers and/or vectors. As used herein, a "heterologous dosing regimen", means a prime dose and boost dose wherein the antigen/immunogens/peptides are presented to the immune system via different delivery carriers and/or vectors. For example, in the instant invention a first composition (as either a prime dose or a boost dose) comprises a viral vectored antigen or immunogen, and a second composition (as either a prime dose or a boost dose) comprises fluorocarbon-linked peptides, wherein the peptide comprises one or more T cell epitopes in common with the viral vectored antigen or immunogen. In other words, in certain embodiments, the present immunogenic composition or vaccine combination is two different T cell inducing immunogenic composition or vaccine compositions, wherein each composition induces antigen specific CD8+ T cells against the same antigen. In alternative embodiments, a first composition (as either a prime dose or a boost dose) comprises a viral vectored antigen or immunogen, and a second composition (as either a prime dose or a boost dose) comprises an RNA immunogenic composition or vaccine composition such as a composition comprising a modified mRNA, a unmodified mRNA or a self-amplifying mRNA formulated in liposomes or lipid nanoparticles, a DNA composition administered by electroporation or using a lipid based formulation, a live attenuated immunogenic composition or vaccine composition, a protein-based composition formulated or not with an adjuvant or delivery system, a killed immunogenic composition or vaccine composition, a different adenoviral vectored immunogenic composition or vaccine composition such as HAdV-1 to 57, a simian adenovirus or a non-adenoviral vector such as but not limited to an adeno-associated virus (AAV), a lentivirus or a poxvirus. The first composition can be administered first to prime the immune response locally or systemically and the second immunogenic composition or vaccine such as the adenovirus can be administered mucosally as a booster to "pull" the primed immune cells locally and re-stimulated them in an antigen specific manner.

In embodiments, the prime and boost dose are administered at least 7 days apart, at least 14 days apart, or longer. In embodiments, the prime dose and boost dose are administered about 7 days apart, about 14 days apart, about 20 days apart, about 25 days apart, about 30 days apart, about 35 days apart, about 40 days apart, about 45 days apart, about 50 days apart, about 55 days apart, about 60 days apart or about 65 days apart. Advantageously, the doses are administered about 40 days apart, about 41 days apart, about 42 days apart, about 43 days apart, about 44 days apart, about 45 days apart, about 46 days apart, about 47 days apart, about 48 days apart, about 49 days apart or about 50 days apart. In certain embodiments, the prime dose and boost dose are administered about 1 week apart, about 2 weeks apart, about 3 weeks apart, about 4 weeks apart, about 5 weeks apart, about 6 weeks apart, about 7 weeks apart, about 8 weeks apart, about 9 weeks apart, about 10 weeks apart, about 11 weeks apart or about 12 weeks apart. In certain other embodiments, the prime dose and boost dose are administered about 1 month apart, about 2 months apart, about 3 months apart, about 4 months apart, about 5 months apart, about 6 months apart, about 7 months apart, about 8 months apart, about 9 months apart, about 10 months apart, about 11 months apart, or about 12 months apart.

In embodiments, the first or second immunogenic composition or vaccine composition is administered as a prime and boost dose administered at least 7 days apart, at least 14 days apart, or longer. In embodiments, the prime dose and boost dose are administered about 7 days apart, about 14 days apart, about 20 days apart, about 25 days apart, about 30 days apart, about 35 days apart, about 40 days apart, about 45 days apart, about 50 days apart, about 55 days apart, about 60 days apart or about 65 days apart. Advantageously, the doses are administered about 40 days apart, about 41 days apart, about 42 days apart, about 43 days apart, about 44 days apart, about 45 days apart, about 46 days apart, about 47 days apart, about 48 days apart, about 49 days apart or about 50 days apart. In certain embodiments, the prime dose and boost dose are administered about 1 week apart, about 2 weeks apart, about 3 weeks apart, about 4 weeks apart, about 5 weeks apart, about 6 weeks apart, about 7 weeks apart, about 8 weeks apart, about 9 weeks apart, about 10 weeks apart, about 11 weeks apart or about 12 weeks apart. In certain other embodiments, the prime dose and boost dose are administered about 1 month apart, about 2 months apart, about 3 months apart, about 4 months apart, about 5 months apart, about 6 months apart, about 7 months apart, about 8 months apart, about 9 months apart, about 10 months apart, about 11 months apart, or about 12 months apart.

In some embodiments, rdAd anti-SARS-CoV-2 vectors (e.g., a SARS-CoV-2 immunogenic composition (which can include more than one type of rdAd anti-SARS-CoV-2 vector)) can be administered with one or more anti-cytokine reagents. As shown in Example 2, administration of AdE to mice was shown to decrease the expression of cytokines known to be involved in the progression and symptoms of infectious diseases caused by viruses such as influenza. For instance, AdE can cause an increase in the expression of monocyte chemoattractant protein (MCP-1 (CCL2)), interferon gamma (IFN-γ), and RANTES (CCL5) upon administration to non-infected mammals, which can be accompanied by a decrease in IL-12 expression. Three days after exposure to influenza, animals to which AdE was administered were found to exhibit decreased expression of IL-1α, IL-6, IL-12, MCP-1, with a significant decrease of IL-1α, and IL-12. Six (6) days after exposure to influenza, the animals exhibited decreased expression of IL-5, IL-6, IL-12, IL-17, MCP-1 and GM-CSF, and increased expression of macrophage inflammatory protein 1 alpha (MIP-1α (CCL3)) and RANTES (CCL5). These results are consistent with the development of a "cytokine storm" during infection by SARS-CoV-2. In some embodiments, then, to prevent and/or treat SARS-CoV-2 infection, a SARS-CoV-2 immunogenic composition can be administered to a mammal, such as a human being, with one or more anti-cytokine reagent(s) (i.e., co-administered). Such co-administration can be carried out as single mixture (e.g., one or more anti-cytokine reagents can be included in the SARS-CoV-2 immunogenic composition), or as separate compositions administered essentially simultaneously and/or at or near the same anatomical site, or at different anatomical sites by an appropriate route (e.g., intranasal administration of the SARS-CoV-2 immunogenic composition and intradermal or intravenous administration of the one or more anti-cytokine reagent(s)), and in an effective amount that can vary for each type of anti-cytokine reagent (and as is known in the art). In some embodiments, the SARS-CoV-2 immunogenic composition can be administered as a single dose, as can the one or more anti-cytokine reagents. In some embodiments, the one or more anti-cytokine reagents can be administered multiple times (e.g., any of about 7, 14, 21 days, or any of about one, two or three months) after administration of the SARS-CoV-2 composition including, in some embodiments, an initial administration with the SARS-CoV-2 composition. Exemplary anti-cytokine reagents for administration to a mammal to prevent and/or treat SARS-CoV-2 can therefore include, but are not limited to, one or more anti-IL-1α reagent(s), one or more anti-IL5 reagent(s), one or more anti-IL-6 reagent(s), one or more anti-IL-12 reagent(s), one or more anti-IL-17 reagent (s), one or more anti-MCP-1 reagent(s), one or more anti-TNF-α reagent(s), one or more anti-GM-CSF reagent(s), and/or one or more anti-RANTES reagent(s). In some embodiments, the one or more anti-cytokine reagents would not include one or more anti-MIPα reagent(s) and/or one or more anti-RANTES reagent(s). Exemplary anti-cytokine reagents that can be used as described herein can include, for example, any of those shown in Table 10.

TABLE 10

| Cytokine | Exemplary Anti-Cytokine Reagents |
|---|---|
| IL-1α | anakinra (Kineret ®), canakinumab (Ilaris ®), rilonacept (Arcalyst ®) |
| IL-5 | mepolizumab (GlaxoSmithKline); benralizumab (Fasenra) |
| IL-6 | tocilzumab (Actemra), sarilumab (Kevzara), siltuximab (Sylvant) |
| IL-12 | briakinumab (ABT-874, Abbott); ustekinumab |
| IL-17 | brodalumab (Siliq; Amgen), ixekizumab (Taltz ®, Eli Lilly), secukinumab (Cosentyx; Novartis) |
| TNF-α | inflixibmab (Remicade), adalimumab (Humira), certolizumab pegol (Cimzia), golimumab (Simponi), etanercept (Enbrel), thalidomide (Immunoprin), lenalidomide (Revlimid), pomalidomide (Pomalyst, Imnovid), a xanthine derivative (e.g., pentoxifylline), bupropion |
| GM-CSF | otilimab (MOR103, GSK3196165) |

In some embodiments, one or more additional anti-SARS-CoV-2 agents can also be administered to the subject(s) before, essentially simultaneously, or after administration of SARS-CoV-2 immunogenic composition such as, for instance, chloroquine (e.g., pharmaceutical salt and/or derivative thereof; e.g., hydroxychloroquine 400 mg per day for 5 days or 200 mg three times per day for 10 days) and/or azithromycin (e.g., 500 mg on first day followed by four daily 250 mg doses) and/or remdesivir (e.g., 200 mg initial followed by 100 mg daily doses) and/or one or more anti-inflammatories (e.g., prednisone, dexamethasone) and/or any other suitable reagent. Other administration/dosing schemes, anti-cytokine reagents, combinations thereof, and combinations with other anti-SARS-CoV-2 agents as are available to those of ordinary skill in the art can be suitable for use as disclosed herein, as would be understood by those of ordinary skill in the art.

In some embodiments, a subject (e.g., human being) can be tested for coronavirus infection by a suitable technique (e.g., polymerase chain reaction (PCR), nasal swab to detect viral particles). An immunogenic composition comprising one or more rdAd anti-SARS-CoV-2 vectors (e.g., as viral particles; SARS-CoV-2 immunogenic composition) can then be administered to individuals that test positive for coronavirus infection. Preferably, such administration can be completed within seven to ten days after initial exposure to the coronavirus. In some embodiments, a SARS-CoV-2 immunogenic composition comprising one or more rdAd anti-SARS-CoV-2 vectors (e.g., as viral particles) can be administered to individuals at high risk for infection and/or symptoms (e.g., respiratory symptoms, death) such as immunocompromised individuals and/or suffering from another disease condition (e.g., kidney failure), and/or persons in high risk situations (e.g., travelers to pandemic areas, enclosed spaces such as cruise ships), whether or not such individuals have tested positive for coronavirus infection.

In some embodiments, the compositions disclosed herein can be administered to a host comprising nostrils, wherein such nostrils are tilted upwards (i.e., the dorsal position), to generate a strong immunogenic response via intranasal administration. Other administration and dosing strategies are also contemplated herein as would be understood by those of ordinary skill in the art.

In some embodiments, this disclosure provides an immunogenic composition comprising a replication defective adenoviral (rdAd) vector, the rdAd vector: a) lacking a coding sequence encoding an exogenous, non-adenoviral, antigen (e.g., AdE); b) comprises an expression cassette comprising a coding sequence encoding at least one SARS-CoV-2 antigen, optionally wherein said antigen comprises a SARS-CoV-2 spike (S) protein receptor binding domain (RBD); c) comprises an expression cassette comprising a coding sequence encoding at least one antigen of an infectious agent other than SARS-CoV-2 (e.g., AdD); d) a combination of the vectors of a) and b), wherein the vectors are administered together or separately; e) a combination of the rdAd vectors of b) and c), wherein the vectors are administered together or separately; f) a combination of any of the rdAd vectors of any of a), b), or c) wherein the rdAd vectors are administered together or separately; and/or, g) a combination of two different types of rdAd vectors of b), wherein each type of rdAd vector comprises an expression cassette encoding at least one SARS-CoV-2 antigen different from that encoded by the other types of rdAd vectors in the combination, wherein the rdAd vectors are administered together or separately; wherein said immunogenic composition is configured to induce neutralizing antibody and/or cellular immune response against SARS-CoV-2 in a mammalian subject to which said immunogenic composition is administered. In some embodiments, the immunogenic composition can comprise a combination of any two of the rdAd vectors of a)-c), such as in a two-part composition comprising at least one composition comprising rdAd vectors of a)-c) and at least a second composition comprising a different rdAd vector of a)-c). In some embodiments, the expression cassette comprises a coding sequence encoding at least one SARS-CoV-2 antigen selected from: the coding sequence for spike (S) protein or S1 domain of the spike protein; a sequence presented in SEQ ID NO: 3, or a sequence having at least 80% homology to SEQ ID NO: 3; comprises at least amino acids 331 to 527 of SEQ ID NO: 3; encodes a spike protein RBD sequence comprises one or more of the following residues (the numbering corresponding to SEQ ID NO: 3): L455, F486, Q493, S494 and/or N501, preferably in some embodiments Q493 and N501, preferably in some embodiments a residue selected from Y455, F455 or S455, preferably in some embodiments a residue selected from L486 or P486, preferably in some embodiments a residue selected from N493, R493 or K493, preferably in some embodiments a residue selected from D494 or G494, preferably in some embodiments a residue selected from T501 or S501; comprises an amino acid sequence of SEQ ID NO: 12, SEQ ID NO: 13, SEQ ID NO: 14, preferably SEQ ID NO: 15, SEQ ID NO: 16 or SEQ ID NO: 17, SEQ ID NO: 446; any of SEQ ID NOS: 412-417 and SEQ ID NOS: 438-445, and SEQ ID NOS: 475-476 or 460; or an immunogenic fragment thereof; comprises an amino acid sequence of SEQ ID NO: 16 or SEQ ID NO: 17, wherein amino acid 455 is selected from Y, F, L or S; amino acid 486 is selected from L, F or P; amino acid 493 is selected from N, Q, R or K; amino acid 494 is selected from D, G or S; and, amino acid 501 is selected from T, S or N; a coding sequence encoding one or more of SARS-CoV-2 structural proteins envelope (E), membrane (M) or nucleocapsid (N). In some embodiments, the expression cassette comprises a coding sequence for a modified version of SEQ ID NO: 411 comprising: one or more substitutions of any one or more of amino acids 333-388, 390-395, 397-399, 401-411, 413-415, 417-419, 424, 426-435, 437, 439-442, 444-446, 449, 450, 452, 453, 455-463, 465, 467-473, 475-479, 481-486, 490, 491, 493-495, 499-510, and/or 513-526; one or more substitutions of any one or more of amino acids 367, 403, 417, 439, 446, 449, 452, 453, 455, 456, 470, 473, 475, 476, 477, 478, 484, 486, 490, 493, 494, 495, 496, 499, 500, 501, 502, 503, 504, and/or 505; and/or, one or more substitutions selected from the group consisting of amino acid 367 (V) by F, I, L S or A, amino acid 403 (R) by K or S, 417 (K) by N or T; amino acid 439 (N) by K, amino acid 446 (G) by V, S or A; amino acid 449 (Y) by N; amino acid 452 (L) by L, M or Q, amino acid 453 (Y) by F; amino acid 455 (L) by F; amino acid 456 (F) by L; amino acid 470 (T) by I, A or N, amino acid 473 (Y) by V; amino acid 475 (A) by V; amino acid 476 (G) by S or A; amino acid 477 (S) by N, R, T, G, A or I; amino acid 476 (G) by S or A, amino acid 477 (S) by N, R, T, G, A or I, amino acid 478 (T) by I, K, R or A, amino acid 484 (E) by Q, K, D, A or R; amino acid 486 (F) by L or S; amino acid 490 (F) by L or S, amino acid 493 (Q) by L or R; amino acid 494 (S) by P or L, amino acid 495 (Y) by N or F; amino-acid 496 (G) by V or S, amino acid 499 (P) by H, S or R, amino acid 500 (T) by I; amino acid 501 (N) by Y, T or S; amino acid 502 (G) by R, D or C; amino acid 503 (V) by L, I or F; and, amino acid 504 (G) by V, D or S amino acid 505 (Y) by H, E, W or C. In some embodiments, the at least one antigen of an infectious agent other than SARS-CoV-2 is derived from an influenza virus. In some embodiments, the immunogenic composition is further configured to induce a combined mucosal, humoral and T cell protective immune response against SARS-CoV-2. In some embodiments, the coding sequence encodes at least one or more B cell epitopes, one or more CD8+ T cell epitopes, and/or one or more CD4+ T cell epitopes. In some embodiments, the coding sequence is codon optimized for a mammalian subject. In some embodiments, the immunogenic composition induces the production of neutralizing antibodies seroprotective against SARS-CoV-2 infection in a mammalian subject, optionally wherein the mammalian subject is a human being. In some embodiments, the replication defective adenoviral vector (rdAd) is a human adenovirus, optionally Ad5 or Ad26. In some embodiments, the rdAd is a primate adenovirus, a chicken adenovirus, or a porcine or swine adenovirus. In some embodiments, the rdAd is an E1, E3, and/or E4 deleted or disrupted adenovirus.

In some embodiments, this disclosure provides pharmaceutical formulations comprising an effective amount of such immunogenic composition (i.e., a composition comprising one or more rdAd anti-SARS-CoV-2 vectors) and, a pharmaceutically acceptable diluent or carrier, optionally wherein the diluent is phosphate-buffered saline. In some embodiments, the pharmaceutical formulation is configured for non-invasive administration, and/or for intranasal administration to the mammalian subject. In some embodiments, administration of the pharmaceutical formulation to the mammalian subject induces a protective immune response in the mammalian subject, optionally a combined mucosal, humoral and T cell protective immune response. In some embodiments, the pharmaceutically acceptable carrier is in a spray or aerosol form. In some embodiments, the effective amount is at least $10^7$ viral particles (vp), at least $10^8$ viral particles (vp), or at least $10^9$ viral particles (vp) (of the rdAd anti-SARS-CoV-2 vector(s)). In some embodiments, the pharmaceutical formulation is configured as a single intranasal dose. In some embodiments, the pharmaceutical formulation is configured as two or more intranasal doses. In some embodiments, this disclosure provides coronavirus pharmaceutical formulation suitable for a single dose intranasal administration to a human subject, comprising: an effective amount of at least $10^7$ viral particle (vp) or infectious units (ifu) (e.g., at least $1\times10^7$, or at least $1\times10^8$, or at least $1\times10^9$, or at least $1\times10^{10}$, or at least $1\times10^{11}$ vp or ifu) of the immunogenic composition comprising at least one replication defective adenoviral vector comprising an expression cassette comprising a coding sequence encoding at least SARS-CoV-2 spike (S) protein receptor binding domain (RBD), or at least one immunogenic fragment thereof, wherein the effective amount induces a combined mucosal, humoral and T cell protective immune response; and, a pharmaceutically acceptable diluent or carrier. In some embodiments, the formulation is configured to provide seroprotection to the human subject for at least 6 months or preferably 9 months against SARS-CoV-2. In some embodiments, this disclosure provides a pharmaceutical dosage for intranasal administration, comprising a pharmaceutical acceptable carrier in a spray or aerosol form admixed with an immunogenic composition disclosed herein, wherein the dosage is configured for intranasal administration to non-invasively induce a protective immune response against SARS-CoV-2. In some embodiments, the immunogenic composition comprises an effective amount of at least $10^7$ viral particles (vp), at least $10^8$ viral particles (vp), or at least $10^9$ viral particles (vp) of the rdAd anti-SARS-CoV-2 vector(s). In some embodiments, the effective amount induces a combined mucosal, humoral and T cell protective immune response against a coronavirus, preferably SARS-CoV-2. In some embodiments, the pharmaceutical dosage formulation is configured as two or more doses to induce a protective immune response against SARS-CoV-2.

In some embodiments, this disclosure provides methods for inducing an immune response against coronavirus, preferably SARS-CoV-2, the method comprising administering an effective amount of an immunogenic composition (or formulation or dosage form) disclosed herein to a mammalian subject, preferably wherein the immune response is protective against SARS-CoV-2. In some embodiments, the method comprises intranasal administration of an effective amount of an immunogenic composition disclosed herein to a mammalian subject, wherein the immune response provides protection against challenge with SARS-CoV-2. In some embodiments, this disclosure provides methods for inducing a combined mucosal, humoral and/or T cell protective immune response in a human subject against coronavirus comprising: administering intranasally to a human subject a single dose of a coronavirus, preferably SARS-CoV-2, pharmaceutical formulation or dosage disclosed herein, wherein the administration induces serum antibodies, mucosal antibodies and T cells against SARS-CoV-2, optionally whereby the human subject is seroprotected for at least about 6 months or preferably for at least about 9 months. Preferably, the seroprotection lasts for at least 12 months, at least 13 months or at least 14 months.

In preferred embodiments, the rdAd anti-SARS-CoV-2 vector comprises SEQ ID NO: 15 (or comprising a nucleic acid sequence encoding SEQ ID NO: 15), preferably within an expression cassette. In preferred embodiments, the rdAd anti-SARS-CoV-2 vector comprises an expression cassette comprising a SARS-CoV-2 spike protein Receptor Binding Domain (RBD) of the S1 domain, pTA signal sequence (italics) and long flanking sequences (underlined), as illustrated in FIG. 19. Variants of SEQ ID NO: 15 are also contemplated. For instance, any of the leader and flanking sequences shown in FIG. 19 can be deleted (i.e., not included) or substituted by other leader and/or flanking sequences. In preferred embodiments, the rdAd anti-SARS-CoV-2 vector comprising SEQ ID NO: 15 (or comprising a nucleic acid sequence encoding SEQ ID NO: 15), or a variant thereof, can be administered as a pharmaceutical composition comprising the effective amount is at least $10^7$ viral particles (vp), at least $10^8$ viral particles (vp), at least $10^9$ viral particles (vp), at least $10^{10}$ viral particles (vp), or at least $10^{11}$ viral particles (vp); preferably administered intranasally (preferably wherein the mammal (preferably a human being) is in the supine position during administration); and preferably as a single administration (dose), but in some embodiments including at least two administrations (doses) separated from one another by time (e.g., 7-21 days). In preferred embodiments, the administration induces the production of anti-SARS-CoV-2 neutralizing antibodies and/or an anti-SARS-CoV-2 cellular response (e.g., T cells) that provides protection (e.g., in some preferred embodiments seroprotection) for at least about 6, 9, 10, 11, 12, 13, or months. In preferred embodiments, administration of the rdAd anti-SARS-CoV-2 vector comprising SEQ ID NO: 15 (or comprising a nucleic acid sequence encoding SEQ ID NO: 15) results in protection against infection by SARS-CoV-2, accelerates recovery from infection by SARS-CoV-2, slows and/or reverses clinical worsening in a patient infected by SARS-CoV-2, and/or reduces or eliminates the need for hospitalization and/or care in in ICU unit for a patient infected by SARS-CoV-2.

In some embodiments, this disclosure provides methods such as those above, further comprising administering one or more anti-cytokine reagents (see, e.g., Table 4) to the human being to prevent and/or treat SARS-CoV-2, optionally wherein the one or more anti-cytokine reagents include one or more anti-IL-1α reagent(s), one or more anti-IL5 reagent(s), one or more anti-IL-6 reagent(s), one or more anti-IL-12 reagent(s), one or more anti-IL-17 reagent(s), one or more anti-MCP-1 reagent(s), one or more anti-TNF-α reagent(s), one or more anti-GM-CSF reagent(s), and/or one or more anti-RANTES reagent(s). In some embodiments, the one or more anti-cytokine reagents does not include one or more anti-MIPα reagent(s) and/or one or more anti-RANTES reagent(s). In some embodiments, the one or more anti-cytokine reagent(s) are co-administered substantially with the effective amount of the immunogenic composition. In some embodiments, the one or more anti-cytokine reagent(s) are not administered substantially with the effective amount of the immunogenic composition. In some embodiments, the immunogenic composition is administered to the mammal once and the one or more anti-cytokine reagent(s) are administered multiple times. In some embodiments, the immunogenic composition is co-administered to the mammal with the one or more anti-cytokine reagent(s), and the one or more anti-cytokine reagent(s) are subsequently administered to the mammal. In some embodiments, this disclosure provides methods for treating and/or inhibiting (e.g., ameliorating) the symptoms of a respiratory viral infection in a mammal, said respiratory viral infection causing elevated expression of interleukin-6 (IL-6), interleukin-1-alpha (IL-1α) and/or interleukin-12 (IL-12) in the lung of said mammal which can cause deleterious effects in a host. In some embodiments, such methods comprise intranasally administering an effective amount of an E1 and E3 deleted adenoviral vector to the subject, whereby expression of IL-6, IL-1α, and/or IL-12 in the lung is reduced thereby alleviating said symptoms for up to about 28 days following administration of the vector. In some embodiments, such methods cause the expression of monocyte chemoattractant protein 1 (MCP-1), tumor necrosis factor alpha (TNF-α), granulocyte macrophage colony stimulating factor (GM-CSF), RANTES, and/or IL-17 are reduced in the lung following administration of the vector. In some embodiments, the expression of macrophage inflammatory protein 1 alpha (MIP-1α) and/or RANTES are not reduced following administration of the vector. In some embodiments, this disclosure provides methods for inducing an anti-viral immune response in a mammalian subject in need thereof with, or at risk of, a respiratory viral infection, the method comprising: intranasal administration of an effective amount of an E1 and E3 deleted adenoviral vector to the subject, wherein the anti-viral immune response generates increased expression of monocyte chemoattractant protein 1 (MCP-1) and/or interferon alpha (IFN-γ) following the administration step. In some embodiments of such methods, the mammalian subject (e.g., human being) is infected by SARS-CoV-2 (e.g., in the hospital being treated for SARS-CoV-2 infection) prior to the administering of the pharmaceutical formulation thereto. In some embodiments, one or more additional anti-SARS-CoV-2 agents can be administered to the subject(s) before, essentially simultaneously, or after administration of SARS-CoV-2 immunogenic composition such as, for instance, chloroquine (e.g., pharmaceutical salt and/or derivative thereof; e.g., hydroxychloroquine 400 mg per day for 5 days or 200 mg three times per day for 10 days) and/or azithromycin (e.g., 500 mg on first day followed by four daily 250 mg doses) and/or remdesivir (e.g., 200 mg initial followed by 100 mg daily doses) and/or any other suitable reagent.

In some embodiments, this disclosure provides SARS-CoV-2 immunogenic compositions comprising one or more rdAd anti-SARS-CoV-2 vectors comprising one or more SARS-CoV-2 antigen coding sequences encoding one or more peptides comprising one or more T cell epitopes of Table 3A, one or more groups of T cell epitopes of Table 3B, or SEQ ID NOS: 27-282; and/or one or more B cell epitopes of SEQ ID NOS: 283-327; and/or one or more of SEQ ID NOS: 328-408 optionally wherein the peptides are concatenated, and optionally separated by a linker amino acid sequence of two to ten amino acids.

In some embodiments, this disclosure provides SARS-CoV-2 immunogenic compositions comprising one or more rdAd anti-SARS-CoV-2 vectors comprising at least one polynucleotide encoding at least one molecular adjuvant selected from the group consisting of: one or more polypeptides or peptides that functions as a co-stimulatory component; one or more cytokines; one or more chemokines; one or more immune inhibitory proteins; one or more TLR agonists, optionally wherein the one or more TLR agonists is selected from the group consisting of SEQ ID NOS: 463-474; and a combination thereof.

In some embodiments, this disclosure provides SARS-CoV-2 immunogenic compositions comprising one or more rdAd anti-SARS-CoV-2 vectors comprising at least one polynucleotide sequence encoding at least one SARS-CoV-2 blocking protein; wherein the at least one polynucleotide sequence encodes at least one peptide or polypeptide: that induces an immune response that interferes with the binding of the SARS-CoV-2 S protein to its cellular receptor, directly interferes with the binding of the SARS-CoV-2 S protein to its cellular receptor, is an RBD binding agent, is an ACE2 binding agent, and/or is both an RBD binding agent and an ACE2 binding agent.

In some embodiments, this disclosure provides one or more polynucleotide(s) encoding a rdAd anti-SARS-CoV-2 vector disclosed herein. In some embodiments, this disclosure provides one or more rdAd anti-SARS-CoV-2 vectors produced upon expression of such polynucleotide(s) in a host cell. In some embodiments, this disclosure provides one or more compositions comprising such polynucleotides and/or rdAd anti-SARS-CoV-2 vectors, which in some embodiments is a pharmaceutical composition or pharmaceutical dosage form.

PREFERRED ASPECTS OF THE DISCLOSURE

Preferred aspects of this disclosure include:

An immunogenic composition comprising a replication defective adenoviral (rdAd) vector, wherein the rdAd vector is selected from:

a) an rdAd vector lacking a coding sequence encoding an exogenous, non-adenoviral, antigen;

b) an rdAd vector comprising an expression cassette comprising a SARS-CoV-2 antigen coding sequence encoding at least one SARS-CoV-2 antigen, optionally wherein said antigen comprises a SARS-CoV-2 spike (S) protein receptor binding domain (RBD);

c) an rdAd vector comprising an expression cassette comprising a coding sequence encoding at least one exogenous antigen of an infectious agent other than SARS-CoV-2;

d) a combination of the vectors of a) and b), wherein the rdAd vectors are administered together or separately;

e) a combination of the vectors of b) and c), wherein the rdAd vectors are administered together or separately;

f) a combination of any of the rdAd vectors of any of a), b), or c), wherein the rdAd vectors are administered together or separately;

g) a combination of two different types of rdAd vectors of b), wherein each type of rdAd vector comprises an expression cassette encoding at least one SARS-CoV-2 antigen different from that encoded by the other types of rdAd vectors in the combination, wherein the rdAd vectors are administered together or separately;

said immunogenic composition being configured to induce neutralizing antibody and/or cellular immune response against SARS-CoV-2 in a mammalian subject to which said immunogenic composition is administered.

The immunogenic composition of the prior aspect, wherein the expression cassette comprises a SARS-CoV-2 antigen coding sequence for spike (S) protein or the S1 domain of the spike protein.

The immunogenic composition of any prior aspect, wherein the expression cassette comprises a SARS-CoV-2 antigen coding sequence selected from the group consisting of SEQ ID NO: 3; a sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%) homology and/or identity to SEQ ID NO: 3; a sequence present in SEQ ID NO: 12; a sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%) homology and/or identity to SEQ ID NO: 12; SEQ ID NO: 15; a sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%) homology and/or identity to SEQ ID NO: 15; SEQ ID NO: 446; a sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%) homology and/or identity to SEQ ID NO: 446; any of SEQ ID NOS: 412-417; any SEQ ID NOS: 438-445, and SEQ ID NOS: 475-476 and 460; a sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%) homology and/or identity to any of SEQ ID NOS: 412-417 and SEQ ID NOS: 438-445, and SEQ ID NOS: 475-476 and 460.

The immunogenic composition of any prior aspect, wherein the SARS-CoV-2 antigen coding sequence encodes a spike protein sequence comprising a sequence where the S1/S2 cleavable site and/or S2' are resistant to proteomic degradation, and/or a sequence where the fusion peptide has been deleted or modified to prevent its fusogenic activity, and/or a sequence where the intracellular domain has been modified or partially to alter the endoplasmic reticulum retention motif. The immunogenic composition of any prior aspect, wherein the expression cassette comprises a SARS-CoV-2 antigen coding sequence selected from the group consisting and/or a sequence including at least one of NSPQQAQSVAS (SEQ ID NO: 451), NSPSGAGSVAS (SEQ ID NO: 456) or NSP VAS (SEQ ID NO: 461) at the S1/S2 cleavage site, KRSFIADA (SEQ ID NO: 453), PSKPSKQSF (SEQ ID NO: 457), PSKPSKNSF (SEQ ID NO: 458), PSKPSNASF (SEQ ID NO: 459) at the S2' cleavage site, or SRLDPPEAEV (SEQ ID NO: 455), and/or any sequence modification presented in Table 1 and/or Table 2.

The immunogenic composition of any prior aspect, wherein the SARS-CoV-2 antigen coding sequence is a sequence presented in SEQ ID NO: 18, SEQ ID NO: 19, SEQ ID NO: 20, or an immunogenic fragment thereof.

The immunogenic composition of any prior aspect, wherein the SARS-CoV-2 antigen coding sequence encodes at least amino acids 331 to 527 of SEQ ID NO: 3.

The immunogenic composition of any prior aspect, wherein the SARS-CoV-2 antigen coding sequence encodes a spike protein receptor binding domain (RBD) sequence comprises one or more of the following substitutions: K417N, K417T, R403K, N439K, G446V, G446S, L452R, G476A, S477N, T478K, E484D, T4781, E484K, F490S, Q493R, S494P, P499H and/or N501Y.

The immunogenic composition of any prior aspect, wherein the SARS-CoV-2 antigen coding sequence encodes a spike protein receptor binding domain (RBD) sequence, or immunogenic fragment thereof, and/or comprises an amino acid sequence of SEQ ID NO: 12, SEQ ID NO: 13, SEQ ID NO 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NOS: 412-417, SEQ ID NOS: 438-445, SEQ ID NO: 446, SEQ ID NO: 460, SEQ ID NO: 475 and SEQ ID NO: 476; or an immunogenic fragment thereof.

The immunogenic composition of any prior aspect, wherein the expression cassette of the replication defective adenoviral vector further comprises a coding sequence encoding one or more of SARS-CoV-2 structural proteins envelope (E), membrane (M) or nucleocapsid (N).

The immunogenic composition of any prior aspect, comprising an additional replication defective adenoviral vector comprises a coding sequence encoding one or more of SARS-CoV-2 structural proteins envelope (E), membrane (M) or nucleocapsid (N).

The immunogenic composition of any prior aspect, wherein the expression cassette of the replication defective adenoviral vector comprises a coding sequence for a modified version of SEQ ID NO: 411 comprising:

one or more substitutions of any one or more of amino acids 333-388, 390-395, 397-399, 401-411, 413-415, 417-419, 424, 426-435, 437, 439-442, 444-446, 449, 450, 452, 453, 455-463, 465, 467-473, 475-479, 481-486, 490, 491, 493-495, 499-510, and/or 513-526; one or more substitutions of any one or more of amino acids 367, 403, 417, 439, 446, 449, 452, 453, 455, 456, 470, 473, 475, 476, 477, 478, 484, 486, 490, 493, 494, 495, 496, 499, 500, 501, 502, 503, 504, and/or 505; one or more substitutions selected from the group consisting of amino acid 367 (V) by F, I, L S or A, amino acid 403 (R) by K or S, 417 (K) by N or T; amino acid 439 (N) by K, amino acid 446 (G) by V, S or A; amino acid 449 (Y) by N; amino acid 452 (L) by L, M or Q, amino acid 453 (Y) by F; amino acid 455 (L) by F; amino acid 456 (F) by L; amino acid 470 (T) by I, A or N, amino acid 473 (Y) by V; amino acid 475 (A) by V; amino acid 476 (G) by S or A; amino acid 477 (S) by N, R, T, G, A or I; amino acid 476 (G) by S or A, amino acid 477 (S) by N, R, T, G, A or I, amino acid 478 (T) by I, K, R or A, amino acid 484 (E) by Q, K, D, A or R; amino acid 486 (F) by L or S; amino acid 490 (F) by L or S, amino acid 493 (Q) by L or R; amino acid 494 (S) by P or L, amino acid 495 (Y) by N or F; amino-acid 496 (G) by V or S, amino acid 499 (P) by H, S or R, amino acid 500 (T) by I; amino acid 501 (N) by Y, T or S; amino acid 502 (G) by R, D or C; amino acid 503 (V) by L, I or F; and, amino acid 504 (G) by V, D or S amino acid 505 (Y) by H, E, W or C.

The immunogenic composition of any prior aspect wherein the at least one antigen of an infectious agent other than SARS-CoV-2 is derived from an influenza virus.

The immunogenic composition of any prior aspect comprising a combination of any two of the rdAd vectors of a)-c).

The immunogenic composition of any prior aspect, wherein said immunogenic composition is a two-part composition comprising at least one composition comprising rdAd vectors of a)-c) and at least a second composition comprising a different rdAd vector of a)-c).

The immunogenic composition of any prior aspect, further configured to induce a combined mucosal, humoral and T cell protective immune response against SARS-CoV-2.

The immunogenic composition of any prior aspect, wherein the coding sequence encodes at least one or more B cell epitopes, one or more CD8+ T cell epitopes, and/or one or more CD4+ T cell epitopes.

The immunogenic composition of any prior aspect, wherein the coding sequence is codon optimized for the mammalian subject.

The immunogenic composition of any prior aspect, wherein the neutralizing antibodies are seroprotective against SARS-CoV-2 infection in a mammalian subject, optionally wherein the mammalian subject is a human being.

The immunogenic composition of any prior aspect, wherein the replication defective adenoviral vector is a human adenovirus, optionally Ad5 or Ad26.

The immunogenic composition of any prior aspect, wherein the replication defective adenoviral vector is a bovine adenovirus, a canine adenovirus, a non-human primate adenovirus, a chicken adenovirus, or a porcine or swine adenovirus.

The immunogenic composition of any prior aspect, wherein the replication defective adenoviral vector is an E1, E3, and/or E4 deleted or disrupted adenovirus.

The immunogenic composition of any prior aspect, wherein the SARS-CoV-2 antigen coding sequence encodes one or more peptides comprising one or more T cell epitopes of Table 3A, one or more groups of T cell epitopes of Table 3B, or SEQ ID NOS: 27-282; and/or one or more B cell epitopes of SEQ ID NOS. 25-68; and/or one or more of SEQ ID NOS. 328-369; optionally wherein the peptides are concatenated, and optionally separated by a linker amino acid sequence of two to ten amino acids.

The immunogenic composition of any prior aspect wherein the rdAd vector further comprises at least one molecular adjuvant selected from the group consisting of: one or more polypeptides or peptides that functions as a co-stimulatory component; one or more cytokines; one or more chemokines; one or more immune inhibitory proteins; one or more TLR agonists, optionally wherein the one or more TLR agonists is selected from the group consisting of SEQ ID NOS: 463-474; and a combination thereof.

The immunogenic composition of any prior aspect, wherein the rdAd vector comprises at least one polynucleotide sequence encoding at least one SARS-CoV-2 blocking protein; wherein the at least one polynucleotide sequence encodes at least one peptide or polypeptide: that induces an immune response that interferes with the binding of the SARS-CoV-2 S protein to its cellular receptor, directly interferes with the binding of the SARS-CoV-2 S protein to its cellular receptor, is an RBD binding agent, is an ACE2 binding agent, and/or is both an RBD binding agent and an ACE2 binding agent.

A polynucleotide encoding a rdAd vector of an immunogenic composition of any prior aspect, an rdAd vector produced upon expression of the polynucleotide in a host cell, and a composition comprising the rdAd vector.

A pharmaceutical formulation, comprising an effective amount of the immunogenic composition of any prior aspect; and, a pharmaceutically acceptable diluent or carrier, optionally wherein the diluent is phosphate-buffered saline.

The pharmaceutical formulation of any prior aspect configured for non-invasive administration.

The pharmaceutical formulation of any prior aspect configured for intranasal administration to the mammalian subject.

The pharmaceutical formulation of any prior aspect, wherein administration of the pharmaceutical formulation to the mammalian subject induces a protective immune response in the mammalian subject, optionally a combined mucosal, humoral and T cell protective immune response.

The pharmaceutical formulation of any prior aspect wherein the pharmaceutically acceptable carrier is in a spray or aerosol form.

The pharmaceutical formulation of any prior aspect, wherein the effective amount is at least $10^7$ viral particles (vp), at least $10^8$ viral particles (vp), or at least $10^9$ viral particles (vp).

The pharmaceutical formulation of any prior aspect, configured as a single intranasal dose.

The pharmaceutical formulation of any prior aspect, configured as two or more intranasal doses.

A pharmaceutical formulation suitable for a single dose intranasal administration to a human subject, comprising:

an effective amount of at least $10^7$ viral particle (vp) of the immunogenic composition of any prior aspect comprising at least one replication defective adenoviral vector comprising an expression cassette comprising a coding sequence encoding at least SARS-CoV-2 spike (S) protein receptor binding domain (RBD), or at least one immunogenic fragment thereof, wherein the effective amount induces a combined mucosal, humoral and T cell protective immune response; and, a pharmaceutically acceptable diluent or carrier.

The pharmaceutical formulation of any prior aspect, wherein the formulation is configured to provide seroprotection to the human subject for at least 6 months against SARS-CoV-2.

The pharmaceutical formulation of any prior aspect, wherein the coding sequence is codon optimized for the human subject.

A pharmaceutical dosage for intranasal administration, comprising:

a pharmaceutical acceptable carrier in a spray or aerosol form admixed with an immunogenic composition of any prior aspect, wherein the dosage is configured for intranasal administration to non-invasively induce a protective immune response against SARS-CoV-2.

The pharmaceutical dosage of any prior aspect, wherein the immunogenic composition comprises an effective amount of at least $10^7$ viral particles (vp), at least $10^8$ viral particles (vp), or at least $10^9$ viral particles (vp).

The pharmaceutical dosage of any prior aspect, wherein the effective amount induces a combined mucosal, humoral and T cell protective immune response.

The pharmaceutical dosage of any one of any prior aspect, configured as a single dose to induce a protective immune response against coronavirus.

The pharmaceutical dosage of any one of any prior aspect, configured as two or more doses to induce a protective immune response against SARS-CoV-2.

A method for inducing an immune response against coronavirus, the method comprising administering an effective amount of the immunogenic composition of any prior aspect to a mammalian subject.

The method of any prior aspect, wherein the immune response is protective against SARS-CoV-2.

A method for inducing an immune response against SARS-CoV-2, the method comprising administering a pharmaceutical formulation of any prior aspect or a pharmaceutical dosage of any prior aspect to a mammalian subject.

The method of any prior aspect wherein the immune response is protective against SARS-CoV-2.

The method of any prior aspect, the method comprising intranasal administration of an effective amount of the immunogenic composition to the mammalian subject, wherein the immune response provides protection against challenge with SARS-CoV-2.

A method of inducing a combined mucosal, humoral and/or T cell protective immune response in a human subject against coronavirus comprising:

administering intranasally to a human subject a single dose of the coronavirus (SARS-CoV-2) pharmaceutical formulation of any prior aspect or a pharmaceutical dosage of any prior aspect, wherein the administration induces serum antibodies, mucosal antibodies and T cells against SARS-CoV-2, optionally whereby the human subject is seroprotected for at least about 6 months or more preferably about 9 months.

The method of any prior aspect, wherein the seroprotection lasts for at least 12 months, at least 13 months or at least 14 months.

The method of any prior aspect further comprising administering one or more anti-cytokine reagents to the human being to prevent and/or treat SARS-CoV-2, optionally wherein the one or more anti-cytokine reagents include one or more anti-IL-1α reagent(s), one or more anti-IL5 reagent(s), one or more anti-IL-6 reagent(s), one or more anti-IL-12 reagent(s), one or more anti-IL-17 reagent(s), one or more anti-MCP-1 reagent(s), one or more anti-TNF-α reagent(s), one or more anti-GM-CSF reagent(s), and/or one or more anti-RANTES reagent(s).

The method of any prior aspect, wherein the one or more anti-cytokine reagents does not include one or more anti-MIPα reagent(s) and/or one or more anti-RANTES reagent(s).

The method of any prior aspect wherein:

the one or more anti-cytokine reagent(s) are co-administered substantially with the effective amount of the immunogenic composition;

the one or more anti-cytokine reagent(s) are not administered substantially with the effective amount of the immunogenic composition;

the immunogenic composition is administered to the mammal once and the one or more anti-cytokine reagent(s) are administered multiple times; or the immunogenic composition is co-administered to the mammal with the one or more anti-cytokine reagent(s), and the one or more anti-cytokine reagent(s) are subsequently administered to the mammal.

A method of treating or inhibiting the symptoms of a respiratory viral infection in a mammal, said respiratory viral infection causing elevated expression of interleukin-6 (IL-6), interleukin-1-alpha (IL-1α) and/or interleukin-12 (IL-12) in the lung of said mammal, the method comprising: intranasally administering an effective amount of an E1 and E3 deleted adenoviral vector, or formulation or composition comprising the same, of any prior aspect to the subject, whereby expression of IL-6, IL-1α, and/or IL-12 in the lung is reduced thereby alleviating said symptoms for up to about 28 days following administration of the vector.

The method of any prior aspect wherein expression of monocyte chemoattractant protein 1 (MCP-1), IFN-γ, and/or RANTES, are increased in the lung following administration of the vector.

The method of any prior aspect wherein the expression of macrophage inflammatory protein 1 alpha (MIP-1α) and/or RANTES are not reduced following administration of the vector.

A method of inducing an anti-viral immune response in a mammalian subject in need thereof with, or at risk of, a respiratory viral infection, the method comprising: intranasal administration of an effective amount of an E1 and E3 deleted adenoviral vector, or formulation or composition comprising the same, of any prior aspect to the subject, wherein the anti-viral immune response generates increased expression of monocyte chemoattractant protein 1 (MCP-1) and/or interferon alpha (IFN-γ) following the administration step.

The method of any prior aspect wherein one or more additional anti-SARS-CoV-2 agents is administered to subjects before, essentially simultaneously, or after administration of E1 and E3 deleted adenoviral vector, optionally wherein said one or more additional agents is selected from the group consisting of chloroquine, azithromycin, remdesivir, an anti-inflammatory agent, and a combination thereof.

The method of any prior aspect wherein the mammalian subject is infected by SARS-CoV-2 prior to the administering of the pharmaceutical formulation thereto.

The method of any prior aspect wherein the mammalian subject is a human being.

An immunogenic composition comprising a replication defective adenoviral (rdAd) vector, wherein the rdAd vector is selected from:

a) an rdAd vector lacking a coding sequence encoding an exogenous, non-adenoviral, antigen;

b) an rdAd vector comprising an expression cassette comprising a SARS-CoV-2 antigen coding sequence encoding at least one SARS-CoV-2 antigen, optionally wherein said antigen comprises a SARS-CoV-2 spike (S) protein receptor binding domain (RBD);

c) an rdAd vector comprising an expression cassette comprising a coding sequence encoding at least one exogenous antigen of an infectious agent other than SARS-CoV-2;

d) a combination of the vectors of a) and b), wherein the rdAd vectors are administered together or separately;

e) a combination of the vectors of b) and c), wherein the rdAd vectors are administered together or separately;

f) a combination of any of the rdAd vectors of any of a), b), or c), wherein the rdAd vectors are administered together or separately;

g) a combination of two different types of rdAd vectors of b), wherein each type of rdAd vector comprises an expression cassette encoding at least one SARS-CoV-2 antigen different from that encoded by the other types of rdAd vectors in the combination, wherein the rdAd vectors are administered together or separately;

said immunogenic composition being configured to induce neutralizing antibody and/or cellular immune response against SARS-CoV-2 in a mammalian subject to which said immunogenic composition is administered, for use in the treatment or prevention of SARS-CoV-2.

Use of an immunogenic composition comprising a replication defective adenoviral (rdAd) vector, wherein the rdAd vector is selected from:

a) an rdAd vector lacking a coding sequence encoding an exogenous, non-adenoviral, antigen;

b) an rdAd vector comprising an expression cassette comprising a SARS-CoV-2 antigen coding sequence encoding at least one SARS-CoV-2 antigen, optionally wherein said antigen comprises a SARS-CoV-2 spike (S) protein receptor binding domain (RBD);

c) an rdAd vector comprising an expression cassette comprising a coding sequence encoding at least one exogenous antigen of an infectious agent other than SARS-CoV-2;

d) a combination of the vectors of a) and b), wherein the rdAd vectors are administered together or separately;

e) a combination of the vectors of b) and c), wherein the rdAd vectors are administered together or separately;

f) a combination of any of the rdAd vectors of any of a), b), or c), wherein the rdAd vectors are administered together or separately;

g) a combination of two different types of rdAd vectors of b), wherein each type of rdAd vector comprises an expression cassette encoding at least one SARS-CoV-2 antigen different from that encoded by the other types of rdAd vectors in the combination, wherein the rdAd vectors are administered together or separately;

said immunogenic composition being configured to induce neutralizing antibody and/or cellular immune response against SARS-CoV-2 in a mammalian subject to which said immunogenic composition is administered, characterized by being in the manufacture of a medicament to provide treatment or prevention of SARS-CoV-2.

An immunogenic composition comprising a replication defective adenoviral (rdAd) vector comprising a nucleic acid sequence encoding SEQ ID NO: 446 or a variant comprising at least 90%, or at least 95% identity to SEQ ID NO: 446.

The immunogenic composition of the prior aspect, wherein the nucleic acid sequence encodes SEQ ID NO: 15.

The immunogenic composition of any prior aspect, wherein the nucleic acid sequence encodes SEQ ID NO: 13.

The immunogenic composition of any prior aspect, wherein the nucleic acid sequence encodes one or more of SEQ ID NOS: 412-417, SEQ ID NOS: 438-445, SEQ ID NOS: 475-476 and SEQ ID NO: 460.

The immunogenic composition of any prior aspect, wherein the nucleic acid sequence encodes a sequence comprising one or more point mutations of SEQ ID NO: 3.

The immunogenic composition of any prior aspect, wherein the nucleic acid sequence encodes a sequence comprising one or more mutations at positions 333-388, 390-395, 397-399, 401-411, 413-415, 417-419, 424, 426-435, 437, 439-442, 444-446, 449, 450, 452, 453, 455-463, 465, 467-473, 475-479, 481-486, 490, 491, 493-495, 499-510, or 513-526 wherein amino acid numbering corresponds to SEQ ID NO: 411.

The immunogenic composition of any prior aspect, wherein the nucleic acid sequence encodes a sequence comprising one or more mutations at amino acid positions 367, 403, 439, 417, 446, 447, 449, 452, 453, 455, 456, 470, 473, 475, 476, 477, 478, 484, 486, 487, 490, 493, 494, 496, 499, 500, 501, 502, 503, 504, and/or 505, wherein amino acid numbering corresponds to SEQ ID NO: 411.

The immunogenic composition of the prior aspect, wherein the one or more mutations are selected from substitution of amino acid 417 (K) by N; substitution of amino acid 446 (G) by V, S or A; substitution of amino acid 449 (Y) by N; substitution at amino acid 453 (Y) by F; substitution of amino acid 455 (L) by F; substitution of amino acid 456 (F) by L; substitution of amino acid 473 (Y) by V; substitution of amino acid 475 (A) by V; substitution of amino acid 476 (G) by S or A; substitution of amino acid 477 (S) by N, R, T, G, A or I; substitution at amino acid 484 (E) by Q, K, D, A or R; substitution of amino acid 486 (F) by L or S; substitution of amino acid 453 (Y) by F; substitution of amino acid 493 (Q) by L or R; substitution of amino acid 495 (Y) by N or F; substitution of amino acid 500 (T) by I; substitution of amino acid 501 (N) by Y, T or S; substitution of amino acid 502 (G) by R, D or C; substitution of amino acid 503 (V) by L, I or F; or, substitution of amino acid 505 (Y) by H, E, W or C, wherein amino acid numbering corresponds to SEQ ID NO: 411.

The immunogenic composition of any prior aspect, wherein the nucleic acid sequence encodes a sequence comprising one or more mutations selected from K417T, K417N, E484K, L452R and/or N501Y, wherein amino acid numbering corresponds to SEQ ID NO: 411.

The immunogenic composition of any prior aspect, wherein the nucleic acid sequence encodes one or more of SEQ ID NOS: 412-417.

The immunogenic composition of any prior aspect, wherein the nucleic acid sequence encodes one or more of SEQ ID NOS: 438-443 or 460.

The immunogenic composition of any prior aspect, wherein the nucleic acid sequence encoding SEQ ID NO: 446 further comprises a leader sequence encoded by a nucleic acid sequence encoding a sequence selected from SEQ ID NOS: 418 to 437.

The immunogenic composition of any prior aspect, wherein the coding sequence is codon optimized for a mammalian subject.

The immunogenic composition of any prior aspect, wherein the replication defective adenoviral vector is a bovine adenovirus, a canine adenovirus, a non-human primate adenovirus, a chicken adenovirus, a porcine or swine adenovirus, or a human adenovirus.

The immunogenic composition of the prior aspect, wherein the non-human primate adenovirus is a chimpanzee or gorilla adenovirus.

The immunogenic composition of any prior aspect, wherein the replication defective adenoviral vector is a human adenovirus.

The immunogenic composition of the prior aspect, wherein the human adenovirus is Ad5 or Ad26.

A pharmaceutical formulation, comprising an effective amount of the immunogenic composition of any prior aspects, the composition comprising at least one pharmaceutically acceptable diluent or carrier, optionally wherein the diluent is phosphate-buffered saline.

The pharmaceutical formulation of the prior aspect, configured for non-invasive or intranasal administration, optionally wherein the pharmaceutically acceptable carrier is in a spray or aerosol form.

A method for inducing an immune response against SARS-CoV-2, the method comprising administering an effective amount of the immunogenic composition of any prior aspect to a human being.

The method of the prior aspect, wherein the effective amount is at least $10^8$ viral particles (vp), at least $10^9$ viral particles (vp), or at least $10^{10}$ viral particles (vp).

The method of any prior aspect, wherein the immunogenic composition is administered intranasally.

The method of any prior aspect, wherein the immune response against SARS-CoV-2 persists for at least 6 months, at least 9 months or at least 12 months after administration to a human subject.

The method of any prior aspect, wherein the immune response against SARS-CoV-2 comprises a mucosal IgA and/or T cell response against SARS-CoV-2 induced after administration of the immunogenic composition.

The method of any prior aspect, wherein the effective amount of the immunogenic composition reduces incidence of mild or moderate COVID-19-related diseases after the administration to the human subject.

The method of any prior aspect, wherein the effective amount of the immunogenic composition reduces incidence of severe COVID-19-related diseases after the administration to the human subject.

The method of any prior aspect, wherein the effective amount of the immunogenic composition reduces severity of COVID-19-related diseases after the administration to the human subject.

The method of any prior aspect, wherein the effective amount of the immunogenic composition reduces incidence of infection with SARS-CoV-2 after the administration to the human subject.

The method of any prior aspect, wherein the effective amount of the immunogenic composition reduces incidence of asymptomatic COVID-19 after the administration to the human subject.

The method of any prior aspect, wherein the effective amount of the immunogenic composition reduces transmission of SARS-CoV-2 after the administration to the human subject.

Other embodiments are also contemplated herein as would be understood by those of ordinary skill in the art.

EXAMPLES

The following examples are put forth so as to provide those of ordinary skill in the art with a complete disclosure and description of how to use the embodiments provided herein and are not intended to limit the scope of the disclosure nor are they intended to represent that the Examples below are all of the experiments or the only experiments performed. Efforts have been made to ensure accuracy with respect to numbers used (e.g. amounts, temperature, etc.) but some experimental errors and deviations should be accounted for. Unless indicated otherwise, parts are parts by volume, and temperature is in degrees Centigrade. It should be understood that variations in the methods as described can be made without changing the fundamental aspects that the Examples are meant to illustrate.

Example 1: Materials and Methods

Recombinant replication deficient adenovirus type 5. Replication defective human Adenovirus 5 (hAd5) are generated using previously described methods (Miravet, et al. Methods Mol Biol 2014, 1089, 159-173). In brief, the defective hAd5 lacks E1 and E3 genes to allow genomic space for the transgene insert. In some embodiments, the hAd5 lacks coding sequences for any exogenous antigens (i.e., non adenoviral antigens as in the AdE vector). In some embodiments, the hAd5 encodes one or more SARS-CoV-2 antigen(s) (referred to herein as "hAd5-SARS-CoV-2"). In some embodiments, the hAd5 encodes one or more influenza antigen(s) (as in the AdD vector). The hAd5-SARS-CoV-2 vectors and AdD vectors can encode any SARS-CoV-2 or influenza antigen, respectively, that is immunogenic regarding such antigen(s) in a human being or non-human animal (e.g., a mammal). For instance, the SARS-CoV-2 antigen insert can encode any protein (and/or any one or more fragment(s) and/or derivative(s) thereof) encoded by SEQ ID NO:1 (FIGS. 1A-J), such as any one or more of SEQ ID Nos. 2-11, 13 or 15 and/or any one or more fragments and/or derivatives thereof (e.g., a peptide of at least 3, 6, 9 or 11 contiguous amino acids thereof). The expression cassette is a cytomegalovirus (CMV) immediate early driven transgene, optionally encoding a tissue plasminogen activator signal sequence (tPA), followed by a codon optimized SARS-CoV-2 spike (S) cassette, inserted into the E1 region of the Adenovirus vector. The present immunogenic compositions are manufactured by propagation of the RD-Ad5 vector in replication-permissive CAP cells (Wölfel, et al. BMC Proceedings, 2011, 5(Supp 8):P133; Cevec), followed by purification of the virus from the infected cell harvest, and the final product may include the following excipients Tris HCl (pH 7.4), histidine, sucrose, sodium chloride, magnesium chloride, polysorbate 80, ethylenediaminetetraacetic acid, and ethanol, the final product stored at −80° C.

For animal and/or clinical studies, the present pharmaceutical formulations are supplied in a single-use glass vials each containing a nominal volume of 0.7 mL of a sterile frozen suspension of immunogenic composition (e.g., vaccine) formulated to deliver the nominal dose of $1\times10^7$, $1\times10^8$, $1\times10^9$, $1\times10^{10}$ or $1\times10^{11}$ viral particles (vp). Alternatively, the present pharmaceutical formulations are supplied in a single-use (pre-filled) syringe, optionally with an atomizer, (e.g., BD Accuspray) containing a nominal volume of 0.5 mL of a sterile frozen suspension of immunogenic composition (e.g., vaccine) formulated to deliver the nominal dose of $1\times10^7$, $1\times10^8$, $1\times10^9$, $1\times10^{10}$ or $1\times10^{11}$ viral particles (vp).

Focus Forming Assay. hAd5 vector (e.g., AdE, hAd5-SARS-CoV-2, AdD) titration is performed by focus forming assay (FFA) or other suitable assay. Briefly, regarding the FFA, cells expressing the viral receptor (e.g., ACE2 receptor (angiotensin converting enzyme 2)) are plated the day before the assay in a 96-well plate then virus stocks, serially diluted, allowed to infect cells, and then, optionally overlayed with methylcellulose. The cells are incubated at 37° C. for 48 hours followed by fixation with paraformaldehyde. Immunostaining using a coronavirus monoclonal antibody and a secondary antibody are used to visualize the formation of foci for individual infected cells for the hAd5-SARS-CoV-2 stock.

Western Blot. To confirm protein expression from the hAd5 (e.g., recombinant hAd5-SARS-CoV-2 virus), 293 cells (e.g, 293, Calu-3, Caco-2 or Vero) are infected with hAd5-SARS-CoV-2. After an incubation period (e.g., 48 hours) at 37° C., 5% $CO_2$ the cells are rinsed once with PBS and harvested using 2×NuPage buffer. Samples are heated at 95° C. for 10 minutes, cooled, and loaded onto NuPage 4-12% gels. Protein are transferred to nitrocellulose membrane, blocked with non-fat milk, and probed with one or more types of primary antibodies in TBST, each having specificity for one or more SARS-CoV-2 antigens. After overnight incubation, membranes are washed 3 times with TBST and blotted with fluorescently conjugated secondary antibodies (molecular probes). After one hour in secondary, membranes are washed three times in TB ST and one time in PBS, then fluorescent signal are captured with an imager.

Intracellular Cytokine stain. Spleens are harvested from vaccinated mice eight days post vaccination. Spleens are ground over a 100 μm cell strainer and brought up in RPMI with 10% FBS and HEPES. Approximately $10^6$ cells are plated per well in a round bottom 96 well plate and stimulated for 6 hours at 37° C., 5% $CO_2$ in the presence of 10 μg/ml brefeldin A and either α-CD3 (2C11 clone) or 10 μg of peptide in 90% DMSO. Following peptide stimulation, cells are washed once with PBS and stained for surface markers. Cells are then fixed and permeabalized and stained for intracellular markers (e.g. IFN-γ). The cells are analyzed by flow cytometry.

ELISA. Polystyrene 96-well plates are coated overnight at 4° C. with 1 μg/ml of SARS-CoV-2 antigen in sodium carbonate buffer (pH 9.3). Plates are washed three times in PBS with 0.02% Tween 20 and blocked with non-fat dried milk for one hour at 37° C. with PBS, 2% BSA, and 0.02% Tween 20. Serum from hAd5 (e.g., hAd5-SARS-CoV-2) vaccinated mice are serially diluted in PBS then incubated at 37° C. Plates are washed four times with PBS with 0.02% Tween 20 and incubated with labeled secondary antibody for one hour. After washing and incubation as needed the plates are read using a microplate reader.

Vaccination with Recombinant replication deficient adenovirus type 5. Mice are anesthetized using Ketamine/Xylazine (90 mg/kg: 10 mg/kg), and then vaccinated with an appropriate volume intranasally of $1\times10^7$ particles of hAd5-SARS-CoV-2 diluted in PBS.

Animal Challenge. SARS-CoV-2 is diluted in sterile PBS pH 7.4 to obtain a suitable final concentration of SARS-CoV-2 per mouse (e.g., those expressing the viral receptor) in a final volume of 10-50 μL. Virus challenge is performed by intranasal administration 21 days post hAd5-SARS-CoV-2 vaccination. Mice are anesthetized during this procedure using Ketamine/Xylazine (90 mg/kg: 10 mg/kg). After challenge, each mouse is examined for visible trauma and, placed back into its cage for recovery.

Clinical Monitoring. Animals are observed for clinical outcomes daily after SARS-CoV-2 challenge. Body weight changes, symptoms of SARS-CoV-2 virus infection, and mortality are recorded for each animal daily.

Example 2: AdE Compositions for Immunization Against Respiratory Infection

The studies described in this example evaluated the immune response following administration of AdE for prevention and/or treatment of respiratory infection (e.g., as may be caused by influenza), including measurement of serum antibody levels by hemagglutination inhibition assay and secretory IgA levels in lung lavage. Cellular immunity was evaluated by quantitation of cells, in lung lavage, releasing IFN-γ and IL-4 by ELISpot assay. In addition, adenovirus-specific immunity was evaluated by adenovirus neutralization using serum from vaccinated mice. This study determined the ability of the empty adenovirus vector (AdE) to provide protection against influenza A H1N1, H3N2, H5N1, and influenza B virus challenge infections in mice. In addition, cytokine levels in lung lavage were evaluated following vaccination and challenge in an attempt to determine the mechanism of protection afforded by the AdE vector.

Materials and Methods

Abbreviations used in this example include: IL—interleukin; MCP—monocyte chemoattractant protein; IFN—interferon; TNF—tumor necrosis factor, MIP—macrophage inflammatory protein; GM-CSF—granulocyte/macrophage colony stimulating factor; and RANTES—regulated upon activation, normal T cell expressed and secreted.

Animals: Female six week-old BALB/c mice were obtained from Charles River Laboratories. The mice were quarantined for 72 hours before use and maintained on Teklad Rodent Diet (Harlan Teklad) and tap water at the Laboratory Animal Research Center of Utah State University.

Virus: Influenza A/California/04/2009 (pandemic H1N1), strain designation 175190, was received from Dr. Elena Govorkova, Department of Infectious Diseases, St. Jude Children's Research Hospital, Memphis Tenn. The virus was adapted to replication in the lungs of BALB/c mice by 9 sequential passages through mouse lungs. Virus was plaque purified in Madin-Darby canine kidney (MDCK) cells (American Type Culture Collection, Manassas, Va.) and a virus stock was prepared by growth in embryonated chicken eggs and then MDCK cells. Influenza A/Victoria/

3/75 (H3N2) virus was obtained from the American Type Culture Collection (Manassas, Va.). The virus became lethal to mice after seven serial passages in the lungs of infected animals. Following mouse-adaptation a virus stock was prepared by growth in MDCK cells. Influenza A/Vietnam/1203/2004 (H5N1) was obtained from the Centers for Disease Control (Atlanta, Ga.). Viral propagation and assays were done in MDCK cells. Parent virus was passaged once to prepare a challenge pool. Influenza B/Sichuan/379/99 virus was obtained from the Centers for Disease Control (Atlanta, Ga.). The virus was propagated twice in MDCK cells, and then passaged serially 10 times in mice. Following mouse-adaptation a virus stock was prepared by growth in MDCK cells.

AdE Composition: The virus titer for the AdE was 6.4×$10^9$ infection forming units (ifu)/ml (3.2×$10^8$ ifu/0.05 ml). The vaccine was administered by the intranasal route in a 50 μl volume on a single occasion (see experimental design).

Experimental design: Animal numbers and study groups are described in Tables 1 to 3. Groups of mice were vaccinated on study day 0 or 20 by the intranasal route. The placebo groups received 50 μl physiological sterile saline (PSS) by the same route. For influenza virus challenge, mice were anesthetized by i.p. injection of ketamine/xylazine (50 mg/kg/5 mg/kg) prior to intranasal challenge with 90 μl of influenza A/CA/04/2009 (H1N1p), A/Victoria/3/1975 (H3N2), B/Sichuan/379/1999 or 75 μl of influenza A/Vietnam/1203/2004 (H5N1). The challenge dose was approximately 3×LD50 CCID50 (cell culture infectious doses) of virus per mouse. All mice were administered virus challenge on study day 22. Following challenge all mice were observed for weight loss and mortality through day 21 post-challenge.

TABLE 11

Study Groups Observed for Morality Rates and Body Weight

| No. Mice | Group No. | Infected Y or N | Vaccine Dosage (IFU/mouse) | Vaccine Day/Route | Challenge Virus | Challenge Day | Observations/ Testing |
|---|---|---|---|---|---|---|---|
| 10 | 1 | Yes | None (Placebo) | Day 0, IN | $I^A$/CA/04/2009 (H1N1) | Day 22 | Survival and weight |
| 10 | 3 | Yes | None (Placebo) | Day 0, IN | $I^A$/Vic/3/1975 (H3N2) | Day 22 | determination |
| 10 | 5 | Yes | None (Placebo) | Day 0, IN | $I^A$/Vietnam/1203/2004 (H5N1) | Day 22 | |
| 10 | 7 | Yes | None (Placebo) | Day 0, IN | $I^B$/Sichuan/379/1999 | Day 22 | |
| 10 | 9 | Yes | AdE (3.2 × $10^8$) | Day 0, IN | $I^A$/CA/04/2009 (H1N1) | Day 22 | |
| 10 | 11 | Yes | AdE (3.2 × $10^8$) | Day 0, IN | $I^A$/Vic/3/1975 (H3N2) | Day 22 | |
| 10 | 13 | Yes | AdE (3.2 × $10^8$) | Day 0, IN | $I^A$/Vietnam/1203/2004 (H5N1) | Day 22 | |
| 10 | 15 | Yes | AdE (3.2 × $10^8$) | Day 0, IN | $I^B$/Sichuan/379/1999 | Day 22 | |
| 10 | 17 | Yes | None (Placebo) | Day 20, IN | $I^A$/CA/04/2009 (H1N1) | Day 22 | |
| 10 | 19 | Yes | None (Placebo) | Day 20, IN | $I^A$/Vic/3/1975 (H3N2) | Day 22 | |
| 10 | 21 | Yes | None (Placebo) | Day 20, IN | $I^A$/Vietnam/1203/2004 (H5N1) | Day 22 | |
| 10 | 23 | Yes | None (Placebo) | Day 20, IN | $I^B$/Sichuan/379/1999 | Day 22 | |
| 10 | 25 | Yes | AdE (3.2 × $10^8$) | Day 20, IN | $I^A$/CA/04/2009 (H1N1) | Day 22 | |
| 10 | 27 | Yes | AdE (3.2 × $10^8$) | Day 20, IN | $I^A$/Vic/3/1975 (H3N2) | Day 22 | |
| 10 | 29 | Yes | AdE (3.2 × $10^8$) | Day 20, IN | $I^A$/Vietnam/1203/2004 (H5N1) | Day 22 | |
| 10 | 31 | Yes | AdE (3.2 × $10^8$) | Day 20, IN | $I^B$/Sichuan/379/1999 | Day 22 | |
| 5 | 2 | No | Normal controls observed for weight gain | | | | |

TABLE 12

Study Group Used for Cytokine Analysis

| No. Mice | Group No. | Infected Y or N | Vaccine Dosage (IFU/mouse) | Vaccine Day/Route | Challenge Virus | Challenge Day | Observations/ Testing |
|---|---|---|---|---|---|---|---|
| 20 | 1a | Yes | None (Placebo) | Day 0, IN | $I^A$/CA/04/2009 (H1N1) | Day 22 | Sac 5 mice per group for lung |
| 20 | 5a | Yes | AdE (3.2 × $10^8$) | Day 0, IN | $I^A$/CA/04/2009 (H1N1) | Day 22 | lavage on day 3 and 6 post- |
| 20 | 9a | Yes | None (Placebo) | Day 20, IN | $I^A$/CA/04/2009 (H1N1) | Day 22 | vacc. Sac 5 mice per |

TABLE 12-continued

Study Group Used for Cytokine Analysis

| No. Mice | Group No. | Infected Y or N | Vaccine Dosage (IFU/mouse) | Vaccine Day/Route | Challenge Virus | Challenge Day | Observations/ Testing |
|---|---|---|---|---|---|---|---|
| 20 | 13a | Yes | AdE (3.2 × $10^8$) | Day 20, IN | $I^A$/CA/04/2009 (H1N1) | Day 22 | group for lung lavage on day 3 and 6 post-challenge. |

TABLE 13

Negative Controls for Cytokine Analysis

| No. Mice | Group No. | Infected Y or N | Vaccine Dosage (IFU/mouse) | Vaccine Day/Route | Observations/Testing |
|---|---|---|---|---|---|
| 6 | 4 | No | None (Placebo) | Day 0, IN | Sac 3 mice per group for lung lavage on days 25 and 28 post-vaccination. |
| 6 | 6 | No | AdE (3.2 × $10^8$) | Day 0, IN | |

Groups of mice were vaccinated on study day 0 or 20 by the intranasal route. The placebo groups received 50 μl physiological sterile saline (PSS) by the same route. For influenza virus challenge, mice were anesthetized by i.p. injection of ketamine/xylazine (50 mg/kg/5 mg/kg) prior to intranasal challenge with 90 μl of influenza A/CA/04/2009 (H1N1p), A/Victoria/3/1975 (H3N2), B/Sichuan/379/1999 or 75 μl of influenza A/Vietnam/1203/2004 (H5N1). The challenge dose was approximately 3×LD50 CCID50 (cell culture infectious doses) of virus per mouse. All mice were administered virus challenge on study day 22. Following challenge all mice were observed for weight loss and mortality through day 21 post-challenge.

Statistical analysis: Kaplan-Meier survival curves were generated and compared by the Log-rank (Mantel-Cox) test followed by pairwise comparison using the Gehan-Breslow-Wilcoxon test in Prism 5.0f (GraphPad Software Inc., La Jolla, Calif.). The mean body weights were analyzed by analysis of variance (ANOVA) followed by Tukey's multiple comparison test using Prism 5.0f.

Bronchioalveolar lavage (BAL): The lavage procedure was begun immediately after blood collection and was completed within 5 to 10 min of each animal's death. A volume of 0.75 ml of phosphate buffered saline (PBS) was slowly delivered into the lung through the tracheal tube. Immediately after delivery the fluid was slowly withdrawn by gentle suction and the samples stored at −80. The procedure was repeated a total of three times and lavage fluids from each mouse were pooled.

Lung virus titer determination: BAL samples were centrifuged at 2000×g for 5 minutes. Varying 10-fold dilutions of BAL supernatants were assayed in triplicate for infectious virus in MDCK cells, with virus titers calculated as described previously (1, 2). Virus titer differences were evaluated by ANOVA on log-transformed values assuming equal variance and normal distribution. Following ANOVA, individual treatment values were compared to placebo control by Tukey's pair-wise comparison test using Prism 5.0f.

Lung cytokine/chemokine determinations: A sample (200 μl) from each lung lavage was tested for cytokines and chemokines using a chemiluminescent ELISA-based assay according to the manufacturer's instructions (Quansys Biosciences Q-Plex™ Array, Logan, Utah). The Quansys multiplex ELISA is a quantitative test in which 16 distinct capture antibodies have been applied to each well of a 96-well plate in a defined array. Each sample supernatant was tested at 2 dilutions for the following: IL-1α, IL-1β, IL-2, IL-3, IL-4, IL-5, IL-6, IL-10, IL-12p70, IL-17, MCP-1, IFN-g, TNF-a, MIP-1a, GM-CSF, and RANTES.

Cytokine and chemokine titers are reported in pg/ml of lung lavage fluid. Titer differences were evaluated by ANOVA on values assuming equal variance and normal distribution. In addition, treatment group mean values were evaluated by two-way ANOVA for effects based on the day post-infection using Prism 5.0f.

Results and Discussion

This study determined the ability of the empty adenovirus vector (AdE) to provide protection against influenza A H1N1, H3N2, H5N1, and influenza B virus challenge infections in mice. In addition, cytokine levels in lung lavage were evaluated following vaccination and challenge with influenza A/CA/04/2009 (pandemic H1N1) virus in an attempt to determine the mechanism of protection afforded by the AdE vector. Mice were vaccinated with 3.2×$10^8$ ifu/50 μl of AdE by the intranasal route. A single vaccination was given three-weeks before challenge infection. In addition, this study evaluated the antiviral effects of the AdE-vector when administered 2 days before challenge infection. Following infection, all mice were observed for weight loss and mortality through day 21 post-challenge.

The AdE vector was found to provide 100% protection from challenge with influenza A/CA/04/2009 (pandemic H1N1) virus when administered 20 days before challenge, and provided 80% protection when administered two (2) days before challenge. The AdE vector provided 90% protection from influenza A/Victoria/3/75 (H3N2) virus when administered 20 days before challenge. However, the protection afforded by the AdE vector administered two (2) days before challenge was not significant. The AdE vector administered 20 days before influenza A/Vietnam/1203/2004 (H5N1) virus challenge did not provide protection from mortality, but did increase the mean day of death significantly. However, no protection from influenza A/Vietnam/1203/2004 (H5N1) was provided when the AdE vector was administered two (2) days before challenge. The AdE vector also provided 100% protection from influenza B/Sichuan/379/9 virus when administered 20 days before challenge. In addition, the AdE vector provided 90% protection when administered two (2) days before challenge with influenza B/Sichuan/379/9 virus. The AdE vector only provided significant protection from weight loss following challenge by the influenza B/Sichuan/379/9 virus. Both times of AdE administration, day 0 and day 20, provided protection from weight loss following challenge. The groups of mice receiving AdE 20 days before challenge showed a 1-2 log reduction in influenza A/CA/04/2009 (pandemic H1N1) virus titer compared to placebo controls on both days.

In an attempt to identify the immune mechanism of protection afforded by immunization with the AdE vector, the expression of cytokines and chemokines in lung lavage following influenza A/CA/04/2009 (pandemic H1N1) virus infection was determined. Expression of of IL-1α, IL-1β, IL-2, IL-3, IL-4, IL-5, IL-6, IL-10, IL-12p70, IL-17, MCP-1, IFN-γ, TNFα, MIP-1α, GM-CSF, and RANTES were measured on days 3 and 6 post-vaccination, days 25 and 28 post-vaccination, and on days 3 and 6 post-challenge (which is the same as days 25 and 28 post-vaccination). Significant changes in cytokine and chemokine levels were observed for IL-1α, IL-6, IL-12p70, MCP-1, IFN-γ, and RANTES. Significant decreases, compared to placebo controls, were observed after challenge infection for IL-1α, IL-6, and IL-12p70. No significant changes were observed for IL-1b, IL-2, IL-3, IL-4, IL-5, IL-10, IL-17, TNF-α, MIP-1α, and GM-CSF. A significant decrease ($p<0.01$) in IL-1α expression was observed on day 3 post-challenge when the AdE was administered 20 days before challenge. A significant decrease ($p<0.01$) in IL-6 expression in lung lavage following vaccination with AdE and challenge was observed (e.g., on day 6 post-challenge when the AdE was administered 20 days before challenge)). A significant decrease ($p<0.01$) in IL-12p70 expression in lung lavage following vaccination with AdE and challenge was observed on day 3 post-challenge when the AdE was administered 20 days before challenge. Significant ($p<0.01$) changes in expression of MCP-1 and IFN-γ in lung lavage were observed after vaccination and after challenge infection. MCP-1 levels increased on days 3, 6, 25, and 28 for all AdE treated groups post-vaccination. However, the MCP-1 levels decreased on day 6 post-challenge when the AdE was administered 20 days before challenge. IFN-γ levels increased on day 6 post-vaccination when the AdE was administered two (2) days before challenge, and remained elevated until days 25 and 28 ($p<0.001$) post-vaccination when AdE was administered 20 days before challenge. In addition, IFNγ levels increased approximately 10-fold on day 6 post-challenge when AdE was administered two (2) days before challenge. Significant changes in levels of RANTES were observed on days 3 ($p<0.0001$), 6 ($p<0.001$) and 25 ($p<0.01$) post-vaccination). This data is summarized in Table 14.

TABLE 14

| AdE Admin. | Infected? | Lung Lavage Collection Post-AdE | Decreased | Increased |
|---|---|---|---|---|
| Day 0 | No | Day 3 | | MCP-1 RANTES (CCL5) |

TABLE 14-continued

| AdE Admin. | Infected? | Lung Lavage Collection Post-AdE | Decreased | Increased |
|---|---|---|---|---|
| Day 0 | No | Day 6 | | MCP-1 IFN-γ RANTES (CCL5) |
| Day 0 | No | Day 25 | | MCP-1 IFN-γ RANTES (CCL5) |
| Day 0 | No | Day 28 | | MCP-1 IFN-γ |
| Challenge on Day 22 of Study | | | | |
| Day 0 | Yes | Day 25 (Day 3 post-challenge) | IL-1α IL-12 | |
| Day 0 | Yes | Day 28 Post-AdE (Day 6 post-challenge) | IL-6 MCP-1 | |
| Day 20 | Yes | Day 5 (Day 3 post-challenge; same as Day 25 of the study) | | |
| Day 20 | Yes | Day 8 (Day 6 post-challenge; same as Day 28 of the study) | | IFN-γ |

Conclusions

This example describes the use of an empty adenovirus vector (AdE) as a vaccine against influenza A H1N1, H3N2, H5N1, and influenza B virus challenge infections in mice. A single vaccination was given either three (3) weeks before challenge infection, or two (2) days before challenge infection. Remarkably, protection was provided against all challenge strains when the AdE was administered 20 days before challenge. The survival effects observed against the H5N1 virus was not actually from mortality, but rather an increase in mean day of death. In addition, protection was provided against the H1N1 and influenza B virus challenge by the AdE vector, when administered two (2) days before challenge. Protection observed two (2) days after vaccination suggests an innate immune mechanism. However, innate immunity is not expected to last longer than four (4) days post-infection. Therefore, the observation that mice can be protected from virus challenge after only two (2) days, in addition to three (3) weeks after vaccination, suggests more than one mechanism of action. One possible mechanism, suggested by the increased levels of MCP-1 and IFN-γ both post-vaccination and post-challenge, is that vaccination with AdE leads to an increase in MCP-1, which recruits monocytes, neutrophils, and/or lymphocytes, which then stimulates production of IFN-γ.

Example 3: AdE Human Clinical Trial for SARS-CoV-2 Vaccination

In this example, the use of intranasal (i.n.) administration of AdE vectors (i.e., replication deficient ΔE1E3 adenovirus type 5 (Ad5)) viral particles without an exogenous non-Ad pathogen antigen encoded in the Ad5 genome) to confer prophylactic therapy against SARS-CoV-2 is described. To establish the immunogenic and/or protective capacity of an immunogenic composition comprising AdE vectors against SARS-CoV-2, an AdE immunogenic composition comprising AdE viral particles (vp), are administered to human being subjects and tested for its effect on the immune response against SARS-CoV-2 therein. To do so, a randomized, double-blind, placebo-controlled, dose-escalation clinical trial to evaluate the safety and immunogenicity of an AdE immunogenic composition in healthy adults 18 to 49 years of age can be carried out. Subjects are typically screened within 28 days of randomization (Day 1).

For instance, a study can comprise two parts; part A which evaluates safety, and part B which evaluates immunogenicity, of the AdE immunogenic composition. In part A, approximately 120 subjects who meet all inclusion and no exclusion criteria and provided written informed consent are enrolled into four sequential cohorts of 30 subjects each defined by the AdE dose ($1\times10^8$, $1\times10^9$, $1\times10^{10}$, and $1\times10^{11}$ vp). Within each cohort (and the sentinel group in the first dose cohort), subjects are randomized in a 4:1:1 ratio to receive one intranasal dose of the AdE immunogenic composition (Day 1) or one intranasal dose of placebo (normal saline) (Day 1). The AdE immunogenic composition and placebo are administered in a double-blind fashion. Reactogenicity can be ascertained by determining counts and percentages of subjects with local events including but not limited to nasal irritation, sneezing, nasal congestion, cough, sore throat, change in smell, change in taste, change in vision, eye pain, pain, tenderness, induration, erythema, regional lymphadenopathy, and systemic events (headache, fatigue, myalgia, nausea, vomiting, diarrhea, coughing, chills, fever) for 14 days after vaccination. Adverse Events (AEs) are determined as counts and percentages of subjects with AEs from Day 1 to Day 57; medically attended AEs (MAAEs), serious AEs (SAEs), and new-onset chronic illnesses (NCIs) from Day 1 to Day 181 following administration of the AdE immunogenic composition. For instance, targeted and symptom-driven physical examinations including vital signs can be carried out on days 4, 8, 15, 22, 29, and 57; an electrocardiogram can be carried out on day 57; safety laboratory tests can be carried out on days 8 and 57; and serum samples taken for immunogenicity testing at days 8, 15, 22, 29, 57, 91, 181, and 361. The primary endpoint for evaluation of the safety profile in Part A is the number and percentage (95% confidence interval (CI)) of subjects with solicited and unsolicited AEs recorded post-vaccination. Safety analyses is performed using the Safety Population. The number (percentage, 95% CI) of subjects with local events and systemic events is summarized by group, as is reactogenicity. The number (percentage, 95% CI) of subjects with AEs from Day 1 to Day 57 (including MAAEs, NCIs, SAEs) is summarized for each Medical Dictionary for Regulatory Activities system organ class (SOC) by preferred term (PT) and group. The number (percentage) of subjects with MAAEs, with NCIs, and with SAEs from Day 1 to Day 181 is summarized in a similar fashion. The number (percentage, 95% CI) of subjects with AEs by severity and by relationship to investigational product (IP) is also summarized. Listings of AEs, MAAEs, NCIs, and SAEs are provided.

In part B, the immunogenicity of the AdE immunogenic composition is determined. Following administration of the AdE immunogenic composition by intranasal spray as a single dose of $1\times10^8$, $1\times10^9$, $1\times10^{10}$, and $1\times10^{11}$ vp and as two doses (3 weeks apart) of the highest well tolerated of these doses to subjects, the immune response can be measured by ELISA of serum to measure anti-SARS-CoV-2 antigen antibodies, and the GMT, geometric mean ratio (GMR) (the ratio of postvaccination and pre-vaccination GMTs within the same dose group), and responder rate (≥four-fold rise in IgG post dose) determined. For instance, approximately 25 subjects who meet all inclusion and no exclusion criteria and provided written informed consent are randomized in a 4:1 ratio to receive two intranasal doses of the AdE immunogenic composition at the highest well tolerated dose from Part A or placebo 21 days apart (Days 1 and 22). The AdE immunogenic composition and placebo are administered in a double-blind fashion. Intranasal doses of the AdE immunogenic composition and placebo are administered to subjects in a sitting or reclined position. In part B, targeted and symptom-driven physical examination including vital signs can be carried out on days 8, 15, 22, 29, 36, 43, 50, and 57; an electrocardiogram can be carried out on day 57; safety laboratory tests on days 8, 29, and 57; serum samples taken for immunogenicity testing at days 8, 15, 22, 29, 57, 91, 181, and 361; and nasopharyngeal swabs collected on days 8, 15, 29, 36, 43, 50, 57, and 91. Nasopharyngeal samples collected at Screening and on Days 29 and 57 can also be subsequently tested for evaluation of mucosal immune response.

In some embodiments, the clinical trial can be carried out using patients already infected by SARS-CoV-2 and time to clinical improvement and/or recovery determined (or, in some embodiments, a cohort of the patients tested). A primary outcome measure is Time to Clinical Improvement (TTCI) and/or Time to Clinical Recovery (TTCR) which are determined for up to 28 days following administration of the AdE composition as described above. TTCI is defined as the time (in days) from initiation of study treatment (active or placebo) until a decline of two categories from status at randomization on a six-category ordinal scale of clinical status which ranges from 1 (discharged) to 6 (death). The six-category ordinal scale is as follows: 6. Death; 5. ICU, requiring extracorporeal membrane oxygenation (ECMO) and/or invasive mechanical ventilation (IMV); 4. Intensive care unit (ICU)/hospitalization, requiring non-invasive mechanical ventilation (NIV)/high-flow nasal cannula (HFNC) therapy; 3. Hospitalization, requiring supplemental oxygen (but not NIV/HFNC); 2. Hospitalization, not requiring supplemental oxygen; and, 1. Hospital discharge or meet discharge criteria (discharge criteria are defined as clinical recovery, i.e. fever, respiratory rate, oxygen saturation return to normal, and cough relief). Secondary outcome TTCI measures include all cause mortality (baseline SpO2 during screening, PaO2/FiO2<300 mmHg or a respiratory rate ≥24 breaths per min without supplemental oxygen); frequency of respiratory progression (SPO2≤94% on room air or PaO2/FiO2<300 mmHg and requirement for supplemental oxygen or more advanced ventilator support); time to defervescence (in those with fever at enrolment); time to cough reported as mild or absent (in those with cough at enrolment rated severe or moderate); time to dyspnea reported as mild or absent (on a scale of severe, moderate, mild absent, in those with dyspnoea at enrolment rated as severe or moderate,); frequency of requirement for supplemental oxygen or non-invasive ventilation; time to SARS-CoV-2 RT-PCR negative in throat swab, sputum, lower respiratory tract specimen, and/or upper respiratory tract specimen; change (reduction) in SARS-CoV-2 viral load in throat swab, sputum, lower respiratory tract specimen, and/or upper respiratory tract specimen as assessed by area under viral load curve (e.g., as determined using polymerase chain reaction (PCR)); frequency of requirement for mechanical ventilation; and, frequency of serious adverse events. TTCI is defined as the time (in hours) from initiation of study treatment (active or placebo) until normalization of fever, respiratory rate, and oxygen saturation, and alleviation of cough, sustained for at least 72 hours. The primary TTCR outcome measures include normalization and alleviation criteria; fever—≤36.9° C. or—axilla, ≤37.2° C. oral; respiratory rate—≤24/minute on room air; oxygen saturation—>94% on room air; and, cough—mild or absent on a patient reported scale of severe, moderate, mild, absent. The secondary TTCR outcome measures are the same as the TTCI secondary outcomes listed above.

Standard clinical trial design and statistical methods are used in the analyses thereof. For instance, the sample size for this study is selected as adequate and reasonable for an initial review of the safety and immunogenicity profile of the AdE immunogenic composition at doses to be well tolerated, rather than for statistical power (e.g., 120 subjects as described above). The sample size permits initial estimates of reactogenicity. For example, given a total of 100 subjects receiving AdE immunogenic composition, the study is designed to have an 80% probability of detecting at least one AE that occurred at a rate of 1.6%. If no SAEs were observed among the 100 subjects who received AdE immunogenic composition, an approximation to the 1-sided upper bound of the 95% confidence interval (CI) on the rate of SAE occurrence would be 3%. Immunology analyses are conducted using the Evaluable and Per-protocol (PP) Populations with primary conclusions drawn from the PP Population. Analyses based on the Evaluable Population are undertaken and presented only if >1 subject in any one group were excluded from the PP Population. With the exception responder analyses, as described below, no imputation for missing data is performed. Data is transformed as appropriate prior to analysis. Baseline is defined as the sample collected prior to AdE immunogenic composition administration on Day 1. The primary variables of interest for assessment of humoral and cellular immune response to SARS-CoV-2 (e.g., cell mediated responses) are determined. In some embodiments, comparisons of responders in each AdE immunogenic composition dose group against the placebo group can also be conducted using Fisher's exact test. To determine the effect of pre-dose Ad5 serum antibody levels on immunogenicity of AdE immunological composition on Day 29 (Part A) or Day 50 (Part B), analyses are performed using ANCOVA with baseline Ad5 titer as a covariate. Mucosal immunogenicity analyses are conducted using the Evaluable and PP Populations. No imputation for missing data is performed. Endpoints analyzed are GMT and GMR for IgA antibody level measured by ELISA. Summary statistics for continuous parameters (safety laboratory tests and vital signs) are presented by group as follows: pre-vaccination, postvaccination, and change from pre-vaccination to postvaccination assessment. The number and percentage of subjects with postvaccination safety laboratory values or vital sign values recorded as newly abnormal (i.e., an event with an increase in the toxicity grade relative to the baseline value and with a severity grade of moderate or higher) after study vaccination are tabulated. Shift tables that cross-tabulate the pre-vaccination and postvaccination safety laboratory values of each subject by severity grade are prepared. Summaries of the number and percentage of subjects with normal, abnormal not clinically significant, and abnormal clinically significant ECG interpretations are presented. For shedding of the Ad5 vector, data are summarized by count and percent positive by time point, along with median copy number. The median duration of Ad5 shedding, interquartile range, minimum and maximum duration of Ad5 shedding are presented for each AdE immunogenic composition group and all immunological composition dose groups combined. Viral culture results for evaluation of adenovirus infection are also listed.

These studies will show that the AdE composition can be used to induce an anti-SARS-CoV-2 immune response in human beings (e.g., it is an immunogenic composition), and exhibits an acceptable safety profile. It is preferred that the immune response is statistically significant, and even more preferably, a protective immune response (i.e., it is a SARS-CoV-2 vaccine). In preferred embodiments, the data shows the AdE composition can be used to treat subjects infected by SARS-CoV-2 (e.g., hospitalized patients).

Example 4

A. Generation of Recombinant Human Adenovirus Type 5 SARS-CoV-2 (hAd5-SARS-CoV-2)

An E1/E3 deleted, replication defective hAd5 that uses optionally the tissue plasminogen activator (tPA) leader sequence followed by a codon optimized nucleotide sequence encoding at least one SARS-CoV-2 protein(s) (e.g., any one or more of SEQ ID NOS. 2-11, and/or one or more fragment(s) and/or derivative(s) thereof). The expression cassette containing the cytomegalovirus (CMV) promoter and SARS-CoV-2 coding sequence are inserted into the E1 region of the hAd5. This vector is referred to herein as "hAd5-SARS-CoV-2".

To investigate the expression level of SARS-CoV-2 protein(s) from the hAd5-SARS-CoV-2 vaccine, the expression of the SARS-CoV-2 protein(s) are compared from SARS-CoV-2-infected Vero cells by western blot with an anti-SARS-CoV-2 rabbit polyclonal specific to S. The western blot shows that the hAd5-SARS-CoV-2 vaccine expresses S in infected cells. The expressed S antigen is also sequenced to verify the native sequence.

B. Immunogenicity of hAd5-SARS-CoV-2 Vaccine.

To understand the immunogenicity of the hAd5-SARS-CoV-2 vaccine, eight-week old mice (e.g., wild type or transgenic provided they expresses the receptor for SARS-CoV-2) are intranasally (i.n.) immunized with sufficient number of (e.g., $1\times10^7$) hAd5-SARS-CoV-2 viral particles. On day eight, the peak of the T cell adaptive immune response, a subset of vaccinated mice are euthanized and SARS-CoV-2 antigen specific $CD8^+$ T cell responses evaluated by intracellular cytokine staining and/or IFN-γ ELISpot. Splenic or PBMCs T cells are stimulated with peptide pools covering the antigen and/or an immunodominant SARS-CoV-2 peptide and the frequency of IFN-γ-producing T cells are determined. Twenty-one days after vaccination mice are bled to evaluate the serum antibody response. A SARS-CoV-2 specific ELISA is used to determine SARS-CoV-2 S specific immunoglobulin (IgG) responses. A single hAd5-SARS-CoV-2 vaccination may generate a SARS-CoV-2 S specific IgG response, e.g., with a higher reciprocal mean endpoint versus naïve animals with a reciprocal mean endpoint titer below the limit of detection. To determine the quantity of neutralizing antibodies, focus reduction neutralization tests are completed.

C. Neutralization of SARS-CoV-2

The virus neutralizing capacity of the vaccine will be determined using sera from immunized mice as described in section B. of this example, using the method of plaque reduction, or infected foci reduction. Either wild type, attenuated or VSV-pseudo-typed with the SARS-CoV-2 S will be mixed with various dilutions of vaccinated mouse serum and incubated for 30 min at room temperature followed by infection of Vero or other appropriate cell line. Virus neutralization then is quantified as the highest antibody dilution capable of reducing the number of plaque or infectious foci by a predetermined value, for example 50%.

D. Protective Capacity of hAd5-SARS-CoV-2 Immunogenic Compositions

To establish the protective capacity of the SARS-CoV-2 immunogenic composition, a sufficient number of hAd5-

SARS-CoV-2 viral particles (e.g., $1\times10^7$) are administered i.n. to mice or other appropriate rodent (e.g. transgenic rodent expressing the virus receptor). Twenty-one days later the animals are challenged with SARS-CoV-2, along with a phosphate buffered saline (PBS)-vaccinated control group and monitored for survival. After stringent challenge all PBS-vaccinated control mice are found to exhibit symptoms and/or succumbed to SARS-CoV-2 infection, while the majority of hAd5-SARS-CoV-2 vaccinated mice survive. Clinical signs of disease are scored for twelve days and found improved in hAd5-SARS-CoV-2 vaccinated mice compared to the non-vaccinated controls. Such results will demonstrate that the hAd5-SARS-CoV-2 vaccine is able to induce a protective response leading to reduced disease severity in this animal model.

E. Other

The tests described above can also be carried out using one or more other rdAd anti-SARS-CoV-2 vectors (e.g., AdE, AdD) by substituting hAd5-SARS-CoV-2 with another such vector (e.g., AdE, AdD), as would be understood by those of ordinary skill in the art. The generation and interpretation of results would be adjusted according to the particular rdAd anti-SARS-CoV-2 vector(s) being tested, as would be understood by those of ordinary skill in the art.

Example 5: hAd5-SARS-CoV-2 Human Clinical Trial for SARS-CoV-2 Vaccination

To establish the immunogenic and/or protective capacity of a hAdv5-SARS-CoV-2 immunogenic composition comprising hAd5-SARS-CoV-2 viral particles (vp) and at least one pharmaceutically acceptable excipient, the same is administered to human subjects and tested for its effect on the immune response against SARS-CoV-2 in such subjects and, for its effect on time to clinical improvement and/or recovery on patients (e.g., hospitalized patients) infected with SARS-CoV-2. To do so, a randomized, double-blind, placebo-controlled, dose-escalation clinical trial to evaluate the safety and immunogenicity of hAdv5-SARS-CoV-2 composition in healthy adults 18 to 49 years of age is carried out. Subjects are typically screened within 28 days of randomization (Day 1).

For instance, a study can comprise two parts; part A which evaluates safety and part B which evaluates immunogenicity of the hAdv5-SARS-CoV-2 immunogenic composition. In part A, approximately 120 subjects who meet all inclusion and no exclusion criteria and provided written informed consent are enrolled into four sequential cohorts of 30 subjects each defined by the hAdv5 SARS-CoV-2 dose ($1\times10^8$, $1\times10^9$, $1\times10^{10}$, and $1\times10^{11}$ vp). Within each cohort (and the sentinel group in the first dose cohort), subjects are randomized in a 4:1:1 ratio to receive one intranasal dose of the hAdv5-SARS-CoV-2 immunogenic composition (Day 1) or one intranasal dose of placebo (normal saline) (Day 1). The hAdv5-SARS-CoV-2 immunogenic composition and placebo are administered in a double-blind fashion. Reactogenicity can be ascertained by determining counts and percentages of subjects with local events including but not limited to nasal irritation, sneezing, nasal congestion, cough, sore throat, change in smell, change in taste, change in vision, eye pain, pain, tenderness, induration, erythema, regional lymphadenopathy, and systemic events (headache, fatigue, myalgia, nausea, vomiting, diarrhea, coughing, chills, fever) for 14 days after vaccination. Adverse Events (AEs) are determined as counts and percentages of subjects with AEs from Day 1 to Day 57; medically attended AEs (MAAEs), serious AEs (SAEs), and new-onset chronic illnesses (NCIs) from Day 1 to Day 181 following administration of the hAdv5-SARS-CoV-2 immunogenic composition. For instance, targeted and symptom-driven physical examinations including vital signs can be carried out on days 4, 8, 15, 22, 29, and 57; an electrocardiogram can be carried out on day 57; safety laboratory tests can be carried out on days 8 and 57; and serum samples taken for immunogenicity testing at days 8, 15, 22, 29, 57, 91, 181, and 361 (e.g., enzyme-linked immunosorbent assay (ELISA) of serum to measure anti-SARS-CoV-2 antigen antibodies, geometric mean titer (GMT) as compared to day 0 (baseline)). Responder rates are also determined as described below (e.g., ≥four-fold rise in IgG post dose). The primary endpoint for evaluation of the safety profile in Part A is the number and percentage (95% confidence interval (CI)) of subjects with solicited and unsolicited AEs recorded post-vaccination. Safety analyses is performed using the Safety Population. The number (percentage, 95% CI) of subjects with local events and systemic events is summarized by group, as is reactogenicity. The number (percentage, 95% CI) of subjects with AEs from Day 1 to Day 57 (including MAAEs, NCIs, SAEs) is summarized for each Medical Dictionary for Regulatory Activities system organ class (SOC) by preferred term (PT) and group. The number (percentage) of subjects with MAAEs, with NCIs, and with SAEs from Day 1 to Day 181 is summarized in a similar fashion. The number (percentage, 95% CI) of subjects with AEs by severity and by relationship to investigational product (IP) is also summarized. Listings of AEs, MAAEs, NCIs, and SAEs are provided.

In part B, the immunogenicity of hAdv5-SARS-CoV-2 immunogenic composition is determined. Following administration of the hAdv5-SARS-CoV-2 immunogenic composition by intranasal spray as a single dose of $1\times10^8$, $1\times10^9$, $1\times10^{10}$, and $1\times10^{11}$ vp and as two doses (3 weeks apart) of the highest well tolerated of these doses to subjects, the immune response can be measured by ELISA of serum to measure anti-SARS-CoV-2 antigen antibodies, and the GMT, geometric mean ratio (GMR) (the ratio of postvaccination and pre-vaccination GMTs within the same dose group), and responder rate (≥four-fold rise in IgG post dose) determined. For instance, approximately 25 subjects who meet all inclusion and no exclusion criteria and provided written informed consent are randomized in a 4:1 ratio to receive two intranasal doses of the hAdv5-SARS-CoV-2 immunogenic composition at the highest well tolerated dose from Part A or placebo 21 days apart (Days 1 and 22). The hAdv5-SARS-CoV-2 immunogenic composition and placebo are administered in a double-blind fashion. Intranasal doses of the hAdv5-SARS-CoV-2 immunogenic composition and placebo are administered to subjects in a sitting position. In part B, targeted and symptom-driven physical examination including vital signs can be carried out on days 8, 15, 22, 29, 36, 43, 50, and 57; an electrocardiogram can be carried out on day 57; safety laboratory tests on days 8, 29, and 57; serum samples taken for immunogenicity testing at days 8, 15, 22, 29, 57, 91, 181, and 361; and nasopharyngeal swabs collected on days 8, 15, 29, 36, 43, 50, 57, and 91. Nasopharyngeal samples collected at Screening and on Days 29 and 57 can also be subsequently tested for evaluation of mucosal immune response.

The clinical trial can be carried out in patients already infected by SARS-CoV-2 and time to clinical improvement and/or recovery determined (or, in some embodiments, a cohort of the patients tested). A primary outcome measure is Time to Clinical Improvement (TTCI) and/or Time to Clinical Recovery (TTCR) which are determined for up to 28 days following administration of the hAdv5-SARS-CoV-2 composition as described above. TTCI is defined as the time (in days) from initiation of study treatment (active or placebo) until a decline of two categories from status at randomization on a six-category ordinal scale of clinical status which ranges from 1 (discharged) to 6 (death). The six-category ordinal scale is as follows: 6. Death; 5. ICU, requiring extracorporeal membrane oxygenation (ECMO) and/or invasive mechanical ventilation (IMV); 4. Intensive care unit (ICU)/hospitalization, requiring non-invasive mechanical ventilation (NIV)/high-flow nasal cannula (HFNC) therapy; 3. Hospitalization, requiring supplemental oxygen (but not NIV/HFNC); 2. Hospitalization, not requiring supplemental oxygen; and, 1. Hospital discharge or meet discharge criteria (discharge criteria are defined as clinical recovery, i.e. fever, respiratory rate, oxygen saturation return to normal, and cough relief). Secondary outcome TTCI measures include all-cause mortality (baseline SpO2 during screening, PaO2/FiO2<300 mmHg or a respiratory rate ⩾24 breaths per min without supplemental oxygen); frequency of respiratory progression (SPO2⩽94% on room air or PaO2/FiO2<300 mmHg and requirement for supplemental oxygen or more advanced ventilator support); time to defervescence (in those with fever at enrolment); time to cough reported as mild or absent (in those with cough at enrollment rated severe or moderate); time to dyspnea reported as mild or absent (on a scale of severe, moderate, mild absent, in those with dyspnea at enrollment rated as severe or moderate,); frequency of requirement for supplemental oxygen or non-invasive ventilation; time to 2019-nCoV-2 RT-PCR negative in throat swab, sputum, lower respiratory tract specimen, and/or upper respiratory tract specimen; change (reduction) in SARS-CoV-2 viral load in throat swab, sputum, lower respiratory tract specimen, and/or upper respiratory tract specimen; change (reduction) in 2019-nCoV-2 viral load in in throat swab, sputum, lower respiratory tract specimen, and/or upper respiratory tract specimen; change (reduction) in SARS-CoV-2 viral load in throat swab, sputum, lower respiratory tract specimen, and/or upper respiratory tract specimen as assessed by area under viral load curve (e.g., as determined using polymerase chain reaction (PCR)); frequency of requirement for mechanical ventilation; and, frequency of serious adverse events. TTCI is defined as the time (in hours) from initiation of study treatment (active or placebo) until normalization of fever, respiratory rate, and oxygen saturation, and alleviation of cough, sustained for at least 72 hours. The primary TTCR outcome measures include normalization and alleviation criteria; fever—⩽36.9° C. or—axilla, ⩽37.2° C. oral; respiratory rate—⩽24/minute on room air; oxygen saturation—>94% on room air; and, cough—mild or absent on a patient reported scale of severe, moderate, mild, absent. The secondary TTCR outcome measures are the same as the TTCI secondary outcomes listed above.

Standard clinical trial design and statistical methods are used in the analyses of the data obtained from the trial. For instance, the sample size for this study is selected as adequate and reasonable for an initial review of the safety and immunogenicity profile of the hAdv5-SARS-CoV-2 composition at doses to be well tolerated, rather than for statistical power (e.g., 120 subjects as described above). The sample size permits initial estimates of reactogenicity. For example, given a total of 100 subjects receiving hAdv5-SARS-CoV-2 composition, the study is designed to have an 80% probability of detecting at least one AE that occurred at a rate of 1.6%. If no SAEs were observed among the 100 subjects who received hAdv5-SARS-CoV-2 immunological composition, an approximation to the 1-sided upper bound of the 95% confidence interval (CI) on the rate of SAE occurrence would be 3%. Immunology analyses are conducted using the Evaluable and Per-protocol (PP) Populations with primary conclusions drawn from the PP Population. Analyses based on the Evaluable Population are undertaken and presented only if >1 subject in any one group were excluded from the PP Population. With the exception responder analyses, as described below, no imputation for missing data is performed. Data is transformed as appropriate prior to analysis. Baseline is defined as the sample collected prior to hAdv5-SARS-CoV-2 composition administration on Day 1. The primary variables of interest for assessment of humoral immune response to SARS-CoV-2 are anti-SARS-CoV-2 antigen IgG titers. GMTs are determined at Baseline and postvaccination on Days 8, 15, 22, 29, 57, 91, and 181 (Part A) and Days 8, 15, 22, 29, 36, 43, 50, 91, and 181 (Part B) and summarized by dose group. Comparisons between hAdv5-SARS-CoV-2 composition doses and placebo are evaluated by analysis of covariance (ANCOVA) with treatment as a fixed effect and baseline log-transformed level as a covariate on the post-baseline log-transformed level of anti-SARS-CoV-2 IgG as a dependent variable. From these analyses, least-square (LS) means, LS treatment differences, and 95% CIs for the treatment differences on log-scale are obtained. The results are transformed back to the original scale by exponentiation to provide treatment geometric LS means, point estimates of the geometric LS mean ratios, and 95% CI for these ratios on each study day. A "responder" is defined as a subject with a 4-fold rise in anti-SARS-CoV-2 antigen titer from baseline on Days 8, 15, 22, 29, 57, 91, and 181 (Part A) and Days 8, 15, 22, 29, 36, 43, 50, 91, and 181 (Part B). Fold change for determination of responder status is computed using the post-imputation values without the +1 transformation, i.e., fold change=current imputed value/baseline imputed value. Responder rates are tabulated by percentages per dose group and the 95% Clopper-Pearson exact CI of the percentage. Differences of 95% CIs are presented to compare the response rate of each hAdv5-SARS-CoV-2 composition dose group to the and placebo group. In some embodiments, comparisons of responders in each hAdv5-SARS-CoV-2 composition dose group against the against the placebo group can also be conducted using Fisher's exact test. To determine the effect of pre-dose Ad5 serum antibody levels on immunogenicity of hAdv5-SARS-CoV-2 composition on Day 29 (Part A) or Day 50 (Part B), analyses are performed using ANCOVA with baseline Ad5 titer as a covariate. Mucosal immunogenicity analyses are conducted using the Evaluable and PP Populations. No imputation for missing data is performed. Endpoints analyzed are GMT and GMR for IgA antibody level measured by ELISA. Methods used are the same as for humoral immunogenicity analyses. Summary statistics for continuous parameters (safety laboratory tests and vital signs) are presented by group as follows: pre-vaccination, postvaccination, and change from pre-vaccination to postvaccination assessment. The number and percentage of subjects with postvaccination safety laboratory values or vital sign values recorded as newly abnormal (ie, an event with an increase in the toxicity grade relative to the baseline value and with a severity grade of moderate or higher) after study vaccination are tabulated. Shift tables that cross-tabulate the pre-vaccination and post-vaccination safety laboratory values of each subject by severity grade are prepared. Summaries of the number and percentage of subjects with normal, abnormal not clinically significant, and abnormal clinically significant ECG interpretations are presented. For shedding of the RD-Ad5 vector, data are summarized by count and percent positive by time point, along with median copy number. The median duration of Ad5 shedding, interquartile range, minimum and maximum duration of Ad5 shedding are presented for each hAdv5-SARS-CoV-2 composition group and all hAdv5-SARS-CoV-2 composition dose groups combined. Viral culture results for evaluation of adenovirus infection are also listed.

These studies will show that the hAdv5-SARS-CoV-2 composition can be used to induce an anti-SARS-CoV-2 immune response in human beings (i.e., it is an immunogenic composition), and exhibits an acceptable safety profile. It is preferred that that immune response be statistically significant, and even more preferably, a protective immune response (i.e., it is a SARS-CoV-2 vaccine). In preferred embodiments, the data shows the hAdv5-SARS-CoV-2 vaccine composition can be used to treat subjects infected by SARS-CoV-2 (e.g., hospitalized patients).

Example 6: AdD Vectors Human Clinical Trial for SARS-CoV-2 Vaccination

In this example, the use of intranasal (i.n.) administration of AdD vectors (i.e., replication deficient ΔE1E3 adenovirus type 5 (Ad5) viral particles encoding a pathogen antigen derived from an infectious agent other than SARS-CoV-2, e.g. influenza such as NasoVAX which is an AdVector (Ad5) expressing influenza hemagglutinin (HA) antigen, described in, e.g., Ser. No. 62/830,444 filed on 6 Apr. 2019 which is incorporated herein by reference and discloses preparation of NasoVAX) to confer prophylactic therapy against SARS-CoV-2 is described. In embodiments, the AdD vector induces an immune response, preferably a protective immune response, against both SARS-CoV-2 and the pathogen associated with the expressed exogenous antigen of the AdD vector. For example, NasoVAX will induce an immune response against both influenza and coronavirus including SARS-CoV-2. In this way, AdD is a dual vaccine inducing an immune response against two respiratory infectious agents.

To establish the immunogenic and/or protective capacity of a composition comprising AdD vectors against SARS-CoV-2, an AdD composition comprising AdD viral particles (vp), are administered to human being subjects and tested for its effect on the immune response against SARS-CoV-2 therein. To do so, a randomized, double-blind, placebo-controlled, dose-escalation clinical trial to evaluate the safety and immunogenicity of a AdD immunological composition in healthy adults 18 to 49 years of age can be carried out. Subjects are typically screened within 28 days of randomization (Day 1).

For instance, a study can comprise two parts; part A which evaluates safety, and part B which evaluates immunogenicity, of the AdD composition (e.g., NasoVax). In part A, approximately 120 subjects who meet all inclusion and no exclusion criteria and provided written informed consent are enrolled into four sequential cohorts of 30 subjects each defined by the AdD dose ($1\times10^8$, $1\times10^9$, $1\times10^{10}$, and $1\times10^{11}$ vp), each subject being administered a single intranasal dose in a total volume of 0.5 ml split evenly between nostrils as a nasal spray ("placebo" subjects receive 0.5 ml of normal saline not including AdD, the does also being split evenly between nostrils as a nasal spray). Within each cohort (and the sentinel group in the first dose cohort), subjects are randomized in a 4:1:1 ratio to receive one intranasal dose of the AdD composition (Day 1) or one intranasal dose of placebo (normal saline) (Day 1). The AdD composition and placebo are administered in a double-blind fashion. Reactogenicity can be ascertained by determining counts and percentages of subjects with local events including but not limited to nasal irritation, sneezing, nasal congestion, cough, sore throat, change in smell, change in taste, change in vision, eye pain, pain, tenderness, induration, erythema, regional lymphadenopathy, and systemic events (headache, fatigue, myalgia, nausea, vomiting, diarrhea, coughing, chills, fever) for 14 days after vaccination. Adverse Events (AEs) are determined as counts and percentages of subjects with AEs from Day 1 to Day 57; medically attended AEs (MAAEs), serious AEs (SAEs), and new-onset chronic illnesses (NCIs) from Day 1 to Day 181 following administration of the AdD composition. For instance, targeted and symptom-driven physical examinations including vital signs can be carried out on days 4, 8, 15, 22, 29, and 57; an electrocardiogram can be carried out on day 57; safety laboratory tests can be carried out on days 8 and 57; and serum samples taken for immunogenicity testing at days 8, 15, 22, 29, 57, 91, 181, and 361 (e.g., enzyme-linked immunosorbent assay (ELISA) of serum to measure anti-SARS-CoV-2 antigen and/or anti-D antigen antibodies, geometric mean titer (GMT) as compared to day 0 (baseline)), and/or anti-SARS-CoV-2 and/or anti-AdD immune cellular responses (e.g., T cell response). Responder rates are also determined as described below (e.g., ≥four-fold rise in IgG post dose). The primary endpoint for evaluation of the safety profile in Part A is the number and percentage (95% confidence interval (CI)) of subjects with solicited and unsolicited AEs recorded postvaccination. Safety analyses is performed using the Safety Population. The number (percentage, 95% CI) of subjects with local events and systemic events is summarized by group, as is reactogenicity. The number (percentage, 95% CI) of subjects with AEs from Day 1 to Day 57 (including MAAEs, NCIs, SAEs) is summarized for each Medical Dictionary for Regulatory Activities system organ class (SOC) by preferred term (PT) and group. The number (percentage) of subjects with MAAEs, with NCIs, and with SAEs from Day 1 to Day 181 is summarized in a similar fashion. The number (percentage, 95% CI) of subjects with AEs by severity and by relationship to investigational product (IP) is also summarized. Listings of AEs, MAAEs, NCIs, and SAEs are provided.

In part B, the immunogenicity of the AdD composition is determined. Following administration of the AdD composition by intranasal spray as a single dose of $1\times10^8$, $1\times10^9$, $1\times10^{10}$, and $1\times10^{11}$ vp in a 0.5 ml volume split evenly between nostrils as a nasal spray (and in some embodiments as two doses (3 weeks apart) of the highest well tolerated of these doses) to subjects, the immune response can be measured by ELISA of serum to measure anti-SARS-CoV-2 antigen antibodies and/or anti-AdD antibodies, and the GMT, geometric mean ratio (GMR) (the ratio of postvaccination and pre-vaccination GMTs within the same dose group), and responder rate (≥four-fold rise in IgG post dose), as well as immune cellular responses (e.g., T cell responses), are determined. For instance, approximately 25 subjects who meet all inclusion and no exclusion criteria and provided written informed consent are randomized in a 4:1 ratio to receive two intranasal doses of the AdD composition at the highest well tolerated dose from Part A or placebo 21 days apart (Days 1 and 22). The AdD composition and placebo are administered in a double-blind fashion. Intranasal doses of the AdD composition and placebo are administered to subjects in a sitting or reclined position. In part B, targeted and symptom-driven physical examination including vital signs can be carried out on days 8, 15, 22, 29, 36, 43, 50, and 57; an electrocardiogram can be carried out on day 57; safety laboratory tests on days 8, 29, and 57; serum samples taken for immunogenicity testing at days 8, 15, 22, 29, 57, 91, 181, and 361; and nasopharyngeal swabs collected on days 8, 15, 29, 36, 43, 50, 57, and 91. Nasopharyngeal samples collected at Screening and on Days 29 and 57 can also be subsequently tested for evaluation of mucosal immune response.

In some embodiments, the clinical trial can be carried out using patients already infected by SARS-CoV-2 and time to clinical improvement and/or recovery determined (or, in some embodiments, a cohort of the patients tested). A primary outcome measure is Time to Clinical Improvement (TTCI) and/or Time to Clinical Recovery (TTCR) which are determined for up to 28 days following administration of the AdD composition as described above. TTCI is defined as the time (in days) from initiation of study treatment (active or placebo) until a decline of two categories from status at randomization on a six-category ordinal scale of clinical status which ranges from 1 (discharged) to 6 (death). The six-category ordinal scale is as follows: 6. Death; 5. ICU, requiring extracorporeal membrane oxygenation (ECMO) and/or invasive mechanical ventilation (IMV); 4. Intensive care unit (ICU)/hospitalization, requiring non-invasive mechanical ventilation (NIV)/high-flow nasal cannula (HFNC) therapy; 3. Hospitalization, requiring supplemental oxygen (but not NIV/HFNC); 2. Hospitalization, not requiring supplemental oxygen; and, 1. Hospital discharge or meet discharge criteria (discharge criteria are defined as clinical recovery, i.e. fever, respiratory rate, oxygen saturation return to normal, and cough relief). Secondary outcome TTCI measures include all-cause mortality (baseline SpO2 during screening, PaO2/FiO2<300 mmHg or a respiratory rate ≥24 breaths per min without supplemental oxygen); frequency of respiratory progression (SPO2≤94% on room air or PaO2/FiO2<300 mmHg and requirement for supplemental oxygen or more advanced ventilator support); time to defervescence (in those with fever at enrolment); time to cough reported as mild or absent (in those with cough at enrolment rated severe or moderate); time to dyspnea reported as mild or absent (on a scale of severe, moderate, mild absent, in those with dyspnoea at enrollment rated as severe or moderate,); frequency of requirement for supplemental oxygen or non-invasive ventilation; time to SARS-CoV-2 RT-PCR negative in upper respiratory tract specimen; change (reduction) in SARS-CoV-2 viral load in upper respiratory tract specimen as assessed by area under viral load curve (e.g., as determined using polymerase chain reaction (PCR)); frequency of requirement for mechanical ventilation; and, frequency of serious adverse events. TTCI is defined as the time (in hours) from initiation of study treatment (active or placebo) until normalization of fever, respiratory rate, and oxygen saturation, and alleviation of cough, sustained for at least 72 hours. The primary TTCR outcome measures include normalization and alleviation criteria; fever—≤36.9° C. or—axilla, ≤37.2° C. oral; respiratory rate—≤24/minute on room air; oxygen saturation—>94% on room air; and, cough—mild or absent on a patient reported scale of severe, moderate, mild, absent. The secondary TTCR outcome measures are the same as the TTCI secondary outcomes listed above.

In some embodiments, a clinical trial can be carried out on approximately 120 subjects testing positive for SARS-CoV-2 aged over 50 years randomized into placebo and treatment groups. The placebo group receives 0.5 ml normal saline not including any AdD vector, administered as a single intranasal dose split evenly between the nostrils as a nasal spray. The treatment group is administered 0.5 ml normal saline including any AdD vector (i.e., NasoVax), administered as a single intranasal dose split evenly between the nostrils as a nasal spray. The primary efficacy endpoints are the proportion of subjects developing acute respiratory distress symptoms (ARDS) and maximum severity of COVID-19 (i.e., the symptoms of SARS-CoV-2 infection) by forced expiratory volume (FEV-1) and radiographic criteria. Secondary endpoints include viral shedding, days on mechanical ventilation and length of hospital stay.

Standard clinical trial design and statistical methods are used in the analyses thereof. For instance, the sample size for this study is selected as adequate and reasonable for an initial review of the safety and immunogenicity profile of the AdD composition at doses to be well tolerated, rather than for statistical power (e.g., 120 subjects as described above). The sample size permits initial estimates of reactogenicity. For example, given a total of 100 subjects receiving AdD composition, the study is designed to have an 80% probability of detecting at least one AE that occurred at a rate of 1.6%. If no SAEs were observed among the 100 subjects who received hAdv5-D (AdD) composition, an approximation to the 1-sided upper bound of the 95% confidence interval (CI) on the rate of SAE occurrence would be 3%. Immunology analyses are conducted using the Evaluable and Per-protocol (PP) Populations with primary conclusions drawn from the PP Population. Analyses based on the Evaluable Population are undertaken and presented only if >1 subject in any one group were excluded from the PP Population. With the exception responder analyses, as described below, no imputation for missing data is performed. Data is transformed as appropriate prior to analysis. Baseline was defined as the sample collected prior to AdD composition administration on Day 1. The primary variables of interest for assessment of humoral and cellular immune response to SARS-CoV-2 (e.g., anti-SARS-CoV-2 and/or anti-AdD antigen IgG titers, T cell responses) are determined. GMTs are determined at Baseline and postvaccination on Days 8, 15, 22, 29, 57, 91, and 181 (Part A) and Days 8, 15, 22, 29, 36, 43, 50, 91, and 181 (Part B) and summarized by dose group. Comparisons between AdD composition doses and placebo were evaluated by analysis of covariance (ANCOVA) with treatment as a fixed effect and baseline log-transformed level as a covariate on, e.g., the post-baseline log-transformed level of anti-SARS-CoV-2 IgG as a dependent variable. From these analyses, least-square (LS) means, LS treatment differences, and 95% CIs for the treatment differences on log-scale are obtained. The results are transformed back to the original scale by exponentiation to provide treatment geometric LS means, point estimates of the geometric LS mean ratios, and 95% CI for these ratios on each study day. A "responder" is defined as a subject with a 4-fold rise in anti-SARS-CoV-2 and/or anti-D antigen titer from baseline on Days 8, 15, 22, 29, 57, 91, and 181 (Part A) and Days 8, 15, 22, 29, 36, 43, 50, 91, and 181 (Part B). Fold change for determination of responder status is computed using the post-imputation values without the +1 transformation, i.e., fold change=current imputed value/baseline imputed value. Responder rates are tabulated by percentages per dose group and the 95% Clopper-Pearson exact CI of the percentage. Differences of 95% CIs are presented to compare the response rate of each AdD composition dose group to the and placebo group. In some embodiments, comparisons of responders in each AdD composition dose group against the against the placebo group can also be conducted using Fisher's exact test. To determine the effect of pre-dose Ad5 serum antibody levels on immunogenicity of AdD composition on Day 29 (Part A) or Day 50 (Part B), analyses are performed using ANCOVA with baseline Ad5 titer as a covariate. Mucosal immunogenicity analyses are conducted using the Evaluable and PP Populations. No imputation for missing data is performed. Endpoints analyzed are GMT and GMR for IgA antibody level measured by ELISA. Methods used are the same as for humoral immunogenicity analyses. Summary statistics for continuous parameters (safety laboratory tests and vital signs) are presented by group as follows: pre-vaccination, postvaccination, and change from pre-vaccination to postvaccination assessment. The number and percentage of subjects with postvaccination safety laboratory values or vital sign values recorded as newly abnormal (ie, an event with an increase in the toxicity grade relative to the baseline value and with a severity grade of moderate or higher) after study vaccination are tabulated. Shift tables that cross-tabulate the pre-vaccination and post-vaccination safety laboratory values of each subject by severity grade are prepared. Summaries of the number and percentage of subjects with normal, abnormal not clinically significant, and abnormal clinically significant ECG interpretations are presented. For shedding of the Ad5 vector, data are summarized by count and percent positive by time point, along with median copy number. The median duration of Ad5 shedding, interquartile range, minimum and maximum duration of Ad5 shedding are presented for each AdD composition group and all immunological composition dose groups combined. Viral culture results for evaluation of adenovirus infection are also listed.

These studies will show that the AdD composition can be used to induce an anti-SARS-CoV-2 immune response in human beings (e.g., it is an immunogenic composition), and exhibits an acceptable safety profile. It is preferred that that immune response be statistically significant, and even more preferably, a protective immune response (i.e., it is a SARS-CoV-2 vaccine). In preferred embodiments, the data shows the AdD composition can be used to treat subjects infected by SARS-CoV-2 (e.g., hospitalized patients).

Example 7: Double-Blind, Randomized, Placebo-Controlled Study of NasoVAX in the Prevention of Clinical Worsening in Patients with Early Onset COVID-19

In this example, NasoVAX is used as therapy for the early phases of infection or as a concomitant therapy with direct antiviral agents. Pertaining to the treatment of COVID-19, NasoVAX (and AdE) were demonstrated in preclinical mouse models to provide protection from lethal challenge with a respiratory virus, an effect that occurred in as little as 2 days and lasted 3 or more weeks. See U.S. Pat. No. 9,175,310. In Example 2 above, use of AdE (no transgene expression) was associated with down-regulation of IL-6, IL-1α and IL-12. Those are cytokines that have been demonstrated to mediate pulmonary interstitial inflammation in COVID-19. The protection afforded by NasoVAX and AdE in the pre-clinical mouse models may be attributed to the adenovirus vector, as the vector had commensurate effects in the presence or absence of a transgene expressing the influenza hemagglutinin (HA) antigen. The protective effects of NasoVAX can be be viewed as a biologic response modulating innate immunity that dampens the excessive and pathogenic immune response to a respiratory pathogen. This would be analogous to the use of IL-6 inhibitors Kevzara (sarilumab) and Actemra (tocilizumab) to modulate lung inflammation associated with COVID-19. In embodiments, an adenoviral vector (with or without expressing a transgene from a respiratory pathogen) when administered intranasally ameliorates COVID-19 disease symptoms.

The strength of the vector approach is that unlike other agents that can be used to modulate lung inflammation associated with COVID-19 (e.g., Kevzara (sarilumab) and Actemra (tocilizumab)), NasoVAX is administered intranasally, leaving IV access ports free for other medication; not limited to a single cytokine; not having a hematological side-effect profile (e.g., neutropenia); and exhibits a prolonged duration of action, which would be useful in very early stages in the disease process to modulate subsequent cytokine damage. Moreover, as shown in Example 9 below, when an adenoviral vectored immunogenic composition is administered intranasally bypasses adenovirus immunity of the subject (e.g., those that are seropositive for the viral vector, i.e. Ad5), allowing for repeated dosing and/or doing to adenovirus seropositive subjects.

Thus, in some embodiments, NasoVAX could be used as therapy for the early phases of infection or as a concomitant therapy for COVID-19, in some embodiments in combination with direct antiviral agents (e.g., chloroquine, azithromycin). At some juncture, the drug substance could transition into a product in which the vector alone (e.g., sans transgene as in AdE) is administered.

NasoVAX is prepared by isolation of bacterial colony harboring the large recombinant adenovirus plasmid bearing the human codon-optimized hemagglutinin cDNA from influenza A/California/04/2009 (pAdcoCA09.HA). AdcoCA09.HA recombinant vector was recovered from PER.C6 cells in suspension following large scale transfection of pAdcoCA09.HA plasmid into approximately $4\times10^9$ cells in a single operation using flow-cell electroporation technology (Model STX-100, Maxcyte Inc. Gaithersburg, Md.). At the time of harvest, the infected cells and growth media containing any released vector were subjected to three cycles of freeze-thaw followed by isolation and purification of the vector by CsCl isopycnic centrifugation and dialysis against final product formation buffer. The purified vector was amplified in PER.C6 cells, released from the infected cell pellet by three cycles of freeze-thaw to create an infected cell lysate that was clarified by centrifugation and sterile filtered as the Pre-Master Virus Seed. The NasoVAX Pre-MVS was released following testing. The manufacture of AdcoCA09.HA includes a vector expansion step whereby vector pre-MVS is amplified under cGMP to increase the available seed stock for infection of the production run. The product of this intermediate expansion step is the AdcoCA09.HA MVS. Production of the AdcoCA09.HA MVS starts with cGMP vector expansion of the pre-MVS followed by derivation, production, and characterization of the MVS. Manufacturing of the drug substance includes AdcoCA09.HA infection of PER.C6 cells in suspension followed by concentration of the vector in the cell pellet, release of the vector from the cell pellet, clarification of the lysate and purification of the vector using two sequential anion exchange chromatography resins. The product eluate is diafiltered against formulation buffer, concentrated if necessary, and sterile filtered to create the bulk drug substance (BDS). Final drug product (FDP) is obtained from BDS following dilution to the appropriate strength with formulation buffer and sterile filtration before filling into the final container. The test product to be used in this example is NasoVAX supplied (e.g., $1\times10^9$, $10^{10}$ and/or $10^{11}$ vp) in single-use glass syringes containing 500 μL of a sterile, frozen suspension in A195 buffer (10 mM Tris, 10 mM histidine, 5% (w/v) sucrose, 75 mM NaCl, 1 mM $MgCl_2$, 0.02% (w/v) polysorbate-80, 0.1 mM EDTA, 0.5% (v/v) ethanol, pH 7.4). The syringes (BD, Accuspray™) are designed to deliver 250 μL of an intranasal spray to each nostril. Alternatively, NasoVAX is supplied in 2 mL glass vials, wherein the dose is removed to a tuberculin syringe and affixed to a LMA MAD300 atomizer device (Teleflex, Israel) before intranasal administration. Stability samples were packaged in the same dosage form and container (BD Accuspray™) as the test product and tested using stability indicating assays including physical stability of the virus particles (viral particles test, HPLC), infectivity of the virus (infectious titer, Adenovirus Fluorescent Focus Unit (FFU) Assay), functionality (transgene expression) of the adenovirus vector (potency), the physical stability of the formulation (appearance and pH), and sterility.

In this example, a clinical trial including approximately 120 patients with early onset COVID-19 randomized 1:1 to NasoVAX ($1\times10^{11}$ vp dose) or placebo and stratified by age is described. Each patient will participate in the study up to approximately 6 weeks (a 2-week Treatment Period and a 1-month follow-up phone call). Patients are included in this study are selected using the following non-limiting criteria: able and willing to provide informed consent; men and women 35 years of age and older; early onset COVID-19, defined as oral temperature ≥38.0° Celsius, onset of symptoms within 48 hours, and confirmation of COVID-19 by a PCR-based diagnostic within 24 hours of randomization; saturated $O_2$ ($SaO_2$)≥96.0% at rest for 5 minutes on two successive measurements; women of childbearing potential (women who are not permanently sterile [documented hysterectomy, bilateral tubal ligation, salpingectomy, or oophorectomy] or postmenopausal [12 months with no menses without an alternative medical cause]) exhibit negative urine pregnancy test at screening and willingness to practice a highly effective method of contraception that includes, but is not limited to, abstinence, sex only with persons of the same sex, monogamous relationship with a postmenopausal partner, monogamous relationship with vasectomized partner, vasectomy, licensed hormonal methods, intrauterine device, or consistent use of a barrier method (e.g., condom, diaphragm) with spermicide for 28 days after the last dose of study medication; men with sexual partners of childbearing potential have a willingness to practice a highly effective method of contraception, as defined above, for 45 days after the last dose of study medication; and the ability and willingness to comply with all aspects of the study through the entire study period. Exclusion criteria include: pregnant or lactating women; moderate or severe shortness of breath at rest; findings on physical examination suggesting rapid disease progression, need for immediate hospitalization, obstructive airway diseases, including chronic obstructive pulmonary disease (COPD) and asthma, or other respiratory diseases that could exacerbate independent of those caused by COVID-19; nasal conditions that might affect the suitability of intranasal medication, such as a history of chronic rhinitis, nasal septal defect, cleft palate, nasal polyps, or nasal surgery other than cosmetic rhinoplasty; use of chloroquine and hydroxychloroquine and other investigational agents for COVID-19 within the past 30 days; history of conditions associated with immunocompromise, or treatments known to affect the immune system, including but not limited to oral or intravenous corticosteroids, alkylating drugs, antimetabolites, cytotoxic drugs, radiation, immune-modulating biologics, within 30 days of screening; and, any medical, psychiatric, or social condition or occupational or other responsibility that in the judgment of the Investigator would interfere with or serve as a contraindication to protocol adherence, assessment of safety (including reactogenicity), or a patient's ability to give informed consent.

Patients are randomized 1:1 to NasoVAX or placebo administered as a single intranasal dose of 0.5 mL (0.25 mL each nostril) within 24 hours of COVID-19 diagnosis. The first 20 study participants (approximately 10 treated with NasoVAX and 10 treated with placebo) consist of a sentinel cohort of patients ages 35 to 49 years. Patients are provided disposable finger-tip oximeters and digital thermometers and return home for the duration of the trial. $SaO_2$, oral temperature, and pulse respiratory rate is monitored remotely at rest for 2 minutes twice daily for 14 days using mobile/smart phone pulse oximetry and web-based diaries to record oral temperature, symptoms and concomitant medications and telephoned daily to document clinical status and adverse events (AEs). Patients are called approximately every 7±2 days after the last day of remote monitoring to document final outcome and adverse events. SAEs, hospital and ICU lengths of stays, and mortality in hospitalized patients will be documented. No in-person visits are expected during the study.

With respect to efficacy, the Primary Objective of this study is to assess the effectiveness of NasoVAX in preventing clinical worsening in patients with early onset COVID-19; and the Secondary Objectives are to assess the effectiveness of NasoVAX in reducing rates of ICU admission and mechanical ventilation in patients with early onset COVID-19 and the severity of COVID-19 in patients with early onset COVID-19 who require hospitalization. The primary endpoint is the proportion of patients with clinical worsening, defined as a 4% decrease in mean $SaO_2$ to a level of 94% or less by mobile pulse oximetry at any measurement during home follow-up, or hospitalization. In ambulatory patients, secondary efficacy endpoints include severity of COVID-19, assessed by maximum decrease in $SaO_2$ and spontaneous ventilation rate by outpatient pulse oximetry during home follow-up and the proportion of patients requiring mechanical ventilation. In hospitalized patients, the secondary efficacy endpoints include ventilator-free days, defined as one point (day) for each day between the dose of study medication on Day 1 and Day 30 (relative to the first dose of study drug) that a patient is both alive and free of mechanical ventilation and the ratio of arterial oxygen partial pressure to fractional inspired oxygen (P/F ratio).

With respect to safety, the Primary Objective is to assess the safety and tolerability of NasoVAX in preventing clinical worsening in patients with early onset COVID-19. These include incidence and severity of adverse events (AEs), mortality, hospital length of stay, and ICU length of stay. Safety endpoints are categorized separately between AEs reported at home vs. those reported during hospitalization for medical care.

Statistical methods include the Power and Sample Size Assumptions that 10% of patients receiving NasoVAX develop clinical worsening vs. 29% receiving placebo, 60 patients per treatment arm provides 77% power at a one-sided a of 0.05 to achieve statistical significance on the primary efficacy variable. Population definitions include: "Safety Analysis Set": all patients who receive any study medication; "Intent to treat" (ITT): all randomized patients who receive any amount of study medication, have a baseline and at least one post-baseline $SaO_2$ measurement. Subjects are analyzed according to the treatment that they receive; and, "Per Protocol" (PP): all randomized patients who receive any amount of study medication according to the correct treatment assignment and who have twice daily results from $SaO_2$ measurements through Day 14 or hospitalization. Baseline is defined as data collected closest to randomization prior to any study medication dosing. All analyses and summary statistics are presented by treatment group (NasoVAX, placebo). Descriptive statistics, including the numbers and percentages for categorical variables and the numbers, means, standard deviations, medians, minimums and maximums for continuous variables are provided by treatment. Patients are randomized 1:1 to NasoVAX or placebo and stratified by age group (35-49 years vs. 50 years and older). To assure a 1:1 distribution of NasoVax and placebo (10 patients each of 20 patients) in the sentinel cohort, randomization in this group are not stratified. For the Efficacy Analyses, descriptive statistics are used to evaluate differences in demographic and baseline characteristics. For the primary analysis, proportions of patients with clinical worsening, defined as a 4% decrease in mean $SaO_2$ to a level of 94% or less by mobile pulse oximetry at any measurement during home follow-up, or hospitalization, are compared between NasoVAX and placebo groups using the Cochrane Mantel Haenszel test at a 0.05% one-sided level of significance. The same approach is applied for secondary or exploratory endpoints that are categorical in nature. Subjects who discontinue prematurely or have missing data are considered non-responders for that endpoint. Sensitivity analyses are performed to assess the effect of site on the response to study medication. Linear and logistic regression are employed to examine the effects of baseline factors, such as age, sex, medications and medical co-morbidities on response. Quantitative safety data are summarized using descriptive statistics and frequency distributions. All summaries are presented by treatment arms. AEs are coded using Medical Dictionary for Regulatory Activities (MedDRA®), Concomitant medications are coded using World Health Organization (WHO) drug dictionary. Changes from baseline in Severity of COVID-19, assessed by maximum decrease in $SaO_2$ and spontaneous ventilation rate by outpatient pulse oximetry during home follow-up, are analyzed using a mixed model for repeated measures (MMRM) model. The model will include the fixed effects of treatment, stratification factor, week, and treatment-by-visit interaction as well as the continuous, covariate of baseline level. The model will employ an unstructured within patient covariance matrix and a restricted maximum likelihood (ReML) estimation method. Ventilator-free days are analyzed using a t-test or Mann-Whitney for continuous data. A Kaplan-Meier model is developed to compare changes between treatment groups in $SaO_2$ over time. No multiplicity adjustments are made for secondary or exploratory endpoints.

These studies will show that the NasoVAX can be used to induce an anti-SARS-CoV-2 immune response in human beings (e.g., it is an immunogenic composition), and exhibits an acceptable safety profile. The data will also show that NasoVAX is effective in reducing rates of ICU admission and mechanical ventilation in patients with early onset COVID-19 and the severity of COVID-19 in patients with early onset COVID-19 who require hospitalization. In some embodiments, a decrease in expression of inflammatory cytokines such as IL-1α, IL-5, IL-6, IL-12, IL-17, MCP-1, tumor necrosis factor alpha (TNF-α), granulocyte macrophage colony stimulating factor (GM-CSF), and/or RANTES (CCL5) (see, e.g., Example 2) following administration of NasoVAX to subjects can occur, and can in some embodiments be used to diagnose COVID-19, and/or predict recovery therefrom and used to adjust treatment protocols (e.g., non-NasoVAX treatments) accordingly. In some embodiments, an increase in MCP1 and/or RANTES shortly after administration of NasoVAX, can be used to predict (e.g., as a marker) recovery from COVID-19 and amelioration of symptoms. It is preferred that that immune response be statistically significant, and even more preferably, a protective immune response (i.e., it is a SARS-CoV-2 vaccine). In preferred embodiments, the data shows that NasoVAX can be used to treat subjects infected by SARS-CoV-2 (e.g., hospitalized patients).

Example 8. NasoVAX Stability at Room Temperature

This example describes the long-term stability of NasoVAX in a liquid formulation at room temperature. Long-term stability at room temperature is desire feature of vaccines that can be used in situations in which refrigeration or other means for stabilizing a formulation may not be available. This would be important in epidemic or pandemic situations during which vaccines need to be shipped to remote areas that may lack the equipment to maintain formulations at a cooler temperature, or shipped directly to end-users, such as individual self-isolating at home or in quarantine. As shown in Tables 9 and 10 below, low dose ($2\times10^9$ vp/mL dose) and high dose ($2\times10^{11}$ vp/mL dose) formulations, respectively, were prepared and maintained at room temperature in glass vials for one, three and six months. Viability of the NasoVAX vectors was determined using the Adenovirus Fluorescent Focus Unit (FFU) assay. Briefly, the FFU assay is carried out by infecting cell monolayers with the appropriate NasoVAX dilution and incubated for 24-48 hours. The cells were then washed, inspected, fixed (e.g., ice-cold 90% methanol for four minutes), and washed again. Anti-Ad5 antibody was then added at various dilutions (antibody omitted in control samples), followed by a detection agent (e.g., NCL-Adeno (Novocastra, Newcastle, UK)) under appropriate conditions (e.g., ten minutes at room temperature with shaking). The cells are then washed, and the total number of infectious particles determined (e.g., by digital light scattering (DLS)). As shown in Tables 15 and 16, the low-dose and high-dose NasoVAX formulations were stable for at least three months at room temperature.

This study shows an adenoviral vectored vaccine composition (e.g., NasoVAX) is stable for about 3 months at an ambient temperature, such as room temperature (e.g., 15 to 30° C., preferably 20-25° C.). In embodiments, an adenoviral vectored vaccine composition can be stored, or shipped, without the need for refrigeration or specific storage conditions. In certain embodiments, the present intranasal adenoviral vectored vaccine is configured to induce an immune response against SARS-CoV-2 virus (a pandemic coronavirus strain) infection and/or to ameliorate COVID-19 disease symptoms and may be shipped directly to the user for intranasal administration.

TABLE 15

| Stability Data for NasoVAX (2 × $10^9$ vp/mL dose) | | | | |
|---|---|---|---|---|
| | Stability Time Point | | | |
| Analysis | T = 0 M | T = 1 M | T = 3 M | T = 6 M |
| Appearance | Liquid, Colorless; Translucent; No visible particulate matter observed | Liquid, Colorless, Translucent; No visible particulate matter observed | Liquid, Colorless; Clear; No visible particulate matter observed | Liquid, Colorless; Transparent; No visible particulate observed |
| pH | 7.5 | 7.5 | 7.7 | 7.5 |
| vp by HPLC | 1.2 × $10^9$ vp/mL | 1.1 × $10^9$ vp/mL | 0.9 × $10^9$ vp/mL | 1.2 × $10^9$ vp/mL |
| Adenovirus Fluorescent Focus Unit (FFU) Assay | 1.1 × $10^8$ FFU/mL | 2.3 × $10^8$ FFU/mL | 0.7 × $10^8$ FFU/mL | 0.1 × $10^8$ FFU/mL |
| % Infectious Particles | 9% | 21% | 8% | 0.4% |
| Aggregation by DLS | 66.7 nm | 139.7 nm (23% PD) | 91.9 nm (14% PD) | 107.5 nm (8% PD) |

TABLE 16

| Stability Data for NasoVAX (2 × $10^{11}$ vp/mL dose) | | | | |
|---|---|---|---|---|
| | Stability Time Point | | | |
| Analysis | T = 0 M | T = 1 M | T = 3 M | T = 6 M |
| Appearance | Liquid, Colorless; Translucent; No visible particulate matter observed | Liquid, Colorless; Translucent; No visible particulate matter observed | Liquid, Colorless; Translucent; No visible particulate matter observed | Liquid, Colorless; Translucent; No visible particulate observed |
| pH | 7.6 | 7.5 | 7.5 | 7.6 |
| vp by HPLC | 1.3 × $10^{11}$ vp/mL | 1.0 × $10^{11}$ vp/mL | 0.4 × $10^{11}$ vp/mL | 1.2 × $10^{11}$ vp/mL |
| Adenovirus Fluorescent Focus Unit (FFU) Assay | 0.9 × $10^{10}$ FFU/mL | 0.9 × $10^{10}$ FFU/mL | 0.5 × $10^{10}$ FFU/mL | 0.1 × $10^{10}$ FFU/mL |
| % Infectious Particles | 7% | 9% | 12% | 0.5% |
| Aggregation by DLS | 122 nm | 118.2 nm (19% PD) | 116.9 nm (13% PD) | 115.5 nm (14% PD) |

Example 9: NasoVAX Shedding and Anti-NasoVAX Vector Antibodies

NasoVAX was previously evaluated in a Phase 2a, randomized, double-blind, placebo-controlled trial to evaluate the safety and immunogenicity of NasoVAX (monovalent Adco.CA.HA), in healthy adults 18 to 49 years of age. The subjects were randomized and given a single dose of 1×$10^9$, 1×$10^{10}$, and 1×$10^{11}$ viral particles (vp) or saline placebo, all given as a 0.5 mL dose split approximately as 0.25 ml nasal spray in each nostril. The protocol was described in U.S. Ser. No. 62/830,442 filed 6 Apr. 2019.

Figures 25, 26:
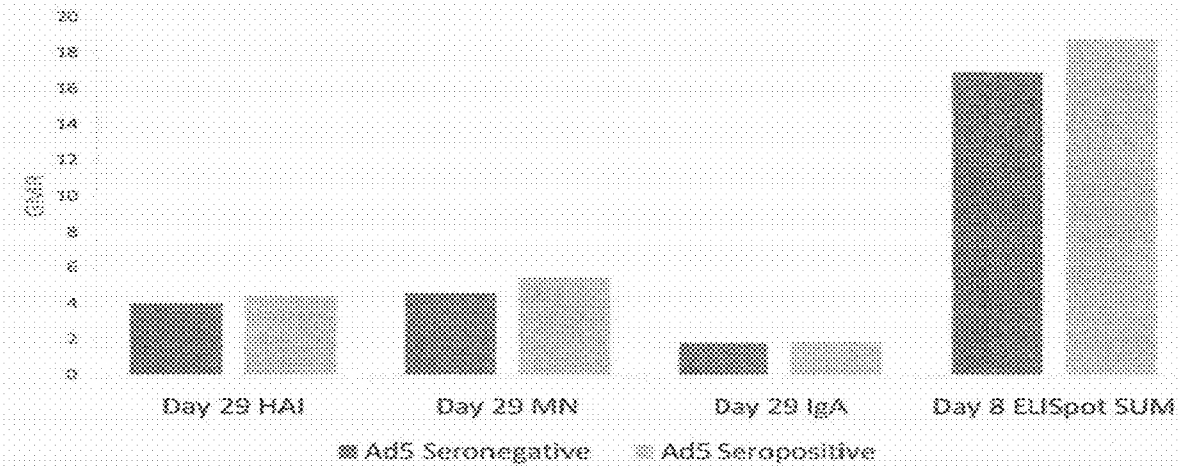
FIG. 25 shows a dose-dependent vector shedding that is absent at 2 weeks post-administration (of the present monovalent influenza vaccine composition (e.g., NasoVAX)) with no replication competent virus found (as determined via polymerase chain reaction ("PCR") assay) and anti-vector antibody presented as GMR at Day 29 vs baseline wherein only a 2.3-fold induction after 1 month at highest dose was demonstrated. The present monovalent influenza vaccine composition demonstrates a transient shedding (Ad-vector) with limited anti-vector (Ad-vector) immune response
FIG. 26 shows the effect of NasoVAX administration (high dose; $11\times10^{11}$ vp) of pre-existing (baseline Ad5 serostatus) anti-vector (Ad5) immunity as measured for humoral ("HAI" or microneutralization "MN" at day 29), mucosal ("IgA" at day 29) and cellular ("ELISpot" at day 8) wherein no difference in an immune response between Ad5 seronegative or Ad5 seropositive subjects was observed. Median titer of Ad5+ subjects was 22-fold above the lower limit of quantification (LLOQ).
Figure 27:
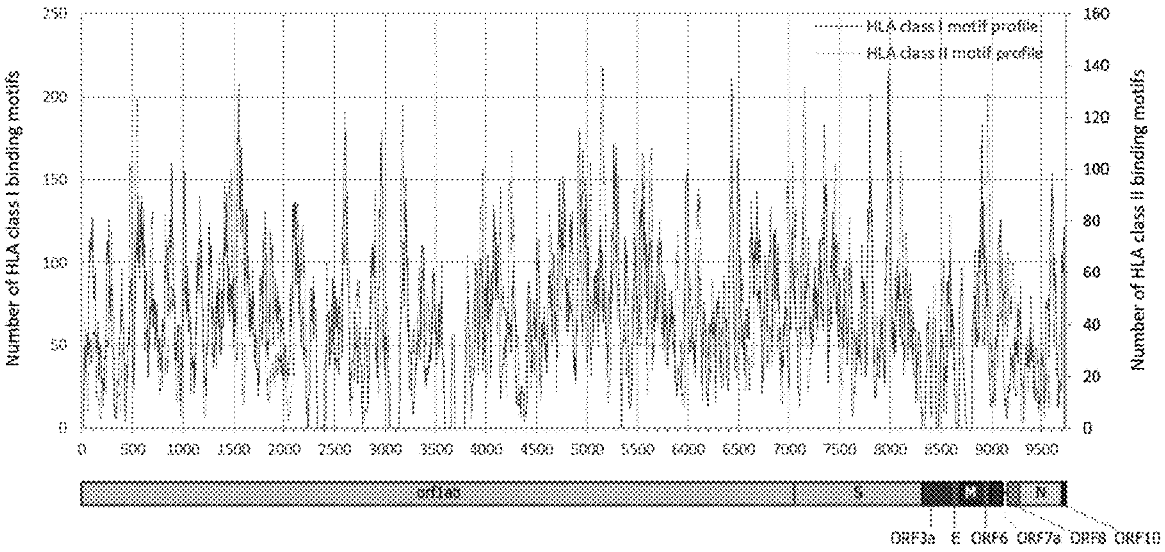
FIG. 27. Profiles of high affinity HLA class I and HLA class II binding motifs across the entire SARS-CoV-2 proteome.
Figure 28:
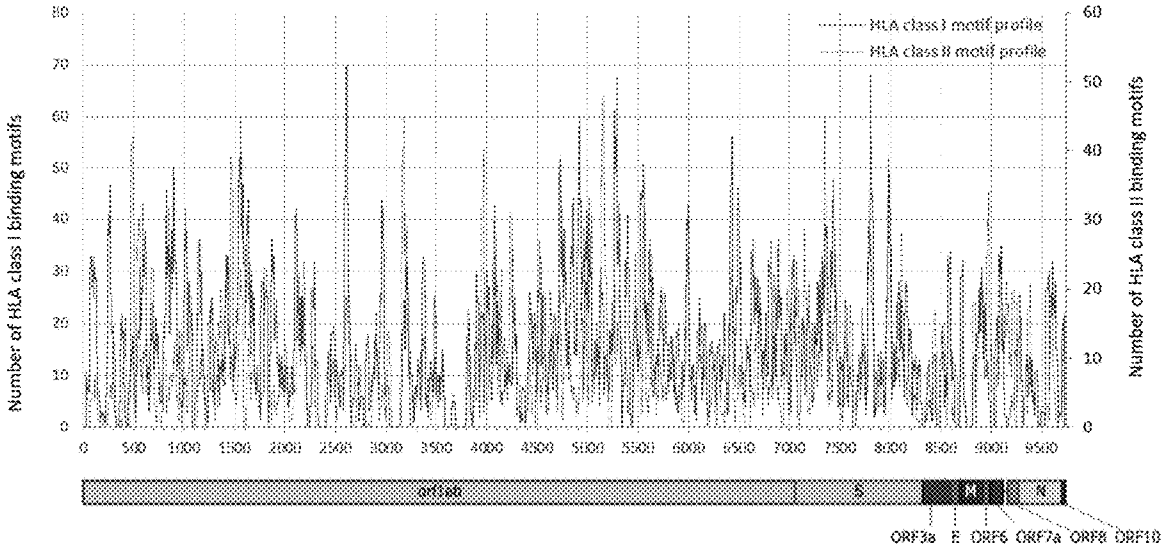
FIG. 28. Profiles of high and moderate affinity HLA class I and HLA class II binding motifs across the entire SARS-CoV-2 proteome.
Figure 29:
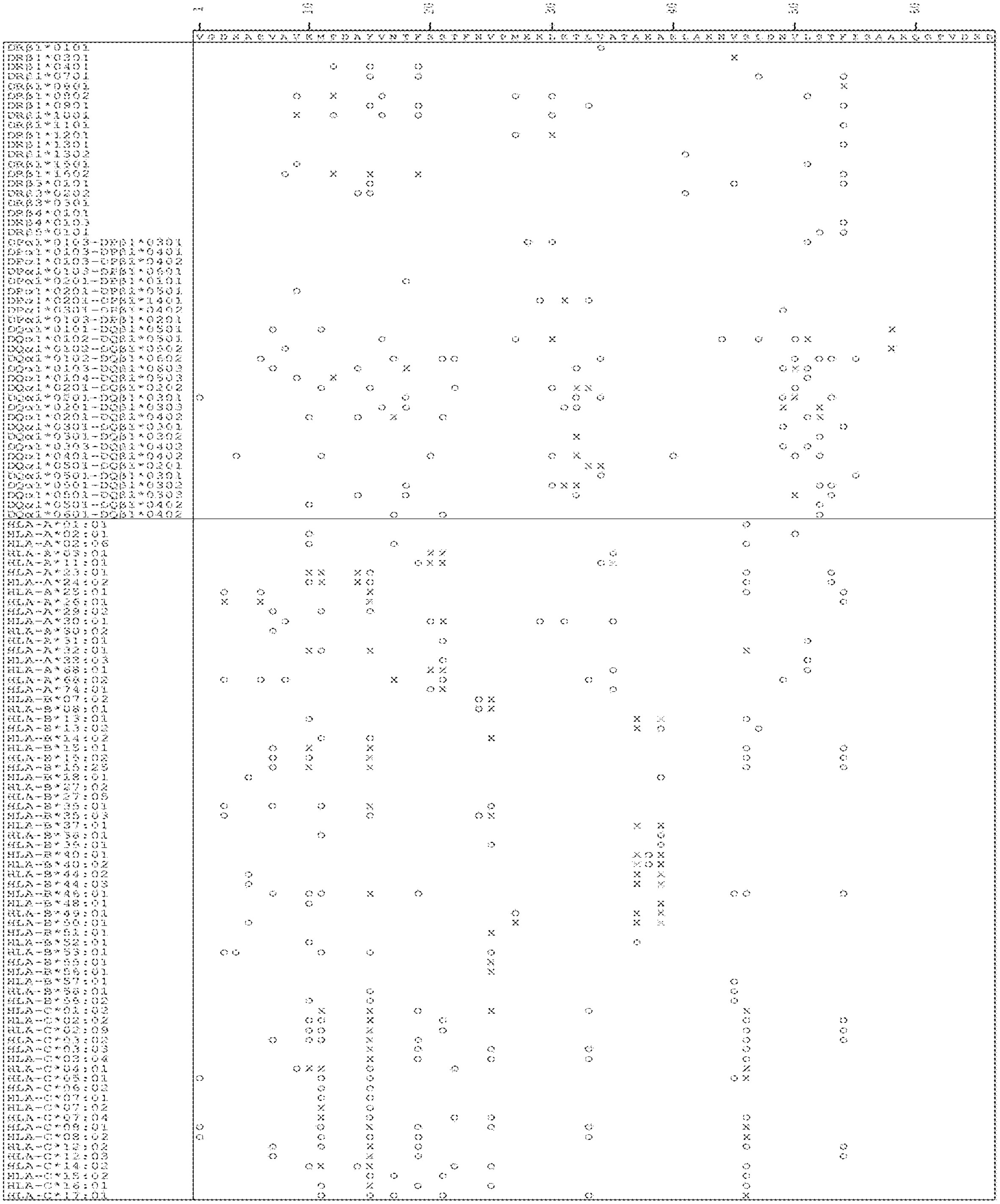
FIG. 29. Map of HLA class I and HLA class II binding motifs for SEQ ID NO: 328.
Figure 30:
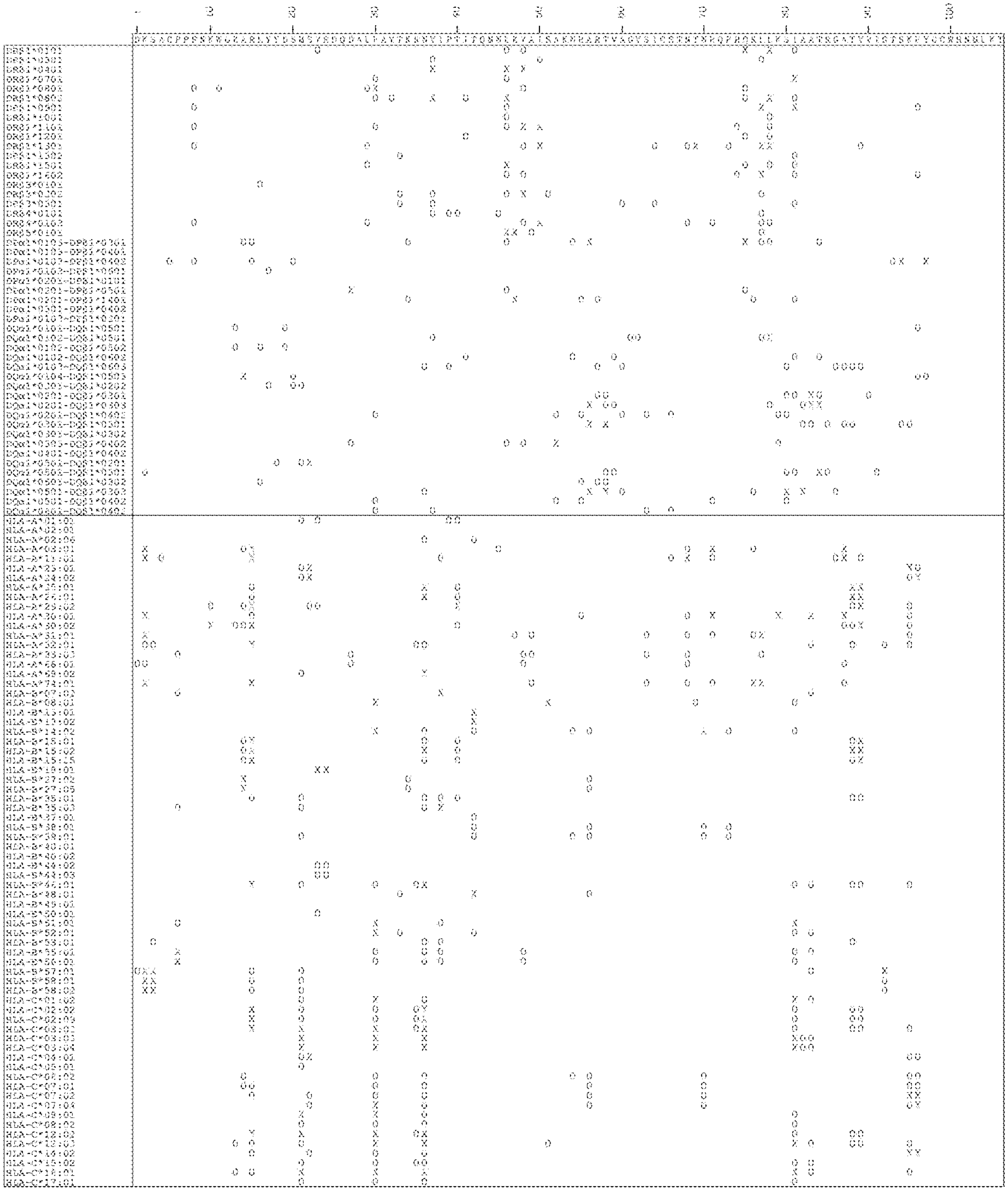
FIG. 30. Map of HLA class I and HLA class II binding motifs for SEQ ID NO: 329.
Figure 31:
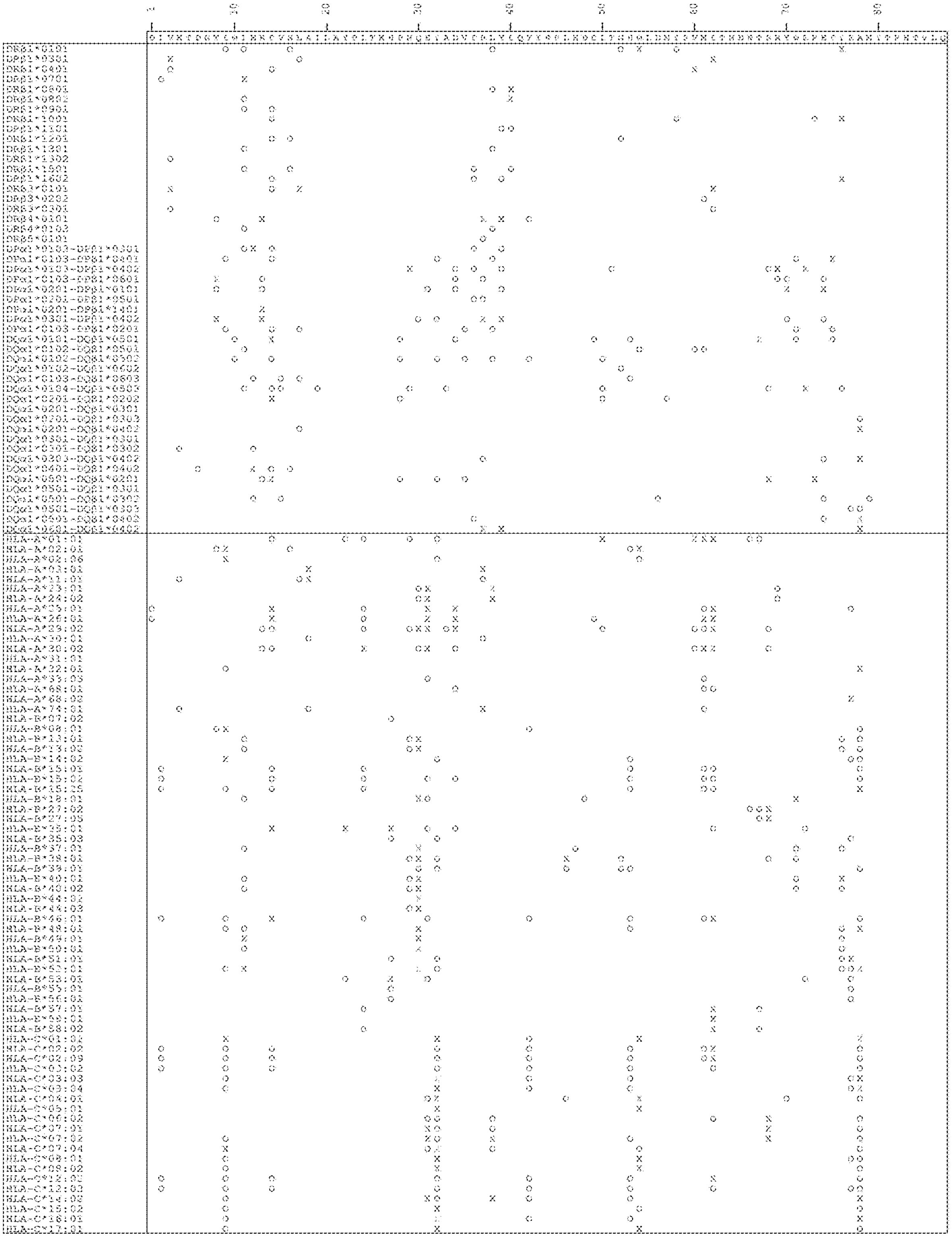
FIG. 31. Map of HLA class I and HLA class II binding motifs for SEQ ID NO: 330.
Figure 32:
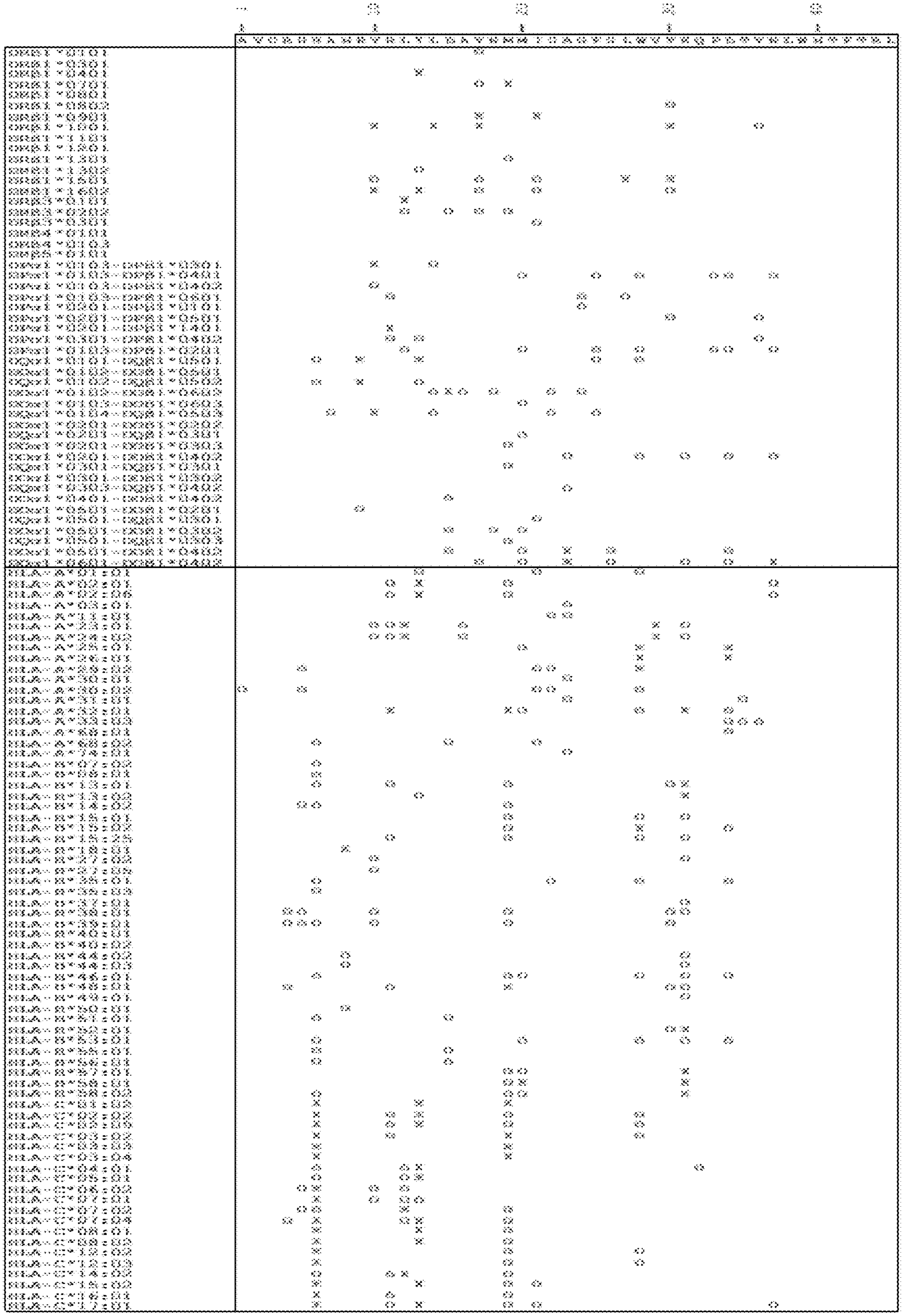
FIG. 32. Map of HLA class I and HLA class II binding motifs for SEQ ID NO: 331.
Figure 33:
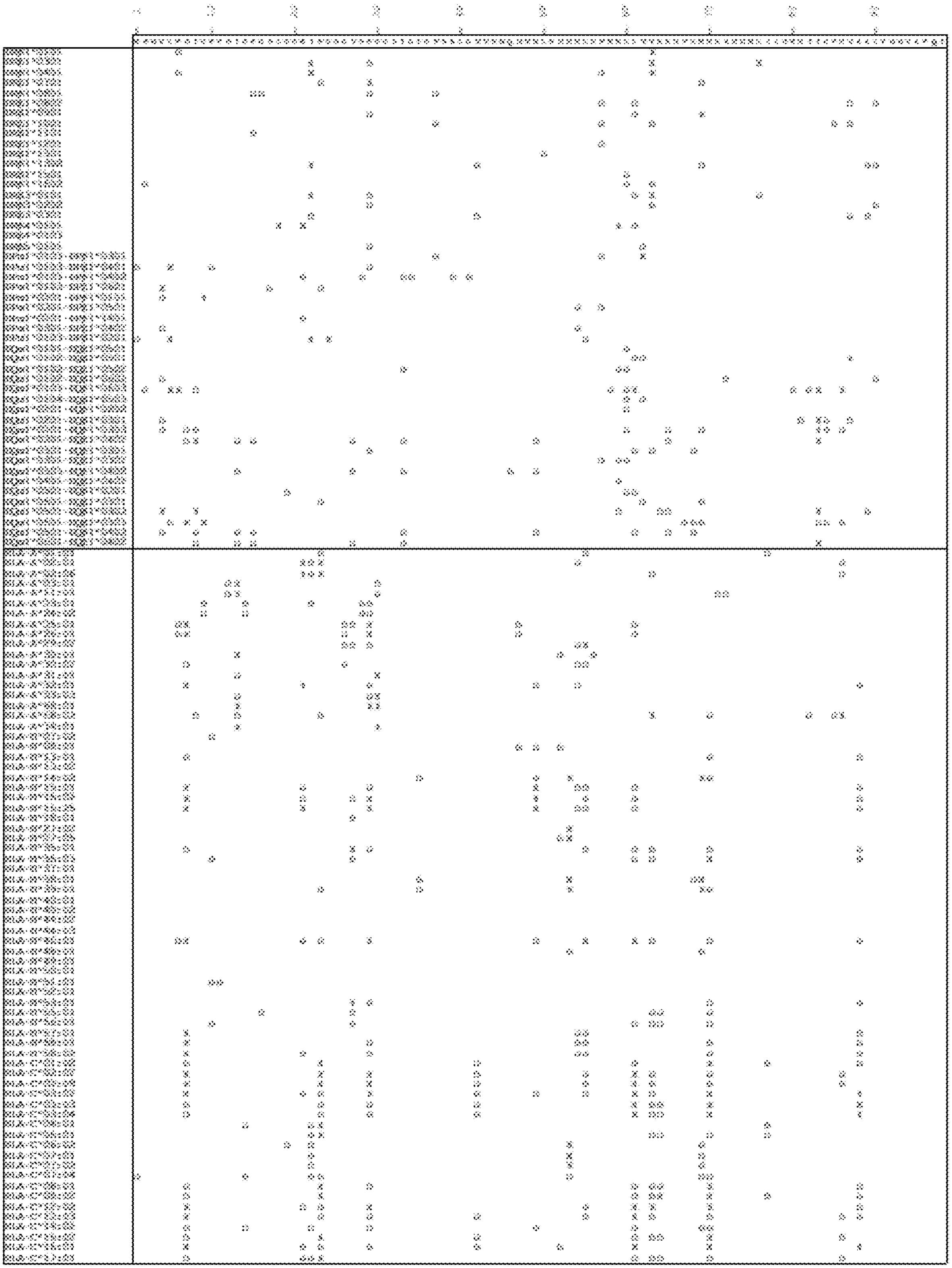
FIG. 33. Map of HLA class I and HLA class II binding motifs for SEQ ID NO: 332.
Figure 34:
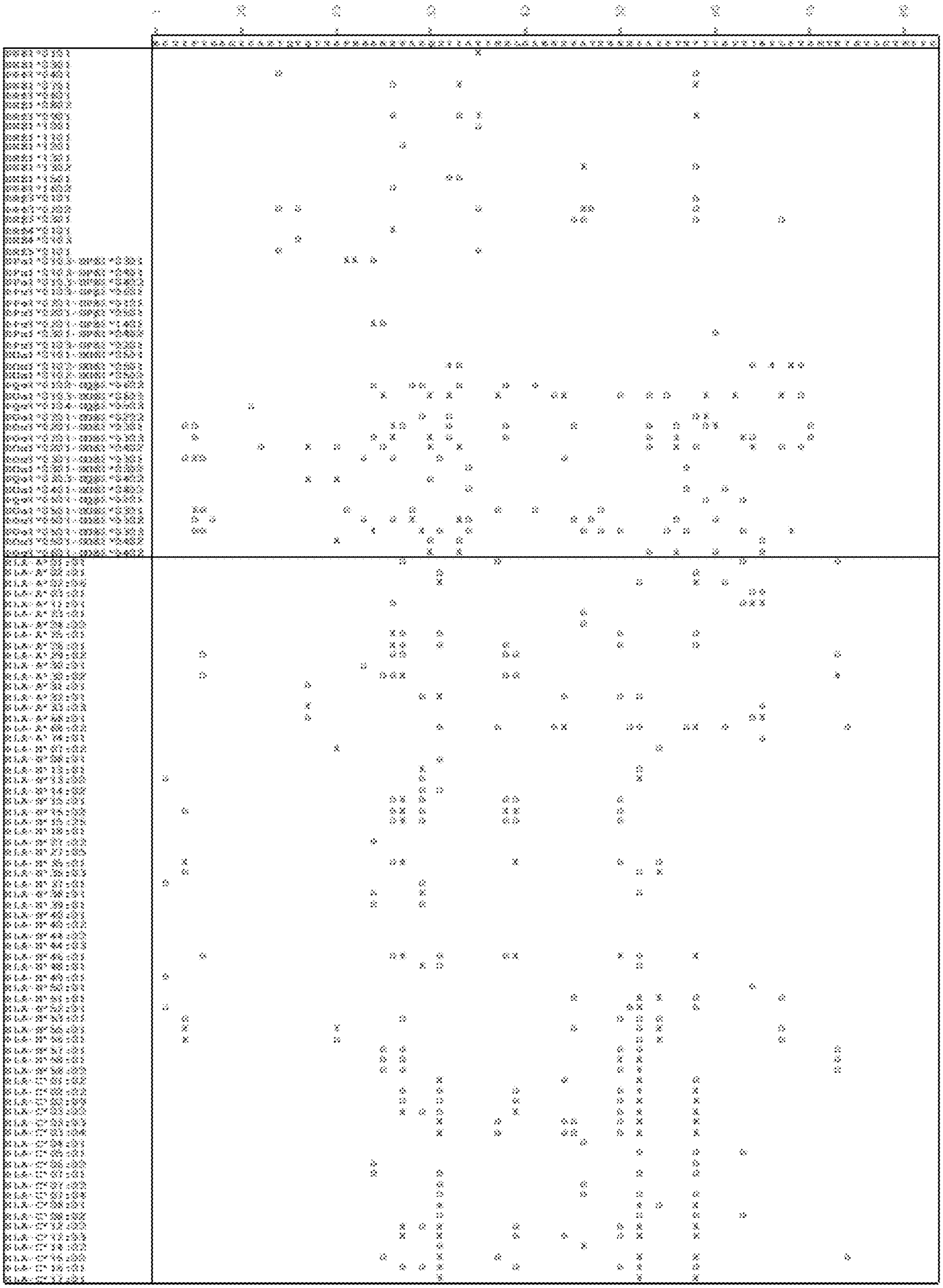
FIG. 34. Map of HLA class I and HLA class II binding motifs for SEQ ID NO: 333.
Figure 35:
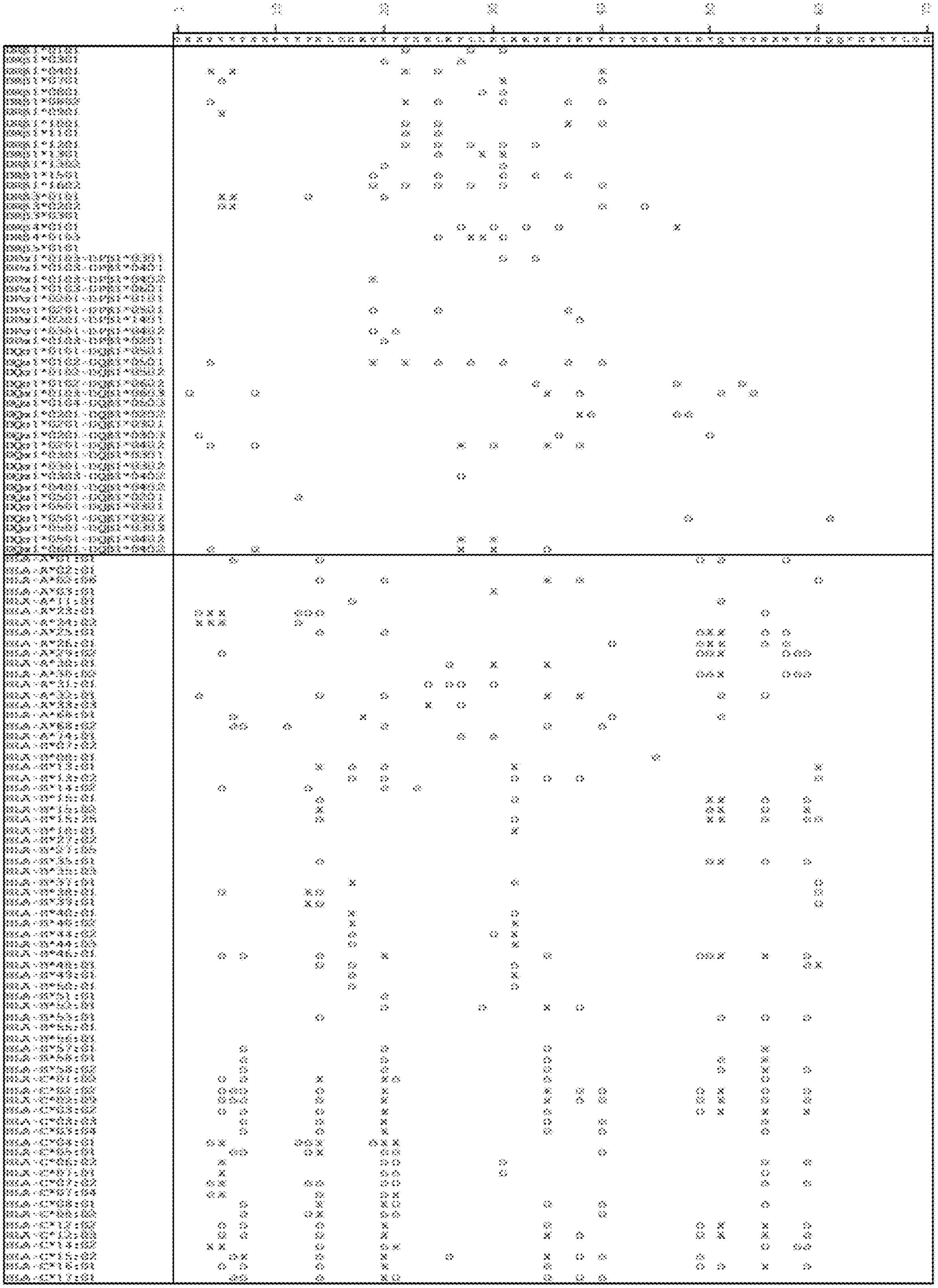
FIG. 35. Map of HLA class I and HLA class II binding motifs for SEQ ID NO: 334.
Figure 36:
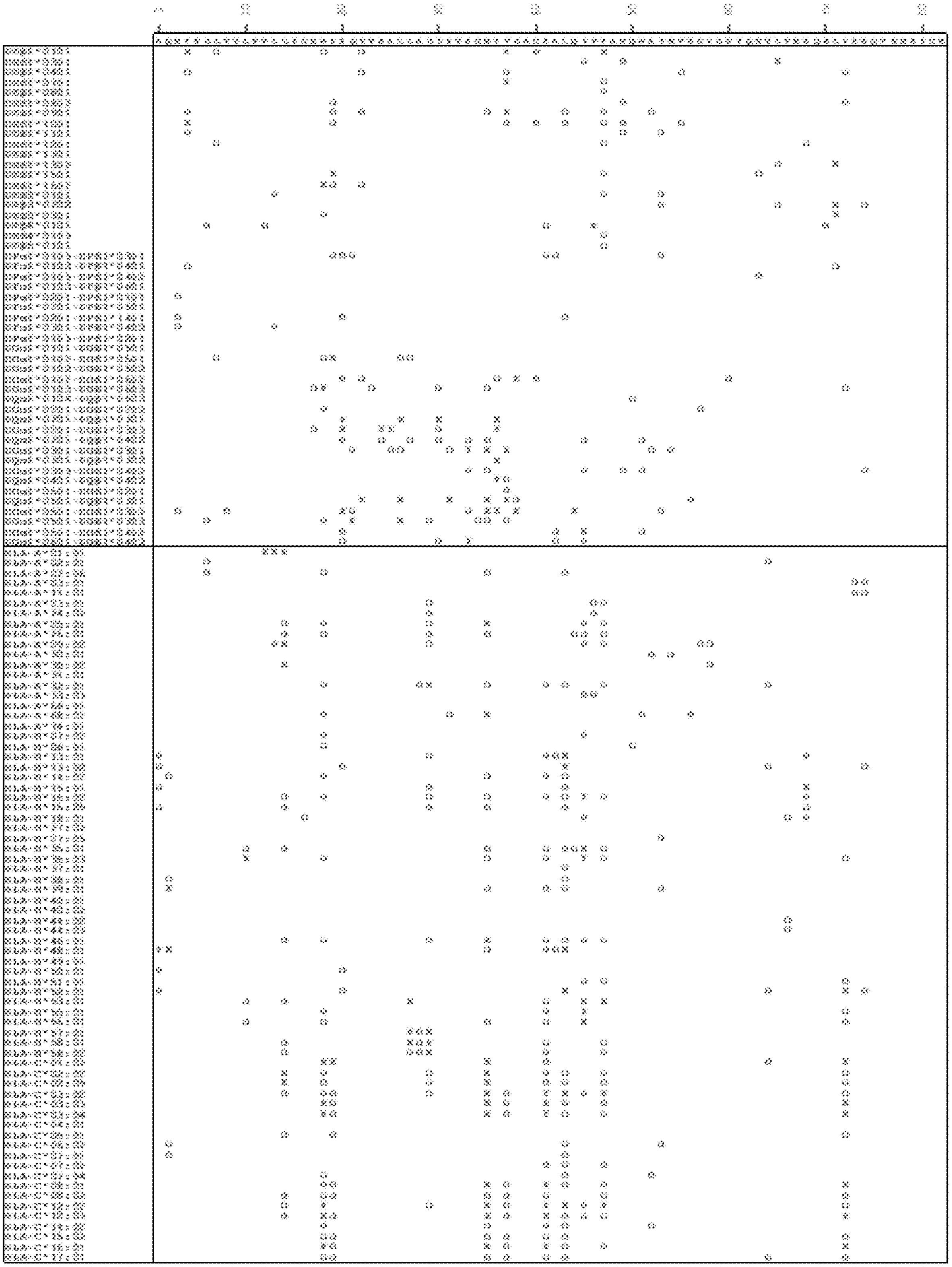
FIG. 36. Map of HLA class I and HLA class II binding motifs for SEQ ID NO: 335.
Figure 37:
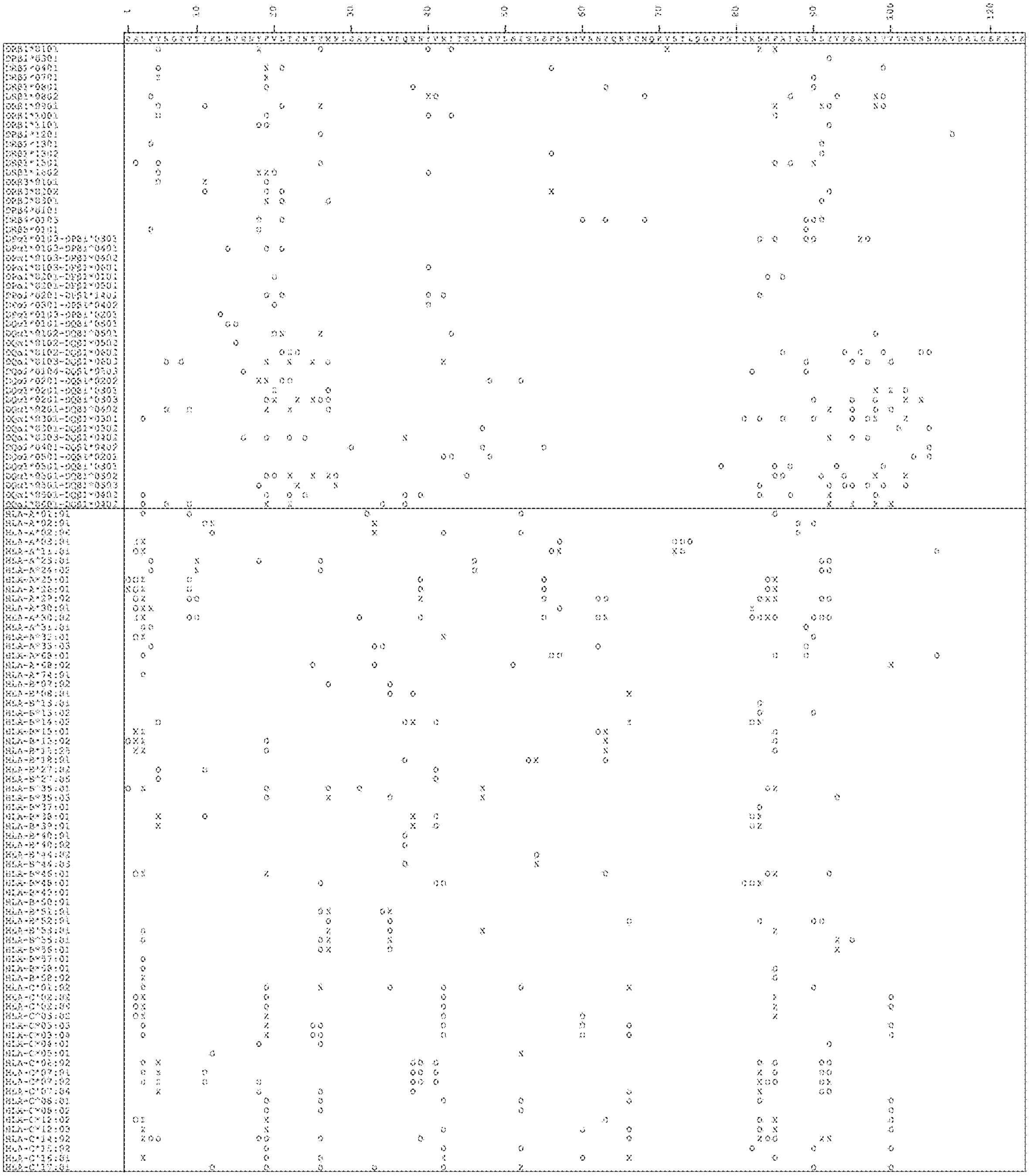
FIG. 37. Map of HLA class I and HLA class II binding motifs for SEQ ID NO: 336.
Figure 38:
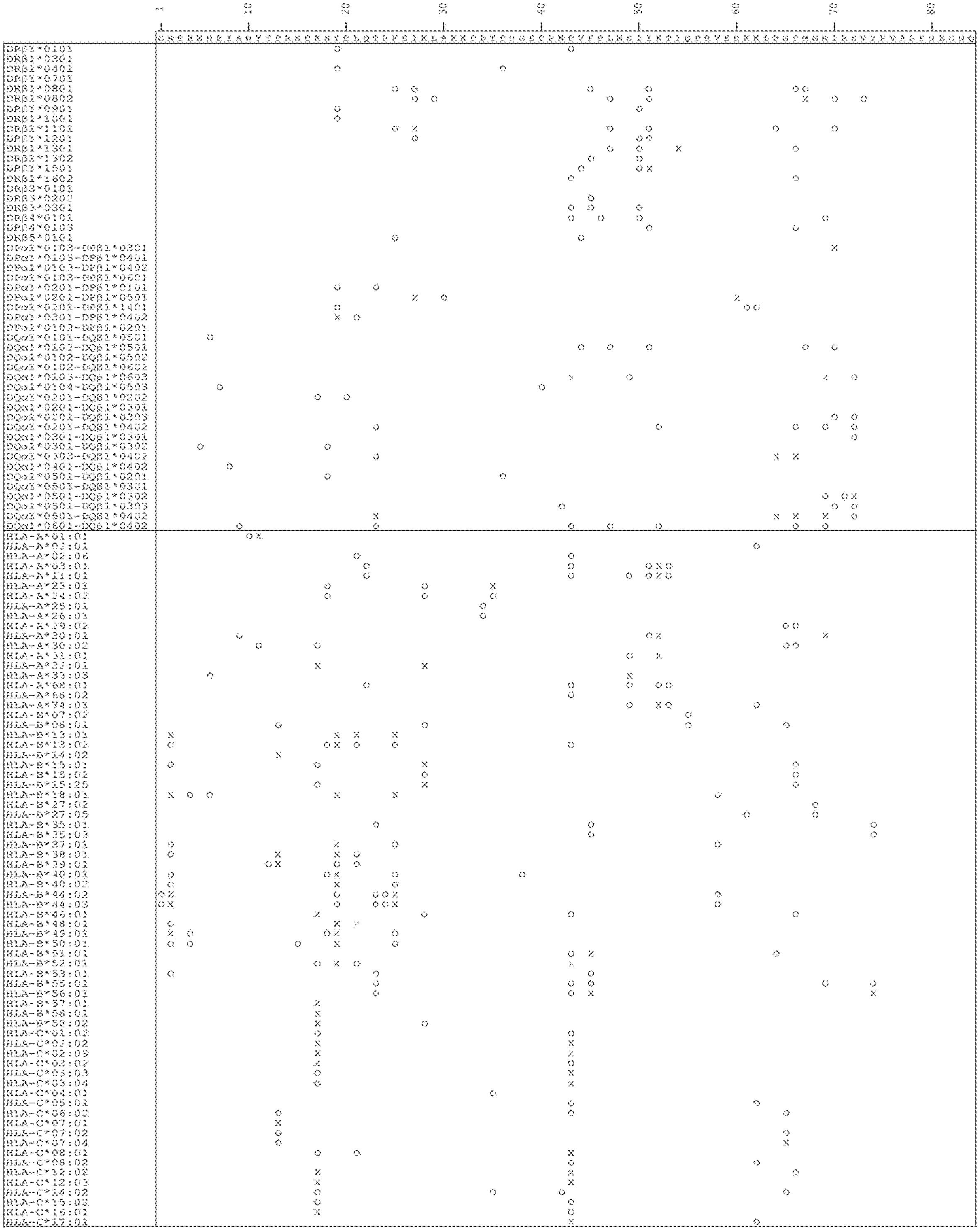
FIG. 38. Map of HLA class I and HLA class II binding motifs for SEQ ID NO: 337.
Figure 39:
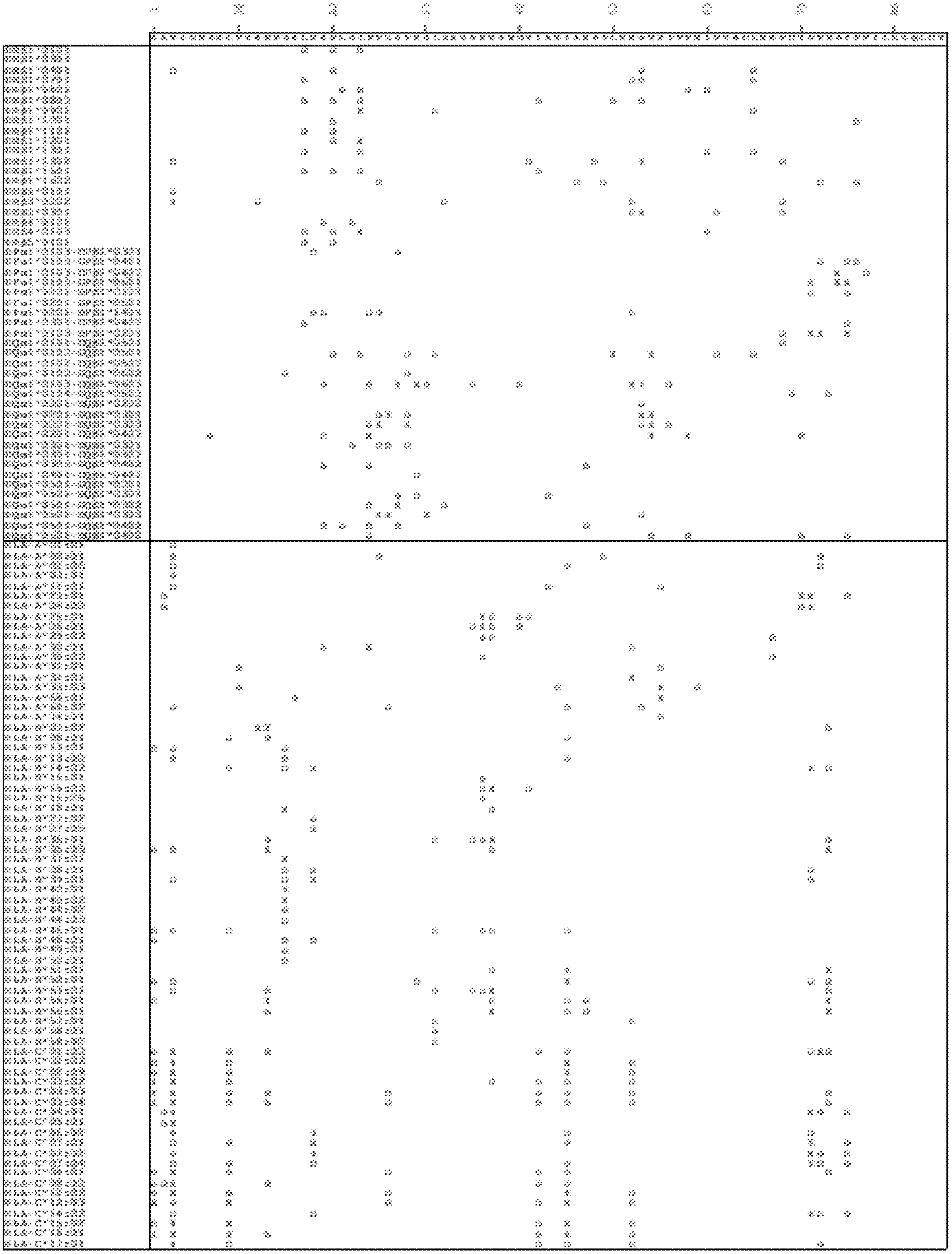
FIG. 39. Map of HLA class I and HLA class II binding motifs for SEQ ID NO: 338.
Figure 40:
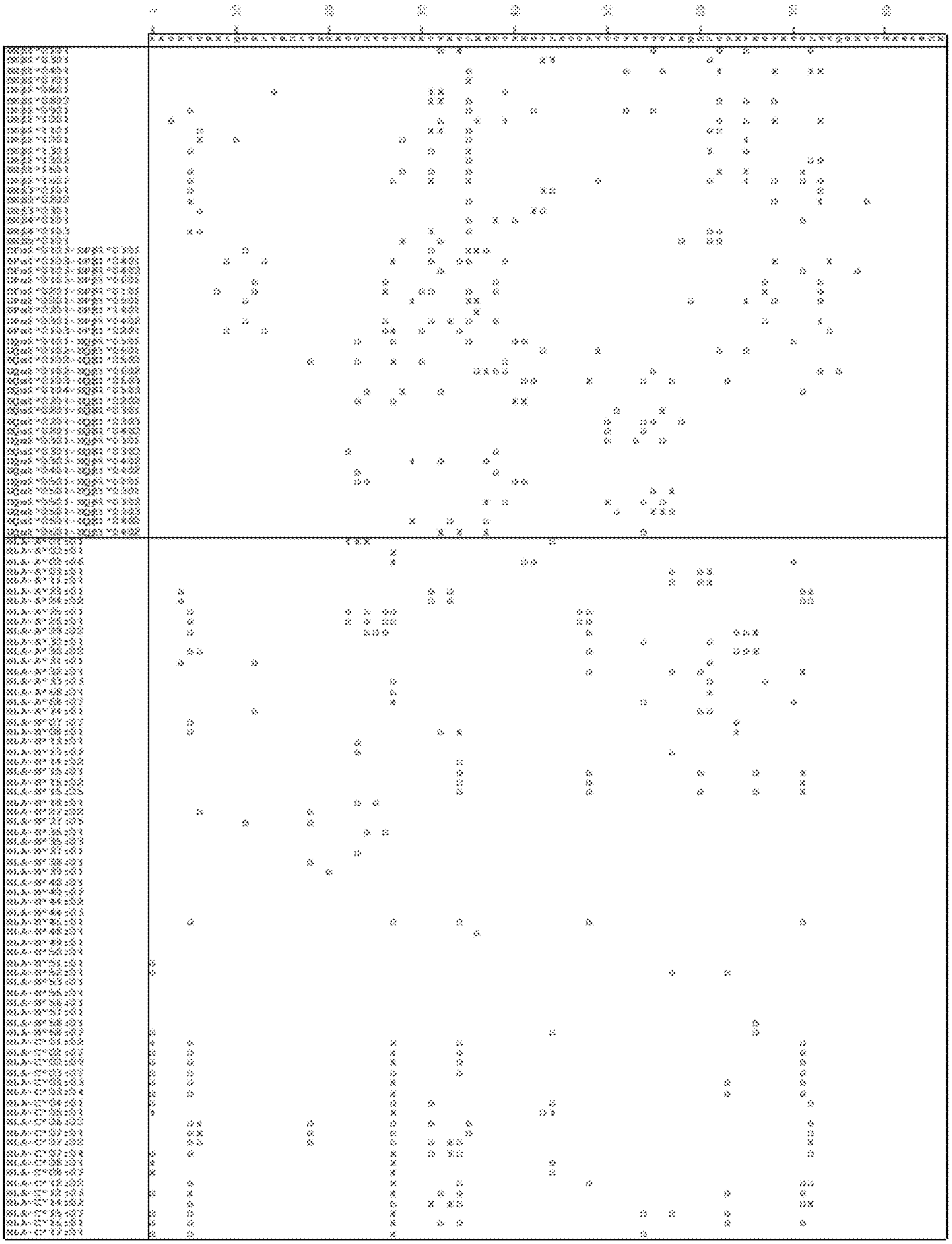
FIG. 40. Map of HLA class I and HLA class II binding motifs for SEQ ID NO: 339.
Figure 41:
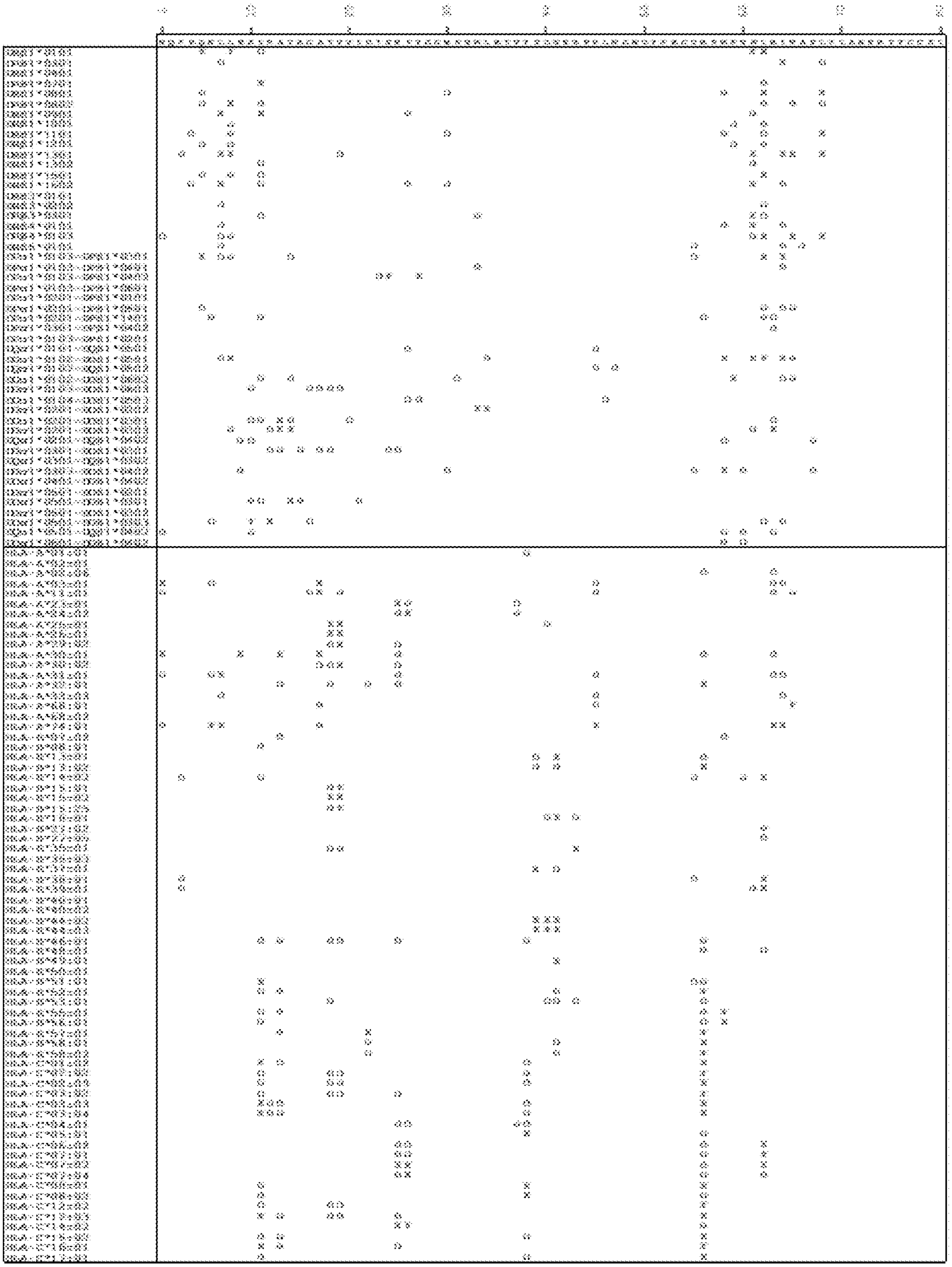
FIG. 41. Map of HLA class I and HLA class II binding motifs for SEQ ID NO: 340.
Figure 42:
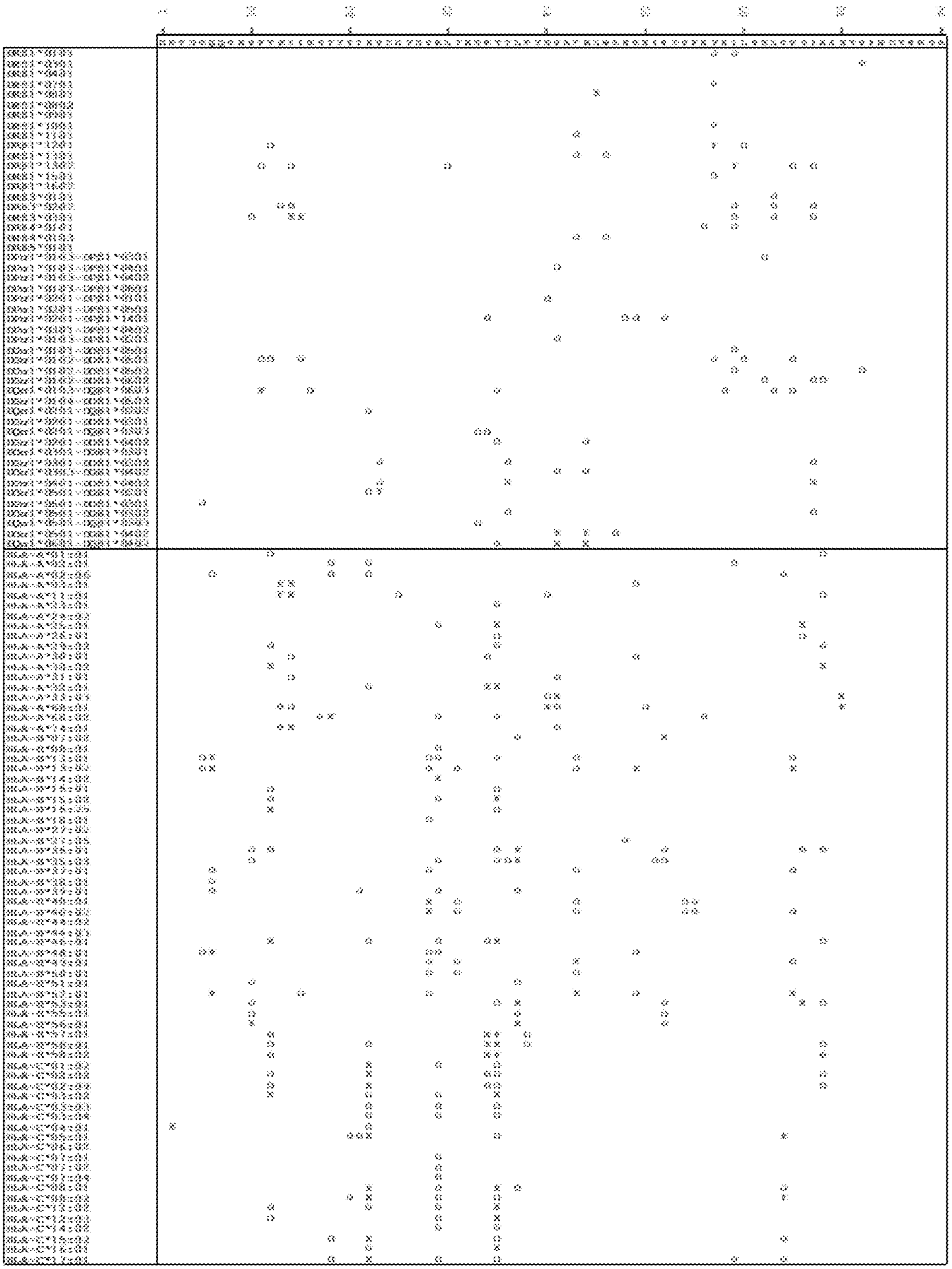
FIG. 42. Map of HLA class I and HLA class II binding motifs for SEQ ID NO: 341.
Figure 43:
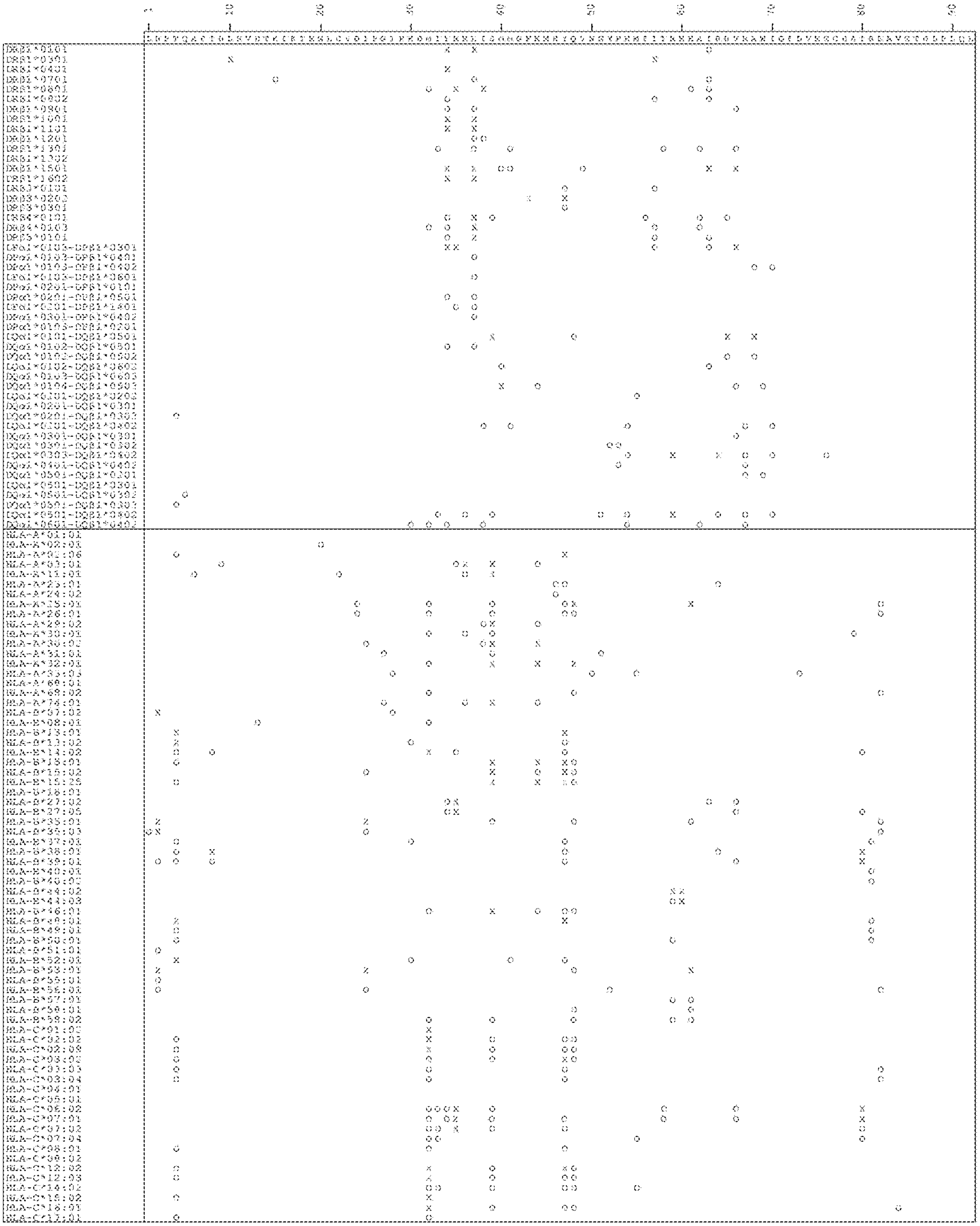
FIG. 43. Map of HLA class I and HLA class II binding motifs for SEQ ID NO: 342.
Figure 44:
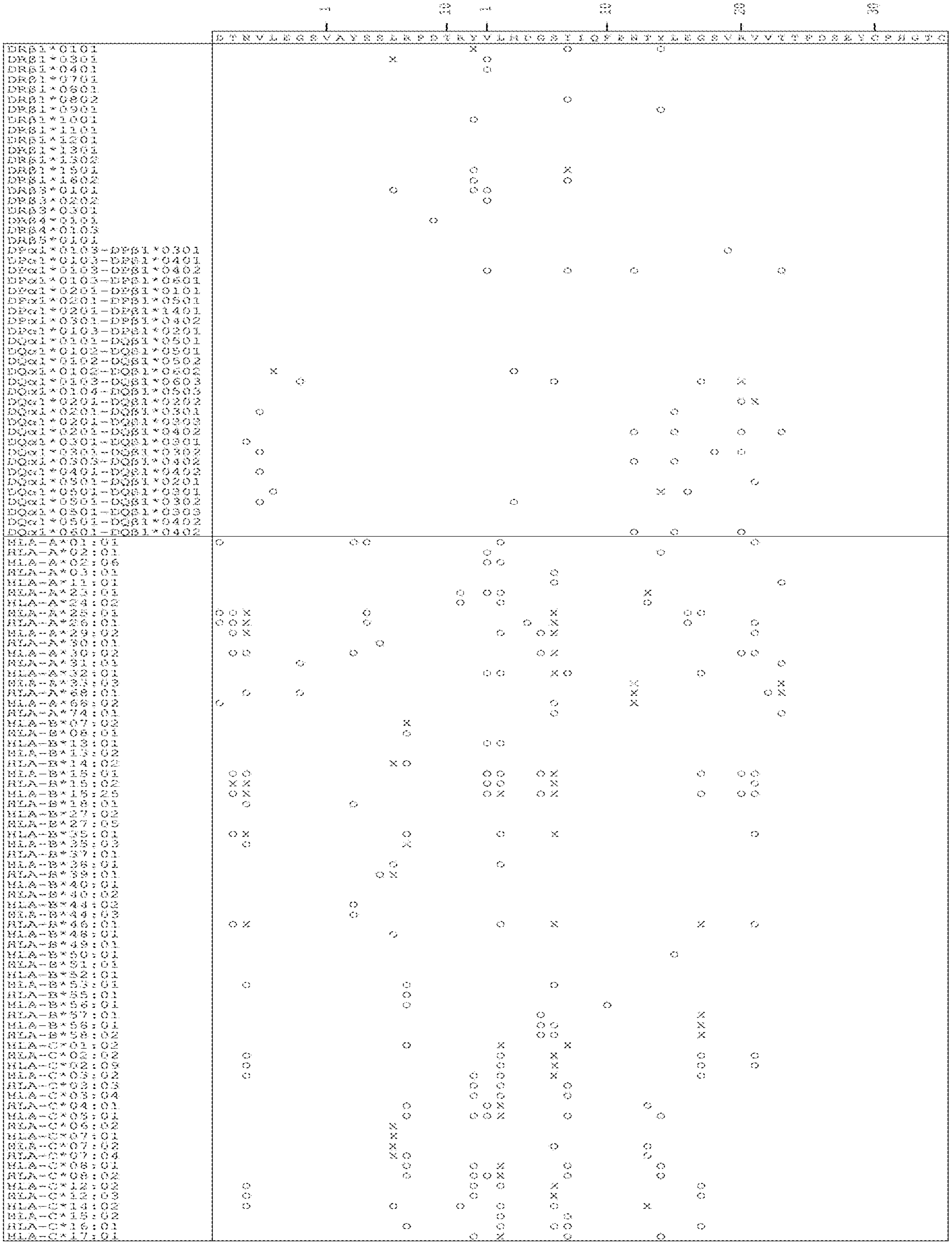
FIG. 44. Map of HLA class I and HLA class II binding motifs for SEQ ID NO: 343.
Figure 45:
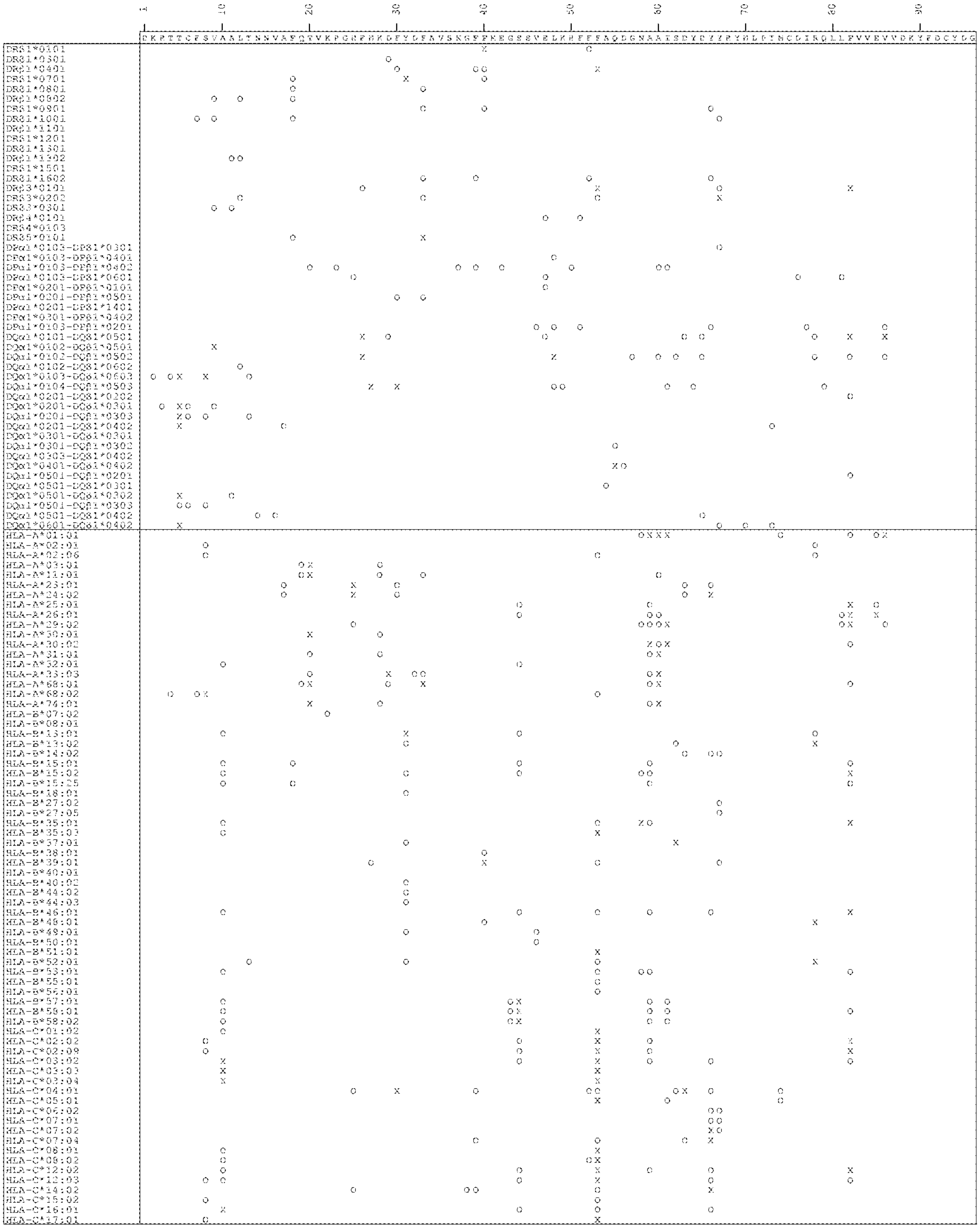
FIG. 45. Map of HLA class I and HLA class II binding motifs for SEQ ID NO: 344.
Figure 46:
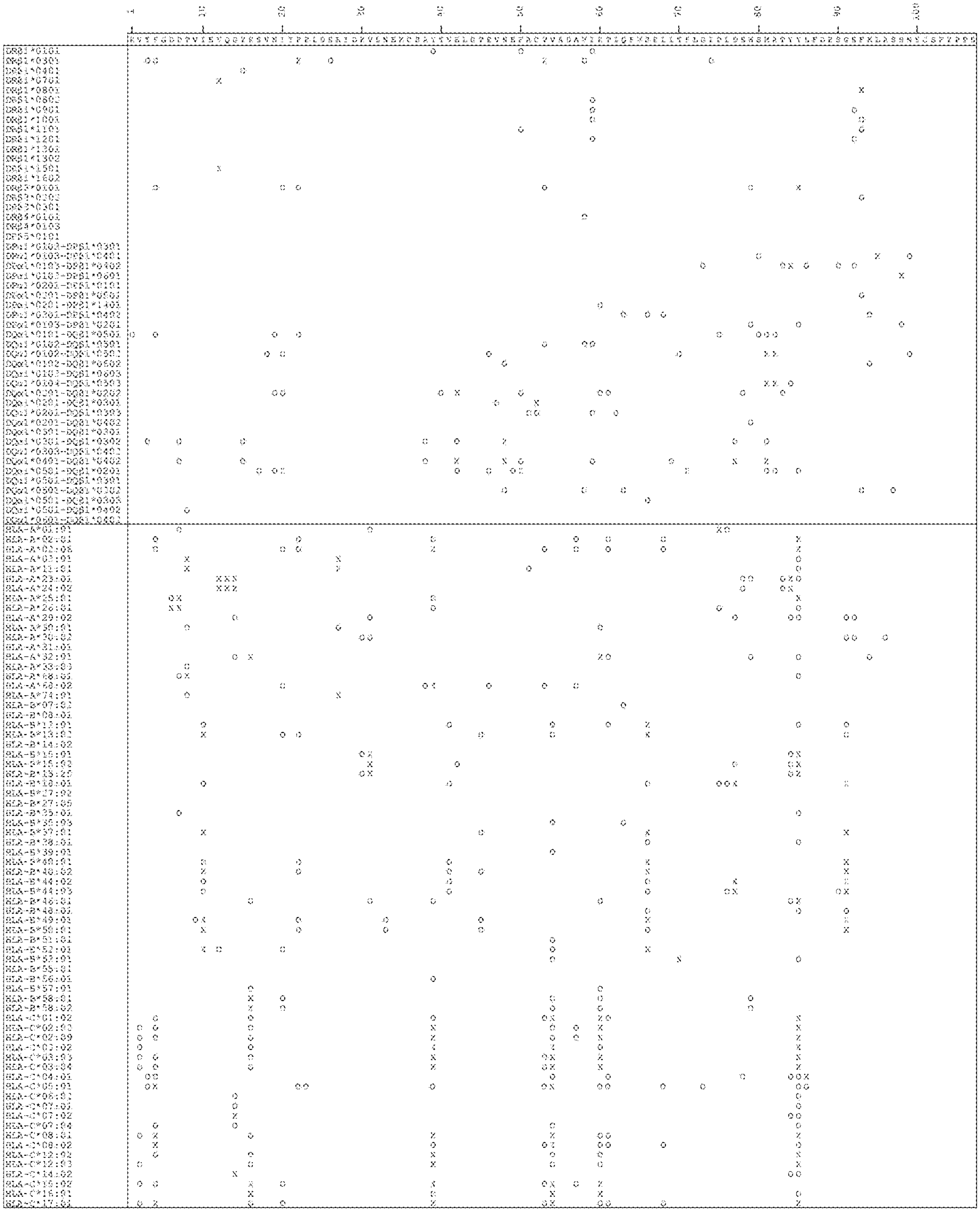
FIG. 46. Map of HLA class I and HLA class II binding motifs for SEQ ID NO: 345.
Figure 47:
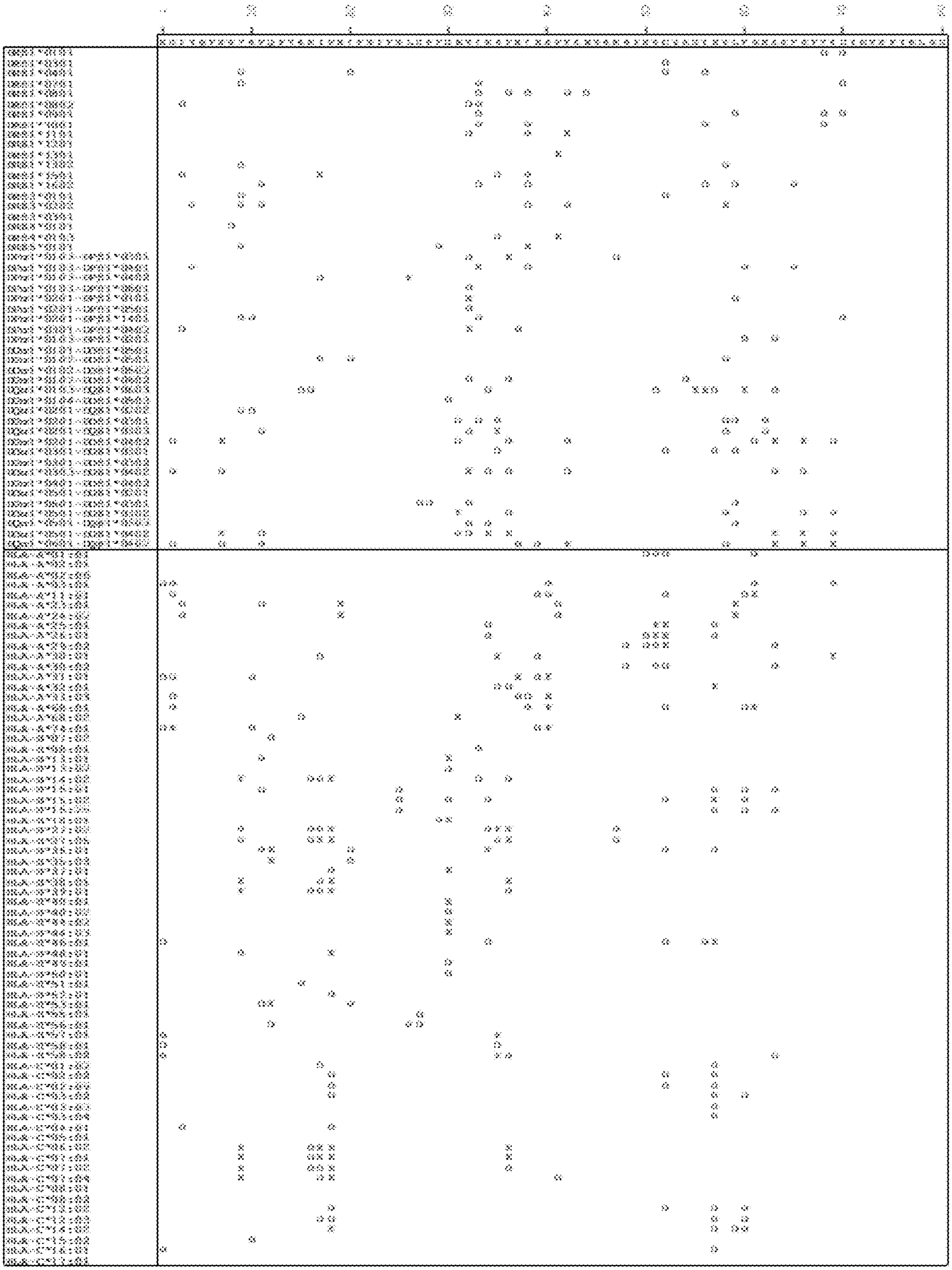
FIG. 47. Map of HLA class I and HLA class II binding motifs for SEQ ID NO: 346.
Figure 48:
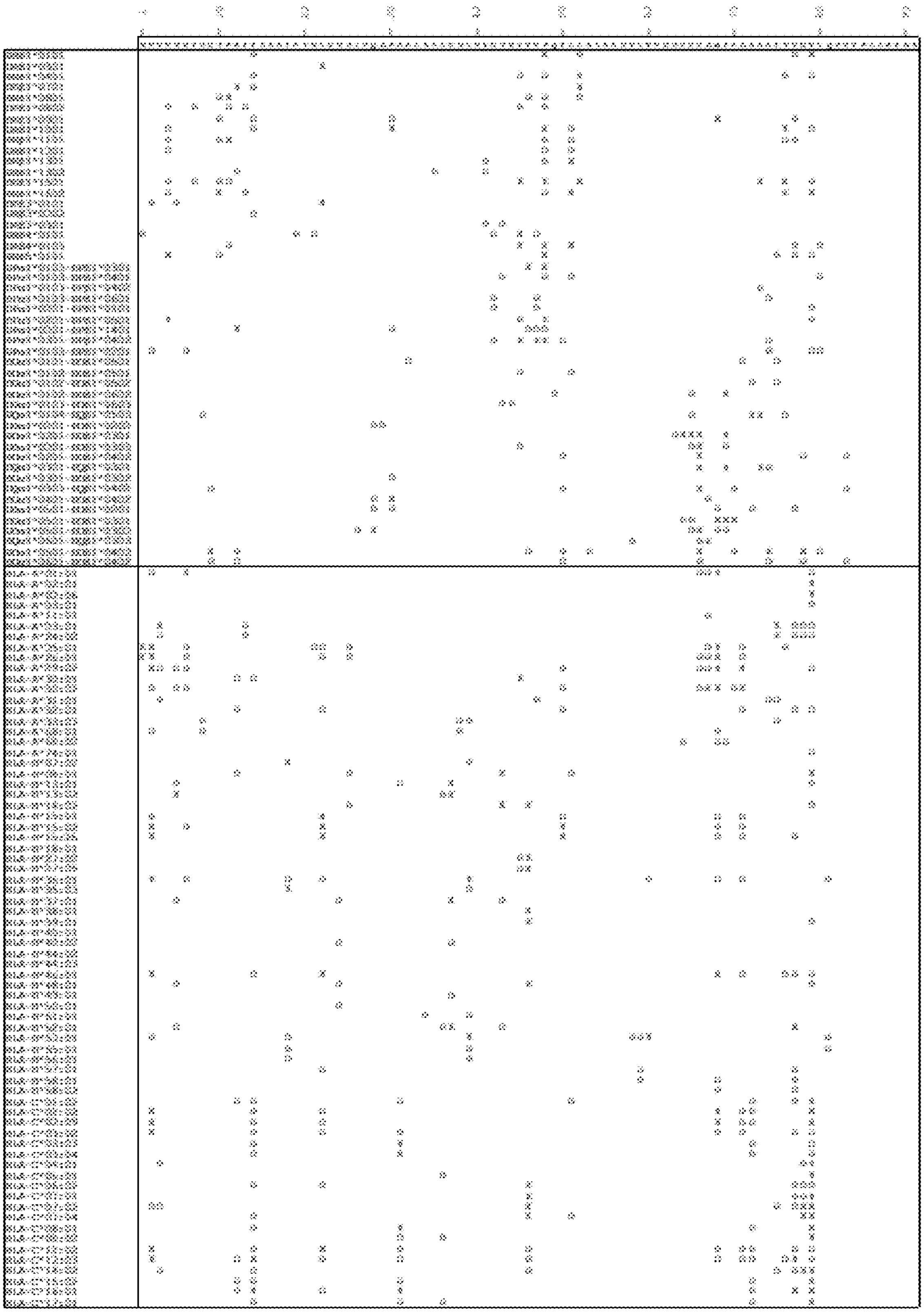
FIG. 48. Map of HLA class I and HLA class II binding motifs for SEQ ID NO: 347.
Figure 49:
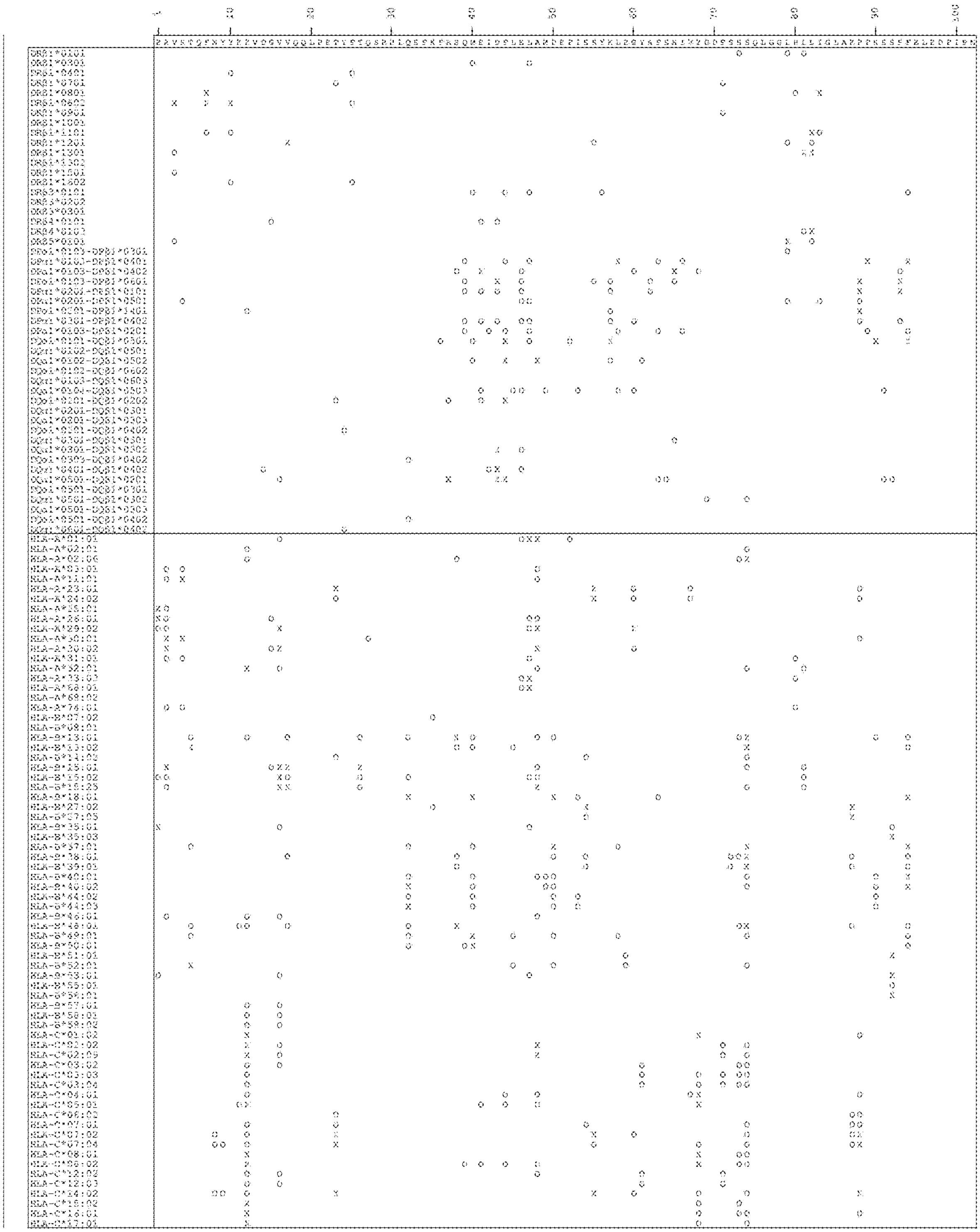
FIG. 49. Map of HLA class I and HLA class II binding motifs for SEQ ID NO: 348.
Figure 50:
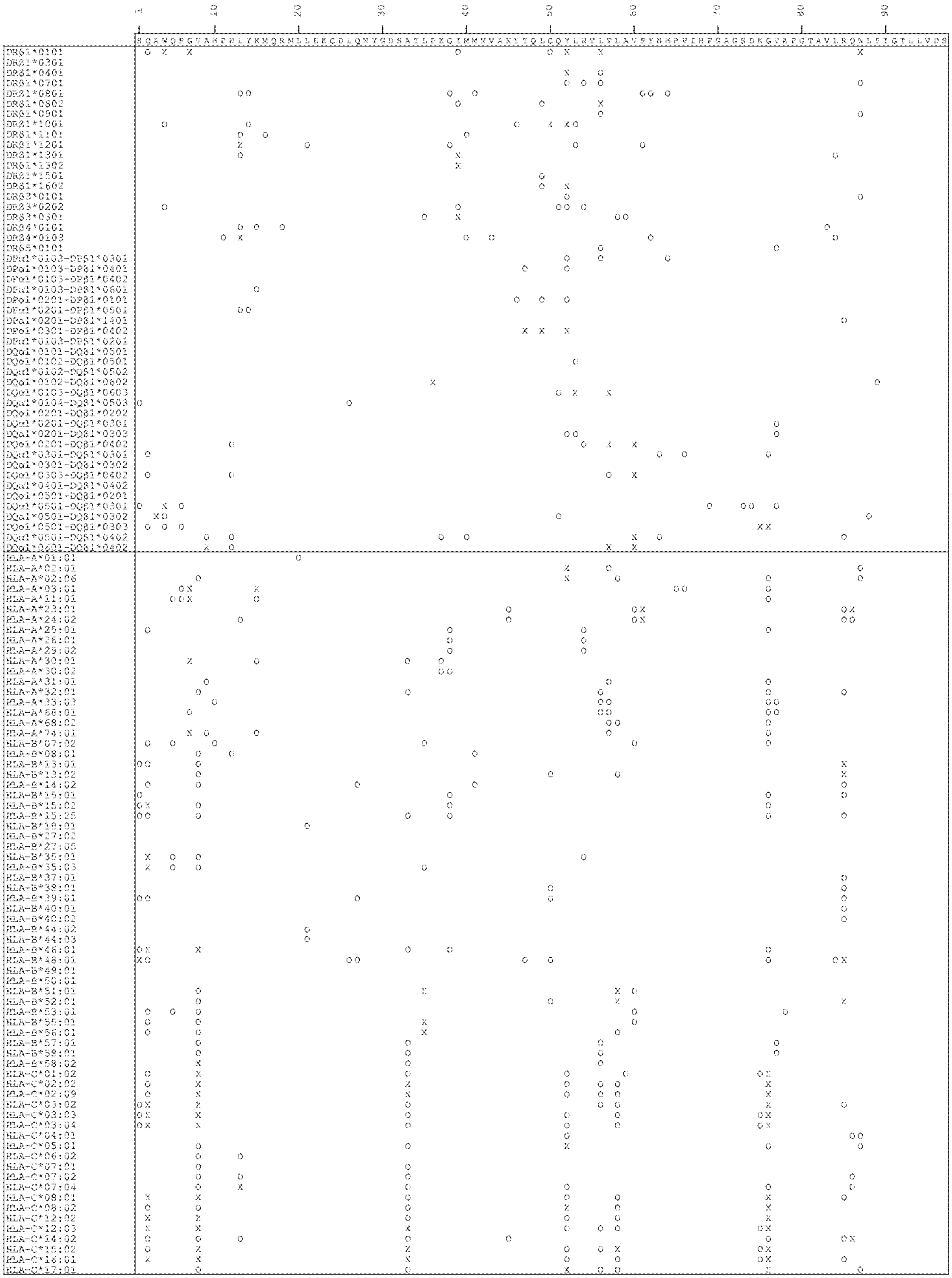
FIG. 50. Map of HLA class I and HLA class II binding motifs for SEQ ID NO: 349.
Figure 51:
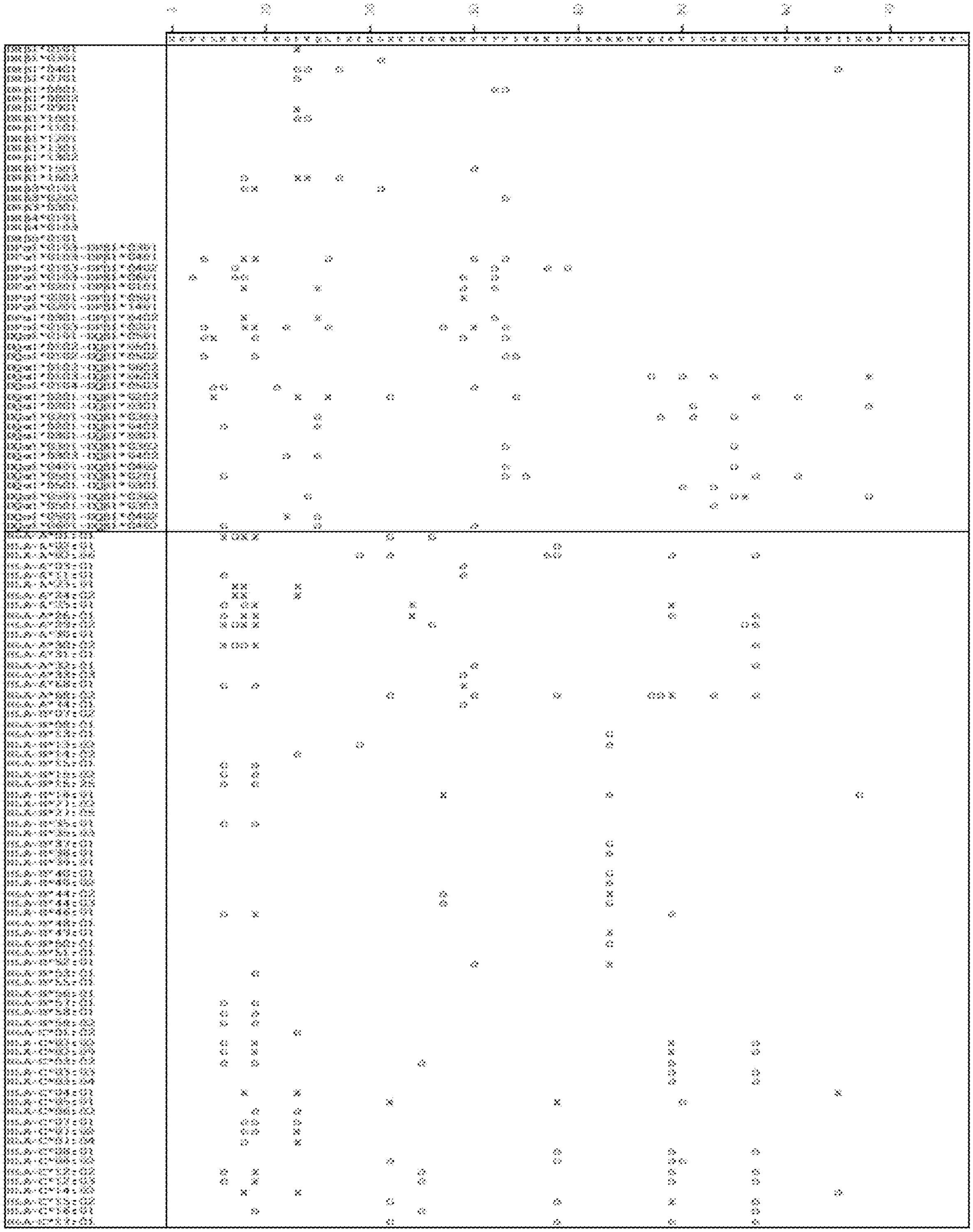
FIG. 51. Map of HLA class I and HLA class II binding motifs for SEQ ID NO: 350.
Figure 52:
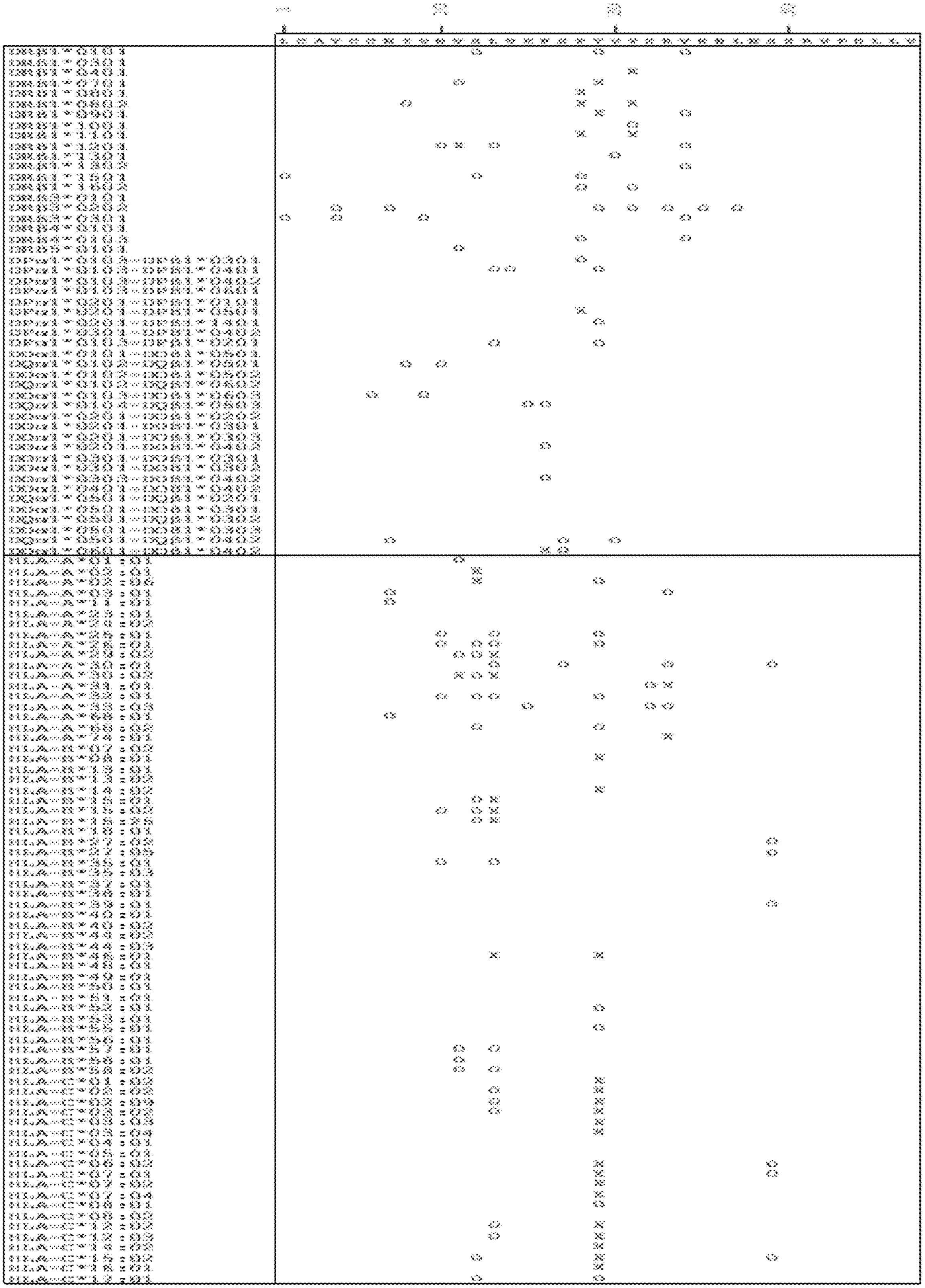
FIG. 52. Map of HLA class I and HLA class II binding motifs for SEQ ID NO: 351.
Figure 53:
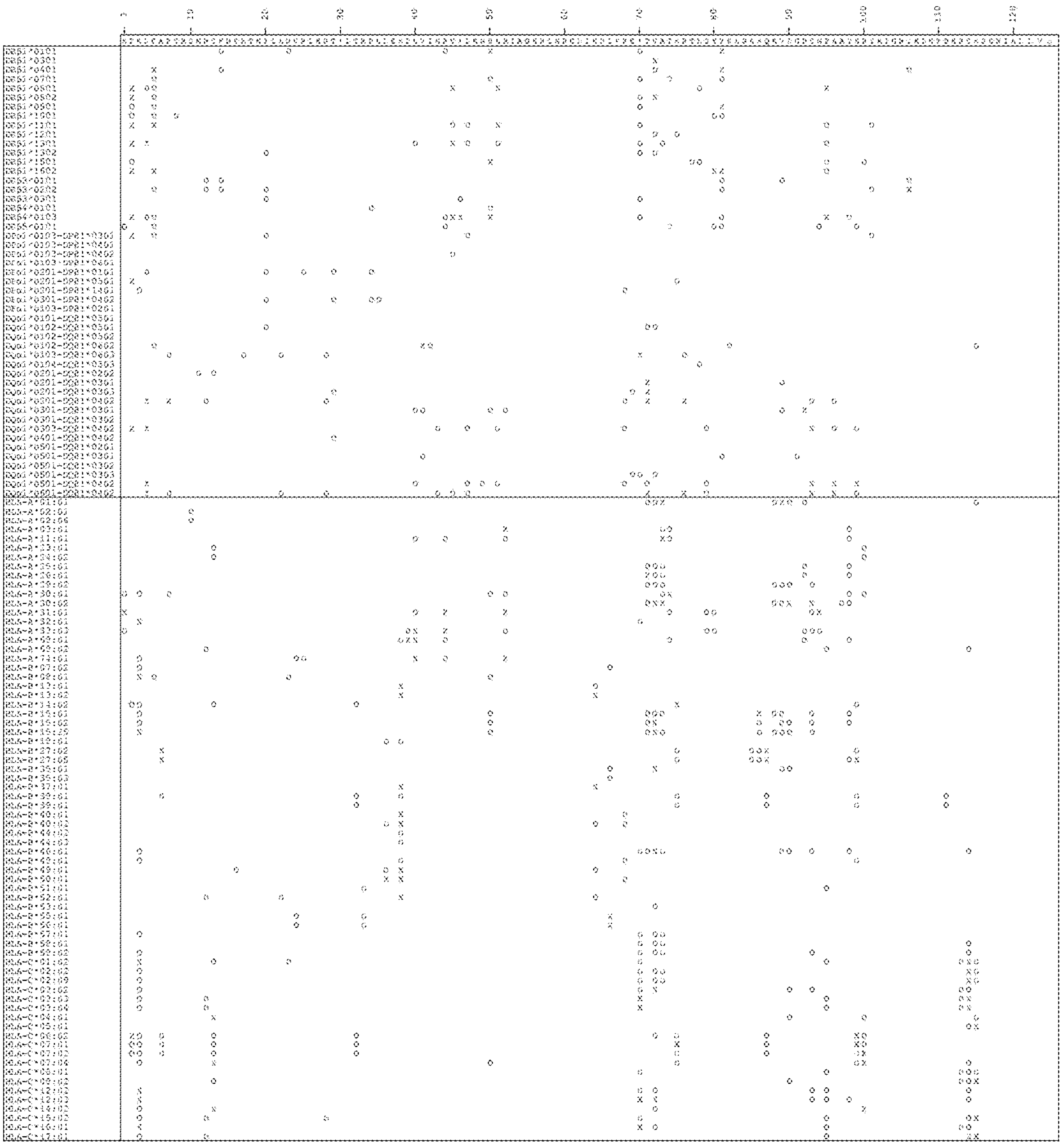
FIG. 53. Map of HLA class I and HLA class II binding motifs for SEQ ID NO: 352.
Figure 54:
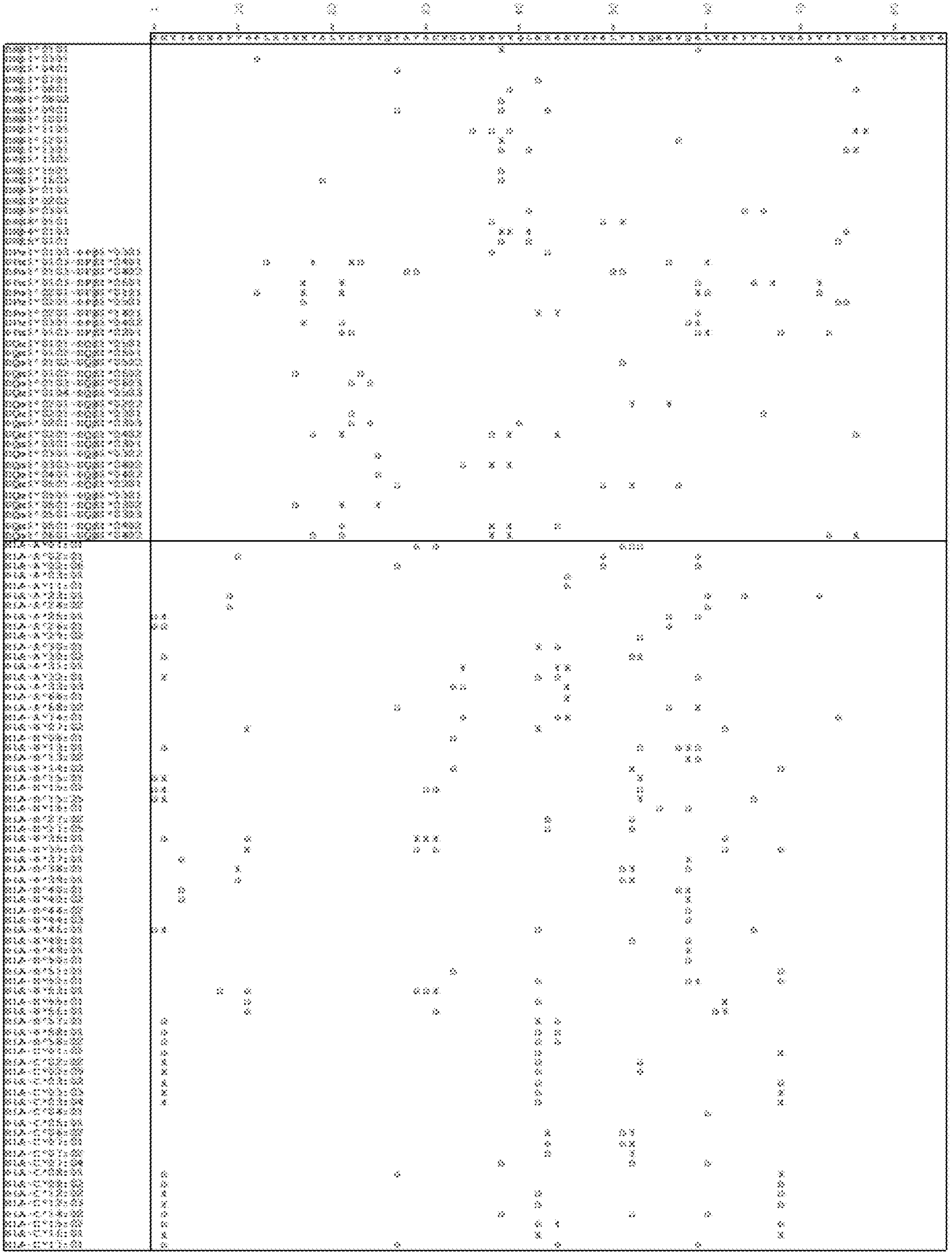
FIG. 54. Map of HLA class I and HLA class II binding motifs for SEQ ID NO: 353.
Figure 55:
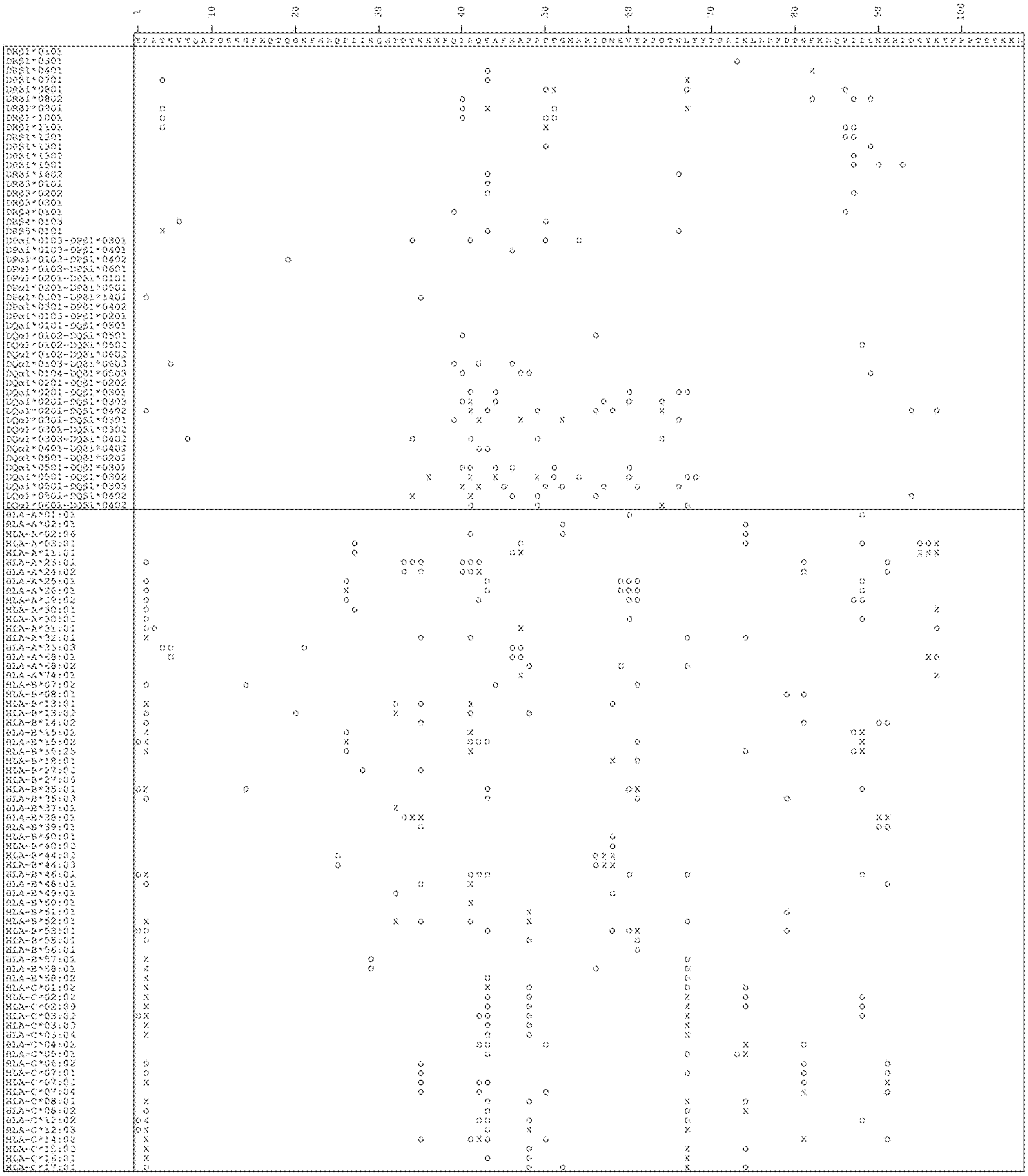
FIG. 55. Map of HLA class I and HLA class II binding motifs for SEQ ID NO: 354.
Figure 56:
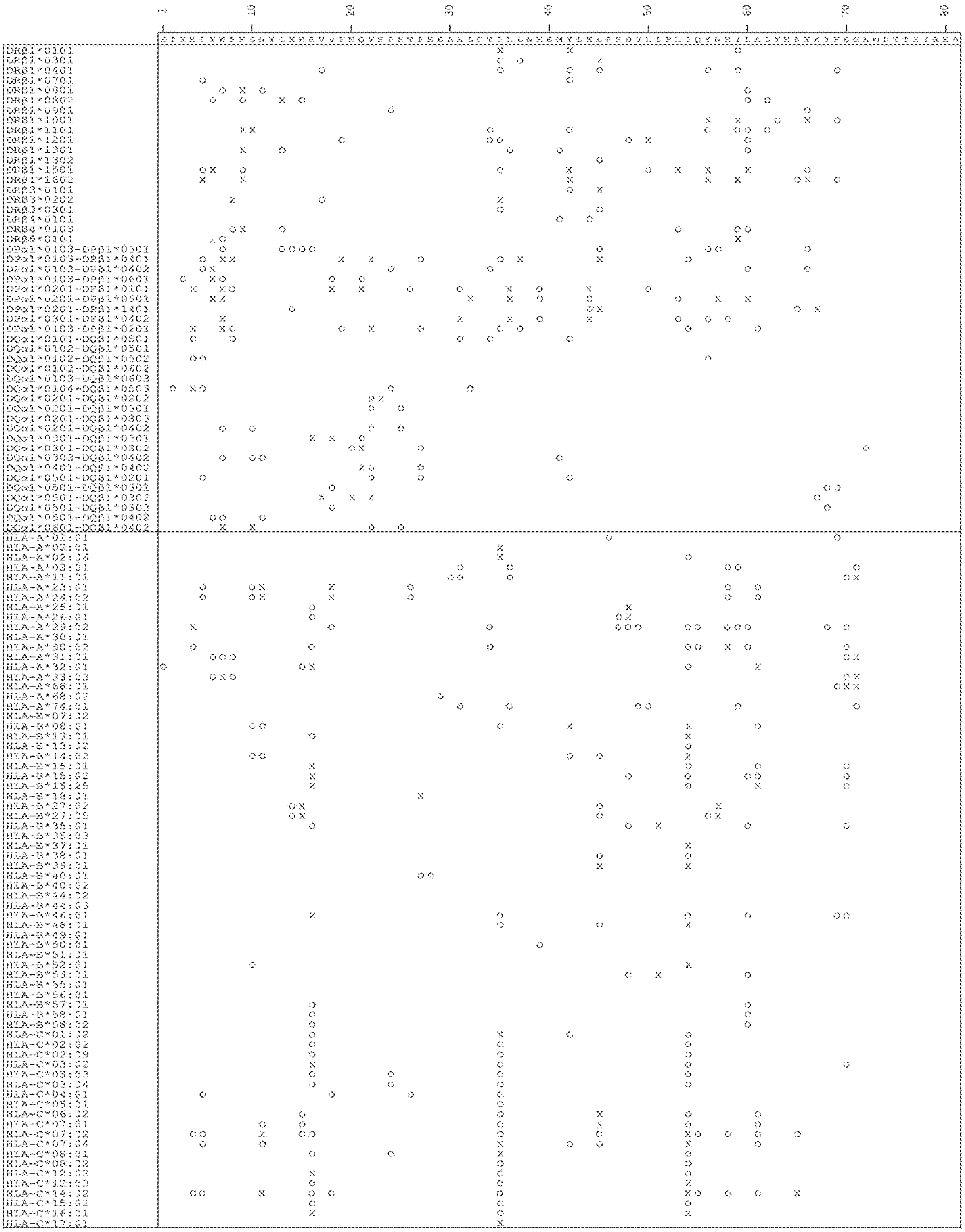
FIG. 56. Map of HLA class I and HLA class II binding motifs for SEQ ID NO: 355.
Figure 57:
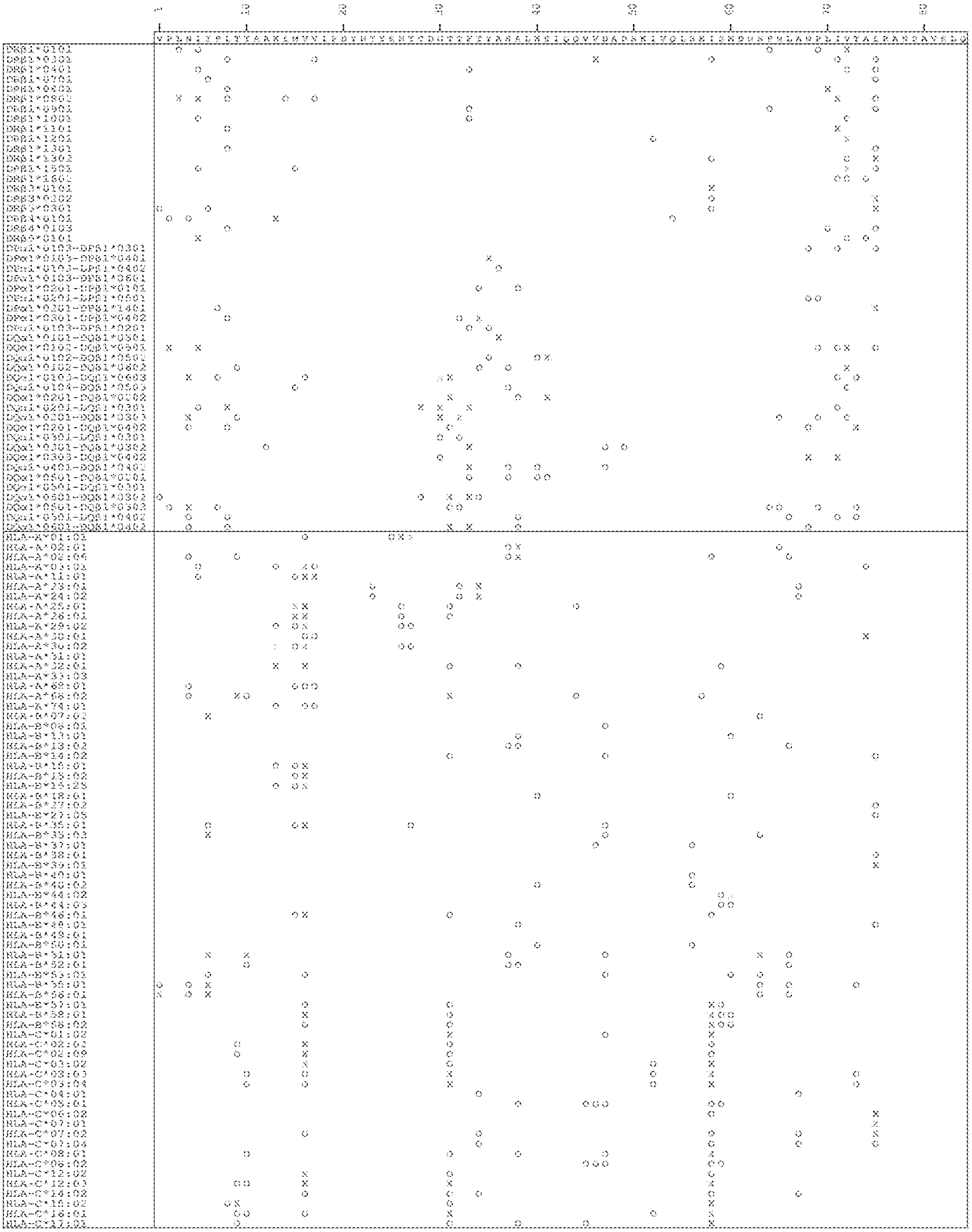
FIG. 57. Map of HLA class I and HLA class II binding motifs for SEQ ID NO: 356.
Figure 58:
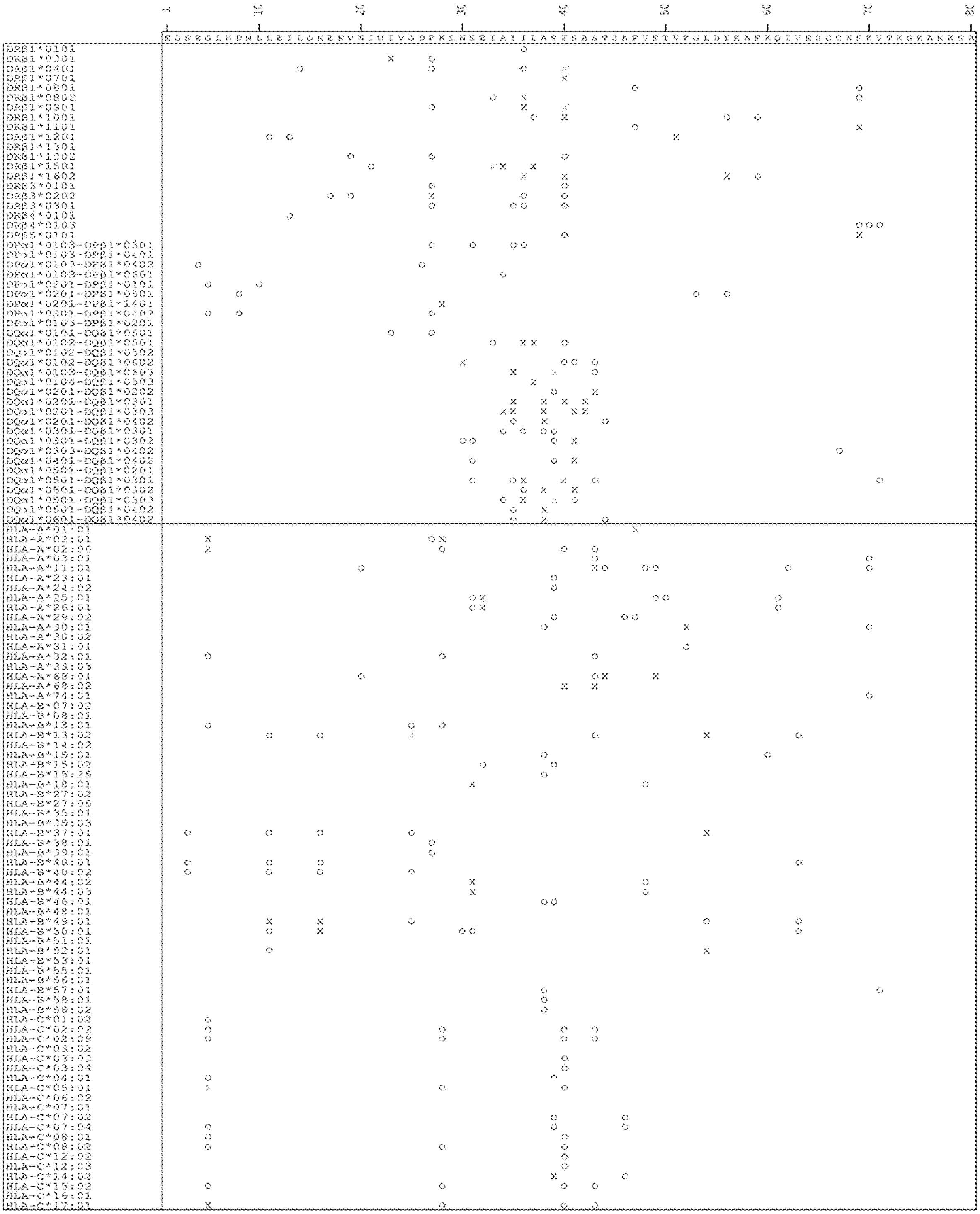
FIG. 58. Map of HLA class I and HLA class II binding motifs for SEQ ID NO: 357.
Figure 59:
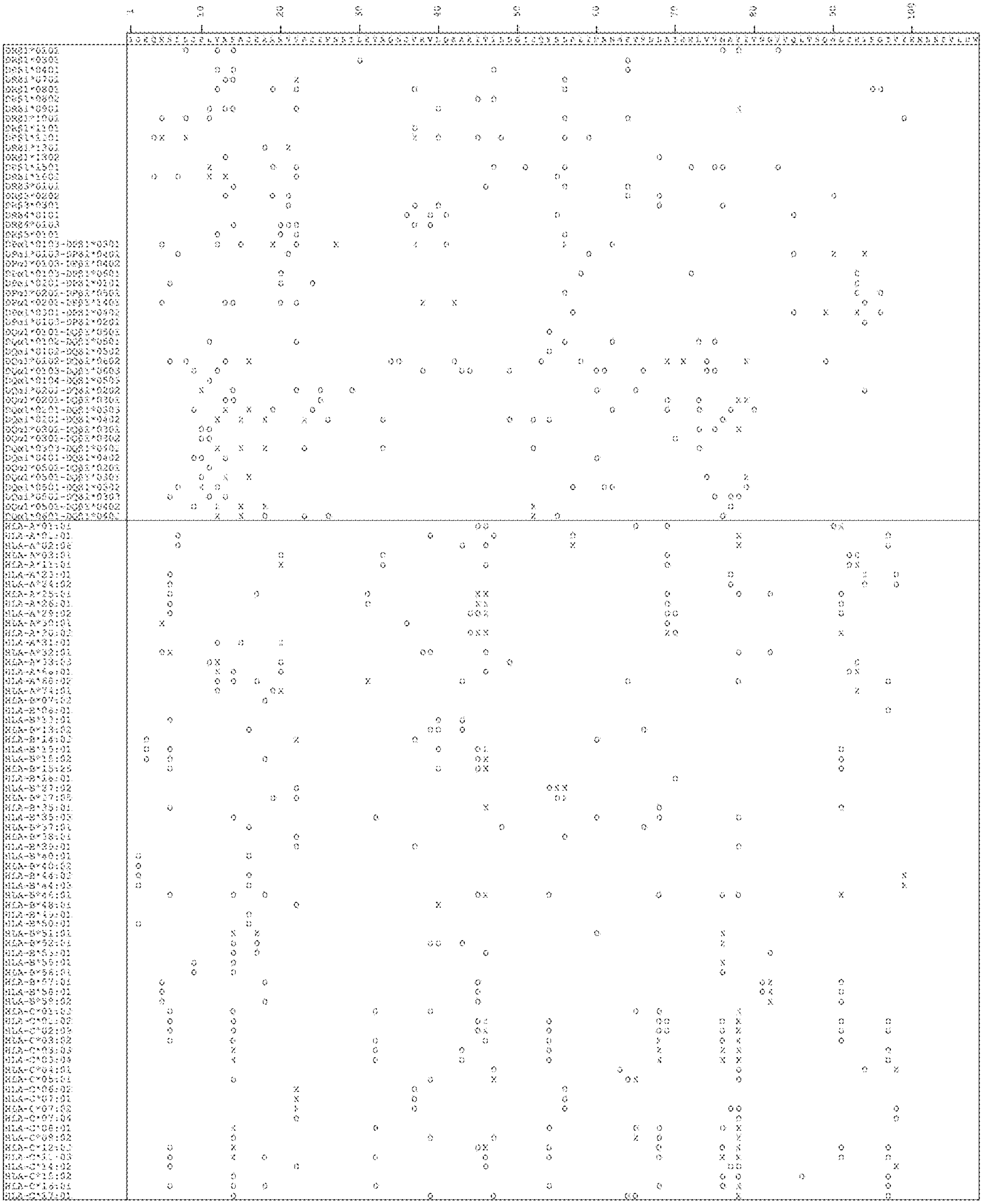
FIG. 59. Map of HLA class I and HLA class II binding motifs for SEQ ID NO: 358.
Figure 60:
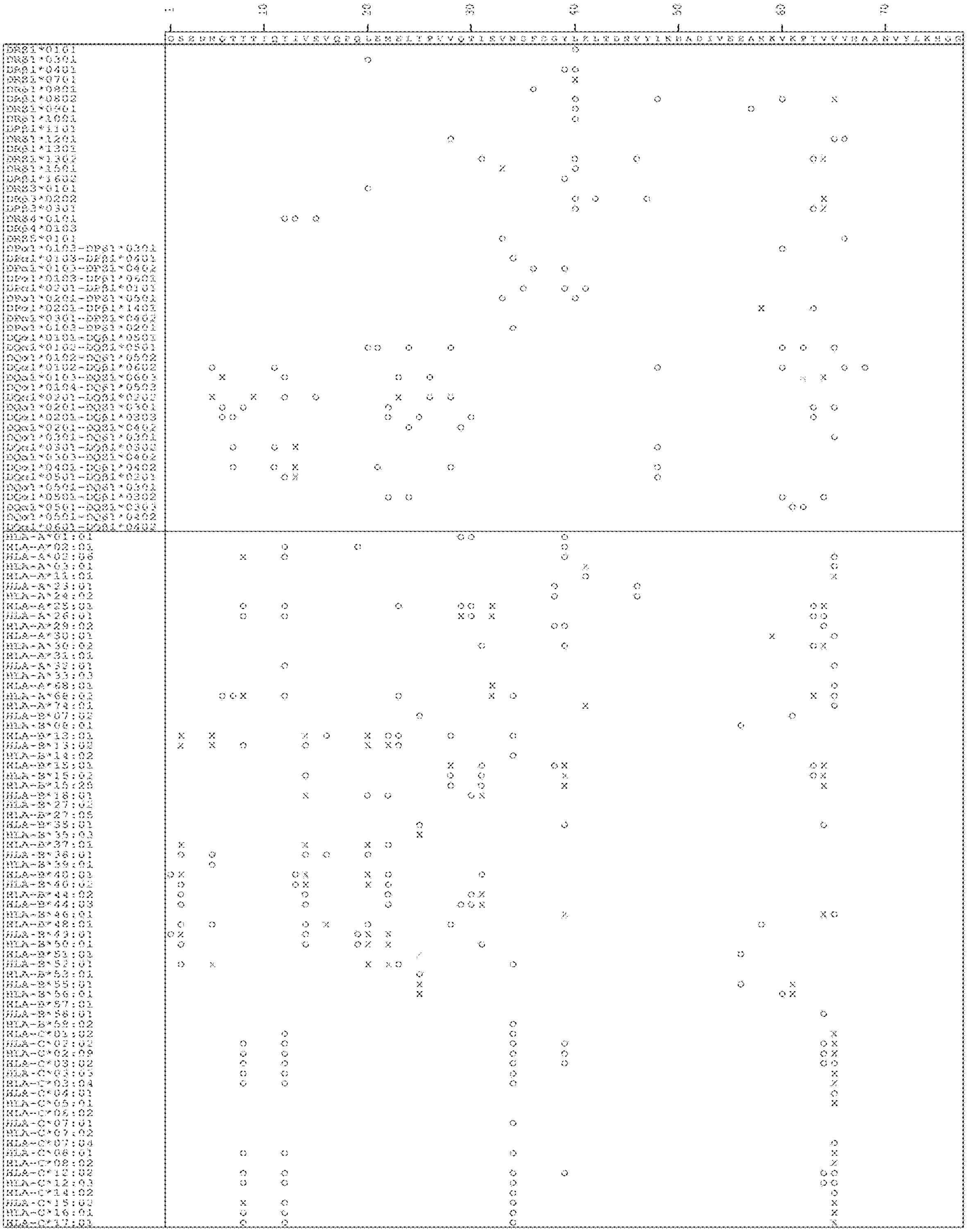
FIG. 60. Map of HLA class I and HLA class II binding motifs for SEQ ID NO: 359.
Figure 61:
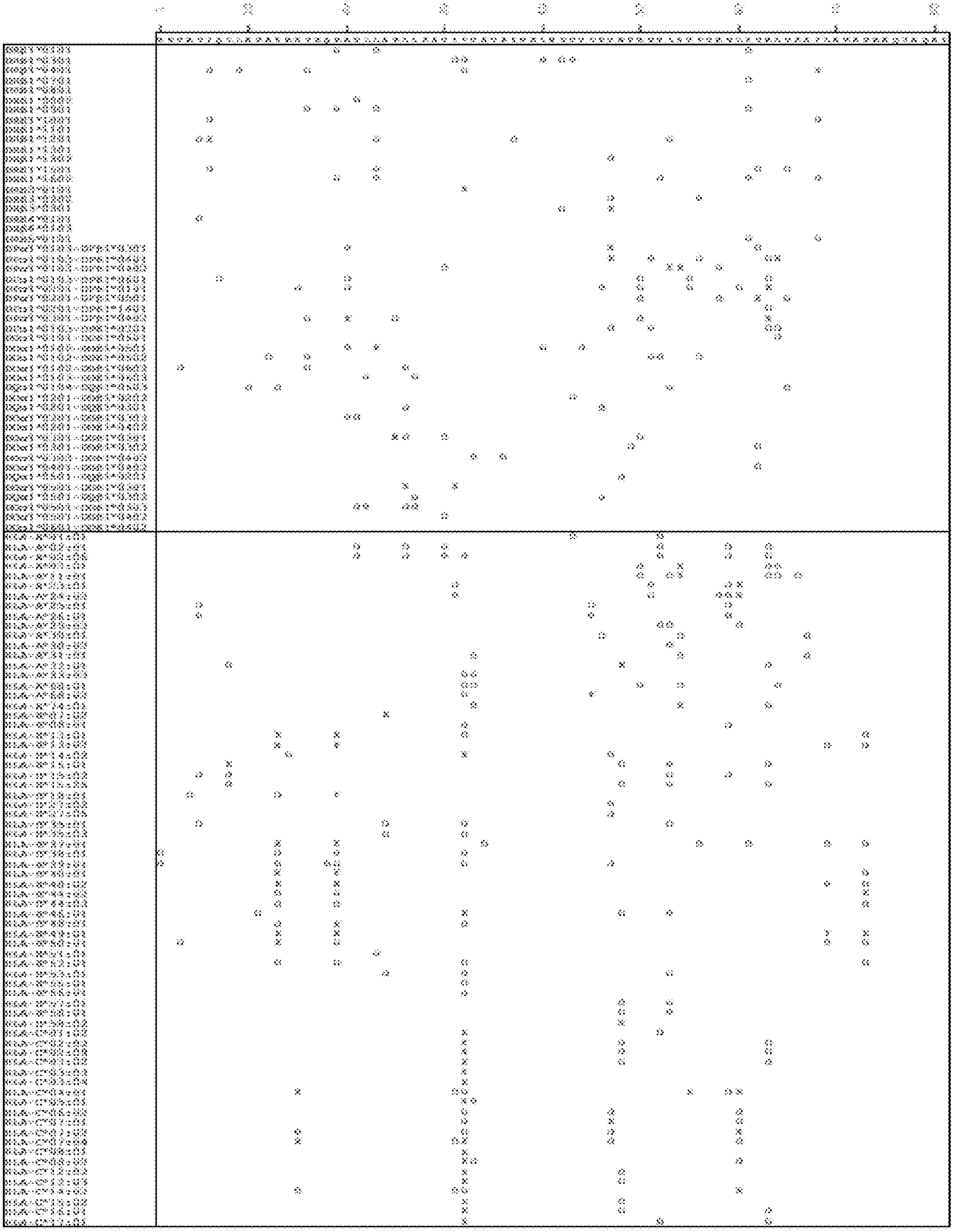
FIG. 61. Map of HLA class I and HLA class II binding motifs for SEQ ID NO: 360.
Figure 62:
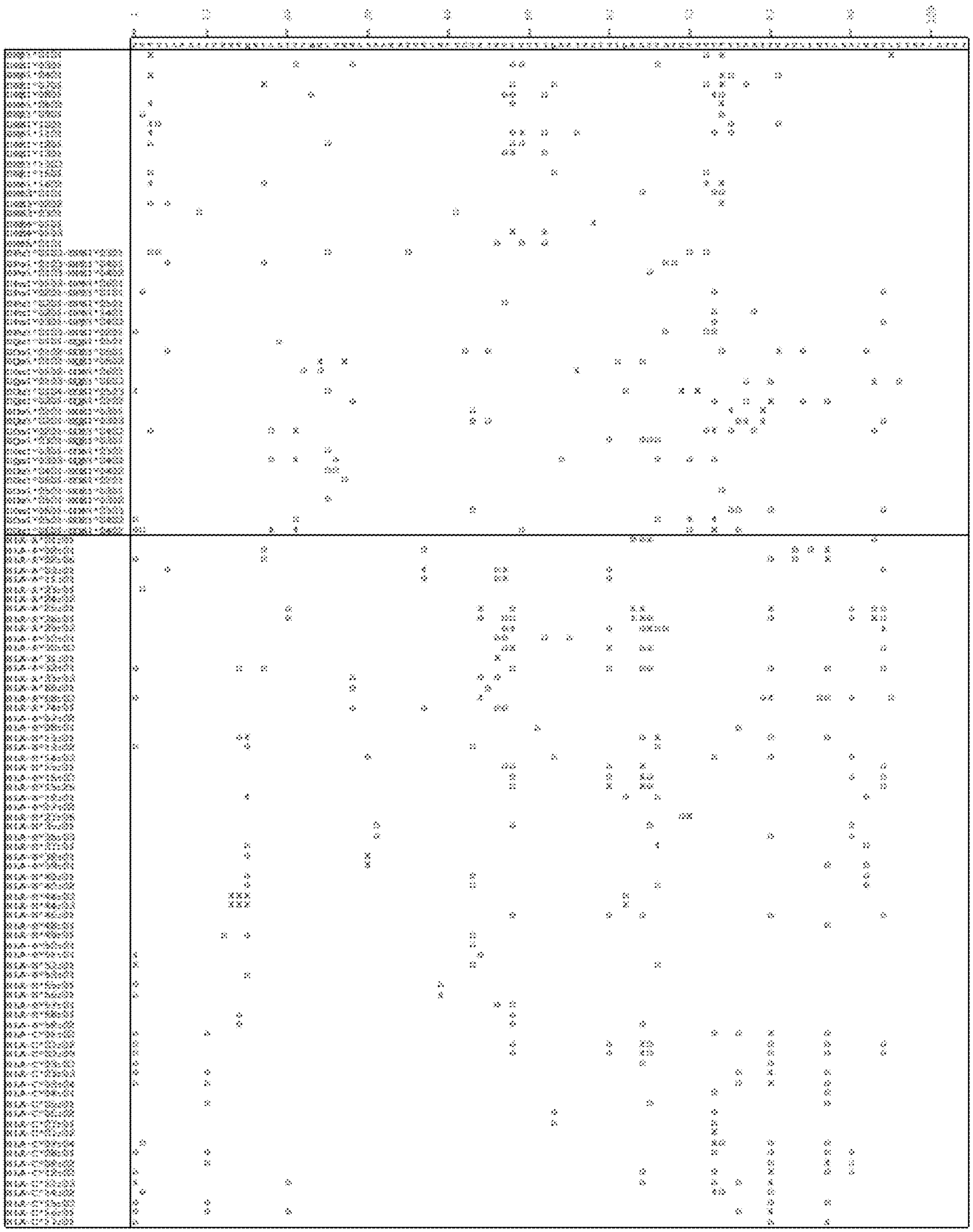
FIG. 62. Map of HLA class I and HLA class II binding motifs for SEQ ID NO: 361.
Figure 63:
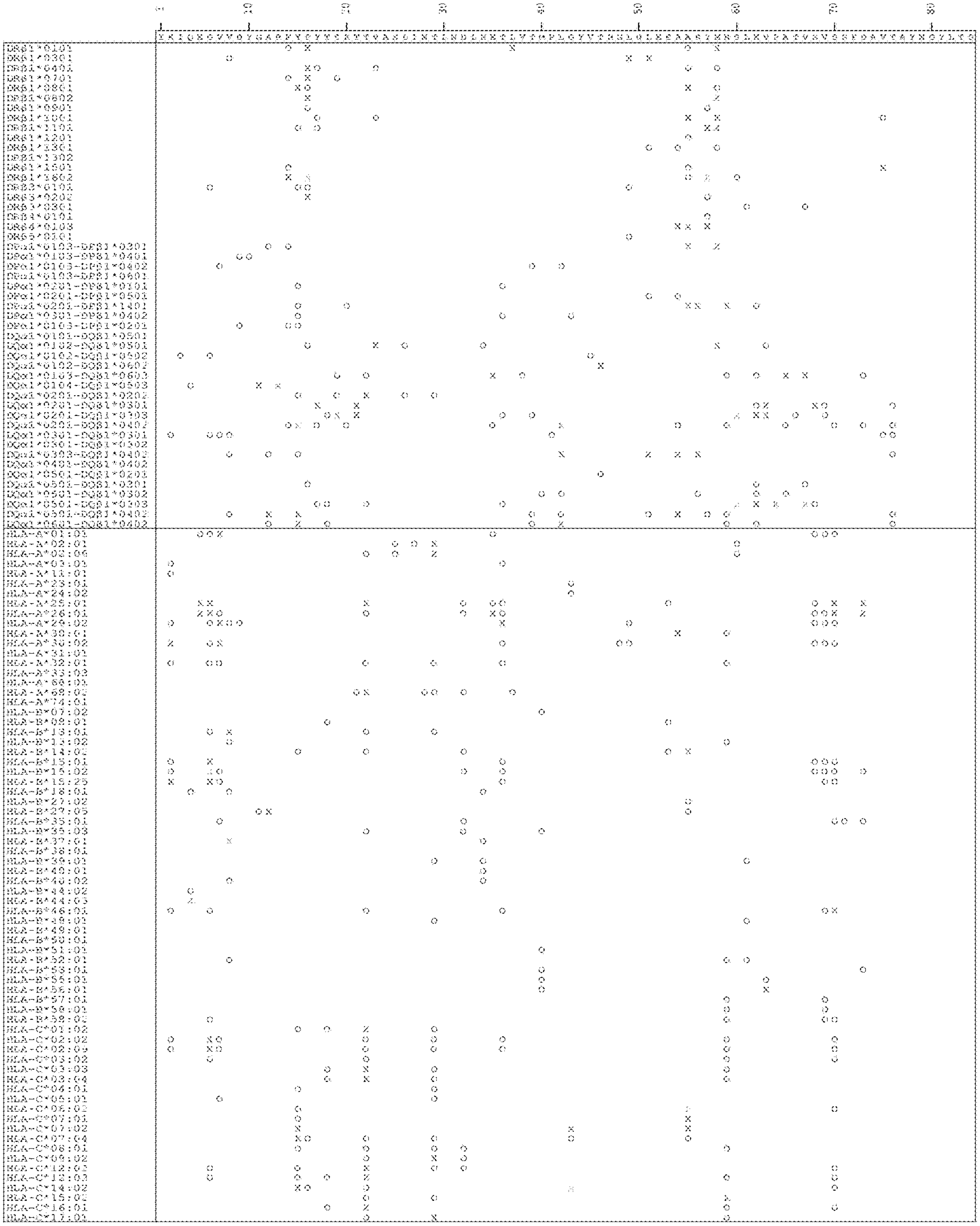
FIG. 63. Map of HLA class I and HLA class II binding motifs for SEQ ID NO: 362.
Figure 64:
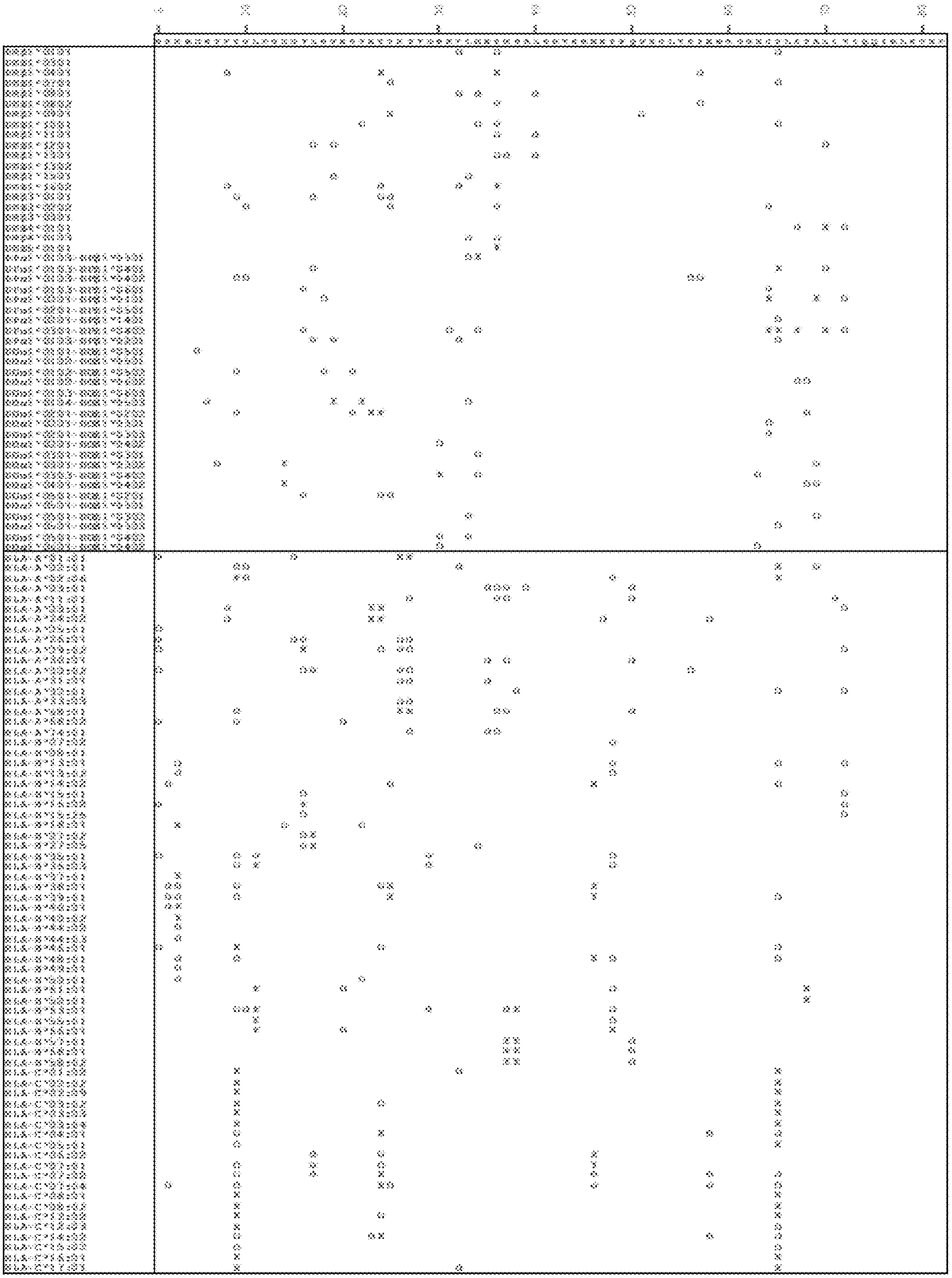
FIG. 64. Map of HLA class I and HLA class II binding motifs for SEQ ID NO: 363.
Figure 65:
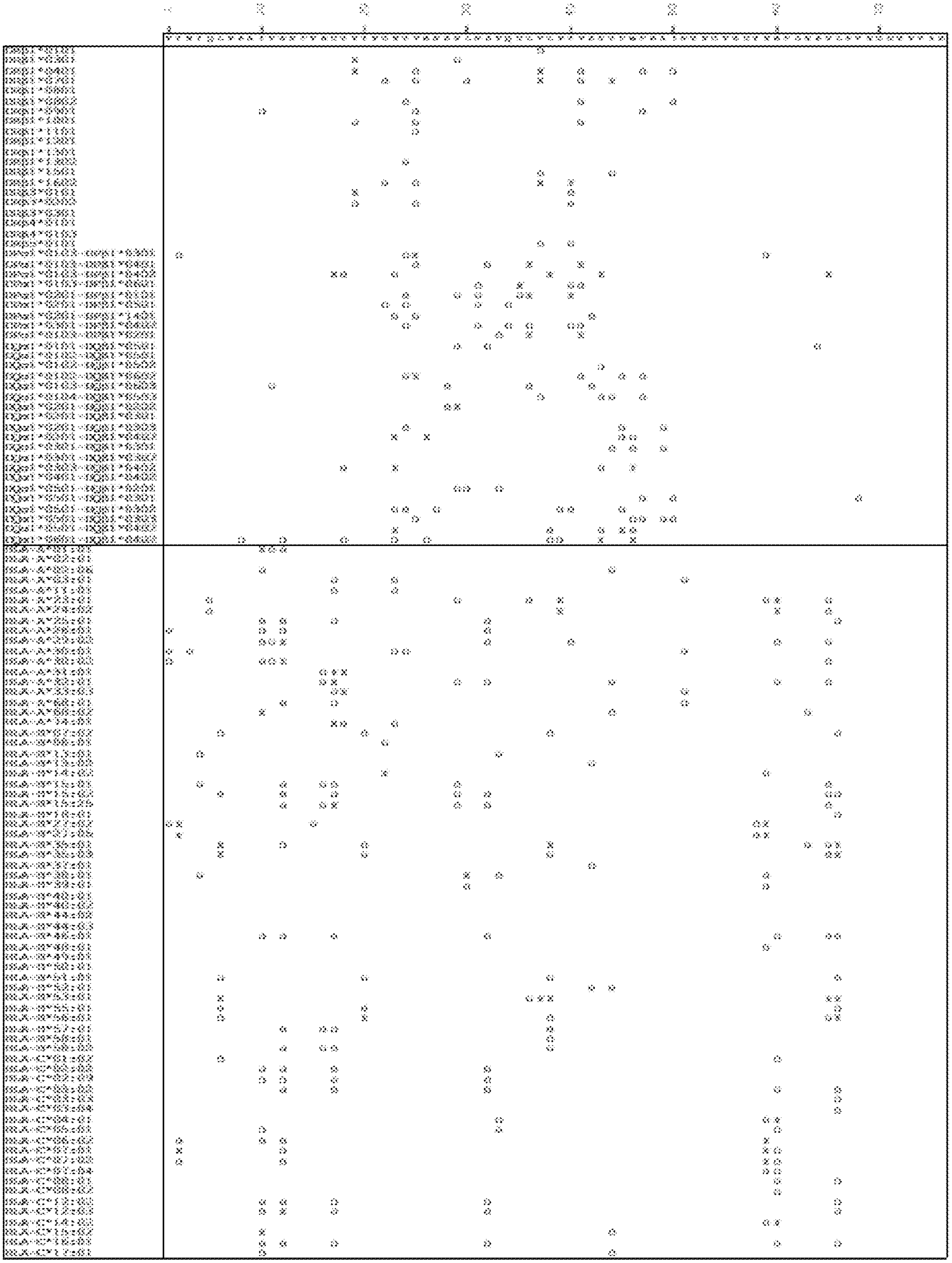
FIG. 65. Map of HLA class I and HLA class II binding motifs for SEQ ID NO: 364.
Figure 66:
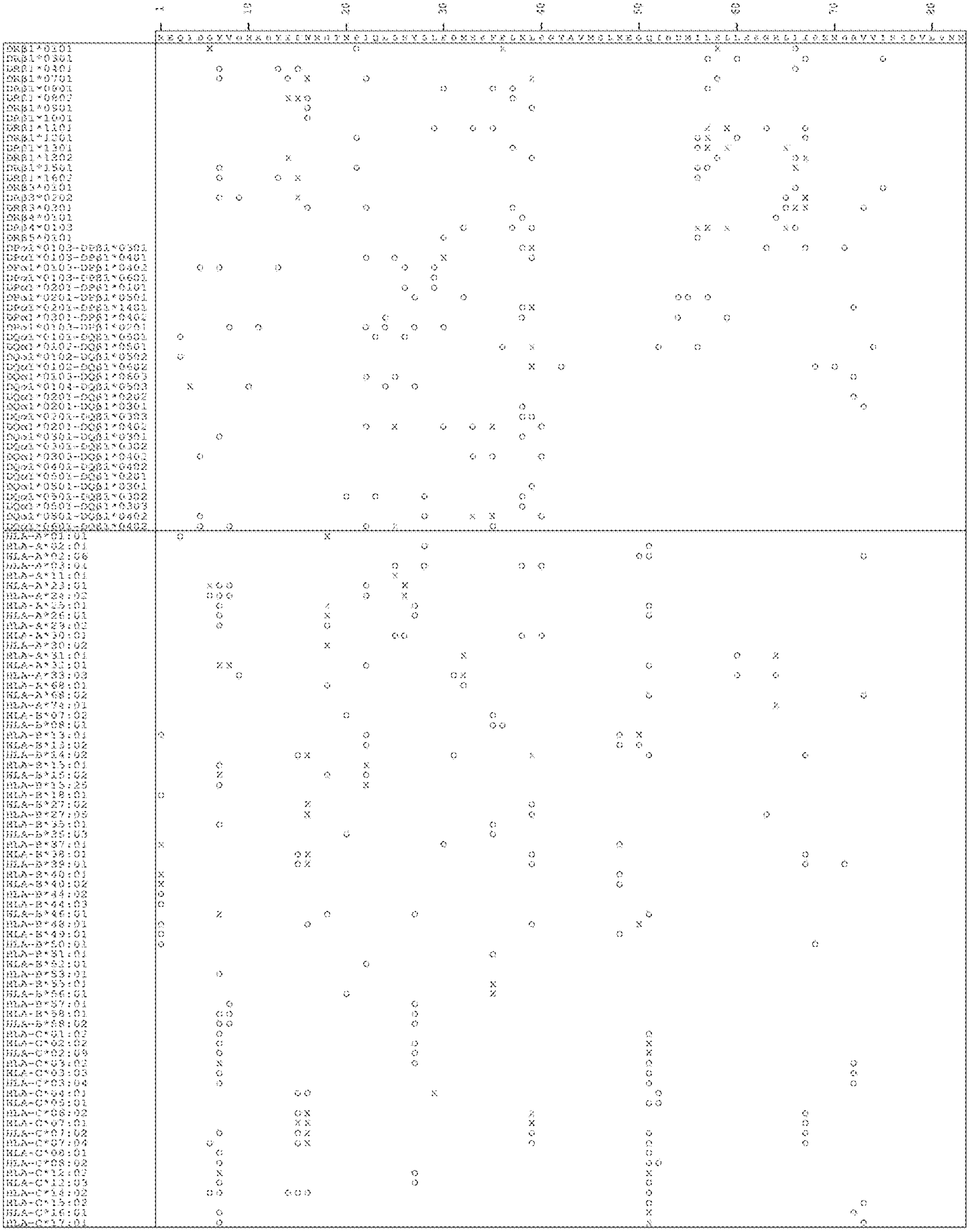
FIG. 66. Map of HLA class I and HLA class II binding motifs for SEQ ID NO: 365.
Figure 67:
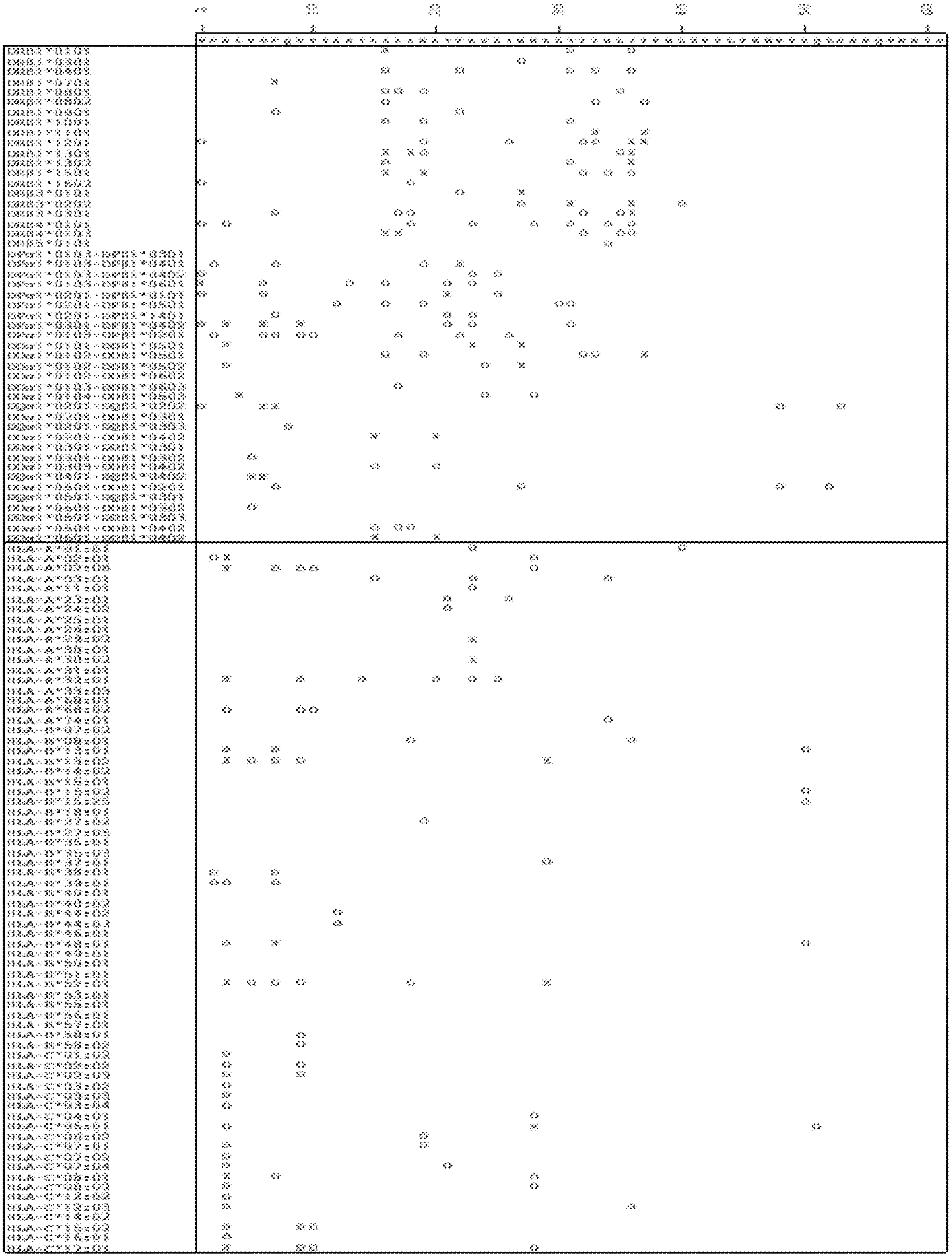
FIG. 67. Map of HLA class I and HLA class II binding motifs for SEQ ID NO: 366.
Figure 68:
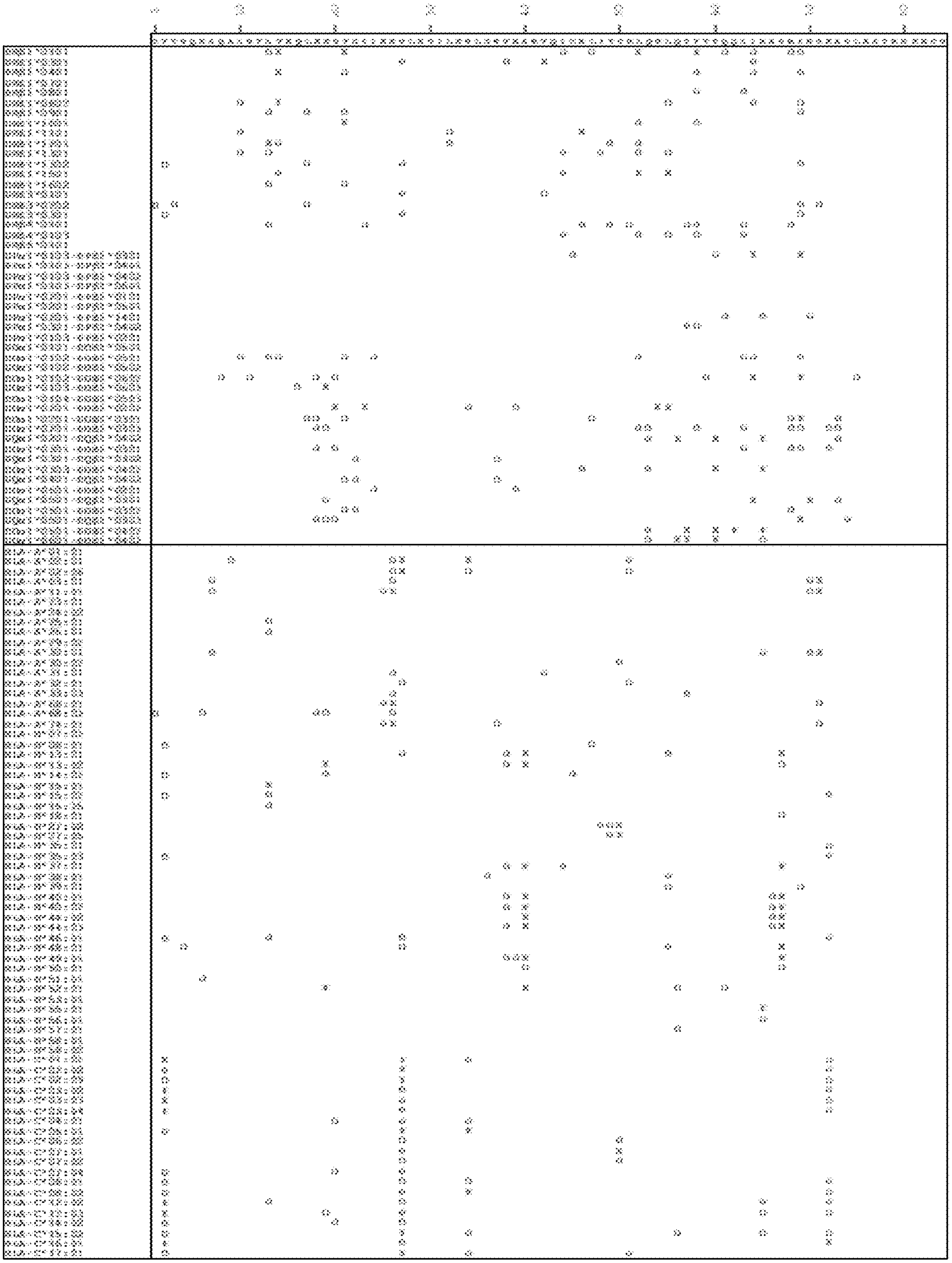
FIG. 68. Map of HLA class I and HLA class II binding motifs for SEQ ID NO: 367.
Figure 69:
FIG. 69. Map of HLA class I and HLA class II binding motifs for SEQ ID NO: 368.
Figure 70:
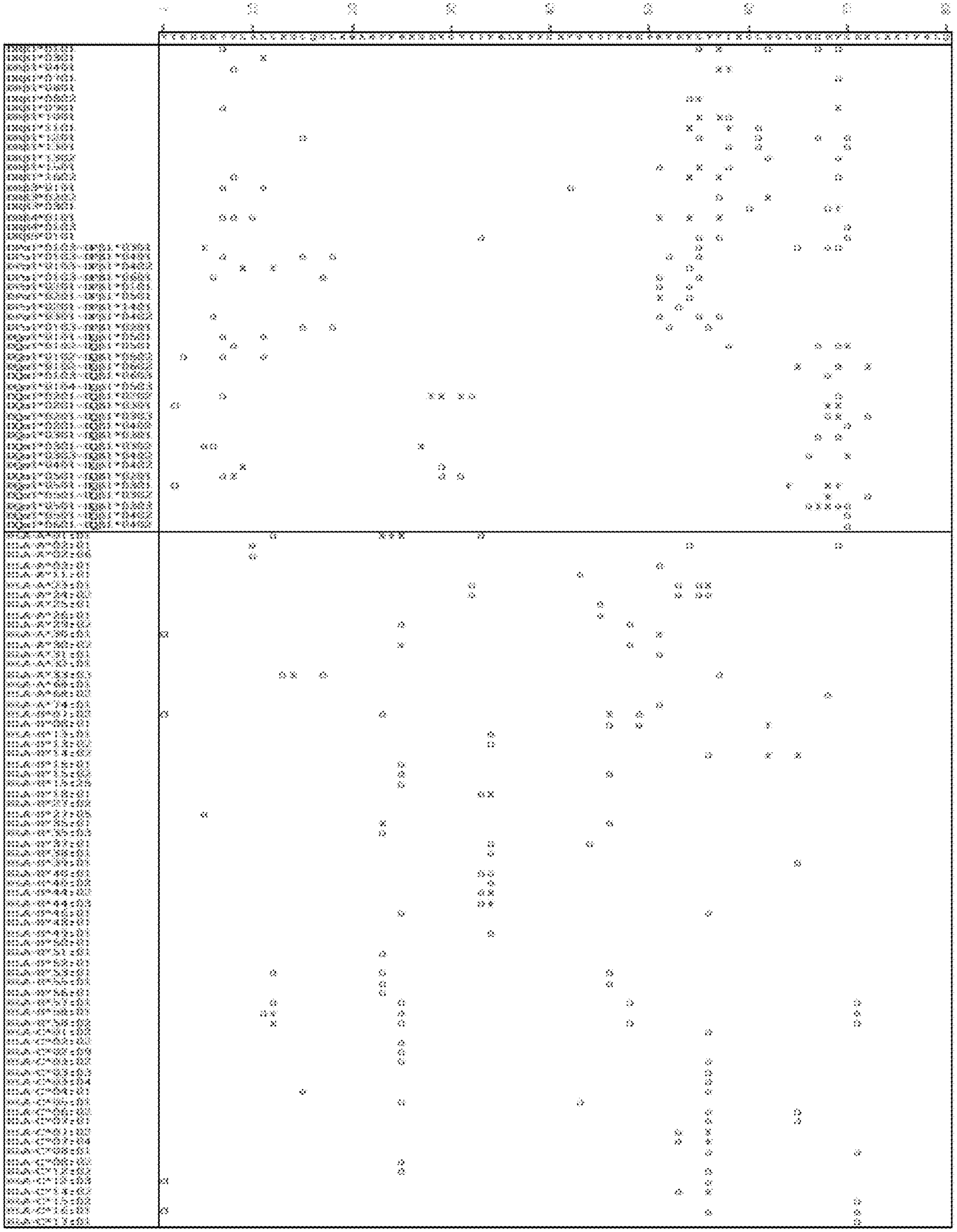
FIG. 70. Map of HLA class I and HLA class II binding motifs for SEQ ID NO: 369.

A secondary objective of that study was to evaluate the immune response against the adenoviral vector (Ad5) for subjects that were seropositive for Ad5 (as compared to subjects that were seronegative) at the time of administration of NasoVAX. At four, eight and 15 days post-dose, nasopharyngeal swab samples were collected from each subject and the concentration of the Ad5 vector shed by each quantified by polymerase chain reaction (PCR) assay. As shown in FIG. 25, dose-dependent shedding of NasoVAX vector was detected until day 8 post-dose and was not detected at day 15. No replication-competent virus was detected.

FIG. 25 also illustrates the GMR of antibodies against the Ad5 vector component of NasoVAX following administration of a single intranasal dose of $10^9$ vp, $10^{10}$ vp, or $10^{11}$ vp of NasoVAX. As shown therein, administration of the highest dose ($10^{11}$ vp) surprisingly only resulted in about a 2.3-fold induction of anti-Ad5 vector antibodies in subjects as compared to control. This is an important finding as it indicates the intranasal route of administration can be used for repeated dosing of NasoVAX, or potentially other adenoviral vectored immunogenic compositions, including Ad5-based vectors.

FIG. 26 shows the effect of pre-existing anti-Ad5 immunity on Ad5 serostatus following administration of a single intranasal dose ($10^{11}$ vp) of NasoVAX to subjects. As shown therein, pre-existing anti-Ad5 immunity ("Ad5 Seropositive" (median titer being 22-fold above the lower limit of quantitation ("LLOQ")) had little effect on humoral (HA1), microneutralization (MN), mucosal (IgA), or cellular (ELISpot) anti-Ad5 immunity following administration of the intranasal dose of NasoVAX. This is another important finding as it indicates that NasoVAX can be administered intranasally even to a subject with pre-existing immunity to Ad5. In embodiments, the present intranasal adenoviral vectored vaccine can be administered repeatedly (e.g., as a seasonal vaccine administered about once every 11-14 months) without inducing a significant immune response against the viral vector.

Example 10: Combination of rdAd Anti-SARS-CoV-2 Vectors Human Clinical Trial as SARS-CoV-2 Vaccine In this example, intranasal (i.n.) administration of a combination of rdAd anti-SARS-CoV-2 vectors (e.g., a "combined SARS-CoV-2 composition") to confer prophylactic therapy against SARS-CoV-2 is described. To establish the immunogenic and/or protective capacity of such immunogenic composition(s), a composition comprising AdE is first administered to a human being, followed seven days later by administration of a composition comprising hAd5-SARS-CoV-2, which is followed by testing of the effect of this combination on the immune response against SARS-CoV-2 in the human being(s). The sequential administration of the composition AdE and then the composition comprising hAd5-SARS-CoV-2 is referred to herein as the "combined SARS-CoV-2 composition". To do so, a randomized, double-blind, placebo-controlled, dose-escalation clinical trial to evaluate the safety and immunogenicity of combined SARS-CoV-2 composition in healthy adults 18 to 49 years of age can be carried out. Subjects are typically screened within 28 days of randomization (Day 1).

For instance, a study can comprise two parts; part A which evaluates safety, and part B which evaluates immunogenicity, of the combined SARS-CoV-2 composition. In part A, approximately 120 subjects who meet all inclusion and no exclusion criteria and provided written informed consent are enrolled into four sequential cohorts of 30 subjects each defined by the combined SARS-CoV-2 composition doses ($1\times10^8$, $1\times10^9$, $1\times10^{10}$, and $1\times10^{11}$ vp in each dose). Within each cohort (and the sentinel group in the first dose cohort), subjects are randomized in a 4:1:1 ratio to receive one intranasal dose of the combined SARS-CoV-2 composition (AdE composition on day 1 followed by hAd5-SARS-CoV-2 composition on day 7) or intranasal doses of placebo (normal saline) (on days 1 and 7). The combined SARS-CoV-2 composition and placebo are administered in a double-blind fashion. Reactogenicity is ascertained by determining counts and percentages of subjects with local events including but not limited to nasal irritation, sneezing, nasal congestion, cough, sore throat, change in smell, change in taste, change in vision, eye pain, pain, tenderness, induration, erythema, regional lymphadenopathy, and systemic events (headache, fatigue, myalgia, nausea, vomiting, diarrhea, coughing, chills, fever) for 14 days after vaccination. Adverse Events (AEs) are determined as counts and percentages of subjects with AEs from Day 1 to Day 57; medically attended AEs (MAAEs), serious AEs (SAEs), and new-onset chronic illnesses (NCIs) from Day 1 to Day 181 following administration of the combined SARS-CoV-2 composition or placebo. For instance, targeted and symptom-driven physical examinations including vital signs can be carried out on days 4, 8, 15, 22, 29, and 57; an electrocardiogram can be carried out on day 57; safety laboratory tests can be carried out on days 8 and 57; and serum samples taken for immunogenicity testing at days 8, 15, 22, 29, 57, 91, 181, and 361 (e.g., enzyme-linked immunosorbent assay (ELISA) of serum to measure anti-SARS-CoV-2 antigen antibodies, geometric mean titer (GMT) as compared to day 0 (baseline)), and/or anti-SARS-CoV-2 immune cellular responses (e.g., T cell response). Responder rates are also determined as described below (e.g., ≥four-fold rise in IgG post dose). The primary endpoint for evaluation of the safety profile in Part A is the number and percentage (95% confidence interval (CI)) of subjects with solicited and unsolicited AEs recorded postvaccination. Safety analyses is performed using the Safety Population. The number (percentage, 95% CI) of subjects with local events and systemic events is summarized by group, as is reactogenicity. The number (percentage, 95% CI) of subjects with AEs from Day 1 to Day 57 (including MAAEs, NCIs, SAEs) is summarized for each Medical Dictionary for Regulatory Activities system organ class (SOC) by preferred term (PT) and group. The number (percentage) of subjects with MAAEs, with NCIs, and with SAEs from Day 1 to Day 181 is summarized in a similar fashion. The number (percentage, 95% CI) of subjects with AEs by severity and by relationship to investigational product (IP) is also summarized. Listings of AEs, MAAEs, NCIs, and SAEs are provided.

In part B, the immunogenicity of the combined SARS-CoV-2 composition is determined. Following administration of the combined SARS-CoV-2 composition by intranasal spray as a single dose of $1\times10^8$, $1\times10^9$, $1\times10^{10}$, and $1\times10^{11}$ vp (i.e., combined SARS-CoV-2 composition (AdE composition on day 1 followed by hAd5-SARS-CoV-2 composition on day 7) of the highest well tolerated of these doses to subjects, the immune response can be measured by ELISA of serum to measure anti-SARS-CoV-2 antigen antibodies, and the GMT, geometric mean ratio (GMR) (the ratio of postvaccination and pre-vaccination GMTs within the same dose group), and responder rate (≥four-fold rise in IgG post dose), as well as immune cellular responses (e.g., T cell responses). For instance, approximately 25 subjects who meet all inclusion and no exclusion criteria and provided written informed consent are randomized in a 4:1 ratio to receive two intranasal doses of the combined SARS-CoV-2 composition at the highest well tolerated dose from Part A or placebo 21 days apart (Days 1 and 22). The combined SARS-CoV-2 composition and placebo are administered in a double-blind fashion. Intranasal doses of the combined SARS-CoV-2 composition immunogenic composition and placebo are administered to subjects in a sitting or reclined position. In part B, targeted and symptom-driven physical examination including vital signs can be carried out on days 8, 15, 22, 29, 36, 43, 50, and 57; an electrocardiogram can be carried out on day 57; safety laboratory tests on days 8, 29, and 57; serum samples taken for immunogenicity testing at days 8, 15, 22, 29, 57, 91, 181, and 361; and nasopharyngeal swabs collected on days 8, 15, 29, 36, 43, 50, 57, and 91. Nasopharyngeal samples collected at screening and on Days 29 and 57 can also be subsequently tested for evaluation of mucosal immune response.

In some embodiments, the clinical trial can be carried out using patients already infected by SARS-CoV-2 and time to clinical improvement and/or recovery determined (or, in some embodiments, a cohort of the patients tested). A primary outcome measure is Time to Clinical Improvement (TTCI) and/or Time to Clinical Recovery (TTCR) which are determined for up to 28 days following administration of the combined SARS-CoV-2 composition as described above. TTCI is defined as the time (in days) from initiation of study treatment (active or placebo) until a decline of two categories from status at randomization on a six-category ordinal scale of clinical status which ranges from 1 (discharged) to 6 (death). The six-category ordinal scale is as follows: 6. Death; 5. ICU, requiring extracorporeal membrane oxygenation (ECMO) and/or invasive mechanical ventilation (IMV); 4. Intensive care unit (ICU)/hospitalization, requiring non-invasive mechanical ventilation (NIV)/high-flow nasal cannula (HFNC) therapy; 3. Hospitalization, requiring supplemental oxygen (but not NIV/HFNC); 2. Hospitalization, not requiring supplemental oxygen; and, 1. Hospital discharge or meet discharge criteria (discharge criteria are defined as clinical recovery, i.e. fever, respiratory rate, oxygen saturation return to normal, and cough relief). Secondary outcome TTCI measures include all cause mortality (baseline SpO2 during screening, PaO2/FiO2<300 mmHg or a respiratory rate ≥24 breaths per min without supplemental oxygen); frequency of respiratory progression (SPO2≤94% on room air or PaO2/FiO2<300 mmHg and requirement for supplemental oxygen or more advanced ventilator support); time to defervescence (in those with fever at enrolment); time to cough reported as mild or absent (in those with cough at enrollment rated severe or moderate); time to dyspnea reported as mild or absent (on a scale of severe, moderate, mild absent, in those with dyspnoea at enrolment rated as severe or moderate,); frequency of requirement for supplemental oxygen or non-invasive ventilation; time to 2019-nCoV RT-PCR negative in in throat swab, sputum, lower respiratory tract specimen, and/or upper respiratory tract specimen; change (reduction) in SARS-CoV-2 viral load in throat swab, sputum, lower respiratory tract specimen, and/or upper respiratory tract specimen; change (reduction) in 2019-nCoV viral load in in throat swab, sputum, lower respiratory tract specimen, and/or upper respiratory tract specimen; change (reduction) in SARS-CoV-2 viral load in throat swab, sputum, lower respiratory tract specimen, and/or upper respiratory tract specimen as assessed by area under viral load curve (e.g., as determined using polymerase chain reaction (PCR)); frequency of requirement for mechanical ventilation; and, frequency of serious adverse events. TTCI is defined as the time (in hours) from initiation of study treatment (active or placebo) until normalization of fever, respiratory rate, and oxygen saturation, and alleviation of cough, sustained for at least 72 hours. The primary TTCR outcome measures include normalization and alleviation criteria; fever—≤36.9° C. or—axilla, ≤37.2° C. oral; respiratory rate—≤24/minute on room air; oxygen saturation—>94% on room air; and, cough—mild or absent on a patient reported scale of severe, moderate, mild, absent. The secondary TTCR outcome measures are the same as the TTCI secondary outcomes listed above.

Standard clinical trial design and statistical methods are used in the analyses thereof. For instance, the sample size for this study is selected as adequate and reasonable for an initial review of the safety and immunogenicity profile of the combined SARS-CoV-2 composition at doses to be well tolerated, rather than for statistical power (e.g., 120 subjects as described above). The sample size permits initial estimates of reactogenicity. For example, given a total of 100 subjects receiving the combined SARS-CoV-2 composition, the study is designed to have an 80% probability of detecting at least one AE that occurred at a rate of 1.6%. If no SAEs were observed among the 100 subjects who received hAdv5-SARS-CoV-2 composition, an approximation to the 1-sided upper bound of the 95% confidence interval (CI) on the rate of SAE occurrence would be 3%. Immunology analyses are conducted using the Evaluable and Per-protocol (PP) Populations with primary conclusions drawn from the PP Population. Analyses based on the Evaluable Population are undertaken and presented only if >1 subject in any one group were excluded from the PP Population. With the exception responder analyses, as described below, no imputation for missing data is performed. Data are transformed as appropriate prior to analysis. Baseline is defined as the sample collected prior to combined SARS-CoV-2 composition administration on days 1 (for the AdE composition) and 7 (for the hAdv5-SARS-CoV-2 composition). The primary variables of interest for assessment of humoral and cellular immune response to SARS-CoV-2 (e.g., anti-SARS-CoV-2 antigen IgG titers, T cell responses) are determined. GMTs are determined at Baseline and postvaccination on Days 8, 15, 22, 29, 57, 91, and 181 (Part A) and Days 8, 15, 22, 29, 36, 43, 50, 91, and 181 (Part B) and summarized by dose group. Comparisons between combined SARS-CoV-2 composition doses and placebo are evaluated by analysis of covariance (ANCOVA) with treatment as a fixed effect and baseline log-transformed level as a covariate on, e.g., the post-baseline log-transformed level of anti-SARS-CoV-2 IgG as a dependent variable. From these analyses, least-square (LS) means, LS treatment differences, and 95% CIs for the treatment differences on log-scale are obtained. The results are transformed back to the original scale by exponentiation to provide treatment geometric LS means, point estimates of the geometric LS mean ratios, and 95% CI for these ratios on each study day. A “responder” is defined as a subject with a 4-fold rise in anti-SARS-CoV-2 antigen titer from baseline on Days 8, 15, 22, 29, 57, 91, and 181 (Part A) and Days 8, 15, 22, 29, 36, 43, 50, 91, and 181 (Part B). Fold change for determination of responder status is computed using the post-imputation values without the +1 transformation, i.e., fold change=current imputed value/baseline imputed value. Responder rates are tabulated by percentages per dose group and the 95% Clopper-Pearson exact CI of the percentage. Differences of 95% CIs are presented to compare the response rate of each combined SARS-CoV2 composition dose group to the and placebo group. In some embodiments, comparisons of responders in each combined SARS-CoV-2 composition dose group against the against the placebo group can also be conducted using Fisher’s exact test. To determine the effect of pre-dose Ad5 serum antibody levels on immunogenicity of combined SARS-CoV-2 composition on Day 29 (Part A) or Day 50 (Part B), analyses are performed using ANCOVA with baseline Ad5 titer as a covariate. Mucosal immunogenicity analyses are conducted using the Evaluable and PP Populations. No imputation for missing data is performed. Endpoints analyzed are GMT and GMR for IgA antibody level measured by ELISA. Methods used are the same as for humoral immunogenicity analyses. Summary statistics for continuous parameters (safety laboratory tests and vital signs) are presented by group as follows: pre-vaccination, postvaccination, and change from pre-vaccination to post-vaccination assessment. The number and percentage of subjects with postvaccination safety laboratory values or vital sign values recorded as newly abnormal (ie, an event with an increase in the toxicity grade relative to the baseline value and with a severity grade of moderate or higher) after study vaccination are tabulated. Shift tables that cross-tabulate the pre-vaccination and postvaccination safety laboratory values of each subject by severity grade are prepared. Summaries of the number and percentage of subjects with normal, abnormal not clinically significant, and abnormal clinically significant ECG interpretations are presented. For shedding of the Ad5 vector, data are summarized by count and percent positive by time point, along with median copy number. The median duration of Ad5 shedding, interquartile range, minimum and maximum duration of Ad5 shedding are presented for each combined SARS-CoV-2 composition group and all immunogenic composition dose groups combined. Viral culture results for evaluation of adenovirus infection are also listed.

These studies will show that the combined SARS-CoV-2 composition can be used to induce an anti-SARS-CoV-2 immune response in human beings (e.g., it is an immunogenic composition), and with an acceptable safety profile. It is preferred that that immune response be statistically significant, and even more preferably, a protective immune response (i.e., it is a SARS-CoV-2 vaccine). In preferred embodiments, the data shows the combined SARS-CoV-2 composition can be used to treat subjects infected by SARS-CoV-2 (e.g., hospitalized patients).

Example 11: Anti-SARS-CoV-2 Human Clinical Trial Using Cytokine Inhibition

As shown in Example 2, administration of AdE to mice was shown to decrease the expression of certain cytokines known to be involved in the progression and symptoms of infectious diseases caused by viruses such as influenza. For instance, it was shown that non-infected mice (by influenza), 25 days after administration of AdE, exhibited an increase in expression of monocyte chemoattractant protein (MCP-1 (CCL2)), interferon gamma (IFN-γ), and RANTES (CCL5). At 28 days post-administration of AdE, such non-infected mice exhibited increased expression of MCP-1 and IFN-γ but also a decrease in IL-12 expression. Mice challenged with influenza at day 3 post-administration of AdE, mice were found to exhibit decreased expression of IL-1α, IL-6, IL-12, MCP-1, tumor necrosis factor alpha (TNF-α), granulocyte macrophage colony stimulating factor (GM-CSF), and RANTES. At day six (6) post-administration of AdE, the infected mice exhibited decreased expression of IL-5, IL-6, IL-12, IL-17, MCP-1 and GM-CSF, and increased expression of macrophage inflammatory protein 1 alpha (MIP-1α (CCL3)) and RANTES (CCL5). These results are consistent with the development of a "cytokine storm" during infection by SARS-CoV-2. In some embodiments, then, to prevent and/or treat SARS-CoV-2 infection by, for instance, inhibiting the development of or suppressing a cytokine storm, aSARS-CoV-2 immunogenic composition is administered to a human being with one or more anti-cytokine reagent(s) (e.g., one or more anti-IL-1α reagent(s), one or more anti-IL5 reagent(s), one or more anti-IL-6 reagent(s), one or more anti-IL-12 reagent(s), one or more anti-IL-17 reagent(s), one or more anti-MCP-1 reagent(s), one or more anti-TNF-α reagent(s), one or more anti-GM-CSF reagent(s), and/or one or more anti-RANTES reagent(s). In some embodiments, the one or more anti-cytokine reagents would not include one or more anti-MIPα reagent(s) and/or one or more anti-RANTES reagent(s). Exemplary anti-cytokine reagents that can be used as described herein can include, for example, any of those shown in Table 10.

Such anti-cytokine reagents are administered with the SARS-CoV-2 immunogenic composition at the same time (i.e., simultaneously), or essentially the same time, by a suitable route appropriate for each reagent (e.g., intranasal administration of the SARS-CoV-2 immunogenic composition and subcutaneous injection for the anti-cytokine reagent(s) in effective amounts. In some embodiments, the one or more anti-cytokine reagent(s) are co-administered with the SARS-CoV-2 composition and, in some embodiments, the one or more anti-cytokine reagents are subsequently administered as the sole active agents. These studies will show that the combination of SARS-CoV-2 composition(s) and one or more anti-cytokine reagent(s) are useful for inducing an anti-SARS-CoV-2 immune response in human beings (e.g., it is an immunogenic composition), with an acceptable safety profile, and with alleviation of symptoms related to the deleterious effects of cytokines experienced by some patients (e.g., the aforementioned cytokine storm). It is preferred that that immune response be statistically significant, and even more preferably, that it is a protective and/or curative immune response (i.e., it is a SARS-CoV-2 vaccine). In preferred embodiments, the data shows the combination of SARS-CoV-2 composition(s) and one or more anti-cytokine reagent(s) can be used to treat subjects infected by SARS-CoV-2 (e.g., hospitalized patients).

Example 12. Animal Study Dosing Strategies

In some embodiments, one or more anti-SARS-CoV-2 vectors and/or combination(s) of anti-SARS-CoV-2 vectors (i.e., "SARS-CoV-2 vaccine") are administered to animals in various dosages to assess pre-clinical validation of the same. In some embodiments, the mechanisms of vaccine-induced protection in animals are determined. In some embodiments, the mechanisms of vaccine-induced protection in animals with pre-existing immunity to the more common circulating coronaviruses (as is the case for most humans) are determined. These studies provide: (i) an assessment of SARS-CoV-2 vaccine-induced pulmonary inflammation; (ii) SARS-CoV-2 vaccine Ab titers with isotype and breadth of reactivity to day 28; (iii) anti-SARS-CoV-2 antibody (Ab) neutralization titers to day 28 post-administration; and, (iv) identification of optimal SARS-CoV-2 vaccine dose/administration schedule.

In some embodiments, the immunity of the animals can be studied using the flow cytometric techniques described by Yu, et al. (PLOS ONE DOI:10.1371/journal.pone.0150606 Mar. 3, 2016) which has been shown to be useful for accurately quantifying eleven distinct immune cell types, including T cells, B cells, natural killer (NK) cells, neutrophils, eosinophils, inflammatory monocytes, resident monocytes, macrophages (e.g., tissue specific macrophages, resident/interstitial macrophages, alveolar macrophages, microglia), mast cells, basophils, and/or plasmacytoid DCs, and/or to perform detailed phenotyping of specific cell types. In some embodiments, for instance, a comparison of SSC vs. MHC Class II expression can be used to separate NK cells and monocytes from mature myeloid cells; and/or, a comparison of CD64 vs. CD24 expression can be used to distinguish macrophages from dendritic cells as can CD11c vs. MHC class two expression (although the former may be more accurate). Other markers may also be studied as is known in the art (e.g., any one or more of CD11b, CD14, CD24, CD68, CD103, CD169, CD206, $CX_3CR1$, CCR2, F4/80, IA-IE, Ly6C, and/or MerTK). In some embodiments, anti-SARS-2-CoV-2 specific antibody titers in the lung airways and serum are determined (e.g., using bead arrays); inflammatory cell infiltrate into the lungs is measured (e.g., using flow cytometry); anti-SARS-CoV-2 neutralization titers are determined (e.g., using SARS-2 microneutralization assays); local and systemic cytokine levels are assessed; the number and functional attributes of anti-SARS-2 specific B cells (e.g., and subsets), T cells (e.g., (using ICCS or cytokine ELISPOTs) and plasma cells (e.g., using antibody ELISPOT) from early (7-14 days) to memory (1-4 months) timepoints following vaccination in naïve mice and those with pre-existing immunity to related endemic coronaviruses are determined. Other types of analyses may also be used as is known in the art, or would otherwise be understood by those of ordinary skill in the art to be applicable.

In some embodiments, the mechanisms of vaccine-induced protection in animals are determined studying animals to which the SARS-CoV-2 vaccine is administered following the dosing scheme shown in Table 17.

TABLE 17

Experiments 1 and 2 (Vaccine Candidate #1 and #2)*

| Vaccine | N strain (C57BL/6 or CD1) | 7 days (n = 10) | 14 days (n = 10) | 21 days (n = 10) | 28 days (n = 10) |
|---|---|---|---|---|---|
| High dose Single admin** | 30 | BAL[a] tissue phenotype[b] Serum[c,d] | BAL[a] tissue phenotype[b] Serum[c,d] | Not done | BAL[a] tissue phenotype[b] Serum[c,d] |
| Mid dose Single admin | 30 | BAL[a] tissue phenotype[b] Serum[c,d] | BAL[a] tissue phenotype[b] Serum[c,d] | Not done | BAL[a] tissue phenotype[b] Serum[c,d] |
| Low dose Single admin | 30 | BAL[a] tissue phenotype[b] Serum[c,d] | BAL[a] tissue phenotype[b] Serum[c,d] | Not done | BAL[a] tissue phenotype[b] Serum[c,d] |
| High dose Two admin. (day 0 & day 14) | 20 | Not done | Not done | BAL[a] tissue phenotype[b] Serum[c,d] | BAL[a] tissue phenotype[b] Serum[c,d] |
| Mock | 10 | BAL[a] tissue phenotype[b] Serum[c,d] | NA | NA | NA |

*Vaccine Candidate #1: S1 vector (SEQ ID NO: 13); Vaccine Candidate #2: RBD vector (SEQ ID NO: 15) admin" represents "administration

[a]Abs in BAL by Bead Array

[b]BAL, lung tissue, medLN, spleen, blood T cell, B cell NK and myeloid lineage subsets (T cells, B cells, NK cells, neutrophils, eosinophils, inflammatory monocytes, resident monocytes, alveolar macrophages, resident/interstitial macrophages, CD11b– DC, and CD11b+ DC) https://www.ncbi.nlm.nih.gov/pmc/articles/PMC4777539/pdf/pone.0150606.pdf

[c]serum Ab COVID specific, domain specific and cross reactivity to endemic coronaviruses by bead array (include isotype and subisotypes)

[d]serum neutralizing or virus reduction assays (selecting most relevant timepoints and vaccine candidate based on binding assays from the serum samples collected)

In some embodiments, such as to evaluate B and T cell responses to vaccine candidates to determine best dosing and administration schedule, the dosing regimen shown in Table 17 is used. In some embodiments, the animals receive the SARS-CoV-2 vaccine (or two different SARS-CoV-2 vaccines as shown in Table 17) using the optimal dosing and administration schedule determined by the scheme presented in Table 18. Data is collected at four timepoints (e.g., n=7/group/timepoint/functional assay, timepoints between 0-120 days). SARS-CoV-2 vaccine-induced pulmonary inflammation and Ab responses are measured to day 28, anti-SARS-CoV-2 Ab titers with isotype and breadth of reactivity are determined to day 120, anti-SARS-CoV-2 Ab neutralization titers are determined to day 120, SARS-CoV-2 vaccine-induced T cell responses are determined to day 28, and SARS-CoV-2 vaccine-induced ASC and memory B cell responses are determined to day 120.

TABLE 18

Anti- SARS-CoV-2 functional and antigen specific assays post-vaccination

| Optimal Vaccine/dose/time | N strain | 7-14 days (n = 20) | 14-28 days (n = 20) | 60 days (n = 10) | 120 days (n = 10) |
|---|---|---|---|---|---|
| SARS-CoV-2 Vaccine #1 (optimal dosing) | 60 (inbred) | BAL[f,g,h] Tissues[i,j,k] Serum[l] | BAL[f,g,h] Tissues[i,j,k] Serum[l,m] | BAL[g] Tissues[i,k] Serum[l,m] | BAL[g] Tissues[i,k] Serum[l,m] |
| SARS-CoV-2 Vaccine #2 (optimal dosing) | 60 (inbred) | BAL[f,g,h] Tissues[i,j,k] Serum[l] | BAL[f,g,h] Tissues[i,j,k] Serum[l,m] | BAL[g] Tissues[i,k] Serum[l,m] | BAL[g] Tissues[i,k] Serum[l,m] |
| Mock | 20 (inbred) | BAL[f,g,h] Tissues[i,j,k] Serum[l] | NA | NA | NA |

[f]Cytokines/Abs in BAL supernatant (e.g. 5 cytokines from this list IL-6, IL-10, TNF-α, IL-5, IFN-α, IFN-β, IFN-γ, MIP-1a and MIP-2)

[g]BAL cells -ELISPOTs (SARS2 specific IgA, M and G).

[h]BAL cells T cell recall IFNg ICCS (CD4 and CD8 restim anti-CD3 and/or EL4 cells expressing SARS2 S protein)

[i]lung tissue, medLN, Spleen, BM ELISPOTs (SARS2 specific IgA, M and G)

[j]lung tissue, medLN, Spleen Antigen-specific T cell recall IFNγ ICCS (CD4 and CD8 restim anti-CD3 and/or EL4 cells expressing SARS2 S protein)

[k]BAL, lung, medLN, Spleen SARS2 specific B cell responses flow cytometry

[l]serum Ab repeats as needed

[m]serum neutralizing or virus reduction assays as needed

In some embodiments, the following protocol is used whether pre-existing immunity to endemic β-coronavirus affects vaccine responses to SARS2. In this experiment (table 3), impact of pre-existing anti-coronavirus Spike protein memory B cells against endemic β-coronaviruses is assessed. Inbred mice (BALB/c or B6) are vaccinated with recombinant OC43 or HKU1 Spike protein using two different adjuvants (CFA or alum) to establish a memory B cell response to the endemic coronavirus Spike protein (i.e., "memory mice"). Immunized mice and control naïve mice then receive the optimal SARS-CoV-2 vaccine(s). Pulmonary inflammation, anti-SARS-CoV-2 Ab and B cell responses, anti-SARS-CoV-2 Ab quality are assessed in the memory mice. Additional details regarding the administration scheme is provided in Table 19.

TABLE 19

Expt #4 - Pre-existing immunity to related Coronavirus S proteins - impact on vaccination with SARS2 Spike protein

| Vaccination #1 Day 0&14 | Vaccination #2 Day 60 | N strain | 7 days post Vac2 (n = 10) | 14 days (n = 10) | 28 days (n = 10) |
|---|---|---|---|---|---|
| HKU1 or OC43 recombinant S in adjuvant 1 | nil | 30 (inbred) | BAL[n,o] Tissue[p,q,r] Serum[s] | BAL[n,o] Tissue[p,q,r] Serum[s] | Serum[s,t] |
| HKU1 or OC43 recombinant S in adjuvant 2 | nil | 30 (inbred) | BAL[n,o] Tissue[p,q,r] Serum[s] | BAL[n,o] Tissue[p,q,r] Serum[s] | Serum[s,t] |
| HKU1 or OC43 recombinant S in adjuvant 1 | SARS2 Ad5 best | 30 (inbred) | BAL[n,o] Tissue[p,q,r] Serum[s] | BAL[n,o] Tissue[p,q,r] Serum[s] | Serum[s,t] |
| HKU1 or OC43 recombinant S in adjuvant 2 | SARS2 Ad5 best | 30 (inbred) | BAL[n,o] Tissue[p,q,r] Serum[s] | BAL[n,o] Tissue[p,q,r] Serum[s] | Serum[s,t] |
| Mock | SARS2 Ad5 best | 30 (inbred) | BAL[n,o] Tissue[p,q,r] Serum[s] | BAL[n,o] Tissue[p,q,r] Serum[s] | Serum[s,t] |

[n]Cytokines in BAL by Luminex (IL-6, IL-10, TNF-α, IL-5, IFN-α, IFN-β and IFN-γ)

[o]Abs in BAL by Bead Array

[p]BAL, lung tissue, medLN, spleen, blood T cell, B cell NK and myeloid lineage subsets (T cells, B cells, NK cells, neutrophils, eosinophils, inflammatory monocytes, resident monocytes, alveolar macrophages, resident/interstitial macrophages, CD11b− DC, and CD11b+ DC) https://www.ncbi.nlm.nih.gov/pmc/articles/PMC4777539/pdf/pone.0150606.pdf

[q]BAL, lung, medLN, Spleen SARS2 specific B cell responses flow cytometry

[r]cloning SARS2 specific B cell receptors and looking at breadth and depth of reactivity (and affinity/avidity)

[s]serum Ab COVID specific, domain specific and cross reactivity to endemic coronaviruses by bead array (include isotype and subisotypes)

[t]serum neutralizing or virus reduction assays (pseudotyped virus first and primary SARS2 second)

Figure 93:
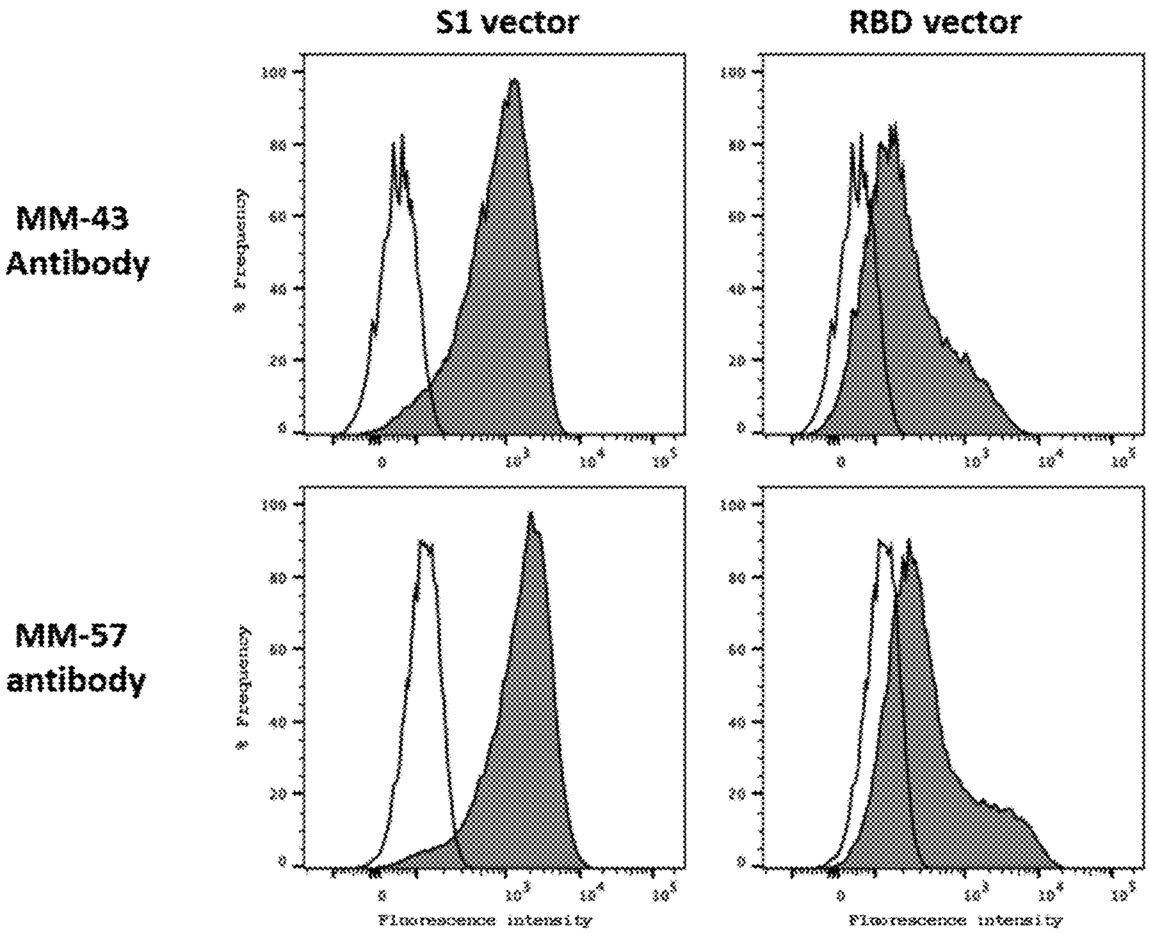
FIG. 93. Expression and detection of spike transgene in S1 or RBD vector infected cells. Per.C6 cells were infected at MOI:5 with S1 (SEQ ID NO: 13) or RBD (SEQ ID NO: 15) vector ("S1 vector" or "RBD vector") respectively. 24 hrs post-infection, cells were harvested, fixed and permeabilized and then stained with mouse neutralizing spike-specific monoclonal antibodies MM-43 (upper panel) or MM-57 (bottom panel) filled histograms. Non-infected cells were used as negative control (open histogram).

Example 13A. Preparation of the Adenoviral Vectors (S1 and RBD) for Preclinical Testing Vaccine candidates utilized in example 13A to 18 were prepared using a replication-deficient, E1- and E3-deleted adenovirus type 5 vector platform (Tang et al 2009) to express the human codon-optimized gene for the S1 domain (residues 16 to 685) or RBD domain (residues 302 to 543) of SARS-CoV-2 spike protein (accession number QHD43416.1). The Ad5-vectored S1 and RBD transgenes included a human tissue plasminogen activator leader sequence and were expressed under the control of the cytomegalovirus immediate early promoter/enhancer, SEQ ID NO: 13 and SEQ ID NO: 15, respectively. Initial seed stocks were obtained from a large-scale transfection of recombinant vector plasmid into E1-complementing PER.C6 cells using a scalable transfection system (Maxcyte STX-100). Cell transfection was performed by a static electroporation using the CL1.1 Processing Assembly procedure (Li L H, Shivakumar R, Feller S, Allen C, Weiss J M, Dzekunov S, Singh V, Holaday J, Fratantoni J, Liu L N. Highly efficient, large volume flow electroporation. Technol Cancer Res Treat. 2002 October; 1(5):341-50.). Following further expansion, infected cells were collected 70 hours post-infection and virus was released from pelleted cells by freeze-thaw cycles. Resulting cell lysate was clarified by centrifugation, then filtered using a 0.22 μm cutoff. RBD and S1 Ad5 vectors were purified over a CsCl gradient, dialyzed against a formulation buffer (A195) containing 10 mM Tris at a pH of 7.4, 75 mM NaCl, 1 mM $MgCl_2$, 10 mM histidine, 5% (wt/vol) sucrose, 0.02% polysorbate-80 (wt/vol), 0.1 mM EDTA, and 0.5% (vol/vol) ethanol and were then frozen and stored at −65° C. To confirm that the S1 and RBD transgenes were expressed and antigenically intact, PerC6 cells were infected with S1 vector or RBD vectors before intracellular staining using two different neutralizing monoclonal antibodies against SARS-CoV-2 S1 (SinoBiologicals Cat: 40591-MM43) and SARS-CoV-2 RBD (SinoBiologicals, Cat: 40592-MM57) and analysis by flow cytometry (FIG. 93).

Example 13B. Intranasal Administration of Ad5 Vector Expressing RDB Domain in C57BL/6 Mice Replication-deficient Ad5 vector expressing the RBD domain from the spike antigen of SARS-CoV-2 (SEQ ID NO: 15) was administered intranasally to C57BL/6 mice to evaluate the induction of systemic and mucosal immunity against SARS-CoV-2. C57BL/6 mice received one or two intranasal administration of the Ad5 vector at three different doses in a volume of 50 μl as indicated in table 18. High dose was 6.7E+09 ifu/ml (3.35E+08 ifu in 50 μL), mid-dose 1.2E+09 ifu/ml (6E+07 ifu in 50 μL) and Low dose 1.2E+08 ifu/ml (6E+06 ifu in 50 μL) in A195 buffer. The control group received an intranasal administration of 50 μl of the A195 buffer alone. At day 7, day 14, day 21 or day 28 post-vaccine administration, sera, bronchoalveolar lavages (BAL) and tissues including lungs, mediastinal lymph nodes and spleens were collected from 10 animals per group according to the table below. Immunological readouts included the measurement of SARS-CoV-2 spike antigen-specific-IgG in the serum and BAL, SARS-CoV-2 spike antigen-specific IgA in the BAL, neutralizing antibody responses against SARS-CoV-2 in the serum and the numeration of immune cells in the lung, lymph nodes, BALs and spleens at different time-points. These parameters are summarized in Table 20.

TABLE 20

| Vaccine/ Control | Intranasal dose | Number of animals per group | Immunization | Sample collection (10 animals per time point) |
|---|---|---|---|---|
| RBD Ad5 | 3.35E+08 ifu in 50 µL | 30 | Day 0 | Day 7, 14, 28 |
| RBD Ad5 | 6E+07 ifu in 50 µL | 30 | Day 0 | Day 7, 14, 28 |
| RBD Ad5 | 6E+06 ifu in 50 µL | 30 | Day 0 | Day 7, 14, 28 |
| RBD Ad5 | 3.35E+08 ifu in 50 µL | 20 | Day 0 & 14 | Day 21, 28 |
| A195 buffer | 50 µL | 10 | Day 0 | Day 7 |

The quantification of SARS-CoV-2 spike IgG and IgA was performed in serum or BAL samples obtained from immunized animals using a cytometric bead array conjugated a recombinant SARS-CoV-2 ectodomain spike protein. To produce recombinant SARS-CoV-2 S ectodomain protein, two codon-optimized constructs were generated with linear sequence order encoding: a human IgG leader sequence, the SARS-CoV-2 S ectodomain (amino acids 14-1211), a GGSG linker, T4 Fibritin Foldon sequence, a GS linker, and finally an AviTag (construct 1) or 6×-HisTag (construct 2). Each construct was engineered with two sets of mutations to stabilize the protein in a pre-fusion conformation. These included substitution of RRAR>SGAG (residues 682 to 685, as in Walls et al 2020) at the S1/S2 cleavage site and the introduction of two proline residues; K983P, V984P, as in Walls et al 2020 and Wrapp et al 2020. Avi/His-tagged trimers were produced by co-transfecting plasmid constructs 1 and 2 (1:2 ratio) into FreeStyle 293-F Cells. Cells were grown for three days and the supernatant (media) was recovered by centrifugation. Recombinant S trimers were purified from media by FPLC using a HisTrap HP Column (GE) and elution with 250 mM of imidazole. After exchanging into either 10 mM Tris-HCl, pH 8.0 or 50 mM Bicine, pH 8.3, purified spike ectodomain trimers were biotinylated by addition of biotin-protein ligase (Avidity, Aurora, Colo.). Biotinylated spike ectodomain trimers were buffer exchanged into PBS, sterile filtered, aliquoted, then stored at −80° C. until used. Following affinity purification of his-tagged protein and enzymatic biotinylation, the resulting recombinant SARS-CoV-2 trimers were passively absorbed onto streptavidin functionalized fluorescent microparticles (Spherotech 3.6 um cat #CPAK-3567-4K, peak 4). 500 µg of biotinylated SARS2-CoV-2 was incubated with 2×1e7 Streptavidin functionalized fluorescent microparticles in 400 ul of 1% BSA PBS. Following coupling, the SARS-CoV-2 spike conjugated beads were washed twice in 1 ml of 1% BSA, PBS, 0.05% NaN3 prior to final resuspension to a concentration of $1\times10^8$ beads/mL. SARS-CoV-2 coupled beads were stored at 4° C. The loading of recombinant SARS2-CoV-2 spike onto the beads was evaluated by staining $1\times10^5$ beads with dilutions ranging from 1 ug to 2 ng/ml of the recombinant anti-SARS spike antibody CR3022 and visualized with an anti-human IgG secondary. IgG and IgA standards were obtained by covalent coupling of isotype specific polyclonal antibodies to fluorescent particles. Briefly, 0.2 mg of goat polyclonal anti-mouse IgG (southern Biotech cat #1013-01), anti-IgM (cat #1 022-01), and anti-IgA (cat #1040-01) antibodies in PBS were mixed with 5×1e7 fluorescent microparticles each with a unique fluorescent intensity in the far red channels (Spherotech 3.6 um cat #CPAK-3567-4K, peaks 1-3) resuspended in 0.1 M MES buffer pH 5.0. An equal volume of EDC (1-Ethyl-3-(3-dimethylaminopropyl)-carbodiimide), 10 mg/mL, in 0.1 M IVIES (2-(N-morpholino) ethanesulfonic acid) buffer pH 5.0, and the mixture was incubated overnight at room temperature. The beads were washed twice by pelleting by centrifugation and resuspension in PBS. Following washing, beads were resuspended in 1% BSA, PBS with 0.005% $NaN_3$ as a preservative. BAL samples, diluted 1/4-8, or serum samples were diluted to 1/1000-5000 in 50 µl of PBS were arrayed in 96 well u-bottom polystyrene plates along with 50 ul of standards consisting of either mouse IgG, IgM, or IgA ranging from 1 µg/ml to 2 ng/ml at 0.75× dilutions (southern biotech IgM: cat #0106-01, IgG: cat #0107-01, IgA cat #0106-01). 5 µl of a suspension containing 5×1e5 of each SARS-CoV-2 spike, anti-IgM, anti-IgA, and anti-IgG beads was added to the diluted samples. The suspensions were mixed by pipetting and incubated for 15 mins at room temperature. The beads were washed by the addition of 200 µl of PBS and centrifugation at 3000 g for 5 min at room temperature. The CBA particles were resuspended in a secondary staining solution consisting of poly-clonal anti-IgG 488 (southern Biotech cat #1010-30), and either a goat polyclonal anti-IgM (southern Biotech cat #1020-09) or anti-IgA (southern Biotech cat #1040-09) conjugated to PE diluted 1/400 in 1% BSA in PBS. The suspension was incubated for 15 min in the dark at room temperature. The beads were washed by the addition of 200 µl of PBS and pelleted by centrifugation at 3000 g for 5 min at room temperature. The particles were resuspended in 75 µl of PBS and directly analyzed on a BD Cytoflex flow cytometer in plate mode at sample rate of 100 ul per minute. Sample collection was stopped following the acquisition of 75 µL. Following acquisition, the resulting FCS files were analyzed in flowJo (treestar). Briefly, the beads were identified by gating on singlet 3.6 um particles in log scale in the forward scatter and side scatter parameters. APC-Cy7 channel fluorescence gates were used to segregate the particles by bead identity. Geometric mean fluorescent intensity was calculated in the PE and 488 channels. Best fit power curves were generated from the Ig capture beads using the know concertation of standards on a plate by plate basis. This formula was applied to the MFI of the SARS-COV-2 spike particles for all samples of the corresponding assay converting MFI to ng/ml or µg/ml. These calculated values were corrected for the dilution factor.

A foci reduction neutralization test (FNRT) was used to quantify the titer of neutralizing antibodies against SARS-CoV-2 isolate USA-WA1/2020. Vero E6 cells were grown on 96-well plates to confluence. On the day of the infection phase of the assay, serial dilutions (1:20-1:2560) of antisera were made and combined and incubated with an equal volume of viral stock, at a specified dilution for 30 min at RT, such that the final dilutions of antisera ranged from (1:40-1:5120). The viral stock was diluted from a concentrated working stock to produce an estimated 30 viral focal units per well. After incubation, the sera:virus mixtures were added to the wells (100 μL), and infection allowed to proceed for 1 hour on the Vero cells at 35° C. At the completion of the 1-hour incubation, a viscous overlay of Eagle's MEM with 4% FBS and antibiotics and 1.2% Avicell were added to sera:virus mixture on the cell monolayers such that the final volume was 200 μL per well. The infection was allowed to proceed for 24 hr. The next day, each plate was fixed by submerging the entire plate and contents in 10% formalin/PBS for 24 h. Detection of virus foci reduction was performed on fixed 96 well plates. Briefly, plates were rinsed in $H_2O$, and methanol:hydrogen peroxide added to the wells for 30 min with rocking to quench endogenous peroxidase activity. After quenching, plates were rinsed in $H_2O$ to remove methanol and 5% Blotto was added to the wells as a blocking solution for 1 hour. For primary antibody detection, a SARS-CoV-2 Spike/RBD antibody (Rabbit, Polyclonal, SinoBiologicals Ct No. 40592-T62) was added to 5% Blotto and incubated on the monolayers overnight. Plates are rinsed in 5 washes with PBS, and further incubated with a secondary antibody of goat anti-rabbit IgG conjugated to horseradish peroxidase (Boster Biological Technology Co., #BA1054-0.5) in 5% Blotto for 1 hour. Plates were rinsed once with 0.05% tween in 1×PBS followed by 5 washes in 1×PBS. Detection of peroxidase activity was by use of Impact DAB detection kit (Vector Labs #SK-4105) per manufacturer's instructions. Brown foci are counted manually from the scanned image of each well, recorded, and the reduction of foci as compared to equivalent naïve mouse sera controls was determined. $FRNT_{50}$ titers were also calculated using a 4PL curve fit.

The analysis of bronchoalveolar lavage (BAL) cells by flow cytometry was performed as follows. BAL cells present were obtained by centrifugation at 700×g for 5 min at 4° C. of the BAL fluids. Cells were resuspended in 500 μl Red Blood Cell Lysis Buffer [ACK buffer (10 mM KHCO3, pH 7.2-7.4, 150 mM NH4Cl and 0.1 mM EDTA)]. After 1 min, 2 ml of staining media (PBS+2% Fetal Bovine Serum) with 2 mM EDTA. This media is referred to as SME. The sample were then filtered by passing it through a 70 um Nitex® Nylon filter membrane and into a clean 15-ml conical tube. Following centrifugation at 700×g for 5 min at 4° C., the cells were resuspended in 225 μl SME. 25 ul of each sample are then transferred into a 96-well plate for cell counting by flow cytometry using Fluoresbrite Carboxylate YG 10 μm microspheres. The remaining of the cells were transferred into a separate V-bottom 96-well plate for antibody staining for flow cytometric analysis. The BAL cell samples were incubated for 10 min at 4° C. in the dark with Fc-Block (1:1000 dilution), and then stained with the following BAL staining panel: Autofluorescence (empty FITC channel), Ly6G-PE (clone 1A8; 1:200 dilution), CD64-PerCP-Cy5.5 (clone X54-5/7.1; 1:150 dilution), CD8a-APC (clone 53-6.7; 1:200 dilution), CD11c-PE-Cy7 (clone N418; 1:200 dilution), CD19-APC-Fire750 (clone 6D5; 1:200 dilution), CD4-eFluor450 (clone GK1.5; 1:200 dilution) and Aqua LIVE/DEAD (1:1000 dilution). After incubation with antibody mix (50 μl total volume) for 20 min at 4° C. in the dark, cells were washed with 200 ul SME. Cells were then resuspension in 200 μl 10% formalin before analysis on FACSCanto II within 2 days.

The analysis of mediastinal lymph node by flow cytometry was performed as follows. Mediastinal lymph node (mLN) were collected and placed into separate wells of a 24-well plate containing 1 ml Staining Media (PBS+2% Fetal Bovine Serum) with added 2 mM EDTA. This media is referred to as SME. The mLN were gently grinded and crushed by rubbing in-between two microscope slides, then rinsed with 1 ml SME before transfer in a 15-ml conical tube. The volume was brought to 10 ml using SME. The cell suspension were then filtered by passing it through a 70 um Nitex® Nylon filter membrane and into a clean 15-ml conical tube before rinsing the filter membrane with an additional 2 ml SME. After centrifugation at 1800 rpm at 4° C. for 5 min, cells were resuspended with 1 ml SME. 50 ul of each sample were transferred into a 96-well plate for cell counting by flow cytometry using Fluoresbrite Carboxylate YG 10 μm microspheres. 200-250 μl of each sample were transferred into 3 separate V-bottom 96-well plates for antibody staining for flow cytometric analysis. mLN tissue were stained with 3 different flow panels. The mLN samples were incubated for 10 min at 4° C. in the dark with Fc-Block (1:1000 dilution), washed with 200 ul SME, and then stained with the following 3 panels. The myeloid panel consisted of B220/CD45R-FITC (clone RA3-6B2; 1:200 dilution), Ly6G-PE (clone 1A8; 1:200 dilution), CD64-PerCP-Cy5.5 (clone X54-5/7.1; 1:150 dilution), CD11b-APC (clone M1/70; 1:200 dilution), CD11c-PE-Cy7 (clone N418; 1:300 dilution), Ly6C-APC-Cy7 (clone AL-21; 1:200 dilution), MHCII-PB (clone M5/114.15.4; 1:600 dilution), CD3-BV510 (clone 17A2; 1:200 dilution), CD19-BV510 (clone HIB19; 1:200 dilution) and Aqua LIVE/DEAD (1:1000 dilution). For this myeloid panel staining, cells are incubated with the antibody mix (50 ul total volume) for 20 min at 4° C. in the dark. Cells were then washed with 200 μl SME and resuspended in 200 μl 10% formalin (fixative) before analysis on FACSCanto II within 2 days. The T cell panel consisted of CXCR5/CD185-FITC (clone J252D4; 1:50 dilution), PD1/CD279-PE (clone J43; 1:200 dilution), CD8a-PerCP-Cy5.5 (clone 53-6.7; 1:200 dilution), CD25-PE-Cy7 (clone PC61; 1:300 dilution), CD4-AF647 (clone GK1.5; 1:200 dilution), CD3-APC-eFluor780 (clone 17A2; 1:200 dilution), NK1.1-eFlour450 (clone PK136; 1:200 dilution) and Aqua LIVE/DEAD (1:1000 dilution). For the T cell panel staining, cells were incubated with anti-CXCR5-FITC alone (30 ul total volume; 1:50 dilution) for 30 min at 4° C. in the dark and then washed with 200 μl SME. Cell were then incubated with the rest of the antibody mix (50 μl total volume) for 15 min at 4° C. in the dark and then washed with 200 ul SME. Cells were resuspended in 200 ul 10% formalin (fixative) before analysis on FACSCanto II within 2 days. The B cell panel consisted of CD95/FAS-FITC (clone Jo2; 1:200 dilution), SPIKE (Covid-19)-PE (1:50 dilution) 7-AAD (1:1000 dilution), F4/80-PerCP-Cy5.5 (clone BM8; 1:200 dilution), CD3-PerCP-Cy5.5 (clone 17A2; 1:200 dilution), SPIKE (Covid-19)-APC (1:50 dilution) CD38-PE-Cy7 (clone 90; 1:400 dilution), CD19-APC-Fire750 (clone 6D5; 1:200 dilution), CD138-BV421 (clone 281-2; 1:200 dilution) and IgD-BV510 (clone 11-26c.2a; 1:500 dilution). For the B cell panel staining, cells were incubated with antibody mix (50 ul total volume) for 20 min at 4° C. in the dark and then washed with 200 ul SME. Cell were resuspended in 200 ul SME (no fixative) and immediately analyzed on FACSCanto II.

The analysis of lung tissues by flow cytometry was performed as follows. Excised lungs were cut into very small pieces using scissors before addition Collagenase/DNase. After incubation at 37° C. for 30 min, lung homogenates were diluted with 1 ml SME. Digested tissues were gently grinded and crushed by using the flat end of a syringe plunger onto a strainer before rinsing with 10-15 ml SME. After centrifugation at 1800 rpm and 4° C. for 5 min, pellets were resuspended in 3 ml Red Blood Cell Lysis Buffer [ACK buffer (10 mM KHCO3, pH 7.2-7.4, 150 mM NH4Cl and 0.1 mM EDTA)]. After incubation at room temperature for 5 min. Samples were diluted 1:2 by adding 3 ml SME to inactivate the lysis buffer. Cells were filtered each lysate by passing it through a Nitex® Nylon filter membrane and into a clean 50-ml conical tube. After rinsing with additional 5-10 ml SME, cells were centrifuged before resuspending the cell pellets in 1 ml SME. 50 µl of each sample were placed into a 96-well plate for cell counting by flow cytometry using Fluoresbrite Carboxylate YG 10 µm microspheres. 200 µl of each sample were placed into 3 separate V-bottom 96-well plates for antibody staining for flow cytometric analysis. Samples were incubated for 10 min at 4° C. in the dark with Fc-Block (1:1000 dilution) and then washed with 200 µl SME before staining with the same 3 panels used for the lymph nodes.

The analysis of splenocytes by flow cytometry was performed as follows. Spleen were transferred into a 70-um cell strainer fitted on a 50-ml conical tube and gently grinded and crushed by using the flat end of a syringe plunger before rinsing the strainer with 10-15 ml SME. After centrifugation at 1800 rpm and 4° C. for 5 min, pellets are resuspended in 5 ml Red Blood Cell Lysis Buffer [ACK buffer (10 mM KHCO3, pH 7.2-7.4, 150 mM NH4Cl and 0.1 mM EDTA)]. After incubation at room temperature for 5 min, 20 ml SME was added to each lysate to dilute the ACK buffer. Cells were then filtered by passing it through a 70 um Nitex® Nylon filter membrane. Filtered were rinse with an additional 5 ml SME. After centrifugation, cell pellets were resuspended in 20 ml SME. 50 µl of each sample were placed into a 96-well plate for cell counting by flow cytometry using Fluoresbrite Carboxylate YG 10 µm microspheres. 200 µl of each sample were placed into 3 separate V-bottom 96-well plates for antibody staining for flow cytometric analysis. Samples were incubated for 10 min at 4° C. in the dark with Fc-Block (1:1000 dilution) and then washed with 200 µl SME before staining with the same 3 panels used for the lymph nodes.

Figure 71:
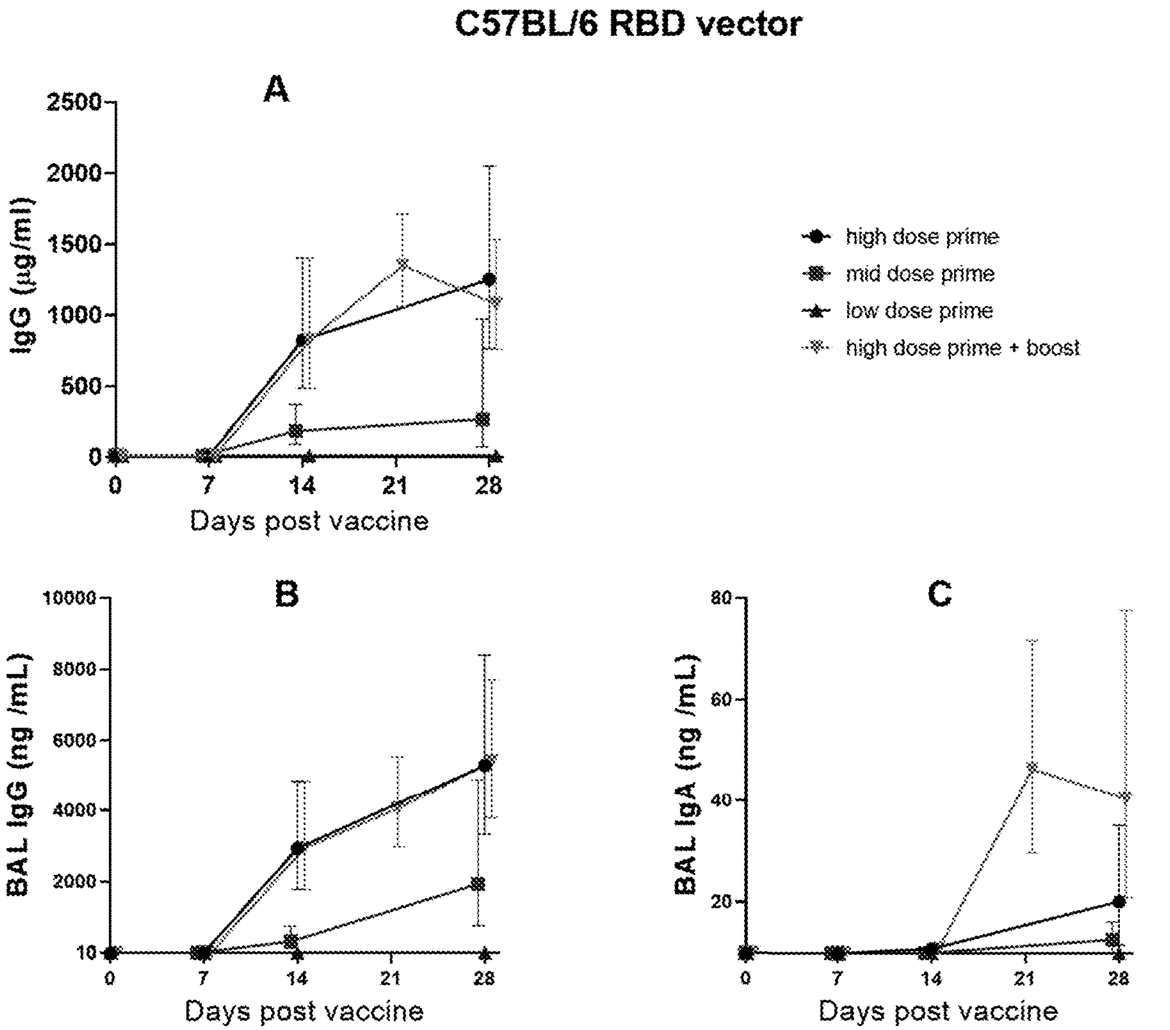
FIG. 71. Measurements of anti-SAR-CoV-2 IgG (μg/ml) in the serum (A), BAL anti-SARS-Cov-2 IgG (ng/ml) (B) and BAL anti-SARS-CoV-2 IgA (ng/ml) (C) from bronchoalveolar lavages obtained at different time points from individual C57BL/6 mice that have received a single intranasal dose of the replication-deficient Ad5 vector expressing the RBD domain (as shown in SEQ ID NO: 15). Results as expressed as the geometric mean response +/−95% confidence interval. Day 0 reports control group values for all groups. Day 7 and day 14 for group receiving 2 intranasal doses report values from group receiving a single administration at the same dose.
Figure 72A:
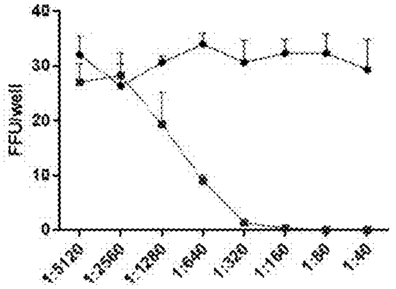
FIG. 72. Serum neutralizing antibodies against SARS-CoV-2 measured by focus reduction neutralization test (PRNT) in ten C57BL/6 mice that have received a single intranasal high dose of the replication-deficient Ad5 vector expressing the RBD domain (SEQ ID NO: 15). Each graph (FIG. 72A through 72J) corresponds to the result obtained from one immunized mouse. Lines in black correspond to the negative control serum and lines in red correspond to the tested serum samples.
Figure 72B:
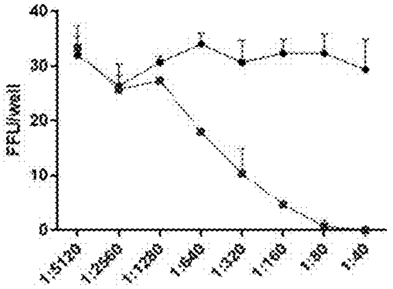
Figure 72C:
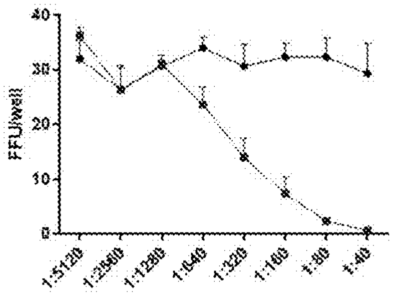
Figure 72D:
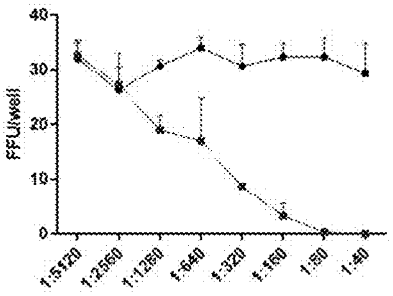
Figure 72E:
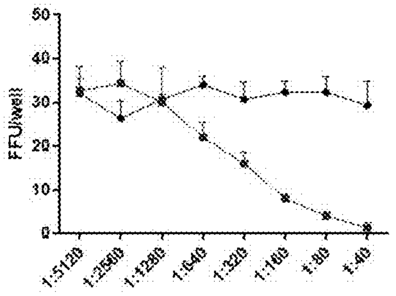
Figure 72F:
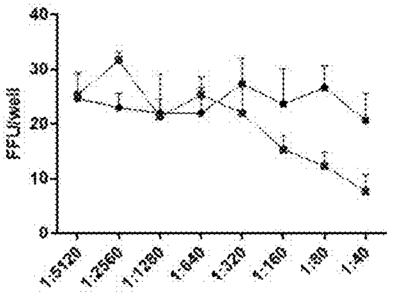
Figure 72G:
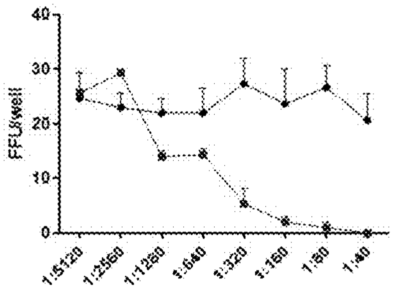
Figure 72H:
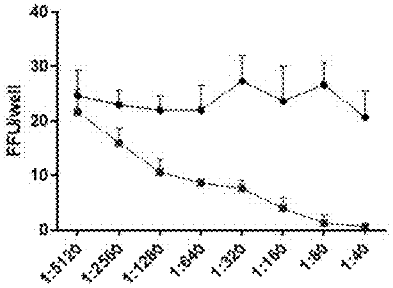
Figure 72I:
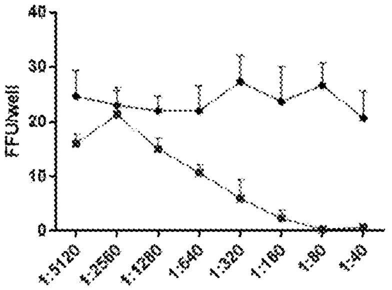
Figure 72J:
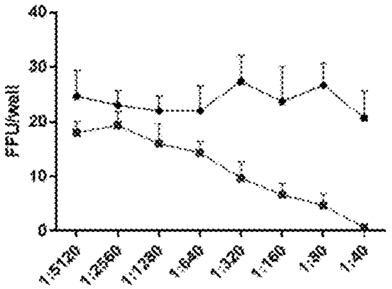
Figure 73:
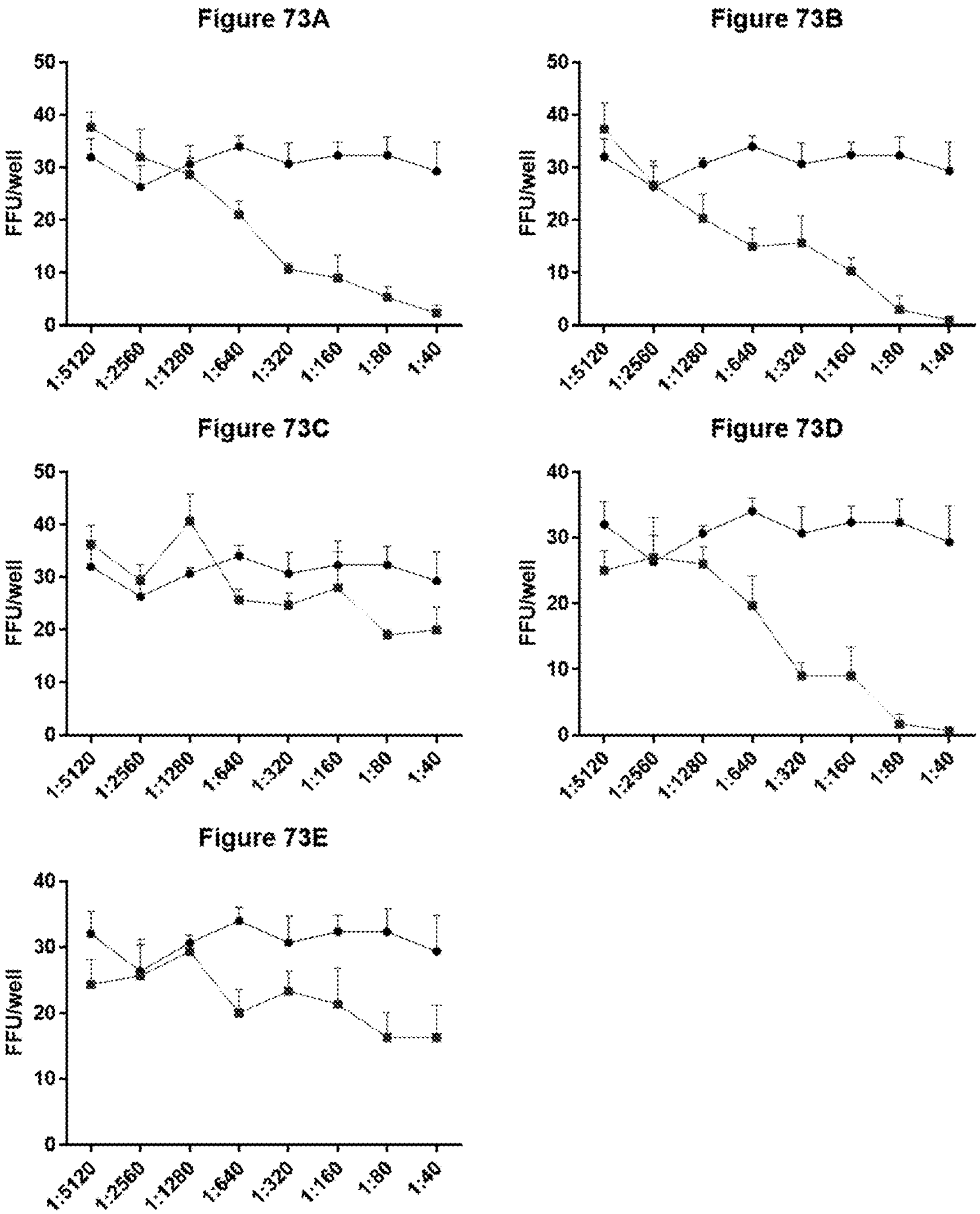
FIG. 73. Serum neutralizing antibodies against SARS-CoV-2 measured by focus reduction neutralization test (PRNT) in five C57BL/6 mice that have received a single intranasal mid-dose of replication-deficient Ad5 vector expressing the RBD domain (SEQ ID NO: 15). Each graph (FIG. 73A through 73E) corresponds to the result obtained from one immunized mouse. Lines in black correspond to the negative control serum and lines in red correspond to the tested serum samples.

Following a single intranasal administration, the replication-deficient Ad5 vector expressing the RBD domain of Spike (SEQ ID NO: 15) was demonstrated to stimulate the production of IgG antibodies in the serum indicating the induction of systemic responses as well as the production of IgG and IgA antibodies in bronchoalveolar lavages indicating the induction of a mucosal responses as shown in FIGS. 71A-71C. A dose response was observed across the different antibody markers with the high dose vaccine leading the highest responses and the low dose leading to a marginal response while the mid-dose generated an intermediate response. It is worth noting that at day 14 and day 28 with a single high dose vaccine, spike-specific IgG response in the serum reached very high level, exceeding 1 milligram per ml representing approximately 5% of the total serum IgG. After an intranasal boost at day 14 with the same vector, the IgA production in the BAL increased significantly above the response induced by a single dose of the vaccine IgG response at day 21 and day 28 while the impact on the IgG responses was limited.

All ten animals (100%) tested from the group that received a single administration of the high dose vaccine showed the presence of neutralizing antibodies against SARS-CoV-2 as measured by focus reduction neutralization test (FRNT) (FIGS. 72A-72J) while only three out of five animals (60%) show significant neutralizing response in the group that has received a single administration of the mid-dose vaccine (FIGS. 73A-73E).

Intranasal administration of the vaccine induces the recruitment and/or proliferation of innate and adaptive immune cells in different immune compartments. FIGS. 74A-74L, 75A-75E, 76A-76J, and 77A-L present the variations in the number of immune cells respectively in the lung, BAL, mediastinal lymph nodes and the spleen following the single intranasal administration of the high dose vaccine. Importantly, elevation on the number of CD19 cells, memory B cells, Germinal Center (GC) B cells and/or T follicular helper (hf) cells observed in the lung, BAL and lymph nodes and to a lesser extend in the spleen are indicative of the ability of the vaccine to stimulate a long-lived humoral and mucosal antibody response. In addition, the elevation of macrophages, dendritic cells, CD4+ and/or CD8+ T cells observed in the lung, BAL and lymph nodes and to a lesser extend in the spleen are indicatives of the ability of the vaccine to stimulate mucosal and systemic, innate and cell-mediated immune responses that are anticipated to be of benefit in the context of SARS-CoV-2 infection. Results obtained with the lower vaccine doses were not presented as they show a similar trend but at a lower level.

Example 14. Intranasal Administration of Ad5 Vector Expressing S1 Domain in C57BL/6 Mice Replication-deficient Ad5 vector expressing the S1 domain from the spike antigen of SARS-CoV-2 (SEQ ID NO: 13) was administered intranasally to C57BL/6 mice to evaluate the induction of systemic and mucosal immunity against SARS-CoV-2. C57BL/6 mice received one or two intranasal administration of the Ad5 vector at three different doses in a volume of 50 µl as indicated in Table 19. High dose was 1.2E+09 ifu/ml (6E+08 ifu in 50 mid-dose 1.2E+09 ifu/ml (6E+07 ifu in 50 µL) and Low dose 1.2E+08 ifu/ml (6E+06 ifu in 50 µL) in A195 buffer. The control group received an intranasal administration of 50 µl of the A195 buffer alone. At day 7, day 14, day 21 or day 28 post-vaccine administration, sera, bronchoalveolar lavages (BAL) and tissues including lungs, mediastinal lymph nodes and spleens were collected from 10 animals per group according to the table below. Immunological readouts included the measurement of SARS-CoV-2 spike antigen-specific-IgG in the serum and BAL, SARS-CoV-2 spike antigen-specific IgA in the BAL, neutralizing antibody responses against SARS-CoV-2 in the serum and the numeration of immune cells in the lung, lymph nodes, BALs and spleens at different time-points. These parameters are summarized in Table 21.

TABLE 21

| Vaccine/ Control | Intranasal dose | Number of animals per group | Immunization | Sample collection (10 animals per time point) |
|---|---|---|---|---|
| S1 Ad5 | 6E+08 ifu in 50 µL | 30 | Day 0 | Day 7, 14, 28 |
| S1 Ad5 | 6E+07 ifu in 50 µL | 30 | Day 0 | Day 7, 14, 28 |
| S1 Ad5 | 6E+06 ifu in 50 µL | 30 | Day 0 | Day 7, 14, 28 |

TABLE 21-continued

| Vaccine/ Control | Intranasal dose | Number of animals per group | Immunization | Sample collection (10 animals per time point) |
|---|---|---|---|---|
| S1 Ad5 | 6E+08 ifu in 50 μL | 20 | Day 0 & 14 | Day 21, 28 |
| A195 buffer | 50 μL | 10 | Day 0 | Day 7 |

Methods for the quantification of SARS-CoV-2 spike IgG and IgA in serum or BAL samples, focus reduction neutralization tests as well as the flow cytometric analysis of bronchoalveolar lavage (BAL) cells, mediastinal lymph nodes, lung tissues and splenocytes are described in Example 13B.

Following a single intranasal administration, the replication-deficient Ad5 vector expressing the S1 domain of Spike (SEQ ID NO: 13) was demonstrated to stimulate the production of IgG antibodies in the serum indicating the induction of systemic responses as well as the production of IgG and IgA antibodies in bronchoalveolar lavages indicating the induction of a mucosal responses as shown in FIGS. 78A-78C. A dose response was observed across the different antibody markers with the high dose vaccine leading to the highest responses and the low dose leading to a marginal response while the mid-dose generated an intermediate response. Overall, IgG responses in the serum and BALs were lower with the S1 vector compared to the results obtained with the RBD vector as presented in Example 13B. After an intranasal boost at day 14 with the same vector, the IgA production in the BAL increased significantly above the response induced by a single dose of the vaccine IgG response at day 21 and day 28 while the impact on the IgG responses was limited.

Three out of five animals tested from the group that received a single administration of the high dose vaccine showed significant induction of neutralizing antibodies against SARS-CoV-2 as measured by focus reduction neutralization test (FRNT) (FIGS. 79A-79E). In the single mid-dose group, two out of five animals (FIGS. 80B and D) show low neutralizing response (FIGS. 80A-80E).

Intranasal administration of the vaccine induces the recruitment and/or proliferation of innate and adaptive immune cells in different immune compartments. FIGS. 81A-81L, 82A-82E, 83A-83J, and 84A-L present the variations in the number of immune cells respectively in the lung, BAL, mediastinal lymph nodes and the spleen following the single intranasal administration of the high dose vaccine. Importantly, elevation on the number of CD19 cells, memory B cells, Germinal Center (GC) B cells and/or T follicular helper (hf) cells observed in the lung, BAL and lymph nodes and to a lesser extend in the spleen are indicative of the ability of the vaccine to stimulate a long-lived humoral and mucosal antibody response. In addition, the elevation of macrophages, dendritic cells, CD4+ and/or CD8+ T cells observed in the lung, BAL and lymph nodes and to a lesser extend in the spleen are indicatives of the ability of the vaccine to stimulate mucosal and systemic, innate and cell-mediated immune responses that are anticipated to be of benefit in the context of SARS-CoV-2 infection. Results obtained with the lower vaccine doses were not presented as they show a similar trend but at a lower level.

Example 15. Intranasal Administration of Ad5 Vector Expressing RBD Domain in CD-1 Mice Replication-deficient Ad5 vector expressing the RBD domain from the spike antigen of SARS-CoV-2 (SEQ ID NO: 15) was administered intranasally to CD-1 mice to evaluate the induction of systemic and mucosal immunity against SARS-CoV-2. CD-1 mice received one or two intranasal administration of the Ad5 vector at three different doses in a volume of 50 μl. High dose was 6.7E+09 ifu/ml (3.35E+08 ifu in 50 mid-dose 1.2E+09 ifu/ml (6E+07 ifu in 50 μL) and Low dose 1.2E+08 ifu/ml (6E+06 ifu in 50 μL) in A195 buffer. The control group received an intranasal administration of 50 μl of the A195 buffer alone. At day 7, day 14 and/or day 21 post-vaccine administration, sera and bronchoalveolar lavages (BAL) were collected from 10 animals per group according to Table 22. Immunological readouts included the measurement of SARS-CoV-2 spike antigen-specific-IgG in the serum and BAL, SARS-CoV-2 spike antigen-specific IgA in the BAL, and neutralizing antibody responses against SARS-CoV-2 in the serum. These parameters are summarized in Table 22.

TABLE 22

| Vaccine/ Control | Intranasal dose | Number of animals per group | Immunization | Sample collection (10 animals per time point) |
|---|---|---|---|---|
| RBD Ad5 | 3.35E+08 ifu in 50 μL | 30 | Day 0 | Day 7, 14, 21 |
| RBD Ad5 | 6E+07 ifu in 50 μL | 30 | Day 0 | Day 7, 14, 21 |
| RBD Ad5 | 6E+06 ifu in 50 μL | 30 | Day 0 | Day 7, 14, 21 |
| RBD Ad5 | 3.35E+08 ifu in 50 μL | 20 | Day 0 & 14 | Day 21 |
| A195 buffer | 50 μL | 10 | Day 0 | Day 7 |

Methods for the quantification of SARS-CoV-2 spike IgG and IgA in serum or BAL samples and focus reduction neutralization tests are described in Example 13B.

Following a single intranasal administration, the replication-deficient Ad5 vector expressing the RBD of the S1 domain of Spike (SEQ ID NO: 15) was demonstrated to stimulate the production of IgG antibodies in the serum indicating the induction of systemic responses as well as the production of IgG and IgA antibodies in bronchoalveolar lavages indicating the induction of a mucosal responses as shown in FIGS. 85A-85C. A dose response was observed across the different antibody markers with the high dose vaccine leading to the highest responses and the low dose leading to a marginal response while the mid-dose generated an intermediate response. After an intranasal boost at day 14 with the same vector, impact on the IgG and IgA responses were limited compared to the single administration at the same dose.

Eight out of 10 animals tested (FIGS. 92A, 92C-92E and 92G to 92J) from the group that received a single administration of the high dose vaccine showed significant induction of neutralizing antibodies against SARS-CoV-2 as measured by focus reduction neutralization test (FRNT) (FIGS. 92A-92J).

Example 16. Intranasal Administration of Ad5 Vector Expressing S1 Domain in CD-1 Mice Replication-deficient Ad5 vector expressing the S1 domain from the spike antigen of SARS-CoV-2 (SEQ ID NO: 13) was administered intranasally to CD-1 mice to evaluate the induction of systemic and mucosal immunity against SARS-CoV-2. CD-1 mice received a single intranasal administration of the Ad5 vector at three different doses in a volume of 50 μl. High dose was 6.7E+09 ifu/ml (3.35E+08 ifu in 50 mid-dose 1.2E+09 ifu/ml (6E+07 ifu in 50 μL) and Low dose 1.2E+08 ifu/ml (6E+06 ifu in 50 μL) in A195 buffer. The control group received an intranasal administration of 50 μl of the A195 buffer alone. At day 7, day 14 and day 21 post-vaccine administration, sera and bronchoalveolar lavages (BAL) were collected from 10 animals per group according to Table 23. Immunological readouts included the measurement of SARS-CoV-2 spike antigen-specific-IgG in the serum and BAL, SARS-CoV-2 spike antigen-specific IgA in the BAL, neutralizing antibody responses against SARS-CoV-2 in the serum. These parameters are summarized in Table 23.

TABLE 23

| Vaccine/ Control | Intranasal dose | Number of animals per group | Immunization | Sample collection (10 animals per time point) |
|---|---|---|---|---|
| S1 Ad5 | 3.35E+08 ifu in 50 μL | 30 | Day 0 | Day 7, 14, 21 |
| S1 Ad5 | 6E+07 ifu in 50 μL | 30 | Day 0 | Day 7, 14, 21 |
| S1 Ad5 | 6E+06 ifu in 50 μL | 30 | Day 0 | Day 7, 14, 21 |
| A195 buffer | 50 μL | 10 | Day 0 | Day 7 |

Methods for the quantification of SARS-CoV-2 spike IgG and IgA in serum or BAL samples and focus reduction neutralization tests are described in Example 13B.

Figure 86:
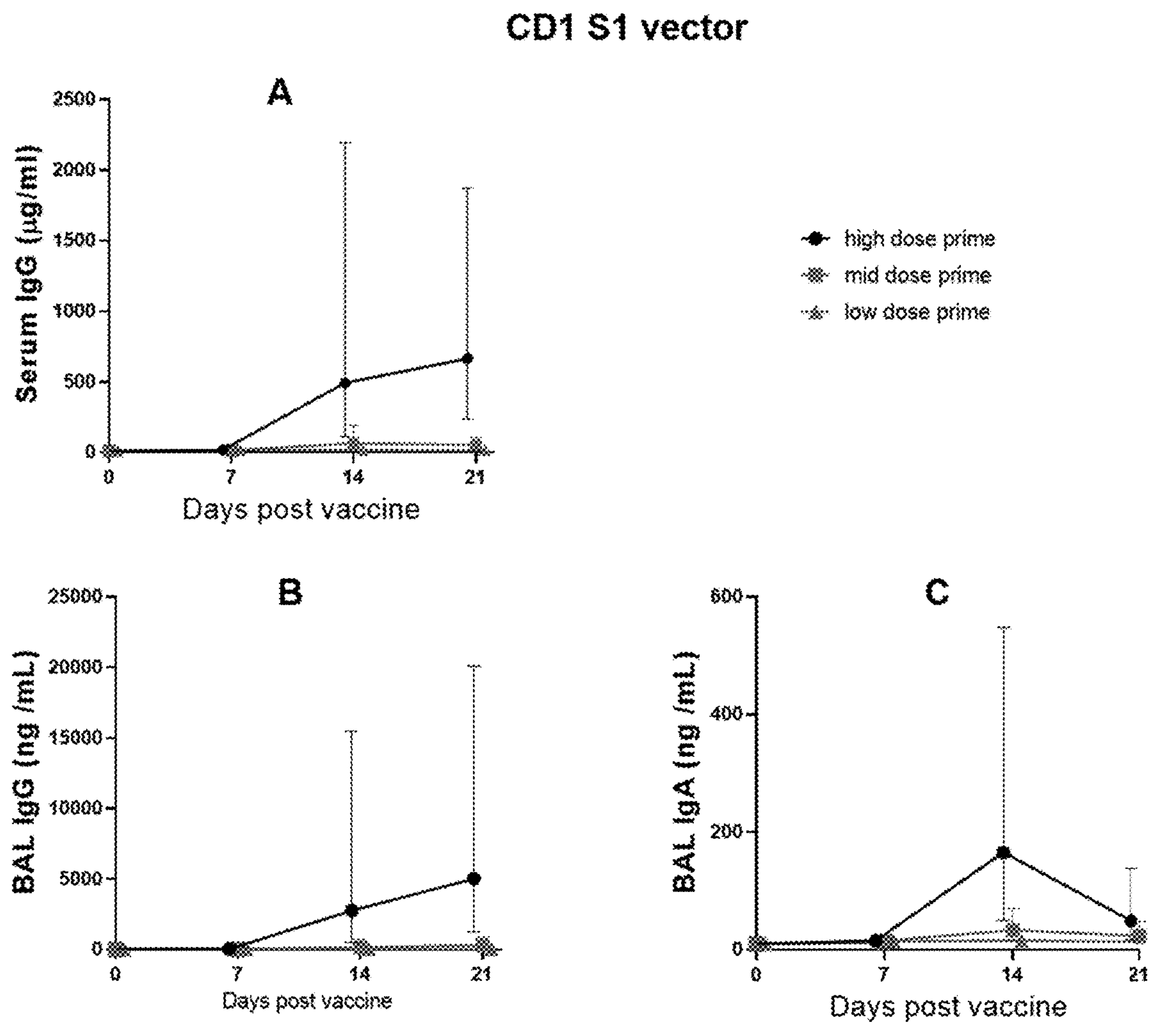
FIG. 86. Measurements of anti-SAR-CoV-2 IgG (µg/ml) in the serum (A), BAL anti-SARS-CoV-2 IgG (ng/ml) (B) and BAL anti-SARS-CoV-2 IgA (ng/ml) (C) from bronchoalveolar lavages obtained at different time points from individual CD-1 mice that have received a single intranasal dose of the replication-deficient Ad5 vector expressing the S1 domain (SEQ ID NO: 13). Results for the groups are expressed as the geometric mean response +/−95% confidence interval. Day 0 reports control group values for all groups.

Following a single intranasal administration, the replication-deficient Ad5 vector expressing the S1 domain of Spike (SEQ ID NO: 13) was demonstrated to stimulate the production of IgG antibodies in the serum indicating the induction of systemic responses as well as the production of IgG and IgA antibodies in bronchoalveolar lavages indicating the induction of a mucosal responses as shown in FIGS. 86A-86C. A dose response was observed across the different antibody markers with the high dose vaccine leading to the highest responses and the low dose and mid dose leading to a marginal immune response.

Example 17. Intranasal Administration of Ad5 Vector Expressing RBD Domain in CD-1 Mice Replication-deficient Ad5 vector expressing the RBD domain from the spike antigen of SARS-CoV-2 (SEQ ID NO: 15) was administered intranasally to CD-1 mice to evaluate the induction of systemic and mucosal T cell immunity against SARS-CoV-2. CD-1 mice received a single intranasal administration of the Ad5 vector at 6.7E+09 ifu/ml (3.35E+08 ifu in 50 μL) in A195 buffer. The control group received an intranasal administration of 50 μl of the A195 buffer alone. At day 10, day 14 and day 28 post-vaccine administration, lungs and spleens from 10 mice in the vaccine group and 3 mice from the control group were collected according to Table 24. Immunological readouts included the measurement of CD4+ and CD8+ T cell responses in the lungs and spleens by flow cytometry, the measurement of T cell response in the lungs and spleens by an IFN-gamma ELISpot assay as well as the measurement of T cell cytokines following in vitro recall with RBD-derived peptides.

TABLE 24

| Vaccine/ Control | Intranasal dose | Number of animals per group | Immunization | Sample collection (10 animals per time point) |
|---|---|---|---|---|
| RBD Ad5 | 3.35E+08 ifu in 50 μL | 30 | Day 0 | Day 7, 14, 28 |
| A195 buffer | 50 μL | 9 | Day 0 | Day 7, 14, 28 |

The analysis of RBD-specific T cell responses by IFN-gamma ELISpot in the spleens and lungs was performed as follows. Spleens were transferred into a 70-um cell strainer fitted on a 50-ml conical tube and gently grinded and crushed by using the flat end of a syringe plunger before rinsing the strainer with 10-15 ml SME. After centrifugation at 1800 rpm and 4° C. for 5 min, pellets are resuspended in 5 ml Red Blood Cell Lysis Buffer [ACK buffer (10 mM KHCO3, pH 7.2-7.4, 150 mM NH4Cl and 0.1 mM EDTA)]. After incubation at room temperature for 5 min, 20 ml SME was added to each lysate to dilute the ACK buffer. Cells were then filtered by passing through a 70 um Nitex® Nylon filter membrane. Filtered cells were rinsed with an additional 5 ml SME. After centrifugation, cell pellets were resuspended in 20 ml SME. 50 μl of each sample were placed into a 96-well plate for cell counting by flow cytometry using Fluoresbrite Carboxylate YG 10 μm microspheres.

Excised lungs were cut into very small pieces using scissors before addition of Collagenase/DNase. After incubation at 37° C. for 30 min, lung homogenates were diluted with 1 ml SME. Digested tissues were gently grinded and crushed by using the flat end of a syringe plunger onto a strainer before rinsing with 10-15 ml SME. After centrifugation at 1800 rpm and 4° C. for 5 min, pellets were resuspended in 3 ml Red Blood Cell Lysis Buffer [ACK buffer (10 mM KHCO3, pH 7.2-7.4, 150 mM NH4Cl and 0.1 mM EDTA)]. After incubation at room temperature for 5 min. Samples were diluted 1:2 by adding 3 ml SME to inactivate the lysis buffer. Cells were filtered by passing it through a Nitex® Nylon filter membrane and into a clean 50-ml conical tube. After rinsing with additional 5-10 ml SME, cells were centrifuged before resuspending the cell pellets in 1 ml SME. 50 μl of each sample were placed into a 96-well plate for cell counting by flow cytometry using Fluoresbrite Carboxylate YG 10 μm microspheres.

For analysis of T cell responses, a pool of 53 peptides derived from a peptide scan through RBD of Spike Glycoprotein of SARS-CoV-2 (319-541) was designed and synthesized by JPT (JPT Peptide technologies, Berlin, Germany). Peptides were designed with a length of 15 a.a. and an overlap of 11a.a. Before use, each vial containing 15 nmol (appr. 25 μg) of each peptide per vial was reconstituted in 50 μl of DMSO before dilution into complete culture media.

Spleen and lung cell suspensions (150,000 cells/well) were placed in individual wells of ELIspot plates (Millipore-Sigma) that were pre-coated with anti-IFN-γ (AN18, (5 μg/ml)). Cells were stimulated with the RBD peptide pool described above at 0.5 to 2.0 μg/peptide/ml. Following 24 hr stimulation, plates were stained with biotinylated anti-IFN-γ (R4-6A2), followed by washing steps, and incubation with streptavidin-ALP. Secreted IFN-γ was detected following incubation with NBT/NCPI substrate for 7-10 min. The number of IFN-γ spot-forming cells were manually counted from digital images of each well. Statistical analysis was performed in GraphPad Prism using a Mann-Whitney test.

The analysis of CD4+ and CD8+ T cell responses in lung tissues and spleens by flow cytometry was performed as follows. Spleen and lung single cell suspensions were stimulated with the RBD peptide pool for 5 hrs in the presence of Brefeldin A (5 hrs, 12.5 ug/mL concentration). Cells were then incubated on ice with a combination of fluorescent dye-labelled antibodies including anti-CD4-V500 (clone GK1.5; 1:200 dilution), anti-CD8α-APC-Fire750 (clone 53-6.7; 1:200 dilution), anti-CD11a/CD18-Pacific Blue (H155-78; 1:200 dilution), anti-CD103-PE (M290; 1:200 dilution), anti-CD69-FITC (H1-2F3; 1:200 dilution), anti-Ly6G-PerCP-Cy5.5 (clone 1A8; 1:200 dilution), anti-CD64-PerCP-Cy5.5 (clone X54-5/7.1; 1:200 dilution), anti-B220/CD45R-PerCP (clone RA3-6B2; 1:200 dilution), and Red LIVE/DEAD (1:1000 dilution). Following surface staining, cells were permeabilized using BD Biosciences Cytofix/Cytoperm kit, and stained with anti-IFN-γ-PE-Cy7 (XMG1.2; 1:200 dilution) and anti-TNF-α-APC (MP6-XT22; 1:200 dilution). Following incubation with the antibodies, cells were washed and resuspended before analysis on FACSCanto II within 12 hours. Statistical analysis was performed in GraphPad Prism using a Mann-Whitney test.

Protein levels of IFNγ, IL-2, IL-4, IL-5, IL-10, IL-13, IL-17A and TNFα were quantified in culture supernatants using the mouse-specific Milliplex® multi-analyte panel kit MT17MAG-47K (Millipore; Sigma) and the MagPix® instrument platform with related xPONENT® software (Luminex Corporation). The readouts were analyzed with the standard version of EMD Millipore's Milliplex® Analyst software. Statistical analysis was performed in GraphPad Prism using a Mann-Whitney test.

Figure 88:
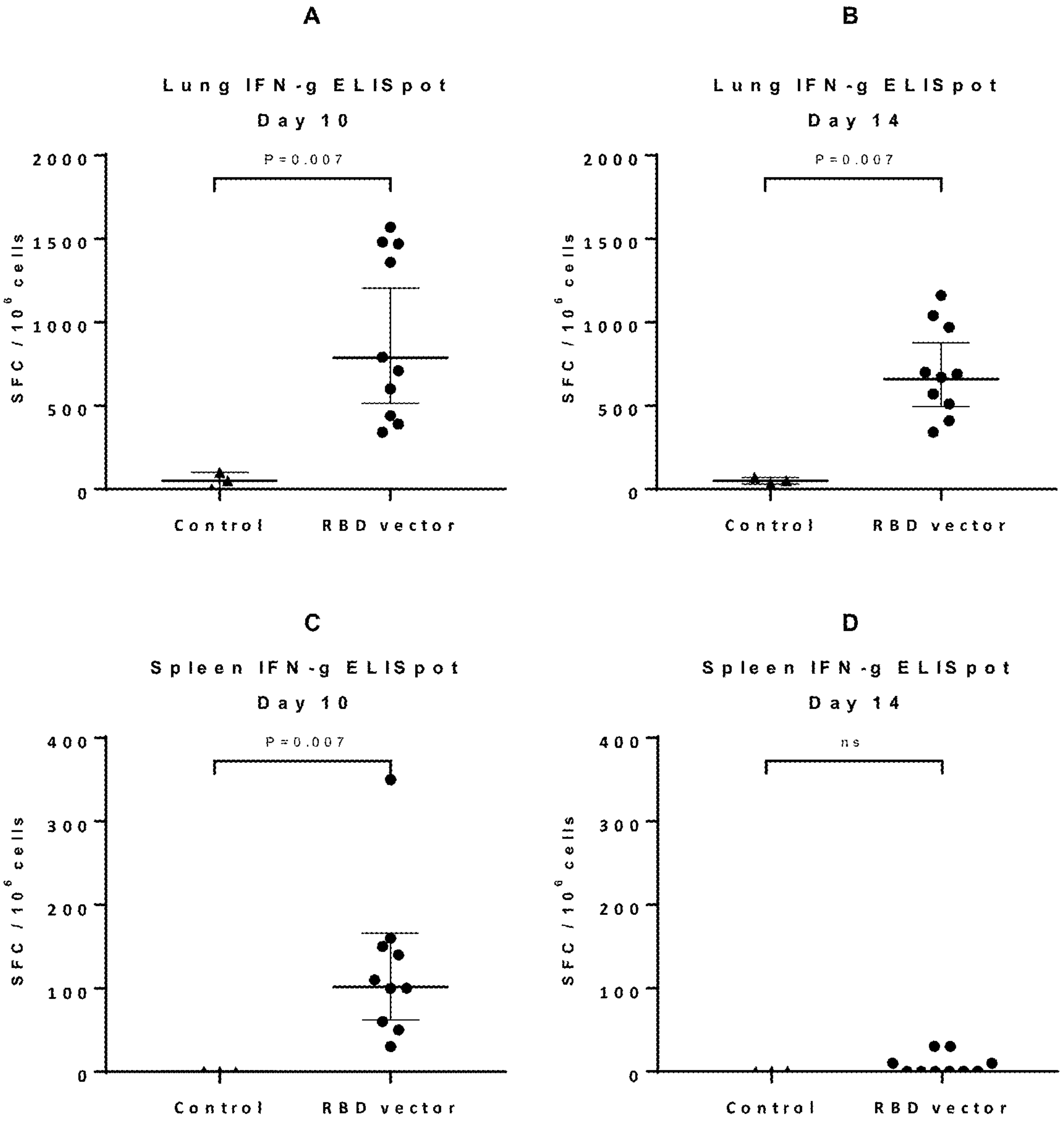
FIG. 88. Measurement of lung T cells at day 10 (A) and day 14 (B) and spleen T cells at day 10 (C) and day 14 (D) from individual CD-1 mice that received a single intranasal dose of the replication-deficient Ad5 vector expressing the RBD domain (SEQ ID NO: 15) ("RBD vector") or control groups that received the A195 buffer only. Results for the groups are expressed as the geometric mean response +/−95% confidence interval.
Figure 89:
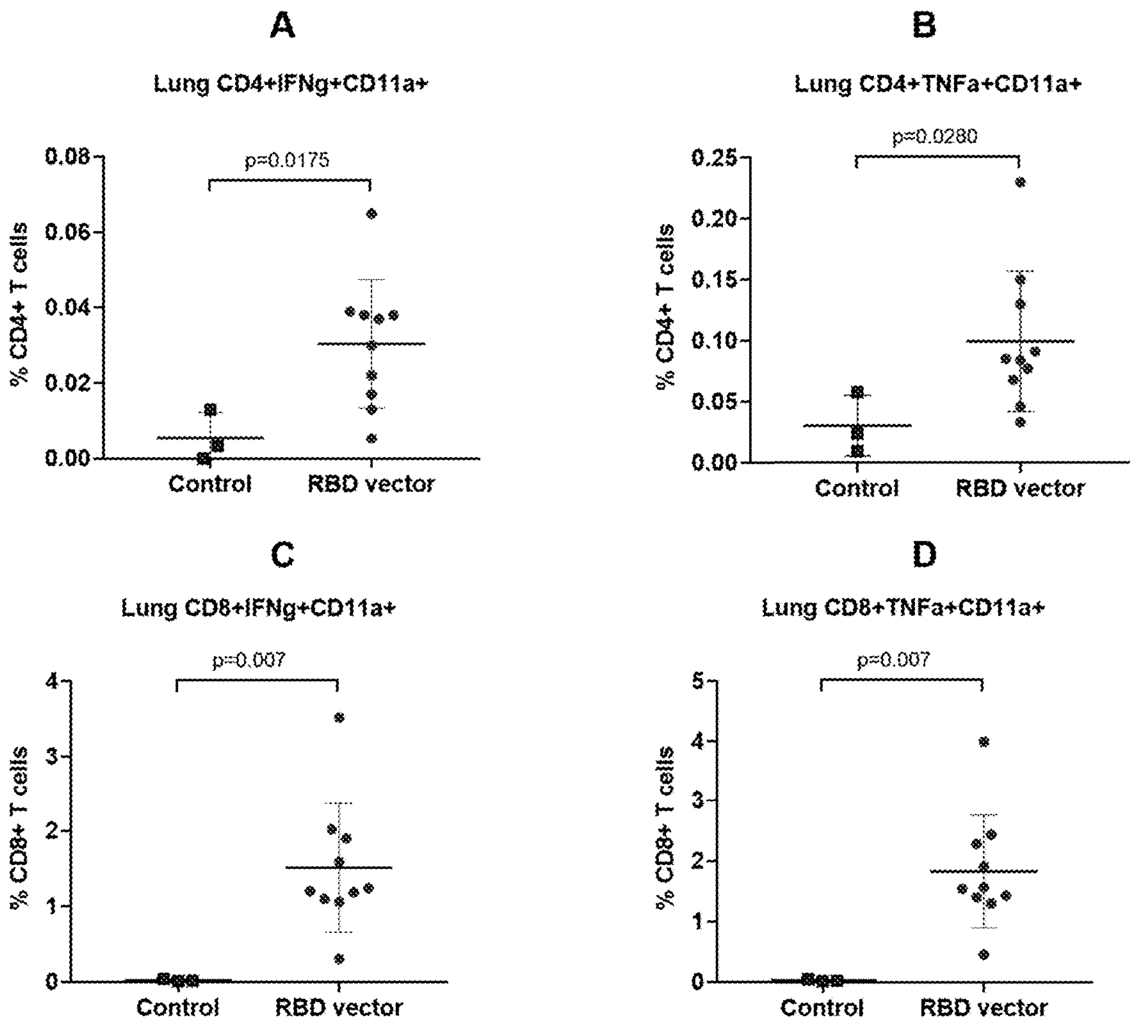
FIG. 89. Measurements of lung CD4+ IFN-g+ CD11a+ T cells (A), Lung CD4+ TNF-a+ CD11a+ T cells (B), Lung CD4+ IFN-g+ CD11a+ T cells (C) and Lung CD4+ TNF-a+ CD11a+ T cells (D) at day 14 from individual CD-1 mice that received a single intranasal dose of the replication-deficient Ad5 vector expressing the RBD domain (SEQ ID NO: 15) ("RBD vector") or that received the control A195 buffer only. Prior to flow cytometry analysis, cells were re-stimulated with a RBD peptide pool at 2 mcg/peptide/mL. Lines correspond to geometric mean response +/−95% confidence interval.
Figure 90:
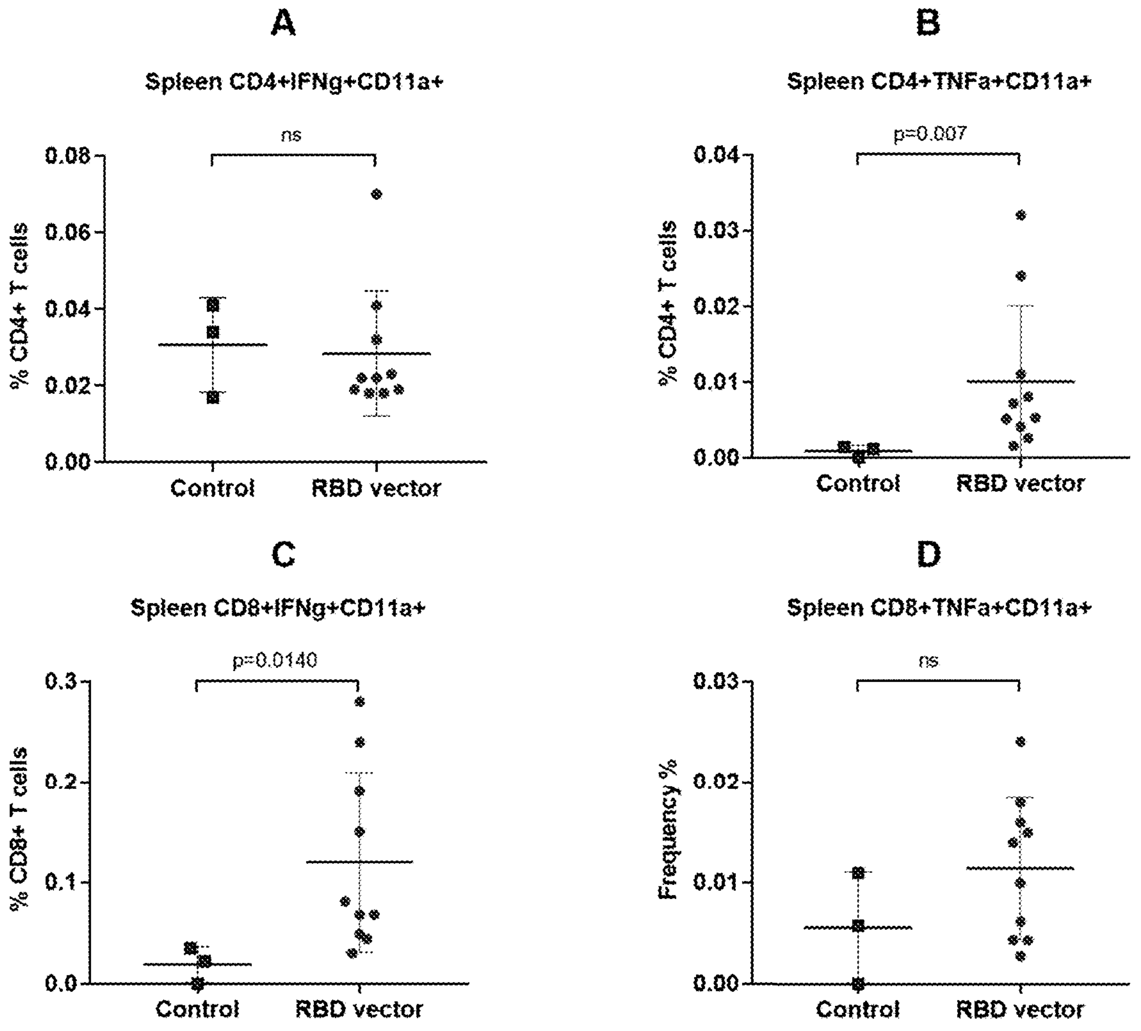
FIG. 90. Measurements of Spleen CD4+ IFN-g+ CD11a+ T cells (A), Spleen CD4+ TNF-a+ CD11a+ T cells (B), Spleen CD4+ IFN-g+ CD11a+ T cells (C) and Spleen CD4+ TNF-a+ CD11a+ T cells (D) at day 14 from individual CD-1 mice that received a single intranasal dose of the replication-deficient Ad5 vector expressing the RBD domain (SEQ ID NO: 15) ("RBD vector") or that received the control A195 buffer only. Lines correspond to geometric mean response +/−95% confidence interval.
Figure 91:
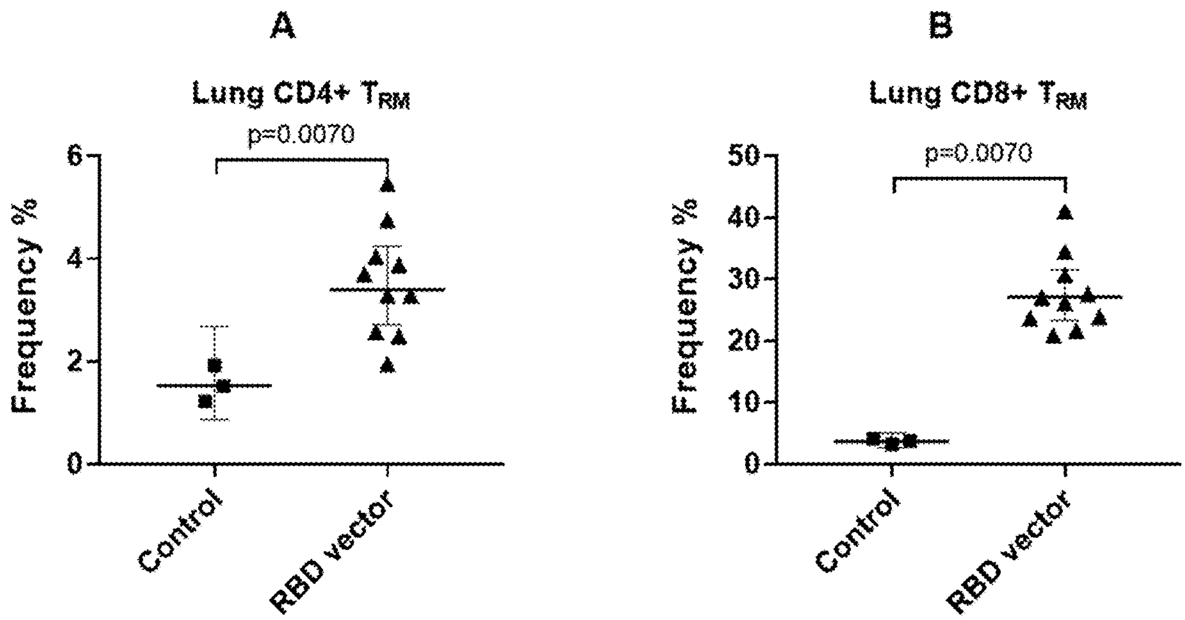
FIG. 91. Measurements of lung resident memory CD4+ (A) and CD8+(B) T cells expressing the tissue-resident memory T cell (TRM) markers CD103 and CD69 at day 14 from individual CD-1 mice that have received a single intranasal dose of the replication-deficient Ad5 vector expressing the RBD domain (SEQ ID NO: 15) ("RBD vector") or that received the control A195 buffer only. Lines correspond to geometric mean response +/−95% confidence interval.
Figure 92:
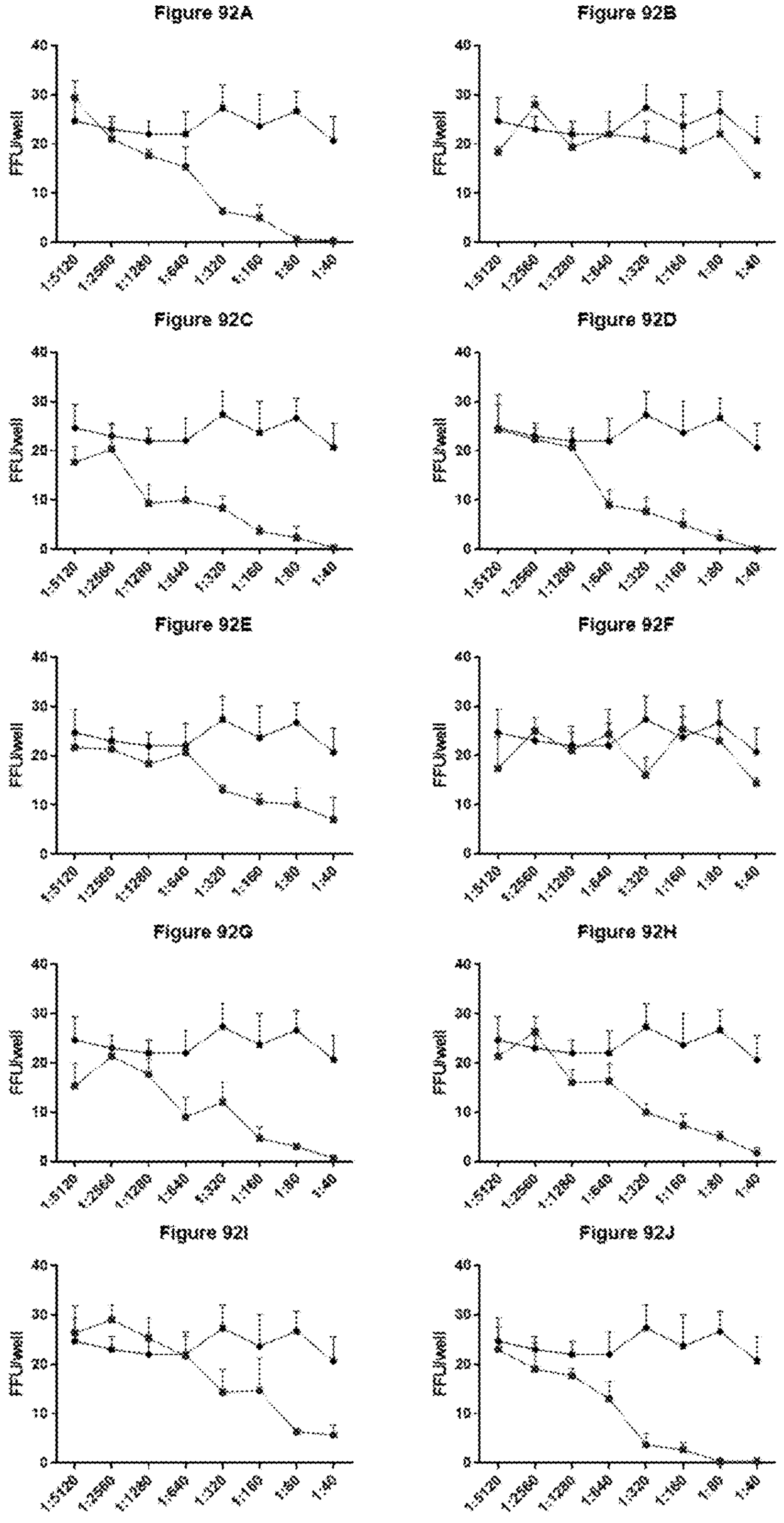
FIG. 92. Serum neutralizing antibodies against SARS-CoV-2 measured by focus reduction neutralization test (FRNT) in ten CD-1 mice that have received a single intranasal high dose of the replication-deficient Ad5 vector expressing the RBD domain (SEQ ID NO: 15). Each graph corresponds to the result obtained from one immunized mouse (FIGS. 92A through 92J). Lines in black correspond to the negative control serum and lines in red correspond to the tested serum samples.

Following a single intranasal administration, the replication-deficient Ad5 vector expressing the RBD domain of Spike (SEQ ID NO: 15) was demonstrated to induce a significant production of IFN-gamma producing T cells in the lung and spleen as shown in FIGS. 88 A to D. A high frequency of IFN-γ-producing RBD-specific T cells were detected in the lung at 10- and 14-days post-vaccination, reaching a mean response of 915 and 706 spot per million input cells respectively. See FIG. 88. IFN-γ producing RBD-specific T cells were also detected by ELISpot in the spleen—albeit at lower frequency compared to the lungs. This suggests that functional effector T cells primed in response to mucosal-delivered antigens can migrate to peripheral lymphoid tissues. In addition, RBD-specific CD4+ and CD8+ T cells expressing the early activation homing markers CD11a and IFN-gamma and/or TNF-alpha were also found at significant levels in the lungs (FIGS. 89 A to D) and spleens (FIGS. 90 A to D). The expression of the integrin CD11a, which is only upregulated in recently activated T cells and is required for optimal vascular adhesion in the tissue and retention within the respiratory tract (Thatte J, Dabak V, Williams M B, Braciale T J, Ley K. LFA-1 is required for retention of effector CD8 T cells in mouse lungs. Blood. 2003 Jun. 15; 101(12):4916-22.), supporting the hypothesis that these cells were recently recruited to the lung. The T cell responses were found at higher levels in the lung and dominated by CD8+ T cells. Intranasal RBD vector also induced high level tissue-resident memory CD4+ and CD8+ T cells (TRM) in the lungs (FIGS. 91 A and B).

Figure 95:
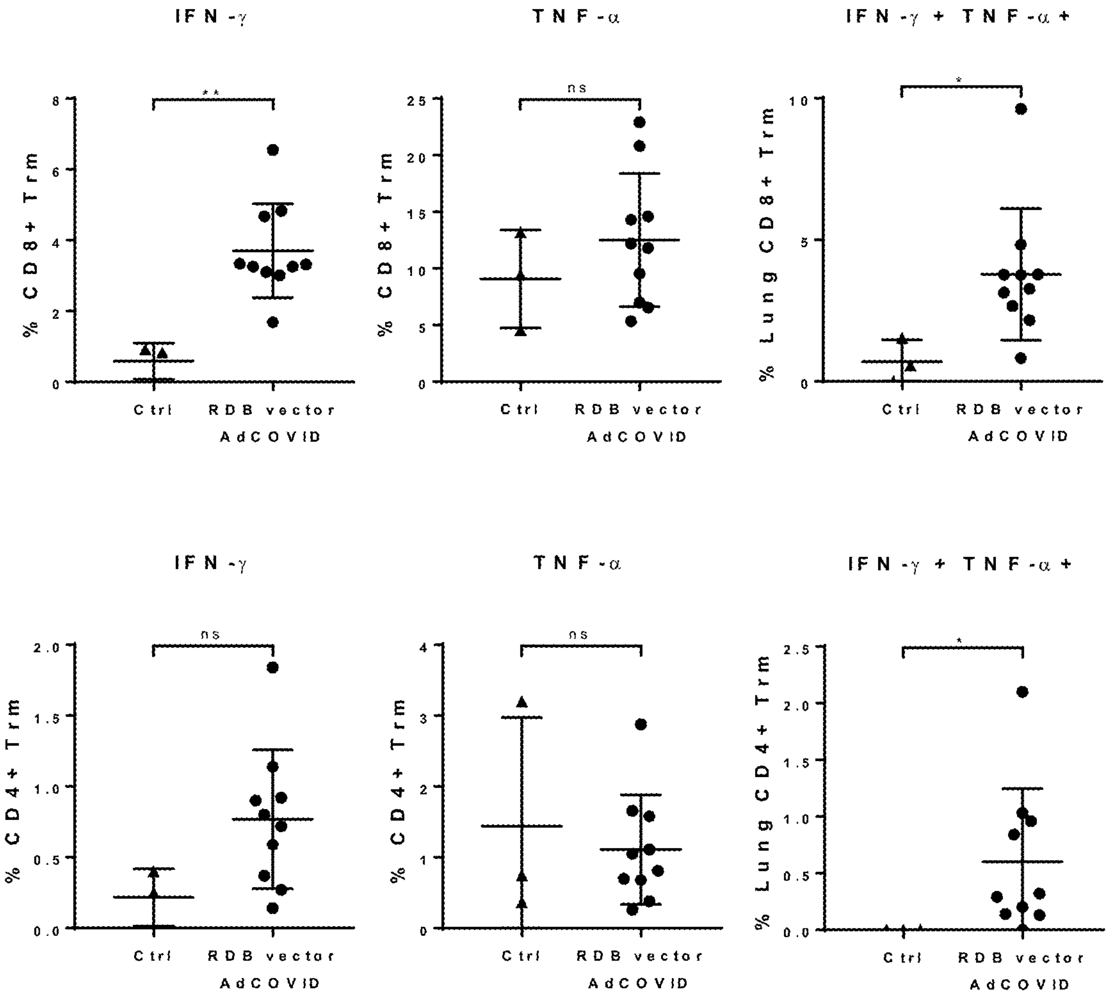
FIG. 95. Intracellular cytokine production by lung resident memory T cells at 14 days after single intranasal administration with the RBD vector. CD-1 mice were given a single intranasal administration of vehicle (Ctrl) or high dose RBD vector as described in Example 17. Lung cells (n=10 mice/vaccine, 3 mice/control) were isolated at day 14, re-stimulated with the RBD peptide pool for 5 hrs and analyzed by flow cytometry to identify $CD69^{+}CD103^{+}$ resident memory T cells (Trm). Results are expressed as the % of CD4+ or CD8+ T cells for individual mice. Lines presented as the mean response +/−SD for the groups. Statistical analysis was performed with a Mann-Whitney test: *, P<0.05; , P<0.01; *, P<0.001; ****, P<0.0001.

To assess whether vaccine-induced T cells might represent resident memory T cells (Trm), the expression of the Trm markers CD103 and CD69 (Takamura S. Persistence in Temporary Lung Niches: A Survival Strategy of Lung-Resident Memory CD8+ T Cells. Viral Immunol. 2017 July/August; 30(6):438-450. doi: 10.1089/vim.2017.0016.) was assessed on the lung $CD4^+$ and $CD8^+$ cells. Consistent with the intranasal administration route, induction of lung RDB-specific $CD4^+$ and $CD8^+$ Trm expressing either IFN-γ, TNF-α or both cytokines were observed (FIG. 95).

Figure 96:
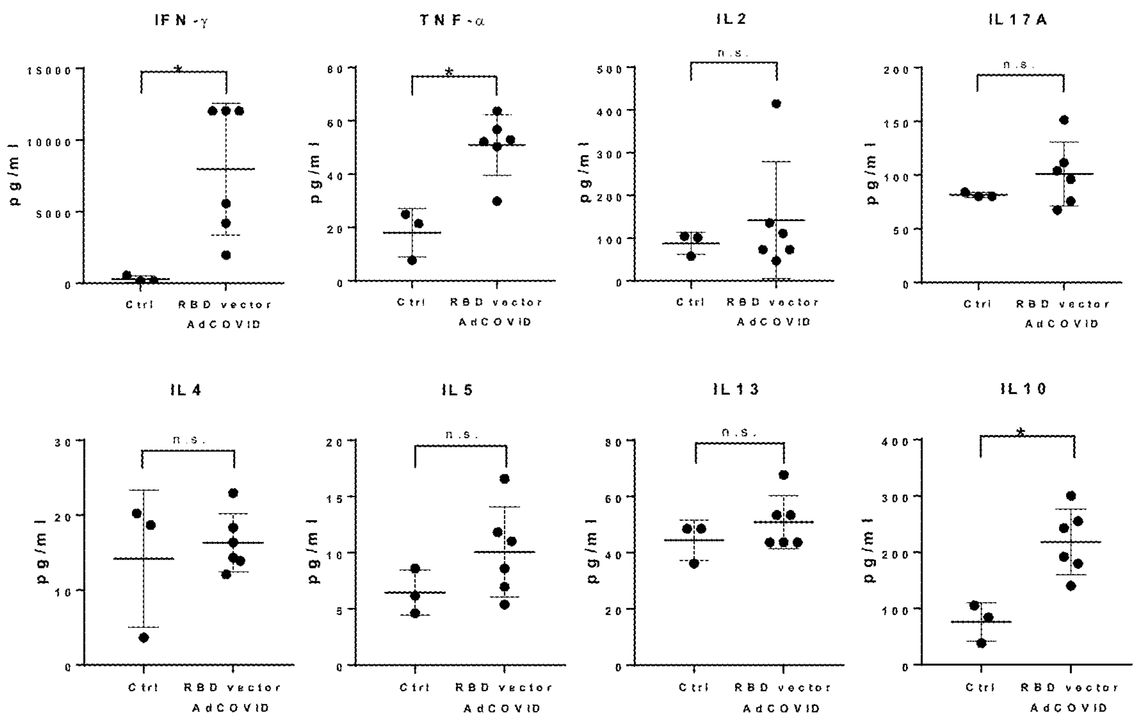
FIG. 96. Secreted cytokine production by splenic T cells 10 days after single intranasal administration with RBD vector. CD-1 mice were given a single intranasal administration of vehicle (Ctrl) or high dose RBD vector as described in Example 18. Spleen cells (n=10 mice/vaccine, 3 mice/control) were isolated at day 10 and re-stimulated with the RBD peptide pool for 48 hrs. Secreted cytokines were detected in the supernatant using a cytokine multiplex assay. Results are expressed in pg/ml. Lines represent mean response +/−SD. Statistical analysis was performed with a Mann-Whitney test: *, P<0.05; , P<0.01; *, P<0.001; ****, P<0.0001.

The data showed that intranasal administration of the RBD vector vaccine induced T cells competent to produce IFN-γ and TNF-α cytokines that are associated with Th-1 biased cellular response. In addition, we observed that the vaccine elicited high frequencies of antigen-specific $CD8^+$ T cells that generally correlate with an IFN-regulated T cell response that is important for control of viral infection. To further assess the cytokine producing potential of the T cells from vaccinated mice, we restimulated the splenic T cells with RBD peptides for 48 hours and then used cytokine bead arrays to measure cytokine levels in the supernatant. As expected, we observed induction of IFN-γ and TNF-α by the T cells, Moreover, we found that the T cells from the vaccinated animals produced moderate levels of IL-10 compared to T cells from the vehicle control treated mice. Importantly, Interleukin (IL)-4, IL-5, IL-13 and IL-17a levels in the supernatant from re-stimulated cells derived from the vaccinated mice were equivalent to that seen in cultures containing peptide-stimulated cells from the vehicle control animals (FIG. 96).

Example 18. Intranasal Administration of Ad5 Vector Expressing RBD Domain in C57BL/6 Mice Elicits Persistent Antibody Responses The immunogenicity of an intranasal replication-defective Ad5 vector encoding the RBD domain residues 302 to 543 (SEQ ID NO: 15) of SARS-Cov-2 was assessed in inbred C57BL/6 mice by measuring spike-specific serum IgG responses over time. At Day 0 prevaccination and Days 15, 30, 63 and 120 post-vaccination (e.g., about 2 weeks, about 1 month, about 2 months and about 4 months), sera were collected after a single intranasal vaccination as described in Table 25. Methods for the quantification of SARS-CoV-2 spike IgG in serum is described in Example 13B.

TABLE 25

| Vaccine/ Vehicle control | Intranasal dose | Number of animals per group | Immunization | Sample collection |
|---|---|---|---|---|
| AdtPAWHSRBD | 3.78E+08 ifu in 30 μL | 20 C57BL/6 | Day 0 | Day 0 (pre-vaccination), 15, 30, 63 and 120 |

Figure 97:
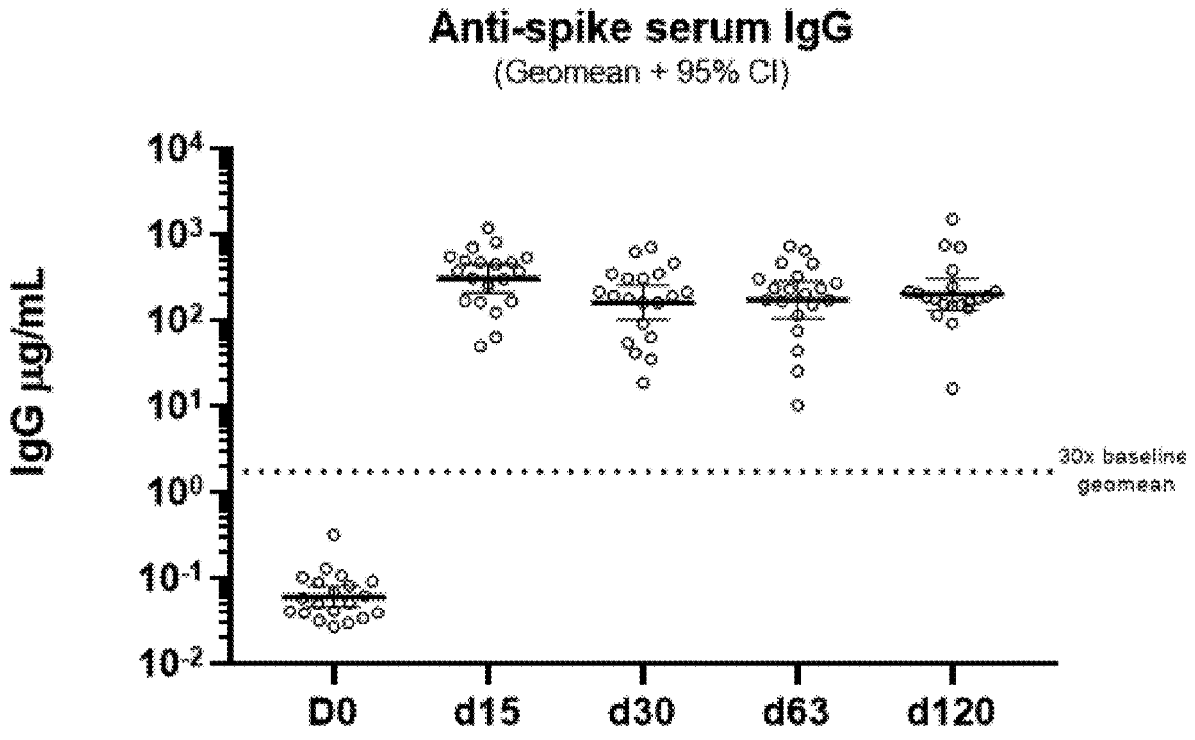
FIG. 97. Longitudinal spike-specific serum IgG responses following single intranasal administration of the RBD vector. C57BL/6J mice (n=20) received a single intranasal administration of the RBD vector. Sera were collected at days 0 pre-vaccination), and at days 15, 30, 63 and 120 post-vaccination and analyzed individually for quantification of spike-specific IgG. Results are expressed in μg/ml. See Example 18.

Results are presented in FIG. 97 wherein the 30× baseline is indicated with the dotted line. After detection of a spike-specific IgG response detected in all 20 vaccinated animals at day 15, responses remain stable up to day 120 with no statistical difference across the different post-vaccination timepoints based on a Wilcoxon matched-pairs signed rank test. This example demonstrated no significant decay in the measured anti-spike IgG from serum between 30 days and 120 days post vaccination. In embodiments, provided herein is a vaccine or RBD vector, that when administered as a single intranasal dose to a mammal induces an antibody response against the spike protein that is durable for at least 4 months. In some embodiments provided herein is a vaccine or RBD vector, that when administered as a single intranasal dose to a mammal induces an antibody response against the spike protein that is durable (given the absence of decay as measured at about 4 months) for at least about 5 months, at least about 6 months, at least about 7 months, at least about 8 months, at least about 9 months, at least about 10 months, at least about 11 months or at least about 12 months (on year).

Example 19. Intranasal Administration of Ad5 Vector Expressing RBD Domain in CD1 Mice Elicits Long-Lived Antibody Secreting Cells in the Bone Marrow and Lung The immunogenicity of an intranasal replication-defective Ad5 vector encoding the RBD domain residues 302 to 543 (SEQ ID NO: 15) of SARS-Cov-2 was assessed in outbred CD-1 mice by measuring RBD-specific plasma cells (antibody secreting cells; ASCs) in the bone marrow (BM) and lung that produce spike-specific IgG and IgA. At Days 69 post-vaccination, bone marrows and lungs were collected after a single intranasal vaccination as described in Table 26.

TABLE 26

| Vaccine/ Vehicle control | Intranasal dose | Number of animals per group | Immunization | Sample collection |
|---|---|---|---|---|
| RBD vector | 3.78E+08 ifu in 30 μL | 5 CD-1 | Day 0 | Day 69 |

The detection of RBD-specific ASCs in the bone marrow (BM) and lung that produce spike-specific IgG and IgA by ELISPOT is summarized as follows. Single cell suspensions from bone marrow (2 tibia+2 femur/mouse) and lung cells were prepared from vaccinated mice. Cells were serially diluted in duplicate in complete media and incubated for 5 hours at 37° C. on multiscreen cellulose filter ELISPOT plates (Millipore) that were previously coated with purified recombinant RBD protein (Sino Biological). RBD-specific antibodies secreted by plasma cells present in these tissues were detected using AP-conjugated goat anti-mouse IgG Ab (Jackson ImmunoResearch) or AP-conjugated goat anti-mouse IgA (Jackson ImmunoResearch). ELISPOTS were imaged and counted using S6 Ultra-V Analyzer (Cellular Technology Limited).

Figure 98:
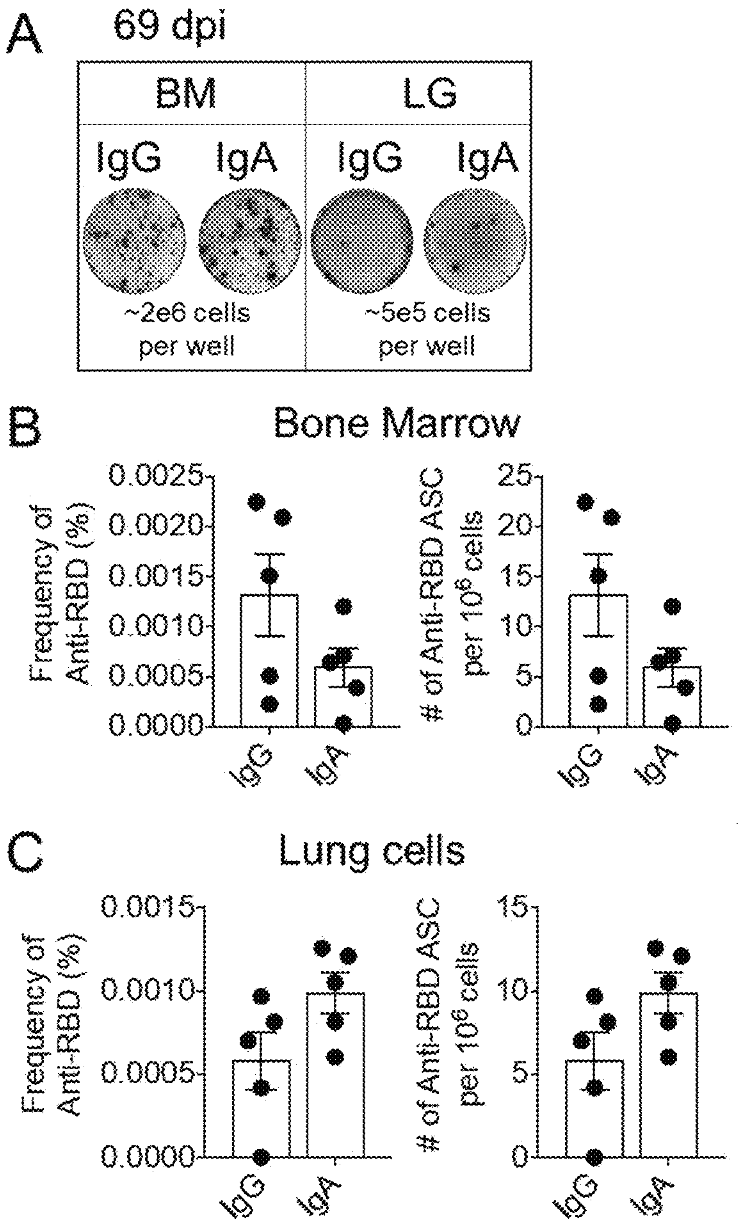
FIG. 98. Quantification of RBD-specific antibody secreting cells ("ASCs") produced IgG and IgA antibodies in the bone marrow and lungs following single intranasal administration of the RBD vector. CD-1 mice (n=5) received a single intranasal administration of the RBD vector. Lung cells (LG) and bone marrow cells (BM) were collected 69 days post-immunization ("69 dpi") and analyzed individually for the quantification of ASCs by ELISpot. (A) shows an example of a B-cell ELIspot plate wells. (B) Shows measurement of RBD-specific ASCs producing IgG and IgA shown as either the frequency or number per $10^6$ total cells in bone marrow. (C) Shows measurement of RBD-specific ASCs producing IgG and IgA shown as either the frequency or number per $10^6$ total cells in lung. See Example 19.

Results are presented in FIG. 98. RBD-specific ASCs were identified in the bone marrow of day 69 vaccinated mice. As these ASCs are located in a niche that specifically supports the long-term survival of ASCs, we predict that the systemic RBD-specific antibody titers induced by the RBD vector will be highly durable. Moreover, intranasal vaccination also resulted in the establishment of a durable ASC population in the lung that included IgA ASCs that can provide mucosal protection at the site of future infection. It is known that infection with respiratory viruses can also establish long-lived ASCs within the lung and that these cells are important in early protection from reinfection. Therefore, it is a reasonable supposition that the presence of these intranasal vaccine-induced ASCs may also provide local protection to the vaccinated animals. In embodiments provided herein are compositions (e.g., RBD vector) and methods for inducing bone marrow and lung resident memory antibody secreting cells. In some embodiments provided herein is a vaccine or RBD vector, that when administered as a single intranasal dose to a mammal induces bone marrow and lung resident memory antibody secreting cells that secrete both anti-spike IgG and IgA.

Example 20. Intranasal Administration of Ad5 Vector Expressing RBD Domain in C57BL/6 Mice Elicits Long-Lived RBD-Specific B Cell Memory The immunogenicity of an intranasal replication-defective Ad5 vector encoding the RBD domain residues 302 to 543 (SEQ ID NO: 15) of SARS-Cov-2 was assessed in inbred C57BL/6 mice by measuring long-lived RBD-specific B cell memory in the mediastinal lymph nodes and RBD-specific plasma cells (antibody secreting cells; ASCs) in the bone marrow (BM). At Day 168 post-vaccination (e.g., 24 weeks or 6 months), mediastinal lymph nodes and bone marrows were collected after a single intranasal vaccination as described in Table 27. Naïve C57BL/6 mice (n=5) were used negative controls.

TABLE 27

| Vaccine/ Vehicle control | Intranasal dose | Number of animals per group | Immunization | Sample collection |
|---|---|---|---|---|
| RBD vector | 3.78E+08 ifu in 30 μL | 5 C57BL/6 | Day 0 | Day 168 |

For the flow cytometry analysis of RBD-specific B cell memory, the B cell antibody panel consisted of CD95/FAS- FITC (clone Jo2; 1:200 dilution), SARS-CoV-2 RBD-PE (1:200 dilution), SARS-CoV-2 RBD-APC (1:200 dilution), 7-AAD (1:1000 dilution), CD3-PerCP-Cy5.5 (clone 17A2; 1:200 dilution), CD38-PE-Cy7 (clone 90; 1:400 dilution), CD19-APC-Fire750 (clone 6D5; 1:200 dilution), CD138-BV421 (clone 281-2; 1:200 dilution) and IgD-BV510 (clone 11-26c.2a; 1:500 dilution). Cells were incubated with antibody mix (50 ul total volume) for 20 min at 4° C. in the dark and then washed with 200 ul SME. Cell were resuspended in 200 ul SME (no fixative) and immediately analyzed on FACSCanto II.

Figure 99:
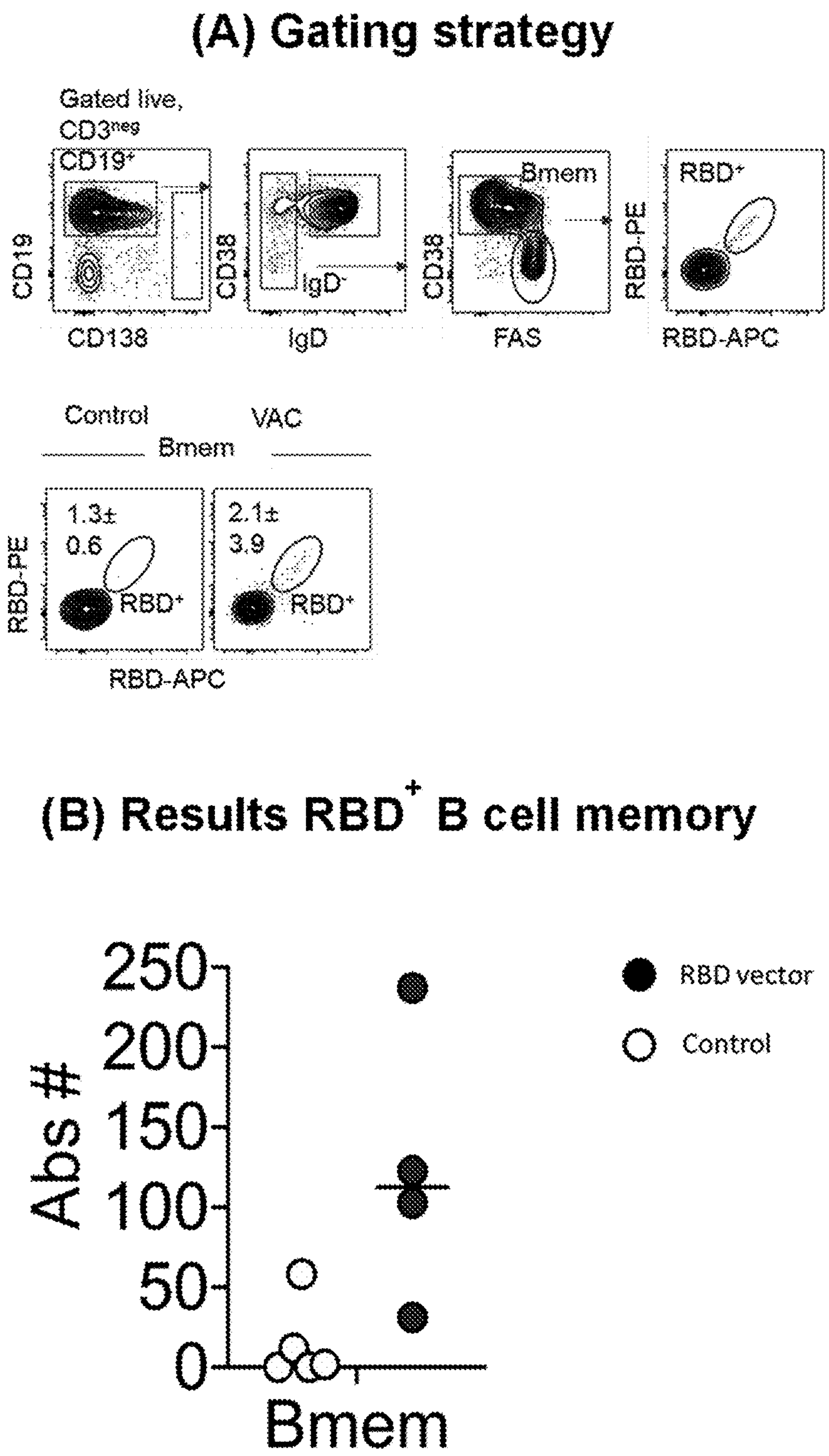
FIG. 99. Quantification of long-lived RBD-specific memory B cells at day 168 after single intranasal administration of the RBD vector. C57BL/6J (n−4) mice received a single intranasal administration of the RBD vector. Mediastinal lymph nodes were collected 168 days (24 weeks) post-immunization and analyzed individually for the quantification of RBD-specific memory B cells by flow cytometry. Naïve C57BL/6J (n=5) were used as negative control. (A) shows the gating strategy for the flow cytometry analysis. (B) Shows the absolute number of RBD specific memory B cells measured in vaccinated animals compared to naïve animals. See Example 20.

Results for RBD-specific memory B cells are presented in FIG. 99. FIG. 99B shows a higher absolute number of RBD-specific memory B cells present in the mediastinal lymph nodes of vaccinated animals compared to naïve animals. Detecting the presence of antigen-specific memory B cells 168 days after a single intranasal administration of the RBD vector provide a strong indication of the long-live nature of RBD-specific B induced by the intranasal vaccine. RBD-specific memory B cell present in mediastinal lymph nodes would be well-suited to be rapidly respond to respiratory infection such as SARS-CoV-2.

Figure 100:
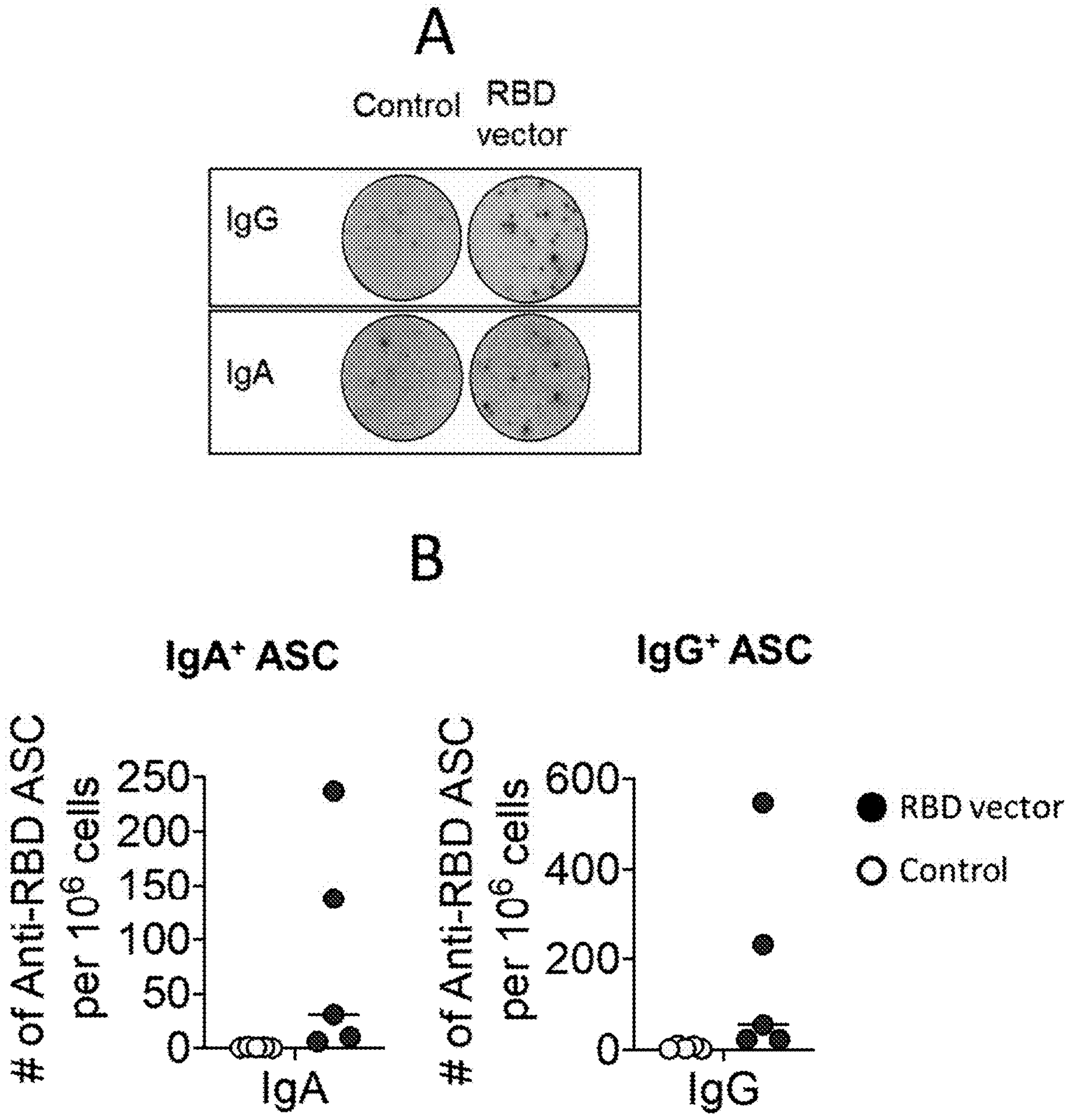
FIG. 100. Quantification of long lived RBD-specific ASCs produced IgG and IgA antibodies in the bone marrow following single intranasal administration of the RBD vector. C57BL/6J (n−4) mice received a single intranasal administration of the RBD vector. Bone marrow cells (BM) were collected 168 days (24 weeks) post-immunization and analyzed individually for the quantification of ASCs by ELISpot. Naïve C57BL/6J (n=5) were used as negative control. (A) Shows an example of B-cell ELIspot plate wells. (B) Shows the measurement of RBD-specific ASCs producing IgG and IgA shown number per 106 total cells in bone marrow. See Example 20.

Measurement of ASCs in bone marrow followed the same method as described in example 19. Results are presented in FIG. 100. Long lived RBD-specific ASCs produced IgG and IgA antibodies were detected in the bone marrow of most animals 168 days after single intranasal administration of the RBD vector.

Discussion—Single-Dose Intranasal Vaccination with 51 and RBD Adenoviral Vector Elicits Rapid and Durable Systemic and Mucosal Immunity Against SARS-CoV-2 in Mice The immunogenicity of the S1 and RBD vectors following a single administration of a replication-defective Ad5 vector encoding the S1 domain (residues 16 to 685) (SEQ ID NO: 13) or the RBD domain (residues 302 to 543) (SEQ ID NO: 15) from the Wuhan-1 strain of SARS-CoV-2 (accession number QHD43416.1) to inbred C57BL/6 and outbred CD-1 mice were assessed by measuring the induction of spike-specific antibody levels in sera and bronchoalveolar lavage (BAL) fluids. Each vaccine was evaluated at three (3) different dose levels (high, medium or low) as described above. Following single vaccine administration on day 0, sera, bronchoalveolar lavage (BAL) samples were collected between days 7-28 (C57BL/6) or days 7-21 (CD-1). IgG and IgA antibodies specific for SARS-CoV-2 spike were measured in serum or BAL samples using a spike cytometric bead array. The functionality of these vaccine-elicited antibodies was measured in live virus neutralization assays. In addition to the induction of robust neutralizing antibody responses and mucosal IgA against SARS-CoV-2, RBD stimulated systemic and mucosal cell-mediated immune responses characterized by a T-helper 1 (Th1) type cytokine profile and through the induction of cytokine-producing $CD4^+$ and $CD8^+$ T cells, including lung-resident memory T (Trm) cells.

Figure 78:
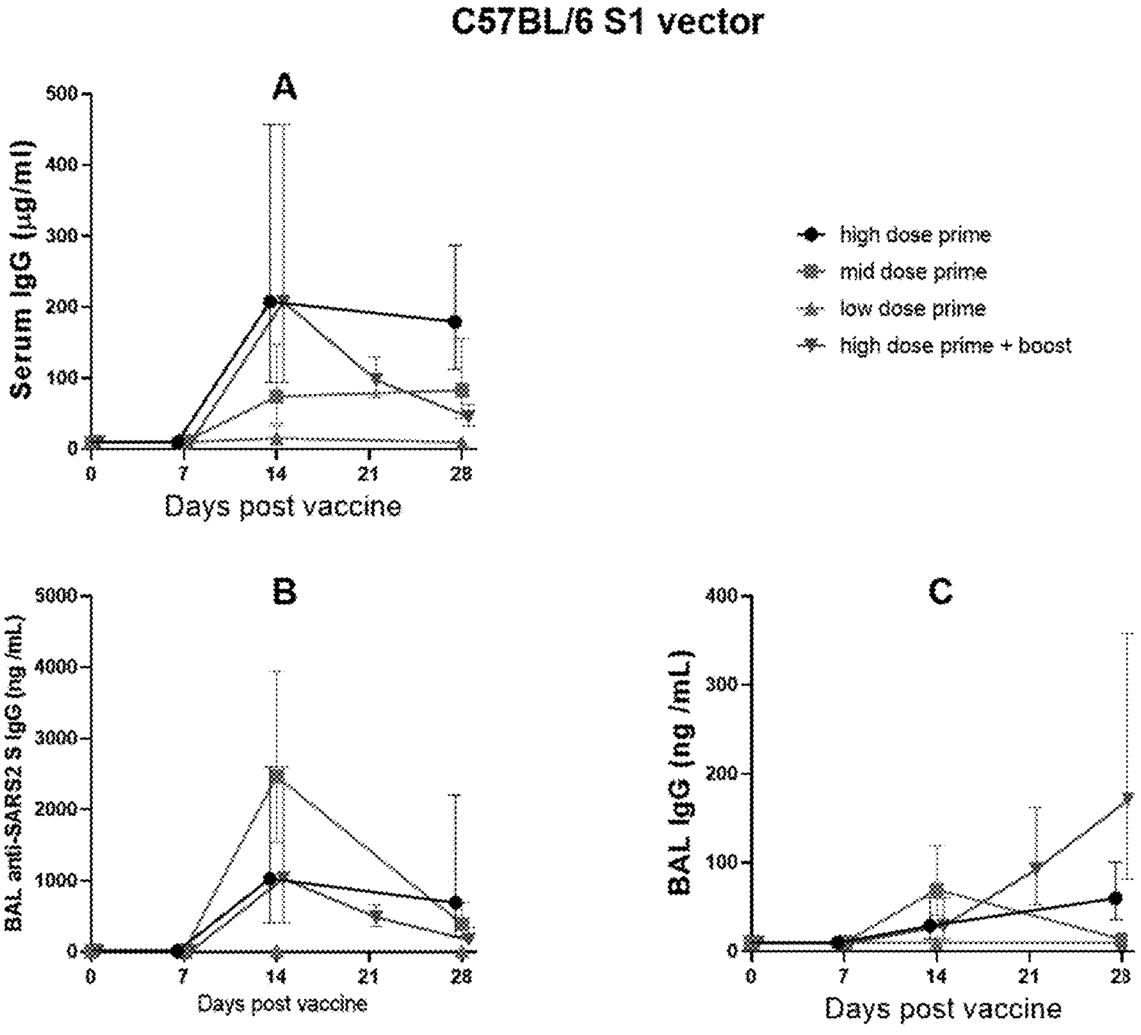
FIG. 78. Measurements of anti-SAR-CoV-2 IgG (μg/ml) in the serum (A), BAL anti-SARS2 S IgG (ng/ml) (B) and, BAL anti-SARS-2 S IgA (ng/ml) (C) from bronchoalveolar lavages (BAL) obtained at different time points from individual C57BL/6 mice that have received a single intranasal dose of the replication-deficient Ad5 vector expressing the S1 domain (SEQ ID NO: 13). Results for the groups as expressed as the geometric mean response +/−95% confidence interval. Day 0 reports control group values for all groups. Day 7 and day 14 for group receiving 2 intranasal doses report values from group receiving a single administration at the same dose.
Figures 79, 79E:
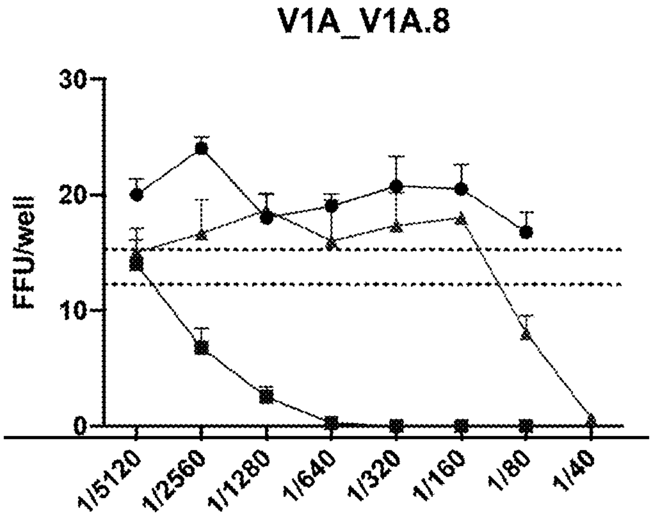
FIG. 79. Serum neutralizing antibodies against SARS-CoV-2 measured by focus reduction neutralization test (PRNT) in five C57BL/6 mice that have received a single intranasal high dose of the replication-deficient Ad5 vector expressing the S1 domain (SEQ ID NO: 13). Each graph corresponds to the result obtained from one immunized mouse (FIG. 79A through 79E). Lines in black correspond to the negative control serum, lines in blue correspond to the positive control and lines in red correspond to the tested serum samples.
Figures 80, 80E:
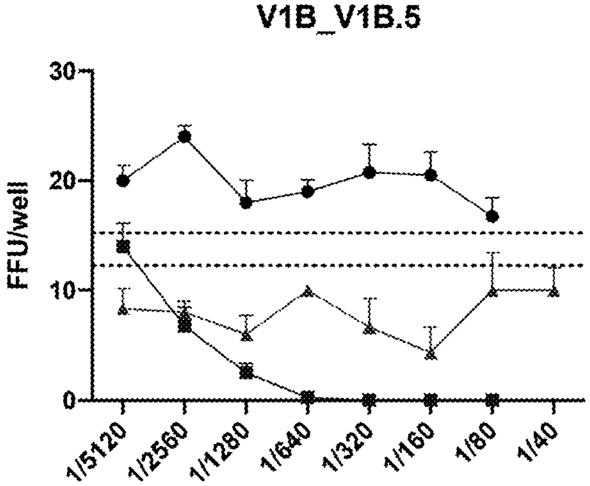
FIG. 80. Serum neutralizing antibodies against SARS-CoV-2 measured by focus reduction neutralization test (PRNT) in five C57BL/6 mice that have received a single intranasal mid-dose of replication-deficient Ad5 vector expressing the S1 domain (SEQ ID NO: 13). Each graph corresponds to the result obtained from one immunized mouse (FIGS. 80A through 80E). Lines in back correspond to the negative control serum, lines un blue correspond to the positive control and lines in red correspond to the tested serum samples.
Figure 81:
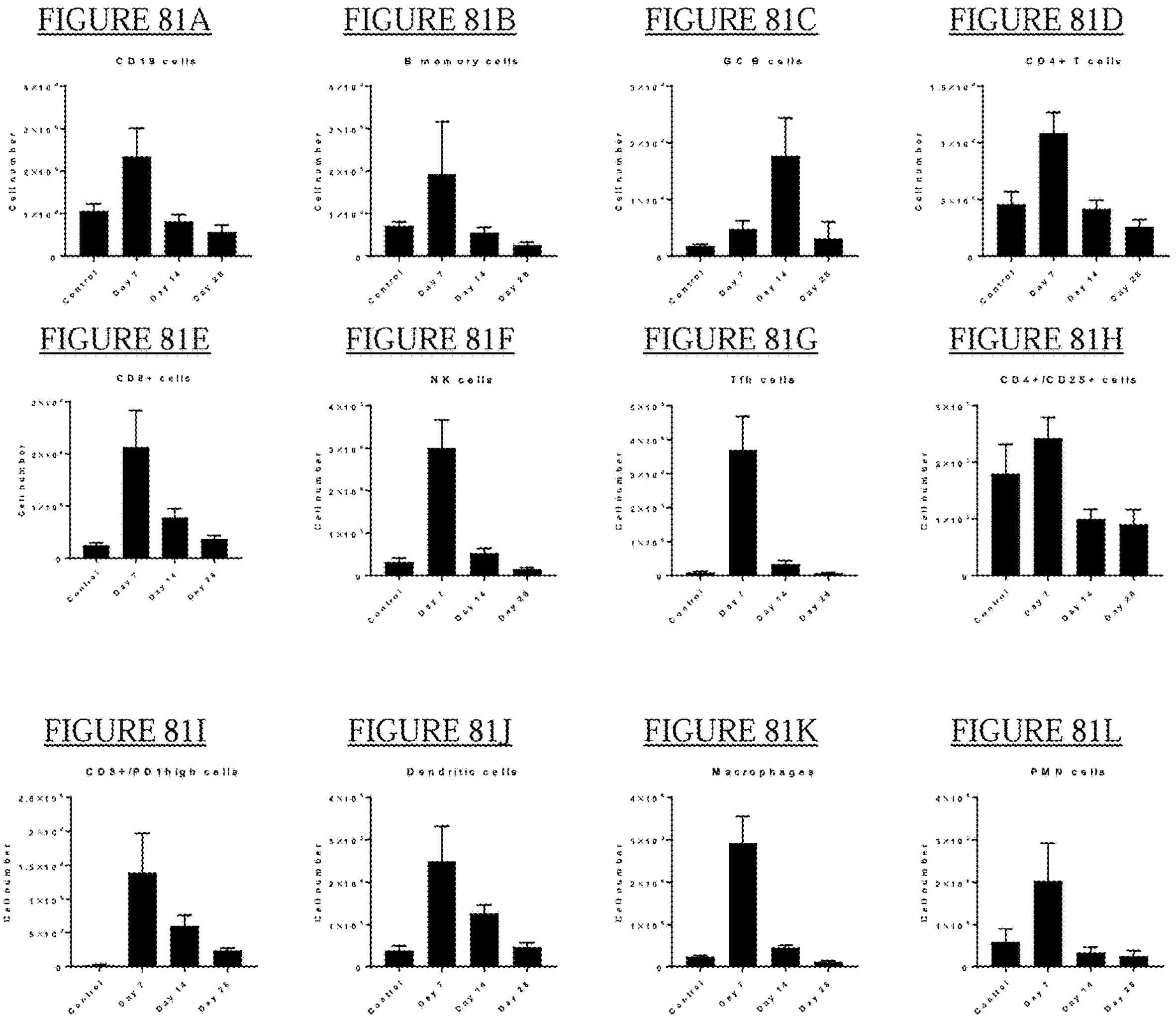
FIG. 81. Flow cytometry analysis of immune cells in lungs from individual C57BL/6 mice that have received a single intranasal high dose of the replication-deficient Ad5 vector expressing the S1 domain (SEQ ID NO: 13). Results for the groups are expressed as the geometric mean response +/95% confidence interval. Each graph (FIG. 81A through FIG. 81L) corresponds to an individual immune cell type at three time points.
Figure 85:
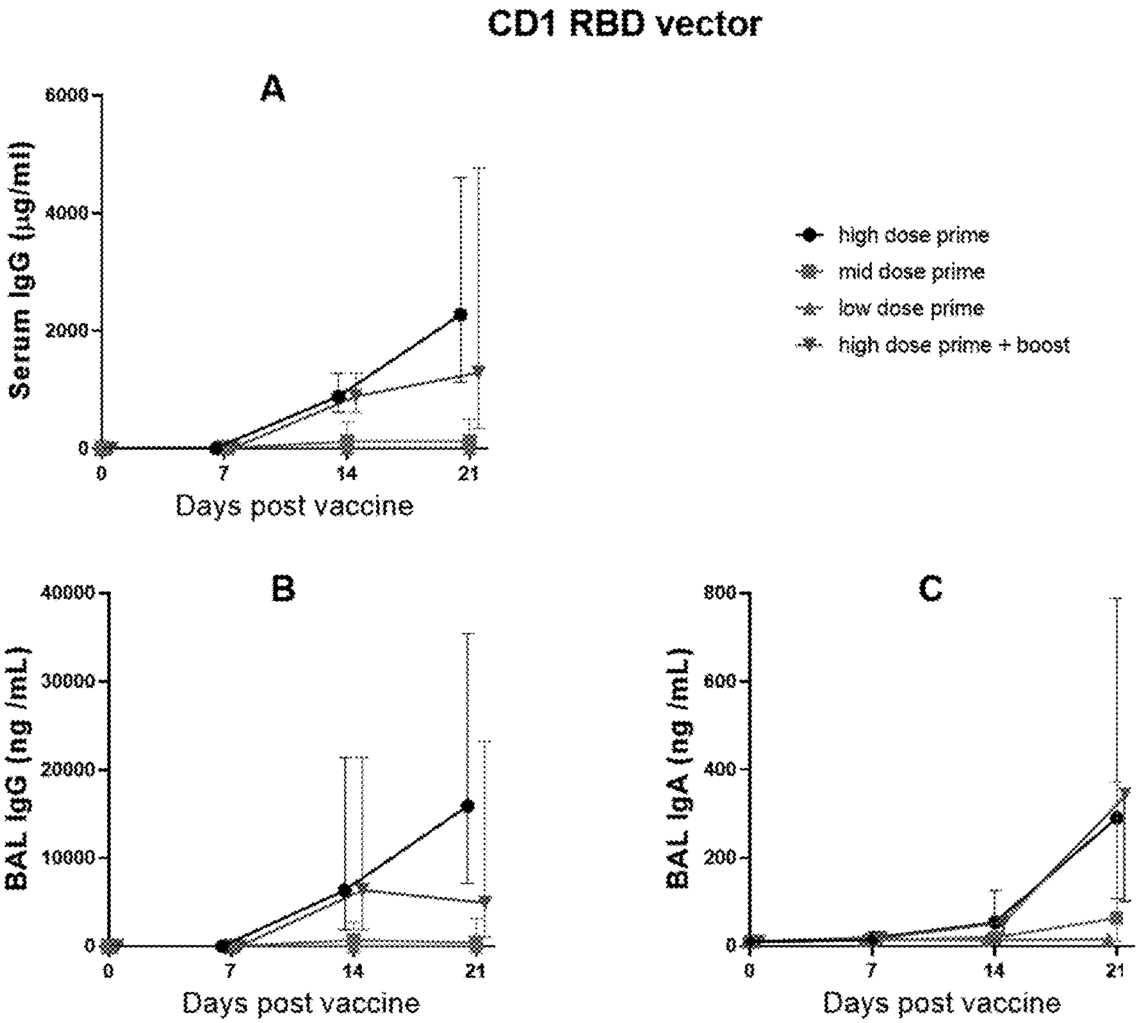
FIG. 85. Measurements of anti-SAR-CoV-2 IgG (µg/ml) in the serum (A), BAL anti-SARS-CoV-2 IgG (ng/ml) (B) and BAL anti-SARS-COV-2 IgA (ng/ml) (C) in bronchoalveolar lavages (BAL) obtained at different time points from individual CD-1 mice that have received one or two intranasal doses of the replication-deficient Ad5 vector expressing the RBD domain (SEQ ID NO: 15). Results for the groups are expressed as the geometric mean response +/−95% confidence interval. Day 0 reports control group values for all groups. Day 7 and day 14 for group receiving 2 intranasal doses report values from group receiving a single administration at the same dose.

Systemic spike-specific IgG antibody responses were detected in both strains of mice receiving a single intranasal administration of either the S1 vector or RBD vector vaccine. FIGS. 78 and 85. At the medium and high vaccine dose, the RBD vector induced a modestly larger serum spike-specific IgG response compared to the S1 vector—an effect that was more pronounced in the C57BL/6 mice compared to CD-1 mice. Moreover, intranasal administration of either S1 or RBD vector led to a rapid elevation of spike-specific IgG in the BAL of both strains of mice. Induction of IgA following a single intranasal dose of S1 or RBD was also demonstrated. Systemic spike-specific IgG antibody responses induced by the RBD vector (encoding SEQ ID NO: 15) following intranasal administration were also demonstrated to be durable with no evidence of decline over time for up to 120 days post-vaccination as presented in example 18. See FIG. 97. Moreover, intranasal vaccination also resulted in the establishment of a durable RBD-specific ASC and long-lived B cell memory population in the lung environment that included IgA ASCs that can provide local protection to the vaccinated animals. See FIGS. 98-100.

Figure 94:
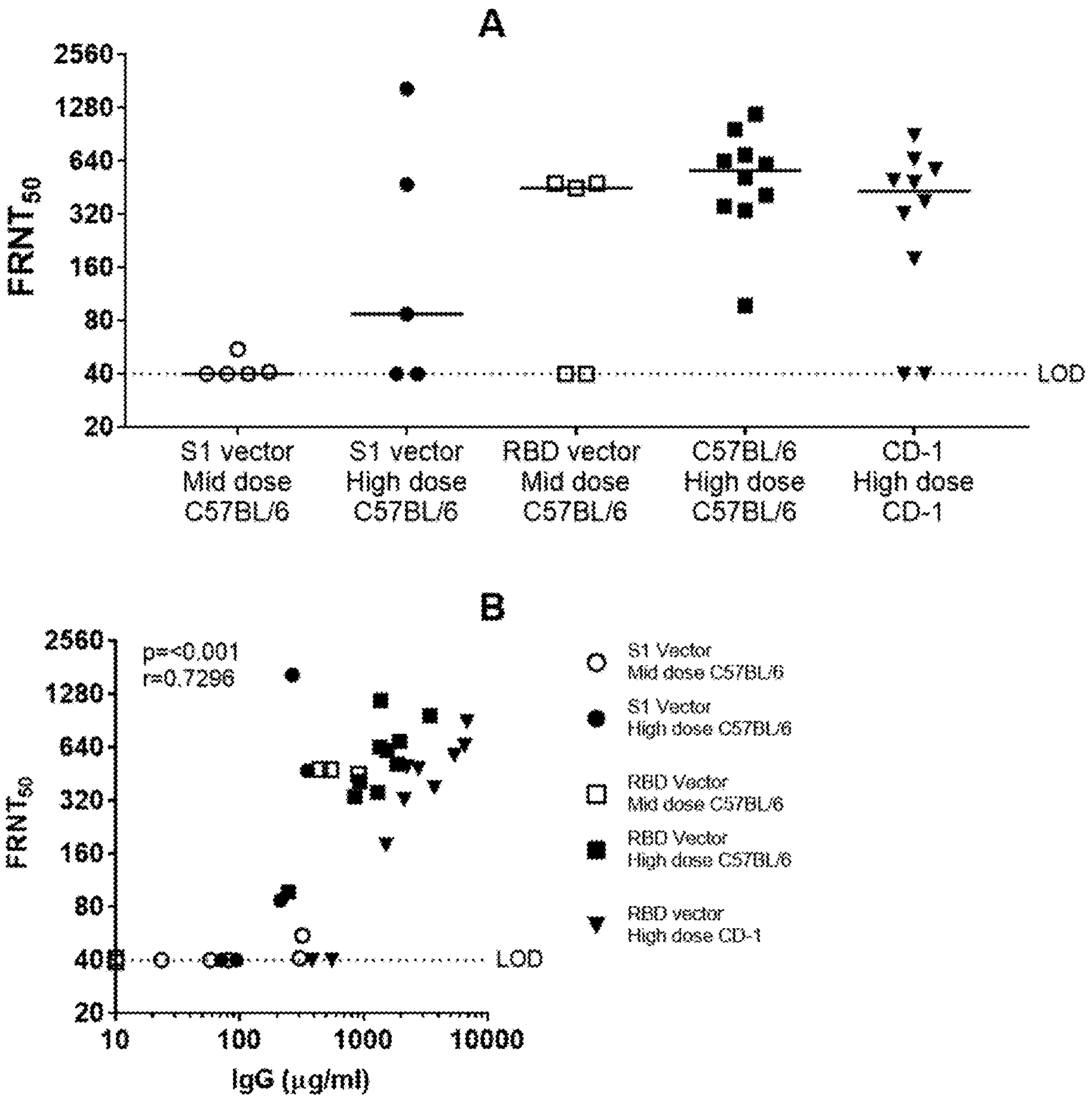
FIG. 94. SARS-CoV-2 neutralizing antibody responses in serum following single intranasal administration of the S1 vector and RBD vector. A: Neutralizing antibody response by C57BL/6 or CD-1 mice vaccinated 28 days earlier with the mid or high dose of the S1 or RBD vector as indicated. Results are expressed as the reciprocal of the dilution of serum samples required to achieve 50% neutralization ($FRNT_{50}$) of wild-type SARS-CoV-2 infection of permissive Vero E6 cells. Line represents the group median value. B: Correlation between neutralizing antibody response and Spike-specific IgG response in serum of vaccinated animals. Correlation analysis was performed with a two-tailed Spearman test. High-dose intranasal vaccination with the RBD vector induced neutralizing antibody responses above background in 10/10 C57BL/6 and 8/10 CD-1 mice.

Intranasal administration of S1 vector or RBD vector elicited neutralizing antibody responses against SARS-CoV-2 were measured in a focus neutralization reduction test (FNRT) (similar as the plaque reduction neutralization test (PRNT)) in infection permissive Vero E6 cells using the wild-type SARS-CoV-2 isolate USA-WA1/2020. The analysis included samples from C57BL/6 mice 4-weeks after vaccination with S1 and RBD using either the mid or high vaccine dose, and samples from CD1 mice 3-weeks after vaccination with the high vaccine dose of RBD vector (FIG. 94A). Intranasal administration of RBD vector elicited significantly greater neutralizing titers compared to use of S1 vector under all conditions evaluated. At the highest dose, intranasal vaccination with RBD vector induced neutralizing antibody responses above background in 10/10 C57BL/6 and 8/10 CD-1 mice with a median titer of 563 and 431 respectively (FIG. 94A). The level of the neutralizing antibody response correlated tightly with magnitude of the spike-specific serum IgG response measured in individual animals (FIG. 94B), indicating that robust antibody responses to administration with RBD vector were associated with the generation of potentially protective neutralizing antibodies.

Examples 13, 15 and 17 demonstrate that a present vaccine composition, e.g., an adenovirus-vectored vaccine encoding the RBD sequence (SEQ ID NO: 15) of the SARS-CoV-2 spike protein configured for intranasal administration, is highly immunogenic in both inbred and outbred mice and elicits robust systemic and local mucosal antibody and T cell responses. Following a single intranasal vaccination, the RBD vector composition elicited a strong and focused immune response against SARS-CoV-2 Spike through the induction of functional antibodies that neutralize wild-type SARS-CoV-2 infection of permissive cells as well as mucosal IgA and cytokine-producing pulmonary $CD4^+$ and $CD8^+$ T cells. Cell-mediated responses induced by the RBD vector composition were biased toward an anti-viral response as demonstrated by the high rates of antigen-specific $CD8^+$ T cells and cytokine expression that included IFN-γ and TNF-α. The establishment of a resident memory CD8+ T cell population in the lungs complements the robust induction of mucosal IgA antibody against the spike protein and represents an important addition to the overall immune response to the RBD vector composition. These data also indicate that intranasal administration of the RBD vector vaccine composition did not initiate a potentially deleterious Th2 response but rather induced the expected anti-viral T cell responses due to the anti-viral response induced with use of an adenoviral vector administered intranasally. See U.S. Pat. No. 9,605,275. Taken altogether, the data show that intranasal administration of the replication incompetent Ad5 vector expressing SARS-CoV-2 spike RBD sequence (SEQ ID NO: 15) generates humoral and cellular immune responses in both systemic and mucosal sites, particularly within the lung, which represents a major site for infection and clinical disease.

While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. An immunogenic composition comprising a replication defective adenoviral (rdAd) vector comprising a nucleic acid sequence encoding SEQ ID NO: 15 or a variant comprising at least 95% identity to SEQ ID NO: 15.

2. The immunogenic composition of claim 1, wherein the nucleic acid sequence encodes SEQ ID NO: 15.

3. The immunogenic composition of claim 1, wherein the nucleic acid sequence encodes a sequence comprising one or more mutations selected from K417T, K417N, E484K, L452R and/or N501Y, wherein amino acid numbering corresponds to SEQ ID NO: 411.

4. The immunogenic composition of claim 1, wherein the nucleic acid sequence encoding SEQ ID NO: 427 of SEQ ID NO: 15 is replaced with a leader sequence encoded by a nucleic acid sequence encoding a sequence selected from SEQ ID NOS: 418 to 437.

5. The immunogenic composition of claim 1, wherein the coding sequence is codon optimized for a mammalian subject.

6. The immunogenic composition of claim 1, wherein the replication defective adenoviral vector is a bovine adenovirus, a canine adenovirus, a non-human primate adenovirus, a chicken adenovirus, a porcine or swine adenovirus, or a human adenovirus.

7. The immunogenic composition of claim 6, wherein the non-human primate adenovirus is a chimpanzee or gorilla adenovirus.

8. The immunogenic composition of claim 1, wherein the replication defective adenoviral vector is a human adenovirus.

9. The immunogenic composition of claim 8, wherein the human adenovirus is Ad5 or Ad26.

10. A pharmaceutical formulation, comprising an effective amount of the immunogenic composition of claim 1, the composition comprising at least one pharmaceutically acceptable diluent or carrier.

11. The pharmaceutical formulation of claim 10, configured for non-invasive or intranasal administration, wherein the pharmaceutically acceptable carrier is in a spray or aerosol form.

12. A method for inducing an immune response against SARS-CoV-2, the method comprising administering an effective amount of the immunogenic composition of claim 1 to a human being.

13. The method of claim 12, wherein the effective amount is at least $10^8$ viral particles (vp), at least $10^9$ viral particles (vp), or at least $10^{10}$ viral particles (vp).

14. The method of claim 12, wherein the immunogenic composition is administered intranasally.

15. The method of claim 12, wherein the immune response against SARS-CoV-2 comprises a mucosal IgA and/or T cell response against SARS-CoV-2 induced after administration of the immunogenic composition.

16. The method of claim 12, wherein the effective amount of the immunogenic composition reduces incidence of mild or moderate COVID-19-related diseases after the administration to the human subject.

17. The method of claim 12, wherein the effective amount of the immunogenic composition reduces incidence of infection with SARS-CoV-2 after the administration to the human subject.

18. The method of claim 12, wherein the effective amount of the immunogenic composition reduces transmission of SARS-CoV-2 after the administration to the human subject.

19. An immunogenic composition comprising an Ad5 human adenovirus replication defective adenoviral (rdAd) vector comprising a nucleic acid sequence encoding SEQ ID NO: 15 or a variant comprising at least 95% identity to SEQ ID NO: 15.

* * * * *